US012486505B2

(12) United States Patent
Frank-Kamenetsky et al.

(10) Patent No.: US 12,486,505 B2
(45) Date of Patent: Dec. 2, 2025

(54) OLIGONUCLEOTIDE COMPOSITIONS AND METHODS THEREOF

(71) Applicant: WAVE LIFE SCIENCES LTD., Singapore (SG)

(72) Inventors: Maria David Frank-Kamenetsky, Brookline, MA (US); Hailin Yang, West Roxbury, MA (US); Aaron Jay Morris, Brighton, MA (US); Chandra Vargeese, Schwenksville, PA (US); Christopher J. Francis, Carlisle, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 55 days.

(21) Appl. No.: 18/305,195

(22) Filed: Apr. 21, 2023

(65) Prior Publication Data

US 2024/0150756 A1 May 9, 2024

Related U.S. Application Data

(60) Division of application No. 16/782,021, filed on Feb. 4, 2020, now Pat. No. 11,634,710, which is a continuation of application No. 15/746,199, filed as application No. PCT/US2016/043598 on Jul. 22, 2016, now abandoned.

(60) Provisional application No. 62/331,960, filed on May 4, 2016, provisional application No. 62/236,847, filed on Oct. 2, 2015, provisional application No. 62/195,779, filed on Jul. 22, 2015.

(51) Int. Cl.

| | |
|---|---|
| ***C07H 21/02*** | (2006.01) |
| ***A61P 25/28*** | (2006.01) |
| ***C12N 15/113*** | (2010.01) |
| ***C12N 15/115*** | (2010.01) |

(52) U.S. Cl.

CPC ............ *C12N 15/113* (2013.01); *A61P 25/28* (2018.01); *C12N 15/115* (2013.01); *C12N 2310/315* (2013.01); *C12N 2310/321* (2013.01); *C12N 2310/322* (2013.01); *C12N 2310/341* (2013.01); *C12N 2310/346* (2013.01)

(58) Field of Classification Search

CPC .................................................... C12N 15/115

See application file for complete search history.

(56) References Cited

U.S. PATENT DOCUMENTS

| | | | |
|---|---|---|---|
| 5,212,295 | A | 5/1993 | Cook |
| 5,521,302 | A | 5/1996 | Cook |
| 5,587,361 | A | 12/1996 | Cook et al. |
| 5,792,615 | A | 8/1998 | Arnold, Jr. et al. |
| 6,146,829 | A | 11/2000 | Cook et al. |
| 6,172,209 | B1 | 1/2001 | Manoharan et al. |
| 6,639,022 | B2 | 10/2003 | Michels et al. |
| 6,867,294 | B1 | 3/2005 | Sanghvi et al. |
| 6,949,520 | B1 | 9/2005 | Hartmann et al. |
| RE39,464 | E | 1/2007 | Cook et al. |
| 7,919,472 | B2 | 4/2011 | Monia et al. |
| 7,947,658 | B2 | 5/2011 | Aronin et al. |
| 7,951,934 | B2 | 5/2011 | Freier |
| 8,415,465 | B2 | 4/2013 | Freier |
| 8,470,987 | B2 | 6/2013 | Wada et al. |
| 8,481,710 | B2 | 7/2013 | Davidson et al. |
| 8,679,750 | B2 | 3/2014 | Hayden et al. |
| 8,680,063 | B2 | 3/2014 | Aronin et al. |
| 8,822,671 | B2 | 9/2014 | Shimizu et al. |
| 8,859,755 | B2 | 10/2014 | Wada et al. |
| 8,906,873 | B2 | 12/2014 | Hung et al. |
| 8,952,145 | B2 | 2/2015 | Freier |
| 8,987,222 | B2 | 3/2015 | Aronin et al. |
| 9,006,198 | B2 | 4/2015 | Bennett et al. |
| 9,057,066 | B2 | 6/2015 | Hung et al. |
| 9,260,716 | B2 | 2/2016 | Davidson et al. |
| 9,353,372 | B2 | 5/2016 | Freier |
| 9,394,333 | B2 | 7/2016 | Wada et al. |
| 9,476,044 | B2 | 10/2016 | Tuschl et al. |
| 9,598,458 | B2 | 3/2017 | Shimizu et al. |
| 9,605,019 | B2 | 3/2017 | Verdine et al. |
| 9,617,547 | B2 | 4/2017 | Gemba |
| 9,683,236 | B2 | 6/2017 | Hung et al. |

(Continued)

FOREIGN PATENT DOCUMENTS

| | | | |
|---|---|---|---|
| EP | 2 873 674 | A1 | 5/2015 |
| JP | H06-220083 | A | 8/1994 |

(Continued)

OTHER PUBLICATIONS

U.S. Appl. No. 17/605,998, filed Oct. 22, 2021, Byrne et al.
U.S. Appl. No. 17/766,680, filed Apr. 5, 2022, Liu et al.
U.S. Appl. No. 17/953,292, filed Sep. 26, 2022, Monian et al.
U.S. Appl. No. 17/956,741, filed Sep. 29, 2022, Vargeese et al.
U.S. Appl. No. 17/960,090, filed Oct. 4, 2022, Vargeese et al.
U.S. Appl. No. 18/062,422, filed Dec. 6, 2022, Butler et al.
U.S. Appl. No. 18/178,470, filed Mar. 3, 2023, Vargeese et al.
U.S. Appl. No. 18/204,895, filed Jun. 1, 2023, Vargeese et al.
U.S. Appl. No. 18/252,029, filed May 5, 2023, Monian et al.
U.S. Appl. No. 18/316,932, filed May 12, 2023, Butler et al.

(Continued)

*Primary Examiner* — Amy Rose Hudson
(74) *Attorney, Agent, or Firm* — Choate, Hall & Stewart LLP; Xiaodong Li; Nnamdi Edokobi

(57) ABSTRACT

Among other things, the present disclosure relates to designed oligonucleotides, compositions, and methods thereof. In some embodiments, provided oligonucleotide compositions provide altered splicing of a transcript. In some embodiments, provided oligonucleotide compositions have low toxicity. In some embodiments, provided oligonucleotide compositions provide improved protein binding profiles. In some embodiments, provided oligonucleotide compositions have improved delivery. In some embodiments, provided oligonucleotide compositions have improved uptake. In some embodiments, the present disclosure provides methods for treatment of diseases using provided oligonucleotide compositions.

15 Claims, 8 Drawing Sheets

Specification includes a Sequence Listing.

(56) References Cited

U.S. PATENT DOCUMENTS

| | | | |
|---|---|---|---|
| 9,695,211 | B2 | 7/2017 | Wada et al. |
| 9,744,183 | B2 | 8/2017 | Verdine et al. |
| 9,982,257 | B2 | 5/2018 | Butler et al. |
| 10,023,865 | B2 | 7/2018 | Tuschl et al. |
| 10,144,933 | B2 | 12/2018 | Gemba et al. |
| 10,149,905 | B2 | 12/2018 | Gemba et al. |
| 10,160,969 | B2 | 12/2018 | Meena et al. |
| 10,167,309 | B2 | 1/2019 | Shimizu et al. |
| 10,280,192 | B2 | 5/2019 | Verdine et al. |
| 10,307,434 | B2 | 6/2019 | Verdine et al. |
| 10,322,173 | B2 | 6/2019 | Gemba et al. |
| 10,329,318 | B2 | 6/2019 | Wada et al. |
| 10,428,019 | B2 | 10/2019 | Wada et al. |
| 10,450,568 | B2 | 10/2019 | Butler et al. |
| 10,479,995 | B2 | 11/2019 | Vargeese et al. |
| 10,590,413 | B2 | 3/2020 | Butler et al. |
| 10,696,711 | B2 | 6/2020 | Shimizu et al. |
| 10,724,035 | B2 | 7/2020 | Vargeese et al. |
| 10,815,482 | B2 | 10/2020 | Meena et al. |
| 11,013,757 | B2 | 5/2021 | Zhang et al. |
| 11,136,346 | B2 | 10/2021 | Shimizu et al. |
| 11,407,775 | B2 | 8/2022 | Butler et al. |
| 11,596,646 | B2 | 3/2023 | Zhang et al. |
| 11,597,927 | B2 | 3/2023 | Vargeese et al. |
| 11,603,532 | B2 | 3/2023 | Vargeese et al. |
| 11,608,355 | B2 | 3/2023 | Bowman et al. |
| 11,634,710 | B2 | 4/2023 | Frank-Kamenetsky et al. |
| 11,643,657 | B2 | 5/2023 | Butler et al. |
| 11,718,638 | B2 | 8/2023 | Butler et al. |
| 11,739,325 | B2 | 8/2023 | Vargeese et al. |
| 11,873,316 | B2 | 1/2024 | Butler et al. |
| 2002/0082227 | A1 | 6/2002 | Henry |
| 2002/0183502 | A1 | 12/2002 | Mesmaeker et al. |
| 2004/0096848 | A1 | 5/2004 | Thrue et al. |
| 2008/0015162 | A1 | 1/2008 | Bhanot et al. |
| 2009/0053205 | A1 | 2/2009 | Kandimalla et al. |
| 2011/0039334 | A1 | 2/2011 | Bennett et al. |
| 2014/0303235 | A1 | 10/2014 | Oestergaard et al. |
| 2014/0303238 | A1 | 10/2014 | Linsley et al. |
| 2014/0309279 | A1 | 10/2014 | Oestergaard et al. |
| 2015/0292015 | A1 | 10/2015 | Bennett et al. |
| 2015/0376625 | A1 | 12/2015 | Oestergaard et al. |
| 2017/0044526 | A1 | 2/2017 | Wan et al. |
| 2017/0130224 | A1 | 5/2017 | Oestergaard et al. |
| 2017/0335323 | A1 | 11/2017 | Hansen et al. |
| 2019/0025288 | A1 | 1/2019 | Boess et al. |
| 2019/0264267 | A1 | 8/2019 | Yang et al. |
| 2019/0375774 | A1 | 12/2019 | Butler et al. |
| 2020/0157545 | A1 | 5/2020 | Vargeese et al. |
| 2020/0362337 | A1 | 11/2020 | Dodart et al. |
| 2021/0032620 | A1 | 2/2021 | Vargeese et al. |
| 2021/0115444 | A1 | 4/2021 | Meena et al. |
| 2021/0254062 | A1 | 8/2021 | Zhang et al. |
| 2022/0098585 | A1 | 3/2022 | Brown et al. |
| 2022/0127301 | A1 | 4/2022 | Shimizu et al. |
| 2022/0145300 | A1 | 5/2022 | Liu et al. |
| 2022/0186217 | A1 | 6/2022 | Zhang et al. |
| 2022/0195429 | A1 | 6/2022 | Vargeese et al. |
| 2022/0306573 | A1 | 9/2022 | Zhang et al. |
| 2022/0307019 | A1 | 9/2022 | Yokota et al. |
| 2022/0401467 | A1 | 12/2022 | Zhang et al. |
| 2023/0089442 | A1 | 3/2023 | Kandasamy et al. |
| 2023/0136645 | A1 | 5/2023 | Butler et al. |
| 2023/0145795 | A1 | 5/2023 | Byrne et al. |
| 2023/0203087 | A1 | 6/2023 | Kandasamy et al. |
| 2023/0220384 | A1 | 7/2023 | Monian et al. |
| 2023/0295617 | A1 | 9/2023 | Vargeese et al. |
| 2023/0295619 | A1 | 9/2023 | Maguire et al. |
| 2023/0329201 | A1 | 10/2023 | Yang et al. |
| 2023/0348524 | A1 | 11/2023 | Bowman et al. |
| 2023/0392137 | A1 | 12/2023 | Monian et al. |
| 2024/0026358 | A1 | 1/2024 | Monian et al. |
| 2024/0109931 | A1 | 4/2024 | Vargeese et al. |
| 2024/0117347 | A1 | 4/2024 | Butler et al. |
| 2024/0132894 | A1 | 4/2024 | Vargeese et al. |
| 2024/0174710 | A1 | 5/2024 | Butler et al. |
| 2024/0175016 | A1 | 5/2024 | Liu et al. |
| 2024/0175018 | A1 | 5/2024 | Vargeese et al. |
| 2024/0229026 | A1 | 7/2024 | Butler et al. |
| 2024/0368207 | A1 | 11/2024 | Butler et al. |
| 2025/0051778 | A1 | 2/2025 | Byrne et al. |

FOREIGN PATENT DOCUMENTS

| | | | |
|---|---|---|---|
| JP | 2003-238586 | A | 8/2003 |
| JP | 2011-184318 | A | 9/2011 |
| RU | 2616283 | C2 | 4/2017 |
| WO | WO-93/08296 | A1 | 4/1993 |
| WO | WO-99/05160 | A2 | 2/1999 |
| WO | WO-2005/014609 | A2 | 2/2005 |
| WO | WO-2005/023828 | A1 | 3/2005 |
| WO | WO-2005/027980 | A1 | 3/2005 |
| WO | WO-2005/028494 | A1 | 3/2005 |
| WO | WO-2005/070859 | A1 | 8/2005 |
| WO | WO-2005/085272 | A1 | 9/2005 |
| WO | WO-2005/092909 | A1 | 10/2005 |
| WO | WO-2005/111057 | A2 | 11/2005 |
| WO | WO-2007/131237 | A2 | 11/2007 |
| WO | WO-2007/131238 | A2 | 11/2007 |
| WO | WO-2007/134014 | A2 | 11/2007 |
| WO | WO-2007/134181 | A2 | 11/2007 |
| WO | WO-2007/136988 | A2 | 11/2007 |
| WO | WO-2007/139190 | A1 | 12/2007 |
| WO | WO-2007/143315 | A2 | 12/2007 |
| WO | WO-2007/143316 | A2 | 12/2007 |
| WO | WO-2007/143317 | A2 | 12/2007 |
| WO | WO-2007/146511 | A2 | 12/2007 |
| WO | WO-2008/049085 | A1 | 4/2008 |
| WO | WO-2010/064146 | A2 | 6/2010 |
| WO | WO-2010/091301 | A1 | 8/2010 |
| WO | WO-2011/005761 | A1 | 1/2011 |
| WO | WO-2011/034072 | A1 | 3/2011 |
| WO | WO-2011/082281 | A2 | 7/2011 |
| WO | WO-2011/108682 | A1 | 9/2011 |
| WO | WO-2012/039448 | A1 | 3/2012 |
| WO | WO-2012/073857 | A1 | 6/2012 |
| WO | WO-2012109395 | A1 | 8/2012 |
| WO | WO-2012/145729 | A2 | 10/2012 |
| WO | WO-2013/012758 | A1 | 1/2013 |
| WO | WO-2013/022984 | A1 | 2/2013 |
| WO | WO-2013/112053 | A1 | 8/2013 |
| WO | WO-2014/010250 | A1 | 1/2014 |
| WO | WO-2014/010718 | A1 | 1/2014 |
| WO | WO-2014/012081 | A2 | 1/2014 |
| WO | WO-2014/118267 | A1 | 8/2014 |
| WO | WO-2014/121287 | A2 | 8/2014 |
| WO | WO-2014/179626 | A2 | 11/2014 |
| WO | WO-2015/051214 | A1 | 4/2015 |
| WO | WO-2015/107425 | A2 | 7/2015 |
| WO | WO-2015/108046 | A1 | 7/2015 |
| WO | WO-2015/108047 | A1 | 7/2015 |
| WO | WO-2015/108048 | A1 | 7/2015 |
| WO | WO-2016/079181 | A1 | 5/2016 |
| WO | WO-2016/096938 | A1 | 6/2016 |
| WO | WO-2016/127000 | A1 | 8/2016 |
| WO | WO-2017/015555 | A1 | 1/2017 |
| WO | WO-2017/015575 | A1 | 1/2017 |
| WO | WO-2017/062862 | A2 | 4/2017 |
| WO | WO-2017/067970 | A1 | 4/2017 |
| WO | WO-2017/160741 | A1 | 9/2017 |
| WO | WO-2017/192664 | A1 | 11/2017 |
| WO | WO-2017/192679 | A1 | 11/2017 |
| WO | WO-2017/210647 | A1 | 12/2017 |
| WO | WO-2018/022473 | A1 | 2/2018 |
| WO | WO-2018/067973 | A1 | 4/2018 |
| WO | WO-2018/098264 | A1 | 5/2018 |
| WO | WO-2018/223056 | A1 | 12/2018 |
| WO | WO-2018/223073 | A1 | 12/2018 |
| WO | WO-2018/223081 | A1 | 12/2018 |
| WO | WO-2018/237194 | A1 | 12/2018 |
| WO | WO-2019/032607 | A1 | 2/2019 |
| WO | WO-2019/032612 | A1 | 2/2019 |
| WO | WO-2019/055951 | A1 | 3/2019 |
| WO | WO-2019/075357 | A1 | 4/2019 |

(56) References Cited

FOREIGN PATENT DOCUMENTS

WO WO-2019/200185 A1 10/2019
WO WO-2019/217784 A1 11/2019
WO WO-2020/118246 A1 6/2020
WO WO-2020/160336 A1 8/2020
WO WO-2020/191252 A1 9/2020
WO WO-2020/196662 A1 10/2020
WO WO-2020/219981 A2 10/2020
WO WO-2020/219983 A2 10/2020
WO WO-2020/227691 A2 11/2020
WO WO-2021/071788 A2 4/2021
WO WO-2021/071858 A1 4/2021
WO WO-2021/178237 A2 9/2021
WO WO-2021/234459 A2 11/2021
WO WO-2021/237223 A1 11/2021
WO WO-2022/046667 A1 3/2022
WO WO-2022/046723 A1 3/2022
WO WO-2022/099159 A1 5/2022
WO WO-2023/049475 A1 3/2023
WO WO-2023/049477 A2 3/2023
WO WO-2023/075766 A1 5/2023
WO WO-2023/076352 A2 5/2023
WO WO-2023/154528 A1 8/2023
WO WO-2023/168014 A2 9/2023
WO WO-2023/201095 A2 10/2023
WO WO-2023/220440 A1 11/2023
WO WO-2024/035946 A1 2/2024
WO WO-2025/030155 A1 2/2025

OTHER PUBLICATIONS

Agrawal, S. et al., Mixed-backbone oligonucleotides as second generation antisense oligonucleotides: In vitro and in vivo studies, Proc. Natl. Acad. Sci. USA, 94: 2620-2625 (1997).
Bilesen, P.H.J. et al., Identification and Allele-Specific Silencing of the Mutant Huntingtin Allele in Huntington's Disease Patient-Derived Fibroblasts, Hum. Gene Thera., 19:710-718 (2008).
Bock, L.C. et al., Selections of single-stranded DNA molecules that bind and inhibit human thrombin, Nature, 355: 564-566 (1992).
Boyanapalli, R. et al., A Novel Quantitative Wild-type Huntingtin (wtHTT) Protein Biomarker Method for Human Cerebrospinal Fluid, Wave Life Sciences, presented at the 17th Annual Huntington's Disease Therapeutics Conference (CHDI Foundation), Palm Springs, CA, on Feb. 28-Mar. 3, 2022.
Carroll, J. B. et al., Potent and Selective Antisense Oligonucleotides Targeting Single-Nucleotide Polymorphisms in the Huntington Disease Gene / Allele-Specific Silencing of Mutant Huntingtin, Mol. Thera., 19(12):2178-2185 (2011).
Chan, J.H.P. et al., Antisense Oligonucleotides: From Design to Therapeutic Application, Clinical and Experimental Pharmacology and Physiology, 33: 544-540 (2006).
Crooke, S. T., Antisense Drug Technology: Principles, Strategies, and Applications, 2nd Edition, pp. 1-66 (2008).
Crooke, S. T., Antisense Strategies, Curr. Mol. Med., 4(5):465-487 (2004).
Crooke, S.T., Progress in Antisense Technology , Annu. Rev. Med., 55: 61-95 (2004).
Dale, E., Enhancing the pharmacologic profiles of CNS targeting therapeutic oligonucleotides, Wave Life Sciences, presented at TIDES USA, on Sep. 23, 2021.
Engelhardt, J.A. et al., Scientific and Regulatory Policy Committee Points-to-consider Paper: Drug-induced Vascular Injury Associated with Nonsmall Molecule Therapeutics in Preclinical Development: Part 2. Antisense Oligonucleotides, Toxicologic Pathology, XX: 1-10 (2015).
Frazier, K. et al., Potential Mechanisms of vascular toxicity in Monkeys with antisense oligonucleotides, TIDES oligo conference, 1-25 (May 15, 2014).
Frazier, K.S. Antisense Oligonucleotide Therapies: The Promise and the Challenges from a Toxicologic Pathologist's Perspective, Toxicology Pathology, 43: 78-89 (2015).
Gagnon, K. T. et al., Allele-Selective Inhibitions of Mutant Huntingtin Expression with Antisense Oligonucleotide Targeting the Expanded CAG Repeat, Biochemistry 49(47): 10166-10178 (2010).
Gagnon, K.T. and Watts, J.K 10th Annual Meeting of the Oligonucleotide Therapeutics Society, San Diego, CA, Summer Summaries (Oct. 12-15, 2014).
Hartmann, G. et al., Delineation of a CpG Phosphorothioate Oligodeoxynucleotide for Activating Primate Immune Responses In Vitro and In Vivo, The Journal of Immunology, 164(3): 1617-1624 (2000).
Henry, S.P. et al., Activation of the Alternative Pathway of Complement by a Phosphorothioate Oligonucleotide: Potential Mechanism of Action, The Journal of Pharmacology and Experimental Therapeutics, 281(2): 810-816 (1997).
Hu, J. et al., Allele-Selective Inhibition of Huntingtin Expression by Switching to an miRNA-like RNAi Mechanism, Chemistry & Biology 17: 1183-1188 (2010).
Hu, J. et al., Exploring the Effect of Sequence Length and Composition on Allele-Selective Inhibition of Human Huntingtin Expression by Single-Stranded Silencing RNAs, Nucleic Acid Therapeutics, 24(3): 199-209 (2014).
Hung, S. Stereopure oligonucleotides as a therapeutic approach to rare neurological diseases. Paper presented at: Huntington's Society of Canada 2017 National Conference (Nov. 2017).
International Search Report for PCT/US2016/043598, 4 pages (Nov. 28, 2016).
Ionis Pharmaceuticals, Inc., Ionis Pharmaceuticals Licenses IONIS-HTT Rx to Partner Following Successful Phase 1/2a Study in Patients with Huntington's Disease, Press Release, 2 pages (Dec. 11, 2017).
Iwamoto, N. et al., Control of phosphorothioate stereochemistry substantially increases the efficacy of antisense oligonucleotides, Nature Biotechnol, 35(9): 845-851 (2017), with Supplemental Data, 14 pages.
Iwamoto, N. et al., Control of phosphorothioate stereochemistry substantially increases the efficacy of antisense oligonucleotides, Nature Biotechnology, 1-7 pages (2017). All Supplemental Data, 8-53 pages (2017).
Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25, 2015-Mar. 28, 2016).
Iwamoto, N. From Stereopurity to precision medicine: Optimizing the properties of antisense nucleic acid therapeutics. Paper presented at: BioJapan, Yokohama, Japan (Oct. 11, 2018).
Kandasamy, P. et al., From stereopurity to precision medicine: Optimizing the properties of antisense nucleic acid therapeutics. Paper presented at: the 45th International Symposium on Nucleic Acid Chemistry, Kyoto, Japan (Nov. 7-9, 2018).
Kaur, H. et al., Activation of natural killer-like YT-INDY cells by oligodeoxynucleotides and binding by homologous pattern recognition proteins, Scandinavian Journal of Immunology, 62: 361-370 (2005).
Kay, C. et al., Personalized gene silencing therapeutics for Huntington disease, Clinical Genetics, 1-8 (2014).
Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).
Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).
Krakowiak, A. et al., Influence of P-Chirality of Phosphorothioate Oligonucleotides on the Activity of Amv-Reverse Transcriptase, Nucleosides & Nucleotides, 17(9-11): 1823-1834 (1998).
Krieg, A.M. et al., P-Chirality-Dependent Immune Activiation by Phosphorothioate CpG Oligodeoxynucleotides, Oligonucleotides, 13:491-499 (2003).
Leviten, M., Wave's Purity Progress, Biocentury, 1-6 (Sep. 28, 2017).
Liu, Y. et al., Impact of Nitrogen-containing Backbone Linkages on Stereopure Antisense Oligonucleotides in the CNS, Wave Life

(56) References Cited

OTHER PUBLICATIONS

Sciences, Presented at TIDES USA: Oligonucleotide & Peptide Therapeutics on Sep. 20-23, 2021 in Boston, Massachusetts.
McBride, J.L. et al., Prelinical Safety of RNAi-Mediated HTT Suppression in the Rhesus Macaque as a Potential Therapy for Huntington's Disease, Molecular Therapy, 19: 1-11 (2011).
Meena, Control of Human RNase H Mediated Cleavage by Stereopure Phosphorothioate Oligonucleotides, WAVE Life Sciences, TIDES Meeting, 23 pages (May 3-6, 2015).
Meena, Development of Allele Specific Antisense Oligonucleotides, WAVE Life Sciences, ACS Central Regional Meeting (CERM), Covington, KY (May 19, 2016).
Meena, Development of Allele Specific Antisense Oligonucleotides, WAVE Life Sciences, TIDES Meeting (May 11, 2016).
Meena, et al., Discovery and Early Clinical Development of the First Allele-Specific Stereopure ASO Drug Candidate with Disease—Modifying Potential for the Treatment of Huntington's Disease, WAVE Life Sciences, Poster, 1 page (2016).
Meena, et al., Therapeutic Implications of Controlling P-Chirality in Phosphorothioate Oligonucleotides, TIDES Poster (May 12-15, 2014).
Meena, et al., Therapeutic Implications of Controlling P-Chirality in Phosphorothioate Oligonucleotides, TIDES, San Diego, WAVE Life Sciences, Poster, 1 page (May 3-6, 2014).
Meena, Optimization of Antisense Drugs by P-Stereochemistry Control, WAVE Life Sciences, OTS Annual Meeting 2014, Oligonucleotide Therapeutics Society, 13 pages (Oct. 12-14, 2014).
Midturi, J. et al., Spectrum of Pulmonary Toxicity Associated with the Use of Interferon Therapy for Hepatitis C: Case Report and Review of the Literature, Clinical Infectious Diseases, 39(11): 1724-1729 (2004).
Miniarikova, J. et al., Design Characterization, and Lead Selection of Therapeutic miRNAs Targeting Huntingtin for Development of Gene Therapy for Huntington's Disease, Molecular Therapy-Nucleic Acids, 5(3): e297 (2016).
Mohapatra, S. LCMS/hybridization ELISA approaches for bioanalysis of stereopure oligonucleotides. Paper presented at: American Association of Pharmaceutical Scientists Annual Meeting, Washington, DC USA (Nov. 4-7, 2018).
Mujeeb, A. et al., High-Resolution NMR of an Antisense DNA. RNA Hybrid Containing Alternating Chirally Pure R p Methylphosphonates in the DNA Backbone+, 36(9): 2371-2379 (1997).
Ostergaard, M.E. et al., Differential effects on allele selective silencing of mutant huntingtin by two stereoisomers of α,β-constrained nucleic acid, ACS Chem. Biol., 9(9):1975-1979 (2014).
Panzara, M. A. Stereopure Oligonucleotides in Development for the Treatment of Genetically Defined Diseases, Wave Life Sciences, presented at TIDES Boston Virtual Conference on Sep. 15-18, 2020.
Panzara, M. et al., Stereopure nucleic acid therapies in development for the treatment of genetic neurological diseases, Poster presented at: 19th Annual Meeting of the American Society of Experimental Neurotherapeutics, Rockville, MD, Poster 39 (Mar. 15, 2017).
Panzara, M. Stereopure nucleic acid therapies in development for the treatment of genetic neurological diseases, Neurotherapeutics, Abstract, 14: 821-822 (2017).
Panzara, M. Stereopure nucleic acid therapies in development for the treatment of genetic neurological diseases, Paper presented at: 19th Annual Meeting of the American Society of Experimental Neurotherapeutics, Rockville, MD USA (Mar. 15, 2017).
Panzara, M. Stereopure nucleic acid therapies in development for the treatment of genetic neurological diseases. Paper presented at: International Society for CNS Drug Development (ISCDD) Annual Meeting, Las Vegas, NV USA (Mar. 24, 2017).
Panzara, M., Innovations that led to SELECT-HD, a phase 1b/2a clinical trial of an allele-selective therapy for Huntington's Disease, Wave Life Sciences, presented on Mar. 3, 2022.
Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).
Pedersen, L. et al., A Kinetic Model Explains Why Shorter and Less Affine Enzyme-recruiting Oligonucleotides Can Be More Potent, Mol Ther Nucleic Acids, 3: e149 1-8 (2014).
Pharmacology Review(s), Application No. 203568Orig1s000, Center for Drug Evaluation and Research, Food and Drug Administration, Department of Health & Human Services, 2013.
Pontarollo, R.A et al., Monocytes are required for optimum in vitro stimulation of bovine peripheral blood mononuclear cells by non-methylated CpG motifs, Veterinary Immunology and Immunopathology, 84(1-2): 43-59 (2002).
Prakash, T.P. et al., 2'-O-[2-(Methylthio )ethyl]-Modified Oligonucleotide: An Analogue of 2'-O-[2-(Methoxy)-ethyl]-Modified Oligonucleotide with Improved Protein Binding Properties and High Binding Affinity to Target RNA, Biochemistry, 41: 11642-11648 (2002).
Robinson, D.S. et al., Predominant TH2-Like Bronchoalveolar T-Lymphocyte Population in Atopic Asthma, The New England Journal of Medicine, 326: 298-304 (1992).
Senn, J.J. et al., Non-CpG-Containing Antisense 2'-Methoxyethyl Oligonucleotides Activate a Proinflammatory Response Independent of Toll-Like Receptor 9 or Myeloid DifferentiationFactor 88, The Journal of Pharmacology and Experimental Therapeutics, 314: 972-979 (2005).
Seth, P., and Olson, R., Nucleic Acid Therapeutics—Making Sense of Antisesnse, 2016 Drug Design and Delivery Symposium, ACS Webinar, 1-36 (Jul. 26, 2016).
Sheehan, J.P. and Phan, T.M. Phosphorothioate Oligonucleotides Inhibit the Intrinsic Tenase Complex by an Allosteric Mechanism, Biochemistry, 40: 4980-4989 (2001).
Singhrao, S.K. et al., Increased Complement Biosynthesis by Microglia and Complement Activation on Neurons in Huntington's Disease, Experimental Neurology, 159: 362-376 (1999).
Soldatow, V.Y. et al., In vitro models for liver toxicity testing, Toxicol Res, 2(1):23-39 (2013).
Southwell, A. L. et al., In Vivo Evaluation of Candidate Allele-specific Mutant Huntingtin Gene Silencing Antisense Oligonucleotides, Mol. Thera., 22(12):2093-2106 (2014).
Stec, W.J. et al., Deoxyribonucleoside 3'-O-(2-Thio- and 2-Oxo-"spiro"-4,4-pentamethylene-1,3,2-oxathiaphospholane)s: Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).
Tosquellas, G. et al., Prooligonucleotides exhibit less serum-protein binding than phosphodiester and phosphorothioate oligonucleotides, Nucleosides, Nucleotides and Nucleic Acids, 19(5-6):995-1003 (2000).
Vargeese, C. From Stereopurity to precision medicine: Optimising the properties of antisense nucleic acid therapeutics, Paper presented at: TIDES Europe: Oligonucleotide and Peptide Therapeutics, Amsterdam, The Netherlands (Nov. 7, 2018).
Vargeese, C. From Stereopurity to precision medicine: Optimizing the properties of antisense nucleic acid therapeutics, Paper presented at: Nature Conference on RNA at the Bench and Bedside, La Jolla, CA USA (Oct. 8, 2018).
Vargeese, C. Pharmacologic properties of stereopure oligonucleotides. Paper presented at: 44th International Symposium on Nucleic Acids Chemistry, Tokyo, Japan (Nov. 14-16, 2017).
Vargeese, C. Stereochemical control of antisense oligonucleotides enhances target efficacy. Paper presented at: the 14th Annual Meeting of the Oligonucleotide Therapeutic Society, Seattle, WA USA (Oct. 3, 2018).
Vergeese, C., Exploring new oligonucleotide backbone chemistries and their deployment to improve the properties of stereopure oligonucleotides, Wave Life Sciences, presented at TIDES USA on Sep. 22, 2021.
Vickers, T. A. et al., Efficient Reduction of Target RNAs by Small Interfering RNA and RNase H-dependent Antisense Agents, Jrnl. Bio. Chem., 278(9):7108-7118 (2003).
Viglietta, V., Select-HD: an adaptive first-in-human clinical trial to evaluate WVE-003, an investigational allele selective mHTT-

(56) References Cited

OTHER PUBLICATIONS lowering oligonucleotide, in early manifest Huntington's disease, Wave Life Sciences, presented at the HSG on Nov. 5, 2021.
Wan, W.B. and Seth, P.P., The Medicinal Chemistry of Therapeutic Oligonucleotides, J. Med. Chem., 59: 9645-9667 (2016).
Wan, W.B. et al., Synthesis, biophysical properties and biological activity of second generation antisense oligonucleotides containing chiral phosphorothioate linkages, Nucleic Acid Research, 42(22):13456-13468 (2014). Supplementary Information, 14 pages.
WAVE Life Sciences, Second Quarter 2022 Earnings Presentation, 27 pages, (2022).
WAVE Life Sciences, WAVE Life Sciences Corporate Presentation, 32 pages, Aug. 3, 2023.
WAVE Life Sciences, WAVE Life Sciences Corporate Presentation, 63 pages, May 12, 2022.
Woolf, T.M. et al., Specificity of antisense oligonucleotides in vivo, Prov. Natl. Aca. Sci. USA, 89: 7305-7309 (1992).
Wozniak, L.A. et al., Chirality at phosphorus: hybrid duplexes of chimeric oligonucleotides containing methylphosphonothioate linkages with complementary DNA and RNA, Journal of Organometallic Chemistry, 690(10): 2658-2663 (2005).
Written Opinion for PCT/US2016/043598, 10 pages (Nov. 28, 2016).
Xu, D. and Esko, J.D., Demystifying Heparan Sulfate- Protein Interactions, Annu. Rev. Biochem., 83: 129-157 (2014).
Zhang, Y. et al., Structural Isosteres of Phosphate Groups in the Protein Data Bank, J. Chem. Inf. Model, 1-18 (2017).
Zhang, Y., Investigating phosphate structural replacements through computational and experimental approaches, Academic Dissertain, University of Helsinki, 119 pages (2014).
Zhong, Z. et al., WAVE Life Sciences: Developing Stereopure Nucleic Acid Therapies for the Treatment of Genetic Neurological Diseases, World CNS Summit 2017, Boston, MA, WAVE Life Sciences, Poster, 1 page (Feb. 20-22, 2017).
Zhong, Z. Stereochemical control of antisense oligonucleotides enhances target efficacy. Paper presented at: TIDES: Oligonucleotide and Peptide Therapeutics, Boston, MA USA (May 9, 2018).
Zhong, Z. WAVE Life Sciences: Developing stereopure nucleic acid therapies for the treatment of serious genetically defined diseases, Paper presented at: ALS Drug Discovery Roundtable Meeting, Boston, MA (Apr. 25, 2017).
Zon, Automated synthesis of phosphorus-sulfur analogs of nucleic acids—25 years on: potential therapeutic agents and proven utility in biotechnology, New J. Chem., 34(5): 795-804 (2010).
U.S. Appl. No. 18/522,146, filed Nov. 28, 2023, Butler et al.
U.S. Appl. No. 18/613,034, filed Mar. 21, 2024, Vargeese et al.
U.S. Appl. No. 18/695,346, filed Mar. 25, 2024, Monian et al.
U.S. Appl. No. 18/695,348, filed Mar. 25, 2024, Acker et al.
U.S. Appl. No. 18/704,629, filed Apr. 25, 2024, Byrne et al.
U.S. Appl. No. 18/836,993, filed Aug. 8, 2024, Kandasamy et al.
U.S. Appl. No. 18/843,171, filed Aug. 30, 2024, Hu et al.
U.S. Appl. No. 18/856,553, filed Oct. 11, 2024, Lu et al.
U.S. Appl. No. 18/864,860, filed Nov. 11, 2024, Shivalila et al.
U.S. Appl. No. 18/864,863, filed Nov. 11, 2024, Liu et al.
U.S. Appl. No. 18/942,334, filed Nov. 8, 2024, Yang et al.
U.S. Appl. No. 18/953,020, filed Nov. 19, 2024, Meena et al.
U.S. Appl. No. 19/008,522, filed Jan. 2, 2025, Vargeese et al.
Wang, L. et al., Phosphorothioation of DNA in bacteria by dnd genes, Nat. Chem. Biol., 3(11):709-710 (2007).

SEQUENCE LISTING

```
Sequence total quantity: 110
SEQ ID NO: 1           moltype = DNA  length = 20
FEATURE                Location/Qualifiers
misc_feature           1..20
                       note = Description of Artificial Sequence: Synthetic
                        oligonucleotide
```

```
source                  1..20
                        mol_type = other DNA
                        organism = synthetic construct
SEQUENCE: 1
gcctcagtct gcttcgcacc                                                20

SEQ ID NO: 2            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 2
gcctcagtct gcttcgcacc                                                20

SEQ ID NO: 3            moltype = DNA  length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 3
aatcgatcga tcg                                                       13

SEQ ID NO: 4            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 4
gcctcagtct gcttcgcacc                                                20

SEQ ID NO: 5            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 5
gcctcagtct gcttcgcacc                                                20

SEQ ID NO: 6            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 6
gcctcagtct gcttcgcacc                                                20

SEQ ID NO: 7            moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 7
gcctcagtct gcttcgcacc                                                20

SEQ ID NO: 8            moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

```
                       organism = synthetic construct
SEQUENCE: 8
aagggcacag                                                   10

SEQ ID NO: 9           moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 9
ggcacaaggg cacagacttc                                        20

SEQ ID NO: 10          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 10
ggcacaaggg cacagacttc                                        20

SEQ ID NO: 11          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 11
aagggcacag                                                   10

SEQ ID NO: 12          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 12
ggcacaaggg cacagacttc                                        20

SEQ ID NO: 13          moltype = DNA  length = 10
FEATURE                Location/Qualifiers
misc_feature           1..10
                       note = Description of Artificial Sequence: Synthetic
                        oligonucleotide
source                 1..10
                       mol_type = other DNA
                       organism = synthetic construct
SEQUENCE: 13
gggacgtctt                                                   10

SEQ ID NO: 14          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 14
ggcacaaggg cacagacttc                                        20

SEQ ID NO: 15          moltype = RNA  length = 25
FEATURE                Location/Qualifiers
misc_feature           1..25
                       note = Description of Artificial Sequence: Synthetic
                        oligonucleotide
source                 1..25
                       mol_type = other RNA
                       organism = synthetic construct
SEQUENCE: 15
```

-continued

```
tttggaagtc tgtgcccttg tgccc                                   25

SEQ ID NO: 16           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 16
gcctcagtct gcttcgcacc                                         20

SEQ ID NO: 17           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 17
gagcagctgc aacctggcaa                                         20

SEQ ID NO: 18           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 18
gggcacaagg gcacagactt                                         20

SEQ ID NO: 19           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 19
gcacaagggc acagacttcc                                         20

SEQ ID NO: 20           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 20
cacaagggca cagacttcca                                         20

SEQ ID NO: 21           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 21
acaagggcac agacttccaa                                         20

SEQ ID NO: 22           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 22
caagggcaca gacttccaaa                                         20
```

-continued

```
SEQ ID NO: 23          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 23
agcagctgca acctggcaac                                              20

SEQ ID NO: 24          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 24
gcagctgcaa cctggcaaca                                              20

SEQ ID NO: 25          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 25
cagctgcaac ctggcaacaa                                              20

SEQ ID NO: 26          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 26
agctgcaacc tggcaacaac                                              20

SEQ ID NO: 27          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 27
gctgcaacct ggcaacaacc                                              20

SEQ ID NO: 28          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 28
gggccaacag ccagcctgca                                              20

SEQ ID NO: 29          moltype = DNA  length = 20
FEATURE                Location/Qualifiers
misc_feature           1..20
                       note = Description of Artificial Sequence: Synthetic
                        oligonucleotide
source                 1..20
                       mol_type = other DNA
                       organism = synthetic construct
SEQUENCE: 29
ggccaacagc cagcctgcag                                              20

SEQ ID NO: 30          moltype = DNA  length = 20
FEATURE                Location/Qualifiers
```

```
misc_feature          1..20
                      note = Description of Artificial Sequence: Synthetic
                       oligonucleotide
source                1..20
                      mol_type = other DNA
                      organism = synthetic construct
SEQUENCE: 30
gccaacagcc agcctgcagg                                              20

SEQ ID NO: 31         moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 31
ccaacagcca gcctgcagga                                              20

SEQ ID NO: 32         moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 32
caacagccag cctgcaggag                                              20

SEQ ID NO: 33         moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 33
aacagccagc ctgcaggagg                                              20

SEQ ID NO: 34         moltype = DNA  length = 20
FEATURE               Location/Qualifiers
misc_feature          1..20
                      note = Description of Artificial Sequence: Synthetic
                       oligonucleotide
source                1..20
                      mol_type = other DNA
                      organism = synthetic construct
SEQUENCE: 34
attaataaat tgtcatcacc                                              20

SEQ ID NO: 35         moltype = DNA  length = 16
FEATURE               Location/Qualifiers
misc_feature          1..16
                      note = Description of Artificial Sequence: Synthetic
                       oligonucleotide
source                1..16
                      mol_type = other DNA
                      organism = synthetic construct
SEQUENCE: 35
ttcagtcatg acttcc                                                  16

SEQ ID NO: 36         moltype = DNA  length = 16
FEATURE               Location/Qualifiers
misc_feature          1..16
                      note = Description of Artificial Sequence: Synthetic
                       oligonucleotide
source                1..16
                      mol_type = other DNA
                      organism = synthetic construct
SEQUENCE: 36
ttcagtcatg acttcc                                                  16

SEQ ID NO: 37         moltype = DNA  length = 20
FEATURE               Location/Qualifiers
misc_feature          1..20
                      note = Description of Artificial Sequence: Synthetic
```

```
                        oligonucleotide
source                  1..20
                        mol_type = other DNA
                        organism = synthetic construct
SEQUENCE: 37
gcctcagtct gcttcgcacc                                            20

SEQ ID NO: 38           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 38
ggcacaaggg cacagacttc                                            20

SEQ ID NO: 39           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 39
ccgtcgccct tcagcacgca                                            20

SEQ ID NO: 40           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 40
ccgtcgccct tcagcacgca                                            20

SEQ ID NO: 41           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 41
ccgtcgccct tcagcacgca                                            20

SEQ ID NO: 42           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 42
ccgtcgccct tcagcacgca                                            20

SEQ ID NO: 43           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 43
ccgtcgccct tcagcacgca                                            20

SEQ ID NO: 44           moltype = DNA  length = 20
FEATURE                 Location/Qualifiers
misc_feature            1..20
                        note = Description of Artificial Sequence: Synthetic
                         oligonucleotide
source                  1..20
```

-continued

```
                        mol_type = other DNA
                        organism = synthetic construct
SEQUENCE: 44
ccgtcgccct tcagcacgca                                              20

SEQ ID NO: 45           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 45
gtccctgaag atgtcaatgc                                              20

SEQ ID NO: 46           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 46
gtccctgaag atgtcaatgc                                              20

SEQ ID NO: 47           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 47
gtccctgaag atgtcaatgc                                              20

SEQ ID NO: 48           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 48
gtccctgaag atgtcaatgc                                              20

SEQ ID NO: 49           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 49
gtccctgaag atgtcaatgc                                              20

SEQ ID NO: 50           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
SEQUENCE: 50
ggcacaaggg cacagacttc                                              20

SEQ ID NO: 51           moltype = RNA  length = 20
FEATURE                 Location/Qualifiers
misc_feature            1..20
                        note = Description of Artificial Sequence: Synthetic
                         oligonucleotide
source                  1..20
                        mol_type = other RNA
                        organism = synthetic construct
```

-continued

```
SEQUENCE: 51
ggcacaaggg cacagacttc                                              20

SEQ ID NO: 52          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 52
ggcacaaggg cacagacttc                                              20

SEQ ID NO: 53          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 53
ggcacaaggg cacagacttc                                              20

SEQ ID NO: 54          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 54
ggcacaaggg cacagacttc                                              20

SEQ ID NO: 55          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 55
ggcacaaggg cacagacttc                                              20

SEQ ID NO: 56          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 56
ggcacaaggg cacagacttc                                              20

SEQ ID NO: 57          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 57
ggcacaaggg cacagacttc                                              20

SEQ ID NO: 58          moltype = RNA  length = 20
FEATURE                Location/Qualifiers
misc_feature           1..20
                       note = Description of Artificial Sequence: Synthetic
                        oligonucleotide
source                 1..20
                       mol_type = other RNA
                       organism = synthetic construct
SEQUENCE: 58
ggcacaaggg cacagacttc                                              20
```

```
SEQ ID NO: 59           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 59
ggcacaaggg cacagacttc                                              20

SEQ ID NO: 60           moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 60
cagtctgctt cg                                                      12

SEQ ID NO: 61           moltype = DNA  length = 20
FEATURE                 Location/Qualifiers
misc_feature            1..20
                        note = Description of Artificial Sequence: Synthetic
                         oligonucleotide
source                  1..20
                        mol_type = other DNA
                        organism = synthetic construct
SEQUENCE: 61
gcctcagtct gcttcgcacc                                              20

SEQ ID NO: 62           moltype = DNA  length = 21
FEATURE                 Location/Qualifiers
misc_feature            1..21
                        note = Description of Combined DNA/RNA Molecule: Synthetic
                         oligonucleotide
modified_base           1..2
                        mod_base = OTHER
                        note = uracil
modified_base           4
                        mod_base = OTHER
                        note = uracil
modified_base           10
                        mod_base = OTHER
                        note = uracil
modified_base           12..15
                        mod_base = OTHER
                        note = uracil
modified_base           18..19
                        mod_base = OTHER
                        note = uracil
source                  1..21
                        mol_type = other DNA
                        organism = synthetic construct
SEQUENCE: 62
ttctagacct gttttgcttt t                                            21

SEQ ID NO: 63           moltype = DNA  length = 21
FEATURE                 Location/Qualifiers
misc_feature            1..21
                        note = Description of Combined DNA/RNA Molecule: Synthetic
                         oligonucleotide
modified_base           1..2
                        mod_base = OTHER
                        note = uracil
modified_base           4
                        mod_base = OTHER
                        note = uracil
modified_base           10
                        mod_base = OTHER
                        note = uracil
modified_base           12..15
                        mod_base = OTHER
                        note = uracil
modified_base           18..19
                        mod_base = OTHER
```

```
                        note = uracil
source                  1..21
                        mol_type = other DNA
                        organism = synthetic construct
SEQUENCE: 63
ttctagacct gttttgcttt t                                           21

SEQ ID NO: 64           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 64
aagcaaaaca ggtctagaat t                                           21

SEQ ID NO: 65           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 65
aagcaaaaca ggtctagaat t                                           21

SEQ ID NO: 66           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 66
aagcaaaaca ggtctagaat t                                           21

SEQ ID NO: 67           moltype = DNA  length = 20
FEATURE                 Location/Qualifiers
misc_feature            1..20
                        note = Description of Combined DNA/RNA Molecule: Synthetic
                         oligonucleotide
modified_base           12
                        mod_base = OTHER
                        note = uracil
modified_base           14
                        mod_base = OTHER
                        note = uracil
source                  1..20
                        mol_type = other DNA
                        organism = synthetic construct
SEQUENCE: 67
agcaaaacag gtctagaatt                                             20

SEQ ID NO: 68           moltype = DNA  length = 20
FEATURE                 Location/Qualifiers
misc_feature            1..20
                        note = Description of Combined DNA/RNA Molecule: Synthetic
```

```
                        oligonucleotide
modified_base           12
                        mod_base = OTHER
                        note = uracil
modified_base           14
                        mod_base = OTHER
                        note = uracil
source                  1..20
                        mol_type = other DNA
                        organism = synthetic construct
SEQUENCE: 68
agcaaaacag gtctagaatt                                            20

SEQ ID NO: 69           moltype = DNA  length = 20
FEATURE                 Location/Qualifiers
misc_feature            1..20
                        note = Description of Combined DNA/RNA Molecule: Synthetic
                         oligonucleotide
modified_base           12
                        mod_base = OTHER
                        note = uracil
modified_base           14
                        mod_base = OTHER
                        note = uracil
source                  1..20
                        mol_type = other DNA
                        organism = synthetic construct
SEQUENCE: 69
agcaaaacag gtctagaatt                                            20

SEQ ID NO: 70           moltype = DNA  length = 21
FEATURE                 Location/Qualifiers
misc_feature            1..21
                        note = Description of Combined DNA/RNA Molecule: Synthetic
                         oligonucleotide
modified_base           1..2
                        mod_base = OTHER
                        note = uracil
modified_base           4
                        mod_base = OTHER
                        note = uracil
modified_base           10
                        mod_base = OTHER
                        note = uracil
modified_base           12..15
                        mod_base = OTHER
                        note = uracil
modified_base           18..19
                        mod_base = OTHER
                        note = uracil
source                  1..21
                        mol_type = other DNA
                        organism = synthetic construct
SEQUENCE: 70
ttctagacct gttttgcttt t                                          21

SEQ ID NO: 71           moltype = DNA  length = 21
FEATURE                 Location/Qualifiers
misc_feature            1..21
                        note = Description of Combined DNA/RNA Molecule: Synthetic
                         oligonucleotide
modified_base           1..2
                        mod_base = OTHER
                        note = uracil
modified_base           4
                        mod_base = OTHER
                        note = uracil
modified_base           10
                        mod_base = OTHER
                        note = uracil
modified_base           12..15
                        mod_base = OTHER
                        note = uracil
modified_base           18..19
                        mod_base = OTHER
                        note = uracil
source                  1..21
                        mol_type = other DNA
                        organism = synthetic construct
```

```
SEQUENCE: 71
ttctagacct gttttgcttt t                                                21

SEQ ID NO: 72          moltype = DNA  length = 21
FEATURE                Location/Qualifiers
misc_feature           1..21
                       note = Description of Combined DNA/RNA Molecule: Synthetic
                        oligonucleotide
modified_base          1..2
                       mod_base = OTHER
                       note = uracil
modified_base          4
                       mod_base = OTHER
                       note = uracil
modified_base          10
                       mod_base = OTHER
                       note = uracil
modified_base          12..15
                       mod_base = OTHER
                       note = uracil
modified_base          18..19
                       mod_base = OTHER
                       note = uracil
source                 1..21
                       mol_type = other DNA
                       organism = synthetic construct
SEQUENCE: 72
ttctagacct gttttgcttt t                                                21

SEQ ID NO: 73          moltype = DNA  length = 21
FEATURE                Location/Qualifiers
misc_feature           1..21
                       note = Description of Combined DNA/RNA Molecule: Synthetic
                        oligonucleotide
modified_base          1..2
                       mod_base = OTHER
                       note = uracil
modified_base          4
                       mod_base = OTHER
                       note = uracil
modified_base          10
                       mod_base = OTHER
                       note = uracil
modified_base          12..15
                       mod_base = OTHER
                       note = uracil
modified_base          18..19
                       mod_base = OTHER
                       note = uracil
source                 1..21
                       mol_type = other DNA
                       organism = synthetic construct
SEQUENCE: 73
ttctagacct gttttgcttt t                                                21

SEQ ID NO: 74          moltype = DNA  length = 21
FEATURE                Location/Qualifiers
misc_feature           1..21
                       note = Description of Combined DNA/RNA Molecule: Synthetic
                        oligonucleotide
modified_base          1..2
                       mod_base = OTHER
                       note = uracil
modified_base          4
                       mod_base = OTHER
                       note = uracil
modified_base          10
                       mod_base = OTHER
                       note = uracil
modified_base          12..15
                       mod_base = OTHER
                       note = uracil
modified_base          18..19
                       mod_base = OTHER
                       note = uracil
source                 1..21
                       mol_type = other DNA
                       organism = synthetic construct
SEQUENCE: 74
```

```
ttctagacct gttttgcttt t                                             21

SEQ ID NO: 75          moltype = DNA  length = 21
FEATURE                Location/Qualifiers
misc_feature           1..21
                       note = Description of Combined DNA/RNA Molecule: Synthetic
                        oligonucleotide
modified_base          1..2
                       mod_base = OTHER
                       note = uracil
modified_base          4
                       mod_base = OTHER
                       note = uracil
modified_base          10
                       mod_base = OTHER
                       note = uracil
modified_base          12..15
                       mod_base = OTHER
                       note = uracil
modified_base          18..19
                       mod_base = OTHER
                       note = uracil
source                 1..21
                       mol_type = other DNA
                       organism = synthetic construct
SEQUENCE: 75
ttctagacct gttttgcttt t                                             21

SEQ ID NO: 76          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
source                 1..21
                       mol_type = other DNA
                       organism = synthetic construct
SEQUENCE: 76
aagcaaaaca ggtctagaat t                                             21

SEQ ID NO: 77          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
source                 1..21
                       mol_type = other DNA
                       organism = synthetic construct
SEQUENCE: 77
aagcaaaaca ggtctagaat t                                             21

SEQ ID NO: 78          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
source                 1..21
                       mol_type = other DNA
                       organism = synthetic construct
SEQUENCE: 78
aagcaaaaca ggtctagaat t                                             21
```

```
SEQ ID NO: 79          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
source                 1..21
                       mol_type = other DNA
                       organism = synthetic construct
SEQUENCE: 79
aagcaaaaca ggtctagaat t                                            21

SEQ ID NO: 80          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
source                 1..21
                       mol_type = other DNA
                       organism = synthetic construct
SEQUENCE: 80
aagcaaaaca ggtctagaat t                                            21

SEQ ID NO: 81          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
source                 1..21
                       mol_type = other DNA
                       organism = synthetic construct
SEQUENCE: 81
aagcaaaaca ggtctagaat t                                            21

SEQ ID NO: 82          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
source                 1..21
                       mol_type = other DNA
                       organism = synthetic construct
SEQUENCE: 82
aagcaaaaca ggtctagaat t                                            21

SEQ ID NO: 83          moltype = DNA  length = 21
FEATURE                Location/Qualifiers
misc_feature           1..21
                       note = Description of Combined DNA/RNA Molecule: Synthetic
                        oligonucleotide
modified_base          13
                       mod_base = OTHER
                       note = uracil
modified_base          15
                       mod_base = OTHER
                       note = uracil
```

```
source                  1..21
                        mol_type = other DNA
                        organism = synthetic construct
SEQUENCE: 83
aagcaaaaca ggtctagaat t                                            21

SEQ ID NO: 84           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 84
aagcaaaaca ggtctagaat t                                            21

SEQ ID NO: 85           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 85
aagcaaaaca ggtctagaat t                                            21

SEQ ID NO: 86           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 86
aagcaaaaca ggtctagaat t                                            21

SEQ ID NO: 87           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 87
aagcaaaaca ggtctagaat t                                            21

SEQ ID NO: 88           moltype = DNA  length = 21
FEATURE                 Location/Qualifiers
misc_feature            1..21
                        note = Description of Combined DNA/RNA Molecule: Synthetic
                         oligonucleotide
```

```
modified_base          1..2
                       mod_base = OTHER
                       note = uracil
modified_base          4
                       mod_base = OTHER
                       note = uracil
modified_base          10
                       mod_base = OTHER
                       note = uracil
modified_base          12..15
                       mod_base = OTHER
                       note = uracil
modified_base          18..19
                       mod_base = OTHER
                       note = uracil
source                 1..21
                       mol_type = other DNA
                       organism = synthetic construct
SEQUENCE: 88
ttctagacct gttttgcttt t                                            21

SEQ ID NO: 89          moltype = DNA  length = 21
FEATURE                Location/Qualifiers
misc_feature           1..21
                       note = Description of Combined DNA/RNA Molecule: Synthetic
                        oligonucleotide
modified_base          1..2
                       mod_base = OTHER
                       note = uracil
modified_base          4
                       mod_base = OTHER
                       note = uracil
modified_base          10
                       mod_base = OTHER
                       note = uracil
modified_base          12..15
                       mod_base = OTHER
                       note = uracil
modified_base          18..19
                       mod_base = OTHER
                       note = uracil
source                 1..21
                       mol_type = other DNA
                       organism = synthetic construct
SEQUENCE: 89
ttctagacct gttttgcttt t                                            21

SEQ ID NO: 90          moltype = DNA  length = 21
FEATURE                Location/Qualifiers
misc_feature           1..21
                       note = Description of Combined DNA/RNA Molecule: Synthetic
                        oligonucleotide
modified_base          1..2
                       mod_base = OTHER
                       note = uracil
modified_base          4
                       mod_base = OTHER
                       note = uracil
modified_base          10
                       mod_base = OTHER
                       note = uracil
modified_base          12..15
                       mod_base = OTHER
                       note = uracil
modified_base          18..19
                       mod_base = OTHER
                       note = uracil
source                 1..21
                       mol_type = other DNA
                       organism = synthetic construct
SEQUENCE: 90
ttctagacct gttttgcttt t                                            21

SEQ ID NO: 91          moltype = DNA  length = 21
FEATURE                Location/Qualifiers
misc_feature           1..21
                       note = Description of Combined DNA/RNA Molecule: Synthetic
                        oligonucleotide
modified_base          1..2
```

```
                         mod_base = OTHER
                         note = uracil
modified_base            4
                         mod_base = OTHER
                         note = uracil
modified_base            10
                         mod_base = OTHER
                         note = uracil
modified_base            12..15
                         mod_base = OTHER
                         note = uracil
modified_base            18..19
                         mod_base = OTHER
                         note = uracil
source                   1..21
                         mol_type = other DNA
                         organism = synthetic construct
SEQUENCE: 91
ttctagacct gttttgcttt t                                                21

SEQ ID NO: 92            moltype = DNA  length = 21
FEATURE                  Location/Qualifiers
misc_feature             1..21
                         note = Description of Combined DNA/RNA Molecule: Synthetic
                          oligonucleotide
modified_base            1..2
                         mod_base = OTHER
                         note = uracil
modified_base            4
                         mod_base = OTHER
                         note = uracil
modified_base            10
                         mod_base = OTHER
                         note = uracil
modified_base            12..15
                         mod_base = OTHER
                         note = uracil
modified_base            18..19
                         mod_base = OTHER
                         note = uracil
source                   1..21
                         mol_type = other DNA
                         organism = synthetic construct
SEQUENCE: 92
ttctagacct gttttgcttt t                                                21

SEQ ID NO: 93            moltype = DNA  length = 21
FEATURE                  Location/Qualifiers
misc_feature             1..21
                         note = Description of Combined DNA/RNA Molecule: Synthetic
                          oligonucleotide
modified_base            1..2
                         mod_base = OTHER
                         note = uracil
modified_base            4
                         mod_base = OTHER
                         note = uracil
modified_base            10
                         mod_base = OTHER
                         note = uracil
modified_base            12..15
                         mod_base = OTHER
                         note = uracil
modified_base            18..19
                         mod_base = OTHER
                         note = uracil
source                   1..21
                         mol_type = other DNA
                         organism = synthetic construct
SEQUENCE: 93
ttctagacct gttttgcttt t                                                21

SEQ ID NO: 94            moltype = DNA  length = 21
FEATURE                  Location/Qualifiers
misc_feature             1..21
                         note = Description of Combined DNA/RNA Molecule: Synthetic
                          oligonucleotide
modified_base            13
                         mod_base = OTHER
```

-continued

```
                        note = uracil
modified_base           15
                        mod_base = OTHER
                        note = uracil
source                  1..21
                        mol_type = other DNA
                        organism = synthetic construct
SEQUENCE: 94
aagcaaaaca ggtctagaat t                                            21

SEQ ID NO: 95           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 95
aagcaaaaca ggtctagaat t                                            21

SEQ ID NO: 96           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 96
aagcaaaaca ggtctagaat t                                            21

SEQ ID NO: 97           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 97
aagcaaaaca ggtctagaat t                                            21

SEQ ID NO: 98           moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 98
aagcaaaaca ggtctagaat t                                            21

SEQ ID NO: 99           moltype = DNA  length = 21
```

-continued

```
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 99
aagcaaaaca ggtctagaat t                                                    21

SEQ ID NO: 100          moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 100
aagcaaaaca ggtctagaat t                                                    21

SEQ ID NO: 101          moltype = DNA  length = 21
FEATURE                 Location/Qualifiers
misc_feature            1..21
                        note = Description of Combined DNA/RNA Molecule: Synthetic
                         oligonucleotide
modified_base           13
                        mod_base = OTHER
                        note = uracil
modified_base           15
                        mod_base = OTHER
                        note = uracil
source                  1..21
                        mol_type = other DNA
                        organism = synthetic construct
SEQUENCE: 101
aagcaaaaca ggtctagaat t                                                    21

SEQ ID NO: 102          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 102
acacacacac                                                                 10

SEQ ID NO: 103          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 103
cccccccccc                                                                 10

SEQ ID NO: 104          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
```

-continued

```
                        organism = synthetic construct
SEQUENCE: 104
cccccccccc                                                          10

SEQ ID NO: 105          moltype = DNA  length = 10
FEATURE                 Location/Qualifiers
misc_feature            1..10
                        note = Description of Artificial Sequence: Synthetic
                         oligonucleotide
source                  1..10
                        mol_type = other DNA
                        organism = synthetic construct
SEQUENCE: 105
cccccccccc                                                          10

SEQ ID NO: 106          moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 106
ggatgttctc ga                                                       12

SEQ ID NO: 107          moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 107
ggatgttctc ga                                                       12

SEQ ID NO: 108          moltype = DNA  length = 12
FEATURE                 Location/Qualifiers
misc_feature            1..12
                        note = Description of Artificial Sequence: Synthetic
                         oligonucleotide
source                  1..12
                        mol_type = other DNA
                        organism = synthetic construct
SEQUENCE: 108
ggatgttctc ga                                                       12

SEQ ID NO: 109          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 109
ttcagtcatg acttcc                                                   16

SEQ ID NO: 110          moltype = DNA  length = 16
FEATURE                 Location/Qualifiers
misc_feature            1..16
                        note = Description of Artificial Sequence: Synthetic
                         oligonucleotide
source                  1..16
                        mol_type = other DNA
                        organism = synthetic construct
SEQUENCE: 110
ttcagtcatg acttcc                                                   16
```

OLIGONUCLEOTIDE COMPOSITIONS AND METHODS THEREOF

CROSS-REFERENCE TO RELATED APPLICATIONS

This application is a Divisional of U.S. application Ser. No. 16/782,021 filed Feb. 4, 2020, issued as U.S. Pat. No. 11,634,710, which is a Continuation of U.S. application Ser. No. 15/746,199, filed Jan. 19, 2018, which is a National Stage Entry of International Application No. PCT/US2016/043598, filed Jul. 22, 2016, which claims priority to United States Provisional Application Nos. 62/195,779, filed Jul. 22, 2015, 62/236,847, filed Oct. 2, 2015, and 62/331,960, filed May 4, 2016, the entirety of each of which is incorporated herein by reference.

SEQUENCE LISTING

The instant application contains a Sequence Listing which has been submitted electronically in XML format and is hereby incorporated by reference in its entirety. Said XML copy, created on Dec. 19, 2023, is named Sequence-Listing.xml and is 209,699 bytes in size.

BACKGROUND

Oligonucleotides are useful in therapeutic, diagnostic, research and nanomaterials applications. The use of naturally occurring nucleic acids (e.g., unmodified DNA or RNA) for therapeutics can be limited, for example, because of their instability against extra- and intracellular nucleases, toxicity, and/or their poor cell penetration and distribution. There is a need for new and improved oligonucleotides and oligonucleotide compositions, such as, e.g., new antisense and siRNA oligonucleotides and oligonucleotide compositions.

SUMMARY

Among other things, the present disclosure encompasses the recognition that structural elements of oligonucleotides, such as base sequence, chemical modifications (e.g., modifications of sugar, base, and/or internucleotidic linkages, and patterns thereof), and/or stereochemistry (e.g., stereochemistry of backbone chiral centers (chiral internucleotidic linkages), and/or patterns thereof), can have significant impact on oligonucleotide properties, e.g., activities, toxicities, e.g., as may be mediated by protein binding characteristics, stability, etc. In some embodiments, the present disclosure demonstrates that oligonucleotide compositions comprising oligonucleotides with controlled structural elements, e.g., controlled chemical modification and/or controlled backbone stereochemistry patterns, provide unexpected properties, including but not limited to certain activities, toxicities, etc. In some embodiments, the present disclosure demonstrates that oligonucleotide properties, e.g., activities, toxicities, etc., can be modulated by chemical modifications (e.g., modifications of sugars, bases, internucleotidic linkages, etc.), chiral structures (e.g., stereochemistry of chiral internucleotidic linkages and patterns thereof, etc.), and/or combination thereof.

The present disclosure recognizes challenges of providing low toxicity oligonucleotide compositions and methods thereof. In some embodiments, the present disclosure provides oligonucleotide compositions and methods with reduced toxicity. In some embodiments, the present disclosure provides oligonucleotide compositions and methods with reduced immune responses. In some embodiments, the present disclosure recognizes that various toxicities induced by oligonucleotides are related to complement activation. In some embodiments, the present disclosure provides oligonucleotide compositions and methods with reduced complement activation. In some embodiments, the present disclosure provides oligonucleotide compositions and methods with reduced complement activation via the alternative pathway. In some embodiments, the present disclosure provides oligonucleotide compositions and methods with reduced complement activation via the classical pathway. In some embodiments, the present disclosure provides oligonucleotide compositions and methods with reduced drug-induced vascular injury. In some embodiments, the present disclosure provides oligonucleotide compositions and methods with reduced injection site inflammation. In some embodiments, reduced toxicity can be evaluated through one or more assays widely known to and practiced by a person having ordinary skill in the art, e.g., evaluation of levels of complete activation product, protein binding, etc. as described herein.

In some embodiments, the present disclosure demonstrates that oligonucleotide properties, e.g., activities, toxicities, etc., can be modulated through chemical modifications. In some embodiments, the present disclosure provides an oligonucleotide composition comprising a first plurality of oligonucleotides which have a common base sequence, and comprise one or more modified sugar moieties, one or more natural phosphate linkages, or combinations thereof. In some embodiments, the present disclosure provides an oligonucleotide composition comprising a first plurality of oligonucleotides which have a common base sequence, comprise one or more modified internucleotidic linkages, and comprise one or more modified sugar moieties, one or more natural phosphate linkages, or combinations thereof. In some embodiments, oligonucleotides of a first plurality have a wing-core-wing structure. In some embodiments, each wing region independently comprises one or more natural phosphate linkages and optionally one or more modified internucleotidic linkages, and the core comprises one or more modified internucleotidic linkages and optionally one or more natural phosphate linkages. In some embodiments, each wing region independently comprises one or more natural phosphate linkages and one or more modified internucleotidic linkages, and the core comprises one or more modified internucleotidic linkages and no natural phosphate linkages. In some embodiments, a wing comprises modified sugar moieties. In some embodiments, a modified internucleotidic linkage is phosphorothioate. In some embodiments, a modified internucleotidic linkage is substituted phosphorothioate. In some embodiments, a modified internucleotidic linkage has the structure of formula I described in this disclosure. In some embodiments, a modified sugar moiety is 2'-modified. In some embodiments, a 2'-modification is 2'-$OR^1$. In some embodiments, such provided compositions have lower toxicity. In some embodiments, provided compositions have lower complement activation.

In some embodiments, the present disclosure provides oligonucleotide compositions with improved protein binding profiles, e.g., lowered harmful protein binding and/or increased beneficial protein binding. In some embodiments, the present disclosure provides methods for improved delivery of oligonucleotide compositions comprising providing oligonucleotide compositions with improved protein binding profile. In some embodiments, the present disclosure demonstrates that protein binding by oligonucleotide compositions can be modulated through chemical modifications, stereochemistry, or combinations thereof. In some embodiments, protein binding by oligonucleotide compositions can be modulated by incorporation of modified internucleotidic linkages. In some embodiments, increased percentage of modified internucleotidic linkages provides increased binding of oligonucleotides to certain proteins. In some embodiments, replacement of one or more modified internucleotidic linkages with natural phosphate linkages provides decreased binding to certain proteins. In some embodiments, replacement of one or more natural phosphate linkages with modified internucleotidic linkages provides increased binding to certain proteins. In some embodiments, certain chemical modifications provide increased protein binding to certain proteins. In some embodiments, certain chemical modifications provide decreased protein binding to certain proteins. In some embodiments, different chemical modifications of the same kind provide different protein binding. For example, in some embodiments, 2'-MOE provides decreased protein binding compared to 2'-OMe (at least in certain contexts—e.g., sequence, stereochemistry, etc.).

Among other things, the present disclosure encompasses the recognition that stereorandom oligonucleotide preparations contain a plurality of distinct chemical entities that differ from one another, e.g., in the stereochemical structure of individual backbone chiral centers within the oligonucleotide chain. Without control of stereochemistry of backbone chiral centers, stereorandom oligonucleotide preparations provide uncontrolled compositions comprising undetermined levels of oligonucleotide stereoisomers. Even though these stereoisomers may have the same base sequence and/or chemical modifications, they are different chemical entities at least due to their different backbone stereochemistry, and they can have, as demonstrated herein, different properties, e.g., activities, toxicities, etc. Among other things, the present disclosure provides chirally controlled compositions that are or contain particular stereoisomers of oligonucleotides of interest. In some embodiments, a particular stereoisomer may be defined, for example, by its base sequence, its length, its pattern of backbone linkages, and its pattern of backbone chiral centers. As is understood in the art, in some embodiments, base sequence may refer to the identity and/or modification status of nucleoside residues (e.g., of sugar and/or base components, relative to standard naturally occurring nucleotides such as adenine, cytosine, guanosine, thymine, and uracil) in an oligonucleotide and/or to the hybridization character (i.e., the ability to hybridize with particular complementary residues) of such residues. In some embodiments, the present disclosure demonstrates that property improvements (e.g., improved activities, lower toxicities, etc.) achieved through inclusion and/or location of particular chiral structures within an oligonucleotide can be comparable to, or even better than those achieved through use of chemical modification, e.g., particular backbone linkages, residue modifications, etc. (e.g., through use of certain types of modified phosphates [e.g., phosphorothioate, substituted phosphorothioate, etc.], sugar modifications [e.g., 2'-modifications, etc.], and/or base modifications [e.g., methylation, etc.]).

Among other things, the present disclosure demonstrates that stereochemistry can be used to modulate toxicity of oligonucleotide compositions. In some embodiments, the present disclosure provides chirally controlled oligonucleotide compositions that have lower toxicity when compared to a corresponding stereorandom (or chirally uncontrolled) oligonucleotide composition of oligonucleotides sharing the same base sequence and chemical modifications. In some embodiments, chirally controlled oligonucleotide compositions of oligonucleotides comprising more Rp chiral internucleotidic linkage have lower toxicity. In some embodiments, chirally controlled oligonucleotide compositions of oligonucleotides having a single Rp chiral internucleotidic linkage have increased toxicity compared to other chirally controlled oligonucleotide compositions and/or the corresponding stereorandom oligonucleotide composition of oligonucleotides sharing the same base sequence and chemical modifications. In some embodiments, a single Rp chiral internucleotidic linkage is in the middle of a sequence. In some embodiments, chirally controlled oligonucleotide compositions of oligonucleotides which comprise one or more Rp chiral internucleotidic linkages at the 5'- and/or the 3'-end provide lower toxicity. In some embodiments, chirally controlled oligonucleotide compositions of oligonucleotides which comprise one or more natural phosphate linkages at the 5'- and/or the 3'-end provide lower toxicity. In some embodiments, a chiral internucleotidic linkage has the structure of formula I. In some embodiments, a chiral internucleotidic linkage is a phosphorothioate linkage. In some embodiments, a chiral internucleotidic linkage is a substituted phosphorothioate linkage.

Among other things, the present disclosure recognizes that, in some embodiments, properties (e.g., activities, toxicities, etc.) of an oligonucleotide can be adjusted by optimizing its pattern of backbone chiral centers, optionally in combination with adjustment/optimization of one or more other features (e.g., chemical modifications, patterns of modifications such as linkage pattern, nucleoside modification pattern, etc.) of the oligonucleotide. In some embodiments, the present disclosure recognizes and demonstrates that chemical modifications, such as modifications of nucleosides and internucleotidic linkages, can provide enhanced properties. In some embodiments, the present disclosure demonstrates that combinations of chemical modifications and stereochemistry can provide unexpected, greatly improved properties (e.g., activities, toxicities, etc.). In some embodiments, chemical combinations, such as modifications of sugars, bases, and/or internucleotidic linkages, are combined with stereochemistry patterns to provide oligonucleotides and compositions thereof with surprisingly enhanced properties including low toxicity, better protein binding profile, etc. In some embodiments, a provided oligonucleotide composition comprising a first plurality of oligonucleotides is chirally controlled, and oligonucleotides of the first plurality comprise a combination of 2'-modification of one or more sugar moieties, one or more natural phosphate linkages, and one or more chiral internucleotidic linkages. In some embodiments, a provided oligonucleotide composition comprising a first plurality of oligonucleotides is chirally controlled, and oligonucleotides of the first plurality comprise a combination of 2'-modification of one or more sugar moieties, one or more natural phosphate linkages, one or more chiral internucleotidic linkages, wherein the 5'- and/or the 3'-end internucleotidic linkages are chiral. In some embodiments, both the 5'- and the 3'-end internucleotidic linkages are chiral. In some embodiments, both the 5'- and the 3'-end internucleotidic linkages are chiral and Sp. In some embodiments, a provided oligonucleotide composition comprising a first plurality of oligonucleotides is chirally controlled, and oligonucleotides of the first plurality comprise a combination of 2'-modification of one or more sugar moieties, one or more natural phosphate linkages, one or more chiral internucleotidic linkages, and a stereochemistry pattern of (Rp)n(Sp)m, (Np)t(Rp)n(Sp)m, or (Sp)t(Rp)n(Sp)m, wherein m>2. In some embodiments, a chiral internucleotidic linkage has the structure of formula I. In some embodiments, a chiral internucleotidic linkage is a phosphorothioate linkage. In some embodiments, a chiral internucleotidic linkage is a substituted phosphorothioate linkage.

In some embodiments, the present disclosure provides oligonucleotide compositions having low toxicity. In some embodiments, the present disclosure provides oligonucleotide compositions having improved protein binding profile. In some embodiments, the present disclosure provides oligonucleotide compositions having improved binding to albumin. In some embodiments, provided compositions have low toxicity and improved binding to certain desired proteins. In some embodiments, provided compositions have low toxicity and improved binding to certain desired proteins. In some embodiments, provided oligonucleotide compositions at the same time provides the same level of, or greatly enhanced, stability and/or activities, e.g., better target-cleavage pattern, better target-cleavage efficiency, better target specificity, etc.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified internucleotidic linkages and optionally one or more natural phosphate linkages, and the core region independently comprises one or more modified internucleotidic linkages; or each wing region independently comprises one or more modified sugar moieties, and the core region comprises one or more un-modified sugar moieties.

In some embodiments, the present disclosure provides an oligonucleotide composition comprising a first plurality of oligonucleotides comprising one or more wing regions and a core region, wherein:

oligonucleotides of the first plurality have the same base sequence;

each wing region independently has a length of two or more bases, and independently comprises one or more modified internucleotidic linkages and optionally one or more natural phosphate linkages; and the core region independently has a length of two or more bases and independently comprises one or more modified internucleotidic linkages.

In some embodiments, the present disclosure provides an oligonucleotide composition comprising a first plurality of oligonucleotides comprising one or more wing regions and a core region, wherein:

oligonucleotides of the first plurality have the same base sequence;

each wing region independently has a length of two or more bases, and independently comprises one or more modified internucleotidic linkages and one or more natural phosphate linkages; and the core region independently has a length of two or more bases and independently comprises one or more modified internucleotidic linkages.

In some embodiments, the present disclosure provides an oligonucleotide composition comprising a first plurality of oligonucleotides comprising two wing regions and a core region, wherein:

oligonucleotides of the first plurality have the same base sequence;

each wing region independently has a length of two or more bases, and independently comprises one or more modified internucleotidic linkages and one or more natural phosphate linkages; and the core region independently has a length of two or more bases and independently comprises one or more modified internucleotidic linkages.

In some embodiments, the present disclosure provides an oligonucleotide composition comprising a first plurality of oligonucleotides comprising two wing regions and a core region, wherein:

oligonucleotides of the first plurality have the same base sequence;

each wing region independently has a length of two or more bases, and independently comprises one or more modified internucleotidic linkages and one or more natural phosphate linkages;

the wing region to the 5'-end of the core region comprises at least one modified internucleotidic linkage followed by a natural phosphate linkage in the wing; and the wing region to the 3'-end of the core region comprises at least one modified internucleotidic linkage preceded by a natural phosphate linkage in the wing;

the core region independently has a length of two or more bases and independently comprises one or more modified internucleotidic linkages.

In some embodiments, the present disclosure provides an oligonucleotide composition comprising a first plurality of oligonucleotides comprising a wing region and a core region, wherein:

oligonucleotides of the first plurality have the same base sequence;

the wing region has a length of two or more bases, and comprises one or more modified internucleotidic linkages and one or more natural phosphate linkages;

the wing region is to the 5'-end of the core region and comprises a natural phosphate linkage between the two nucleosides at its 3'-end, or the wing region to the 3'-end of the core region and comprises a natural phosphate linkage between the two nucleosides at its 5'-end; and the core region independently has a length of two or more bases and independently comprises one or more modified internucleotidic linkages.

In some embodiments, the present disclosure provides an oligonucleotide composition comprising a first plurality of oligonucleotides comprising two wing regions and a core region, wherein:

oligonucleotides of the first plurality have the same base sequence;

each wing region independently has a length of two or more bases, and independently comprises one or more modified internucleotidic linkages and one or more natural phosphate linkages;

the wing region to the 5'-end of the core region comprises a natural phosphate linkage between the two nucleosides at its 3'-end;

the wing region to the 3'-end of a core region comprises a natural phosphate linkage between the two nucleosides at its 5'-end; and the core region independently has a length of two or more bases and independently comprises one or more modified internucleotidic linkages.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified internucleotidic linkages and optionally one or more natural phosphate linkages, and the core region independently comprises one or more modified internucleotidic linkages; and each wing region independently comprises one or more modified sugar moieties, and the core region comprises one or more un-modified sugar moieties.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified internucleotidic linkages and one or more natural phosphate linkages, and the core region independently comprises one or more modified internucleotidic linkages; and each wing region independently comprises one or more modified sugar moieties, and the core region comprises one or more un-modified sugar moieties.

In some embodiments, the present disclosure provides an oligonucleotide composition comprising a first plurality of oligonucleotides which:

1) have a common base sequence; and 2) comprise one or more wing regions and a core region;

wherein:

each wing region comprises at least one modified sugar moiety; and each core region comprises at least one un-modified sugar moiety.

In some embodiments, the present disclosure provides a chirally controlled oligonucleotide composition comprising oligonucleotides defined by having:

1) a common base sequence and length;

2) a common pattern of backbone linkages; and 3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, the present disclosure provides a chirally controlled oligonucleotide composition comprising oligonucleotides of a particular oligonucleotide type characterized by:

1) a common base sequence and length;

2) a common pattern of backbone linkages; and 3) a common pattern of backbone chiral centers;

which composition is chirally controlled in that it is enriched, relative to a substantially racemic preparation of oligonucleotides having the same base sequence and length, for oligonucleotides of the particular oligonucleotide type.

In some embodiments, the present disclosure provides a chirally controlled oligonucleotide composition comprising oligonucleotides of a particular oligonucleotide type characterized by:

1) a common base sequence and length;

2) a common pattern of backbone linkages; and 3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

Among other things, the present disclosure recognizes that combinations of oligonucleotide structural elements (e.g., patterns of chemical modifications, backbone linkages, backbone chiral centers, and/or backbone phosphorus modifications) can provide surprisingly improved properties such as low toxicity and/or desired protein binding. In some embodiments, the present disclosure provides an oligonucleotide composition comprising a predetermined level of oligonucleotides which comprise one or more wing regions and a common core region, wherein:

each wing region independently has a length of two or more bases, and independently and optionally comprises one or more chiral internucleotidic linkages;

the core region independently has a length of two or more bases, and independently comprises one or more chiral internucleotidic linkages, and the common core region has:

1) a common base sequence and length;

2) a common pattern of backbone linkages; and 3) a common pattern of backbone chiral centers.

A wing and core can be defined by any structural elements. In some embodiments, a wing and core is defined by nucleoside modifications, wherein a wing comprises a nucleoside modification that the core region does not have. In some embodiments, oligonucleotides in provided compositions have a wing-core structure of nucleoside modification. In some embodiments, oligonucleotides in provided compositions have a core-wing structure of nucleoside modification. In some embodiments, oligonucleotides in provided compositions have a wing-core-wing structure of nucleoside modification. In some embodiments, a wing and core is defined by modifications of the sugar moieties. In some embodiments, a wing and core is defined by modifications of the base moieties. In some embodiments, each sugar moiety in the wing region has the same 2'-modification which is not found in the core region. In some embodiments, each sugar moiety in the wing region has the same 2'-modification which is different than any sugar modifications in the core region. In some embodiments, each sugar moiety in the wing region has the same 2'-modification, and the core region has no 2'-modifications. In some embodiments, when two or more wings are present, each sugar moiety in a wing region has the same 2'-modification, yet the common 2'-modification in a first wing region can either be the same as or different from the common 2'-modification in a second wing region. In some embodiments, a wing and core is defined by pattern of backbone internucleotidic linkages. In some embodiments, a wing comprises a type of internucleotidic linkage, and/or a pattern of internucleotidic linkages, that are not found in a core. In some embodiments, a wing region comprises both a modified internucleotidic linkage and a natural phosphate linkage. In some embodiments, the internucleotidic linkage at the 5'-end of a wing to the 5'-end of the core region is a modified internucleotidic linkage. In some embodiments, the internucleotidic linkage at the 3'-end of a wing to the 3'-end of the core region is a modified internucleotidic linkage. In some embodiments, a modified internucleotidic linkage is a chiral internucleotidic linkage.

In some embodiments, each wing comprises at least one chiral internucleotidic linkage and at least one natural phosphate linkage. In some embodiments, each wing comprises at least one modified sugar moiety. In some embodiments, each wing sugar moiety is modified. In some embodiments, a wing sugar moiety is modified by a modification that is absent from the core region. In some embodiments, a wing region only has modified internucleotidic linkages at one or both of its ends. In some embodiments, a wing region only has a modified internucleotidic linkage at its 5'-end. In some embodiments, a wing region only has a modified internucleotidic linkage at its 3'-end. In some embodiments, a wing region only has modified internucleotidic linkages at its 5'- and 3'-ends. In some embodiments, a wing is to the 5'-end of a core, and the wing only has a modified internucleotidic linkage at its 5'-end. In some embodiments, a wing is to the 5'-end of a core, and the wing only has a modified internucleotidic linkage at its 3'-end. In some embodiments, a wing is to the 5'-end of a core, and the wing only has modified internucleotidic linkages at both its 5'- and 3'-ends. In some embodiments, a wing is to the 3'-end of a core, and the wing only has a modified internucleotidic linkage at its 5'-end. In some embodiments, a wing is to the 3'-end of a core, and the wing only has a modified internucleotidic linkage at its 3'-end. In some embodiments, a wing is to the 3'-end of a core, and the wing only has modified internucleotidic linkages at both its 5'- and 3'-ends.

In some embodiments, each internucleotidic linkage within a core region is modified. In some embodiments, each internucleotidic linkage within a core region is chiral. In some embodiments, a core region comprises a pattern of backbone chiral centers of (Sp)m(Rp)n, (Rp)n(Sp)m, (Np)t(Rp)n(Sp)m, or (Sp)t(Rp)n(Sp)m. In some embodiments, the pattern of backbone chiral centers of a core region is (Sp)m(Rp)n, (Rp)n(Sp)m, (Np)t(Rp)n(Sp)m, or (Sp)t(Rp)n(Sp)m. In some embodiments, a core region comprises a pattern of backbone chiral centers of (Rp)n(Sp)m, (Np)t(Rp)n(Sp)m, or (Sp)t(Rp)n(Sp)m, wherein m>2. In some embodiments, the pattern of backbone chiral centers of a core region is (Sp)m(Rp)n, (Rp)n(Sp)m, (Np)t(Rp)n(Sp)m, or (Sp)t(Rp)n(Sp)m, wherein m>2. Among other things, in some embodiments such patterns can provide or enhance controlled cleavage of a target sequence, e.g., an RNA sequence.

In some embodiments, oligonucleotides in provided compositions have a common pattern of backbone phosphorus modifications. In some embodiments, a provided composition is an oligonucleotide composition that is chirally controlled in that the composition contains a predetermined level of oligonucleotides of an individual oligonucleotide type, wherein an oligonucleotide type is defined by:

1) base sequence;
2) pattern of backbone linkages;
3) pattern of backbone chiral centers; and
4) pattern of backbone phosphorus modifications.

As noted above and understood in the art, in some embodiments, base sequence of an oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

In some embodiments, a particular oligonucleotide type may be defined by 1A) base identity;
1B) pattern of base modification;
1C) pattern of sugar modification;
2) pattern of backbone linkages;
3) pattern of backbone chiral centers; and
4) pattern of backbone phosphorus modifications.

Thus, in some embodiments, oligonucleotides of a particular type may share identical bases but differ in their pattern of base modifications and/or sugar modifications. In some embodiments, oligonucleotides of a particular type may share identical bases and pattern of base modifications (including, e.g., absence of base modification), but differ in pattern of sugar modifications.

In some embodiments, oligonucleotides of a particular type are chemically identical in that they have the same base sequence (including length), the same pattern of chemical modifications to sugar and base moieties, the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications (e.g., pattern of modifications on the internucleotidic phosphorus atom, such as $—S^-$, and $-L-R^1$ of formula I).

In some embodiments, the present disclosure provides chirally controlled oligonucleotide compositions of oligonucleotides comprising multiple (e.g., more than 5, 6, 7, 8, 9, or 10) internucleotidic linkages, and particularly for oligonucleotides comprising multiple (e.g., more than 5, 6, 7, 8, 9, or 10) chiral internucleotidic linkages. In some embodiments, in a stereorandom or racemic preparation of oligonucleotides, at least one chiral internucleotidic linkage is formed with less than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 95:5 diastereoselectivity. In some embodiments, for a stereoselective or chirally controlled preparation of oligonucleotides, each chiral internucleotidic linkage is formed with greater than 96:4 diastereoselectivity. In some embodiments, for a stereoselective or chirally controlled preparation of oligonucleotides, each chiral internucleotidic linkage is formed with greater than 97:3 diastereoselectivity. In some embodiments, for a stereoselective or chirally controlled preparation of oligonucleotides, each chiral internucleotidic linkage is formed with greater than 98:2 diastereoselectivity. In some embodiments, for a stereoselective or chirally controlled preparation of oligonucleotides, each chiral internucleotidic linkage is formed with greater than 99:1 diastereoselectivity. In some embodiments, diastereoselectivity of a chiral internucleotidic linkage in an oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage.

Among other things, the present disclosure provides oligonucleotide compositions and technologies for optimizing properties, e.g., activities, toxicities, etc. In some embodiments, the present disclosure provides methods for lowering toxicity of oligonucleotides and compositions thereof. In some embodiments, the present disclosure provides methods for lowering immune response associated with administration of oligonucleotides and compositions thereof (i.e., of administering oligonucleotide compositions so that undesirable immune responses to oligonucleotides in the compositions are reduced, for example relative to those observed with a reference composition of nucleotides of comparable or identical nucleotide sequence). In some embodiments, the present disclosure provides methods for lowering complement activation associated with administration of oligonucleotides and compositions thereof. In some embodiments, the present disclosure provides methods for improving protein binding profile of oligonucleotides and compositions thereof. In some embodiments, the present disclosure provides methods for increasing binding to certain proteins by oligonucleotides and compositions thereof. In some embodiments, the present disclosure provides methods for increasing binding to certain proteins by oligonucleotides and compositions thereof. In some embodiments, the present disclosure provides methods for enhancing delivery of oligonucleotides and compositions thereof. Among other things, the present disclosure encompasses the recognition that optimal delivery of oligonucleotides to their targets, in some embodiments, involves balance of oligonucleotides binding to certain proteins so that oligonucleotides can be transported to the desired locations, and oligonucleotide release so that oligonucleotides can be properly released from certain proteins to perform their desired functions, for example, hybridization with their targets, cleavage of their targets, inhibition of translation, modulation of transcript processing, etc. As exemplified in this disclosure, the present disclosure recognizes, among other things, that improvement of oligonucleotide properties can be achieved through chemical modifications and/or stereochemistry.

In some embodiments, the present disclosure provides a method of administering an oligonucleotide composition comprising a first plurality of oligonucleotides having a common nucleotide sequence, the improvement that comprises:

administering an oligonucleotide composition comprising the first plurality of oligonucleotides that is chirally controlled and that is characterized by reduced toxicity relative to a reference oligonucleotide composition of the same common nucleotide sequence.

In some embodiments, the present disclosure provides a method of administering an oligonucleotide composition comprising a first plurality of oligonucleotides having a common nucleotide sequence, the improvement that comprises:

administering an oligonucleotide composition in which each oligonucleotide in the plurality comprises one or more modified sugar moieties and the composition is characterized by reduced toxicity relative to a reference oligonucleotide composition of the same common nucleotide sequence but lacking at least one of the one or more modified sugar moieties.

In some embodiments, the present disclosure provides a method of administering an oligonucleotide composition comprising a first plurality of oligonucleotides having a common nucleotide sequence, the improvement that comprises:

administering an oligonucleotide composition in which each oligonucleotide in the plurality includes one or more natural phosphate linkages and one or more modified phosphate linkages;

wherein the oligonucleotide composition is characterized by reduced toxicity when tested in at least one assay that is observed with an otherwise comparable reference composition whose oligonucleotides do not comprise natural phosphate linkages.

In some embodiments, the present disclosure provides a method of administering an oligonucleotide composition comprising a first plurality of oligonucleotides having a common nucleotide sequence, the improvement that comprises:

administering an oligonucleotide composition in which each oligonucleotide in the plurality comprises one or more modified sugar moieties and the composition is characterized by reduced toxicity relative to a reference oligonucleotide composition of the same common nucleotide sequence but lacking at least one of the one or more modified sugar moieties.

In some embodiments, the present disclosure provides a method comprising steps of administering to a subject an oligonucleotide composition comprising a first plurality of oligonucleotides each of which has a common base sequence and comprises a modified sugar moiety, wherein the oligonucleotide composition is characterized by reduced toxicity when tested in at least one assay that is observed with an otherwise comparable reference composition that comprises a reference plurality of oligonucleotides which have the same common base sequence but have no modified sugar moieties.

In some embodiments, the present disclosure provides a method comprising steps of administering to a subject an oligonucleotide composition comprising a first plurality of oligonucleotides each of which has a common base sequence and comprises one or more natural phosphate linkages and one or more modified phosphate linkages, wherein the oligonucleotide composition is characterized by reduced toxicity when tested in at least one assay that is observed with an otherwise comparable reference composition that comprises a reference plurality of oligonucleotides which have the same common base sequence but have no natural phosphate linkages.

In some embodiments, the present disclosure provides a method comprising steps of administering a chirally controlled oligonucleotide composition to a subject, wherein the chirally controlled oligonucleotide composition is characterized by reduced toxicity when tested in at least one assay that is observed with an otherwise comparable reference composition that includes a different chirally controlled oligonucleotide composition, or a stereorandom oligonucleotide composition, comprising oligonucleotides having the same base sequence.

In some embodiments, reduced toxicity is or comprises reduced complement activation. In some embodiments, reduced toxicity comprises reduced complement activation. In some embodiments, reduced toxicity is or comprises reduced complement activation. In some embodiments, reduced toxicity comprises reduced complement activation via the alternative pathway.

In some embodiments, oligonucleotides can elicit proinflammatory responses. In some embodiments, the present disclosure provides compositions and methods for reducing inflammation. In some embodiments, the present disclosure provides compositions and methods for reducing proinflammatory responses. In some embodiments, the present disclosure provides methods for reducing injection site inflammation using provided compositions. In some embodiments, the present disclosure provides methods for reducing drug-induced vascular injury using provided compositions.

In some embodiments, the present disclosure provides a method, comprising administering a composition comprising a first plurality of oligonucleotides, which composition displays reduced injection site inflammation as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

In some embodiments, the present disclosure provides a method of administering an oligonucleotide composition comprising a first plurality of oligonucleotides having a common nucleotide sequence, the improvement that comprises:

- administering an oligonucleotide comprising a first plurality of oligonucleotides that is characterized by reduced injection site inflammation relative to a reference oligonucleotide composition of the same common nucleotide sequence.

In some embodiments, the present disclosure provides a method, comprising administering a composition comprising a first plurality of oligonucleotides, which composition displays altered protein binding as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

In some embodiments, the present disclosure provides a method of administering an oligonucleotide composition comprising a first plurality of oligonucleotides having a common nucleotide sequence, the improvement that comprises:

- administering an oligonucleotide composition comprising a first plurality of oligonucleotides that is characterized by altered protein binding relative to a reference oligonucleotide composition of the same common nucleotide sequence.

In some embodiments, the present disclosure provides a method comprising administering a composition comprising a first plurality of oligonucleotides, which composition displays improved delivery as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

In some embodiments, the present disclosure provides a method of administering an oligonucleotide composition comprising a first plurality of oligonucleotides having a common nucleotide sequence, the improvement that comprises:

- administering an oligonucleotide comprising a first plurality of oligonucleotides that is characterized by improved delivery relative to a reference oligonucleotide composition of the same common nucleotide sequence.

In general, properties of oligonucleotide compositions as described herein can be assessed using any appropriate assay. Relative toxicity and/or protein binding properties for different compositions (e.g., stereocontrolled vs non-stereocontrolled, and/or different stereocontrolled compositions) are typically desirably determined in the same assay, in some embodiments substantially simultaneously and in some embodiments with reference to historical results.

Those of skill in the art will be aware of and/or will readily be able to develop appropriate assays for particular oligonucleotide compositions. The present disclosure provides descriptions of certain particular assays, for example that may be useful in assessing one or more features of oligonucleotide composition behavior e.g., complement activation, injection site inflammation, protein biding, etc.

For example, certain assays that may be useful in the assessment of toxicity and/or protein binding properties of oligonucleotide compositions may include any assay described and/or exemplified herein.

Definitions

Aliphatic: The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic or polycyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. In some embodiments, aliphatic groups contain 1-50 aliphatic carbon atoms. Unless otherwise specified, aliphatic groups contain 1-10 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic or bicyclic $C_3$-$C_{10}$ hydrocarbon that is completely saturated or that contains one or more units of unsaturation, but which is not aromatic, that has a single point of attachment to the rest of the molecule. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkylene: The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

Alkenylene: The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl" used alone or as part of a larger moiety as in "aralkyl," "aralkoxy," or "aryloxyalkyl," refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring." In certain embodiments of the present disclosure, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Characteristic structural element: The term "characteristic structural element" refers to a distinctive structural element (e.g., core structure, collection of pendant moieties, sequence element, etc) that is found in all members of a family of polypeptides, small molecules, or nucleic acids, and therefore can be used by those of ordinary skill in the art to define members of the family.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Equivalent agents: Those of ordinary skill in the art, reading the present disclosure, will appreciate that the scope of useful agents in the context of the present disclosure is not limited to those specifically mentioned or exemplified herein. In particular, those skilled in the art will recognize that active agents typically have a structure that consists of a core and attached pendant moieties, and furthermore will appreciate that simple variations of such core and/or pendant moieties may not significantly alter activity of the agent. For example, in some embodiments, substitution of one or more pendant moieties with groups of comparable three-dimensional structure and/or chemical reactivity characteristics may generate a substituted compound or portion equivalent to a parent reference compound or portion. In some embodiments, addition or removal of one or more pendant moieties may generate a substituted compound equivalent to a parent reference compound. In some embodiments, alteration of core structure, for example by addition or removal of a small number of bonds (typically not more than 5, 4, 3, 2, or 1 bonds, and often only a single bond) may generate a substituted compound equivalent to a parent reference compound. In many embodiments, equivalent compounds may be prepared by methods illustrated in general reaction schemes as, for example, described below, or by modifications thereof, using readily available starting materials, reagents and conventional or provided synthesis procedures.

In these reactions, it is also possible to make use of variants, which are in themselves known, but are not mentioned here.

Equivalent Dosage: The term "equivalent dosage" is used herein to compare dosages of different pharmaceutically active agents that effect the same biological result. Dosages of two different agents are considered to be "equivalent" to one another in accordance with the present disclosure if they achieve a comparable level or extent of the biological result. In some embodiments, equivalent dosages of different pharmaceutical agents for use in accordance with the present disclosure are determined using in vitro and/or in vivo assays as described herein. In some embodiments, one or more lysosomal activating agents for use in accordance with the present disclosure is utilized at a dose equivalent to a dose of a reference lysosomal activating agent; in some such embodiments, the reference lysosomal activating agent for such purpose is selected from the group consisting of small molecule allosteric activators (e.g., pyrazolpyrimidines), imminosugars (e.g., isofagomine), antioxidants (e.g., n-acetyl-cysteine), and regulators of cellular trafficking (e.g., Rab1a polypeptide).

Heteroaliphatic: The term "heteroaliphatic" refers to an aliphatic group wherein one or more units selected from C, CH, $CH_2$, or $CH_3$ are independently replaced by a heteroatom. In some embodiments, a heteroaliphatic group is heteroalkyl. In some embodiments, a heteroaliphatic group is heteroalkenyl.

Heteroaryl: The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Heteroatom: The term "heteroatom" means one or more of oxygen, sulfur, nitrogen, phosphorus, boron, selenium, or silicon (including, any oxidized form of nitrogen, boron, selenium, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

Heterocycle: As used herein, the terms "heterocycle," "heterocyclyl," "heterocyclic radical," and "heterocyclic ring" are used interchangeably and refer to a stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Intraperitoneal: The phrases "intraperitoneal administration" and "administered intraperitonealy" as used herein have their art-understood meaning referring to administration of a compound or composition into the peritoneum of a subject.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Lower alkyl: The term "lower alkyl" refers to a $C_{1-4}$ straight or branched alkyl group. Example lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Optionally substituted: As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable,"

as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^\circ$; $—(CH_2)_{0-4}R^\circ$; $—O(CH_2)_{0-4}R^\circ$, $—O—(CH_2)_{0-4}C(O)OR^\circ$; $—(CH_2)_{0-4}CH(OR^\circ)_2$; $—(CH_2)_{0-4}SR^\circ$; $—(CH_2)_{0-4}Ph$, which may be substituted with $R^\circ$; $—(CH_2)_{0-4}O(CH_2)_{0-1}Ph$ which may be substituted with $R^\circ$; —CH═CHPh, which may be substituted with $R^\circ$; $—(CH_2)_{0-4}O(CH_2)_{0-1}$-pyridyl which may be substituted with $R^\circ$; $—NO_2$; —CN; $—N_3$; $—(CH_2)_{0-4}N(R^\circ)_2$; $—(CH_2)_{0-4}N(R^\circ)C(O)R^\circ$; $—N(R^\circ)C(S)R^\circ$; $—(CH_2)_{0-4}N(R^\circ)C(O)NR^\circ_2$; $—N(R^\circ)C(S)NR^\circ_2$; $—(CH_2)_{0-4}N(R^\circ)C(O)OR^\circ$; $—N(R^\circ)N(R^\circ)C(O)R^\circ$; $—N(R^\circ)N(R^\circ)C(O)NR^\circ_2$; $—N(R^\circ)N(R^\circ)C(O)OR^\circ$; $—(CH_2)_{0-4}C(O)R^\circ$; $—C(S)R^\circ$; $—(CH_2)_{0-4}C(O)OR^\circ$; $—(CH_2)_{0-4}C(O)SR^\circ$; $—(CH_2)_{0-4}C(O)OSiR^\circ_3$; $—(CH_2)_{0-4}C(O)R^\circ$; $—OC(O)(CH_2)_{0-4}SR$, $—SC(S)SR^\circ$; $—(CH_2)_{0-4}SC(O)R^\circ$; $—(CH_2)_{0-4}C(O)NR^\circ_2$; $—C(S)NR^\circ_2$; $—C(S)SR^\circ$; $—SC(S)SR^\circ$, $—(CH_2)_{0-4}C(O)NR^\circ_2$; $—C(O)N(OR^\circ)R^\circ$; $—C(O)C(O)R^\circ$; $—C(O)CH_2C(O)R^\circ$; $—C(NOR^\circ)R^\circ$; $—(CH_2)_{0-4}SSR^\circ$; $—(CH_2)_{0-4}S(O)_2R^\circ$; $—(CH_2)_{0-4}S(O)_2OR^\circ$; $—(CH_2)_{0-4}OS(O)_2R^\circ$; $—S(O)_2NR^\circ_2$; $—(CH_2)_{0-4}S(O)R^\circ$; $—N(R^\circ)S(O)_2NR^\circ_2$; $—N(R^\circ)S(O)_2R^\circ$; $—N(OR^\circ)R^\circ$; $—C(NH)NR^\circ_2$; $—P(O)_2R^\circ$; $—P(O)R^\circ_2$; $—OP(O)R^\circ_2$; $—OP(O)(OR^\circ)_2$; $—SiR^\circ_3$; $—(C_{1-4}$ straight or branched alkylene)$O—N(R^\circ)_2$; or $—(C_{1-4}$ straight or branched alkylene)$C(O)O—N(R^\circ)_2$, wherein each $R^\circ$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6 membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12 membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^\bullet$, -(halo$R^\bullet$), $—(CH_2)_{0-2}OH$, $—(CH_2)_{0-2}OR^\bullet$, $—(CH_2)_{0-2}CH(OR^\bullet)_2$; —O(halo$R^\bullet$), —CN, $—N_3$, $—(CH_2)_{0-2}C(O)R^\bullet$, $—(CH_2)_{0-2}C(O)OH$, $—(CH_2)_{0-2}C(O)OR^\bullet$, $—(CH_2)_{0-2}SR^\bullet$, $—(CH_2)_{0-2}SH$, $—(CH_2)_{0-2}NH_2$, $—(CH_2)_{0-2}NHR^\bullet$, $—(CH_2)_{0-2}NR^\bullet_2$, $—NO_2$, $—SiR^\bullet_3$, $—OSiR^\bullet_3$, $—C(O)SR^\bullet$, $—(C_{1-4}$ straight or branched alkylene)$C(O)OR^\bullet$, or $—SSR^\bullet$ wherein each $R^\bullet$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6 membered saturated, partially unsaturated, or aryl ring having 0-4 heteroatoms independently selected from nitrogen, oxygen, or sulfur. Suitable divalent substituents on a saturated carbon atom of $R^\circ$ include ═O and ═S.

Suitable divalent substituents on a saturated carbon atom of an "optionally substituted" group include the following: ═O, ═S, $═NNR^*_2$, $═NNHC(O)R^*$, $═NNHC(O)OR^\bullet$, $═NNHS(O)_2R^*$, $═NR^*$, $═NOR^\bullet$, $—O(C(R^*_2))_{2-3}O—$, or $—S(C(R^*_2))_{2-3}S—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $—R^\bullet$, -(halo$R^\bullet$), —OH, $—OR^\bullet$, —O(halo$R^\bullet$), —CN, —C(O)OH, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6 membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, —C(O)RY, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6 membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12 membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $—R^\bullet$, -(halo$R^\bullet$), —OH, $—OR^\bullet$, —O(halo$R^\bullet$), —CN, —C(O)OH, $—C(O)OR^\bullet$, $—NH_2$, $—NHR^\bullet$, $—NR^\bullet_2$, or $—NO_2$, wherein each $R^\bullet$ is unsubstituted or where preceded by "halo" is substituted only with one or more halogens, and is independently $C_{1-4}$ aliphatic, $—CH_2Ph$, $—O(CH_2)_{0-1}Ph$, or a 5-6 membered saturated, partially unsaturated, or aryl ring having 0-4 heteroatoms independently selected from nitrogen, oxygen, or sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase “pharmaceutically acceptable” refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term “pharmaceutically acceptable carrier” means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be “acceptable” in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; pH buffered solutions; polyesters, polycarbonates and/or polyanhydrides; and other nontoxic compatible substances employed in pharmaceutical formulations.

Pharmaceutically acceptable salt: The term “pharmaceutically acceptable salt”, as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prodrug: A general, a “prodrug,” as that term is used herein and as is understood in the art, is an entity that, when administered to an organism, is metabolized in the body to deliver an active (e.g., therapeutic or diagnostic) agent of interest. Typically, such metabolism involves removal of at least one “prodrug moiety” so that the active agent is formed. Various forms of “prodrugs” are known in the art. For examples of such prodrug moieties, see:

a) *Design of Prodrugs*, edited by H. Bundgaard, (Elsevier, 1985) and *Methods in Enzymology,* 42:309-396, edited by K. Widder, et al. (*Academic Press,* 1985);
b) *Prodrugs and Targeted Delivery*, edited by J. Rautio (Wiley, 2011);
c) *Prodrugs and Targeted Delivery*, edited by J. Rautio (Wiley, 2011);
d) *A Textbook of Drug Design and Development*, edited by Krogsgaard-Larsen;
e) Bundgaard, Chapter 5 *“Design and Application of Prodrugs*”, by H. Bundgaard, p. 113-191 (1991);
f) Bundgaard, *Advanced Drug Delivery Reviews,* 8:1-38 (1992);
g) Bundgaard, et al., *Journal of Pharmaceutical Sciences,* 77:285 (1988); and
h) Kakeya, et al., *Chem. Pharm. Bull.,* 32:692 (1984).

As with other compounds described herein, prodrugs may be provided in any of a variety of forms, e.g., crystal forms, salt forms etc. In some embodiments, prodrugs are provided as pharmaceutically acceptable salts thereof.

Protecting group: The term “protecting group,” as used herein, is well known in the art and includes those described in detail in *Protecting Groups in Organic Synthesis*, T. W. Greene and P. G. M. Wuts, $3^{rd}$ edition, John Wiley & Sons, 1999, the entirety of which is incorporated herein by reference. Also included are those protecting groups specially adapted for nucleoside and nucleotide chemistry described in *Current Protocols in Nucleic Acid* Chemistry, edited by Serge L. Beaucage et al. June 2012, the entirety of Chapter 2 is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl–1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifiuoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group.

In some embodiments, a phosphorus protecting group is a group attached to the internucleotide phosphorus linkage throughout oligonucleotide synthesis. In some embodiments, the phosphorus protecting group is attached to the sulfur atom of the internucleotide phosphorothioate linkage. In some embodiments, the phosphorus protecting group is attached to the oxygen atom of the internucleotide phosphorothioate linkage. In some embodiments, the phosphorus protecting group is attached to the oxygen atom of the internucleotide phosphate linkage. In some embodiments the phosphorus protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl) aminoethyl, 4-[N-methyl-N-(2,2,2-trifluoroacetyl)amino] butyl.

Protein: As used herein, the term “protein” refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc). In some embodiments, a protein includes more than one polypeptide chain, for example linked by one or more disulfide bonds or associated by other means. In some embodiments, proteins contain L-amino acids, D-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Sample: A "sample" as used herein is a specific organism or material obtained therefrom. In some embodiments, a sample is a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, a sample is an organism. In some embodiments, a sample is a plant. In some embodiments, a sample is an animal. In some embodiments, a sample is a human. In some embodiments, a sample is an organism other than a human.

Stereochemically isomeric forms: The phrase "stereochemically isomeric forms," as used herein, refers to different compounds made up of the same atoms bonded by the same sequence of bonds but having different three-dimensional structures which are not interchangeable. In some embodiments of the disclosure, provided chemical compositions may be or include pure preparations of individual stereochemically isomeric forms of a compound; in some embodiments, provided chemical compositions may be or include mixtures of two or more stereochemically isomeric forms of the compound. In certain embodiments, such mixtures contain equal amounts of different stereochemically isomeric forms; in certain embodiments, such mixtures contain different amounts of at least two different stereochemically isomeric forms. In some embodiments, a chemical composition may contain all diastereomers and/or enantiomers of the compound. In some embodiments, a chemical composition may contain less than all diastereomers and/or enantiomers of a compound. In some embodiments, if a particular enantiomer of a compound of the present disclosure is desired, it may be prepared, for example, by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, diastereomeric salts are formed with an appropriate optically-active acid, and resolved, for example, by fractional crystallization.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the disclosure, chemical compositions may be provided that are or include pure preparations of a single tautomeric form of a compound. In some embodiments of the disclosure, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the disclosure, chemical compositions may contain all tautomeric forms of a compound. In some embodiments of the disclosure, chemical compositions may contain less than all tautomeric forms of a compound. In some embodiments of the disclosure, chemical compositions may contain one or more tautomeric forms of a compound in amounts that vary over time as a result of interconversion. In some embodiments of the disclosure, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an enol derivative that may subsequently be isolated using one or more suitable techniques known in the art. Unless otherwise indicated, the present disclosure encompasses all tautomeric forms of relevant compounds, whether in pure form or in admixture with one another.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Nucleic acid: The term "nucleic acid" includes any nucleotides, analogs thereof, and polymers thereof. The term "polynucleotide" as used herein refer to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges (also referred to herein as "internucleotide linkages"). The term encompasses nucleic acids containing any combinations of nucleobases, modified nucleobases, sugars, modified sugars, phosphate bridges or modified phosphorus atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. The prefix poly-refers to a nucleic acid containing 2 to about 10,000 nucleotide monomer units and wherein the prefix oligo-refers to a nucleic acid containing 2 to about 200 nucleotide monomer units.

Nucleotide: The term "nucleotide" as used herein refers to a monomeric unit of a polynucleotide that consists of a heterocyclic base, a sugar, and one or more phosphate groups or phosphorus-containing internucleotidic linkages. The naturally occurring bases, (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein.

Nucleoside: The term "nucleoside" refers to a moiety wherein a nucleobase or a modified nucleobase is covalently bound to a sugar or modified sugar.

Sugar: The term "sugar" refers to a monosaccharide in closed and/or open form. Sugars include, but are not limited to, ribose, deoxyribose, pentofuranose, pentopyranose, and hexopyranose moieties. As used herein, the term also encompasses structural analogs used in lieu of conventional sugar molecules, such as glycol, polymer of which forms the backbone of the nucleic acid analog, glycol nucleic acid ("GNA").

Modified sugar: The term "modified sugar" refers to a moiety that can replace a sugar. The modified sugar mimics the spatial arrangement, electronic properties, or some other physicochemical property of a sugar.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex.

Chiral ligand: The term "chiral ligand" or "chiral auxiliary" refers to a moiety that is chiral and can be incorporated into a reaction so that the reaction can be carried out with certain stereoselectivity.

Condensing reagent: In a condensation reaction, the term "condensing reagent" refers to a reagent that activates a less reactive site and renders it more susceptible to attack by another reagent. In some embodiments, such another reagent is a nucleophile.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule.

Solid support: The term "solid support" refers to any support which enables synthesis of nucleic acids. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Linking moiety: The term "linking moiety" refers to any moiety optionally positioned between the terminal nucleoside and the solid support or between the terminal nucleoside and another nucleoside, nucleotide, or nucleic acid.

DNA molecule: A "DNA molecule" refers to the polymeric form of deoxyribonucleotides (adenine, guanine, thymine, or cytosine) in its either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences can be described herein according to the normal convention of giving only the sequence in the 5' to 3' direction along the non-transcribed strand of DNA (i.e., the strand having a sequence homologous to the mRNA).

Coding sequence: A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence is, usually, be located 3' to the coding sequence. The term "non-coding sequence" or "non-coding region" refers to regions of a polynucleotide sequence that are not translated into amino acids (e.g. 5' and 3' un-translated regions).

Reading frame: The term "reading frame" refers to one of the six possible reading frames, three in each direction, of the double stranded DNA molecule. The reading frame that is used determines which codons are used to encode amino acids within the coding sequence of a DNA molecule.

Antisense: As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can associate via hydrogen bonds to a sense nucleic acid molecule.

Wobble position: As used herein, a "wobble position" refers to the third position of a codon. Mutations in a DNA molecule within the wobble position of a codon, in some embodiments, result in silent or conservative mutations at the amino acid level. For example, there are four codons that encode Glycine, i.e., GGU, GGC, GGA and GGG, thus mutation of any wobble position nucleotide, to any other nucleotide selected from A, U, C and G, does not result in a change at the amino acid level of the encoded protein and, therefore, is a silent substitution.

Silent substitution: a "silent substitution" or "silent mutation" is one in which a nucleotide within a codon is modified, but does not result in a change in the amino acid residue encoded by the codon. Examples include mutations in the third position of a codon, as well in the first position of certain codons such as in the codon "CGG" which, when mutated to AGG, still encodes Arg.

Gene: The terms "gene," "recombinant gene" and "gene construct" as used herein, refer to a DNA molecule, or portion of a DNA molecule, that encodes a protein or a portion thereof. The DNA molecule can contain an open reading frame encoding the protein (as exon sequences) and can further include intron sequences. The term "intron" as used herein, refers to a DNA sequence present in a given gene which is not translated into protein and is found in some, but not all cases, between exons. It can be desirable for the gene to be operably linked to, (or it can comprise), one or more promoters, enhancers, repressors and/or other regulatory sequences to modulate the activity or expression of the gene, as is well known in the art.

Complementary DNA: As used herein, a "complementary DNA" or "cDNA" includes recombinant polynucleotides synthesized by reverse transcription of mRNA and from which intervening sequences (introns) have been removed.

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, wordlength=12 to obtain nucleotide sequences homologous to nucleic acid molecules of the disclosure. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

Heterologous: A “heterologous” region of a DNA sequence is an identifiable segment of DNA within a larger DNA sequence that is not found in association with the larger sequence in nature. Thus, when the heterologous region encodes a mammalian gene, the gene can usually be flanked by DNA that does not flank the mammalian genomic DNA in the genome of the source organism. Another example of a heterologous coding sequence is a sequence where the coding sequence itself is not found in nature (e.g., a cDNA where the genomic coding sequence contains introns or synthetic sequences having codons or motifs different than the unmodified gene). Allelic variations or naturally-occurring mutational events do not give rise to a heterologous region of DNA as defined herein.

Transition mutation: The term “transition mutations” refers to base changes in a DNA sequence in which a pyrimidine (cytidine (C) or thymidine (T) is replaced by another pyrimidine, or a purine (adenosine (A) or guanosine (G) is replaced by another purine.

Transversion mutation: The term “transversion mutations” refers to base changes in a DNA sequence in which a pyrimidine (cytidine (C) or thymidine (T) is replaced by a purine (adenosine (A) or guanosine (G), or a purine is replaced by a pyrimidine.

Oligonucleotide: the term “oligonucleotide” refers to a polymer or oligomer of nucleotide monomers, containing any combination of nucleobases, modified nucleobases, sugars, modified sugars, phosphate bridges, or modified phosphorus atom bridges (also referred to herein as “internucleotidic linkage”, defined further herein).

Oligonucleotides can be single-stranded or double-stranded. As used herein, the term “oligonucleotide strand” encompasses a single-stranded oligonucleotide. A single-stranded oligonucleotide can have double-stranded regions and a double-stranded oligonucleotide can have single-stranded regions. Example oligonucleotides include, but are not limited to structural genes, genes including control and termination regions, self-replicating systems such as viral or plasmid DNA, single-stranded and double-stranded siRNAs and other RNA interference reagents (RNAi agents or iRNA agents), shRNA, antisense oligonucleotides, ribozymes, microRNAs, microRNA mimics, supermirs, aptamers, antimirs, antagomirs, U1 adaptors, triplex-forming oligonucleotides, G-quadruplex oligonucleotides, RNA activators, immuno-stimulatory oligonucleotides, and decoy oligonucleotides.

Double-stranded and single-stranded oligonucleotides that are effective in inducing RNA interference are also referred to as siRNA, RNAi agent, or iRNA agent, herein. In some embodiments, these RNA interference inducing oligonucleotides associate with a cytoplasmic multi-protein complex known as RNAi-induced silencing complex (RISC). In many embodiments, single-stranded and double-stranded RNAi agents are sufficiently long that they can be cleaved by an endogenous molecule, e.g., by Dicer, to produce smaller oligonucleotides that can enter the RISC machinery and participate in RISC mediated cleavage of a target sequence, e.g. a target mRNA.

Oligonucleotides of the present disclosure can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, from about 20 to about 30 nucleotides in length. In some embodiments, the oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length.

Internucleotidic linkage: As used herein, the phrase “internucleotidic linkage” refers generally to the phosphorus-containing linkage between nucleotide units of an oligonucleotide, and is interchangeable with “inter-sugar linkage” and “phosphorus atom bridge,” as used above and herein. In some embodiments, an internucleotidic linkage is a phosphodiester linkage, as found in naturally occurring DNA and RNA molecules. In some embodiments, an internucleotidic linkage is a “modified internucleotidic linkage” wherein each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —N(R')$_2$, B(R')$_3$, —S—, —Se—, and —N(R')—, wherein each R' is independently as defined and described below. In some embodiments, an internucleotidic linkage is a phosphotriester linkage, phosphorothioate diester linkage (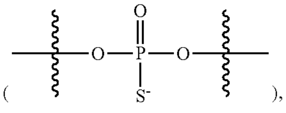), or modified phosphorothioate triester linkage. It is understood by a person of ordinary skill in the art that the internucleotidic linkage may exist as an anion or cation at a given pH due to the existence of acid or base moieties in the linkage.

Unless otherwise specified, when used with an oligonucleotide sequence, each of s, s1, s2, s3, s4, s5, s6 and s7 independently represents the following modified internucleotidic linkage as illustrated in Table 1, below.

TABLE 1
Example Modified Internucleotidic Linkage.
| Symbol | Modified Internucleotidic Linkage |
| --- | --- |
| s | phosphorothioate( 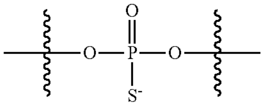 ) |
| s1 | 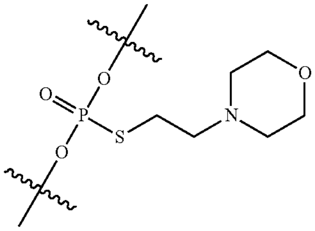 [SMILES: *OP(=O)(O*)SCCN1CCOCC1] |
| s2 | 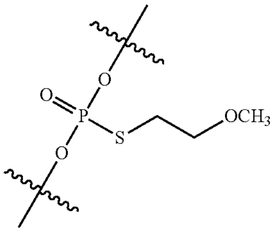 [SMILES: *OP(=O)(O*)SCCOC] |
| s3 | 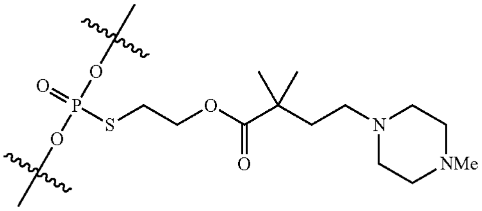 [SMILES: *OP(=O)(O*)SCCOC(=O)C(C)(C)CCN1CCN(C)CC1] |
| s4 | 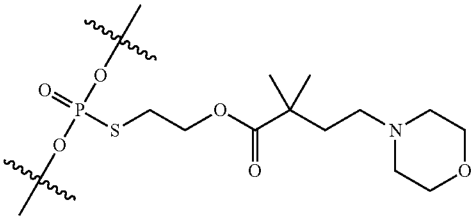 [SMILES: *OP(=O)(O*)SCCOC(=O)C(C)(C)CCN1CCOCC1] |
| s5 | 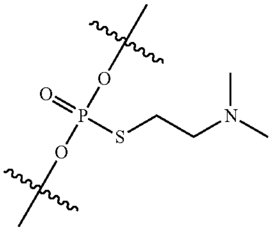 [SMILES: *OP(=O)(O*)SCCN(C)C] |
| s6 | 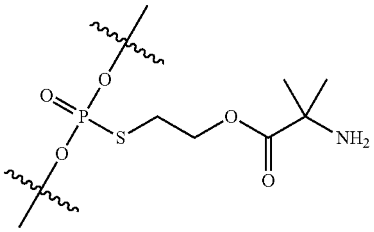 [SMILES: *OP(=O)(O*)SCCOC(=O)C(C)(C)N] |
TABLE 1-continued
Example Modified Internucleotidic Linkage.
| Symbol | Modified Internucleotidic Linkage |
| --- | --- |
| s7 | 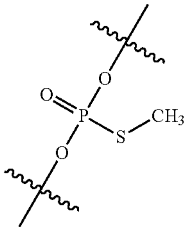 [SMILES: *OP(=O)(O*)SC] |
| s8 | 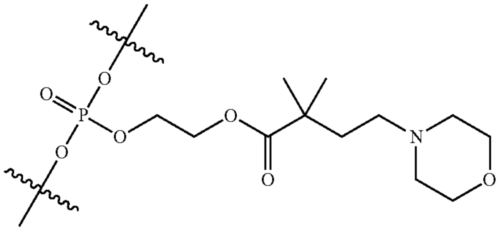 [SMILES: *OP(=O)(O*)OCCOC(=O)C(C)(C)CCN1CCOCC1] |
| s9 | 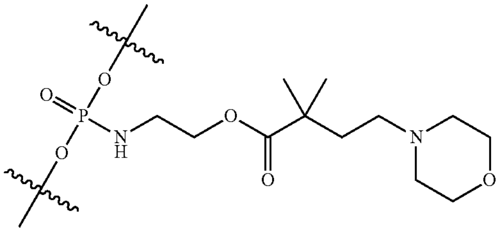 [SMILES: *OP(=O)(NCCOC(=O)C(C)(C)CCN1CCOCC1)O*] |
| s10 | 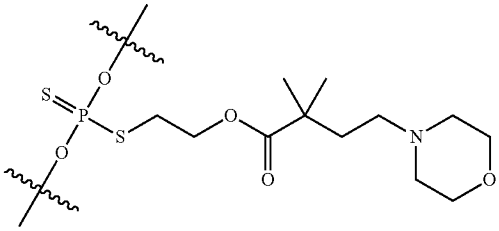 [SMILES: *OP(=S)(O*)SCCOC(=O)C(C)(C)CCN1CCOCC1] |
| s11 | 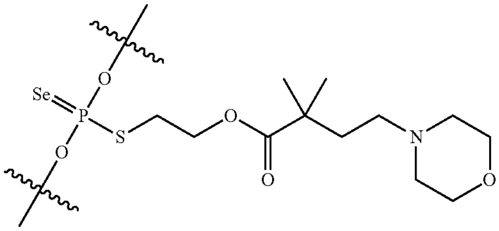 [SMILES: *OP(=[Se])(O*)SCCOC(=O)C(C)(C)CCN1CCOCC1] |
| s12 | 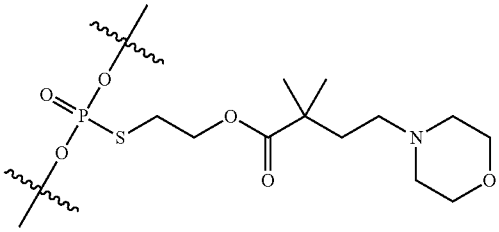 [SMILES: *OP(=O)(O*)SCCOC(=O)C(C)(C)CCN1CCOCC1] |

TABLE 1-continued

| Example Modified Internucleotidic Linkage. | |
|---|---|
| Symbol | Modified Internucleotidic Linkage |
| s13 | 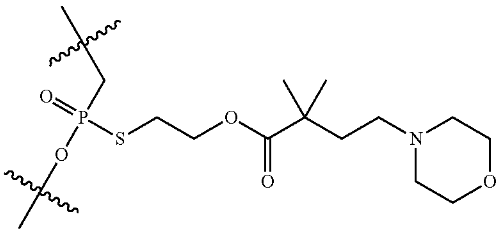 [SMILES: *CP(=O)(O*)SCCOC(=O)C(C)(C)CCN1CCOCC1] |
| s14 | 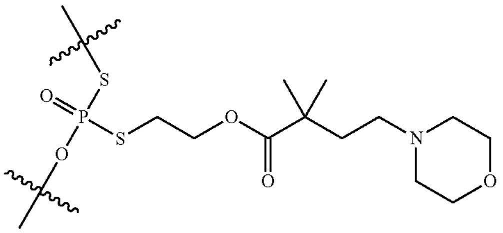 [SMILES: *OP(=O)(S*)SCCOC(=O)C(C)(C)CCN1CCOCC1] |
| s15 | 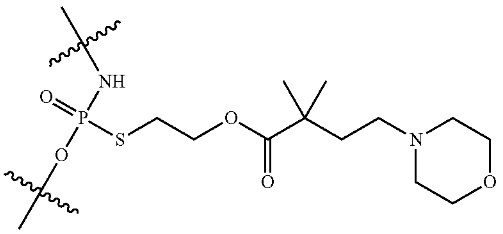 [SMILES: *NP(=O)(O*)SCCOC(=O)C(C)(C)CCN1CCOCC1] |
| s16 | 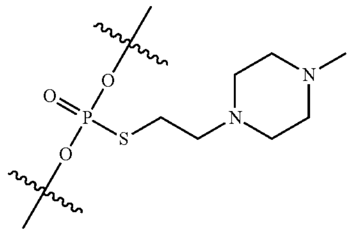 [SMILES: *OP(=O)(O*)SCCN1CCN(C)CC1] |
| s17 | 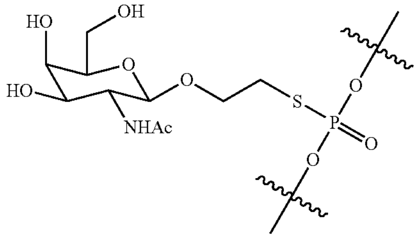 [SMILES: *OP(=O)(O*)SCCOC1OC(CO)C(O)C(O)C1NC(C)=O] |
| s18 | 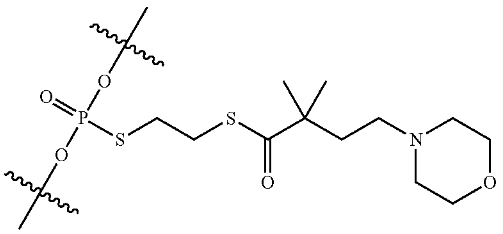 [SMILES: *OP(=O)(O*)SCCSC(=O)C(C)(C)CCN1CCOCC1] |

For instance, (Rp, Sp)-ATsCs1GA has 1) a phosphorothioate internucleotidic linkage

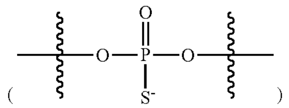

between T and C; and 2) a phosphorothioate triester internucleotidic linkage having the structure of

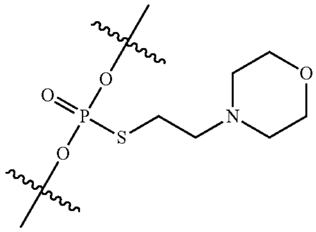 [SMILES: *OP(=O)(O*)SCCN1CCOCC1]

between C and G. Unless otherwise specified, the Rp/Sp designations preceding an oligonucleotide sequence describe the configurations of chiral linkage phosphorus atoms in the internucleotidic linkages sequentially from 5' to 3' of the oligonucleotide sequence. For instance, in (Rp, Sp)-ATsCs1GA, the phosphorus in the "s" linkage between T and C has Rp configuration and the phosphorus in "s1" linkage between C and G has Sp configuration. In some embodiments, "All-(Rp)" or "All-(Sp)" is used to indicate that all chiral linkage phosphorus atoms in oligonucleotide have the same Rp or Sp configuration, respectively. For instance, All-(Rp)-GsCsCsTsCsAsGsTsCsTSGsCsTSTsCsGsCsAsCsC (SEQ ID NO: 1) indicates that all the chiral linkage phosphorus atoms in the oligonucleotide have Rp configuration; All-(Sp)-GsCsCsTsCsAsGsTsCsTSGsCsTSTsCsGsCsAsCsC (SEQ ID NO: 2) indicates that all the chiral linkage phosphorus atoms in the oligonucleotide have Sp configuration.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—$XLR^1$" groups in formula I). Oligonucleotides of a common designated "type" are structurally identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. The present disclosure provides compositions comprising or consisting of a plurality of oligonucleotide molecules (e.g., chirally controlled oligonucleotide compositions). In some embodiments, all such molecules are of the same type (i.e., are structurally identical to one another). In many embodiments, however, provided compositions comprise a plurality of oligonucleotides of different types, typically in predetermined relative amounts.

Chiral control: As used herein, "chiral control" refers to an ability to control the stereochemical designation of every chiral linkage phosphorus within an oligonucleotide strand. The phrase "chirally controlled oligonucleotide" refers to an oligonucleotide which exists in a single diastereomeric form with respect to the chiral linkage phosphorus.

Chirally controlled oligonucleotide composition: As used herein, the phrase "chirally controlled oligonucleotide composition" refers to an oligonucleotide composition that contains predetermined levels of individual oligonucleotide types. For instance, in some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises a mixture of multiple oligonucleotide types. Example chirally controlled oligonucleotide compositions are described further herein.

Chirally pure: as used herein, the phrase "chirally pure" is used to describe a chirally controlled oligonucleotide composition in which all of the oligonucleotides exist in a single diastereomeric form with respect to the linkage phosphorus.

Chirally uniform: as used herein, the phrase "chirally uniform" is used to describe an oligonucleotide molecule or type in which all nucleotide units have the same stereochemistry at the linkage phosphorus. For instance, an oligonucleotide whose nucleotide units all have Rp stereochemistry at the linkage phosphorus is chirally uniform. Likewise, an oligonucleotide whose nucleotide units all have Sp stereochemistry at the linkage phosphorus is chirally uniform.

Predetermined: By predetermined is meant deliberately selected, for example as opposed to randomly occurring or achieved. Those of ordinary skill in the art, reading the present specification, will appreciate that the present disclosure provides new and surprising technologies that permit selection of particular oligonucleotide types for preparation and/or inclusion in provided compositions, and further permits controlled preparation of precisely the selected particular types, optionally in selected particular relative amounts, so that provided compositions are prepared. Such provided compositions are "predetermined" as described herein. Compositions that may contain certain individual oligonucleotide types because they happen to have been generated through a process that cannot be controlled to intentionally generate the particular oligonucleotide types is not a "predetermined" composition. In some embodiments, a predetermined composition is one that can be intentionally reproduced (e.g., through repetition of a controlled process).

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester of an internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is P* of formula I. In some embodiments, a linkage phosphorus atom is chiral. In some embodiments, a chiral linkage phosphorus atom is P* of formula I.

P-modification: as used herein, the term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X-L-$R^1$ wherein each of X, L and $R^1$ is independently as defined and described herein and below.

Blockmer: the term "blockmer," as used herein, refers to an oligonucleotide strand whose pattern of structural features characterizing each individual nucleotide unit is characterized by the presence of at least two consecutive nucleotide units sharing a common structural feature at the internucleotidic phosphorus linkage. By common structural feature is meant common stereochemistry at the linkage phosphorus or a common modification at the linkage phosphorus. In some embodiments, the at least two consecutive nucleotide units sharing a common structure feature at the internucleotidic phosphorus linkage are referred to as a "block".

In some embodiments, a blockmer is a "stereoblockmer," e.g., at least two consecutive nucleotide units have the same stereochemistry at the linkage phosphorus. Such at least two consecutive nucleotide units form a "stereoblock." For instance, (Sp, Sp)-ATsCs1GA is a stereoblockmer because at least two consecutive nucleotide units, the Ts and the Cs1, have the same stereochemistry at the linkage phosphorus (both Sp). In the same oligonucleotide (Sp, Sp)-ATsCs1GA, TsCs1 forms a block, and it is a stereoblock.

In some embodiments, a blockmer is a "P-modification blockmer," e.g., at least two consecutive nucleotide units have the same modification at the linkage phosphorus. Such at least two consecutive nucleotide units form a "P-modification block". For instance, (Rp, Sp)-ATsCsGA is a P-modification blockmer because at least two consecutive nucleotide units, the Ts and the Cs, have the same P-modification (i.e., both are a phosphorothioate diester). In the same oligonucleotide of (Rp, Sp)-ATsCsGA, TsCs forms a block, and it is a P-modification block.

In some embodiments, a blockmer is a "linkage blockmer," e.g., at least two consecutive nucleotide units have identical stereochemistry and identical modifications at the linkage phosphorus. At least two consecutive nucleotide units form a "linkage block". For instance, (Rp, Rp)-ATsCsGA is a linkage blockmer because at least two consecutive nucleotide units, the Ts and the Cs, have the same stereochemistry (both Rp) and P-modification (both phosphorothioate). In the same oligonucleotide of (Rp, Rp)-ATsCsGA, TsCs forms a block, and it is a linkage block.

In some embodiments, a blockmer comprises one or more blocks independently selected from a stereoblock, a P-modification block and a linkage block. In some embodiments, a blockmer is a stereoblockmer with respect to one block, and/or a P-modification blockmer with respect to another block, and/or a linkage blockmer with respect to yet another block. For instance, (Rp, Rp, Rp, Rp, Rp, Sp, Sp, Sp)-AAsTsCsGsAs1Ts1Cs1Gs1ATCG (SEQ ID NO: 3) is a stereoblockmer with respect to the stereoblock AsTsCsGsAs1 (all Rp at linkage phosphorus) or Ts1Cs1Gs1 (all Sp at linkage phosphorus), a P-modification blockmer with respect to the P-modification block AsTsCsGs (all s linkage) or As1Ts1Cs1Gs1 (all s1 linkage), or a linkage blockmer with respect to the linkage block AsTsCsGs (all Rp at linkage phosphorus and all s linkage) or Ts1Cs1Gs1 (all Sp at linkage phosphorus and all s1 linkage).

Altmer: the term "altmer," as used herein, refers to an oligonucleotide strand whose pattern of structural features characterizing each individual nucleotide unit is characterized in that no two consecutive nucleotide units of the oligonucleotide strand share a particular structural feature at the internucleotidic phosphorus linkage. In some embodiments, an altmer is designed such that it comprises a repeating pattern. In some embodiments, an altmer is designed such that it does not comprise a repeating pattern.

In some embodiments, an altmer is a "stereoaltmer," e.g., no two consecutive nucleotide units have the same stereochemistry at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCsCsTsCsAsGsTsCsTSGsCsTSTsCsGsCsAsCsC (SEQ ID NO: 4).

In some embodiments, an altmer is a "P-modification altmer" e.g., no two consecutive nucleotide units have the same modification at the linkage phosphorus. For instance, All-(Sp)-CAs1GsT, in which each linkage phosphorus has a different P-modification than the others.

In some embodiments, an altmer is a "linkage altmer," e.g., no two consecutive nucleotide units have identical stereochemistry or identical modifications at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCs1CsTs1CsAs1GsTs1CsTs1GsCs1TSTs2CsGs3CsAs-4CsC (SEQ ID NO: 5).

Unimer: the term "unimer," as used herein, refers to an oligonucleotide strand whose pattern of structural features characterizing each individual nucleotide unit is such that all nucleotide units within the strand share at least one common structural feature at the internucleotidic phosphorus linkage. By common structural feature is meant common stereochemistry at the linkage phosphorus or a common modification at the linkage phosphorus.

In some embodiments, a unimer is a "stereounimer," e.g., all nucleotide units have the same stereochemistry at the linkage phosphorus. For instance, All-(Sp)-CsAs1GsT, in which all the linkages have Sp phosphorus.

In some embodiments, a unimer is a "P-modification unimer", e.g., all nucleotide units have the same modification at the linkage phosphorus. For instance, (Rp, Sp, Rp, Sp, Rp, Sp, Rp, Sp, Rp, Sp Rp, Sp, Rp, Sp, Rp, Sp, Rp, Sp, Rp)-GsCsCsTsCsAsGsTsCsTSGsCsTSTsCsGsCsAsCsC (SEQ ID NO: 6), in which all the internucleotidic linkages are phosphorothioate diester.

In some embodiments, a unimer is a "linkage unimer," e.g., all nucleotide units have the same stereochemistry and the same modifications at the linkage phosphorus. For instance, All-(Sp)-GsCsCsTsCsAsGsTsCsTSGsCsTSTsCsGsCsAsCsC (SEQ ID NO: 7), in which all the internucleotidic linkages are phosphorothioate diester having Sp linkage phosphorus.

Gapmer: as used herein, the term "gapmer" refers to an oligonucleotide strand characterized in that at least one internucleotidic phosphorus linkage of the oligonucleotide strand is a phosphate diester linkage, for example such as those found in naturally occurring DNA or RNA. In some embodiments, more than one internucleotidic phosphorus linkage of the oligonucleotide strand is a phosphate diester linkage such as those found in naturally occurring DNA or RNA. For instance, All-(Sp)-CAs1GsT, in which the internucleotidic linkage between C and A is a phosphate diester linkage.

Skipmer: as used herein, the term "skipmer" refers to a type of gapmer in which every other internucleotidic phosphorus linkage of the oligonucleotide strand is a phosphate diester linkage, for example such as those found in naturally occurring DNA or RNA, and every other internucleotidic phosphorus linkage of the oligonucleotide strand is a modified internucleotidic linkage. For instance, All-(Sp)-AsTCs1GAs2TCs3G.

For purposes of this disclosure, the chemical elements are identified in accordance with the Periodic Table of the Elements, CAS version, *Handbook of Chemistry and Physics,* 67th Ed., 1986-87, inside cover.

The methods and structures described herein relating to compounds and compositions of the disclosure also apply to the pharmaceutically acceptable acid or base addition salts and all stereoisomeric forms of these compounds and compositions.

DETAILED DESCRIPTION OF CERTAIN EMBODIMENTS

Figure 1:
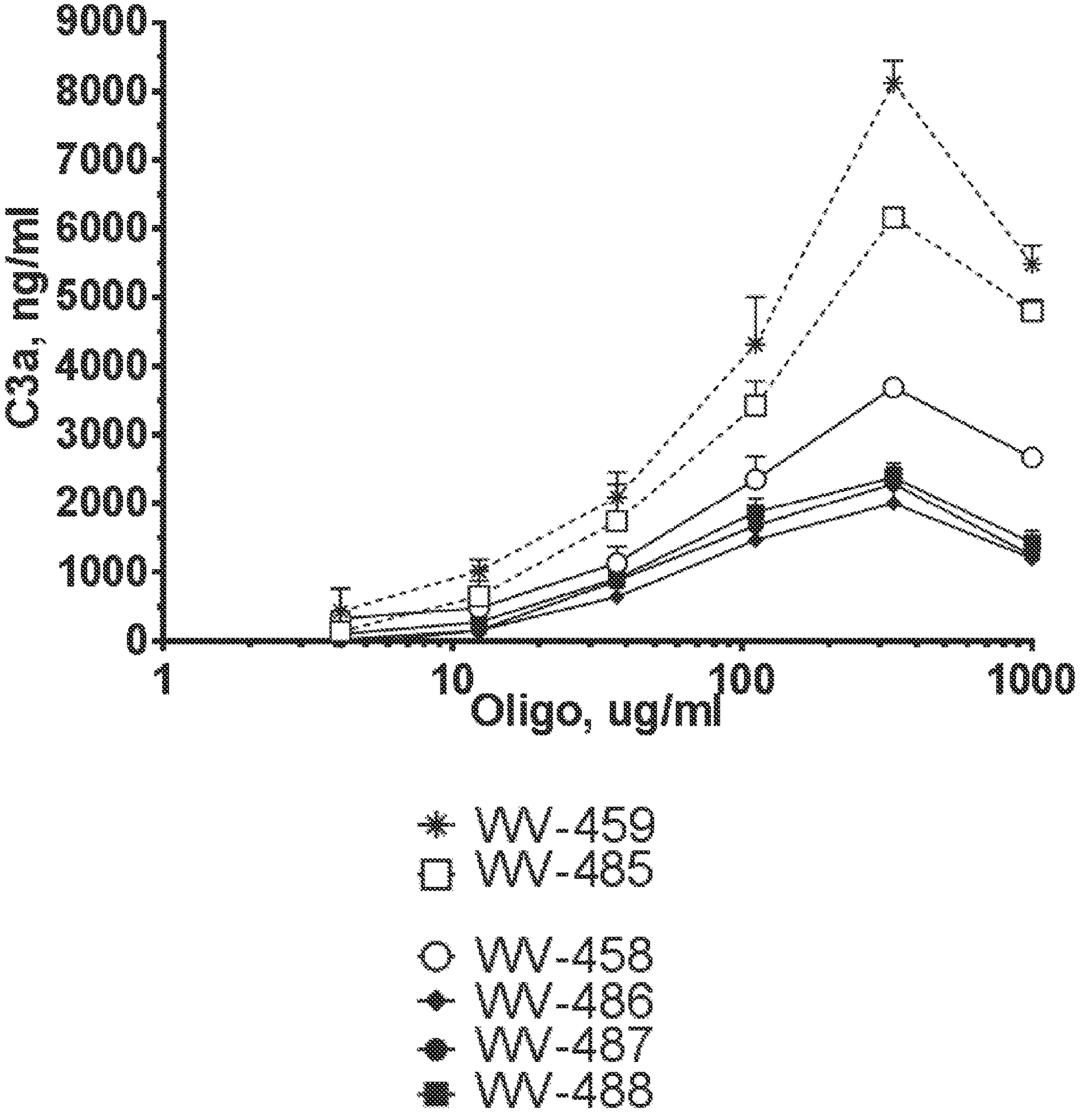
FIG. 1. Example dose response of C3a complement activation (measured via C3a) by oligonucleotides targeting human SOD1 in pooled serum (three individual cynomolgus monkeys). 40 min incubation; 37° C.
Figure 2:
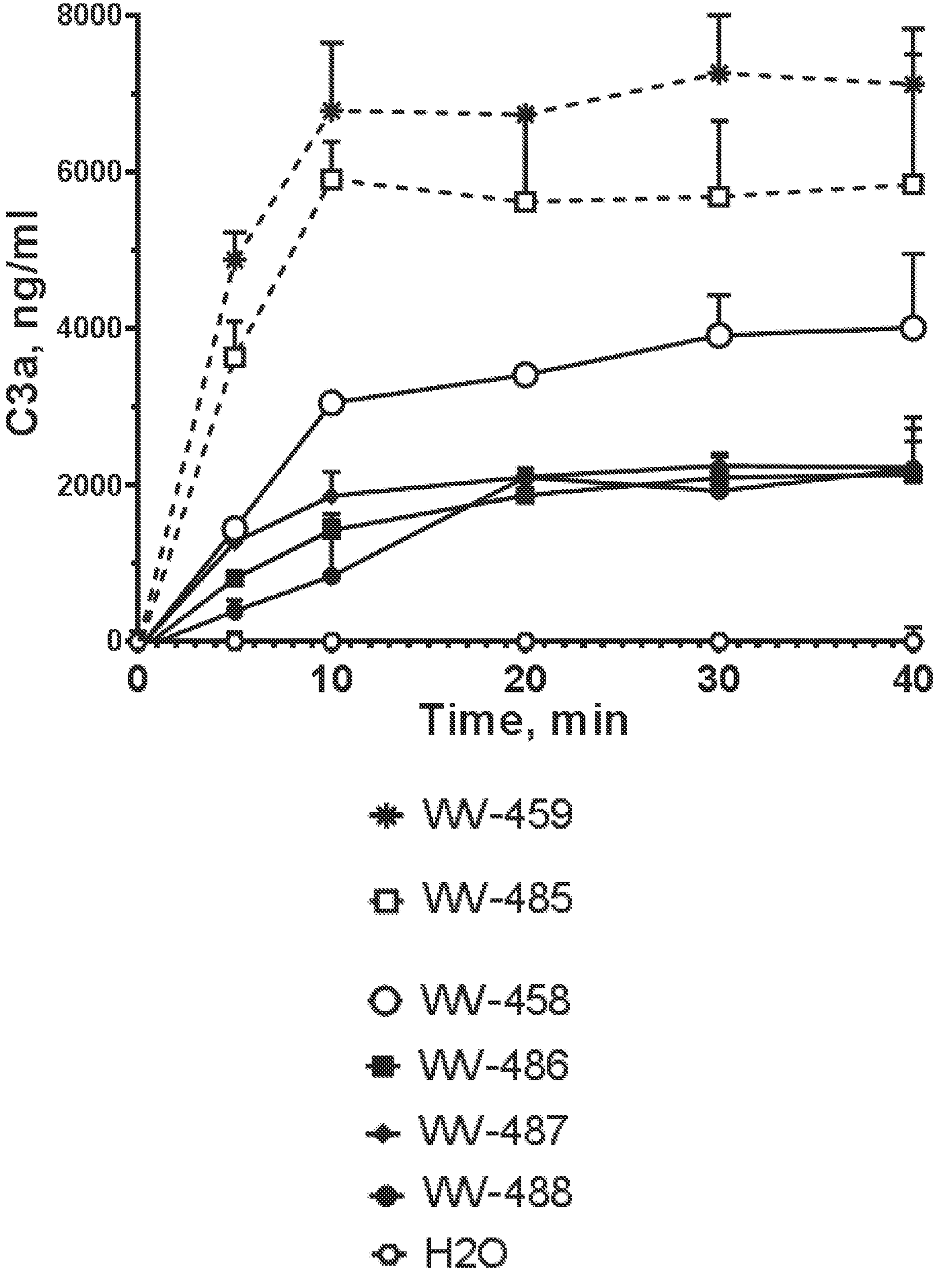
FIG. 2. Example time course of 3Ca complement activation (measured via C3a) by SOD1 oligonucleotides in pooled serum (three individual cynomolgus monkeys). Oligonucleotide concentration: 330 μg/mL; 37° C.
Figure 3:
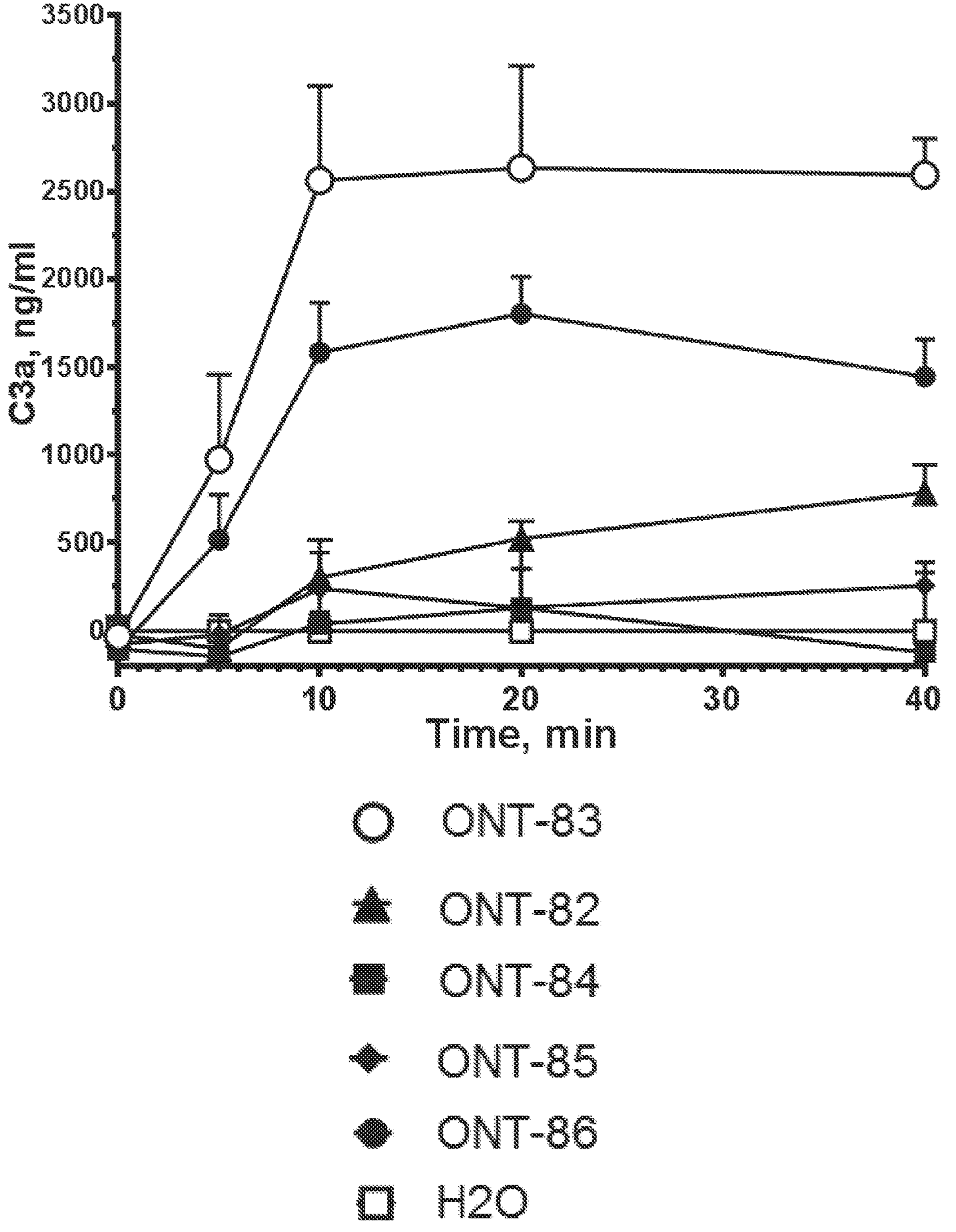
FIG. 3. Example time course of 3Ca complement activation (measured via C3a) by oligonucleotides targeting mouse ApoB in pooled serum (three individual cynomolgus monkeys). Oligonucleotide concentration: 330 μg/mL; 37° C.
Figure 4:
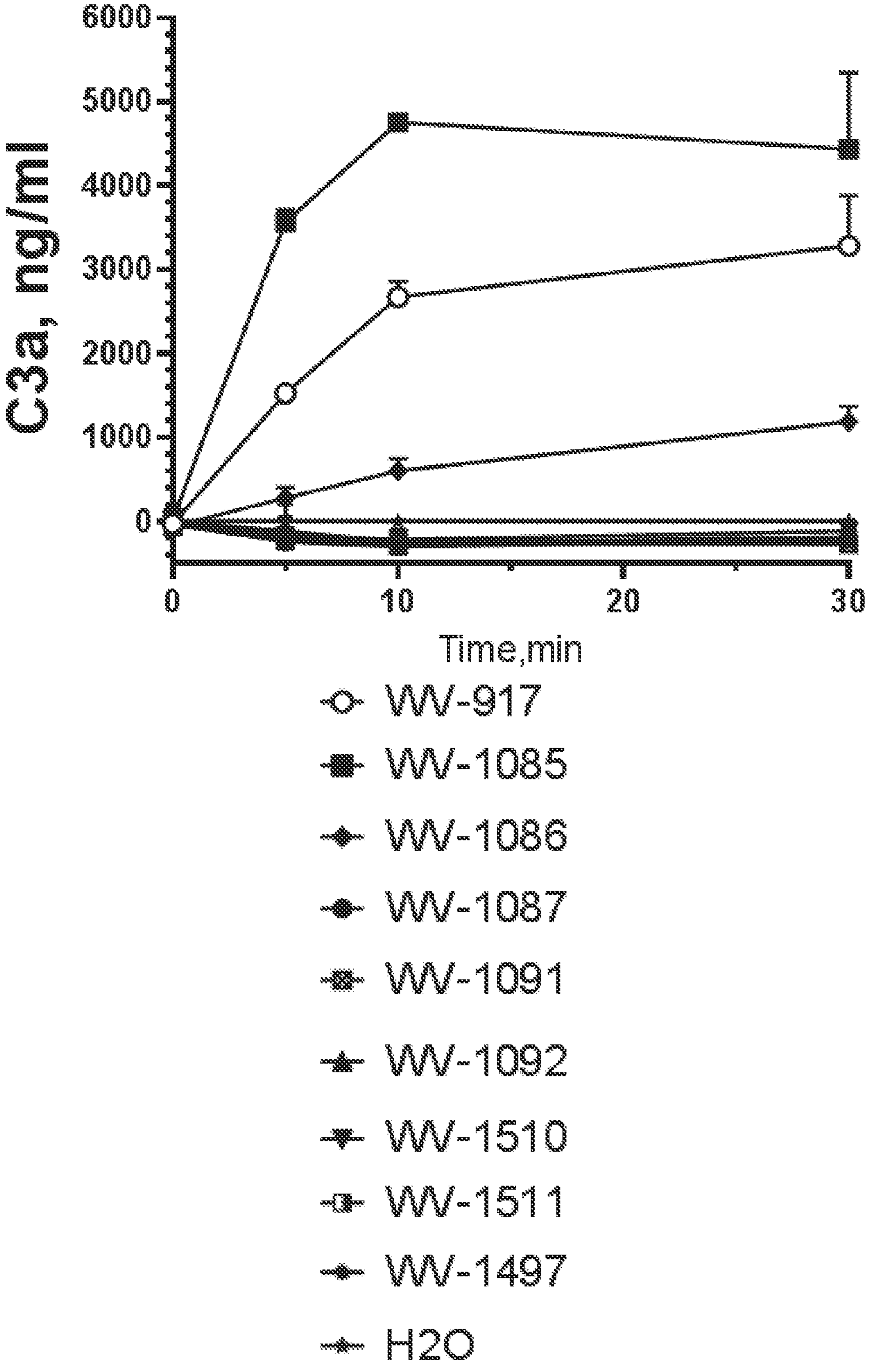
FIG. 4. Example time course of 3Ca complement activation (measured via C3a) by oligonucleotides targeting human HTT in pooled serum (three individual cynomolgus monkeys). Oligonucleotide concentration: 330 μg/mL; 37° C.
Figure 5:
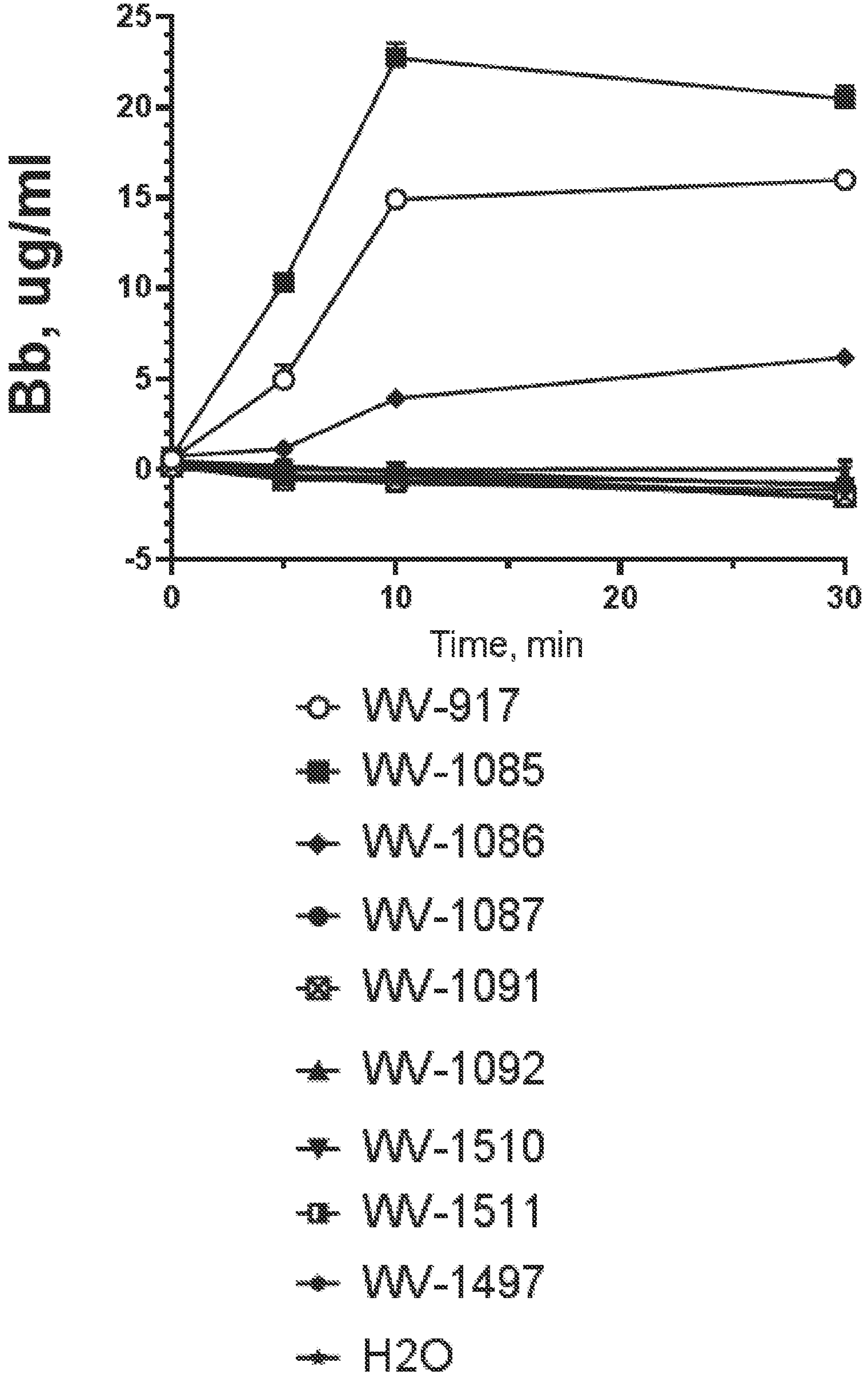
FIG. 5. Example time course of Bb complement activation (measured via Bb) by oligonucleotides targeting human HTT in pooled serum (three individual cynomolgus monkeys). Oligonucleotide concentration: 330 μg/mL; 37° C.

Synthetic oligonucleotides provide useful molecular tools in a wide variety of applications. For example, oligonucleotides are useful in therapeutic, diagnostic, research, and new nanomaterials applications. The use of naturally occurring nucleic acids (e.g., unmodified DNA or RNA) is limited, for example, by their susceptibility to endo- and exo-nucleases. As such, various synthetic counterparts have been developed to circumvent these shortcomings. These include synthetic oligonucleotides that contain chemical modification, e.g., base modifications, sugar modifications, backbone modifications, etc., which, among other things, render these molecules less susceptible to degradation and improve other properties of oligonucleotides. Chemical modifications may also lead to certain undesired effects, such as increased toxicities, etc. From a structural point of view, modifications to internucleotide phosphate linkages introduce chirality, and certain properties of oligonucleotides may be affected by the configurations of the phosphorus atoms that form the backbone of the oligonucleotides. For example, in vitro studies have shown that the properties of antisense nucleotides such as binding affinity, sequence specific binding to the complementary RNA, stability to nucleases are affected by, inter alia, chirality of the backbone (e.g., the configurations of the phosphorus atoms).

Among other things, the present disclosure encompasses the recognition that structural elements of oligonucleotides, such as base sequence, chemical modifications (e.g., modifications of sugar, base, and/or internucleotidic linkages, and patterns thereof), and/or stereochemistry (e.g., stereochemistry of backbone chiral centers (chiral internucleotidic linkages), and/or patterns thereof), can have significant impact on properties, e.g., activities, toxicities, etc., of oligonucleotides and can be adjusted to modulate oligonucleotide properties. In some embodiments, oligonucleotide properties can be adjusted by optimizing chemical modifications (modifications of base, sugar, and/or internucleotidic linkage) and/or stereochemistry (pattern of backbone chiral centers).

In some embodiments, the present disclosure demonstrates that oligonucleotide compositions comprising oligonucleotides with controlled structural elements, e.g., controlled chemical modification and/or controlled backbone stereochemistry patterns, provide unexpected properties, including but not limited to those described herein. In some embodiments, provided compositions comprising oligonucleotides having chemical modifications (e.g., base modifications, sugar modification, internucleotidic linkage modifications, etc.) have improved properties, such as lower toxicity, or improved protein binding profile, or improved delivery, etc. In some embodiments, provided oligonucleotides in provided compositions, e.g., oligonucleotides of a first plurality, comprise base modifications, sugar modifications, and/or internucleotidic linkage modifications. In some embodiments, provided oligonucleotides comprise base modifications and sugar modifications. In some embodiments, provided oligonucleotides comprise base modifications and internucleotidic linkage modifications. In some embodiments, provided oligonucleotides comprise sugar modifications and internucleotidic modifications. In some embodiments, provided compositions comprise base modifications, sugar modifications, and internucleotidic linkage modifications. Example chemical modifications, such as base modifications, sugar modifications, internucleotidic linkage modifications, etc. are widely known in the art including but not limited to those described in this disclosure. In some embodiments, a modified base is substituted A, T, C, G or U. In some embodiments, a sugar modification is 2'-modification. In some embodiments, a 2'-modification is 2-F modification. In some embodiments, a 2'-modification is 2'-$OR^1$. In some embodiments, a 2'-modification is 2'-$OR^1$, wherein $R^1$ is optionally substituted alkyl. In some embodiments, a 2'-modification is 2'-OMe. In some embodiments, a 2'-modification is 2'-MOE. In some embodiments, a modified sugar moiety is a bridged bicyclic or polycyclic ring. In some embodiments, a modified sugar moiety is a bridged bicyclic or polycyclic ring having 5-20 ring atoms wherein one or more ring atoms are optionally and independently heteroatoms. Example ring structures are widely known in the art, such as those found in BNA, LNA, etc. In some embodiments, provided oligonucleotides comprise both one or more modified internucleotidic linkages and one or more natural phosphate linkages. In some embodiments, oligonucleotides comprising both modified internucleotidic linkage and natural phosphate linkage and compositions thereof provide improved properties, e.g., activities and toxicities, etc. In some embodiments, a modified internucleotidic linkage is a chiral internucleotidic linkage. In some embodiments, a modified internucleotidic linkage is a phosphorothioate linkage. In some embodiments, a modified internucleotidic linkage is a substituted phosphorothioate linkage.

Among other things, the present disclosure encompasses the recognition that stereorandom oligonucleotide preparations contain a plurality of distinct chemical entities that differ from one another, e.g., in the stereochemical structure of individual backbone chiral centers within the oligonucleotide chain. Without control of stereochemistry of backbone chiral centers, stereorandom oligonucleotide preparations provide uncontrolled compositions comprising undetermined levels of oligonucleotide stereoisomers. Even though these stereoisomers may have the same base sequence, they are different chemical entities at least due to their different backbone stereochemistry, and they can have, as demonstrated herein, different properties, e.g., activities, toxicities, etc. Among other things, the present disclosure provides new compositions that are or contain particular stereoisomers of oligonucleotides of interest. In some embodiments, a particular stereoisomer may be defined, for example, by its base sequence, its length, its pattern of backbone linkages, and its pattern of backbone chiral centers. As is understood in the art, in some embodiments, base sequence may refer to the identity and/or modification status of nucleoside residues (e.g., of sugar and/or base components, relative to standard naturally occurring nucleotides such as adenine, cytosine, guanosine, thymine, and uracil) in an oligonucleotide and/or to the hybridization character (i.e., the ability to hybridize with particular complementary residues) of such residues. In some embodiments, oligonucleotides in provided compositions comprise sugar modifications, e.g., 2'-modifications, at e.g., a wing region. In some embodiments, oligonucleotides in provided compositions comprise a region in the middle, e.g., a core region, that has no sugar modifications. In some embodiments, the present disclosure provide an oligonucleotide composition comprising a predetermined level of oligonucleotides of an individual oligonucleotide type which are chemically identical, e.g., they have the same base sequence, the same pattern of nucleoside modifications (modifications to sugar and base moieties, if any), the same pattern of backbone chiral centers, and the same pattern of backbone phosphorus modifications. The present disclosure demonstrates, among other things, that individual stereoisomers of a particular oligonucleotide can show different stability and/or activity (e.g., functional and/or toxicity properties) from each other. In some embodiments, property improvements achieved through inclusion and/or location of particular chiral structures within an oligonucleotide can be comparable to, or even better than those achieved through use of particular backbone linkages, residue modifications, etc. (e.g., through use of certain types of modified phosphates [e.g., phosphorothioate, substituted phosphorothioate, etc.], sugar modifications [e.g., 2'-modifications, etc.], and/or base modifications [e.g., methylation, etc.]). Among other things, the present disclosure recognizes that, in some embodiments, properties (e.g., activities, toxicities, etc.) of an oligonucleotide can be adjusted by optimizing its pattern of backbone chiral centers, optionally in combination with adjustment/optimization of one or more other features (e.g., linkage pattern, nucleoside modification pattern, etc.) of the oligonucleotide. As exemplified by various examples in the present disclosure, provided chirally controlled oligonucleotide compositions can demonstrate improved properties, such as lower toxicity, improved protein binding profile, improved delivery, etc.

In some embodiments, oligonucleotide properties can be adjusted by optimizing stereochemistry (pattern of backbone chiral centers) and chemical modifications (modifications of base, sugar, and/or internucleotidic linkage). Among other things, the present disclosure demonstrates that stereochemistry can further improve properties of oligonucleotides comprising chemical modifications. In some embodiments, the present disclosure provides oligonucleotide compositions wherein the oligonucleotides comprise nucleoside modifications, chiral internucleotidic linkages and natural phosphate linkages. For example, WV-1092 comprises 2'-OMe modifications, phosphate and phosphorothioate linkages in its 5'- and 3'-wing regions, and phosphorothioate linkages in its core regions.

In some embodiments, the present disclosure provides oligonucleotide compositions which, unexpectedly, greatly improve properties of oligonucleotides. In some embodiments, provided oligonucleotide compositions provides surprisingly low toxicity. In some embodiments, provided oligonucleotide compositions provides surprisingly improved protein binding profile. In some embodiments, provided oligonucleotide compositions provides surprisingly enhanced delivery. In some embodiments, certain property improvement, such as lower toxicity, improved protein binding profile, and/or enhanced delivery, etc., are achieved without sacrificing other properties, e.g., activities, specificity, etc. In some embodiments, provided compositions provides lower toxicity, improved protein binding profile, and/or enhanced delivery, and improved activity, stability, and/or specificity (e.g., target-specificity, cleavage site specificity, etc.). Example improved activities (e.g., enhanced cleavage rates, increased target-specificity, cleavage site specificity, etc.) include but are not limited to those described in WO/2014/012081 and WO/2015/107425.

In some embodiments, a pattern of backbone chiral centers provides increased stability. In some embodiments, a pattern of backbone chiral centers provides surprisingly increased activity. In some embodiments, a pattern of backbone chiral centers provides increased stability and activity. In some embodiments, a pattern of backbone chiral centers provides surprisingly low toxicity. In some embodiments, a pattern of backbone chiral centers provides surprisingly low immune response. In some embodiments, a pattern of backbone chiral centers provides surprisingly low complement activation. In some embodiments, a pattern of backbone chiral centers provides surprisingly low complement activation via the alternative pathway. In some embodiments, a pattern of backbone chiral centers provides surprisingly improved protein binding profile. In some embodiments, a pattern of backbone chiral centers provides surprisingly increased binding to certain proteins. In some embodiments, a pattern of backbone chiral centers provides surprisingly enhanced delivery. In some embodiments, a pattern of backbone chiral centers comprises or is (Sp)m(Rp)n, (Rp)n(Sp)m, (Np)t(Rp)n(Sp)m, or (Sp)t(Rp)n(Sp)m. In some embodiments, a pattern of backbone chiral centers comprises or is (Rp)n(Sp)m, (Np)t(Rp)n(Sp)m, or (Sp)t(Rp)n(Sp)m, wherein m>2. In some embodiments, a pattern of backbone chiral centers comprises or is (Rp)n(Sp)m, (Np)t(Rp)n(Sp)m, or (Sp)t(Rp)n(Sp)m, wherein n is 1, t>1, and m>2. In some embodiments, m>3. In some embodiments, m>4. In some embodiments, a pattern of backbone chiral centers comprises one or more achiral natural phosphate linkages. In some embodiments, a pattern of backbone chiral centers comprises, comprises one or more repeats of, or is $(Sp)_m(Rp)_n$, $(Rp)_n(Sp)_m$, $(Np)_t(Rp)_n(Sp)_m$, or $(Sp)_t(Rp)_n(Sp)_m$. In some embodiments described herein, m is 1-50; and n is 1-10; and t is 1-50. In some embodiments, a pattern of backbone chiral centers comprises or is (Sp)m(Rp)n, (Rp)n(Sp)m, (Np)t(Rp)n(Sp)m, or (Sp)t(Rp)n(Sp)m. In some embodiments, a pattern of backbone chiral centers comprises or is $(Rp)_n(Sp)_m$, $(Np)_t(Rp)_n$(Sp)m, or $(Sp)_t(Rp)_n(Sp)_m$, wherein m>2. In some embodiments, a pattern of backbone chiral centers is a sequence comprising at least 5, 6, 7, 8, 9, or 10 or more consecutive (Sp) positions. In some embodiments, a pattern of backbone chiral centers is a sequence comprising at least 5 consecutive (Sp) positions. In some embodiments, a pattern of backbone chiral centers is a sequence comprising at least 8 consecutive (Sp) positions. In some embodiments, a pattern of backbone chiral centers is a sequence comprising at least 10 consecutive (Sp) positions. In some embodiments, a pattern of backbone chiral centers is a sequence consisting of all (Sp) with a single (Rp). In some embodiments, a pattern of backbone chiral centers is a sequence consisting of all (Sp) with a single (Rp) at or adjacent to the position of a SNP. In some embodiments, a pattern of backbone chiral centers is a sequence consisting of all (Sp) with a single (Rp), wherein the molecule has a wing-core-wing format. In some embodiments, a pattern of backbone chiral centers is a sequence consisting of all (Sp) with a single (Rp), wherein the molecule has a wing-core-wing format, wherein the wing on the 5' end is 1-9 nt long, the core is 1-15 nt long, and the wing on the 3' end is 1-9 nt long. In some embodiments, a pattern of backbone chiral centers is a sequence consisting of all (Sp) with a single (Rp), wherein the molecule has a wing-core-wing format, wherein the wing on the 5' end is 5 nt long, the core is 1-15 nt long, and the wing on the 3' end is 5 nt long. In some embodiments, a pattern of backbone chiral centers is a sequence consisting of all (Sp) with a single (Rp), wherein the molecule has a wing-core-wing format, wherein the wing on the 5' end is 1-9 nt long, the core is 10 nt long, and the wing on the 3' end is 1-9 nt long. In some embodiments, a pattern of backbone chiral centers is a sequence consisting of all (Sp) with a single (Rp), wherein the molecule has a wing-core-wing format, wherein the wing on the 5' end is 5 nt long, the core is 10 nt long, and the wing on the 3' end is 5 nt long. In some embodiments, a pattern of backbone chiral centers is a sequence consisting of all (Sp) with a single (Rp), wherein the molecule has a wing-core-wing format, wherein the wing on the 5' end is 5 nt long, the core is 10 nt long, and the wing on the 3' end is 5 nt long, and at least one wing comprises a nucleotide with a 2'-OMe modification. In some embodiments, a pattern of backbone chiral centers is a sequence consisting of all (Sp) with a single (Rp), wherein the molecule has a wing-core-wing format, wherein each wing comprises at least one nucleotide with a 2'-OMe modification. In some embodiments, a pattern of backbone chiral centers is a sequence consisting of all (Sp) with a single (Rp), wherein the molecule has a wing-core-wing format, wherein each nucleotide in both wings has a 2'-OMe modification. In some embodiments, a pattern of backbone chiral centers is a sequence consisting of all (Sp) with a single (Rp), wherein the molecule has a wing-core-wing format, wherein the wing on the 5' end is 5 nt long, the core is 10 nt long, and the wing on the 3' end is 5 nt long, and each nucleotide in each wing has a 2'-OMe modification. In some embodiments, the oligonucleotide is single-stranded and has a wing-core-wing format, wherein the wing on the 5' end of the molecule comprises 4 to 8 nt, each of which has a 2'-OMe modification and wherein the nt at the 5' end of the molecule has a phosphorothioate in the Sp conformation; the core comprises 8 to 12 nt, each of which is DNA (2'-H), wherein each has a phosphorothioate in the Sp position except one nt which has the phosphorothioate in the Rp position; and wherein the wing on the 3' end of the molecule comprises 4 to 8 nt, each of which has a 2'-OMe modification, and wherein the nt at the 3' end of the molecule comprises a phosphorothioate in the Sp conformation. In some embodiments, the oligonucleotide is single-stranded and has a wing-core-wing format, wherein the wing on the 5' end of the molecule comprises 6 nt, each of which has a 2'-OMe modification and wherein the nt at the 5' end of the molecule has a phosphorothioate in the Sp conformation; the core comprises 10 nt, each of which is DNA (2'-H), wherein each has a phosphorothioate in the Sp position except one nt which has the phosphorothioate in the Rp position; and wherein the wing on the 3' end of the molecule comprises 6 nt, each of which has a 2'-OMe modification, and wherein the nt at the 3' end of the molecule comprises a phosphorothioate in the Sp conformation.

In some embodiments, the present disclosure recognizes that chemical modifications, such as modifications of nucleosides and internucleotidic linkages, can provide enhanced properties. In some embodiments, the present disclosure demonstrates that combinations of chemical modifications and stereochemistry can provide unexpected, greatly improved properties (e.g., bioactivity, selectivity, etc.). In some embodiments, chemical combinations, such as modifications of sugars, bases, and/or internucleotidic linkages, are combined with stereochemistry patterns, e.g., (Rp)n(Sp)m, (Np)t(Rp)n(Sp)m, or (Sp)t(Rp)n(Sp)m, to provide oligonucleotides and compositions thereof with surprisingly enhanced properties. In some embodiments, a provided oligonucleotide composition is chirally controlled, and comprises a combination of 2'-modification of one or more sugar moieties, one or more natural phosphate linkages, one or more phosphorothioate linkages, and a stereochemistry pattern of (Rp)n(Sp)m, (Np)t(Rp)n(Sp)m, or (Sp)t(Rp)n(Sp)m, wherein m>2. In some embodiments, n is 1, t>1, and m>2. In some embodiments, m>3. In some embodiments, m>4.

In some embodiments, the present disclosure provides an oligonucleotide composition comprising a first plurality of oligonucleotides, wherein:

- oligonucleotides of the first plurality have the same base sequence; and
- oligonucleotides of the first plurality comprise one or more modified sugar moieties, or comprise one or more natural phosphate linkages and one or more modified internucleotidic linkages.

In some embodiments, oligonucleotides of the first plurality comprise one or more modified sugar moieties. In some embodiments, provided oligonucleotides comprise one or more modified sugar moieties. In some embodiments, provided oligonucleotides comprise 2 or more modified sugar moieties. In some embodiments, provided oligonucleotides comprise 3 or more modified sugar moieties. In some embodiments, provided oligonucleotides comprise 4 or more modified sugar moieties. In some embodiments, provided oligonucleotides comprise 5 or more modified sugar moieties. In some embodiments, provided oligonucleotides comprise 6 or more modified sugar moieties. In some embodiments, provided oligonucleotides comprise 7 or more modified sugar moieties. In some embodiments, provided oligonucleotides comprise 8 or more modified sugar moieties. In some embodiments, provided oligonucleotides comprise 9 or more modified sugar moieties. In some embodiments, provided oligonucleotides comprise 10 or more modified sugar moieties. In some embodiments, provided oligonucleotides comprise 15 or more modified sugar moieties. In some embodiments, provided oligonucleotides comprise 20 or more modified sugar moieties. In some embodiments, provided oligonucleotides comprise 25 or more modified sugar moieties. In some embodiments, provided oligonucleotides comprise 30 or more modified sugar moieties.

In some embodiments, 5% or more of the sugar moieties of provided oligonucleotides are modified. In some embodiments, 10% or more of the sugar moieties of provided oligonucleotides are modified. In some embodiments, 15% or more of the sugar moieties of provided oligonucleotides are modified. In some embodiments, 20% or more of the sugar moieties of provided oligonucleotides are modified. In some embodiments, 25% or more of the sugar moieties of provided oligonucleotides are modified. In some embodiments, 30% or more of the sugar moieties of provided oligonucleotides are modified. In some embodiments, 35% or more of the sugar moieties of provided oligonucleotides are modified. In some embodiments, 40% or more of the sugar moieties of provided oligonucleotides are modified. In some embodiments, 45% or more of the sugar moieties of provided oligonucleotides are modified. In some embodiments, 50% or more of the sugar moieties of provided oligonucleotides are modified. In some embodiments, 55% or more of the sugar moieties of provided oligonucleotides are modified. In some embodiments, 60% or more of the sugar moieties of provided oligonucleotides are modified. In some embodiments, 65% or more of the sugar moieties of provided oligonucleotides are modified. In some embodiments, 70% or more of the sugar moieties of provided oligonucleotides are modified. In some embodiments, 75% or more of the sugar moieties of provided oligonucleotides are modified. In some embodiments, 80% or more of the sugar moieties of provided oligonucleotides are modified. In some embodiments, 85% or more of the sugar moieties of provided oligonucleotides are modified. In some embodiments, 90% or more of the sugar moieties of provided oligonucleotides are modified. In some embodiments, 95% or more of the sugar moieties of provided oligonucleotides are modified. In some embodiments, each sugar moiety of provided oligonucleotides is modified.

In some embodiments, oligonucleotides of the first plurality comprise one or more natural phosphate linkages and one or more modified internucleotidic linkages.

Provided oligonucleotides can comprise various number of natural phosphate linkages. In some embodiments, provided oligonucleotides comprise no natural phosphate linkages. In some embodiments, provided oligonucleotides comprise one natural phosphate linkage. In some embodiments, provided oligonucleotides comprise 2 or more natural phosphate linkages. In some embodiments, provided oligonucleotides comprise 3 or more natural phosphate linkages. In some embodiments, provided oligonucleotides comprise 4 or more natural phosphate linkages. In some embodiments, provided oligonucleotides comprise 5 or more natural phosphate linkages. In some embodiments, provided oligonucleotides comprise 6 or more natural phosphate linkages. In some embodiments, provided oligonucleotides comprise 7 or more natural phosphate linkages. In some embodiments, provided oligonucleotides comprise 8 or more natural phosphate linkages. In some embodiments, provided oligonucleotides comprise 9 or more natural phosphate linkages. In some embodiments, provided oligonucleotides comprise 10 or more natural phosphate linkages. In some embodiments, provided oligonucleotides comprise 15 or more natural phosphate linkages. In some embodiments, provided oligonucleotides comprise 20 or more natural phosphate linkages. In some embodiments, provided oligonucleotides comprise 25 or more natural phosphate linkages. In some embodiments, provided oligonucleotides comprise 30 or more natural phosphate linkages.

In some embodiments, 5% or more of the internucleotidic linkages of provided oligonucleotides are natural phosphate linkages. In some embodiments, 10% or more of the internucleotidic linkages of provided oligonucleotides are natural phosphate linkages. In some embodiments, 15% or more of the internucleotidic linkages of provided oligonucleotides are natural phosphate linkages. In some embodiments, 20% or more of the internucleotidic linkages of provided oligonucleotides are natural phosphate linkages. In some embodiments, 25% or more of the internucleotidic linkages of provided oligonucleotides are natural phosphate linkages. In some embodiments, 30% or more of the internucleotidic linkages of provided oligonucleotides are natural phosphate linkages. In some embodiments, 35% or more of the internucleotidic linkages of provided oligonucleotides are natural phosphate linkages. In some embodiments, 40% or more of the internucleotidic linkages of provided oligonucleotides are natural phosphate linkages. In some embodiments, 45% or more of the internucleotidic linkages of provided oligonucleotides are natural phosphate linkages. In some embodiments, 50% or more of the internucleotidic linkages of provided oligonucleotides are natural phosphate linkages. In some embodiments, 55% or more of the internucleotidic linkages of provided oligonucleotides are natural phosphate linkages. In some embodiments, 60% or more of the internucleotidic linkages of provided oligonucleotides are natural phosphate linkages. In some embodiments, 65% or more of the internucleotidic linkages of provided oligonucleotides are natural phosphate linkages. In some embodiments, 70% or more of the internucleotidic linkages of provided oligonucleotides are natural phosphate linkages. In some embodiments, 75% or more of the internucleotidic linkages of provided oligonucleotides are natural phosphate linkages. In some embodiments, 80% or more of the internucleotidic linkages of provided oligonucleotides are natural phosphate linkages. In some embodiments, 85% or more of the internucleotidic linkages of provided oligonucleotides are natural phosphate linkages. In some embodiments, 90% or more of the internucleotidic linkages of provided oligonucleotides are natural phosphate linkages. In some embodiments, 95% or more of the internucleotidic linkages of provided oligonucleotides are natural phosphate linkages.

Provided oligonucleotides can comprise various number of modified internucleotidic linkages. In some embodiments, provided oligonucleotides comprise one modified internucleotidic linkage. In some embodiments, provided oligonucleotides comprise 2 or more modified internucleotidic linkages. In some embodiments, provided oligonucleotides comprise 3 or more modified internucleotidic linkages. In some embodiments, provided oligonucleotides comprise 4 or more modified internucleotidic linkages. In some embodiments, provided oligonucleotides comprise 5 or more modified internucleotidic linkages. In some embodiments, provided oligonucleotides comprise 6 or more modified internucleotidic linkages. In some embodiments, provided oligonucleotides comprise 7 or more modified internucleotidic linkages. In some embodiments, provided oligonucleotides comprise 8 or more modified internucleotidic linkages. In some embodiments, provided oligonucleotides comprise 9 or more modified internucleotidic linkages. In some embodiments, provided oligonucleotides comprise 10 or more modified internucleotidic linkages. In some embodiments, provided oligonucleotides comprise 15 or more modified internucleotidic linkages. In some embodiments, provided oligonucleotides comprise 20 or more modified internucleotidic linkages. In some embodiments, provided oligonucleotides comprise 25 or more modified internucleotidic linkages. In some embodiments, provided oligonucleotides comprise 30 or more modified internucleotidic linkages.

In some embodiments, 5% or more of the internucleotidic linkages of provided oligonucleotides are modified internucleotidic linkages. In some embodiments, 10% or more of the internucleotidic linkages of provided oligonucleotides are modified internucleotidic linkages. In some embodiments, 15% or more of the internucleotidic linkages of provided oligonucleotides are modified internucleotidic linkages. In some embodiments, 20% or more of the internucleotidic linkages of provided oligonucleotides are modified internucleotidic linkages. In some embodiments, 25% or more of the internucleotidic linkages of provided oligonucleotides are modified internucleotidic linkages. In some embodiments, 30% or more of the internucleotidic linkages of provided oligonucleotides are modified internucleotidic linkages. In some embodiments, 35% or more of the internucleotidic linkages of provided oligonucleotides are modified internucleotidic linkages. In some embodiments, 40% or more of the internucleotidic linkages of provided oligonucleotides are modified internucleotidic linkages. In some embodiments, 45% or more of the internucleotidic linkages of provided oligonucleotides are modified internucleotidic linkages. In some embodiments, 50% or more of the internucleotidic linkages of provided oligonucleotides are modified internucleotidic linkages. In some embodiments, 55% or more of the internucleotidic linkages of provided oligonucleotides are modified internucleotidic linkages. In some embodiments, 60% or more of the internucleotidic linkages of provided oligonucleotides are modified internucleotidic linkages. In some embodiments, 65% or more of the internucleotidic linkages of provided oligonucleotides are modified internucleotidic linkages. In some embodiments, 70% or more of the internucleotidic linkages of provided oligonucleotides are modified internucleotidic linkages. In some embodiments, 75% or more of the internucleotidic linkages of provided oligonucleotides are modified internucleotidic linkages. In some embodiments, 80% or more of the internucleotidic linkages of provided oligonucleotides are modified internucleotidic linkages. In some embodiments, 85% or more of the internucleotidic linkages of provided oligonucleotides are modified internucleotidic linkages. In some embodiments, 90% or more of the internucleotidic linkages of provided oligonucleotides are modified internucleotidic linkages. In some embodiments, 95% or more of the internucleotidic linkages of provided oligonucleotides are modified internucleotidic linkages. In some embodiments, each internucleotidic linkage of provided oligonucleotides is a modified internucleotidic linkage.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified internucleotidic linkages and optionally one or more natural phosphate linkages, and the core region independently comprises one or more modified internucleotidic linkages; or each wing region independently comprises one or more modified sugar moieties, and the core region comprises one or more un-modified sugar moieties.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified internucleotidic linkages and optionally one or more natural phosphate linkages, and the core region independently comprises one or more modified internucleotidic linkages.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified sugar moieties, and the core region comprises one or more un-modified sugar moieties.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified internucleotidic linkages and optionally one or more natural phosphate linkages, and the core region independently comprises one or more modified internucleotidic linkages; and each wing region independently comprises one or more modified sugar moieties, and the core region comprises one or more un-modified sugar moieties.

In some embodiments, the present disclosure provides an oligonucleotide composition comprising a first plurality of oligonucleotides comprising one or more wing regions and a core region, wherein:

oligonucleotides of the first plurality have the same base sequence; and each wing region independently comprises one or more modified internucleotidic linkages and one or more natural phosphate linkages, and the core region independently comprises one or more modified internucleotidic linkages; and each wing region independently comprises one or more modified sugar moieties, and the core region comprises one or more un-modified sugar moieties.

In some embodiments, the present disclosure provides an oligonucleotide composition comprising a first plurality of oligonucleotides comprising one or more wing regions and a core region, wherein:

oligonucleotides of the first plurality have the same base sequence;

each wing region independently has a length of two or more bases, and independently comprises one or more modified internucleotidic linkages and optionally one or more natural phosphate linkages; and the core region independently has a length of two or more bases and independently comprises one or more modified internucleotidic linkages.

In some embodiments, the present disclosure provides an oligonucleotide composition comprising a first plurality of oligonucleotides comprising one or more wing regions and a core region, wherein:

oligonucleotides of the first plurality have the same base sequence;

each wing region independently has a length of two or more bases, and independently comprises one or more modified internucleotidic linkages and one or more natural phosphate linkages; and the core region independently has a length of two or more bases and independently comprises one or more modified internucleotidic linkages.

In some embodiments, the present disclosure provides an oligonucleotide composition comprising a first plurality of oligonucleotides comprising two wing regions and a core region, wherein:

oligonucleotides of the first plurality have the same base sequence;

each wing region independently has a length of two or more bases, and independently comprises one or more modified internucleotidic linkages and one or more natural phosphate linkages; and the core region independently has a length of two or more bases and independently comprises one or more modified internucleotidic linkages.

In some embodiments, the present disclosure provides an oligonucleotide composition comprising a first plurality of oligonucleotides comprising two wing regions and a core region, wherein:

oligonucleotides of the first plurality have the same base sequence;

each wing region independently has a length of two or more bases, and independently comprises one or more modified internucleotidic linkages and one or more natural phosphate linkages;

the wing region to the 5'-end of the core region comprises at least one modified internucleotidic linkage followed by a natural phosphate linkage in the wing; and the wing region to the 3'-end of the core region comprises at least one modified internucleotidic linkage preceded by a natural phosphate linkage in the wing;

the core region independently has a length of two or more bases and independently comprises one or more modified internucleotidic linkages.

In some embodiments, the present disclosure provides an oligonucleotide composition comprising a first plurality of oligonucleotides comprising a wing region and a core region, wherein:

oligonucleotides of the first plurality have the same base sequence;

the wing region has a length of two or more bases, and comprises one or more modified internucleotidic linkages and one or more natural phosphate linkages;

the wing region is to the 5'-end of the core region and comprises a modified internucleotidic linkage between the two nucleosides at its 3'-end, or the wing region to the 3'-end of the core region and comprises a modified internucleotidic linkage between the two nucleosides at its 5'-end; and the core region independently has a length of two or more bases and independently comprises one or more modified internucleotidic linkages.

In some embodiments, the present disclosure provides an oligonucleotide composition comprising a first plurality of oligonucleotides comprising two wing regions and a core region, wherein:

oligonucleotides of the first plurality have the same base sequence;

each wing region independently has a length of two or more bases, and independently comprises one or more modified internucleotidic linkages and one or more natural phosphate linkages;

the wing region to the 5'-end of the core region comprises a modified internucleotidic linkage between the two nucleosides at its 3'-end;

the wing region to the 3'-end of a core region comprises a modified internucleotidic linkage between the two nucleosides at its 5'-end; and the core region independently has a length of two or more bases and independently comprises one or more modified internucleotidic linkages.

An example composition is WV-1497, wherein the core region is *A*A*A*G*G*G*C*A*C*A*G* (SEQ ID NO: 8), the wing region to the 5'-end of the core region is mG*mGmCmAmC, and the wing region to the 3'-end of the core region is mAmCmUmU*mC. In some embodiments, a wing region comprises a modified internucleotidic linkage between the two nucleosides at its 3'-end. In some embodiments, a wing region to the 5'-end of a core region comprises a modified internucleotidic linkage between the two nucleosides at its 3'-end. For example, in WV-1497, mG*mGmCmAmC is a wing to the 5'-end of the core region (*A*A*A*G*G*G*C*A*C*A*G* (SEQ ID NO: 8)), and it comprise a modified internucleotidic linkage between the two nucleosides at its 3'-end (mG*mGmC<u>mAmC</u>). In some embodiments, a wing region comprises a modified internucleotidic linkage between the two nucleosides at its 5'-end. In some embodiments, a wing region to the 3'-end of a core region comprises a modified internucleotidic linkage between the two nucleosides at its 5'-end. For example, in WV-1497, mAmCmUmU*mC is a wing to the 3'-end of the core region (*A*A*A*G*G*G*C*A*C*A*G* (SEQ ID NO: 8)), and it comprise a modified internucleotidic linkage between the two nucleosides at its 5'-end (<u>mAmC</u>mUmU*mC).

In some embodiments, oligonucleotides of the first plurality have two wing and one core regions. In some embodiments, the two wing regions are identical. In some embodiments, the two wing regions are different.

In some embodiments, a wing region comprises 2 or more modified internucleotidic linkages. In some embodiments, a wing region comprises 3 or more modified internucleotidic linkages. In some embodiments, a wing region comprises 4 or more modified internucleotidic linkages. In some embodiments, a wing region comprises 5 or more modified internucleotidic linkages. In some embodiments, a wing region comprises 6 or more modified internucleotidic linkages. In some embodiments, a wing region comprises 7 or more modified internucleotidic linkages. In some embodiments, a wing region comprises 8 or more modified internucleotidic linkages. In some embodiments, a wing region comprises 9 or more modified internucleotidic linkages. In some embodiments, a wing region comprises 10 or more modified internucleotidic linkages. In some embodiments, a wing region comprises 11 or more modified internucleotidic linkages. In some embodiments, a wing region comprises 12 or more modified internucleotidic linkages. In some embodiments, a wing region comprises 13 or more modified internucleotidic linkages. In some embodiments, a wing region comprises 14 or more modified internucleotidic linkages. In some embodiments, a wing region comprises 15 or more modified internucleotidic linkages. In some embodiments, a wing region comprises 2 or consecutive modified internucleotidic linkages. In some embodiments, a wing region comprises 3 or consecutive modified internucleotidic linkages. In some embodiments, a wing region comprises 4 or consecutive modified internucleotidic linkages. In some embodiments, a wing region comprises 5 or consecutive modified internucleotidic linkages. In some embodiments, a wing region comprises 6 or consecutive modified internucleotidic linkages. In some embodiments, a wing region comprises 7 or consecutive modified internucleotidic linkages. In some embodiments, a wing region comprises 8 or consecutive modified internucleotidic linkages. In some embodiments, a wing region comprises 9 or consecutive modified internucleotidic linkages. In some embodiments, a wing region comprises 10 or consecutive modified internucleotidic linkages. In some embodiments, a wing region comprises 11 or consecutive modified internucleotidic linkages. In some embodiments, a wing region comprises 12 or consecutive modified internucleotidic linkages. In some embodiments, a wing region comprises 13 or consecutive modified internucleotidic linkages. In some embodiments, a wing region comprises 14 or consecutive modified internucleotidic linkages. In some embodiments, a wing region comprises 15 or consecutive modified internucleotidic linkages. In some embodiments, each internucleotidic linkage in a wing region is independently a modified internucleotidic linkage.

In some embodiments, 5% or more of the internucleotidic linkages of provided oligonucleotides are modified internucleotidic linkages. In some embodiments, 10% or more of the internucleotidic linkages of provided oligonucleotides are modified internucleotidic linkages. In some embodiments, 15% or more of the internucleotidic linkages of provided oligonucleotides are modified internucleotidic linkages. In some embodiments, 20% or more of the internucleotidic linkages of provided oligonucleotides are modified internucleotidic linkages. In some embodiments, 25% or more of the internucleotidic linkages of provided oligonucleotides are modified internucleotidic linkages. In some embodiments, 30% or more of the internucleotidic linkages of provided oligonucleotides are modified internucleotidic linkages. In some embodiments, 35% or more of the internucleotidic linkages of provided oligonucleotides are modified internucleotidic linkages. In some embodiments, 40% or more of the internucleotidic linkages of provided oligonucleotides are modified internucleotidic linkages. In some embodiments, 45% or more of the internucleotidic linkages of a wing region are modified internucleotidic linkages. In some embodiments, 50% or more of the internucleotidic linkages of a wing region are modified internucleotidic linkages. In some embodiments, 55% or more of the internucleotidic linkages of a wing region are modified internucleotidic linkages. In some embodiments, 60% or more of the internucleotidic linkages of a wing region are modified internucleotidic linkages. In some embodiments, 65% or more of the internucleotidic linkages of a wing region are modified internucleotidic linkages. In some embodiments, 70% or more of the internucleotidic linkages of a wing region are modified internucleotidic linkages. In some embodiments, 75% or more of the internucleotidic linkages of a wing region are modified internucleotidic linkages. In some embodiments, 80% or more of the internucleotidic linkages of a wing region are modified internucleotidic linkages. In some embodiments, 85% or more of the internucleotidic linkages of a wing region are modified internucleotidic linkages. In some embodiments, 90% or more of the internucleotidic linkages of a wing region are modified internucleotidic linkages. In some embodiments, 95% or more of the internucleotidic linkages of a wing region are modified internucleotidic linkages. In some embodiments, each internucleotidic linkage of a wing region is a modified internucleotidic linkage.

In some embodiments, a wing region comprises 2 or more natural phosphate linkages. In some embodiments, a wing region comprises 3 or more natural phosphate linkages. In some embodiments, a wing region comprises 4 or more natural phosphate linkages. In some embodiments, a wing region comprises 5 or more natural phosphate linkages. In some embodiments, a wing region comprises 6 or more natural phosphate linkages. In some embodiments, a wing region comprises 7 or more natural phosphate linkages. In some embodiments, a wing region comprises 8 or more natural phosphate linkages. In some embodiments, a wing region comprises 9 or more natural phosphate linkages. In some embodiments, a wing region comprises 10 or more natural phosphate linkages. In some embodiments, a wing region comprises 11 or more natural phosphate linkages. In some embodiments, a wing region comprises 12 or more natural phosphate linkages. In some embodiments, a wing region comprises 13 or more natural phosphate linkages. In some embodiments, a wing region comprises 14 or more natural phosphate linkages. In some embodiments, a wing region comprises 15 or more natural phosphate linkages. In some embodiments, a wing region comprises 2 or consecutive natural phosphate linkages. In some embodiments, a wing region comprises 3 or consecutive natural phosphate linkages. In some embodiments, a wing region comprises 4 or consecutive natural phosphate linkages. In some embodiments, a wing region comprises 5 or consecutive natural phosphate linkages. In some embodiments, a wing region comprises 6 or consecutive natural phosphate linkages. In some embodiments, a wing region comprises 7 or consecutive natural phosphate linkages. In some embodiments, a wing region comprises 8 or consecutive natural phosphate linkages. In some embodiments, a wing region comprises 9 or consecutive natural phosphate linkages. In some embodiments, a wing region comprises 10 or consecutive natural phosphate linkages. In some embodiments, a wing region comprises 11 or consecutive natural phosphate linkages. In some embodiments, a wing region comprises 12 or consecutive natural phosphate linkages. In some embodiments, a wing region comprises 13 or consecutive natural phosphate linkages. In some embodiments, a wing region comprises 14 or consecutive natural phosphate linkages. In some embodiments, a wing region comprises 15 or consecutive natural phosphate linkages. In some embodiments, each internucleotidic linkage in a wing region is independently a natural phosphate linkage.

In some embodiments, 5% or more of the internucleotidic linkages of provided oligonucleotides are natural phosphate linkages. In some embodiments, 10% or more of the internucleotidic linkages of provided oligonucleotides are natural phosphate linkages. In some embodiments, 15% or more of the internucleotidic linkages of provided oligonucleotides are natural phosphate linkages. In some embodiments, 20% or more of the internucleotidic linkages of provided oligonucleotides are natural phosphate linkages. In some embodiments, 25% or more of the internucleotidic linkages of provided oligonucleotides are natural phosphate linkages. In some embodiments, 30% or more of the internucleotidic linkages of provided oligonucleotides are natural phosphate linkages. In some embodiments, 35% or more of the internucleotidic linkages of provided oligonucleotides are natural phosphate linkages. In some embodiments, 40% or more of the internucleotidic linkages of provided oligonucleotides are natural phosphate linkages. In some embodiments, 45% or more of the internucleotidic linkages of a wing region are natural phosphate linkages. In some embodiments, 50% or more of the internucleotidic linkages of a wing region are natural phosphate linkages. In some embodiments, 55% or more of the internucleotidic linkages of a wing region are natural phosphate linkages. In some embodiments, 60% or more of the internucleotidic linkages of a wing region are natural phosphate linkages. In some embodiments, 65% or more of the internucleotidic linkages of a wing region are natural phosphate linkages. In some embodiments, 70% or more of the internucleotidic linkages of a wing region are natural phosphate linkages. In some embodiments, 75% or more of the internucleotidic linkages of a wing region are natural phosphate linkages. In some embodiments, 80% or more of the internucleotidic linkages of a wing region are natural phosphate linkages. In some embodiments, 85% or more of the internucleotidic linkages of a wing region are natural phosphate linkages. In some embodiments, 90% or more of the internucleotidic linkages of a wing region are natural phosphate linkages. In some embodiments, 95% or more of the internucleotidic linkages of a wing region are natural phosphate linkages. In some embodiments, each internucleotidic linkage of a wing region is a natural phosphate linkage.

In some embodiments, a core region comprises 2 or more modified internucleotidic linkages. In some embodiments, a core region comprises 3 or more modified internucleotidic linkages. In some embodiments, a core region comprises 4 or more modified internucleotidic linkages. In some embodiments, a core region comprises 5 or more modified internucleotidic linkages. In some embodiments, a core region comprises 6 or more modified internucleotidic linkages. In some embodiments, a core region comprises 7 or more modified internucleotidic linkages. In some embodiments, a core region comprises 8 or more modified internucleotidic linkages. In some embodiments, a core region comprises 9 or more modified internucleotidic linkages. In some embodiments, a core region comprises 10 or more modified internucleotidic linkages. In some embodiments, a core region comprises 11 or more modified internucleotidic linkages. In some embodiments, a core region comprises 12 or more modified internucleotidic linkages. In some embodiments, a core region comprises 13 or more modified internucleotidic linkages. In some embodiments, a core region comprises 14 or more modified internucleotidic linkages. In some embodiments, a core region comprises 15 or more modified internucleotidic linkages. In some embodiments, a core region comprises 2 or consecutive modified internucleotidic linkages. In some embodiments, a core region comprises 3 or consecutive modified internucleotidic linkages. In some embodiments, a core region comprises 4 or consecutive modified internucleotidic linkages. In some embodiments, a core region comprises 5 or consecutive modified internucleotidic linkages. In some embodiments, a core region comprises 6 or consecutive modified internucleotidic linkages. In some embodiments, a core region comprises 7 or consecutive modified internucleotidic linkages. In some embodiments, a core region comprises 8 or consecutive modified internucleotidic linkages. In some embodiments, a core region comprises 9 or consecutive modified internucleotidic linkages. In some embodiments, a core region comprises 10 or consecutive modified internucleotidic linkages. In some embodiments, a core region comprises 11 or consecutive modified internucleotidic linkages. In some embodiments, a core region comprises 12 or consecutive modified internucleotidic linkages. In some embodiments, a core region comprises 13 or consecutive modified internucleotidic linkages. In some embodiments, a core region comprises 14 or consecutive modified internucleotidic linkages. In some embodiments, a core region comprises 15 or consecutive modified internucleotidic linkages. In some embodiments, each internucleotidic linkage in a core region is independently a modified internucleotidic linkage.

In some embodiments, 5% or more of the internucleotidic linkages of provided oligonucleotides are modified internucleotidic linkages. In some embodiments, 10% or more of the internucleotidic linkages of provided oligonucleotides are modified internucleotidic linkages. In some embodiments, 15% or more of the internucleotidic linkages of provided oligonucleotides are modified internucleotidic linkages. In some embodiments, 20% or more of the internucleotidic linkages of provided oligonucleotides are modified internucleotidic linkages. In some embodiments, 25% or more of the internucleotidic linkages of provided oligonucleotides are modified internucleotidic linkages. In some embodiments, 30% or more of the internucleotidic linkages of provided oligonucleotides are modified internucleotidic linkages. In some embodiments, 35% or more of the internucleotidic linkages of provided oligonucleotides are modified internucleotidic linkages. In some embodiments, 40% or more of the internucleotidic linkages of provided oligonucleotides are modified internucleotidic linkages. In some embodiments, 45% or more of the internucleotidic linkages of a core region are modified internucleotidic linkages. In some embodiments, 50% or more of the internucleotidic linkages of a core region are modified internucleotidic linkages. In some embodiments, 55% or more of the internucleotidic linkages of a core region are modified internucleotidic linkages. In some embodiments, 60% or more of the internucleotidic linkages of a core region are modified internucleotidic linkages. In some embodiments, 65% or more of the internucleotidic linkages of a core region are modified internucleotidic linkages. In some embodiments, 70% or more of the internucleotidic linkages of a core region are modified internucleotidic linkages. In some embodiments, 75% or more of the internucleotidic linkages of a core region are modified internucleotidic linkages. In some embodiments, 80% or more of the internucleotidic linkages of a core region are modified internucleotidic linkages. In some embodiments, 85% or more of the internucleotidic linkages of a core region are modified internucleotidic linkages. In some embodiments, 90% or more of the internucleotidic linkages of a core region are modified internucleotidic linkages. In some embodiments, 95% or more of the internucleotidic linkages of a core region are modified internucleotidic linkages. In some embodiments, each internucleotidic linkage of a core region is a modified internucleotidic linkage.

In some embodiments, the present disclosure provides a chirally controlled oligonucleotide composition comprising a first plurality of oligonucleotides defined by having:

1) a common base sequence and length;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, a common base sequence and length may be referred to as a common base sequence. In some embodiments, oligonucleotides having a common base sequence may have the same pattern of nucleoside modifications, e.g., sugar modifications, base modifications, etc. In some embodiments, a pattern of nucleoside modifications may be represented by a combination of locations and modifications. For example, for WV-1092, the pattern of nucleoside linkage is 5×2'-OMe (2'-OMe modification on sugar moieties)-DNA (no 2'-modifications on the sugar moiety)-5×2'-OMe from the 5'-end to the 3'-end. In some embodiments, a pattern of backbone linkages comprises locations and types (e.g., phosphate, phosphorothioate, substituted phosphorothioate, etc.) of each internucleotidic linkages. For example, for WV-1092, the pattern of backbone linkages is 1×PS(phosphorothioate)-3×PO (phosphate)-11×PS-3×PO-1×PS. A pattern of backbone chiral centers of an oligonucleotide can be designated by a combination of linkage phosphorus stereochemistry (Rp/Sp) from 5' to 3'. For example, WV-1092 has a pattern of 1S-3PO (phosphate)-8S-1R-2S-3PO-1S. In some embodiments, all non-chiral linkages (e.g., PO) may be omitted. As exemplified above, locations of non-chiral linkages may be obtained, for example, from pattern of backbone linkages.

In some embodiments, the present disclosure provides a chirally controlled oligonucleotide composition comprising a first plurality of oligonucleotides of a particular oligonucleotide type characterized by:

1) a common base sequence and length;
2) a common pattern of backbone linkages; and
3) a common pattern of backbone chiral centers;

which composition is chirally controlled in that it is enriched, relative to a substantially racemic preparation of oligonucleotides having the same base sequence and length, for oligonucleotides of the particular oligonucleotide type.

As understood by a person having ordinary skill in the art, a stereorandom or racemic preparation of oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of oligonucleotides, all or most coupling steps are not chirally controlled in that the coupling steps are not specifically conducted to provide enhanced stereoselectivity. An example substantially racemic preparation of oligonucleotides is the preparation of phosphorothioate oligonucleotides through sulfurizing phosphite triesters from commonly used phosphoramidite oligonucleotide synthesis with either tteraethylthiuram disulfide or (TETD) or 3H-1, 2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions). In some embodiments, at least one coupling of a nucleotide monomer has a diastereoselectivity lower than about 60:40, 70:30, 80:20, 85:15, 90:10, 91:9, 92:8, 97:3, 98:2, or 99:1. In some embodiments, at least two couplings of a nucleotide monomer have a diastereoselectivity lower than about 60:40, 70:30, 80:20, 85:15, 90:10, 91:9, 92:8, 97:3, 98:2, or 99:1. In some embodiments, at least three couplings of a nucleotide monomer have a diastereoselectivity lower than about 60:40, 70:30, 80:20, 85:15, 90:10, 91:9, 92:8, 97:3, 98:2, or 99:1. In some embodiments, at least four couplings of a nucleotide monomer have a diastereoselectivity lower than about 60:40, 70:30, 80:20, 85:15, 90:10, 91:9, 92:8, 97:3, 98:2, or 99:1. In some embodiments, at least five couplings of a nucleotide monomer have a diastereoselectivity lower than about 60:40, 70:30, 80:20, 85:15, 90:10, 91:9, 92:8, 97:3, 98:2, or 99:1. In some embodiments, in a stereorandom or racemic preparations, at least one internucleotidic linkage has a diastereoselectivity lower than about 60:40, 70:30, 80:20, 85:15, 90:10, 91:9, 92:8, 97:3, 98:2, or 99:1. In some embodiments, at least two internucleotidic linkages have a diastereoselectivity lower than about 60:40, 70:30, 80:20, 85:15, 90:10, 91:9, 92:8, 97:3, 98:2, or 99:1. In some embodiments, at least three internucleotidic linkages have a diastereoselectivity lower than about 60:40, 70:30, 80:20, 85:15, 90:10, 91:9, 92:8, 97:3, 98:2, or 99:1. In some embodiments, at least four internucleotidic linkages have a diastereoselectivity lower than about 60:40, 70:30, 80:20, 85:15, 90:10, 91:9, 92:8, 97:3, 98:2, or 99:1. In some embodiments, at least five internucleotidic linkages have a diastereoselectivity lower than about 60:40, 70:30, 80:20, 85:15, 90:10, 91:9, 92:8, 97:3, 98:2, or 99:1. In some embodiments, a diastereoselectivity is lower than about 60:40. In some embodiments, a diastereoselectivity is lower than about 70:30. In some embodiments, a diastereoselectivity is lower than about 80:20. In some embodiments, a diastereoselectivity is lower than about 90:10. In some embodiments, a diastereoselectivity is lower than about 91:9. In some embodiments, a diastereoselectivity is lower than about 92:8. In some embodiments, a diastereoselectivity is lower than about 93:7. In some embodiments, a diastereoselectivity is lower than about 94:6. In some embodiments, a diastereoselectivity is lower than about 95:5. In some embodiments, a diastereoselectivity is lower than about 96:4. In some embodiments, a diastereoselectivity is lower than about 97:3. In some embodiments, a diastereoselectivity is lower than about 98:2. In some embodiments, a diastereoselectivity is lower than about 99:1. In some embodiments, at least one coupling has a diastereoselectivity lower than about 90:10. In some embodiments, at least two couplings have a diastereoselectivity lower than about 90:10. In some embodiments, at least three couplings have a diastereoselectivity lower than about 90:10. In some embodiments, at least four couplings have a diastereoselectivity lower than about 90:10. In some embodiments, at least five couplings have a diastereoselectivity lower than about 90:10. In some embodiments, at least one internucleotidic linkage has a diastereoselectivity lower than about 90:10. In some embodiments, at least two internucleotidic linkages have a diastereoselectivity lower than about 90:10. In some embodiments, at least three internucleotidic linkages have a diastereoselectivity lower than about 90:10. In some embodiments, at least four internucleotidic linkages have a diastereoselectivity lower than about 90:10. In some embodiments, at least five internucleotidic linkages have a diastereoselectivity lower than about 90:10.

As understood by a person having ordinary skill in the art, in some embodiments, diastereoselectivity of a coupling or a linkage can be assessed through the diastereoselectivity of a dimer formation under the same or comparable conditions, wherein the dimer has the same 5'- and 3'-nucleosides and internucleotidic linkage. For example, diastereoselectivity of the underlined coupling or linkage in WV-1092 mG*SmGmCmAmC*SA*SA*SG*SG*S G*SC*SA*SC* RA*SG*SmAmCmUmU*SmC (SEQ ID NO: 9) can be assessed from coupling two G moieties under the same or comparable conditions, e.g., monomers, chiral auxiliaries, solvents, activators, temperatures, etc.

In some embodiments, the present disclosure provides chirally controlled (and/or stereochemically pure) oligonucleotide compositions comprising a first plurality of oligonucleotides defined by having:

1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

In some embodiments, the present disclosure provides chirally controlled oligonucleotide composition of a first plurality of oligonucleotides in that the composition is enriched, relative to a substantially racemic preparation of the same oligonucleotides, for oligonucleotides of a single oligonucleotide type. In some embodiments, the present disclosure provides chirally controlled oligonucleotide composition of a first plurality of oligonucleotides in that the composition is enriched, relative to a substantially racemic preparation of the same oligonucleotides, for oligonucleotides of a single oligonucleotide type that share:

1) a common base sequence and length;
2) a common pattern of backbone linkages; and
3) a common pattern of backbone chiral centers.

In some embodiments, the present disclosure provides a chirally controlled oligonucleotide composition comprising a first plurality of oligonucleotides of a particular oligonucleotide type characterized by:

1) a common base sequence and length;
2) a common pattern of backbone linkages; and
3) a common pattern of backbone chiral centers;

which composition is chirally controlled in that it is enriched, relative to a substantially racemic preparation of oligonucleotides having the same base sequence and length, for oligonucleotides of the particular oligonucleotide type.

In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have identical structures.

In some embodiments, oligonucleotides of an oligonucleotide type have a common pattern of backbone phosphorus modifications and a common pattern of sugar modifications. In some embodiments, oligonucleotides of an oligonucleotide type have a common pattern of backbone phosphorus modifications and a common pattern of base modifications. In some embodiments, oligonucleotides of an oligonucleotide type have a common pattern of backbone phosphorus modifications and a common pattern of nucleoside modifications. In some embodiments, oligonucleotides of an oligonucleotide type are identical.

In some embodiments, a chirally controlled oligonucleotide composition is a substantially pure preparation of an oligonucleotide type in that oligonucleotides in the composition that are not of the oligonucleotide type are impurities form the preparation process of said oligonucleotide type, in some case, after certain purification procedures.

In some embodiments, at least about 20% of the oligonucleotides in the composition have a common base sequence and length, a common pattern of backbone linkages, and a common pattern of backbone chiral centers. In some embodiments, at least about 25% of the oligonucleotides in the composition have a common base sequence and length, a common pattern of backbone linkages, and a common pattern of backbone chiral centers. In some embodiments, at least about 30% of the oligonucleotides in the composition have a common base sequence and length, a common pattern of backbone linkages, and a common pattern of backbone chiral centers. In some embodiments, at least about 35% of the oligonucleotides in the composition have a common base sequence and length, a common pattern of backbone linkages, and a common pattern of backbone chiral centers. In some embodiments, at least about 40% of the oligonucleotides in the composition have a common base sequence and length, a common pattern of backbone linkages, and a common pattern of backbone chiral centers. In some embodiments, at least about 45% of the oligonucleotides in the composition have a common base sequence and length, a common pattern of backbone linkages, and a common pattern of backbone chiral centers. In some embodiments, at least about 50% of the oligonucleotides in the composition have a common base sequence and length, a common pattern of backbone linkages, and a common pattern of backbone chiral centers. In some embodiments, at least about 55% of the oligonucleotides in the composition have a common base sequence and length, a common pattern of backbone linkages, and a common pattern of backbone chiral centers. In some embodiments, at least about 60% of the oligonucleotides in the composition have a common base sequence and length, a common pattern of backbone linkages, and a common pattern of backbone chiral centers. In some embodiments, at least about 65% of the oligonucleotides in the composition have a common base sequence and length, a common pattern of backbone linkages, and a common pattern of backbone chiral centers. In some embodiments, at least about 70% of the oligonucleotides in the composition have a common base sequence and length, a common pattern of backbone linkages, and a common pattern of backbone chiral centers. In some embodiments, at least about 75% of the oligonucleotides in the composition have a common base sequence and length, a common pattern of backbone linkages, and a common pattern of backbone chiral centers. In some embodiments, at least about 80% of the oligonucleotides in the composition have a common base sequence and length, a common pattern of backbone linkages, and a common pattern of backbone chiral centers. In some embodiments, at least about 85% of the oligonucleotides in the composition have a common base sequence and length, a common pattern of backbone linkages, and a common pattern of backbone chiral centers. In some embodiments, at least about 90% of the oligonucleotides in the composition have a common base sequence and length, a common pattern of backbone linkages, and a common pattern of backbone chiral centers. In some embodiments, at least about 92% of the oligonucleotides in the composition have a common base sequence and length, a common pattern of backbone linkages, and a common pattern of backbone chiral centers. In some embodiments, at least about 94% of the oligonucleotides in the composition have a common base sequence and length, a common pattern of backbone linkages, and a common pattern of backbone chiral centers. In some embodiments, at least about 95% of the oligonucleotides in the composition have a common base sequence and length, a common pattern of backbone linkages, and a common pattern of backbone chiral centers. In some embodiments, at least about 91%, 92%, 93%, 94%, 95%, 96%, 97%, 98%, or 99% of the oligonucleotides in the composition have a common base sequence and length, a common pattern of backbone linkages, and a common pattern of backbone chiral centers. In some embodiments, greater than about 99% of the oligonucleotides in the composition have a common base sequence and length, a common pattern of backbone linkages, and a common pattern of backbone chiral centers. In some embodiments, purity of a chirally controlled oligonucleotide composition of an oligonucleotide can be expressed as the percentage of oligonucleotides in the composition that have a common base sequence and length, a common pattern of backbone linkages, and a common pattern of backbone chiral centers.

In some embodiments, oligonucleotides having a common base sequence and length, a common pattern of backbone linkages, and a common pattern of backbone chiral centers have a common pattern of backbone phosphorus modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have a common pattern of backbone phosphorus modifications and a common pattern of sugar modifications. In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers are identical.

In some embodiments, oligonucleotides in provided compositions have a common pattern of backbone phosphorus modifications. In some embodiments, a common base sequence is a base sequence of an oligonucleotide type. In some embodiments, a provided composition is an oligonucleotide composition that is chirally controlled in that the composition contains a predetermined level of a first plurality of oligonucleotides of an individual oligonucleotide type, wherein an oligonucleotide type is defined by:

1) base sequence;
2) pattern of backbone linkages;
3) pattern of backbone chiral centers; and
4) pattern of backbone phosphorus modifications.

As noted above and understood in the art, in some embodiments, base sequence of an oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

In some embodiments, a particular oligonucleotide type may be defined by 1A) base identity;
1B) pattern of base modification;
1C) pattern of sugar modification;
2) pattern of backbone linkages;
3) pattern of backbone chiral centers; and
4) pattern of backbone phosphorus modifications.

Thus, in some embodiments, oligonucleotides of a particular type may share identical bases but differ in their pattern of base modifications and/or sugar modifications. In some embodiments, oligonucleotides of a particular type may share identical bases and pattern of base modifications (including, e.g., absence of base modification), but differ in pattern of sugar modifications.

In some embodiments, oligonucleotides of a particular type are identical in that they have the same base sequence (including length), the same pattern of chemical modifications to sugar and base moieties, the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications (e.g., pattern of modifications on the internucleotidic phosphorus atom, such as —S—, and -L-$R^1$ of formula I).

In some embodiments, purity of a chirally controlled oligonucleotide composition of an oligonucleotide type is expressed as the percentage of oligonucleotides in the composition that are of the oligonucleotide type. In some embodiments, at least about 10% of the oligonucleotides in a chirally controlled oligonucleotide composition are of the same oligonucleotide type. In some embodiments, at least about 20% of the oligonucleotides in a chirally controlled oligonucleotide composition are of the same oligonucleotide type. In some embodiments, at least about 30% of the oligonucleotides in a chirally controlled oligonucleotide composition are of the same oligonucleotide type. In some embodiments, at least about 40% of the oligonucleotides in a chirally controlled oligonucleotide composition are of the same oligonucleotide type. In some embodiments, at least about 50% of the oligonucleotides in a chirally controlled oligonucleotide composition are of the same oligonucleotide type. In some embodiments, at least about 60% of the oligonucleotides in a chirally controlled oligonucleotide composition are of the same oligonucleotide type. In some embodiments, at least about 70% of the oligonucleotides in a chirally controlled oligonucleotide composition are of the same oligonucleotide type. In some embodiments, at least about 80% of the oligonucleotides in a chirally controlled oligonucleotide composition are of the same oligonucleotide type. In some embodiments, at least about 90% of the oligonucleotides in a chirally controlled oligonucleotide composition are of the same oligonucleotide type. In some embodiments, at least about 92% of the oligonucleotides in a chirally controlled oligonucleotide composition are of the same oligonucleotide type. In some embodiments, at least about 94% of the oligonucleotides in a chirally controlled oligonucleotide composition are of the same oligonucleotide type. In some embodiments, at least about 95% of the oligonucleotides in a chirally controlled oligonucleotide composition are of the same oligonucleotide type. In some embodiments, at least about 96% of the oligonucleotides in a chirally controlled oligonucleotide composition are of the same oligonucleotide type. In some embodiments, at least about 97% of the oligonucleotides in a chirally controlled oligonucleotide composition are of the same oligonucleotide type. In some embodiments, at least about 98% of the oligonucleotides in a chirally controlled oligonucleotide composition are of the same oligonucleotide type. In some embodiments, at least about 99% of the oligonucleotides in a chirally controlled oligonucleotide composition are of the same oligonucleotide type.

In some embodiments, purity of a chirally controlled oligonucleotide composition can be controlled by stereoselectivity of each coupling step in its preparation process. In some embodiments, a coupling step has a stereoselectivity (e.g., diastereoselectivity) of 60% (60% of the new internucleotidic linkage formed from the coupling step has the intended stereochemistry). After such a coupling step, the new internucleotidic linkage formed may be referred to have a 60% purity. In some embodiments, each coupling step has a stereoselectivity of at least 60%. In some embodiments, each coupling step has a stereoselectivity of at least 70%. In some embodiments, each coupling step has a stereoselectivity of at least 80%. In some embodiments, each coupling step has a stereoselectivity of at least 85%. In some embodiments, each coupling step has a stereoselectivity of at least 90%. In some embodiments, each coupling step has a stereoselectivity of at least 91%. In some embodiments, each coupling step has a stereoselectivity of at least 92%. In some embodiments, each coupling step has a stereoselectivity of at least 93%. In some embodiments, each coupling step has a stereoselectivity of at least 94%. In some embodiments, each coupling step has a stereoselectivity of at least 95%. In some embodiments, each coupling step has a stereoselectivity of at least 96%. In some embodiments, each coupling step has a stereoselectivity of at least 97%. In some embodiments, each coupling step has a stereoselectivity of at least 98%. In some embodiments, each coupling step has a stereoselectivity of at least 99%. In some embodiments, each coupling step has a stereoselectivity of at least 99.5%. In some embodiments, each coupling step has a stereoselectivity of virtually 100%. In some embodiments, a coupling step has a stereoselectivity of virtually 100% in that all detectable product from the coupling step by an analytical method (e.g., NMR, HPLC, etc) has the intended stereoselectivity.

Among other things, the present disclosure recognizes that combinations of oligonucleotide structural elements (e.g., patterns of chemical modifications, backbone linkages, backbone chiral centers, and/or backbone phosphorus modifications) can provide surprisingly improved properties such as bioactivities.

In some embodiments, the present disclosure provides an oligonucleotide composition comprising a predetermined level of a first plurality of oligonucleotides which comprise one or more wing regions and a common core region, wherein:

- each wing region independently has a length of two or more bases, and independently and optionally comprises one or more chiral internucleotidic linkages;
- the core region independently has a length of two or more bases, and independently comprises one or more chiral internucleotidic linkages, and the common core region has:

1) a common base sequence and length;
2) a common pattern of backbone linkages; and
3) a common pattern of backbone chiral centers.

In some embodiments, a wing region comprises a structural feature that is not in a core region. In some embodiments, a wing and core can be defined by any structural elements, e.g., base modifications (e.g., methylated/non-methylated, methylation at position 1/methylation at position 2, etc.), sugar modifications (e.g., modified/non-modified, 2'-modification/another type of modification, one type of 2'-modification/another type of 2'-modification, etc.), backbone linkage types (e.g., phosphate/phosphorothioate, phosphorothioate/substituted phosphorothioate, etc.), backbone chiral center stereochemistry (e.g., all Sp/all Rp, (SpRp) repeats/all Rp, etc.), backbone phosphorus modification types (e.g., s1/s2, s1/s3, etc.), etc.

In some embodiments, a wing and core is defined by nucleoside modifications, wherein a wing comprises a nucleoside modification that the core region does not have. In some embodiments, a wing and core is defined by sugar modifications, wherein a wing comprises a sugar modification that the core region does not have. In some embodiments, a sugar modification is a 2'-modification. In some embodiments, a sugar modification is 2'-$OR^1$. In some embodiments, a sugar modification is 2'-MOE. In some embodiments, a sugar modification is 2'-OMe. Additionally example sugar modifications are described in the present disclosure. In some embodiments, a wing and core is defined by internucleotidic linkages, wherein a wing comprises a internucleotidic linkage type (e.g., natural phosphate linkage, a type of modified internucleotidic linkage, etc.) that the core region does not have. In some embodiments, a wing and core is defined by internucleotidic linkages, wherein a wing has a pattern of backbone linkage that is different from that of the core.

In some embodiments, oligonucleotides in provided compositions have a wing-core structure (hemimer). In some embodiments, oligonucleotides in provided compositions have a wing-core structure of nucleoside modifications. In some embodiments, oligonucleotides in provided compositions have a core-wing structure (another type of hemimer). In some embodiments, oligonucleotides in provided compositions have a core-wing structure of nucleoside modifications. In some embodiments, oligonucleotides in provided compositions have a wing-core-wing structure (gapmer). In some embodiments, oligonucleotides in provided compositions have a wing-core-wing structure of nucleoside modifications. In some embodiments, a wing and core is defined by modifications of the sugar moieties. In some embodiments, a wing and core is defined by modifications of the base moieties. In some embodiments, each sugar moiety in the wing region has the same 2'-modification which is not found in the core region. In some embodiments, each sugar moiety in the wing region has the same 2'-modification which is different than any sugar modifications in the core region. In some embodiments, a core region has no sugar modification. In some embodiments, each sugar moiety in the wing region has the same 2'-modification, and the core region has no 2'-modifications. In some embodiments, when two or more wings are present, each wing is defined by its own modifications. In some embodiments, each wing has its own characteristic sugar modification. In some embodiments, each wing has the same characteristic sugar modification differentiating it from a core. In some embodiments, each wing sugar moiety has the same modification. In some embodiments, each wing sugar moiety has the same 2'-modification. In some embodiments, each sugar moiety in a wing region has the same 2'-modification, yet the common 2'-modification in a first wing region can either be the same as or different from the common 2'-modification in a second wing region. In some embodiments, each sugar moiety in a wing region has the same 2'-modification, and the common 2'-modification in a first wing region is the same as the common 2'-modification in a second wing region. In some embodiments, each sugar moiety in a wing region has the same 2'-modification, and the common 2'-modification in a first wing region is different from the common 2'-modification in a second wing region.

In some embodiments, provided chirally controlled (and/or stereochemically pure) preparations are antisense oligonucleotides (e.g., chiromersen). In some embodiments, provided chirally controlled (and/or stereochemically pure) preparations are siRNA oligonucleotides. In some embodiments, a provided chirally controlled oligonucleotide composition is of oligonucleotides that can be antisense oligonucleotide, antagomir, microRNA, pre-microRNs, antimir, supermir, ribozyme, U1 adaptor, RNA activator, RNAi agent, decoy oligonucleotide, triplex forming oligonucleotide, aptamer or adjuvant. In some embodiments, a chirally controlled oligonucleotide composition is of antisense oligonucleotides. In some embodiments, a chirally controlled oligonucleotide composition is of antagomir oligonucleotides. In some embodiments, a chirally controlled oligonucleotide composition is of microRNA oligonucleotides. In some embodiments, a chirally controlled oligonucleotide composition is of pre-microRNA oligonucleotides. In some embodiments, a chirally controlled oligonucleotide composition is of antimir oligonucleotides. In some embodiments, a chirally controlled oligonucleotide composition is of supermir oligonucleotides. In some embodiments, a chirally controlled oligonucleotide composition is of ribozyme oligonucleotides. In some embodiments, a chirally controlled oligonucleotide composition is of U1 adaptor oligonucleotides. In some embodiments, a chirally controlled oligonucleotide composition is of RNA activator oligonucleotides. In some embodiments, a chirally controlled oligonucleotide composition is of RNAi agent oligonucleotides. In some embodiments, a chirally controlled oligonucleotide composition is of decoy oligonucleotides. In some embodiments, a chirally controlled oligonucleotide composition is of triplex forming oligonucleotides. In some embodiments, a chirally controlled oligonucleotide composition is of aptamer oligonucleotides. In some embodiments, a chirally controlled oligonucleotide composition is of adjuvant oligonucleotides.

In some embodiments, provided chirally controlled (and/or stereochemically pure) preparations are of oligonucleotides that include one or more modified backbone linkages, bases, and/or sugars.

In some embodiments, a provided oligonucleotide comprises one or more chiral, modified phosphate linkages. In some embodiments, a provided oligonucleotide comprises two or more chiral, modified phosphate linkages. In some embodiments, a provided oligonucleotide comprises three or more chiral, modified phosphate linkages. In some embodiments, a provided oligonucleotide comprises four or more chiral, modified phosphate linkages. In some embodiments, a provided oligonucleotide comprises five or more chiral, modified phosphate linkages. In some embodiments, a provided oligonucleotide comprises 1, 2, 3, 4, 5, 6, 7, 8, 9, 10, 11, 12, 13, 14, 15, 16, 17, 18, 19, 20, 21, 22, 23, 24, or 25 chiral, modified phosphate linkages. In some embodiments, a provided oligonucleotide type comprises 5 or more chiral, modified phosphate linkages. In some embodiments, a provided oligonucleotide type comprises 6 or more chiral, modified phosphate linkages. In some embodiments, a provided oligonucleotide type comprises 7 or more chiral, modified phosphate linkages. In some embodiments, a provided oligonucleotide type comprises 8 or more chiral, modified phosphate linkages. In some embodiments, a provided oligonucleotide type comprises 9 or more chiral, modified phosphate linkages. In some embodiments, a provided oligonucleotide type comprises 10 or more chiral, modified phosphate linkages. In some embodiments, a provided oligonucleotide type comprises 11 or more chiral, modified phosphate linkages. In some embodiments, a provided oligonucleotide type comprises 12 or more chiral, modified phosphate linkages. In some embodiments, a provided oligonucleotide type comprises 13 or more chiral, modified phosphate linkages. In some embodiments, a provided oligonucleotide type comprises 14 or more chiral, modified phosphate linkages. In some embodiments, a provided oligonucleotide type comprises 15 or more chiral, modified phosphate linkages. In some embodiments, a provided oligonucleotide type comprises 16 or more chiral, modified phosphate linkages. In some embodiments, a provided oligonucleotide type comprises 17 or more chiral, modified phosphate linkages. In some embodiments, a provided oligonucleotide type comprises 18 or more chiral, modified phosphate linkages. In some embodiments, a provided oligonucleotide type comprises 19 or more chiral, modified phosphate linkages. In some embodiments, a provided oligonucleotide type comprises 20 or more chiral, modified phosphate linkages. In some embodiments, a provided oligonucleotide type comprises 21 or more chiral, modified phosphate linkages. In some embodiments, a provided oligonucleotide type comprises 22 or more chiral, modified phosphate linkages. In some embodiments, a provided oligonucleotide type comprises 23 or more chiral, modified phosphate linkages. In some embodiments, a provided oligonucleotide type comprises 24 or more chiral, modified phosphate linkages. In some embodiments, a provided oligonucleotide type comprises 25 or more chiral, modified phosphate linkages.

In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages. Example such chiral, modified phosphate linkages are described above and herein. In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral, modified phosphate linkages in the Sp configuration.

In some embodiments, provided chirally controlled (and/or stereochemically pure) preparations are of a stereochemical purity of greater than about 80%. In some embodiments, provided chirally controlled (and/or stereochemically pure) preparations are of a stereochemical purity of greater than about 85%. In some embodiments, provided chirally controlled (and/or stereochemically pure) preparations are of a stereochemical purity of greater than about 90%. In some embodiments, provided chirally controlled (and/or stereochemically pure) preparations are of a stereochemical purity of greater than about 91%. In some embodiments, provided chirally controlled (and/or stereochemically pure) preparations are of a stereochemical purity of greater than about 92%. In some embodiments, provided chirally controlled (and/or stereochemically pure) preparations are of a stereochemical purity of greater than about 93%. In some embodiments, provided chirally controlled (and/or stereochemically pure) preparations are of a stereochemical purity of greater than about 94%. In some embodiments, provided chirally controlled (and/or stereochemically pure) preparations are of a stereochemical purity of greater than about 95%. In some embodiments, provided chirally controlled (and/or stereochemically pure) preparations are of a stereochemical purity of greater than about 96%. In some embodiments, provided chirally controlled (and/or stereochemically pure) preparations are of a stereochemical purity of greater than about 97%. In some embodiments, provided chirally controlled (and/or stereochemically pure) preparations are of a stereochemical purity of greater than about 98%. In some embodiments, provided chirally controlled (and/or stereochemically pure) preparations are of a stereochemical purity of greater than about 99%.

In some embodiments, a chiral, modified phosphate linkage is a chiral phosphorothioate linkage, i.e., phosphorothioate internucleotidic linkage. In some embodiments, a provided oligonucleotide comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10, 20, 30, 40, 50, 60, 70, 80, or 90% chiral phosphorothioate internucleotidic linkages of a provided oligonucleotide are of the Sp conformation. In some embodiments, at least about 10% chiral phosphorothioate internucleotidic linkages of a provided oligonucleotide are of the Sp conformation. In some embodiments, at least about 20% chiral phosphorothioate internucleotidic linkages of a provided oligonucleotide are of the Sp conformation. In some embodiments, at least about 30% chiral phosphorothioate internucleotidic linkages of a provided oligonucleotide are of the Sp conformation. In some embodiments, at least about 40% chiral phosphorothioate internucleotidic linkages of a provided oligonucleotide are of the Sp conformation. In some embodiments, at least about 50% chiral phosphorothioate internucleotidic linkages of a provided oligonucleotide are of the Sp conformation. In some embodiments, at least about 60% chiral phosphorothioate internucleotidic linkages of a provided oligonucleotide are of the Sp conformation. In some embodiments, at least about 70% chiral phosphorothioate internucleotidic linkages of a provided oligonucleotide are of the Sp conformation. In some embodiments, at least about 80% chiral phosphorothioate internucleotidic linkages of a provided oligonucleotide are of the Sp conformation. In some embodiments, at least about 90% chiral phosphorothioate internucleotidic linkages of a provided oligonucleotide are of the Sp conformation. In some embodiments, at least about 95% chiral phosphorothioate internucleotidic linkages of a provided oligonucleotide are of the Sp conformation.

In some embodiments, at least about 10, 20, 30, 40, 50, 60, 70, 80, or 90% chiral phosphorothioate internucleotidic linkages of a provided oligonucleotide are of the Rp conformation. In some embodiments, at least about 10% chiral phosphorothioate internucleotidic linkages of a provided oligonucleotide are of the Rp conformation. In some embodiments, at least about 20% chiral phosphorothioate internucleotidic linkages of a provided oligonucleotide are of the Rp conformation. In some embodiments, at least about 30% chiral phosphorothioate internucleotidic linkages of a provided oligonucleotide are of the Rp conformation. In some embodiments, at least about 40% chiral phosphorothioate internucleotidic linkages of a provided oligonucleotide are of the Rp conformation. In some embodiments, at least about 50% chiral phosphorothioate internucleotidic linkages of a provided oligonucleotide are of the Rp conformation. In some embodiments, at least about 60% chiral phosphorothioate internucleotidic linkages of a provided oligonucleotide are of the Rp conformation. In some embodiments, at least about 70% chiral phosphorothioate internucleotidic linkages of a provided oligonucleotide are of the Rp conformation. In some embodiments, at least about 80% chiral phosphorothioate internucleotidic linkages of a provided oligonucleotide are of the Rp conformation. In some embodiments, at least about 90% chiral phosphorothioate internucleotidic linkages of a provided oligonucleotide are of the Rp conformation. In some embodiments, at least about 95% chiral phosphorothioate internucleotidic linkages of a provided oligonucleotide are of the Rp conformation.

In some embodiments, less than about 10, 20, 30, 40, 50, 60, 70, 80, or 90% chiral phosphorothioate internucleotidic linkages of a provided oligonucleotide are of the Rp conformation. In some embodiments, less than about 10% chiral phosphorothioate internucleotidic linkages of a provided oligonucleotide are of the Rp conformation. In some embodiments, less than about 20% chiral phosphorothioate internucleotidic linkages of a provided oligonucleotide are of the Rp conformation. In some embodiments, less than about 30% chiral phosphorothioate internucleotidic linkages of a provided oligonucleotide are of the Rp conformation. In some embodiments, less than about 40% chiral phosphorothioate internucleotidic linkages of a provided oligonucleotide are of the Rp conformation. In some embodiments, less than about 50% chiral phosphorothioate internucleotidic linkages of a provided oligonucleotide are of the Rp conformation. In some embodiments, less than about 60% chiral phosphorothioate internucleotidic linkages of a provided oligonucleotide are of the Rp conformation. In some embodiments, less than about 70% chiral phosphorothioate internucleotidic linkages of a provided oligonucleotide are of the Rp conformation. In some embodiments, less than about 80% chiral phosphorothioate internucleotidic linkages of a provided oligonucleotide are of the Rp conformation. In some embodiments, less than about 90% chiral phosphorothioate internucleotidic linkages of a provided oligonucleotide are of the Rp conformation. In some embodiments, less than about 95% chiral phosphorothioate internucleotidic linkages of a provided oligonucleotide are of the Rp conformation. In some embodiments, a provided oligonucleotide has only one Rp chiral phosphorothioate internucleotidic linkages. In some embodiments, a provided oligonucleotide has only one Rp chiral phosphorothioate internucleotidic linkages, wherein all internucleotide linkages are chiral phosphorothioate internucleotidic linkages.

In some embodiments, a chiral phosphorothioate internucleotidic linkage is a chiral phosphorothioate diester linkage. In some embodiments, each chiral phosphorothioate internucleotidic linkage is independently a chiral phosphorothioate diester linkage. In some embodiments, each internucleotidic linkage is independently a chiral phosphorothioate diester linkage. In some embodiments, each internucleotidic linkage is independently a chiral phosphorothioate diester linkage, and only one is Rp.

In some embodiments, provided chirally controlled (and/or stereochemically pure) preparations are of oligonucleotides that contain one or more modified bases. In some embodiments, provided chirally controlled (and/or stereochemically pure) preparations are of oligonucleotides that contain no modified bases. Example such modified bases are described above and herein.

In some embodiments, oligonucleotides of provided compositions comprise at least 2, 3, 4, 5, 6, 7, 8, 9 or 10 natural phosphate linkages. In some embodiments, oligonucleotides of provided compositions comprise at least one natural phosphate linkage. In some embodiments, oligonucleotides of provided compositions comprise at least two natural phosphate linkages. In some embodiments, oligonucleotides of provided compositions comprise at least three natural phosphate linkages. In some embodiments, oligonucleotides of provided compositions comprise at least four natural phosphate linkages. In some embodiments, oligonucleotides of provided compositions comprise at least five natural phosphate linkages. In some embodiments, oligonucleotides of provided compositions comprise at least six natural phosphate linkages. In some embodiments, oligonucleotides of provided compositions comprise at least seven natural phosphate linkages. In some embodiments, oligonucleotides of provided compositions comprise at least eight natural phosphate linkages. In some embodiments, oligonucleotides of provided compositions comprise at least nine natural phosphate linkages. In some embodiments, oligonucleotides of provided compositions comprise at least ten natural phosphate linkages.

In some embodiments, oligonucleotides of provided compositions comprise 2, 3, 4, 5, 6, 7, 8, 9 or 10 natural phosphate linkages. In some embodiments, oligonucleotides of provided compositions comprise one natural phosphate linkage. In some embodiments, oligonucleotides of provided compositions comprise two natural phosphate linkages. In some embodiments, oligonucleotides of provided compositions comprise three natural phosphate linkages. In some embodiments, oligonucleotides of provided compositions comprise four natural phosphate linkages. In some embodiments, oligonucleotides of provided compositions comprise five natural phosphate linkages. In some embodiments, oligonucleotides of provided compositions comprise six natural phosphate linkages. In some embodiments, oligonucleotides of provided compositions comprise seven natural phosphate linkages. In some embodiments, oligonucleotides of provided compositions comprise eight natural phosphate linkages. In some embodiments, oligonucleotides of provided compositions comprise nine natural phosphate linkages. In some embodiments, oligonucleotides of provided compositions comprise ten natural phosphate linkages.

In some embodiments, oligonucleotides of provided compositions comprise at least 2, 3, 4, 5, 6, 7, 8, 9 or 10 consecutive natural phosphate linkages. In some embodiments, oligonucleotides of provided compositions comprise at least two consecutive natural phosphate linkages. In some embodiments, oligonucleotides of provided compositions comprise at least three consecutive natural phosphate linkages. In some embodiments, oligonucleotides of provided compositions comprise at least four consecutive natural phosphate linkages. In some embodiments, oligonucleotides of provided compositions comprise at least five consecutive natural phosphate linkages. In some embodiments, oligonucleotides of provided compositions comprise at least six consecutive natural phosphate linkages. In some embodiments, oligonucleotides of provided compositions comprise at least seven consecutive natural phosphate linkages. In some embodiments, oligonucleotides of provided compositions comprise at least eight consecutive natural phosphate linkages. In some embodiments, oligonucleotides of provided compositions comprise at least nine consecutive natural phosphate linkages. In some embodiments, oligonucleotides of provided compositions comprise at least ten consecutive natural phosphate linkages.

In some embodiments, oligonucleotides of provided compositions comprise 2, 3, 4, 5, 6, 7, 8, 9 or 10 consecutive natural phosphate linkages. In some embodiments, oligonucleotides of provided compositions comprise two consecutive natural phosphate linkages. In some embodiments, oligonucleotides of provided compositions comprise three consecutive natural phosphate linkages. In some embodiments, oligonucleotides of provided compositions comprise four consecutive natural phosphate linkages. In some embodiments, oligonucleotides of provided compositions comprise five consecutive natural phosphate linkages. In some embodiments, oligonucleotides of provided compositions comprise six consecutive natural phosphate linkages. In some embodiments, oligonucleotides of provided compositions comprise seven consecutive natural phosphate linkages. In some embodiments, oligonucleotides of provided compositions comprise eight consecutive natural phosphate linkages. In some embodiments, oligonucleotides of provided compositions comprise nine consecutive natural phosphate linkages. In some embodiments, oligonucleotides of provided compositions comprise ten consecutive natural phosphate linkages.

In some embodiments, provided chirally controlled (and/or stereochemically pure) preparations are of oligonucleotides having a common base sequence of at least 8 bases. In some embodiments, provided chirally controlled (and/or stereochemically pure) preparations are of oligonucleotides having a common base sequence of at least 9 bases. In some embodiments, provided chirally controlled (and/or stereochemically pure) preparations are of oligonucleotides having a common base sequence of at least 10 bases. In some embodiments, provided chirally controlled (and/or stereochemically pure) preparations are of oligonucleotides having a common base sequence of at least 11 bases. In some embodiments, provided chirally controlled (and/or stereochemically pure) preparations are of oligonucleotides having a common base sequence of at least 12 bases. In some embodiments, provided chirally controlled (and/or stereochemically pure) preparations are of oligonucleotides having a common base sequence of at least 13 bases. In some embodiments, provided chirally controlled (and/or stereochemically pure) preparations are of oligonucleotides having a common base sequence of at least 14 bases. In some embodiments, provided chirally controlled (and/or stereochemically pure) preparations are of oligonucleotides having a common base sequence of at least 15 bases. In some embodiments, provided chirally controlled (and/or stereochemically pure) preparations are of oligonucleotides having a common base sequence of at least 16 bases. In some embodiments, provided chirally controlled (and/or stereochemically pure) preparations are of oligonucleotides having a common base sequence of at least 17 bases. In some embodiments, provided chirally controlled (and/or stereochemically pure) preparations are of oligonucleotides having a common base sequence of at least 18 bases. In some embodiments, provided chirally controlled (and/or stereochemically pure) preparations are of oligonucleotides having a common base sequence of at least 19 bases. In some embodiments, provided chirally controlled (and/or stereochemically pure) preparations are of oligonucleotides having a common base sequence of at least 20 bases. In some embodiments, provided chirally controlled (and/or stereochemically pure) preparations are of oligonucleotides having a common base sequence of at least 21 bases. In some embodiments, provided chirally controlled (and/or stereochemically pure) preparations are of oligonucleotides having a common base sequence of at least 22 bases. In some embodiments, provided chirally controlled (and/or stereochemically pure) preparations are of oligonucleotides having a common base sequence of at least 23 bases. In some embodiments, provided chirally controlled (and/or stereochemically pure) preparations are of oligonucleotides having a common base sequence of at least 24 bases. In some embodiments, provided chirally controlled (and/or stereochemically pure) preparations are of oligonucleotides having a common base sequence of at least 25 bases. In some embodiments, provided chirally controlled (and/or stereochemically pure) preparations are of oligonucleotides having a common base sequence of at least 30, 35, 40, 45, 50, 55, 60, 65, 70, or 75 bases.

In some embodiments, provided compositions comprise oligonucleotides containing one or more residues which are modified at the sugar moiety. In some embodiments, provided compositions comprise oligonucleotides containing one or more residues which are modified at the 2' position of the sugar moiety (referred to herein as a "2'-modification"). Example such modifications are described above and herein and include, but are not limited to, 2'-OMe, 2'-MOE, 2'-LNA, 2'-F, FRNA, FANA, S-cEt, etc. In some embodiments, provided compositions comprise oligonucleotides containing one or more residues which are 2'-modified. For example, in some embodiments, provided oligonucleotides contain one or more residues which are 2'-O-methoxyethyl (2'-MOE)-modified residues. In some embodiments, provided compositions comprise oligonucleotides which do not contain any 2'-modifications. In some embodiments, provided compositions are oligonucleotides which do not contain any 2'-MOE residues. That is, in some embodiments, provided oligonucleotides are not MOE-modified. Additional example sugar modifications are described in the present disclosure.

In some embodiments, provided oligonucleotides are of a general motif of wing-core or core-wing (hemimer, also represented herein generally as X-Y or Y-X, respectively). In some embodiments, provided oligonucleotides are of a general motif of wing-core-wing (gapmer, also represented herein generally as X-Y-X). In some embodiments, each wing region independently contains one or more residues having a particular modification, which modification is absent from the core "Y" portion. In some embodiments, each wing region independently contains one or more residues having a particular nucleoside modification, which modification is absent from the core "Y" portion. In some embodiments, each wing region independently contains one or more residues having a particular base modification, which modification is absent from the core "Y" portion. In some embodiments, each wing region independently contains one or more residues having a particular sugar modification, which modification is absent from the core "Y" portion. Example sugar modifications are widely known in the art. In some embodiments, a sugar modification is a modification selected from those modifications described in U.S. Pat. No. 9,006,198, which sugar modifications are incorporated herein by references. Additional example sugar modifications are described in the present disclosure. In some embodiment, each wing contains one or more residues having a 2' modification that is not present in the core portion. In some embodiments, a 2'-modification is 2'-$OR^1$, wherein $R^1$ is as defined and described in the present disclosure.

In some embodiments, provided oligonucleotides have a wing-core motif represented as X-Y, or a core-wing motif represented as Y-X, wherein the residues at the "X" portion are sugar modified residues of a particular type and the residues in the core "Y" portion are not sugar modified residues of the same particular type. In some embodiments, provided oligonucleotides have a wing-core-wing motif represented as X-Y-X, wherein the residues at each "X" portion are sugar modified residues of a particular type and the residues in the core "Y" portion are not sugar modified residues of the same particular type. In some embodiments, provided oligonucleotides have a wing-core motif represented as X-Y, or a core-wing motif represented as Y-X, wherein the residues at the "X" portion are 2'-modified residues of a particular type and the residues in the core "Y" portion are not 2'-modified residues of the same particular type. In some embodiments, provided oligonucleotides have a wing-core motif represented as X-Y, wherein the residues at the "X" portion are 2'-modified residues of a particular type and the residues in the core "Y" portion are not 2'-modified residues of the same particular type. In some embodiments, provided oligonucleotides have a core-wing motif represented as Y-X, wherein the residues at the "X" portion are 2'-modified residues of a particular type and the residues in the core "Y" portion are not 2'-modified residues of the same particular type. In some embodiments, provided oligonucleotides have a wing-core-wing motif represented as X-Y-X, wherein the residues at each "X" portion are 2'-modified residues of a particular type and the residues in the core "Y" portion are not 2'-modified residues of the same particular type. In some embodiments, provided oligonucleotides have a wing-core motif represented as X-Y, wherein the residues at the "X" portion are 2'-modified residues of a particular type and the residues in the core "Y" portion are 2'-deoxyribonucleoside. In some embodiments, provided oligonucleotides have a core-wing motif represented as Y-X, wherein the residues at the "X" portion are 2'-modified residues of a particular type and the residues in the core "Y" portion are 2'-deoxyribonucleoside. In some embodiments, provided oligonucleotides have a wing-core-wing motif represented as X-Y-X, wherein the residues at each "X" portion are 2'-modified residues of a particular type and the residues in the core "Y" portion are 2'-deoxyribonucleoside. In some embodiments, provided oligonucleotides have a wing-core-wing motif represented as X-Y-X, wherein the residues at each "X" portion are 2'-modified residues of a particular type and the residues in the core "Y" portion are 2'-deoxyribonucleoside. For instance, in some embodiments, provided oligonucleotides have a wing-core-wing motif represented as X-Y-X, wherein the residues at each "X" portion are 2'-MOE-modified residues and the residues in the core "Y" portion are not 2'-MOE-modified residues. In some embodiments, provided oligonucleotides have a wing-core-wing motif represented as X-Y-X, wherein the residues at each "X" portion are 2'-MOE-modified residues and the residues in the core "Y" portion are 2'-deoxyribonucleoside. One of skill in the relevant arts will recognize that all such 2'-modifications described above and herein are contemplated in the context of such X-Y, Y-X and/or X-Y-X motifs.

In some embodiments, a wing has a length of one or more bases. In some embodiments, a wing has a length of two or more bases. In some embodiments, a wing has a length of three or more bases. In some embodiments, a wing has a length of four or more bases. In some embodiments, a wing has a length of five or more bases. In some embodiments, a wing has a length of six or more bases. In some embodiments, a wing has a length of seven or more bases. In some embodiments, a wing has a length of eight or more bases. In some embodiments, a wing has a length of nine or more bases. In some embodiments, a wing has a length of ten or more bases. In some embodiments, a wing has a length of 11 or more bases. In some embodiments, a wing has a length of 12 or more bases. In some embodiments, a wing has a length of 13 or more bases. In some embodiments, a wing has a length of 14 or more bases. In some embodiments, a wing has a length of 15 or more bases. In some embodiments, a wing has a length of 16 or more bases. In some embodiments, a wing has a length of 17 or more bases. In some embodiments, a wing has a length of 18 or more bases. In some embodiments, a wing has a length of 19 or more bases. In some embodiments, a wing has a length of ten or more bases.

In some embodiments, a wing has a length of one base. In some embodiments, a wing has a length of two bases. In some embodiments, a wing has a length of three bases. In some embodiments, a wing has a length of four bases. In some embodiments, a wing has a length of five bases. In some embodiments, a wing has a length of six bases. In some embodiments, a wing has a length of seven bases. In some embodiments, a wing has a length of eight bases. In some embodiments, a wing has a length of nine bases. In some embodiments, a wing has a length of ten bases. In some embodiments, a wing has a length of 11 bases. In some embodiments, a wing has a length of 12 bases. In some embodiments, a wing has a length of 13 bases. In some embodiments, a wing has a length of 14 bases. In some embodiments, a wing has a length of 15 bases. In some embodiments, a wing has a length of 16 bases. In some embodiments, a wing has a length of 17 bases. In some embodiments, a wing has a length of 18 bases. In some embodiments, a wing has a length of 19 bases. In some embodiments, a wing has a length of ten bases.

In some embodiments, a wing comprises one or more chiral internucleotidic linkages. In some embodiments, a wing comprises one or more natural phosphate linkages. In some embodiments, a wing comprises one or more chiral internucleotidic linkages and one or more natural phosphate linkages. In some embodiments, a wing comprises one or more chiral internucleotidic linkages and two or more natural phosphate linkages. In some embodiments, a wing comprises one or more chiral internucleotidic linkages and two or more natural phosphate linkages, wherein two or more natural phosphate linkages are consecutive. In some embodiments, a wing comprises no chiral internucleotidic linkages. In some embodiments, each wing linkage is a natural phosphate linkage. In some embodiments, a wing comprises no phosphate linkages. In some embodiments, each wing is independently a chiral internucleotidic linkage.

In some embodiments, each wing region independently comprises one or more chiral internucleotidic linkages. In some embodiments, each wing region independently comprises one or more natural phosphate linkages. In some embodiments, each wing region independently comprises one or more chiral internucleotidic linkages and one or more natural phosphate linkages. In some embodiments, each wing region independently comprises one or more chiral internucleotidic linkages and two or more natural phosphate linkages. In some embodiments, each wing region independently comprises one or more chiral internucleotidic linkages and two or more natural phosphate linkages, wherein two or more natural phosphate linkages are consecutive.

In some embodiments, each wing region independently comprises at least one chiral internucleotidic linkage. In some embodiments, each wing region independently comprises at least two chiral internucleotidic linkages. In some embodiments, each wing region independently comprises at least three chiral internucleotidic linkages. In some embodiments, each wing region independently comprises at least four chiral internucleotidic linkages. In some embodiments, each wing region independently comprises at least five chiral internucleotidic linkages. In some embodiments, each wing region independently comprises at least six chiral internucleotidic linkages. In some embodiments, each wing region independently comprises at least seven chiral internucleotidic linkages. In some embodiments, each wing region independently comprises at least eight chiral internucleotidic linkages. In some embodiments, each wing region independently comprises at least nine chiral internucleotidic linkages. In some embodiments, each wing region independently comprises at least ten chiral internucleotidic linkages. In some embodiments, each wing region independently comprises at least 11 chiral internucleotidic linkages. In some embodiments, each wing region independently comprises at least 12 chiral internucleotidic linkages. In some embodiments, each wing region independently comprises at least 13 chiral internucleotidic linkages. In some embodiments, each wing region independently comprises at least 14 chiral internucleotidic linkages. In some embodiments, each wing region independently comprises at least 15 chiral internucleotidic linkages. In some embodiments, each wing region independently comprises at least 16 chiral internucleotidic linkages. In some embodiments, each wing region independently comprises at least 17 chiral internucleotidic linkages. In some embodiments, each wing region independently comprises at least 18 chiral internucleotidic linkages. In some embodiments, each wing region independently comprises at least 19 chiral internucleotidic linkages. In some embodiments, each wing region independently comprises at least 20 chiral internucleotidic linkages.

In some embodiments, each wing region independently comprises one chiral internucleotidic linkage. In some embodiments, each wing region independently comprises two chiral internucleotidic linkages. In some embodiments, each wing region independently comprises three chiral internucleotidic linkages. In some embodiments, each wing region independently comprises four chiral internucleotidic linkages. In some embodiments, each wing region independently comprises five chiral internucleotidic linkages. In some embodiments, each wing region independently comprises six chiral internucleotidic linkages. In some embodiments, each wing region independently comprises seven chiral internucleotidic linkages. In some embodiments, each wing region independently comprises eight chiral internucleotidic linkages. In some embodiments, each wing region independently comprises nine chiral internucleotidic linkages. In some embodiments, each wing region independently comprises ten chiral internucleotidic linkages. In some embodiments, each wing region independently comprises 11 chiral internucleotidic linkages. In some embodiments, each wing region independently comprises 12 chiral internucleotidic linkages. In some embodiments, each wing region independently comprises 13 chiral internucleotidic linkages. In some embodiments, each wing region independently comprises 14 chiral internucleotidic linkages. In some embodiments, each wing region independently comprises 15 chiral internucleotidic linkages. In some embodiments, each wing region independently comprises 16 chiral internucleotidic linkages. In some embodiments, each wing region independently comprises 17 chiral internucleotidic linkages. In some embodiments, each wing region independently comprises 18 chiral internucleotidic linkages. In some embodiments, each wing region independently comprises 19 chiral internucleotidic linkages. In some embodiments, each wing region independently comprises 20 chiral internucleotidic linkages.

In some embodiments, each wing region independently comprises at least one consecutive natural phosphate linkage. In some embodiments, each wing region independently comprises at least two consecutive chiral internucleotidic linkages. In some embodiments, each wing region independently comprises at least three consecutive chiral internucleotidic linkages. In some embodiments, each wing region independently comprises at least four consecutive chiral internucleotidic linkages. In some embodiments, each wing region independently comprises at least five consecutive chiral internucleotidic linkages. In some embodiments, each wing region independently comprises at least six consecutive chiral internucleotidic linkages. In some embodiments, each wing region independently comprises at least seven consecutive chiral internucleotidic linkages. In some embodiments, each wing region independently comprises at least eight consecutive chiral internucleotidic linkages. In some embodiments, each wing region independently comprises at least nine consecutive chiral internucleotidic linkages. In some embodiments, each wing region independently comprises at least ten consecutive chiral internucleotidic linkages. In some embodiments, each wing region independently comprises at least 11 consecutive chiral internucleotidic linkages. In some embodiments, each wing region independently comprises at least 12 consecutive chiral internucleotidic linkages. In some embodiments, each wing region independently comprises at least 13 consecutive chiral internucleotidic linkages. In some embodiments, each wing region independently comprises at least 14 consecutive chiral internucleotidic linkages. In some embodiments, each wing region independently comprises at least 15 consecutive chiral internucleotidic linkages. In some embodiments, each wing region independently comprises at least 16 consecutive chiral internucleotidic linkages. In some embodiments, each wing region independently comprises at least 17 consecutive chiral internucleotidic linkages. In some embodiments, each wing region independently comprises at least 18 consecutive chiral internucleotidic linkages. In some embodiments, each wing region independently comprises at least 19 consecutive chiral internucleotidic linkages. In some embodiments, each wing region independently comprises at least 20 consecutive chiral internucleotidic linkages.

In some embodiments, each wing region independently comprises one consecutive natural phosphate linkage. In some embodiments, each wing region independently comprises two consecutive chiral internucleotidic linkages. In some embodiments, each wing region independently comprises three consecutive chiral internucleotidic linkages. In some embodiments, each wing region independently comprises four consecutive chiral internucleotidic linkages. In some embodiments, each wing region independently comprises five consecutive chiral internucleotidic linkages. In some embodiments, each wing region independently comprises six consecutive chiral internucleotidic linkages. In some embodiments, each wing region independently comprises seven consecutive chiral internucleotidic linkages. In some embodiments, each wing region independently comprises eight consecutive chiral internucleotidic linkages. In some embodiments, each wing region independently comprises nine consecutive chiral internucleotidic linkages. In some embodiments, each wing region independently comprises ten consecutive chiral internucleotidic linkages. In some embodiments, each wing region independently comprises 11 consecutive chiral internucleotidic linkages. In some embodiments, each wing region independently comprises 12 consecutive chiral internucleotidic linkages. In some embodiments, each wing region independently comprises 13 consecutive chiral internucleotidic linkages. In some embodiments, each wing region independently comprises 14 consecutive chiral internucleotidic linkages. In some embodiments, each wing region independently comprises 15 consecutive chiral internucleotidic linkages. In some embodiments, each wing region independently comprises 16 consecutive chiral internucleotidic linkages. In some embodiments, each wing region independently comprises 17 consecutive chiral internucleotidic linkages. In some embodiments, each wing region independently comprises 18 consecutive chiral internucleotidic linkages. In some embodiments, each wing region independently comprises 19 consecutive chiral internucleotidic linkages. In some embodiments, each wing region independently comprises 20 consecutive chiral internucleotidic linkages.

In some embodiments, each wing region independently comprises at least one natural phosphate linkage. In some embodiments, each wing region independently comprises at least two natural phosphate linkages. In some embodiments, each wing region independently comprises at least three natural phosphate linkages. In some embodiments, each wing region independently comprises at least four natural phosphate linkages. In some embodiments, each wing region independently comprises at least five natural phosphate linkages. In some embodiments, each wing region independently comprises at least six natural phosphate linkages. In some embodiments, each wing region independently comprises at least seven natural phosphate linkages. In some embodiments, each wing region independently comprises at least eight natural phosphate linkages. In some embodiments, each wing region independently comprises at least nine natural phosphate linkages. In some embodiments, each wing region independently comprises at least ten natural phosphate linkages. In some embodiments, each wing region independently comprises at least 11 natural phosphate linkages. In some embodiments, each wing region independently comprises at least 12 natural phosphate linkages. In some embodiments, each wing region independently comprises at least 13 natural phosphate linkages. In some embodiments, each wing region independently comprises at least 14 natural phosphate linkages. In some embodiments, each wing region independently comprises at least 15 natural phosphate linkages. In some embodiments, each wing region independently comprises at least 16 natural phosphate linkages. In some embodiments, each wing region independently comprises at least 17 natural phosphate linkages. In some embodiments, each wing region independently comprises at least 18 natural phosphate linkages. In some embodiments, each wing region independently comprises at least 19 natural phosphate linkages. In some embodiments, each wing region independently comprises at least 20 natural phosphate linkages.

In some embodiments, each wing region independently comprises one natural phosphate linkage. In some embodiments, each wing region independently comprises two natural phosphate linkages. In some embodiments, each wing region independently comprises three natural phosphate linkages. In some embodiments, each wing region independently comprises four natural phosphate linkages. In some embodiments, each wing region independently comprises five natural phosphate linkages. In some embodiments, each wing region independently comprises six natural phosphate linkages. In some embodiments, each wing region independently comprises seven natural phosphate linkages. In some embodiments, each wing region independently comprises eight natural phosphate linkages. In some embodiments, each wing region independently comprises nine natural phosphate linkages. In some embodiments, each wing region independently comprises ten natural phosphate linkages. In some embodiments, each wing region independently comprises 11 natural phosphate linkages. In some embodiments, each wing region independently comprises 12 natural phosphate linkages. In some embodiments, each wing region independently comprises 13 natural phosphate linkages. In some embodiments, each wing region independently comprises 14 natural phosphate linkages. In some embodiments, each wing region independently comprises 15 natural phosphate linkages. In some embodiments, each wing region independently comprises 16 natural phosphate linkages. In some embodiments, each wing region independently comprises 17 natural phosphate linkages. In some embodiments, each wing region independently comprises 18 natural phosphate linkages. In some embodiments, each wing region independently comprises 19 natural phosphate linkages. In some embodiments, each wing region independently comprises 20 natural phosphate linkages.

In some embodiments, each wing region independently comprises at least one consecutive natural phosphate linkage. In some embodiments, each wing region independently comprises at least two consecutive natural phosphate linkages. In some embodiments, each wing region independently comprises at least three consecutive natural phosphate linkages. In some embodiments, each wing region independently comprises at least four consecutive natural phosphate linkages. In some embodiments, each wing region independently comprises at least five consecutive natural phosphate linkages. In some embodiments, each wing region independently comprises at least six consecutive natural phosphate linkages. In some embodiments, each wing region independently comprises at least seven consecutive natural phosphate linkages. In some embodiments, each wing region independently comprises at least eight consecutive natural phosphate linkages. In some embodiments, each wing region independently comprises at least nine consecutive natural phosphate linkages. In some embodiments, each wing region independently comprises at least ten consecutive natural phosphate linkages. In some embodiments, each wing region independently comprises at least 11 consecutive natural phosphate linkages. In some embodiments, each wing region independently comprises at least 12 consecutive natural phosphate linkages. In some embodiments, each wing region independently comprises at least 13 consecutive natural phosphate linkages. In some embodiments, each wing region independently comprises at least 14 consecutive natural phosphate linkages. In some embodiments, each wing region independently comprises at least 15 consecutive natural phosphate linkages. In some embodiments, each wing region independently comprises at least 16 consecutive natural phosphate linkages. In some embodiments, each wing region independently comprises at least 17 consecutive natural phosphate linkages. In some embodiments, each wing region independently comprises at least 18 consecutive natural phosphate linkages. In some embodiments, each wing region independently comprises at least 19 consecutive natural phosphate linkages. In some embodiments, each wing region independently comprises at least 20 consecutive natural phosphate linkages.

In some embodiments, each wing region independently comprises one consecutive natural phosphate linkage. In some embodiments, each wing region independently comprises two consecutive natural phosphate linkages. In some embodiments, each wing region independently comprises three consecutive natural phosphate linkages. In some embodiments, each wing region independently comprises four consecutive natural phosphate linkages. In some embodiments, each wing region independently comprises five consecutive natural phosphate linkages. In some embodiments, each wing region independently comprises six consecutive natural phosphate linkages. In some embodiments, each wing region independently comprises seven consecutive natural phosphate linkages. In some embodiments, each wing region independently comprises eight consecutive natural phosphate linkages. In some embodiments, each wing region independently comprises nine consecutive natural phosphate linkages. In some embodiments, each wing region independently comprises ten consecutive natural phosphate linkages. In some embodiments, each wing region independently comprises 11 consecutive natural phosphate linkages. In some embodiments, each wing region independently comprises 12 consecutive natural phosphate linkages. In some embodiments, each wing region independently comprises 13 consecutive natural phosphate linkages. In some embodiments, each wing region independently comprises 14 consecutive natural phosphate linkages. In some embodiments, each wing region independently comprises 15 consecutive natural phosphate linkages. In some embodiments, each wing region independently comprises 16 consecutive natural phosphate linkages. In some embodiments, each wing region independently comprises 17 consecutive natural phosphate linkages. In some embodiments, each wing region independently comprises 18 consecutive natural phosphate linkages. In some embodiments, each wing region independently comprises 19 consecutive natural phosphate linkages. In some embodiments, each wing region independently comprises 20 consecutive natural phosphate linkages.

In some embodiments, a wing is to the 5'-end of a core (5'-end wing). In some embodiments, a wing is to the 3'-end of a core (3'-end wing). For example, in WV-1092 (mG*SmGmCmAmC*SA*SA*SG*SG*SG*SC*SA*SC*RA*SG*SmAmCmUmU*SmC (SEQ ID NO: 10)), mG*SmGmCmAmC is a 5'-end wing, *SA*SA*SG*SG*SG*SC*SA*SC*RA*SG*S (SEQ ID NO: 11) is a core, and mAmCmUmU*SmC is a 3'-end wing.

In some embodiments, a 5'-end wing comprises one or more modified internucleotidic linkages and one or more natural phosphate internucleotidic linkages. In some embodiments, a 3'-end wing comprises one or more modified internucleotidic linkages and one or more natural phosphate internucleotidic linkages. In some embodiments, each wing independently comprises one or more modified internucleotidic linkages and one or more natural phosphate internucleotidic linkages. For example, WV-1092 has a 5'-end wing comprises one or more modified internucleotidic linkages and one or more natural phosphate internucleotidic linkages, and a 3'-end wing comprises one or more modified internucleotidic linkages and one or more natural phosphate internucleotidic linkages.

In some embodiments, a 5'-end wing comprises a modified internucleotidic linkage having one or more natural phosphate linkages connecting two or more nucleosides after (to the 3'-end) the modified internucleotidic linkage in the 5'-end wing. For example, a 5'-end wing mG*SmGmCmAmC comprises a modified internucleotidic linkage (mG*SmG) which has three natural phosphate linkages connecting four nucleosides (mGmCmAmC) after the modified internucleotidic linkage in the 5'-end wing. In some embodiments, a 5'-end wing comprises a modified internucleotidic linkages followed by one or more natural phosphate linkages and/or one or more modified internucleotidic linkages, which are followed by one or more natural phosphate linkages in the 5'-end wing (for example, mG*SmG and mG*SmC in mG*SmG*SmCmAmC). In some embodiments, a 5'-end wing comprises a modified internucleotidic linkages followed by one or more natural phosphate linkages in the 5'-end wing. In some embodiments, a 5'-end wing comprises a modified internucleotidic linkages followed by one or more consecutive natural phosphate linkages in the 5'-end wing. In some embodiments, a 5'-end wing comprises a natural phosphate linkage between the two nucleosides at its 3'-end. For example, a 5'-end wing mG*SmGmCmAmC has a natural phosphate linkage between the two nucleosides at its 3'-end (mG*SmGmCmAmC).

In some embodiments, a 3'-end wing comprises a modified internucleotidic linkage having one or more natural phosphate linkages connecting two or more nucleosides before (to the 5'-end) the modified internucleotidic linkage in the 3'-end wing. For example, a 3'-end wing mAmCmUmU*SmC comprises a modified internucleotidic linkage (mU*SmC) which has three natural phosphate linkages connecting four nucleosides (mAmCmUmU) before the modified internucleotidic linkage in the 3'-end wing. In some embodiments, a 3'-end wing comprises a modified internucleotidic linkages preceded by one or more natural phosphate linkages and/or one or more modified internucleotidic linkages, which are preceded by one or more natural phosphate linkages in the 3'-end wing (for example, mU*SmU and mU*SmC in mAmCmU*SmU*SmC). In some embodiments, a 3'-end wing comprises a modified internucleotidic linkages preceded by one or more natural phosphate linkages in the 3'-end wing. In some embodiments, a 3'-end wing comprises a modified internucleotidic linkages preceded by one or more consecutive natural phosphate linkages in the 3'-end wing. In some embodiments, a 3'-end wing comprises a natural phosphate linkage between the two nucleosides at its 5'-end. For example, a 3'-end wing having the structure of mAmCmUmU*SmC has a natural phosphate linkage between the two nucleosides at its 5'-end (mAmCmUmU*SmC).

In some embodiments, one or more is one. In some embodiments, one or more is two. In some embodiments, one or more is three. In some embodiments, one or more is four. In some embodiments, one or more is five. In some embodiments, one or more is six. In some embodiments, one or more is seven. In some embodiments, one or more is eight. In some embodiments, one or more is nine. In some embodiments, one or more is ten. In some embodiments, one or more is at least one. In some embodiments, one or more is at least two. In some embodiments, one or more is at least three. In some embodiments, one or more is at least four. In some embodiments, one or more is at least five. In some embodiments, one or more is at least six. In some embodiments, one or more is at least seven. In some embodiments, one or more is at least eight. In some embodiments, one or more is at least nine. In some embodiments, one or more is at least ten.

In some embodiments, a wing comprises only one chiral internucleotidic linkage. In some embodiments, a 5'-end wing comprises only one chiral internucleotidic linkage. In some embodiments, a 5'-end wing comprises only one chiral internucleotidic linkage at the 5'-end of the wing. In some embodiments, a 5'-end wing comprises only one chiral internucleotidic linkage at the 5'-end of the wing, and the chiral internucleotidic linkage is Rp. In some embodiments, a 5'-end wing comprises only one chiral internucleotidic linkage at the 5'-end of the wing, and the chiral internucleotidic linkage is Sp. In some embodiments, a 3'-end wing comprises only one chiral internucleotidic linkage at the 3'-end of the wing. In some embodiments, a 3'-end wing comprises only one chiral internucleotidic linkage at the 3'-end of the wing, and the chiral internucleotidic linkage is Rp. In some embodiments, a 3'-end wing comprises only one chiral internucleotidic linkage at the 3'-end of the wing, and the chiral internucleotidic linkage is Sp.

In some embodiments, a wing comprises two or more natural phosphate linkages. In some embodiments, all phosphate linkages within a wing are consecutive, and there are no non-phosphate linkages between any two phosphate linkages within a wing.

In some embodiments, a linkage connecting a wing and a core is considered part of the core when describing linkages, e.g., linkage chemistry, linkage stereochemistry, etc. For example, in WV-1092, mG*SmGmCmAmC*SA* SA*SG*SG*SG*SC*S A*SC*RA*SG*SmAmCmUmU* SmC (SEQ ID NO: 12), the underlined linkages may be considered as part of the core (bold), its 5'-wing (having 2'-OMe on sugar moieties) has one single Sp phosphorothioate linkages at its 5'-end, its 3'-wing (having 2'-OMe on sugar moieties) has one Sp phosphorothioate linkage at its 3'-end, and its core has no 2'-modifications on sugar).

In some embodiments, a 5'-internucleotidic linkage connected to a sugar moiety without a 2'-modification is a modified linkage. In some embodiments, a 5'-internucleotidic linkage connected to a sugar moiety without a 2'-modification is a linkage having the structure of formula I. In some embodiments, a 5'-internucleotidic linkage connected to a sugar moiety without a 2'-modification is phosphorothioate linkage. In some embodiments, a 5'-internucleotidic linkage connected to a sugar moiety without a 2'-modification is a substituted phosphorothioate linkage. In some embodiments, a 5'-internucleotidic linkage connected to a sugar moiety without a 2'-modification is a phosphorothioate triester linkage. In some embodiments, each 5'-internucleotidic linkage connected to a sugar moiety without a 2'-modification is a modified linkage. In some embodiments, each 5'-internucleotidic linkage connected to a sugar moiety without a 2'-modification is a linkage having the structure of formula I. In some embodiments, each 5'-internucleotidic linkage connected to a sugar moiety without a 2'-modification is phosphorothioate linkage. In some embodiments, each 5'-internucleotidic linkage connected to a sugar moiety without a 2'-modification is a substituted phosphorothioate linkage. In some embodiments, each 5'-internucleotidic linkage connected to a sugar moiety without a 2'-modification is a phosphorothioate triester linkage.

In some embodiments, a 3'-internucleotidic linkage connected to a sugar moiety without a 2'-modification is a modified linkage. In some embodiments, a 3'-internucleotidic linkage connected to a sugar moiety without a 2'-modification is a linkage having the structure of formula I. In some embodiments, a 3'-internucleotidic linkage connected to a sugar moiety without a 2'-modification is phosphorothioate linkage. In some embodiments, a 3'-internucleotidic linkage connected to a sugar moiety without a 2'-modification is a substituted phosphorothioate linkage. In some embodiments, a 3'-internucleotidic linkage connected to a sugar moiety without a 2'-modification is a phosphorothioate triester linkage. In some embodiments, each 3'-internucleotidic linkage connected to a sugar moiety without a 2'-modification is a modified linkage. In some embodiments, each 3'-internucleotidic linkage connected to a sugar moiety without a 2'-modification is a linkage having the structure of formula I. In some embodiments, each 3'-internucleotidic linkage connected to a sugar moiety without a 2'-modification is phosphorothioate linkage. In some embodiments, each 3'-internucleotidic linkage connected to a sugar moiety without a 2'-modification is a substituted phosphorothioate linkage. In some embodiments, each 3'-internucleotidic linkage connected to a sugar moiety without a 2'-modification is a phosphorothioate triester linkage.

In some embodiments, both internucleotidic linkages connected to a sugar moiety without a 2'-modification are modified linkages. In some embodiments, both internucleotidic linkages connected to a sugar moiety without a 2'-modification are linkage having the structure of formula I. In some embodiments, both internucleotidic linkages connected to a sugar moiety without a 2'-modification are phosphorothioate linkages. In some embodiments, both internucleotidic linkages connected to a sugar moiety without a 2'-modification are substituted phosphorothioate linkages. In some embodiments, both internucleotidic linkages connected to a sugar moiety without a 2'-modification are phosphorothioate triester linkages. In some embodiments, each internucleotidic linkage connected to a sugar moiety without a 2'-modification is a modified linkage. In some embodiments, each internucleotidic linkage connected to a sugar moiety without a 2'-modification is a linkage having the structure of formula I. In some embodiments, each internucleotidic linkage connected to a sugar moiety without a 2'-modification is phosphorothioate linkage. In some embodiments, each internucleotidic linkage connected to a sugar moiety without a 2'-modification is a substituted phosphorothioate linkage. In some embodiments, each internucleotidic linkage connected to a sugar moiety without a 2'-modification is a phosphorothioate triester linkage.

In some embodiments, a sugar moiety without a 2'-modification is a sugar moiety found in a natural DNA nucleoside.

In some embodiments, for a wing-core-wing structure, the 5'-end wing comprises only one chiral internucleotidic linkage. In some embodiments, for a wing-core-wing structure, the 5'-end wing comprises only one chiral internucleotidic linkage at the 5'-end of the wing. In some embodiments, for a wing-core-wing structure, the 3'-end wing comprises only one chiral internucleotidic linkage. In some embodiments, for a wing-core-wing structure, the 3'-end wing comprises only one chiral internucleotidic linkage at the 3'-end of the wing. In some embodiments, for a wing-core-wing structure, each wing comprises only one chiral internucleotidic linkage. In some embodiments, for a wing-core-wing structure, each wing comprises only one chiral internucleotidic linkage, wherein the 5'-end wing comprises only one chiral internucleotidic linkage at its 5'-end; and the 3'-end wing comprises only one chiral internucleotidic linkage at its 3'-end. In some embodiments, the only chiral internucleotidic linkage in the 5'-wing is Rp. In some embodiments, the only chiral internucleotidic linkage in the 5'-wing is Sp. In some embodiments, the only chiral internucleotidic linkage in the 3'-wing is Rp. In some embodiments, the only chiral internucleotidic linkage in the 3'-wing is Sp. In some embodiments, the only chiral internucleotidic linkage in both the 5'- and the 3'-wings are Sp. In some embodiments, the only chiral internucleotidic linkage in both the 5'- and the 3'-wings are Rp. In some embodiments, the only chiral internucleotidic linkage in the 5'-wing is Sp, and the only chiral internucleotidic linkage in the 3'-wing is Rp. In some embodiments, the only chiral internucleotidic linkage in the 5'-wing is Rp, and the only chiral internucleotidic linkage in the 3'-wing is Sp.

In some embodiments, a wing comprises two chiral internucleotidic linkages. In some embodiments, a wing comprises only two chiral internucleotidic linkages, and one or more natural phosphate linkages. In some embodiments, a wing comprises only two chiral internucleotidic linkages, and two or more natural phosphate linkages. In some embodiments, a wing comprises only two chiral internucleotidic linkages, and two or more consecutive natural phosphate linkages. In some embodiments, a wing comprises only two chiral internucleotidic linkages, and two consecutive natural phosphate linkages. In some embodiments, a wing comprises only two chiral internucleotidic linkages, and three consecutive natural phosphate linkages. In some embodiments, a 5'-wing (to a core) comprises only two chiral internucleotidic linkages, one at its 5'-end and the other at its 3'-end, with one or more natural phosphate linkages in between. In some embodiments, a 5'-wing (to a core) comprises only two chiral internucleotidic linkages, one at its 5'-end and the other at its 3'-end, with two or more natural phosphate linkages in between. In some embodiments, a 3'-wing (to a core) comprises only two chiral internucleotidic linkages, one at its 3'-end and the other at its 3'-end, with one or more natural phosphate linkages in between. In some embodiments, a 3'-wing (to a core) comprises only two chiral internucleotidic linkages, one at its 3'-end and the other at its 3'-end, with two or more natural phosphate linkages in between.

In some embodiments, a 5'-wing comprises only two chiral internucleotidic linkages, one at its 5'-end and the other at its 3'-end, with one or more natural phosphate linkages in between, and the 3'-wing comprise only one internucleotidic linkage at its 3'-end. In some embodiments, a 5'-wing (to a core) comprises only two chiral internucleotidic linkages, one at its 5'-end and the other at its 3'-end, with two or more natural phosphate linkages in between, and the 3'-wing comprise only one internucleotidic linkage at its 3'-end. In some embodiments, each chiral internucleotidic linkage independently has its own stereochemistry. In some embodiments, both chiral internucleotidic linkages in the 5'-wing have the same stereochemistry. In some embodiments, both chiral internucleotidic linkages in the 5'-wing have different stereochemistry. In some embodiments, both chiral internucleotidic linkages in the 5'-wing are Rp. In some embodiments, both chiral internucleotidic linkages in the 5'-wing are Sp. In some embodiments, chiral internucleotidic linkages in the 5'- and 3'-wings have the same stereochemistry. In some embodiments, chiral internucleotidic linkages in the 5'- and 3'-wings are Rp. In some embodiments, chiral internucleotidic linkages in the 5'- and 3'-wings are Sp. In some embodiments, chiral internucleotidic linkages in the 5'- and 3'-wings have different stereochemistry.

In some embodiments, a chiral, modified phosphate linkage is a chiral phosphorothioate linkage, i.e., phosphorothioate internucleotidic linkage. In some embodiments, a wing region comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10%, 20%, 30%, 40%, 50%, 60%, 70%, 80%, or 90% chiral phosphorothioate internucleotidic linkages of a wing region are of the Sp conformation. In some embodiments, at least about 10% chiral phosphorothioate internucleotidic linkages of a wing region are of the Sp conformation. In some embodiments, at least about 20% chiral phosphorothioate internucleotidic linkages of a wing region are of the Sp conformation. In some embodiments, at least about 30% chiral phosphorothioate internucleotidic linkages of a wing region are of the Sp conformation. In some embodiments, at least about 40% chiral phosphorothioate internucleotidic linkages of a wing region are of the Sp conformation. In some embodiments, at least about 50% chiral phosphorothioate internucleotidic linkages of a wing region are of the Sp conformation. In some embodiments, at least about 60% chiral phosphorothioate internucleotidic linkages of a wing region are of the Sp conformation. In some embodiments, at least about 70% chiral phosphorothioate internucleotidic linkages of a wing region are of the Sp conformation. In some embodiments, at least about 80% chiral phosphorothioate internucleotidic linkages of a wing region are of the Sp conformation. In some embodiments, at least about 90% chiral phosphorothioate internucleotidic linkages of a wing region are of the Sp conformation. In some embodiments, at least about 95% chiral phosphorothioate internucleotidic linkages of a wing region are of the Sp conformation.

In some embodiments, at least about 10%, 20%, 30%, 40%, 50%, 60%, 70%, 80%, or 90% chiral phosphorothioate internucleotidic linkages of a wing region are of the Rp conformation. In some embodiments, at least about 10% chiral phosphorothioate internucleotidic linkages of a wing region are of the Rp conformation. In some embodiments, at least about 20% chiral phosphorothioate internucleotidic linkages of a wing region are of the Rp conformation. In some embodiments, at least about 30% chiral phosphorothioate internucleotidic linkages of a wing region are of the Rp conformation. In some embodiments, at least about 40% chiral phosphorothioate internucleotidic linkages of a wing region are of the Rp conformation. In some embodiments, at least about 50% chiral phosphorothioate internucleotidic linkages of a wing region are of the Rp conformation. In some embodiments, at least about 60% chiral phosphorothioate internucleotidic linkages of a wing region are of the Rp conformation. In some embodiments, at least about 70% chiral phosphorothioate internucleotidic linkages of a wing region are of the Rp conformation. In some embodiments, at least about 80% chiral phosphorothioate internucleotidic linkages of a wing region are of the Rp conformation. In some embodiments, at least about 90% chiral phosphorothioate internucleotidic linkages of a wing region are of the Rp conformation. In some embodiments, at least about 95% chiral phosphorothioate internucleotidic linkages of a wing region are of the Rp conformation.

In some embodiments, less than about 10%, 20%, 30%, 40%, 50%, 60%, 70%, 80%, or 90% chiral phosphorothioate internucleotidic linkages of a wing region are of the Rp conformation. In some embodiments, less than about 10% chiral phosphorothioate internucleotidic linkages of a wing region are of the Rp conformation. In some embodiments, less than about 20% chiral phosphorothioate internucleotidic linkages of a wing region are of the Rp conformation. In some embodiments, less than about 30% chiral phosphorothioate internucleotidic linkages of a wing region are of the Rp conformation. In some embodiments, less than about 40% chiral phosphorothioate internucleotidic linkages of a wing region are of the Rp conformation. In some embodiments, less than about 50% chiral phosphorothioate internucleotidic linkages of a wing region are of the Rp conformation. In some embodiments, less than about 60% chiral phosphorothioate internucleotidic linkages of a wing region are of the Rp conformation. In some embodiments, less than about 70% chiral phosphorothioate internucleotidic linkages of a wing region are of the Rp conformation. In some embodiments, less than about 80% chiral phosphorothioate internucleotidic linkages of a wing region are of the Rp conformation. In some embodiments, less than about 90% chiral phosphorothioate internucleotidic linkages of a wing region are of the Rp conformation. In some embodiments, less than about 95% chiral phosphorothioate internucleotidic linkages of a wing region are of the Rp conformation. In some embodiments, a wing region has only one Rp chiral phosphorothioate internucleotidic linkages. In some embodiments, a wing region has only one Rp chiral phosphorothioate internucleotidic linkages, wherein all internucleotide linkages are chiral phosphorothioate internucleotidic linkages.

In some embodiments, a core region has a length of one or more bases. In some embodiments, a core region has a length of two or more bases. In some embodiments, a core region has a length of three or more bases. In some embodiments, a core region has a length of four or more bases. In some embodiments, a core region has a length of five or more bases. In some embodiments, a core region has a length of six or more bases. In some embodiments, a core region has a length of seven or more bases. In some embodiments, a core region has a length of eight or more bases. In some embodiments, a core region has a length of nine or more bases. In some embodiments, a core region has a length of ten or more bases. In some embodiments, a core region has a length of 11, 12, 13, 14, 15, 16, 17, 18, 19, 20, 25, or more bases. In certain embodiments, a core region has a length of 11 or more bases. In certain embodiments, a core region has a length of 12 or more bases. In certain embodiments, a core region has a length of 13 or more bases. In certain embodiments, a core region has a length of 14 or more bases. In certain embodiments, a core region has a length of 15 or more bases. In certain embodiments, a core region has a length of 16 or more bases. In certain embodiments, a core region has a length of 17 or more bases. In certain embodiments, a core region has a length of 18 or more bases. In certain embodiments, a core region has a length of 19 or more bases. In certain embodiments, a core region has a length of 20 or more bases. In certain embodiments, a core region has a length of more than 20 bases. In certain embodiments, a core region has a length of 2 bases. In certain embodiments, a core region has a length of 3 bases. In certain embodiments, a core region has a length of 4 bases. In certain embodiments, a core region has a length of 5 bases. In certain embodiments, a core region has a length of 6 bases. In certain embodiments, a core region has a length of 7 bases. In certain embodiments, a core region has a length of 8 bases. In certain embodiments, a core region has a length of 9 bases. In certain embodiments, a core region has a length of 10 bases. In certain embodiments, a core region has a length of 11 bases. In certain embodiments, a core region has a length of 12 bases. In certain embodiments, a core region has a length of 13 bases. In certain embodiments, a core region has a length of 14 bases. In certain embodiments, a core region has a length of 15 bases. In certain embodiments, a core region has a length of 16 bases. In certain embodiments, a core region has a length of 17 bases. In certain embodiments, a core region has a length of 18 bases. In certain embodiments, a core region has a length of 19 bases. In certain embodiments, a core region has a length of 20 bases.

In some embodiments, a core comprises one or more modified internucleotidic linkages. In some embodiments, a core comprises one or more natural phosphate linkages. In some embodiments, a core independently comprises one or more modified internucleotidic linkages and one or more natural phosphate linkages. In some embodiments, a core comprises no natural phosphate linkages. In some embodiments, each core linkage is a modified internucleotidic linkage.

In some embodiments, a core comprises at least one natural phosphate linkage. In some embodiments, a core comprises at least two modified internucleotidic linkages. In some embodiments, a core comprises at least three modified internucleotidic linkages. In some embodiments, a core comprises at least four modified internucleotidic linkages. In some embodiments, a core comprises at least five modified internucleotidic linkages. In some embodiments, a core comprises at least six modified internucleotidic linkages. In some embodiments, a core comprises at least seven modified internucleotidic linkages. In some embodiments, a core comprises at least eight modified internucleotidic linkages. In some embodiments, a core comprises at least nine modified internucleotidic linkages. In some embodiments, a core comprises at least ten modified internucleotidic linkages. In some embodiments, a core comprises at least 11 modified internucleotidic linkages. In some embodiments, a core comprises at least 12 modified internucleotidic linkages. In some embodiments, a core comprises at least 13 modified internucleotidic linkages. In some embodiments, a core comprises at least 14 modified internucleotidic linkages. In some embodiments, a core comprises at least 15 modified internucleotidic linkages. In some embodiments, a core comprises at least 16 modified internucleotidic linkages. In some embodiments, a core comprises at least 17 modified internucleotidic linkages. In some embodiments, a core comprises at least 18 modified internucleotidic linkages. In some embodiments, a core comprises at least 19 modified internucleotidic linkages. In some embodiments, a core comprises at least 20 modified internucleotidic linkages.

In some embodiments, a core comprises one or more chiral internucleotidic linkages. In some embodiments, a core comprises one or more natural phosphate linkages. In some embodiments, a core independently comprises one or more chiral internucleotidic linkages and one or more natural phosphate linkages. In some embodiments, a core comprises no natural phosphate linkages. In some embodiments, each core linkage is a chiral internucleotidic linkage.

In some embodiments, a core comprises at least one natural phosphate linkage. In some embodiments, a core comprises at least two chiral internucleotidic linkages. In some embodiments, a core comprises at least three chiral internucleotidic linkages. In some embodiments, a core comprises at least four chiral internucleotidic linkages. In some embodiments, a core comprises at least five chiral internucleotidic linkages. In some embodiments, a core comprises at least six chiral internucleotidic linkages. In some embodiments, a core comprises at least seven chiral internucleotidic linkages. In some embodiments, a core comprises at least eight chiral internucleotidic linkages. In some embodiments, a core comprises at least nine chiral internucleotidic linkages. In some embodiments, a core comprises at least ten chiral internucleotidic linkages. In some embodiments, a core comprises at least 11 chiral internucleotidic linkages. In some embodiments, a core comprises at least 12 chiral internucleotidic linkages. In some embodiments, a core comprises at least 13 chiral internucleotidic linkages. In some embodiments, a core comprises at least 14 chiral internucleotidic linkages. In some embodiments, a core comprises at least 15 chiral internucleotidic linkages. In some embodiments, a core comprises at least 16 chiral internucleotidic linkages. In some embodiments, a core comprises at least 17 chiral internucleotidic linkages. In some embodiments, a core comprises at least 18 chiral internucleotidic linkages. In some embodiments, a core comprises at least 19 chiral internucleotidic linkages. In some embodiments, a core comprises at least 20 chiral internucleotidic linkages.

In some embodiments, a core comprises one natural phosphate linkage. In some embodiments, a core comprises two chiral internucleotidic linkages. In some embodiments, a core comprises three chiral internucleotidic linkages. In some embodiments, a core comprises four chiral internucleotidic linkages. In some embodiments, a core comprises five chiral internucleotidic linkages. In some embodiments, a core comprises six chiral internucleotidic linkages. In some embodiments, a core comprises seven chiral internucleotidic linkages. In some embodiments, a core comprises eight chiral internucleotidic linkages. In some embodiments, a core comprises nine chiral internucleotidic linkages. In some embodiments, a core comprises ten chiral internucleotidic linkages. In some embodiments, a core comprises 11 chiral internucleotidic linkages. In some embodiments, a core comprises 12 chiral internucleotidic linkages. In some embodiments, a core comprises 13 chiral internucleotidic linkages. In some embodiments, a core comprises 14 chiral internucleotidic linkages. In some embodiments, a core comprises 15 chiral internucleotidic linkages. In some embodiments, a core comprises 16 chiral internucleotidic linkages. In some embodiments, a core comprises 17 chiral internucleotidic linkages. In some embodiments, a core comprises 18 chiral internucleotidic linkages. In some embodiments, a core comprises 19 chiral internucleotidic linkages. In some embodiments, a core comprises 20 chiral internucleotidic linkages.

In some embodiments, a core region has a pattern of backbone chiral centers comprising (Sp)m(Rp)n, (Rp)n(Sp)m, (Np)t(Rp)n(Sp)m, or (Sp)t(Rp)n(Sp)m, wherein each of m, n, t and Np is independently as defined and described in the present disclosure. In some embodiments, a core region has a pattern of backbone chiral centers comprising (Sp)m(Rp)n, (Rp)n(Sp)m, (Np)t(Rp)n(Sp)m, or (Sp)t(Rp)n(Sp)m. In some embodiments, a core region has a pattern of backbone chiral centers comprising (Sp)m(Rp)n. In some embodiments, a core region has a pattern of backbone chiral centers comprising (Sp)m(Rp)n, wherein m>2 and n is 1. In some embodiments, a core region has a pattern of backbone chiral centers comprising (Rp)n(Sp)m. In some embodiments, a core region has a pattern of backbone chiral centers comprising (Rp)n(Sp)m, wherein m>2 and n is 1. In some embodiments, a core region has a pattern of backbone chiral centers comprising (Np)t(Rp)n(Sp)m. In some embodiments, a core region has a pattern of backbone chiral centers comprising (Np)t(Rp)n(Sp)m, wherein m>2 and n is 1. In some embodiments, a core region has a pattern of backbone chiral centers comprising (Np)t(Rp)n(Sp)m, wherein t>2, m>2 and n is 1. In some embodiments, a core region has a pattern of backbone chiral centers comprising (Sp)t(Rp)n(Sp)m. In some embodiments, a core region has a pattern of backbone chiral centers comprising (Sp)t(Rp)n(Sp)m, wherein m>2 and n is 1. In some embodiments, a core region has a pattern of backbone chiral centers comprising (Sp)t(Rp)n(Sp)m, wherein t>2, m>2 and n is 1. Among other things, the present disclosure demonstrates that, in some embodiments, such patterns can provide and/or enhance controlled cleavage, improved cleavage rate, selectivity, etc., of a target sequence, e.g., an RNA sequence. Example patterns of backbone chiral centers are described in the present disclosure.

In some embodiments, at least 60% of the chiral internucleotidic linkages in the core region are Sp. In some embodiments, at least 65% of the chiral internucleotidic linkages in the core region are Sp. In some embodiments, at least 66% of the chiral internucleotidic linkages in the core region are Sp. In some embodiments, at least 67% of the chiral internucleotidic linkages in the core region are Sp. In some embodiments, at least 70% of the chiral internucleotidic linkages in the core region are Sp. In some embodiments, at least 75% of the chiral internucleotidic linkages in the core region are Sp. In some embodiments, at least 80% of the chiral internucleotidic linkages in the core region are Sp. In some embodiments, at least 85% of the chiral internucleotidic linkages in the core region are Sp. In some embodiments, at least 90% of the chiral internucleotidic linkages in the core region are Sp. In some embodiments, at least 95% of the chiral internucleotidic linkages in the core region are Sp.

In some embodiments, a wing-core-wing (i.e., X-Y-X) motif is represented numerically as, e.g., 5-10-4, meaning the wing to the 5'-end of the core is 5 bases in length, the core region is 10 bases in length, and the wing region to the 3'-end of the core is 4-bases in length. In some embodiments, a wing-core-wing motif is any of, e.g. 2-16-2, 3-14-3, 4-12-4, 5-10-5, 2-9-6, 3-9-3, 3-9-4, 3-9-5, 4-7-4, 4-9-3, 4-9-4, 4-9-5, 4-10-5, 4-11-4, 4-11-5, 5-7-5, 5-8- 6, 8-7-5, 7-7-6, 5-9-3, 5-9-5, 5-10-4, 5-10-5, 6-7-6, 6-8-5, and 6-9-2, etc. In certain embodiments, a wing-core-wing motif is 5-10-5. In certain embodiments, a wing-core-wing motif is 7-7-6. In certain embodiments, a wing-core-wing motif is 8-7-5.

In some embodiments, a wing-core motif is 5-15, 6-14, 7-13, 8-12, 9-12, etc. In some embodiments, a core-wing motif is 5-15, 6-14, 7-13, 8-12, 9-12, etc.

In some embodiments, the internucleosidic linkages of provided oligonucleotides of such wing-core-wing (i.e., X-Y-X) motifs are all chiral, modified phosphate linkages. In some embodiments, the internucleosidic linkages of provided oligonucleotides of such wing-core-wing (i.e., X-Y-X) motifs are all chiral phosphorothioate internucleotidic linkages. In some embodiments, chiral internucleotidic linkages of provided oligonucleotides of such wing-core-wing motifs are at least about 10, 20, 30, 40, 50, 50, 70, 80, or 90% chiral, modified phosphate internucleotidic linkages. In some embodiments, chiral internucleotidic linkages of provided oligonucleotides of such wing-core-wing motifs are at least about 10, 20, 30, 40, 50, 60, 70, 80, or 90% chiral phosphorothioate internucleotidic linkages. In some embodiments, chiral internucleotidic linkages of provided oligonucleotides of such wing-core-wing motifs are at least about 10, 20, 30, 40, 50, 50, 70, 80, or 90% chiral phosphorothioate internucleotidic linkages of the Sp conformation.

In some embodiments, each wing region of a wing-core-wing motif optionally contains chiral, modified phosphate internucleotidic linkages. In some embodiments, each wing region of a wing-core-wing motif optionally contains chiral phosphorothioate internucleotidic linkages. In some embodiments, each wing region of a wing-core-wing motif contains chiral phosphorothioate internucleotidic linkages. In some embodiments, the two wing regions of a wing-core-wing motif have the same internucleotidic linkage stereochemistry. In some embodiments, the two wing regions have different internucleotidic linkage stereochemistry. In some embodiments, each internucleotidic linkage in the wings is independently a chiral internucleotidic linkage.

In some embodiments, the core region of a wing-core-wing motif optionally contains chiral, modified phosphate internucleotidic linkages. In some embodiments, the core region of a wing-core-wing motif optionally contains chiral phosphorothioate internucleotidic linkages. In some embodiments, the core region of a wing-core-wing motif comprises a repeating pattern of internucleotidic linkage stereochemistry. In some embodiments, the core region of a wing-core-wing motif has a repeating pattern of internucleotidic linkage stereochemistry. In some embodiments, the core region of a wing-core-wing motif comprises repeating pattern of internucleotidic linkage stereochemistry, wherein the repeating pattern is (Sp)mRp or Rp(Sp)m, wherein m is 1-50. In some embodiments, the core region of a wing-core-wing motif comprises repeating pattern of internucleotidic linkage stereochemistry, wherein the repeating pattern is (Sp)mRp or Rp(Sp)m, wherein m is 1-50. In some embodiments, the core region of a wing-core-wing motif comprises repeating pattern of internucleotidic linkage stereochemistry, wherein the repeating pattern is (Sp)mRp, wherein m is 1-50. In some embodiments, the core region of a wing-core-wing motif comprises repeating pattern of internucleotidic linkage stereochemistry, wherein the repeating pattern is Rp(Sp)m, wherein m is 1-50. In some embodiments, the core region of a wing-core-wing motif has repeating pattern of internucleotidic linkage stereochemistry, wherein the repeating pattern is (Sp)mRp or Rp(Sp)m, wherein m is 1-50. In some embodiments, the core region of a wing-core-wing motif has repeating pattern of internucleotidic linkage stereochemistry, wherein the repeating pattern is (Sp)mRp, wherein m is 1-50. In some embodiments, the core region of a wing-core-wing motif has repeating pattern of internucleotidic linkage stereochemistry, wherein the repeating pattern is Rp(Sp)m, wherein m is 1-50. In some embodiments, the core region of a wing-core-wing motif has repeating pattern of internucleotidic linkage stereochemistry, wherein the repeating pattern is a motif comprising at least 33% of internucleotidic linkage in the S conformation. In some embodiments, the core region of a wing-core-wing motif has repeating pattern of internucleotidic linkage stereochemistry, wherein the repeating pattern is a motif comprising at least 50% of internucleotidic linkage in the S conformation. In some embodiments, the core region of a wing-core-wing motif has repeating pattern of internucleotidic linkage stereochemistry, wherein the repeating pattern is a motif comprising at least 66% of internucleotidic linkage in the S conformation. In some embodiments, the core region of a wing-core-wing motif has repeating pattern of internucleotidic linkage stereochemistry, wherein the repeating pattern is a repeating triplet motif selected from RpRpSp and SpSpRp. In some embodiments, the core region of a wing-core-wing motif has repeating pattern of internucleotidic linkage stereochemistry, wherein the repeating pattern is a repeating RpRpSp. In some embodiments, the core region of a wing-core-wing motif has repeating pattern of internucleotidic linkage stereochemistry, wherein the repeating pattern is a repeating SpSpRp.

In some embodiments, the present disclosure provides a chirally controlled oligonucleotide composition of an oligonucleotide type whose pattern of backbone chiral centers in the core region comprises (Sp)mRp or Rp(Sp)m. In some embodiments, the present disclosure provides a chirally controlled oligonucleotide composition of an oligonucleotide type whose pattern of backbone chiral centers in the core region comprises Rp(Sp)m. In some embodiments, the present disclosure provides a chirally controlled oligonucleotide composition of an oligonucleotide type whose pattern of backbone chiral centers in the core region comprises (Sp)mRp. In some embodiments, m is 2. In some embodiments, the present disclosure provides a chirally controlled oligonucleotide composition of an oligonucleotide type whose pattern of backbone chiral centers in the core region comprises $Rp(Sp)_2$. In some embodiments, the present disclosure provides a chirally controlled oligonucleotide composition of an oligonucleotide type whose pattern of backbone chiral centers in the core region comprises $(Sp)_2Rp(Sp)_2$. In some embodiments, the present disclosure provides a chirally controlled oligonucleotide composition of an oligonucleotide type whose pattern of backbone chiral centers in the core region comprises $(Rp)_2Rp(Sp)_2$. In some embodiments, the present disclosure provides a chirally controlled oligonucleotide composition of an oligonucleotide type whose pattern of backbone chiral centers in the core region comprises $RpSpRp(Sp)_2$. In some embodiments, the present disclosure provides a chirally controlled oligonucleotide composition of an oligonucleotide type whose pattern of backbone chiral centers in the core region comprises $SpRpRp(Sp)_2$. In some embodiments, the present disclosure provides a chirally controlled oligonucleotide composition of an oligonucleotide type whose pattern of backbone chiral centers in the core region comprises $(Sp)_2Rp$.

In some embodiments, the present disclosure provides a chirally controlled oligonucleotide composition of an oligonucleotide type whose pattern of backbone chiral centers comprises (Sp)mRp or Rp(Sp)m. In some embodiments, the present disclosure provides a chirally controlled oligonucleotide composition of an oligonucleotide type whose pattern of backbone chiral centers comprises Rp(Sp)m. In some embodiments, the present disclosure provides a chirally controlled oligonucleotide composition of an oligonucleotide type whose pattern of backbone chiral centers comprises (Sp)mRp. In some embodiments, m is 2. In some embodiments, the present disclosure provides a chirally controlled oligonucleotide composition of an oligonucleotide type whose pattern of backbone chiral centers comprises $Rp(Sp)_2$. In some embodiments, the present disclosure provides a chirally controlled oligonucleotide composition of an oligonucleotide type whose pattern of backbone chiral centers comprises $(Sp)_2Rp(Sp)_2$. In some embodiments, the present disclosure provides a chirally controlled oligonucleotide composition of an oligonucleotide type whose pattern of backbone chiral centers comprises $(Rp)_2Rp(Sp)_2$. In some embodiments, the present disclosure provides a chirally controlled oligonucleotide composition of an oligonucleotide type whose pattern of backbone chiral centers comprises $RpSpRp(Sp)_2$. In some embodiments, the present disclosure provides a chirally controlled oligonucleotide composition of an oligonucleotide type whose pattern of backbone chiral centers comprises $SpRpRp(Sp)_2$. In some embodiments, the present disclosure provides a chirally controlled oligonucleotide composition of an oligonucleotide type whose pattern of backbone chiral centers comprises $(Sp)_2Rp$.

As defined herein, m is 1-50. In some embodiments, m is 1. In some embodiments, m is 2-50. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is greater than 25.

In some embodiments, a repeating pattern is (Sp)m(Rp)n, wherein n is 1-10, and m is independently as defined above and described herein. In some embodiments, the present disclosure provides a chirally controlled oligonucleotide composition of an oligonucleotide type whose pattern of backbone chiral centers comprises (Sp)m(Rp)n. In some embodiments, the present disclosure provides a chirally controlled oligonucleotide composition of an oligonucleotide type whose pattern of backbone chiral centers in the core region comprises (Sp)m(Rp)n. In some embodiments, a repeating pattern is (Rp)n(Sp)m, wherein n is 1-10, and m is independently as defined above and described herein. In some embodiments, the present disclosure provides a chirally controlled oligonucleotide composition of an oligonucleotide type whose pattern of backbone chiral centers comprises (Rp)n(Sp)m. In some embodiments, the present disclosure provides a chirally controlled oligonucleotide composition of an oligonucleotide type whose pattern of backbone chiral centers in the core region comprises (Rp)n(Sp)m. In some embodiments, (Rp)n(Sp)m is $(Rp)(Sp)_2$. In some embodiments, (Sp)n (Rp)m is $(Sp)_2(Rp)$.

In some embodiments, the present disclosure provides a chirally controlled oligonucleotide composition of an oligonucleotide type whose pattern of backbone chiral centers comprises (Sp)m(Rp)n(Sp)t. In some embodiments, a repeating pattern is (Sp)m(Rp)n(Sp)t, wherein n is 1-10, t is 1-50, and m is as defined above and described herein. In some embodiments, the present disclosure provides a chirally controlled oligonucleotide composition of an oligonucleotide type whose pattern of backbone chiral centers in the core region comprises (Sp)m(Rp)n(Sp)t. In some embodiments, a repeating pattern is (Sp)t(Rp)n(Sp)m, wherein n is 1-10, t is 1-50, and m is as defined above and described herein. In some embodiments, the present disclosure provides a chirally controlled oligonucleotide composition of an oligonucleotide type whose pattern of backbone chiral centers comprises (Sp)t(Rp)n(Sp)m. In some embodiments, the present disclosure provides a chirally controlled oligonucleotide composition of an oligonucleotide type whose pattern of backbone chiral centers in the core region comprises (Sp)t(Rp)n(Sp)m.

In some embodiments, a repeating pattern is (Np)t(Rp)n (Sp)m, wherein n is 1-10, t is 1-50, Np is independently Rp or Sp, and m is as defined above and described herein. In some embodiments, the present disclosure provides a chirally controlled oligonucleotide composition of an oligonucleotide type whose pattern of backbone chiral centers comprises (Np)t(Rp)n(Sp)m. In some embodiments, the present disclosure provides a chirally controlled oligonucleotide composition of an oligonucleotide type whose pattern of backbone chiral centers in the core region comprises (Np)t(Rp)n(Sp)m. In some embodiments, a repeating pattern is (Np)m(Rp)n(Sp)t, wherein n is 1-10, t is 1-50, Np is independently Rp or Sp, and m is as defined above and described herein. In some embodiments, the present disclosure provides a chirally controlled oligonucleotide composition of an oligonucleotide type whose pattern of backbone chiral centers comprises (Np)m(Rp)n(Sp)t. In some embodiments, the present disclosure provides a chirally controlled oligonucleotide composition of an oligonucleotide type whose pattern of backbone chiral centers in the core region comprises (Np)m(Rp)n(Sp)t. In some embodiments, Np is Rp. In some embodiments, Np is Sp. In some embodiments, all Np are the same. In some embodiments, all Np are Sp. In some embodiments, at least one Np is different from the other Np. In some embodiments, t is 2.

As defined herein, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

As defined herein, t is 1-50. In some embodiments, t is 1. In some embodiments, t is 2-50. In some embodiments, t is 2, 3, 4, 5, 6, 7 or 8. In some embodiments, t is 3, 4, 5, 6, 7 or 8. In some embodiments, t is 4, 5, 6, 7 or 8. In some embodiments, t is 5, 6, 7 or 8. In some embodiments, t is 6, 7 or 8. In some embodiments, t is 7 or 8. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20. In some embodiments, t is 21. In some embodiments, t is 22. In some embodiments, t is 23. In some embodiments, t is 24. In some embodiments, t is 25. In some embodiments, t is greater than 25.

In some embodiments, at least one of m and t is greater than 2. In some embodiments, at least one of m and t is greater than 3. In some embodiments, at least one of m and t is greater than 4. In some embodiments, at least one of m and t is greater than 5. In some embodiments, at least one of m and t is greater than 6. In some embodiments, at least one of m and t is greater than 7. In some embodiments, at least one of m and t is greater than 8. In some embodiments, at least one of m and t is greater than 9. In some embodiments, at least one of m and t is greater than 10. In some embodiments, at least one of m and t is greater than 11. In some embodiments, at least one of m and t is greater than 12. In some embodiments, at least one of m and t is greater than 13. In some embodiments, at least one of m and t is greater than 14. In some embodiments, at least one of m and t is greater than 15. In some embodiments, at least one of m and t is greater than 16. In some embodiments, at least one of m and t is greater than 17. In some embodiments, at least one of m and t is greater than 18. In some embodiments, at least one of m and t is greater than 19. In some embodiments, at least one of m and t is greater than 20. In some embodiments, at least one of m and t is greater than 21. In some embodiments, at least one of m and t is greater than 22. In some embodiments, at least one of m and t is greater than 23. In some embodiments, at least one of m and t is greater than 24. In some embodiments, at least one of m and t is greater than 25.

In some embodiments, each one of m and t is greater than 2. In some embodiments, each one of m and t is greater than 3. In some embodiments, each one of m and t is greater than 4. In some embodiments, each one of m and t is greater than 5. In some embodiments, each one of m and t is greater than 6. In some embodiments, each one of m and t is greater than 7. In some embodiments, each one of m and t is greater than 8. In some embodiments, each one of m and t is greater than 9. In some embodiments, each one of m and t is greater than 10. In some embodiments, each one of m and t is greater than 11. In some embodiments, each one of m and t is greater than 12. In some embodiments, each one of m and t is greater than 13. In some embodiments, each one of m and t is greater than 14. In some embodiments, each one of m and t is greater than 15. In some embodiments, each one of m and t is greater than 16. In some embodiments, each one of m and t is greater than 17. In some embodiments, each one of m and t is greater than 18. In some embodiments, each one of m and t is greater than 19. In some embodiments, each one of m and t is greater than 20.

In some embodiments, the sum of m and t is greater than 3. In some embodiments, the sum of m and t is greater than 4. In some embodiments, the sum of m and t is greater than 5. In some embodiments, the sum of m and t is greater than 6. In some embodiments, the sum of m and t is greater than 7. In some embodiments, the sum of m and t is greater than 8. In some embodiments, the sum of m and t is greater than 9. In some embodiments, the sum of m and t is greater than 10. In some embodiments, the sum of m and t is greater than 11. In some embodiments, the sum of m and t is greater than 12. In some embodiments, the sum of m and t is greater than 13. In some embodiments, the sum of m and t is greater than 14. In some embodiments, the sum of m and t is greater than 15. In some embodiments, the sum of m and t is greater than 16. In some embodiments, the sum of m and t is greater than 17. In some embodiments, the sum of m and t is greater than 18. In some embodiments, the sum of m and t is greater than 19. In some embodiments, the sum of m and t is greater than 20. In some embodiments, the sum of m and t is greater than 21. In some embodiments, the sum of m and t is greater than 22. In some embodiments, the sum of m and t is greater than 23. In some embodiments, the sum of m and t is greater than 24. In some embodiments, the sum of m and t is greater than 25.

In some embodiments, n is 1, and at least one of m and t is greater than 1. In some embodiments, n is 1 and each of m and t is independently greater than 1. In some embodiments, m>n and t>n. In some embodiments, (Sp)m(Rp)n (Sp)t is $(Sp)_2Rp(Sp)_2$. In some embodiments, (Sp)t(Rp)n (Sp)m is $(Sp)_2Rp(Sp)_2$. In some embodiments, (Sp)t(Rp)n (Sp)m is $SpRp(Sp)_2$. In some embodiments, (Np)t(Rp)n (Sp)m is (Np)tRp(Sp)m. In some embodiments, (Np)t(Rp)n (Sp)m is $(Np)_2Rp(Sp)m$. In some embodiments, (Np)t(Rp)n (Sp)m is $(Rp)_2Rp(Sp)m$. In some embodiments, (Np)t(Rp)n (Sp)m is $(Sp)_2Rp(Sp)m$. In some embodiments, (Np)t(Rp)n (Sp)m is RpSpRp(Sp)m. In some embodiments, (Np)t(Rp)n (Sp)m is SpRpRp(Sp)m.

In some embodiments, (Sp)t(Rp)n(Sp)m is SpRpSpSp. In some embodiments, (Sp)t(Rp)n(Sp)m is $(Sp)_2Rp(Sp)_2$. In some embodiments, (Sp)t(Rp)n(Sp)m is $(Sp)_3Rp(Sp)_3$. In some embodiments, (Sp)t(Rp)n(Sp)m is $(Sp)_4Rp(Sp)_4$. In some embodiments, (Sp)t(Rp)n(Sp)m is $(Sp)tRp(Sp)_5$. In some embodiments, (Sp)t(Rp)n(Sp)m is $SpRp(Sp)_5$. In some embodiments, (Sp)t(Rp)n(Sp)m is $(Sp)_2Rp(Sp)_5$. In some embodiments, (Sp)t(Rp)n(Sp)m is $(Sp)_3Rp(Sp)_5$. In some embodiments, (Sp)t(Rp)n(Sp)m is $(Sp)_4Rp(Sp)_5$. In some embodiments, (Sp)t(Rp)n(Sp)m is $(Sp)_5Rp(Sp)_5$.

In some embodiments, (Sp)m(Rp)n(Sp)t is $(Sp)_2Rp(Sp)_2$. In some embodiments, (Sp)m(Rp)n(Sp)t is $(Sp)_3Rp(Sp)_3$. In some embodiments, (Sp)m(Rp)n(Sp)t is $(Sp)_4Rp(Sp)_4$. In some embodiments, (Sp)m(Rp)n(Sp)t is $(Sp)mRp(Sp)_5$. In some embodiments, (Sp)m(Rp)n(Sp)t is $(Sp)_2Rp(Sp)_5$. In some embodiments, (Sp)m(Rp)n(Sp)t is $(Sp)_3Rp(Sp)_5$. In some embodiments, (Sp)m(Rp)n(Sp)t is $(Sp)_4Rp(Sp)_5$. In some embodiments, (Sp)m(Rp)n(Sp)t is $(Sp)_5Rp(Sp)_5$.

In some embodiments, the core region comprises at least one Rp internucleotidic linkage. In some embodiments, the core region of a wing-core-wing motif comprises at least one Rp internucleotidic linkage. In some embodiments, a core region comprises at least one Rp phosphorothioate internucleotidic linkage. In some embodiments, the core region of a wing-core-wing motif comprises at least one Rp phosphorothioate internucleotidic linkage. In some embodiments, the core region of a wing-core-wing motif comprises only one Rp phosphorothioate internucleotidic linkage. In some embodiments, a core region motif comprises at least two Rp internucleotidic linkages. In some embodiments, the core region of a wing-core-wing motif comprises at least two Rp internucleotidic linkages. In some embodiments, the core region of a wing-core-wing motif comprises at least two Rp phosphorothioate internucleotidic linkages. In some embodiments, a core region comprises at least three Rp internucleotidic linkages. In some embodiments, the core region of a wing-core-wing motif comprises at least three Rp internucleotidic linkages. In some embodiments, the core region comprises at least three Rp phosphorothioate internucleotidic linkages. In some embodiments, the core region of a wing-core-wing motif comprises at least three Rp phosphorothioate internucleotidic linkages. In some embodiments, a core region comprises at least 4, 5, 6, 7, 8, 9, or 10 Rp internucleotidic linkages. In some embodiments, the core region of a wing-core-wing motif comprises at least 4, 5, 6, 7, 8, 9, or 10 Rp internucleotidic linkages. In some embodiments, a core region comprises at least 4, 5, 6, 7, 8, 9, or 10 Rp phosphorothioate internucleotidic linkages. In some embodiments, the core region of a wing-core-wing motif comprises at least 4, 5, 6, 7, 8, 9, or 10 Rp phosphorothioate internucleotidic linkages.

In certain embodiments, a wing-core-wing motif is a 5-10-5 motif wherein the residues at each wing region are 2'-modified residues. In certain embodiments, a wing-core-wing motif is a 5-10-5 motif wherein the residues at each wing region are 2'-$OR^1$-modified residues. In certain embodiments, a wing-core-wing motif is a 5-10-5 motif wherein the residues at each wing region are 2'-MOE-modified residues. In certain embodiments, a wing-core-wing motif is a 5-10-5 motif wherein the residues at each wing region are 2'-OMe-modified residues. In certain embodiments, a wing-core-wing motif is a 5-10-5 motif wherein the residues in the core region are 2'-deoxyribonucleoside residues. In certain embodiments, a wing-core-wing motif is a 5-10-5 motif, wherein all internucleotidic linkages are phosphorothioate linkages. In certain embodiments, a wing-core-wing motif is a 5-10-5 motif, wherein all internucleotidic linkages are chiral phosphorothioate linkages. In certain embodiments, a wing-core-wing motif is a 5-10-5 motif wherein the residues at each wing region are 2'-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-$OR^1$-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-MOE-modified residues, the residues in the core region are 2'-deoxyribonucleoside residues, and all internucleotidic linkages in the core region are chiral phosphorothioate linkages. In certain embodiments, a wing-core-wing motif is a 5-10-5 motif wherein the residues at each wing region are 2'-OMe-modified residues, the residues in the core region are 2'-deoxyribonucleoside residues, and all internucleotidic linkages in the core region are chiral phosphorothioate linkages.

In some embodiments, residues at the "X" wing region are not 2'-MOE-modified residues. In certain embodiments, a wing-core motif is a motif wherein the residues at the "X" wing region are not 2'-MOE-modified residues. In certain embodiments, a core-wing motif is a motif wherein the residues at the "X" wing region are not 2'-MOE-modified residues. In certain embodiments, a wing-core-wing motif is a motif wherein the residues at each "X" wing region are not 2'-MOE-modified residues. In certain embodiments, a wing-core-wing motif is a 5-10-5 motif wherein the residues at each "X" wing region are not 2'-MOE-modified residues. In certain embodiments, a wing-core-wing motif is a 5-10-5 motif wherein the residues in the core "Y" region are 2'-deoxyribonucleoside residues. In certain embodiments, a wing-core-wing motif is a 5-10-5 motif, wherein all internucleotidic linkages are phosphorothioate internucleotidic linkages. In certain embodiments, a wing-core-wing motif is a 5-10-5 motif, wherein all internucleotidic linkages are chiral phosphorothioate internucleotidic linkages. In certain embodiments, a wing-core-wing motif is a 5-10-5 motif wherein the residues at each "X" wing region are not 2'-MOE-modified residues, the residues in the core "Y" region are 2'-deoxyribonucleoside, and all internucleotidic linkages are chiral phosphorothioate internucleotidic linkages.

In some embodiments, a chiral, modified phosphate linkage is a chiral phosphorothioate linkage, i.e., phosphorothioate internucleotidic linkage. In some embodiments, a core region comprises at least 5%, 10%, 15%, 20%, 25%, 30%, 35%, 40%, 45%, 50%, 55%, 60%, 65%, 70%, 75%, 80%, 85%, 90%, 95%, or 100% chiral phosphorothioate internucleotidic linkages. In some embodiments, all chiral, modified phosphate linkages are chiral phosphorothioate internucleotidic linkages. In some embodiments, at least about 10%, 20%, 30%, 40%, 50%, 60%, 70%, 80%, or 90% chiral phosphorothioate internucleotidic linkages of a core region are of the Sp conformation. In some embodiments, at least about 10% chiral phosphorothioate internucleotidic linkages of a core region are of the Sp conformation. In some embodiments, at least about 20% chiral phosphorothioate internucleotidic linkages of a core region are of the Sp conformation. In some embodiments, at least about 30% chiral phosphorothioate internucleotidic linkages of a core region are of the Sp conformation. In some embodiments, at least about 40% chiral phosphorothioate internucleotidic linkages of a core region are of the Sp conformation. In some embodiments, at least about 50% chiral phosphorothioate internucleotidic linkages of a core region are of the Sp conformation. In some embodiments, at least about 60% chiral phosphorothioate internucleotidic linkages of a core region are of the Sp conformation. In some embodiments, at least about 70% chiral phosphorothioate internucleotidic linkages of a core region are of the Sp conformation. In some embodiments, at least about 80% chiral phosphorothioate internucleotidic linkages of a core region are of the Sp conformation. In some embodiments, at least about 90% chiral phosphorothioate internucleotidic linkages of a core region are of the Sp conformation. In some embodiments, at least about 95% chiral phosphorothioate internucleotidic linkages of a core region are of the Sp conformation.

In some embodiments, at least about 10%, 20%, 30%, 40%, 50%, 60%, 70%, 80%, or 90% chiral phosphorothioate internucleotidic linkages of a core region are of the Rp conformation. In some embodiments, at least about 10% chiral phosphorothioate internucleotidic linkages of a core region are of the Rp conformation. In some embodiments, at least about 20% chiral phosphorothioate internucleotidic linkages of a core region are of the Rp conformation. In some embodiments, at least about 30% chiral phosphorothioate internucleotidic linkages of a core region are of the Rp conformation. In some embodiments, at least about 40% chiral phosphorothioate internucleotidic linkages of a core region are of the Rp conformation. In some embodiments, at least about 50% chiral phosphorothioate internucleotidic linkages of a core region are of the Rp conformation. In some embodiments, at least about 60% chiral phosphorothioate internucleotidic linkages of a core region are of the Rp conformation. In some embodiments, at least about 70% chiral phosphorothioate internucleotidic linkages of a core region are of the Rp conformation. In some embodiments, at least about 80% chiral phosphorothioate internucleotidic linkages of a core region are of the Rp conformation. In some embodiments, at least about 90% chiral phosphorothioate internucleotidic linkages of a core region are of the Rp conformation. In some embodiments, at least about 95% chiral phosphorothioate internucleotidic linkages of a core region are of the Rp conformation.

In some embodiments, less than about 10%, 20%, 30%, 40%, 50%, 60%, 70%, 80%, or 90% chiral phosphorothioate internucleotidic linkages of a core region are of the Rp conformation. In some embodiments, less than about 10% chiral phosphorothioate internucleotidic linkages of a core region are of the Rp conformation. In some embodiments, less than about 20% chiral phosphorothioate internucleotidic linkages of a core region are of the Rp conformation. In some embodiments, less than about 30% chiral phosphorothioate internucleotidic linkages of a core region are of the Rp conformation. In some embodiments, less than about 40% chiral phosphorothioate internucleotidic linkages of a core region are of the Rp conformation. In some embodiments, less than about 50% chiral phosphorothioate internucleotidic linkages of a core region are of the Rp conformation. In some embodiments, less than about 60% chiral phosphorothioate internucleotidic linkages of a core region are of the Rp conformation. In some embodiments, less than about 70% chiral phosphorothioate internucleotidic linkages of a core region are of the Rp conformation. In some embodiments, less than about 80% chiral phosphorothioate internucleotidic linkages of a core region are of the Rp conformation. In some embodiments, less than about 90% chiral phosphorothioate internucleotidic linkages of a core region are of the Rp conformation. In some embodiments, less than about 95% chiral phosphorothioate internucleotidic linkages of a core region are of the Rp conformation. In some embodiments, a core region has only one Rp chiral phosphorothioate internucleotidic linkages. In some embodiments, a core region has only one Rp chiral phosphorothioate internucleotidic linkages, wherein all internucleotide linkages are chiral phosphorothioate internucleotidic linkages.

As understood by a person having ordinary skill in the art, provided oligonucleotides and compositions, among other things, can target a great number of nucleic acid polymers. For instance, in some embodiments, provided oligonucleotides and compositions may target a transcript of a nucleic acid sequence, wherein a common base sequence of oligonucleotides (e.g., a base sequence of an oligonucleotide type) comprises or is a sequence complementary to a sequence of the transcript. In some embodiments, a common base sequence comprises a sequence complimentary to a sequence of a target. In some embodiments, a common base sequence is a sequence complimentary to a sequence of a target. In some embodiments, a common base sequence comprises or is a sequence 100% complimentary to a sequence of a target. In some embodiments, a common base sequence comprises a sequence 100% complimentary to a sequence of a target. In some embodiments, a common base sequence is a sequence 100% complimentary to a sequence of a target. In some embodiments, a common base sequence in a core comprises or is a sequence complimentary to a sequence of a target. In some embodiments, a common base sequence in a core comprises a sequence complimentary to a sequence of a target. In some embodiments, a common base sequence in a core is a sequence % complimentary to a sequence of a target. In some embodiments, a common base sequence in a core comprises or is a sequence 100% complimentary to a sequence of a target. In some embodiments, a common base sequence in a core comprises a sequence 100% complimentary to a sequence of a target. In some embodiments, a common base sequence in a core is a sequence 100% complimentary to a sequence of a target.

In some embodiments, as described in this disclosure, provided oligonucleotides and compositions may provide new cleavage patterns, higher cleavage rate, higher cleavage degree, higher cleavage selectivity, etc. In some embodiments, provided compositions can selectively suppress (e.g., cleave) a transcript from a target nucleic acid sequence which has one or more similar sequences exist within a subject or a population, each of the target and its similar sequences contains a specific nucleotidic characteristic sequence element that defines the target sequence relative to the similar sequences. In some embodiments, for example, a target sequence is a wild-type allele or copy of a gene, and a similar sequence is a sequence has very similar base sequence, e.g., a sequence having SNP, mutations, etc.; In some embodiments, a characteristic sequence element defines that target sequence relative to the similar sequence: for example, when a target sequence is a Huntington's disease-causing allele with T at rs362307 (U in the corresponding RNA; C for the non-disease-causing allele), a characteristic sequence comprises this SNP.

In some embodiments, a similar sequence has greater than 60%, 65%, 70%, 75%, 80%, 85%, 90%, 91%, 92%, 93%, 94%, 95%, 96%, 97%, 98% or 99% sequence homology with a target sequence. In some embodiments, a target sequence is a disease-causing copy of a nucleic acid sequence comprising one or more mutations and/or SNPs, and a similar sequence is a copy not causing the disease (wild type). In some embodiments, a target sequence comprises a mutation, wherein a similar sequence is the corresponding wild-type sequence. In some embodiments, a target sequence is a mutant allele, while a similar sequence is a wild-type allele. In some embodiments, a target sequence comprises an SNP that is associated with a disease-causing allele, while a similar sequence comprises the same SNP that is not associates with the disease-causing allele. In some embodiments, the region of a target sequence that is complementary to a common base sequence of a provided oligonucleotide composition has greater than 60%, 65%, 70%, 75%, 80%, 85%, 90%, 91%, 92%, 93%, 94%, 95%, 96%, 97%, 98% or 99% sequence homology with the corresponding region of a similar sequence. In some embodiments, the region of a target sequence that is complementary to a common base sequence of a provided oligonucleotide composition differs from the corresponding region of a similar sequence at less than 5, less than 4, less than 3, less than 2, or only 1 base pairs. In some embodiments, the region of a target sequence that is complementary to a common base sequence of a provided oligonucleotide composition differs from the corresponding region of a similar sequence only at a mutation site or SNP site. In some embodiments, the region of a target sequence that is complementary to a common base sequence of a provided oligonucleotide composition differs from the corresponding region of a similar sequence only at a mutation site. In some embodiments, the region of a target sequence that is complementary to a common base sequence of a provided oligonucleotide composition differs from the corresponding region of a similar sequence only at an SNP site.

In some embodiments, a common base sequence comprises or is a sequence complementary to a characteristic sequence element. In some embodiments, a common base sequence comprises a sequence complementary to a characteristic sequence element. In some embodiments, a common base sequence is a sequence complementary to a characteristic sequence element. In some embodiments, a common base sequence comprises or is a sequence 100% complementary to a characteristic sequence element. In some embodiments, a common base sequence comprises a sequence 100% complementary to a characteristic sequence element. In some embodiments, a common base sequence is a sequence 100% complementary to a characteristic sequence element. In some embodiments, a common base sequence in a core comprises or is a sequence complementary to a characteristic sequence element. In some embodiments, a common base sequence in a core comprises a sequence complementary to a characteristic sequence element. In some embodiments, a common base sequence in a core is a sequence complementary to a characteristic sequence element. In some embodiments, a common base sequence in a core comprises or is a sequence 100% complementary to a characteristic sequence element. In some embodiments, a common base sequence in a core comprises a sequence 100% complementary to a characteristic sequence element. In some embodiments, a common base sequence in a core is a sequence 100% complementary to a characteristic sequence element.

In some embodiments, a characteristic sequence element comprises or is a mutation. In some embodiments, a characteristic sequence element comprises a mutation. In some embodiments, a characteristic sequence element is a mutation. In some embodiments, a characteristic sequence element comprises or is a point mutation. In some embodiments, a characteristic sequence element comprises a point mutation. In some embodiments, a characteristic sequence element is a point mutation. In some embodiments, a characteristic sequence element comprises or is an SNP. In some embodiments, a characteristic sequence element comprises an SNP. In some embodiments, a characteristic sequence element is an SNP.

In some embodiments, a common base sequence 100% matches a target sequence, which it does not 100% match a similar sequence of the target sequence. For example, in some embodiments, a common base sequence matches a mutation in the disease-causing copy or allele of a target nucleic acid sequence, but does not match a non-disease-causing copy or allele at the mutation site; in some other embodiments, a common base sequence matches an SNP in the disease-causing allele of a target nucleic acid sequence, but does not match a non-disease-causing allele at the corresponding site. In some embodiments, a common base sequence in a core 100% matches a target sequence, which it does not 100% match a similar sequence of the target sequence. For example, in WV-1092, its common base sequence (and its common base sequence in its core) matches the disease-causing U, but not the non-disease causing (wild-type) C at rs362307.

Among other things, the present disclosure recognizes that a base sequence may have impact on oligonucleotide properties. In some embodiments, a base sequence may have impact on cleavage pattern of a target when oligonucleotides having the base sequence are utilized for suppressing a target, e.g., through a pathway involving RNase H: for example, FIG. 33 demonstrates that structurally similar (all phosphorothioate linkages, all stereorandom) oligonucleotides have different sequences may have different cleavage patterns. In some embodiments, a common base sequence of a non-stereorandom oligonucleotide compositions (e.g., certain oligonucleotide compositions provided in the present disclosure) is a base sequence that when applied to a DNA oligonucleotide composition (e.g., ONT-415) or a stereorandom all-phosphorothioate oligonucleotide composition (e.g., WV-905), cleavage pattern of the DNA (DNA cleavage pattern) and/or the stereorandom all-phosphorothioate (stereorandom cleavage pattern) composition has a cleavage site within or in the vicinity of a characteristic sequence element. In some embodiments, a cleavage site within or in the vicinity is within a sequence complementary to a core region of a common sequence. In some embodiments, a cleavage site within or in the vicinity is within a sequence 100% complementary to a core region of a common sequence.

In some embodiments, a common base sequence is a base sequence that has a cleavage site within or in the vicinity of a characteristic sequence element in its DNA cleavage pattern. In some embodiments, a common base sequence is a base sequence that has a cleavage site within a characteristic sequence element in its DNA cleavage pattern. In some embodiments, a common base sequence is a base sequence that has a cleavage site in the vicinity of a characteristic sequence element in its DNA cleavage pattern. In some embodiments, a common base sequence is a base sequence that has a cleavage site in the vicinity of a mutation or SNP of a characteristic sequence element in its DNA cleavage pattern. In some embodiments, a common base sequence is a base sequence that has a cleavage site in the vicinity of a mutation in its DNA cleavage pattern. In some embodiments, a common base sequence is a base sequence that has a cleavage site in the vicinity of an SNP in its DNA cleavage pattern.

In some embodiments, a common base sequence is a base sequence that has a cleavage site within or in the vicinity of a characteristic sequence element in its stereorandom cleavage pattern. In some embodiments, a common base sequence is a base sequence that has a cleavage site within a characteristic sequence element in its stereorandom cleavage pattern. In some embodiments, a common base sequence is a base sequence that has a cleavage site in the vicinity of a characteristic sequence element in its stereorandom cleavage pattern. In some embodiments, a common base sequence is a base sequence that has a cleavage site in the vicinity of a mutation or SNP of a characteristic sequence element in its stereorandom cleavage pattern. In some embodiments, a common base sequence is a base sequence that has a cleavage site in the vicinity of a mutation in its stereorandom cleavage pattern. In some embodiments, a common base sequence is a base sequence that has a cleavage site in the vicinity of an SNP in its stereorandom cleavage pattern.

In some embodiments, a common base sequence is a base sequence that has a cleavage site in the vicinity of a mutation of a characteristic sequence element in its DNA and/or stereorandom cleavage pattern. In some embodiments, a common base sequence is a base sequence that has a cleavage site in the vicinity of a mutation in its DNA and/or stereorandom cleavage pattern. In some embodiments, a common base sequence is a base sequence that has a cleavage site in the vicinity of a mutation in its DNA cleavage pattern. In some embodiments, a cleavage site in the vicinity of a mutation is at a mutation, i.e., a cleavage site is at the internucleotidic linkage of a mutated nucleotide (e.g., if a mutation is at A in the target sequence of GGGACGTCTT (SEQ ID NO: 13), the cleavage is between A and C). In some embodiments, a cleavage site in the vicinity is a cleavage site 0, 1, 2, 3, 4, 5, 6, 7, 8, 9, or 10 internucleotidic linkages away from a mutation, where 0 means cleavage at the mutation site (e.g., if a mutation is at A in the target sequence of GGGACGTCTT (SEQ ID NO: 13), the cleavage is between A and C for 0 internucleotidic linkage away; a cleavage site 1 internucleotidic linkage away from the mutation is between G and A to the 5' from the mutation or between C and G to the 3' from the mutation). In some embodiments, a cleavage site in the vicinity is a cleavage site 0, 1, 2, 3, 4, or 5 internucleotidic linkages away from a mutation. In some embodiments, a cleavage site in the vicinity is a cleavage site 0, 1, 2, 3, 4, or 5 internucleotidic linkages away to the 5' from a mutation. In some embodiments, a cleavage site in the vicinity is a cleavage site 0, 1, 2, 3, 4, or 5 internucleotidic linkages away to the 3' from a mutation. In some embodiments, a cleavage site in the vicinity is a cleavage site 0, 1, 2, 3, 4, or 5 internucleotidic linkages away from a mutation. In some embodiments, a cleavage site in the vicinity is a cleavage site 0, 1, 2, 3, 4, or 5 internucleotidic linkages away to the 5' from a mutation. In some embodiments, a cleavage site in the vicinity is a cleavage site 0, 1, 2, 3, 4, or 5 internucleotidic linkages away to the 3' from a mutation. In some embodiments, a cleavage site in the vicinity is a cleavage site 0, 1, 2, 3, or 4 internucleotidic linkages away from a mutation. In some embodiments, a cleavage site in the vicinity is a cleavage site 0, 1, 2, 3, or 4 internucleotidic linkages away to the 5' from a mutation. In some embodiments, a cleavage site in the vicinity is a cleavage site 0, 1, 2, 3, or 4 internucleotidic linkages away to the 3' from a mutation. In some embodiments, a cleavage site in the vicinity is a cleavage site 0, 1, 2, or 3 internucleotidic linkages away from a mutation. In some embodiments, a cleavage site in the vicinity is a cleavage site 0, 1, 2, or 3 internucleotidic linkages away to the 5' from a mutation. In some embodiments, a cleavage site in the vicinity is a cleavage site 0, 1, 2, or 3 internucleotidic linkages away to the 3' from a mutation. In some embodiments, a cleavage site in the vicinity is a cleavage site 0, 1, or 2 internucleotidic linkages away from a mutation. In some embodiments, a cleavage site in the vicinity is a cleavage site 0, 1, or 2 internucleotidic linkages away to the 5' from a mutation. In some embodiments, a cleavage site in the vicinity is a cleavage site 0, 1, or 2 internucleotidic linkages away to the 3' from a mutation. In some embodiments, a cleavage site in the vicinity is a cleavage site 0 or 1 internucleotidic linkage away from a mutation. In some embodiments, a cleavage site in the vicinity is a cleavage site 0 or 1 internucleotidic linkage away to the 5' from a mutation. In some embodiments, a cleavage site in the vicinity is a cleavage site 0 or 1 internucleotidic linkage away to the 3' from a mutation. In some embodiments, a cleavage site in the vicinity is a cleavage site 0 internucleotidic linkage away from a mutation. In some embodiments, a cleavage site in the vicinity is a cleavage site one internucleotidic linkage away from a mutation. In some embodiments, a cleavage site in the vicinity is a cleavage site one internucleotidic linkage away to the 5' from a mutation. In some embodiments, a cleavage site in the vicinity is a cleavage site one internucleotidic linkage away to the 3' from a mutation. In some embodiments, a cleavage site in the vicinity is a cleavage site two internucleotidic linkages away from a mutation. In some embodiments, a cleavage site in the vicinity is a cleavage site two internucleotidic linkages away to the 5' from a mutation. In some embodiments, a cleavage site in the vicinity is a cleavage site two internucleotidic linkages away to the 3' from a mutation. In some embodiments, a cleavage site in the vicinity is a cleavage site three internucleotidic linkages away from a mutation. In some embodiments, a cleavage site in the vicinity is a cleavage site three internucleotidic linkages away to the 5' from a mutation. In some embodiments, a cleavage site in the vicinity is a cleavage site three internucleotidic linkages away to the 3' from a mutation. In some embodiments, a cleavage site in the vicinity is a cleavage site four internucleotidic linkages away from a mutation. In some embodiments, a cleavage site in the vicinity is a cleavage site four internucleotidic linkages away to the 5' from a mutation. In some embodiments, a cleavage site in the vicinity is a cleavage site four internucleotidic linkages away to the 3' from a mutation. In some embodiments, a cleavage site in the vicinity is a cleavage site five internucleotidic linkages away from a mutation. In some embodiments, a cleavage site in the vicinity is a cleavage site five internucleotidic linkages away to the 5' from a mutation. In some embodiments, a cleavage site in the vicinity is a cleavage site five internucleotidic linkages away to the 3' from a mutation.

In some embodiments, a common base sequence is a base sequence that has a cleavage site in the vicinity of an SNP of a characteristic sequence element in its DNA and/or stereorandom cleavage pattern. In some embodiments, a common base sequence is a base sequence that has a cleavage site in the vicinity of an SNP in its DNA and/or stereorandom cleavage pattern. In some embodiments, a common base sequence is a base sequence that has a cleavage site in the vicinity of an SNP in its DNA cleavage pattern. In some embodiments, a cleavage site in the vicinity of an SNP is at an SNP, i.e., a cleavage site is at the internucleotidic linkage of a nucleotide at an SNP (e.g., for the target of WV-905, G*G*C*A*C*A*A*G*G*G*C*A*C*A*G*A*C*T*T*C (SEQ ID NO: 14), which comprises rUrUrUrGrGrArArGrUrCrUrGrUrGrCrCrCrUrUrGrUrGrCrCrC (SEQ ID NO: 15) (rs362307 bolded), the cleavage is between the bolded rU and the underlined rG immediately after it). In some embodiments, a cleavage site in the vicinity is a cleavage site 0, 1, 2, 3, 4, 5, 6, 7, 8, 9, Or 10 internucleotidic linkages away from an SNP, where 0 means cleavage at an SNP (e.g., for the target of WV-905, G*G*C*A*C*A*A*G*G*G*C*A*C*A*G*A*C*T*T*C (SEQ ID NO: 14), which comprises rUrUrUrGrGrArArGrUrCrUrGrUrGrCrCrCrUrUrGrUrGrCrCrC (SEQ ID NO: 15) (rs362307 bolded), the cleavage is between the bolded rU and the underlined rG immediately after it for 0 internucleotidic linkage away; a cleavage site 1 internucleotidic linkage away from an SNP is between the rG and rU to the 5' from the SNP (underlined: rUrUrUrGrGrArArGrUrCrUrGrUrGrCrCrCrUrUrGrUrGrCrCrC (SEQ ID NO: 15)), or between rG and rC to the 3'-end of the SNP (underlined: rUrUrUrGrGrArArGrUrCrUrGrUrGrCrCrCrUrUrGrUrGrCrCrC (SEQ ID NO: 15))). In some embodiments, a cleavage site in the vicinity is a cleavage site 0, 1, 2, 3, 4, or 5 internucleotidic linkages away from an SNP. In some embodiments, a cleavage site in the vicinity is a cleavage site 0, 1, 2, 3, 4, or 5 internucleotidic linkages away to the 5' from an SNP. In some embodiments, a cleavage site in the vicinity is a cleavage site 0, 1, 2, 3, 4, or 5 internucleotidic linkages away to the 3' from an SNP. In some embodiments, a cleavage site in the vicinity is a cleavage site 0, 1, 2, 3, 4, or 5 internucleotidic linkages away from an SNP. In some embodiments, a cleavage site in the vicinity is a cleavage site 0, 1, 2, 3, 4, or 5 internucleotidic linkages away to the 5' from an SNP. In some embodiments, a cleavage site in the vicinity is a cleavage site 0, 1, 2, 3, 4, or 5 internucleotidic linkages away to the 3' from an SNP. In some embodiments, a cleavage site in the vicinity is a cleavage site 0, 1, 2, 3, or 4 internucleotidic linkages away from an SNP. In some embodiments, a cleavage site in the vicinity is a cleavage site 0, 1, 2, 3, or 4 internucleotidic linkages away to the 5' from an SNP. In some embodiments, a cleavage site in the vicinity is a cleavage site 0, 1, 2, 3, or 4 internucleotidic linkages away to the 3' from an SNP. In some embodiments, a cleavage site in the vicinity is a cleavage site 0, 1, 2, or 3 internucleotidic linkages away from an SNP. In some embodiments, a cleavage site in the vicinity is a cleavage site 0, 1, 2, or 3 internucleotidic linkages away to the 5' from an SNP. In some embodiments, a cleavage site in the vicinity is a cleavage site 0, 1, 2, or 3 internucleotidic linkages away to the 3' from an SNP. In some embodiments, a cleavage site in the vicinity is a cleavage site 0, 1, or 2 internucleotidic linkages away from an SNP. In some embodiments, a cleavage site in the vicinity is a cleavage site 0, 1, or 2 internucleotidic linkages away to the 5' from an SNP. In some embodiments, a cleavage site in the vicinity is a cleavage site 0, 1, or 2 internucleotidic linkages away to the 3' from an SNP. In some embodiments, a cleavage site in the vicinity is a cleavage site 0 or 1 internucleotidic linkage away from an SNP. In some embodiments, a cleavage site in the vicinity is a cleavage site 0 or 1 internucleotidic linkage away to the 5' from an SNP. In some embodiments, a cleavage site in the vicinity is a cleavage site 0 or 1 internucleotidic linkage away to the 3' from an SNP. In some embodiments, a cleavage site in the vicinity is a cleavage site 0 internucleotidic linkage away from an SNP. In some embodiments, a cleavage site in the vicinity is a cleavage site one internucleotidic linkage away from an SNP. In some embodiments, a cleavage site in the vicinity is a cleavage site one internucleotidic linkage away to the 5' from an SNP. In some embodiments, a cleavage site in the vicinity is a cleavage site one internucleotidic linkage away to the 3' from an SNP. In some embodiments, a cleavage site in the vicinity is a cleavage site two internucleotidic linkages away from an SNP. In some embodiments, a cleavage site in the vicinity is a cleavage site two internucleotidic linkages away to the 5' from an SNP. In some embodiments, a cleavage site in the vicinity is a cleavage site two internucleotidic linkages away to the 3' from an SNP. In some embodiments, a cleavage site in the vicinity is a cleavage site three internucleotidic linkages away from an SNP. In some embodiments, a cleavage site in the vicinity is a cleavage site three internucleotidic linkages away to the 5' from an SNP. In some embodiments, a cleavage site in the vicinity is a cleavage site three internucleotidic linkages away to the 3' from an SNP. In some embodiments, a cleavage site in the vicinity is a cleavage site four internucleotidic linkages away from an SNP. In some embodiments, a cleavage site in the vicinity is a cleavage site four internucleotidic linkages away to the 5' from an SNP. In some embodiments, a cleavage site in the vicinity is a cleavage site four internucleotidic linkages away to the 3' from an SNP. In some embodiments, a cleavage site in the vicinity is a cleavage site five internucleotidic linkages away from an SNP. In some embodiments, a cleavage site in the vicinity is a cleavage site five internucleotidic linkages away to the 5' from an SNP. In some embodiments, a cleavage site in the vicinity is a cleavage site five internucleotidic linkages away to the 3' from an SNP. For example, FIG. 33 demonstrates that stereorandom cleavage pattern of the WV-905 sequence has cleavage sites at the SNP (between CUGU and GCCC), two internucleotidic linkages away (between GUCU and GUGC, and between GUGC and CCUU), three internucleotidic linkages away (between UGCC and CUUG); four internucleotidic linkages away (between GCCC and UUGU, and AAGU and CUGU), and five internucleotidic linkages away (between CCCU and UGUG).

In some embodiments, a cleavage site within or in the vicinity of a characteristic sequence element, e.g., in the vicinity of a mutation, an SNP, etc., is a major cleavage site of a DNA and/or stereorandom cleavage pattern. In some embodiments, a cleavage site within or in the vicinity of a characteristic sequence element is a major cleavage site of a DNA cleavage pattern. In some embodiments, a cleavage site within or in the vicinity of a characteristic sequence element is a major cleavage site of a stereorandom cleavage pattern. In some embodiments, a cleavage site in the vicinity of a mutation is a major cleavage site of a DNA cleavage pattern. In some embodiments, a cleavage site in the vicinity of a mutation is a major cleavage site of a stereorandom cleavage pattern. In some embodiments, a cleavage site in the vicinity of an SNP is a major cleavage site of a DNA cleavage pattern. In some embodiments, a cleavage site in the vicinity of an SNP is a major cleavage site of a stereorandom cleavage pattern. In some embodiments, a major cleavage site is within a sequence complementary to a core region of a common sequence. In some embodiments, a major cleavage site is within a sequence 100% complementary to a core region of a common sequence.

In some embodiments, a major cleavage site is a site having the most, or the second, third, fourth or fifth most cleavage. In some embodiments, a major cleavage site is a site having the most, or the second, third, or fourth most cleavage. In some embodiments, a major cleavage site is a site having the most, or the second, or third most cleavage. In some embodiments, a major cleavage site is a site having the most or the second most cleavage. In some embodiments, a major cleavage site is a site having the most cleavage. In some embodiments, a major cleavage site is a site having the second most cleavage. In some embodiments, a major cleavage site is a site having the third most cleavage. In some embodiments, a major cleavage site is a site having the fourth most cleavage. In some embodiments, a major cleavage site is a site having the fifth most cleavage.

In some embodiments, a major cleavage site is a site wherein greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of cleavage occurs. In some embodiments, a major cleavage site is a site wherein greater than 5% of cleavage occurs. In some embodiments, a major cleavage site is a site wherein greater than 10% of cleavage occurs. In some embodiments, a major cleavage site is a site wherein greater than 15% of cleavage occurs. In some embodiments, a major cleavage site is a site wherein greater than 20% of cleavage occurs. In some embodiments, a major cleavage site is a site wherein greater than 25% of cleavage occurs. In some embodiments, a major cleavage site is a site wherein greater than 30% of cleavage occurs. In some embodiments, a major cleavage site is a site wherein greater than 35% of cleavage occurs. In some embodiments, a major cleavage site is a site wherein greater than 40% of cleavage occurs. In some embodiments, a major cleavage site is a site wherein greater than 45% of cleavage occurs. In some embodiments, a major cleavage site is a site wherein greater than 50% of cleavage occurs. In some embodiments, a major cleavage site is a site wherein greater than 55% of cleavage occurs. In some embodiments, a major cleavage site is a site wherein greater than 60% of cleavage occurs. In some embodiments, a major cleavage site is a site wherein greater than 65% of cleavage occurs. In some embodiments, a major cleavage site is a site wherein greater than 70% of cleavage occurs. In some embodiments, a major cleavage site is a site wherein greater than 75% of cleavage occurs. In some embodiments, a major cleavage site is a site wherein greater than 80% of cleavage occurs. In some embodiments, a major cleavage site is a site wherein greater than 85% of cleavage occurs. In some embodiments, a major cleavage site is a site wherein greater than 90% of cleavage occurs. In some embodiments, a major cleavage site is a site wherein greater than 91% of cleavage occurs. In some embodiments, a major cleavage site is a site wherein greater than 92% of cleavage occurs. In some embodiments, a major cleavage site is a site wherein greater than 93% of cleavage occurs. In some embodiments, a major cleavage site is a site wherein greater than 94% of cleavage occurs. In some embodiments, a major cleavage site is a site wherein greater than 95% of cleavage occurs. In some embodiments, a major cleavage site is a site wherein greater than 96% of cleavage occurs. In some embodiments, a major cleavage site is a site wherein greater than 97% of cleavage occurs. In some embodiments, a major cleavage site is a site wherein greater than 98% of cleavage occurs. In some embodiments, a major cleavage site is a site wherein greater than 99% of cleavage occurs. In some embodiments, a major cleavage site is a site wherein 100% of cleavage occurs.

In some embodiments, a major cleavage site is a site wherein greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of a target is cleaved. In some embodiments, a major cleavage site is a site wherein greater than 5% of a target is cleaved. In some embodiments, a major cleavage site is a site wherein greater than 10% of a target is cleaved. In some embodiments, a major cleavage site is a site wherein greater than 15% of a target is cleaved. In some embodiments, a major cleavage site is a site wherein greater than 20% of a target is cleaved. In some embodiments, a major cleavage site is a site wherein greater than 25% of a target is cleaved. In some embodiments, a major cleavage site is a site wherein greater than 30% of a target is cleaved. In some embodiments, a major cleavage site is a site wherein greater than 35% of a target is cleaved. In some embodiments, a major cleavage site is a site wherein greater than 40% of a target is cleaved. In some embodiments, a major cleavage site is a site wherein greater than 45% of a target is cleaved. In some embodiments, a major cleavage site is a site wherein greater than 50% of a target is cleaved. In some embodiments, a major cleavage site is a site wherein greater than 55% of a target is cleaved. In some embodiments, a major cleavage site is a site wherein greater than 60% of a target is cleaved. In some embodiments, a major cleavage site is a site wherein greater than 65% of a target is cleaved. In some embodiments, a major cleavage site is a site wherein greater than 70% of a target is cleaved. In some embodiments, a major cleavage site is a site wherein greater than 75% of a target is cleaved. In some embodiments, a major cleavage site is a site wherein greater than 80% of a target is cleaved. In some embodiments, a major cleavage site is a site wherein greater than 85% of a target is cleaved. In some embodiments, a major cleavage site is a site wherein greater than 90% of a target is cleaved. In some embodiments, a major cleavage site is a site wherein greater than 91% of a target is cleaved. In some embodiments, a major cleavage site is a site wherein greater than 92% of a target is cleaved. In some embodiments, a major cleavage site is a site wherein greater than 93% of a target is cleaved. In some embodiments, a major cleavage site is a site wherein greater than 94% of a target is cleaved. In some embodiments, a major cleavage site is a site wherein greater than 95% of a target is cleaved. In some embodiments, a major cleavage site is a site wherein greater than 96% of a target is cleaved. In some embodiments, a major cleavage site is a site wherein greater than 97% of a target is cleaved. In some embodiments, a major cleavage site is a site wherein greater than 98% of a target is cleaved. In some embodiments, a major cleavage site is a site wherein greater than 99% of a target is cleaved. In some embodiments, a major cleavage site is a site wherein 100% of a target is cleaved. In some embodiments, a cleavage pattern may not have a major cleavage site as no site reaches an absolute cleavage threshold level.

As a person having ordinary skill in the art understands, provided oligonucleotide compositions and methods have various uses as known by a person having ordinary skill in the art. Methods for assessing provided compositions, and properties and uses thereof, are also widely known and practiced by a person having ordinary skill in the art. Example properties, uses, and/or methods include but are not limited to those described in WO/2014/012081 and WO/2015/107425.

In some embodiments, a common base sequence comprises or is a sequence complementary to a nucleic acid sequence. In some embodiments, a common base sequence comprises or is a sequence 100% complementary to a nucleic acid sequence. In some embodiments, a common base sequence comprises or is a sequence complementary to a disease-causing nucleic acid sequence. In some embodiments, a common base sequence comprises or is a sequence 100% complementary to a disease-causing nucleic acid sequence. In some embodiments, a common base sequence comprises or is a sequence complementary to a characteristic sequence element of disease-causing nucleic acid sequence, which characteristic sequences differentiate a disease-causing nucleic acid sequence from a non-disease-causing nucleic acid sequence. In some embodiments, a common base sequence comprises or is a sequence 100% complementary to a characteristic sequence element of disease-causing nucleic acid sequence, which characteristic sequences differentiate a disease-causing nucleic acid sequence from a non-disease-causing nucleic acid sequence. In some embodiments, a common base sequence comprises or is a sequence complementary to a disease-associated nucleic acid sequence. In some embodiments, a common base sequence comprises or is a sequence 100% complementary to a disease-associated nucleic acid sequence. In some embodiments, a common base sequence comprises or is a sequence complementary to a characteristic sequence element of disease-associated nucleic acid sequence, which characteristic sequences differentiate a disease-associated nucleic acid sequence from a non-disease-associated nucleic acid sequence. In some embodiments, a common base sequence comprises or is a sequence 100% complementary to a characteristic sequence element of disease-associated nucleic acid sequence, which characteristic sequences differentiate a disease-associated nucleic acid sequence from a non-disease-associated nucleic acid sequence.

In some embodiments, a common base sequence comprises or is a sequence complementary to a gene. In some embodiments, a common base sequence comprises or is a sequence 100% complementary to a gene. In some embodiments, a common base sequence comprises or is a sequence complementary to a characteristic sequence element of a gene, which characteristic sequences differentiate the gene from a similar sequence sharing homology with the gene. In some embodiments, a common base sequence comprises or is a sequence 100% complementary to a characteristic sequence element of a gene, which characteristic sequences differentiate the gene from a similar sequence sharing homology with the gene. In some embodiments, a common base sequence comprises or is a sequence complementary to characteristic sequence element of a target gene, which characteristic sequences comprises a mutation that is not found in other copies of the gene, e.g., the wild-type copy of the gene, another mutant copy the gene, etc. In some embodiments, a common base sequence comprises or is a sequence 100% complementary to characteristic sequence element of a target gene, which characteristic sequences comprises a mutation that is not found in other copies of the gene, e.g. the wild-type copy of the gene, another mutant copy the gene, etc.

In some embodiments, a common base sequence comprises or is a sequence complementary to a sequence comprising an SNP. In some embodiments, a common base sequence comprises or is a sequence complementary to a sequence comprising an SNP, and the common base sequence is 100% complementary to the SNP that is associated with a disease. For example, in some embodiments, a common base sequence is 100% complementary to an SNP associated with a Huntington's disease-associated (or -causing) allele. In some embodiments, a common base sequence is that of WV-1092, which is 100% complementary to the disease-causing allele in many Huntington's disease patients at rs362307. In some embodiments, an SNP is rs362307. In some embodiments, an SNP is rs7685686. In some embodiments, an SNP is rs362268. In some embodiments, an SNP is rs362306. In some embodiments, other example SNP site may be any of the Huntingtin site disclosed in the present disclosure.

In some embodiments, a common base sequence comprises a sequence found in GCCTCAGTCTGCTTCGCACC (SEQ ID NO: 16). In some embodiments, a common base sequence comprises a sequence found in GCCTCAGT CTGCTTCGCACC (SEQ ID NO: 16), wherein the sequence found in GCCTCAGTCTGCTTCGCACC (SEQ ID NO: 16) comprises at least 15 nucleotides. In some embodiments, a common base sequence is GCCTCA GTCTGCTTCGCACC (SEQ ID NO: 16).

In some embodiments, a common base sequence comprises a sequence found in GAGCAGCT GCAACCTGGCAA (SEQ ID NO: 17). In some embodiments, a common base sequence comprises a sequence found in GAGCAGCTGCAACCTGGCAA (SEQ ID NO: 17), wherein the sequence found in GAGCAGCTG CAACCTGGCAA (SEQ ID NO: 17) comprises at least 15 nucleotides. In some embodiments, a common base sequence is GAGCAGCTGCAACCTGGCAA (SEQ ID NO: 17). In some embodiments, a common base sequence is GGGCACAAGGGCACAGACTT (SEQ ID NO: 18). In some embodiments, a common base sequence is GAGCAGCTGCAACCTGGCAA (SEQ ID NO: 17). In some embodiments, a common base sequence is GCACAAGGGCACAGACTTCC (SEQ ID NO: 19). In some embodiments, a common base sequence is CACAAGGGCACAGACTTCCA (SEQ ID NO: 20). In some embodiments, a common base sequence is ACAAGGGCACAGACTTCCAA (SEQ ID NO: 21). In some embodiments, a common base sequence is CAAGGGCACAGACTTCCAAA (SEQ ID NO: 22). In some embodiments, a common base sequence comprises a sequence found in GAGCAGCTGCAACCTGGCAA (SEQ ID NO: 17). In some embodiments, a common base sequence comprises a sequence found in GAGCAGCTGCAACCTGGCAA (SEQ ID NO: 17), wherein the sequence found in GAGCAGCTGCAACCTGGCAA (SEQ ID NO: 17) comprises at least 15 nucleotides. In some embodiments, a common base sequence is GAGCAGCTGCAACCTGGCAA (SEQ ID NO: 17). In some embodiments, a common base sequence is GAGCAGCTGCAACCTGGCAA (SEQ ID NO: 17). In some embodiments, a common base sequence is AGCAGCTGCAACCTGGCAAC (SEQ ID NO: 23). In some embodiments, a common base sequence is GCAGCTGCAACCTGGCAACA (SEQ ID NO: 24). In some embodiments, a common base sequence is CAGCTGCAACCTGGCAACAA (SEQ ID NO: 25). In some embodiments, a common base sequence is AGCTGCAACCTGGCAACAAC (SEQ ID NO: 26). In some embodiments, a common base sequence is GCTGCAACCTGGCAACAACC (SEQ ID NO: 27). In some embodiments, a common base sequence comprises a sequence found in GGGCCAACAGCCAGCCTGCA (SEQ ID NO: 28). In some embodiments, a common base sequence comprises a sequence found in GGGCCAACAGCCAGCCTGCA (SEQ ID NO: 28), wherein the sequence found in GGGCCAACAGCCAGCCTGCA (SEQ ID NO: 28) comprises at least 15 nucleotides. In some embodiments, a common base sequence is GGGCCAACAGCCAGCCTGCA (SEQ ID NO: 28). In some embodiments, a common base sequence is GGGCCAACAGCCAGCCTGCA (SEQ ID NO: 28). In some embodiments, a common base sequence is GGCCAACAGCCAGCCTGCAG (SEQ ID NO: 29). In some embodiments, a common base sequence is GCCAACAGCCAGCCTGCAGG (SEQ ID NO: 30). In some embodiments, a common base sequence is CCAACAGCCAGCCTGCAGGA (SEQ ID NO: 31). In some embodiments, a common base sequence is CAACAGCCAGCCTGCAGGAG (SEQ ID NO: 32). In some embodiments, a common base sequence is AACAGCCAGCCTGCAGGAGG (SEQ ID NO: 33). In some embodiments, a common base sequence comprises a sequence found in ATTAATAAATTGTCATCACC (SEQ ID NO: 34). In some embodiments, a common base sequence comprises a sequence found in ATTAATAAATTGTCATCACC (SEQ ID NO: 34), wherein the sequence found in ATTAATAAATTGTCATCACC (SEQ ID NO: 34) comprises at least 15 nucleotides. In some embodiments, a common base sequence is ATTAATAAATTGTCATCACC (SEQ ID NO: 34). In some embodiments, a common base sequence is ATTAATAAATTGTCATCACC (SEQ ID NO: 34).

In some embodiments, a chiral internucleotidic linkage has the structure of formula I. In some embodiments, a chiral internucleotidic linkage is phosphorothioate. In some embodiments, each chiral internucleotidic linkage in a single oligonucleotide of a provided composition independently has the structure of formula I. In some embodiments, each chiral internucleotidic linkage in a single oligonucleotide of a provided composition is a phosphorothioate.

In some embodiments, oligonucleotides of the present disclosure comprise one or more modified sugar moieties. In some embodiments, oligonucleotides of the present disclosure comprise one or more modified base moieties. As known by a person of ordinary skill in the art and described in the disclosure, various modifications can be introduced to a sugar and/or moiety. For example, in some embodiments, a modification is a modification described in U.S. Pat. No. 9,006,198, WO2014/012081 and WO/2015/107425, the sugar and base modifications of each of which are incorporated herein by reference.

In some embodiments, a sugar modification is a 2'-modification. Commonly used 2'-modifications include but are not limited to 2'-$OR^1$, wherein $R^1$ is not hydrogen. In some embodiments, a modification is 2'-OR, wherein R is optionally substituted aliphatic. In some embodiments, a modification is 2'-OMe. In some embodiments, a modification is 2'-MOE. In some embodiments, the present disclosure demonstrates that inclusion and/or location of particular chirally pure internucleotidic linkages can provide stability improvements comparable to or better than those achieved through use of modified backbone linkages, bases, and/or sugars. In some embodiments, a provided single oligonucleotide of a provided composition has no modifications on the sugars. In some embodiments, a provided single oligonucleotide of a provided composition has no modifications on 2'-positions of the sugars (i.e., the two groups at the 2'-position are either —H/—H or —H/—OH). In some embodiments, a provided single oligonucleotide of a provided composition does not have any 2'-MOE modifications.

In some embodiments, a 2'-modification is —O-L- or -L- which connects the 2'-carbon of a sugar moiety to another carbon of a sugar moiety. In some embodiments, a 2'-modification is —O-L- or -L- which connects the 2'-carbon of a sugar moiety to the 4'-carbon of a sugar moiety. In some embodiments, a 2'-modification is S-cEt. In some embodiments, a modified sugar moiety is an LNA moiety.

In some embodiments, a 2'-modification is —F. In some embodiments, a 2'-modification is FANA. In some embodiments, a 2'-modification is FRNA.

In some embodiments, a sugar modification is a 5'-modification, e.g., R-5'-Me, S-5'-Me, etc.

In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Example such moieties are widely known in the art, including but not limited to those used in morpholio (optionally with its phosphorodiamidate linkage), glycol nucleic acids, etc.

In some embodiments, a single oligonucleotide in a provided composition has at least about 25% of its internucleotidic linkages in Sp configuration. In some embodiments, a single oligonucleotide in a provided composition has at least about 30% of its internucleotidic linkages in Sp configuration. In some embodiments, a single oligonucleotide in a provided composition has at least about 35% of its internucleotidic linkages in Sp configuration. In some embodiments, a single oligonucleotide in a provided composition has at least about 40% of its internucleotidic linkages in Sp configuration. In some embodiments, a single oligonucleotide in a provided composition has at least about 45% of its internucleotidic linkages in Sp configuration. In some embodiments, a single oligonucleotide in a provided composition has at least about 50% of its internucleotidic linkages in Sp configuration. In some embodiments, a single oligonucleotide in a provided composition has at least about 55% of its internucleotidic linkages in Sp configuration. In some embodiments, a single oligonucleotide in a provided composition has at least about 60% of its internucleotidic linkages in Sp configuration. In some embodiments, a single oligonucleotide in a provided composition has at least about 65% of its internucleotidic linkages in Sp configuration. In some embodiments, a single oligonucleotide in a provided composition has at least about 70% of its internucleotidic linkages in Sp configuration. In some embodiments, a single oligonucleotide in a provided composition has at least about 75% of its internucleotidic linkages in Sp configuration. In some embodiments, a single oligonucleotide in a provided composition has at least about 80% of its internucleotidic linkages in Sp configuration. In some embodiments, a single oligonucleotide in a provided composition has at least about 85% of its internucleotidic linkages in Sp configuration. In some embodiments, a single oligonucleotide in a provided composition has at least about 90% of its internucleotidic linkages in Sp configuration.

In some embodiments, oligonucleotides in a provided composition is not an oligonucleotide selected from: $T_kT_k{}^mC_kAGT{}^mCATGA{}^mCT_kT{}^mC_k{}^mC_k$ (SEQ ID NO: 35), wherein each nucleoside followed by a subscript 'k' indicates a (S)-cEt modification, R is Rp phosphorothioate linkage, S is Sp phosphorothioate linkage, each ${}^mC$ is a 5-methylcytosine modified nucleoside, and all internucleoside linkages are phosphorothioates (PS) with stereochemistry patterns selected from RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

In some embodiments, a single oligonucleotide in a provided composition is not an oligonucleotide selected from: $T_kT_k{}^mC_kAGT{}^mCATGA{}^mCTT_k{}^mC_k{}^mC_k$ (SEQ ID NO: 36), wherein each nucleoside followed by a subscript 'k' indicates a (S)-cEt modification, R is Rp phosphorothioate linkage, S is Sp phosphorothioate linkage, each ${}^mC$ is a 5-methylcytosine modified nucleoside and all core internucleoside linkages are phosphorothioates (PS) with stereochemistry patterns selected from: RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

Chirally Controlled Oligonucleotides and Chirally Controlled Oligonucleotide Compositions The present disclosure provides chirally controlled oligonucleotides, and chirally controlled oligonucleotide compositions which are of high crude purity and of high diastereomeric purity. In some embodiments, the present disclosure provides chirally controlled oligonucleotides, and chirally controlled oligonucleotide compositions which are of high crude purity. In some embodiments, the present disclosure provides chirally controlled oligonucleotides, and chirally controlled oligonucleotide compositions which are of high diastereomeric purity.

In some embodiments, a chirally controlled oligonucleotide composition is a substantially pure preparation of an oligonucleotide type in that oligonucleotides in the composition that are not of the oligonucleotide type are impurities form the preparation process of said oligonucleotide type, in some case, after certain purification procedures.

In some embodiments, the present disclosure provides oligonucleotides comprising one or more diastereomerically pure internucleotidic linkages with respect to the chiral linkage phosphorus. In some embodiments, the present disclosure provides oligonucleotides comprising one or more diastereomerically pure internucleotidic linkages having the structure of formula I. In some embodiments, the present disclosure provides oligonucleotides comprising one or more diastereomerically pure internucleotidic linkages with respect to the chiral linkage phosphorus, and one or more phosphate diester linkages. In some embodiments, the present disclosure provides oligonucleotides comprising one or more diastereomerically pure internucleotidic linkages having the structure of formula I, and one or more phosphate diester linkages. In some embodiments, the present disclosure provides oligonucleotides comprising one or more diastereomerically pure internucleotidic linkages having the structure of formula I-c, and one or more phosphate diester linkages. In some embodiments, such oligonucleotides are prepared by using stereoselective oligonucleotide synthesis, as described in this application, to form pre-designed diastereomerically pure internucleotidic linkages with respect to the chiral linkage phosphorus. For instance, in one example oligonucleotide of (Rp/Sp, Rp/Sp, Rp/Sp, Rp, Rp, Sp, Sp, Sp, Sp, Sp Sp, Sp, Sp, Sp, Rp, Rp, Rp, Rp, Rp)-d [GsCsCsTsCsAsGsTsCsTSGsCsTSTsCsGs1Cs1As1CsC] (SEQ ID NO: 37), the first three internucleotidic linkages are constructed using traditional oligonucleotide synthesis method, and the diastereomerically pure internucleotidic linkages are constructed with stereochemical control as described in this application. Example internucleotidic linkages, including those having structures of formula I, are further described below.

In some embodiments, the present disclosure provides a chirally controlled oligonucleotide, wherein at least two of the individual internucleotidic linkages within the oligonucleotide have different stereochemistry and/or different P-modifications relative to one another. In certain embodiments, the present disclosure provides a chirally controlled oligonucleotide, wherein at least two individual internucleotidic linkages within the oligonucleotide have different P-modifications relative to one another. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate diester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphorothioate triester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate triester internucleotidic linkage.

In certain embodiments, a modified internucleotidic linkages has the structure of formula I:

(I)

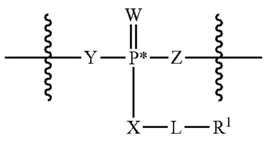

wherein each variable is as defined and described below. In some embodiments, a linkage of formula I is chiral. In some embodiments, the present disclosure provides a chirally controlled oligonucleotide comprising one or more modified internucleotidic linkages of formula I. In some embodiments, the present disclosure provides a chirally controlled oligonucleotide comprising one or more modified internucleotidic linkages of formula I, and wherein individual internucleotidic linkages of formula I within the oligonucleotide have different P-modifications relative to one another. In some embodiments, the present disclosure provides a chirally controlled oligonucleotide comprising one or more modified internucleotidic linkages of formula I, and wherein individual internucleotidic linkages of formula I within the oligonucleotide have different —X-L-$R^1$ relative to one another. In some embodiments, the present disclosure provides a chirally controlled oligonucleotide comprising one or more modified internucleotidic linkages of formula I, and wherein individual internucleotidic linkages of formula I within the oligonucleotide have different X relative to one another. In some embodiments, the present disclosure provides a chirally controlled oligonucleotide comprising one or more modified internucleotidic linkages of formula I, and wherein individual internucleotidic linkages of formula I within the oligonucleotide have different -L-$R^1$ relative to one another. In some embodiments, a chirally controlled oligonucleotide is an oligonucleotide in a provided composition that is of the particular oligonucleotide type. In some embodiments, a chirally controlled oligonucleotide is an oligonucleotide in a provided composition that has the common base sequence and length, the common pattern of backbone linkages, and the common pattern of backbone chiral centers.

In some embodiments, the present disclosure provides a chirally controlled oligonucleotide, wherein at least two of the individual internucleotidic linkages within the oligonucleotide have different stereochemistry and/or different P-modifications relative to one another. In some embodiments, the present disclosure provides a chirally controlled oligonucleotide, wherein at least two of the individual internucleotidic linkages within the oligonucleotide have different stereochemistry relative to one another, and wherein at least a portion of the structure of the chirally controlled oligonucleotide is characterized by a repeating pattern of alternating stereochemistry.

In some embodiments, the present disclosure provides a chirally controlled oligonucleotide, wherein at least two of the individual internucleotidic linkages within the oligonucleotide have different P-modifications relative to one another, in that they have different X atoms in their —$XLR^1$ moieties, and/or in that they have different L groups in their —$XLR^1$ moieties, and/or that they have different $R^1$ atoms in their —$XLR^1$ moieties.

In some embodiments, the present disclosure provides a chirally controlled oligonucleotide, wherein at least two of the individual internucleotidic linkages within the oligonucleotide have different stereochemistry and/or different P-modifications relative to one another and the oligonucleotide has a structure represented by the following formula:

$$[S^{B}n1R^{B}n2S^{B}n3R^{B}n4 \ldots S^{B}nxR^{B}ny]$$

wherein:

each $R^B$ independently represents a block of nucleotide units having the R configuration at the linkage phosphorus;

each $S^B$ independently represents a block of nucleotide units having the S configuration at the linkage phosphorus;

each of n1-ny is zero or an integer, with the requirement that at least one odd n and at least one even n must be non-zero so that the oligonucleotide includes at least two individual internucleotidic linkages with different stereochemistry relative to one another; and wherein the sum of n1-ny is between 2 and 200, and in some embodiments is between a lower limit selected from the group consisting of 2, 3, 4, 5, 6, 7, 8, 9, 10, 11, 12, 13, 14, 15, 16, 17, 18, 19, 20, 21, 22, 23, 24, 25 or more and an upper limit selected from the group consisting of 5, 10, 15, 20, 25, 30, 35, 40, 45, 50, 55, 60, 65, 70, 75, 80, 85, 90, 95, 100, 110, 120, 130, 140, 150, 160, 170, 180, 190, and 200, the upper limit being larger than the lower limit.

In some such embodiments, each n has the same value; in some embodiments, each even n has the same value as each other even n; in some embodiments, each odd n has the same value each other odd n; in some embodiments, at least two even ns have different values from one another; in some embodiments, at least two odd ns have different values from one another.

In some embodiments, at least two adjacent ns are equal to one another, so that a provided oligonucleotide includes adjacent blocks of S stereochemistry linkages and R stereochemistry linkages of equal lengths. In some embodiments, provided oligonucleotides include repeating blocks of S and R stereochemistry linkages of equal lengths. In some embodiments, provided oligonucleotides include repeating blocks of S and R stereochemistry linkages, where at least two such blocks are of different lengths from one another; in some such embodiments each S stereochemistry block is of the same length, and is of a different length from each R stereochemistry length, which may optionally be of the same length as one another.

In some embodiments, at least two skip-adjacent ns are equal to one another, so that a provided oligonucleotide includes at least two blocks of linkages of a first stereochemistry that are equal in length to one another and are separated by a block of linkages of the other stereochemistry, which separating block may be of the same length or a different length from the blocks of first stereochemistry.

In some embodiments, ns associated with linkage blocks at the ends of a provided oligonucleotide are of the same length. In some embodiments, provided oligonucleotides have terminal blocks of the same linkage stereochemistry. In some such embodiments, the terminal blocks are separated from one another by a middle block of the other linkage stereochemistry.

In some embodiments, a provided oligonucleotide of formula [$S^B$n1$R^B$n2$S^B$n3$R^B$n4 . . . $S^B$nx$R^B$ny] is a stereoblockmer. In some embodiments, a provided oligonucleotide of formula [$S^B$n1$R^B$n2$S^B$n3$R^B$n4 . . . $S^B$nx$R^B$ny] is a stereoskipmer. In some embodiments, a provided oligonucleotide of formula [$S^B$n1$R^B$n2$S^B$n3$R^B$n4 . . . $S^B$nx$R^B$ny] is a stereoaltmer. In some embodiments, a provided oligonucleotide of formula [$S^B$n1$R^B$n2$S^B$n3$R^B$n4 . . . $S^B$nx$R^B$ny] is a gapmer.

In some embodiments, a provided oligonucleotide of formula [$S^B$n1$R^B$n2$S^B$n3$R^B$n4 . . . $S^B$nx$R^B$ny] is of any of the above described patterns and further comprises patterns of P-modifications. For instance, in some embodiments, a provided oligonucleotide of formula [$S^B$n1$R^B$n2$S^B$n3$R^B$n4 . . . $S^B$nx$R^B$ny] and is a stereoskipmer and P-modification skipmer. In some embodiments, a provided oligonucleotide of formula [$S^B$n1$R^B$n2$S^B$n3$R^B$n4 . . . $S^B$nx$R^B$ny] and is a stereoblockmer and P-modification altmer. In some embodiments, a provided oligonucleotide of formula [$S^B$n1$R^B$n2$S^B$n3$R^B$n4 . . . $S^B$nx$R^B$ny] and is a stereoaltmer and P-modification blockmer.

In some embodiments, a provided oligonucleotide of formula [$S^B$n1$R^B$n2$S^B$n3$R^B$n4 . . . $S^B$nx$R^B$ny] is a chirally controlled oligonucleotide comprising one or more modified internuceotidic linkages independently having the structure of formula I:

(I)

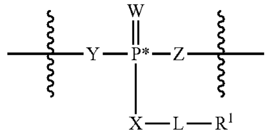

wherein:

P* is an asymmetric phosphorus atom and is either Rp or Sp;

W is O, S or Se;

each of X, Y and Z is independently —O—, —S—, —N(-L-$R^1$)—, or L;

L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—;

$R^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O— each R' is independently —R, —C(O)R, —$CO_2$R, or —$SO_2$R, or:

two R' are taken together with their intervening atoms to form an optionally substituted aryl, carbocyclic, heterocyclic, or heteroaryl ring;

-Cy- is an optionally substituted bivalent ring selected from phenylene, carbocyclylene, arylene, heteroarylene, and heterocyclylene;

each R is independently hydrogen, or an optionally substituted group selected from $C_1$-$C_6$ aliphatic, carbocyclyl, aryl, heteroaryl, and heterocyclyl; and each

independently represents a connection to a nucleoside.

In some embodiments, L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

each R' is independently —R, —C(O)R, —$CO_2$R, or —$SO_2$R, or:

two R' on the same nitrogen are taken together with their intervening atoms to form an optionally substituted heterocyclic or heteroaryl ring, or two R' on the same carbon are taken together with their intervening atoms to form an optionally substituted aryl, carbocyclic, heterocyclic, or heteroaryl ring;

Cy- is an optionally substituted bivalent ring selected from phenylene, carbocyclylene, arylene, heteroarylene, or heterocyclylene;

each R is independently hydrogen, or an optionally substituted group selected from $C_1$-$C_6$ aliphatic, phenyl, carbocyclyl, aryl, heteroaryl, or heterocyclyl; and each

independently represents a connection to a nucleoside.

In some embodiments, a chirally controlled oligonucleotide comprises one or more modified internucleotidic phosphorus linkages. In some embodiments, a chirally controlled oligonucleotide comprises, e.g., a phosphorothioate or a phosphorothioate triester linkage. In some embodiments, a chirally controlled oligonucleotide comprises a phosphorothioate triester linkage. In some embodiments, a chirally controlled oligonucleotide comprises at least two phosphorothioate triester linkages. In some embodiments, a chirally controlled oligonucleotide comprises at least three phosphorothioate triester linkages. In some embodiments, a chirally controlled oligonucleotide comprises at least four phosphorothioate triester linkages. In some embodiments, a chirally controlled oligonucleotide comprises at least five phosphorothioate triester linkages. Example such modified internucleotidic phosphorus linkages are described further herein.

In some embodiments, a chirally controlled oligonucleotide comprises different internucleotidic phosphorus linkages. In some embodiments, a chirally controlled oligonucleotide comprises at least one phosphate diester internucleotidic linkage and at least one modified internucleotidic linkage. In some embodiments, a chirally controlled oligonucleotide comprises at least one phosphate diester internucleotidic linkage and at least one phosphorothioate triester linkage. In some embodiments, a chirally controlled oligonucleotide comprises at least one phosphate diester internucleotidic linkage and at least two phosphorothioate triester linkages. In some embodiments, a chirally controlled oligonucleotide comprises at least one phosphate diester internucleotidic linkage and at least three phosphorothioate triester linkages. In some embodiments, a chirally controlled oligonucleotide comprises at least one phosphate diester internucleotidic linkage and at least four phosphorothioate triester linkages. In some embodiments, a chirally controlled oligonucleotide comprises at least one phosphate diester internucleotidic linkage and at least five phosphorothioate triester linkages. Example such modified internucleotidic phosphorus linkages are described further herein.

In some embodiments, a phosphorothioate triester linkage comprises a chiral auxiliary, which, for example, is used to control the stereoselectivity of a reaction. In some embodiments, a phosphorothioate triester linkage does not comprise a chiral auxiliary. In some embodiments, a phosphorothioate triester linkage is intentionally maintained until and/or during the administration to a subject.

In some embodiments, a chirally controlled oligonucleotide is linked to a solid support. In some embodiments, a chirally controlled oligonucleotide is cleaved from a solid support.

In some embodiments, a chirally controlled oligonucleotide comprises at least one phosphate diester internucleotidic linkage and at least two consecutive modified internucleotidic linkages. In some embodiments, a chirally controlled oligonucleotide comprises at least one phosphate diester internucleotidic linkage and at least two consecutive phosphorothioate triester internucleotidic linkages.

In some embodiments, a chirally controlled oligonucleotide is a blockmer. In some embodiments, a chirally controlled oligonucleotide is a stereoblockmer. In some embodiments, a chirally controlled oligonucleotide is a P-modification blockmer. In some embodiments, a chirally controlled oligonucleotide is a linkage blockmer.

In some embodiments, a chirally controlled oligonucleotide is an altmer. In some embodiments, a chirally controlled oligonucleotide is a stereoaltmer. In some embodiments, a chirally controlled oligonucleotide is a P-modification altmer. In some embodiments, a chirally controlled oligonucleotide is a linkage altmer.

In some embodiments, a chirally controlled oligonucleotide is a unimer. In some embodiments, a chirally controlled oligonucleotide is a stereounimer. In some embodiments, a chirally controlled oligonucleotide is a P-modification unimer. In some embodiments, a chirally controlled oligonucleotide is a linkage unimer.

In some embodiments, a chirally controlled oligonucleotide is a gapmer.

In some embodiments, a chirally controlled oligonucleotide is a skipmer.

In some embodiments, the present disclosure provides oligonucleotides comprising one or more modified internucleotidic linkages independently having the structure of formula I:

(I)

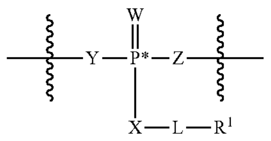

wherein:

P* is an asymmetric phosphorus atom and is either Rp or Sp;

W is O, S or Se;

each of X, Y and Z is independently —O—, —S—, —N(-L-$R^1$)—, or L;

L is a covalent bond or an optionally substituted, linear or branched $C_1$-$C_{10}$ alkylene, wherein one or more methylene units of L are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—;

$R^1$ is halogen, R, or an optionally substituted $C_1$-$C_{50}$ aliphatic wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O— each R' is independently —R, —C(O)R, —$CO_2$R, or —$SO_2$R, or:

two R' are taken together with their intervening atoms to form an optionally substituted aryl, carbocyclic, heterocyclic, or heteroaryl ring;

Cy- is an optionally substituted bivalent ring selected from phenylene, carbocyclylene, arylene, heteroarylene, and heterocyclylene;

each R is independently hydrogen, or an optionally substituted group selected from $C_1$-$C_6$ aliphatic, carbocyclyl, aryl, heteroaryl, and heterocyclyl; and each

independently represents a connection to a nucleoside.

In some embodiments, L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2N(R')$—, —$N(R')S(O)_2$—, —SC(O)—, —C(O)S—, —OC(O)—, or —C(O)O—;

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2N(R')$—, —$N(R')S(O)_2$—, —SC(O)—, —C(O)S—, —OC(O)—, or —C(O)O—;

each R' is independently —R, —C(O)R, —$CO_2R$, or —$SO_2R$, or:

two R' on the same nitrogen are taken together with their intervening atoms to form an optionally substituted heterocyclic or heteroaryl ring, or two R' on the same carbon are taken together with their intervening atoms to form an optionally substituted aryl, carbocyclic, heterocyclic, or heteroaryl ring;

Cy- is an optionally substituted bivalent ring selected from phenylene, carbocyclylene, arylene, heteroarylene, or heterocyclylene;

each R is independently hydrogen, or an optionally substituted group selected from $C_1$-$C_6$ aliphatic, phenyl, carbocyclyl, aryl, heteroaryl, or heterocyclyl; and each

independently represents a connection to a nucleoside.

In some embodiments, P* is an asymmetric phosphorus atom and is either Rp or Sp. In some embodiments, P* is Rp. In other embodiments, P* is Sp. In some embodiments, an oligonucleotide comprises one or more internucleotidic linkages of formula I wherein each P* is independently Rp or Sp. In some embodiments, an oligonucleotide comprises one or more internucleotidic linkages of formula I wherein each P* is Rp. In some embodiments, an oligonucleotide comprises one or more internucleotidic linkages of formula I wherein each P* is Sp. In some embodiments, an oligonucleotide comprises at least one internucleotidic linkage of formula I wherein P* is Rp. In some embodiments, an oligonucleotide comprises at least one internucleotidic linkage of formula I wherein P* is Sp. In some embodiments, an oligonucleotide comprises at least one internucleotidic linkage of formula I wherein P* is Rp, and at least one internucleotidic linkage of formula I wherein P* is Sp.

In some embodiments, W is O, S, or Se. In some embodiments, W is O. In some embodiments, W is S. In some embodiments, W is Se. In some embodiments, an oligonucleotide comprises at least one internucleotidic linkage of formula I wherein W is O. In some embodiments, an oligonucleotide comprises at least one internucleotidic linkage of formula I wherein W is S. In some embodiments, an oligonucleotide comprises at least one internucleotidic linkage of formula I wherein W is Se.

In some embodiments, each R is independently hydrogen, or an optionally substituted group selected from $C_1$-$C_6$ aliphatic, phenyl, carbocyclyl, aryl, heteroaryl, or heterocyclyl.

In some embodiments, R is hydrogen. In some embodiments, R is an optionally substituted group selected from $C_1$-$C_6$ aliphatic, phenyl, carbocyclyl, aryl, heteroaryl, or heterocyclyl.

In some embodiments, R is an optionally substituted $C_1$-$C_6$ aliphatic. In some embodiments, R is an optionally substituted $C_1$-$C_6$ alkyl. In some embodiments, R is optionally substituted, linear or branched hexyl. In some embodiments, R is optionally substituted, linear or branched pentyl. In some embodiments, R is optionally substituted, linear or branched butyl. In some embodiments, R is optionally substituted, linear or branched propyl. In some embodiments, R is optionally substituted ethyl. In some embodiments, R is optionally substituted methyl.

In some embodiments, R is optionally substituted phenyl. In some embodiments, R is substituted phenyl. In some embodiments, R is phenyl.

In some embodiments, R is optionally substituted carbocyclyl. In some embodiments, R is optionally substituted $C_3$-$C_{10}$ carbocyclyl. In some embodiments, R is optionally substituted monocyclic carbocyclyl. In some embodiments, R is optionally substituted cycloheptyl. In some embodiments, R is optionally substituted cyclohexyl. In some embodiments, R is optionally substituted cyclopentyl. In some embodiments, R is optionally substituted cyclobutyl. In some embodiments, R is an optionally substituted cyclopropyl. In some embodiments, R is optionally substituted bicyclic carbocyclyl.

In some embodiments, R is an optionally substituted aryl. In some embodiments, R is an optionally substituted bicyclic aryl ring.

In some embodiments, R is an optionally substituted heteroaryl. In some embodiments, R is an optionally substituted 5-6 membered monocyclic heteroaryl ring having 1-3 heteroatoms independently selected from nitrogen, sulfur, or oxygen. In some embodiments, R is a substituted 5-6 membered monocyclic heteroaryl ring having 1-3 heteroatoms independently selected from nitrogen, oxygen, or sulfur. In some embodiments, R is an unsubstituted 5-6 membered monocyclic heteroaryl ring having 1-3 heteroatoms independently selected from nitrogen, sulfur, or oxygen.

In some embodiments, R is an optionally substituted 5 membered monocyclic heteroaryl ring having 1-3 heteroatoms independently selected from nitrogen, oxygen or sulfur. In some embodiments, R is an optionally substituted 6 membered monocyclic heteroaryl ring having 1-3 heteroatoms independently selected from nitrogen, oxygen, or sulfur.

In some embodiments, R is an optionally substituted 5-membered monocyclic heteroaryl ring having 1 heteroatom selected from nitrogen, oxygen, or sulfur. In some embodiments, R is selected from pyrrolyl, furanyl, or thienyl.

In some embodiments, R is an optionally substituted 5-membered heteroaryl ring having 2 heteroatoms independently selected from nitrogen, oxygen, or sulfur. In certain embodiments, R is an optionally substituted 5-membered heteroaryl ring having 1 nitrogen atom, and an additional heteroatom selected from sulfur or oxygen. Example R groups include optionally substituted pyrazolyl, imidazolyl, thiazolyl, isothiazolyl, oxazolyl or isoxazolyl.

In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having 2 nitrogen atoms. In certain embodiments, R is an optionally substituted 6-membered heteroaryl ring having 1 nitrogen. Example R groups include optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having 1 heteroatom independently selected from nitrogen, oxygen, or sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, or sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, or sulfur.

In certain embodiments, R is an optionally substituted 6,6-fused heteroaryl ring having 1-4 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having 1 heteroatom independently selected from nitrogen, oxygen, or sulfur. In some embodiments, R is an optionally substituted quinolinyl. In some embodiments, R is an optionally substituted isoquinolinyl. According to one aspect, R is an optionally substituted 6,6-fused heteroaryl ring having 2 heteroatoms independently selected from nitrogen, oxygen, or sulfur. In some embodiments, R is a quinazoline or a quinoxaline.

In some embodiments, R is an optionally substituted heterocyclyl. In some embodiments, R is an optionally substituted 3-7 membered saturated or partially unsaturated heterocyclic ring having 1-2 heteroatoms independently selected from nitrogen, oxygen, or sulfur. In some embodiments, R is a substituted 3-7 membered saturated or partially unsaturated heterocyclic ring having 1-2 heteroatoms independently selected from nitrogen, oxygen, or sulfur. In some embodiments, R is an unsubstituted 3-7 membered saturated or partially unsaturated heterocyclic ring having 1-2 heteroatoms independently selected from nitrogen, oxygen, or sulfur.

In some embodiments, R is an optionally substituted heterocyclyl. In some embodiments, R is an optionally substituted 6 membered saturated or partially unsaturated heterocyclic ring having 1-2 heteroatoms independently selected from nitrogen, oxygen, or sulfur. In some embodiments, R is an optionally substituted 6 membered partially unsaturated heterocyclic ring having 2 heteroatoms independently selected from nitrogen, oxygen, or sulfur. In some embodiments, R is an optionally substituted 6 membered partially unsaturated heterocyclic ring having 2 oxygen atom.

In certain embodiments, R is a 3-7 membered saturated or partially unsaturated heterocyclic ring having 1-2 heteroatoms independently selected from nitrogen, oxygen, or sulfur. In certain embodiments, R is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, R is an optionally substituted 5 membered saturated or partially unsaturated heterocyclic ring having 1-2 heteroatoms independently selected from nitrogen, oxygen, or sulfur.

In certain embodiments, R is an optionally substituted 5-6 membered partially unsaturated monocyclic ring having 1-2 heteroatoms independently selected from nitrogen, oxygen, or sulfur. In certain embodiments, R is an optionally substituted tetrahydropyridinyl, dihydrothiazolyl, dihydrooxazolyl, or oxazolinyl group.

In some embodiments, R is an optionally substituted 8-10 membered bicyclic saturated or partially unsaturated heterocyclic ring having 1-4 heteroatoms independently selected from nitrogen, oxygen, or sulfur. In some embodiments, R is an optionally substituted indolinyl. In some embodiments, R is an optionally substituted isoindolinyl. In some embodiments, R is an optionally substituted 1, 2, 3, 4-tetrahydroquinoline. In some embodiments, R is an optionally substituted 1, 2, 3, 4-tetrahydroisoquinoline.

In some embodiments, each R' is independently —R, —C(O)R, —$CO_2$R, or —$SO_2$R, or:

two R' on the same nitrogen are taken together with their intervening atoms to form an optionally substituted heterocyclic or heteroaryl ring, or two R' on the same carbon are taken together with their intervening atoms to form an optionally substituted aryl, carbocyclic, heterocyclic, or heteroaryl ring.

In some embodiments, R' is —R, —C(O)R, —$CO_2$R, or —$SO_2$R, wherein R is as defined above and described herein.

In some embodiments, R' is —R, wherein R is as defined and described above and herein. In some embodiments, R' is hydrogen.

In some embodiments, R' is —C(O)R, wherein R is as defined above and described herein. In some embodiments, R' is —$CO_2$R, wherein R is as defined above and described herein. In some embodiments, R' is —$SO_2$R, wherein R is as defined above and described herein.

In some embodiments, two R' on the same nitrogen are taken together with their intervening atoms to form an optionally substituted heterocyclic or heteroaryl ring. In some embodiments, two R' on the same carbon are taken together with their intervening atoms to form an optionally substituted aryl, carbocyclic, heterocyclic, or heteroaryl ring.

In some embodiments, -Cy- is an optionally substituted bivalent ring selected from phenylene, carbocyclylene, arylene, heteroarylene, or heterocyclylene.

In some embodiments, -Cy- is optionally substituted phenylene. In some embodiments, -Cy- is optionally substituted carbocyclylene. In some embodiments, -Cy- is optionally substituted arylene. In some embodiments, -Cy- is optionally substituted heteroarylene. In some embodiments, -Cy- is optionally substituted heterocyclylene.

In some embodiments, each of X, Y and Z is independently —O—, —S—, —N(-L-$R^1$)—, or L, wherein each of L and $R^1$ is independently as defined above and described below.

In some embodiments, X is —O—. In some embodiments, X is —S—. In some embodiments, X is —O— or —S—. In some embodiments, an oligonucleotide comprises at least one internucleotidic linkage of formula I wherein X is —O—. In some embodiments, an oligonucleotide comprises at least one internucleotidic linkage of formula I wherein X is —S—. In some embodiments, an oligonucleotide comprises at least one internucleotidic linkage of formula I wherein X is —O—, and at least one internucleotidic linkage of formula I wherein X is —S—. In some embodiments, an oligonucleotide comprises at least one internucleotidic linkage of formula I wherein X is —O—, and at least one internucleotidic linkage of formula I wherein X is —S—, and at least one internucleotidic linkage of formula I wherein L is an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, X is —N(-L-$R^1$)—. In some embodiments, X is —N(R')—. In some embodiments, X is —N(R')—. In some embodiments, X is —N(R)—. In some embodiments, X is —NH—.

In some embodiments, X is L. In some embodiments, X is a covalent bond. In some embodiments, X is or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, X is an optionally substituted $C_1$-$C_{10}$ alkylene or $C_1$-$C_{10}$ alkenylene. In some embodiments, X is methylene.

In some embodiments, Y is —O—. In some embodiments, Y is —S—.

In some embodiments, Y is —N(-L-$R^1$)—. In some embodiments, Y is —N(R')—. In some embodiments, Y is —N(R')—. In some embodiments, Y is —N(R)—. In some embodiments, Y is —NH—.

In some embodiments, Y is L. In some embodiments, Y is a covalent bond. In some embodiments, Y is or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Y is an optionally substituted $C_1$-$C_{10}$ alkylene or $C_1$-$C_{10}$ alkenylene. In some embodiments, Y is methylene.

In some embodiments, Z is —O—. In some embodiments, Z is —S—.

In some embodiments, Z is —N(-L-$R^1$)—. In some embodiments, Z is —N(R')—. In some embodiments, Z is —N(R')—. In some embodiments, Z is —N(R)—. In some embodiments, Z is —NH—.

In some embodiments, Z is L. In some embodiments, Z is a covalent bond. In some embodiments, Z is or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Z is an optionally substituted $C_1$-$C_{10}$ alkylene or $C_1$-$C_{10}$ alkenylene. In some embodiments, Z is methylene.

In some embodiments, L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, L is a covalent bond. In some embodiments, L is an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)

O—, —OC(O)N(R')—, —S(O)—, —$S(O)_2$—, —$S(O)_2$N(R')—, —N(R')$S(O)_2$—, —SC(O)—, —C(O)S—, —OC(O)—, or —C(O)O—.

In some embodiments, L has the structure of -$L^1$-V—, wherein: $L^1$ is an optionally substituted group selected from

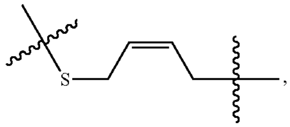,

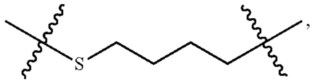,

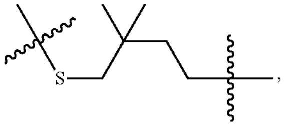,

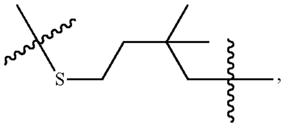,

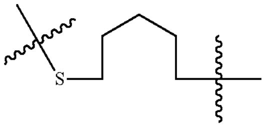,

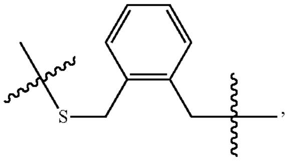,

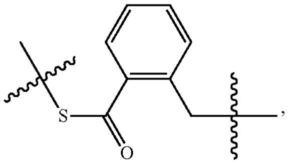,

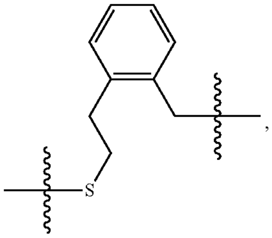,

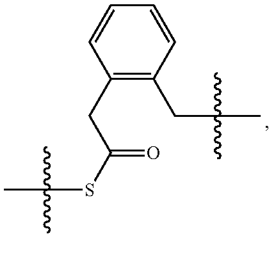 [SMILES: *Cc1ccccc1CC(=O)S*], $C_1$-$C_6$ alkylene, $C_1$-$C_6$ alkenylene, carbocyclylene, arylene, $C_1$-$C_6$ heteroalkylene, heterocyclylene, and heteroarylene;

V is selected from —O—, —S—, —NR'—, $C(R')_2$, —S—S—, —B—S—S—C—, B C,

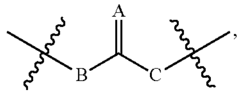, or an optionally substituted group selected from $C_1$-$C_6$ alkylene, arylene, $C_1$-$C_6$ heteroalkylene, heterocyclylene, and heteroarylene;

A is =O, =S, =NR', or =$C(R')_2$;

each of B and C is independently —O—, —S—, —NR'—, —$C(R')_2$—, or an optionally substituted group selected from $C_1$-$C_6$ alkylene, carbocyclylene, arylene, heterocyclylene, or heteroarylene; and each R' is independently as defined above and described herein.

In some embodiments, $L^1$ is

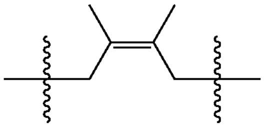,

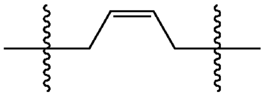, 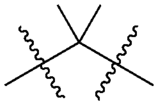,

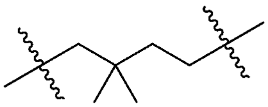, 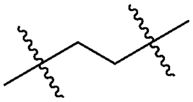,

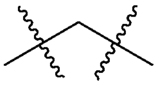, or 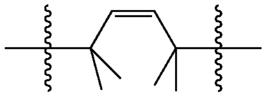.

In some embodiments, $L^1$ is

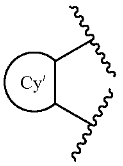, wherein Ring Cy' is an optionally substituted arylene, carbocyclylene, heteroarylene, or heterocyclylene. In some embodiments, $L^1$ is optionally substituted

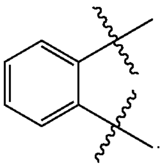 [SMILES: *c1ccccc1*].

In some embodiments, $L^1$ is
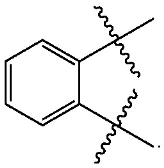 [SMILES: *c1ccccc1*]
In some embodiments, $L^1$ is connected to X. In some embodiments, $L^1$ is an optionally substituted group selected from
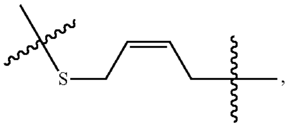
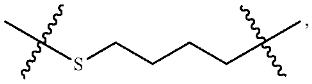
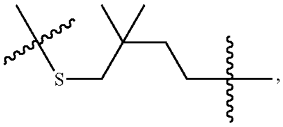
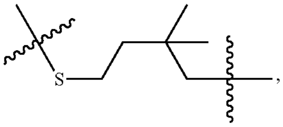
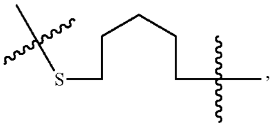
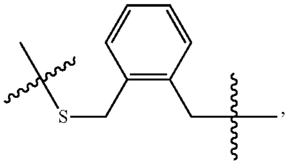
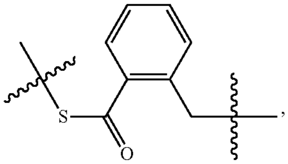
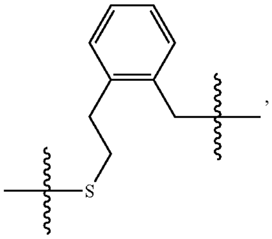
, and
-continued
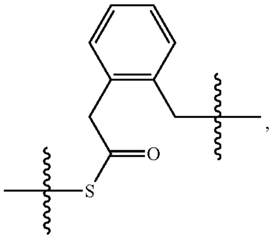 [SMILES: *Cc1ccccc1CC(=O)S*]
and the sulfur atom is connect to V. In some embodiments, $L^1$ is an optionally substituted group selected from
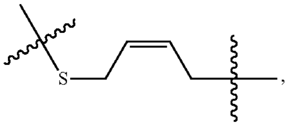
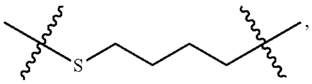
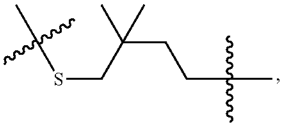
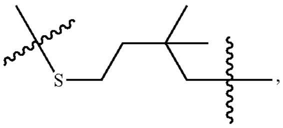
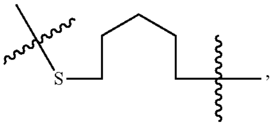
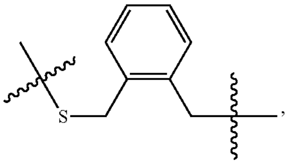
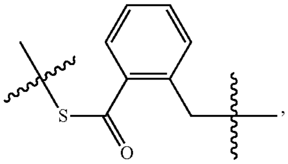
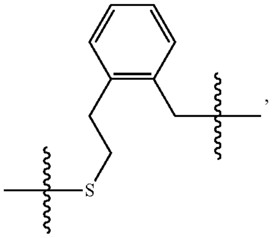
, and -continued

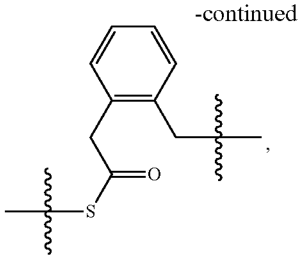

and the carbon atom is connect to X.

In some embodiments, L has the structure of:

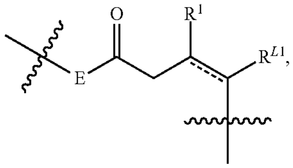

wherein:

E is —O—, —S—, —NR'— or —C(R')$_2$—;

⋯⋯ is a single or double bond;

the two $R^{L1}$ are taken together with the two carbon atoms to which they are bound to form an optionally substituted aryl, carbocyclic, heteroaryl or heterocyclic ring; and each R' is independently as defined above and described herein.

In some embodiments, L has the structure of:

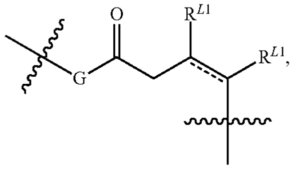

wherein:

G is —O—, —S—, or —NR';

⋯⋯ is a single or double bond; and the two $R^{L1}$ are taken together with the two carbon atoms to which they are bound to form an optionally substituted aryl, $C_3$-$C_{10}$ carbocyclic, heteroaryl or heterocyclic ring.

In some embodiments, L has the structure of:

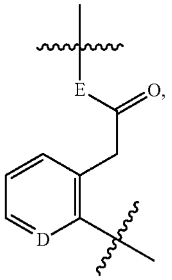

wherein:

E is —O—, —S—, —NR'— or —C(R')$_2$—;

D is =N—, =C(F)—, =C(Cl)—, =C(Br)—, =C(I)—, =C(CN)—, =C($NO_2$)—, =C($CO_2$—($C_1$-$C_6$ aliphatic))-, or =C($CF_3$)—; and each R' is independently as defined above and described herein.

In some embodiments, L has the structure of:

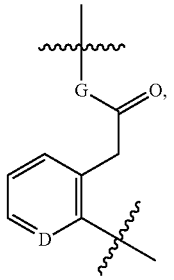

wherein:

G is —O—, —S—, or —NR';

D is =N—, =C(F)—, =C(Cl)—, =C(Br)—, =C(I)—, =C(CN)—, =C($NO_2$)—, =C($CO_2$—($C_1$-$C_6$ aliphatic))-, or =C($CF_3$)—.

In some embodiments, L has the structure of:

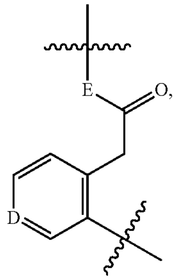

wherein:

E is —O—, —S—, —NR'— or —C(R')$_2$—;

D is =N—, =C(F)—, =C(Cl)—, =C(Br)—, =C(I)—, =C(CN)—, =C($NO_2$)—, =C($CO_2$—($C_1$-$C_6$ aliphatic))-, or =C($CF_3$)—; and each R' is independently as defined above and described herein.

In some embodiments, L has the structure of:

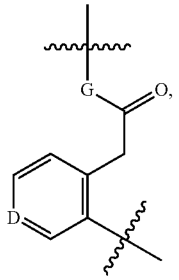

wherein:

G is —O—, —S—, or —NR';

D is =N—, =C(F)—, =C(Cl)—, =C(Br)—, =C(I)—, =C(CN)—, =C($NO_2$)—, =C($CO_2$—($C_1$-$C_6$ aliphatic))-, or =C($CF_3$)—.

In some embodiments, L has the structure of:

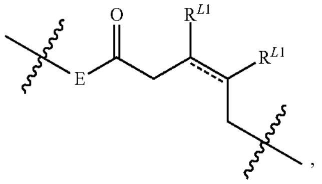

wherein:

E is —O—, —S—, —NR'— or —C(R')$_2$—;

---- is a single or double bond;

the two $R^{L1}$ are taken together with the two carbon atoms to which they are bound to form an optionally substituted aryl, $C_3$-$C_{10}$ carbocyclic, heteroaryl or heterocyclic ring;

and each R' is independently as defined above and described herein.

In some embodiments, L has the structure of:

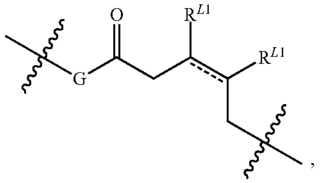

wherein:

G is —O—, —S—, or —NR';

---- is a single or double bond;

the two $R^{L1}$ are taken together with the two carbon atoms to which they are bound to form an optionally substituted aryl, $C_3$-$C_{10}$ carbocyclic, heteroaryl or heterocyclic ring;

and each R' is independently as defined above and described herein.

In some embodiments, L has the structure of:

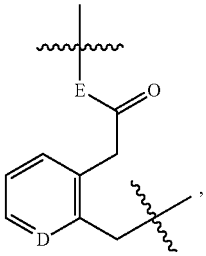

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

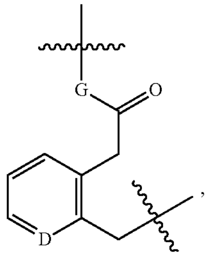

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

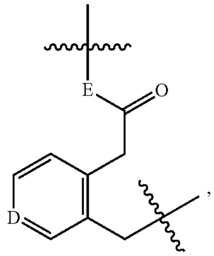

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

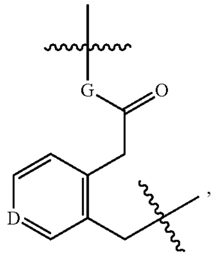

wherein:

G is —O—, —S—, or —NR';

D is =N—, =C(F)—, =C(Cl)—, =C(Br)—, =C(I)—, =C(CN)—, =C(NO$_2$)—, =C(CO$_2$—(C$_1$-C$_6$ aliphatic))-, or =C(CF$_3$)—; and each R' is independently as defined above and described herein.

In some embodiments, L has the structure of:

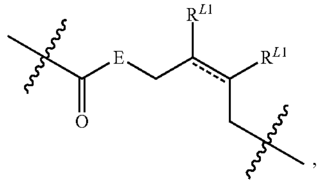

wherein:

E is —O—, —S—, —NR'— or —C(R')$_2$—;

⎓ is a single or double bond;

the two $R^{L1}$ are taken together with the two carbon atoms to which they are bound to form an optionally substituted aryl, $C_3$-$C_{10}$ carbocyclic, heteroaryl or heterocyclic ring; and each R' is independently as defined above and described herein.

In some embodiments, L has the structure of:

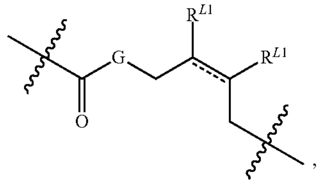

wherein:

G is —O—, —S—, or —NR';

⎓ is a single or double bond;

the two $R^{L1}$ are taken together with the two carbon atoms to which they are bound to form an optionally substituted aryl, $C_3$-$C_{10}$ carbocyclic, heteroaryl or heterocyclic ring; and each R' is independently as defined above and described herein.

In some embodiments, L has the structure of:

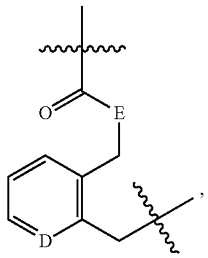

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—($C_1$-$C_6$ aliphatic))-, or =C(CF$_3$)—; and each R' is independently as defined above and described herein.

In some embodiments, L has the structure of:

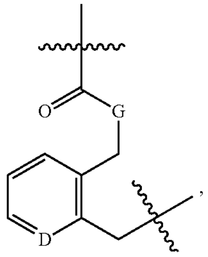

wherein:

G is —O—, —S—, or —NR';

D is =N—, =C(F)—, =C(Cl)—, =C(Br)—, =C(I)—, =C(CN)—, =C(NO$_2$)—, =C(CO$_2$—($C_1$-$C_6$ aliphatic))-, or =C(CF$_3$)—; and R' is as defined above and described herein.

In some embodiments, L has the structure of:

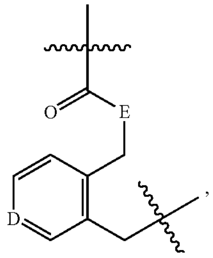

wherein:

E is —O—, —S—, —NR'— or —C(R')$_2$—;

D is =N—, =C(F)—, =C(Cl)—, =C(Br)—, =C(I)—, =C(CN)—, =C(NO$_2$)—, =C(CO$_2$—($C_1$-$C_6$ aliphatic))-, or =C(CF$_3$)—; and each R' is independently as defined above and described herein.

In some embodiments, L has the structure of:

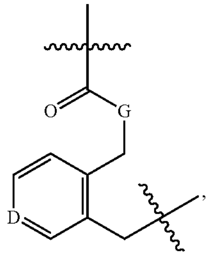

wherein:

G is —O—, —S—, or —NR';

D is =N—, =C(F)—, =C(Cl)—, =C(Br)—, =C(I)—, =C(CN)—, =C(NO$_2$)—, =C(CO$_2$—($C_1$-$C_6$ aliphatic))-, or =C(CF$_3$)—; and R' is as defined above and described herein.

In some embodiments, L has the structure of:

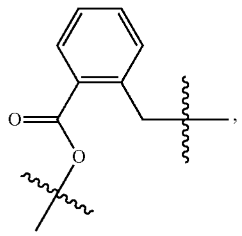

wherein the phenyl ring is optionally substituted. In some embodiments, the phenyl ring is not substituted. In some embodiments, the phenyl ring is substituted.

In some embodiments, L has the structure of:

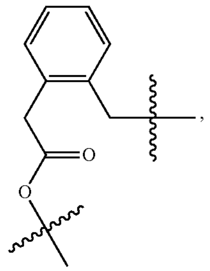 [SMILES: *Cc1ccccc1CC(=O)O*]

wherein the phenyl ring is optionally substituted. In some embodiments, the phenyl ring is not substituted. In some embodiments, the phenyl ring is substituted.

In some embodiments, L has the structure of:

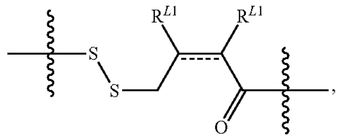

wherein:

---- is a single or double bond; and the two $R^{L1}$ are taken together with the two carbon atoms to which they are bound to form an optionally substituted aryl, $C_3$-$C_{10}$ carbocyclic, heteroaryl or heterocyclic ring.

In some embodiments, L has the structure of:

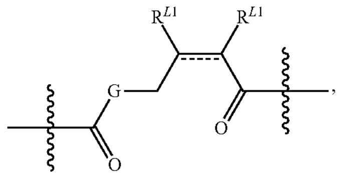

wherein:

G is —O—, —S—, or —NR';

---- is a single or double bond; and the two $R^{L1}$ are taken together with the two carbon atoms to which they are bound to form an optionally substituted aryl, $C_3$-$C_{10}$ carbocyclic, heteroaryl or heterocyclic ring.

In some embodiments, E is —O—, —S—, —NR'— or —$C(R')_2$—, wherein each R' independently as defined above and described herein. In some embodiments, E is —O—, —S—, or —NR'—. In some embodiments, E is —O—, —S—, or —NH—. In some embodiments, E is —O—. In some embodiments, E is —S—. In some embodiments, E is —NH—.

In some embodiments, G is —O—, —S—, or —NR', wherein each R' independently as defined above and described herein. In some embodiments, G is —O—, —S—, or —NH—. In some embodiments, G is —O—. In some embodiments, G is —S—. In some embodiments, G is —NH—.

In some embodiments, L is -$L^3$-G-, wherein:

$L^3$ is an optionally substituted $C_1$-$C_5$ alkylene or alkenylene, wherein one or more methylene units are optionally and independently replaced by —O—, —S—, —N(R')—, —C(O)—, —C(S)—, —C(NR')—, —S(O)—, —$S(O)_2$—, or

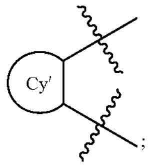 [SMILES: *CC*]

and wherein each of G, R' and Ring Cy' is independently as defined above and described herein.

In some embodiments, L is -$L^3$-S—, wherein $L^3$ is as defined above and described herein. In some embodiments, L is -$L^3$-O—, wherein $L^3$ is as defined above and described herein. In some embodiments, L is -$L^3$-N(R')—, wherein each of $L^3$ and R' is independently as defined above and described herein. In some embodiments, L is -$L^3$-NH—, wherein each of $L^3$ and R' is independently as defined above and described herein.

In some embodiments, $L^3$ is an optionally substituted $C_5$ alkylene or alkenylene, wherein one or more methylene units are optionally and independently replaced by —O—, —S—, —N(R')—, —C(O)—, —C(S)—, —C(NR')—, —S(O)—, —$S(O)_2$—, or

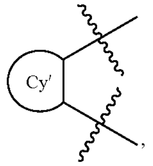 [SMILES: *CC*]

and each of R' and Ring Cy' is independently as defined above and described herein. In some embodiments, $L^3$ is an optionally substituted $C_5$ alkylene. In some embodiments, -$L^3$-G- is

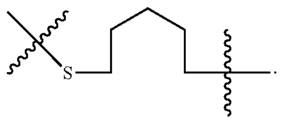 [SMILES: *CCCCCS*]

In some embodiments, $L^3$ is an optionally substituted $C_4$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

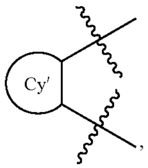 [SMILES: *CC*], and each of R' and Cy' is independently as defined above and described herein.

In some embodiments, -$L^3$-G- is

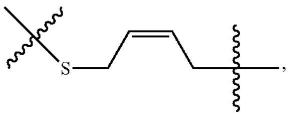,

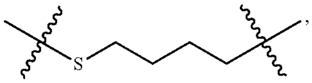,

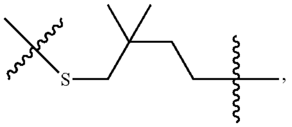,

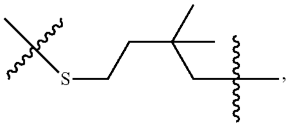,

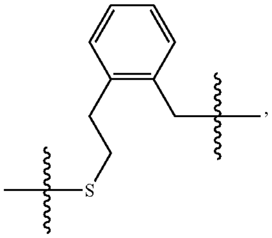,

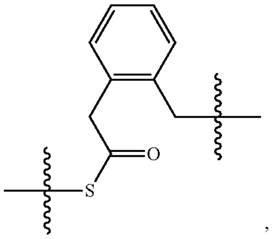, or 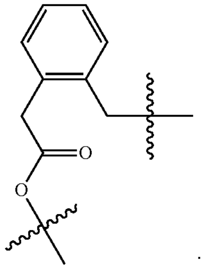.

In some embodiments, $L^3$ is an optionally substituted $C_3$ alkylene or alkenylene, wherein one or more methylene units are optionally and independently replaced by —O—, —S—, —N(R')—, —C(O)—, —C(S)—, —C(NR')—, —S(O)—, —S(O)$_2$—, or

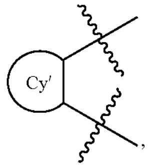, and each of R' and Cy' is independently as defined above and described herein.

In some embodiments, -$L^3$-G- is

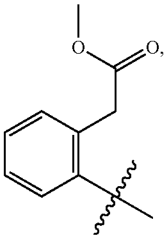, 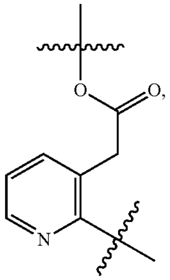, 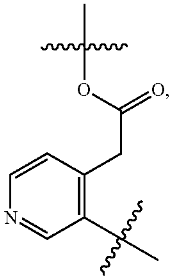,

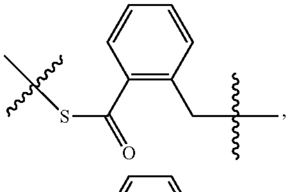,

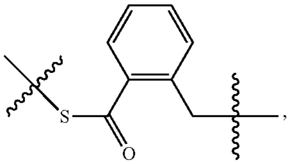, or

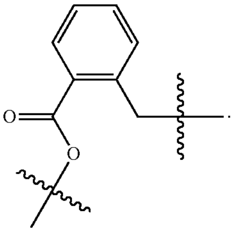.

In some embodiments, L is

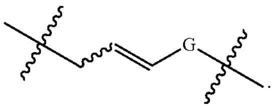.

In some embodiments, L is

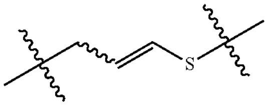 or 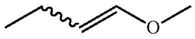.

In some embodiments, L is

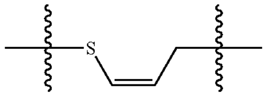 or

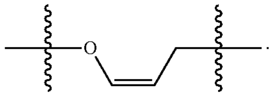.

In some embodiments, $L^3$ is an optionally substituted $C_2$ alkylene or alkenylene, wherein one or more methylene units are optionally and independently replaced by —O—, —S—, —N(R')—, —C(O)—, —C(S)—, —C(NR')—, —S(O)—, —$S(O)_2$—, or

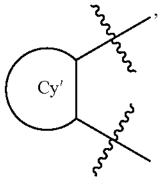 [SMILES: *CC*], and each of R' and Cy' is independently as defined above and described herein.

In some embodiments, $-L^3$-G- is

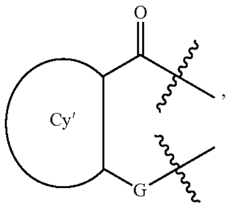, wherein each of G and Cy' is independently as defined above and described herein. In some embodiments, L is

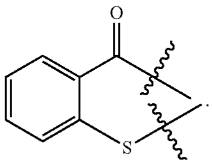 [SMILES: *Sc1ccccc1C(*)=O].

In some embodiments, L is $-L^4$-G-, wherein $L^4$ is an optionally substituted $C_1$-$C_2$ alkylene; and G is as defined above and described herein. In some embodiments, L is $-L^4$-G-, wherein $L^4$ is an optionally substituted $C_1$-$C_2$ alkylene; G is as defined above and described herein; and G is connected to $R^1$. In some embodiments, L is $-L^4$-G-, wherein $L^4$ is an optionally substituted methylene; G is as defined above and described herein; and G is connected to $R^1$. In some embodiments, L is $-L^4$-G-, wherein $L^4$ is methylene; G is as defined above and described herein; and G is connected to $R^1$. In some embodiments, L is $-L^4$-G-, wherein $L^4$ is an optionally substituted —$(CH_2)_2$—; G is as defined above and described herein; and G is connected to $R^1$. In some embodiments, L is $-L^4$-G-, wherein $L^4$ is —$(CH_2)_2$—; G is as defined above and described herein; and G is connected to $R^1$.

In some embodiments, L is

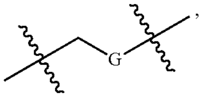, or 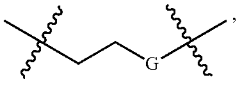, wherein G is as defined above and described herein, and G is connected to $R^1$. In some embodiments, L is

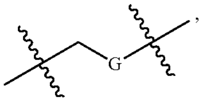, wherein G is as defined above and described herein, and G is connected to $R^1$. In some embodiments, L is

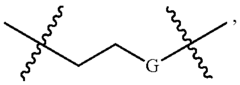, wherein G is as defined above and described herein, and G is connected to $R^1$. In some embodiments, L is

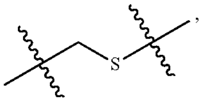, or 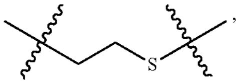, wherein the sulfur atom is connected to $R^1$. In some embodiments, L is

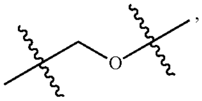, or 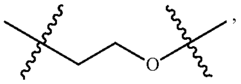, wherein the oxygen atom is connected to $R^1$.

In some embodiments, L is

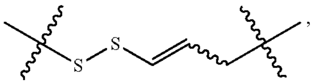,

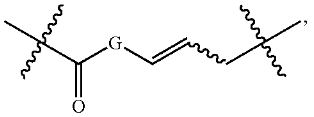, or

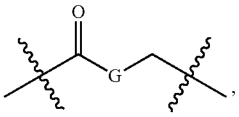, wherein G is as defined above and described herein.

In some embodiments, L is —S—$R^{L3}$— or —S—C(O)—$R^{L3}$—, wherein $R^{L3}$ is an optionally substituted, linear or branched, $C_1$-$C_9$ alkylene, wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each of R' and -Cy- is independently as defined above and described herein. In some embodiments, L is —S—$R^{L3}$— or —S—C(O)—$R^{L3}$—, wherein $R^{L3}$ is an optionally substituted $C_1$-$C_6$ alkylene. In some embodiments, L is —S—$R^{L3}$— or —S—C(O)—$R^{L3}$—, wherein $R^{L3}$ is an optionally substituted $C_1$-$C_6$ alkenylene. In some embodiments, L is —S—$R^{L3}$— or —S—C(O)—$R^{L3}$—, wherein $R^{L3}$ is an optionally substituted $C_1$-$C_6$ alkylene wherein one or more methylene units are optionally and independently replaced by an optionally substituted $C_1$-$C_6$ alkenylene, arylene, or heteroarylene. In some embodiments, In some embodiments, $R^{L3}$ is an optionally substituted —S—($C_1$-$C_6$ alkenylene)-, —S—($C_1$-$C_6$ alkylene)-, —S—($C_1$-$C_6$ alkylene)-arylene-($C_1$-$C_6$ alkylene)-, —S—CO-arylene-($C_1$-$C_6$ alkylene)-, or —S—CO—($C_1$-$C_6$ alkylene)-arylene-($C_1$-$C_6$ alkylene)-.

In some embodiments, L is

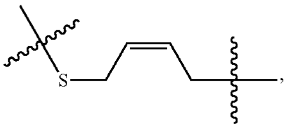
,

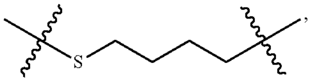
,

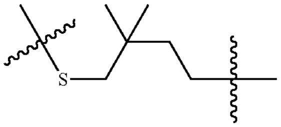
,

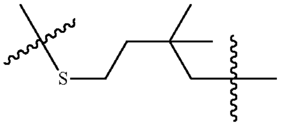
,

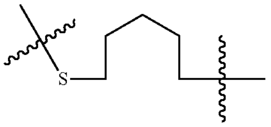
,

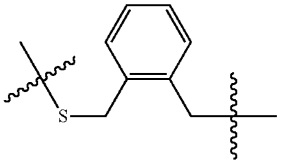
,

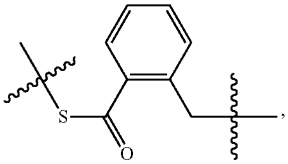
,

-continued

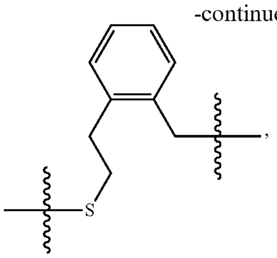
, or

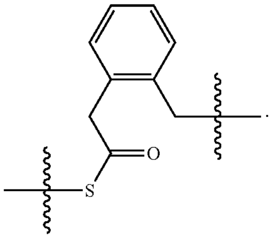
.

In some embodiments, L is

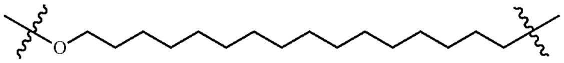
.

In some embodiments, L is

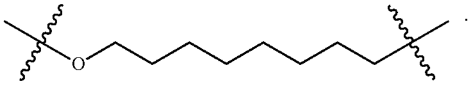 [SMILES: *CCCCCCCCO*]
.

In some embodiments,

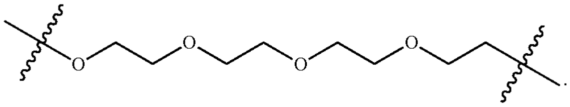 [SMILES: *CCOCCOCCOCCO*]
.

In some embodiments, the sulfur atom in the L embodiments described above and herein is connected to X. In some embodiments, the sulfur atom in the L embodiments described above and herein is connected to $R^1$.

In some embodiments, $R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is halogen, R, or an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N (R')—, —N(R')S(O)$_2$—, —SC(O)—, —C(O)S—, —OC(O)—, or —C(O)O—, wherein each variable is independently as defined above and described herein.

In some embodiments, $R^1$ is hydrogen. In some embodiments, $R^1$ is halogen. In some embodiments, $R^1$ is —F. In some embodiments, $R^1$ is —$C_1$. In some embodiments, $R^1$ is —Br. In some embodiments, $R^1$ is —I.

In some embodiments, $R^1$ is R wherein R is as defined above and described herein.

In some embodiments, $R^1$ is hydrogen. In some embodiments, $R^1$ is an optionally substituted group selected from $C_1$-$C_{50}$ aliphatic, phenyl, carbocyclyl, aryl, heteroaryl, or heterocyclyl.

In some embodiments, $R^1$ is an optionally substituted $C_1$-$C_{50}$ aliphatic. In some embodiments, $R^1$ is an optionally substituted $C_1$-$C_{10}$ aliphatic. In some embodiments, $R^1$ is an optionally substituted $C_1$-$C_6$ aliphatic. In some embodiments, $R^1$ is an optionally substituted $C_1$-$C_6$alkyl. In some embodiments, $R^1$ is optionally substituted, linear or branched hexyl. In some embodiments, $R^1$ is optionally substituted, linear or branched pentyl. In some embodiments, $R^1$ is optionally substituted, linear or branched butyl. In some embodiments, $R^1$ is optionally substituted, linear or branched propyl. In some embodiments, $R^1$ is optionally substituted ethyl. In some embodiments, $R^1$ is optionally substituted methyl.

In some embodiments, $R^1$ is optionally substituted phenyl. In some embodiments, $R^1$ is substituted phenyl. In some embodiments, $R^1$ is phenyl.

In some embodiments, $R^1$ is optionally substituted carbocyclyl. In some embodiments, $R^1$ is optionally substituted $C_3$-$C_{10}$ carbocyclyl. In some embodiments, $R^1$ is optionally substituted monocyclic carbocyclyl. In some embodiments, $R^1$ is optionally substituted cycloheptyl. In some embodiments, $R^1$ is optionally substituted cyclohexyl. In some embodiments, $R^1$ is optionally substituted cyclopentyl. In some embodiments, $R^1$ is optionally substituted cyclobutyl. In some embodiments, $R^1$ is an optionally substituted cyclopropyl. In some embodiments, $R^1$ is optionally substituted bicyclic carbocyclyl.

In some embodiments, $R^1$ is an optionally substituted $C_1$-$C_{50}$ polycyclic hydrocarbon. In some embodiments, $R^1$ is an optionally substituted $C_1$-$C_{50}$ polycyclic hydrocarbon wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is optionally substituted

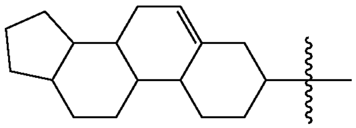.

In some embodiments, $R^1$ is

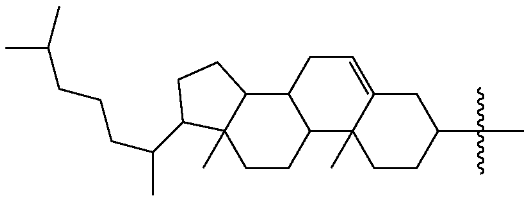.

In some embodiments, $R^1$ is optionally substituted

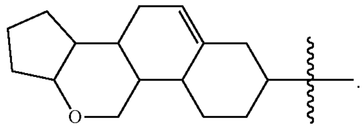 [SMILES: *C1CCC2C(=CCC3C4CCCC4OCC23)C1].

In some embodiments, $R^1$ is an optionally substituted $C_1$-$C_{50}$ aliphatic comprising one or more optionally substituted polycyclic hydrocarbon moieties. In some embodiments, $R^1$ is an optionally substituted $C_1$-$C_{50}$ aliphatic comprising one or more optionally substituted polycyclic hydrocarbon moieties, wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is an optionally substituted $C_1$-$C_{50}$ aliphatic comprising one or more optionally substituted

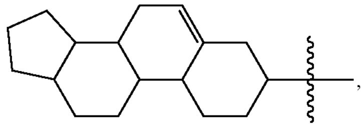,

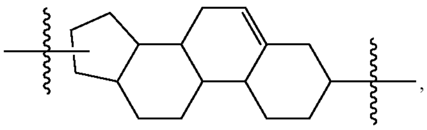,

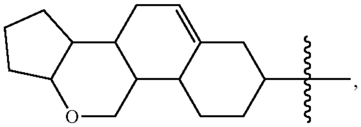, or

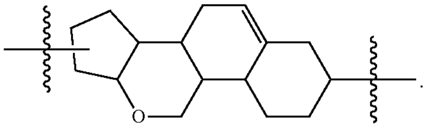.

In some embodiments, $R^1$ is

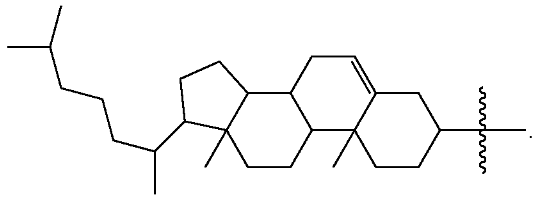 [SMILES: *C1CCC2(C)C(=CCC3C2CCC2(C)C(C(C)CCCC(C)C)CCC32)C1]

In some embodiments, $R^1$ is

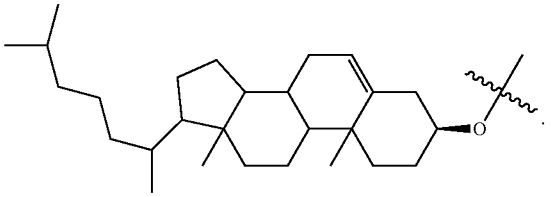 [SMILES: *O[C@H]1CCC2(C)C(=CCC3C2CCC2(C)C(C(C)CCCC(C)C)CCC32)C1]

In some embodiments, $R^1$ is

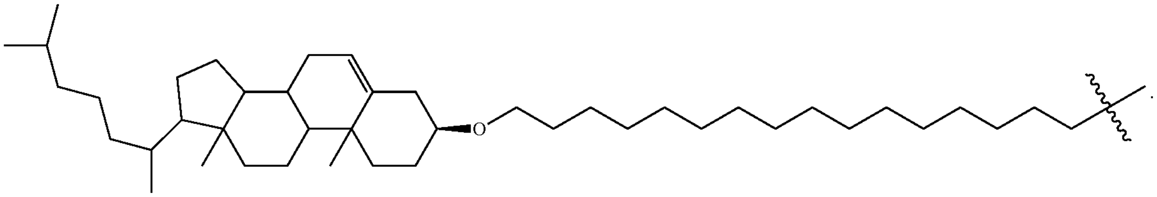 [SMILES: *CCCCCCCCCCCCCCCCO[C@H]1CCC2(C)C(=CCC3C2CCC2(C)C(C(C)CCCC(C)C)CCC32)C1]

In some embodiments, $R^1$ is

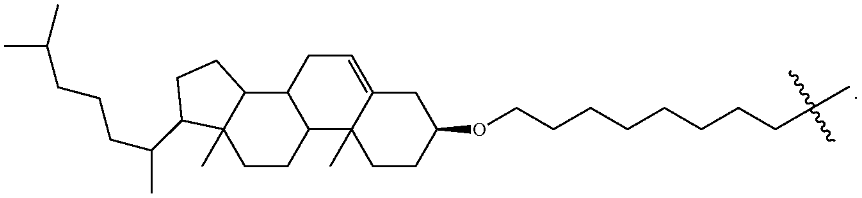 [SMILES: *CCCCCCCCO[C@H]1CCC2(C)C(=CCC3C2CCC2(C)C(C(C)CCCC(C)C)CCC32)C1]

In some embodiments, $R^1$ is

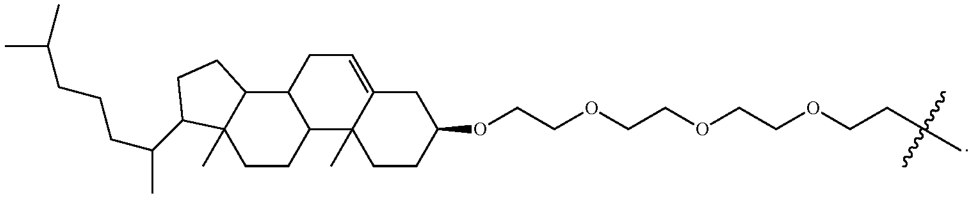 [SMILES: *CCOCCOCCOCCO[C@H]1CCC2(C)C(=CCC3C2CCC2(C)C(C(C)CCCC(C)C)CCC32)C1]

In some embodiments, $R^1$ is an optionally substituted aryl. In some embodiments, $R^1$ is an optionally substituted bicyclic aryl ring.

In some embodiments, $R^1$ is an optionally substituted heteroaryl. In some embodiments, $R^1$ is an optionally substituted 5-6 membered monocyclic heteroaryl ring having 1-3 heteroatoms independently selected from nitrogen, sulfur, or oxygen. In some embodiments, $R^1$ is a substituted 5-6 membered monocyclic heteroaryl ring having 1-3 heteroatoms independently selected from nitrogen, oxygen, or sulfur. In some embodiments, $R^1$ is an unsubstituted 5-6 membered monocyclic heteroaryl ring having 1-3 heteroatoms independently selected from nitrogen, sulfur, or oxygen.

In some embodiments, $R^1$ is an optionally substituted 5 membered monocyclic heteroaryl ring having 1-3 heteroatoms independently selected from nitrogen, oxygen or sulfur. In some embodiments, $R^1$ is an optionally substituted 6 membered monocyclic heteroaryl ring having 1-3 heteroatoms independently selected from nitrogen, oxygen, or sulfur.

In some embodiments, $R^1$ is an optionally substituted 5-membered monocyclic heteroaryl ring having 1 heteroatom selected from nitrogen, oxygen, or sulfur. In some embodiments, $R^1$ is selected from pyrrolyl, furanyl, or thienyl.

In some embodiments, $R^1$ is an optionally substituted 5-membered heteroaryl ring having 2 heteroatoms independently selected from nitrogen, oxygen, or sulfur. In certain embodiments, $R^1$ is an optionally substituted 5-membered heteroaryl ring having 1 nitrogen atom, and an additional heteroatom selected from sulfur or oxygen. Example $R^1$ groups include optionally substituted pyrazolyl, imidazolyl, thiazolyl, isothiazolyl, oxazolyl or isoxazolyl.

In some embodiments, $R^1$ is a 6-membered heteroaryl ring having 1-3 nitrogen atoms. In other embodiments, $R^1$ is an optionally substituted 6-membered heteroaryl ring having 1-2 nitrogen atoms. In some embodiments, $R^1$ is an optionally substituted 6-membered heteroaryl ring having 2 nitrogen atoms. In certain embodiments, $R^1$ is an optionally substituted 6-membered heteroaryl ring having 1 nitrogen. Example $R^1$ groups include optionally substituted pyridinyl, pyrimidinyl, pyrazinyl, pyridazinyl, triazinyl, or tetrazinyl.

In certain embodiments, $R^1$ is an optionally substituted 8-10 membered bicyclic heteroaryl ring having 1-4 heteroatoms independently selected from nitrogen, oxygen, or sulfur. In some embodiments, $R^1$ is an optionally substituted 5,6-fused heteroaryl ring having 1-4 heteroatoms independently selected from nitrogen, oxygen, or sulfur. In other embodiments, $R^1$ is an optionally substituted 5,6-fused heteroaryl ring having 1-2 heteroatoms independently selected from nitrogen, oxygen, or sulfur. In certain embodiments, $R^1$ is an optionally substituted 5,6-fused heteroaryl ring having 1 heteroatom independently selected from nitrogen, oxygen, or sulfur. In some embodiments, $R^1$ is an optionally substituted indolyl. In some embodiments, $R^1$ is an optionally substituted azabicyclo[3.2.1]octanyl. In certain embodiments, $R^1$ is an optionally substituted 5,6-fused heteroaryl ring having 2 heteroatoms independently selected from nitrogen, oxygen, or sulfur. In some embodiments, $R^1$ is an optionally substituted azaindolyl. In some embodiments, $R^1$ is an optionally substituted benzimidazolyl. In some embodiments, $R^1$ is an optionally substituted benzothiazolyl. In some embodiments, $R^1$ is an optionally substituted benzoxazolyl. In some embodiments, $R^1$ is an optionally substituted indazolyl. In certain embodiments, $R^1$ is an optionally substituted 5,6-fused heteroaryl ring having 3 heteroatoms independently selected from nitrogen, oxygen, or sulfur.

In certain embodiments, $R^1$ is an optionally substituted 6,6-fused heteroaryl ring having 1-4 heteroatoms independently selected from nitrogen, oxygen, or sulfur. In some embodiments, $R^1$ is an optionally substituted 6,6-fused heteroaryl ring having 1-2 heteroatoms independently selected from nitrogen, oxygen, or sulfur. In other embodiments, $R^1$ is an optionally substituted 6,6-fused heteroaryl ring having 1 heteroatom independently selected from nitrogen, oxygen, or sulfur. In some embodiments, $R^1$ is an optionally substituted quinolinyl. In some embodiments, $R^1$ is an optionally substituted isoquinolinyl. According to one aspect, $R^1$ is an optionally substituted 6,6-fused heteroaryl ring having 2 heteroatoms independently selected from nitrogen, oxygen, or sulfur. In some embodiments, $R^1$ is a quinazoline or a quinoxaline.

In some embodiments, $R^1$ is an optionally substituted heterocyclyl. In some embodiments, $R^1$ is an optionally substituted 3-7 membered saturated or partially unsaturated heterocyclic ring having 1-2 heteroatoms independently selected from nitrogen, oxygen, or sulfur. In some embodiments, $R^1$ is a substituted 3-7 membered saturated or partially unsaturated heterocyclic ring having 1-2 heteroatoms independently selected from nitrogen, oxygen, or sulfur. In some embodiments, $R^1$ is an unsubstituted 3-7 membered saturated or partially unsaturated heterocyclic ring having 1-2 heteroatoms independently selected from nitrogen, oxygen, or sulfur.

In some embodiments, $R^1$ is an optionally substituted heterocyclyl. In some embodiments, $R^1$ is an optionally substituted 6 membered saturated or partially unsaturated heterocyclic ring having 1-2 heteroatoms independently selected from nitrogen, oxygen, or sulfur. In some embodiments, $R^1$ is an optionally substituted 6 membered partially unsaturated heterocyclic ring having 2 heteroatoms independently selected from nitrogen, oxygen, or sulfur. In some embodiments, $R^1$ is an optionally substituted 6 membered partially unsaturated heterocyclic ring having 2 oxygen atoms.

In certain embodiments, $R^1$ is a 3-7 membered saturated or partially unsaturated heterocyclic ring having 1-2 heteroatoms independently selected from nitrogen, oxygen, or sulfur. In certain embodiments, $R^1$ is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, $R^1$ is an optionally substituted 5 membered saturated or partially unsaturated heterocyclic ring having 1-2 heteroatoms independently selected from nitrogen, oxygen, or sulfur.

In certain embodiments, $R^1$ is an optionally substituted 5-6 membered partially unsaturated monocyclic ring having 1-2 heteroatoms independently selected from nitrogen, oxygen, or sulfur. In certain embodiments, $R^1$ is an optionally substituted tetrahydropyridinyl, dihydrothiazolyl, dihydrooxazolyl, or oxazolinyl group.

In some embodiments, $R^1$ is an optionally substituted 8-10 membered bicyclic saturated or partially unsaturated heterocyclic ring having 1-4 heteroatoms independently selected from nitrogen, oxygen, or sulfur. In some embodiments, $R^1$ is an optionally substituted indolinyl. In some embodiments, $R^1$ is an optionally substituted isoindolinyl. In some embodiments, $R^1$ is an optionally substituted 1, 2, 3, 4-tetrahydroquinoline. In some embodiments, $R^1$ is an optionally substituted 1, 2, 3, 4-tetrahydroisoquinoline.

In some embodiments, $R^1$ is an optionally substituted $C_1$-$C_{10}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently as defined above and described herein. In some embodiments, $R^1$ is an optionally substituted $C_1$-$C_{10}$ aliphatic wherein one or more methylene units are optionally and independently replaced by an optionally-Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —OC(O)—, or —C(O)O—, wherein each R' is independently as defined above and described herein. In some embodiments, $R^1$ is an optionally substituted $C_1$-$C_{10}$ aliphatic wherein one or more methylene units are optionally and independently replaced by an optionally-Cy-, —O—, —S—, —S—S—, —N(R')—, —C(O)—, —OC(O)—, or —C(O)O—, wherein each R' is independently as defined above and described herein.

In some embodiments, $R^1$ is

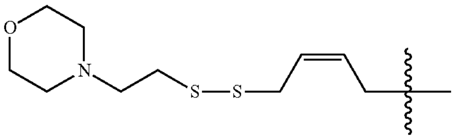,

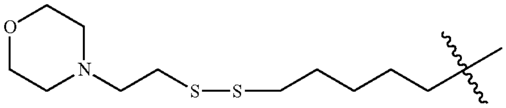,

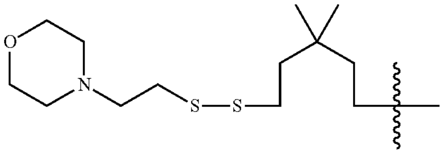,

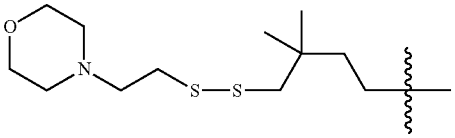,

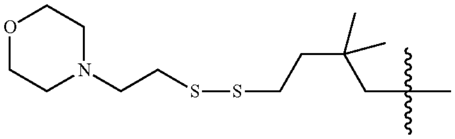,

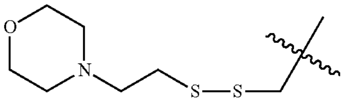,

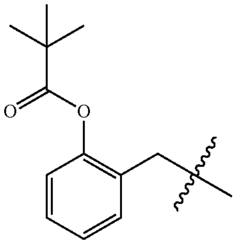, 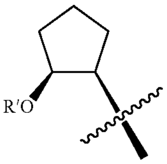,

-continued

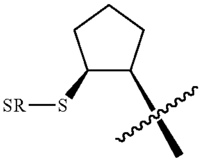, 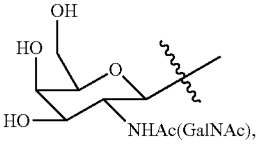,

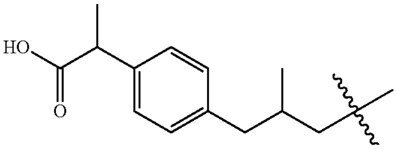,

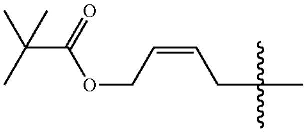,

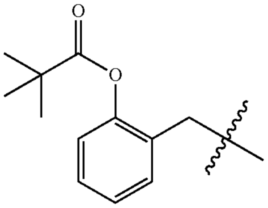,

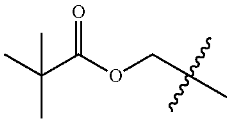,

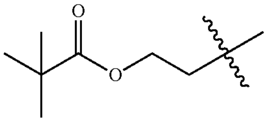,

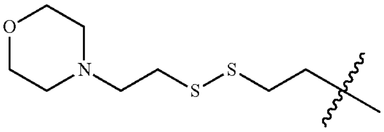,

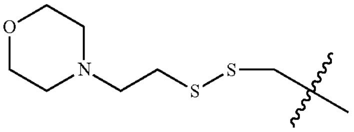,

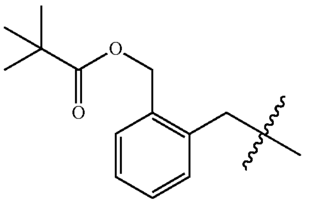,

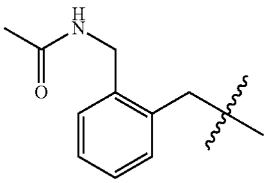,

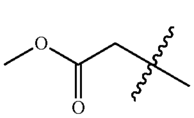, 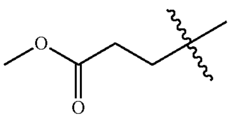,

-continued
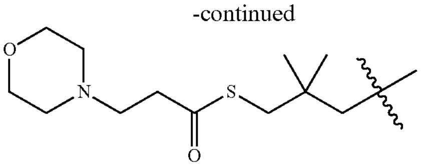,
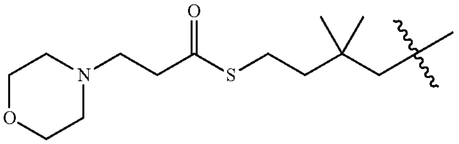,
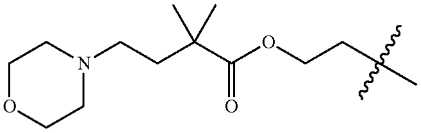,
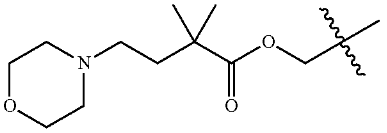,
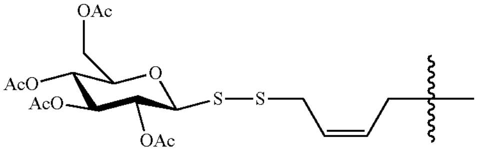,
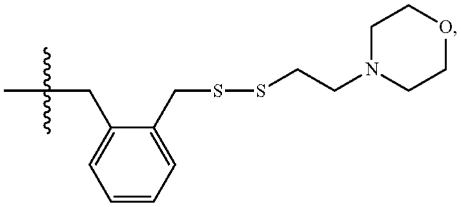
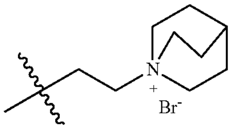, 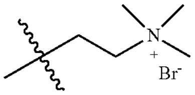,
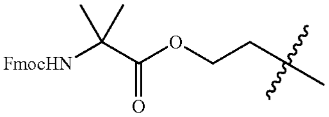,
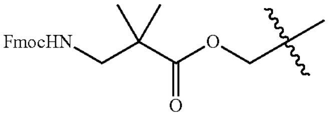,
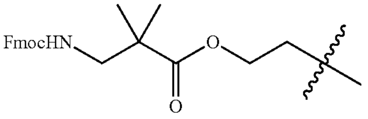,
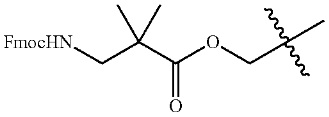,
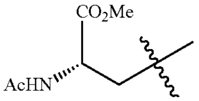,
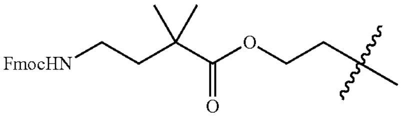,
-continued
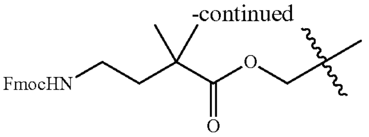,
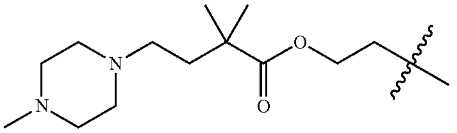,
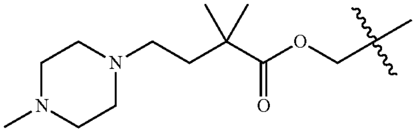,
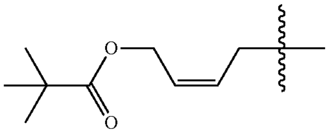,
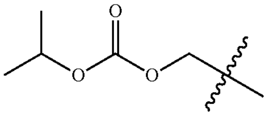, $CH_3$—,
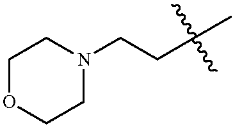, 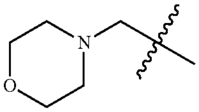,
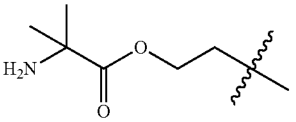,
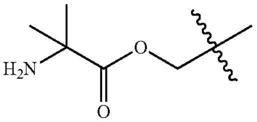, 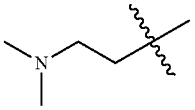,
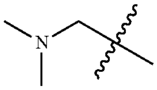, 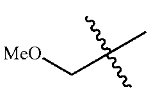, or
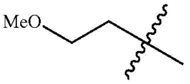.
In some embodiments, $R^1$ is $CH_3$—,
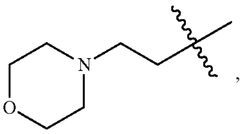,
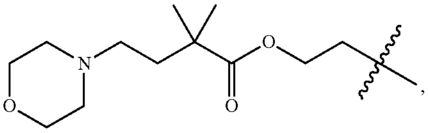,
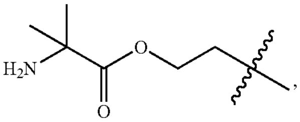, 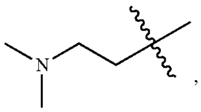, -continued

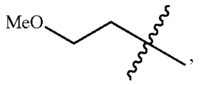, or

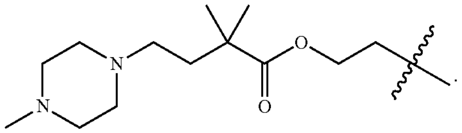.

In some embodiments, $R^1$ comprises a terminal optionally substituted —$(CH_2)_2$-moiety which is connected to L. Example such $R^1$ groups are depicted below:

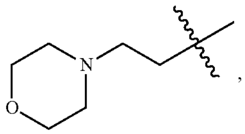,

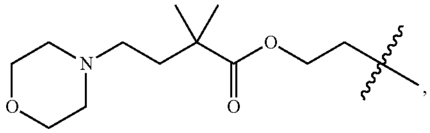,

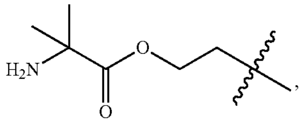, 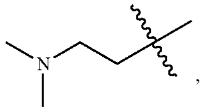,

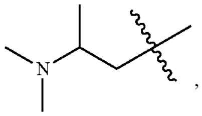, 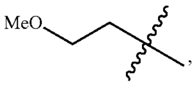, and

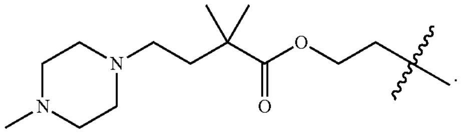.

In some embodiments, $R^1$ comprises a terminal optionally substituted —$(CH_2)$— moiety which is connected to L. Example such $R^1$ groups are depicted below:

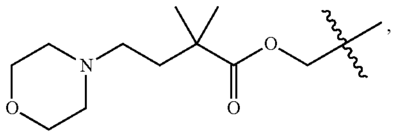,

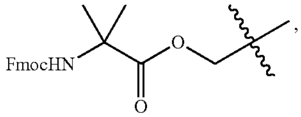,

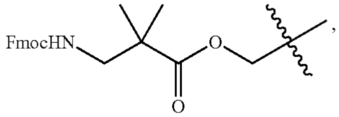,

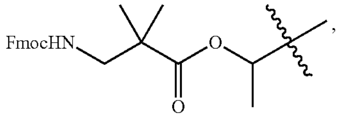,

-continued

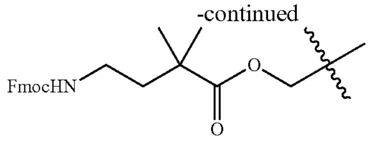,

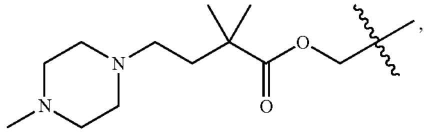,

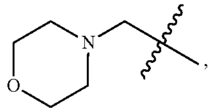, 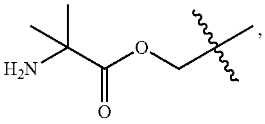,

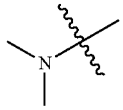, and 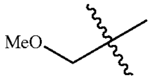.

In some embodiments, $R^1$ is —S—$R^{L2}$, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2$N(R')—, —N(R')$S(O)_2$—, —SC(O)—, —C(O)S—, —OC(O)—, or —C(O)O—, and each of R' and -Cy- is independently as defined above and described herein. In some embodiments, $R^1$ is —S—$R^{L2}$, wherein the sulfur atom is connected with the sulfur atom in L group.

In some embodiments, $R^1$ is —C(O)—$R^{L2}$, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —$S(O)_2$—, —$S(O)_2$N(R')—, —N(R')$S(O)_2$—, —SC(O)—, —C(O)S—, —OC(O)—, or —C(O)O—, and each of R' and -Cy- is independently as defined above and described herein. In some embodiments, $R^1$ is —C(O)—$R^{L2}$, wherein the carbonyl group is connected with G in L group. In some embodiments, $R^1$ is —C(O)—$R^{L2}$, wherein the carbonyl group is connected with the sulfur atom in L group.

In some embodiments, $R^{L2}$ is optionally substituted $C_1$-$C_9$ aliphatic. In some embodiments, $R^{L2}$ is optionally substituted $C_1$-$C_9$ alkyl. In some embodiments, $R^{L2}$ is optionally substituted $C_1$-$C_9$ alkenyl. In some embodiments, $R^{L2}$ is optionally substituted $C_1$-$C_9$ alkynyl. In some embodiments, $R^{L2}$ is an optionally substituted $C_1$-$C_9$ aliphatic wherein one or more methylene units are optionally and independently replaced by -Cy- or —C(O)—. In some embodiments, $R^{L2}$ is an optionally substituted $C_1$-$C_9$ aliphatic wherein one or more methylene units are optionally and independently replaced by -Cy-. In some embodiments, $R^{L2}$ is an optionally substituted $C_1$-$C_9$ aliphatic wherein one or more methylene units are optionally and independently replaced by an optionally substituted heterocyclene. In some embodiments, $R^{L2}$ is an optionally substituted $C_1$-$C_9$ aliphatic wherein one or more methylene units are optionally and independently replaced by an optionally substituted arylene.

In some embodiments, $R^{L2}$ is an optionally substituted $C_1$-$C_9$ aliphatic wherein one or more methylene units are optionally and independently replaced by an optionally substituted heteroarylene. In some embodiments, $R^{L2}$ is an optionally substituted $C_1$-$C_9$ aliphatic wherein one or more methylene units are optionally and independently replaced by an optionally substituted $C_3$-$C_{10}$ carbocyclylene. In some embodiments, $R^{L2}$ is an optionally substituted $C_1$-$C_9$ aliphatic wherein two methylene units are optionally and independently replaced by -Cy- or —C(O)—. In some embodiments, $R^{L2}$ is an optionally substituted $C_1$-$C_9$ aliphatic wherein two methylene units are optionally and independently replaced by -Cy- or —C(O)—. Example $R^{L2}$ groups are depicted below:

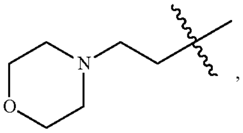
,
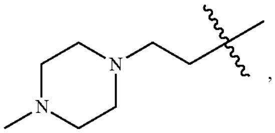
,
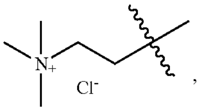
,
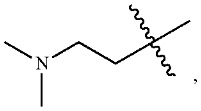
,
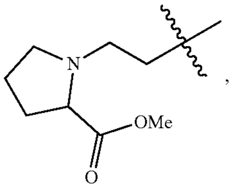
,
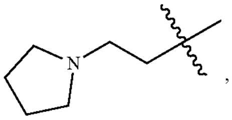
, and
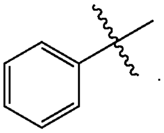
.

In some embodiments, $R^1$ is hydrogen, or an optionally substituted group selected from

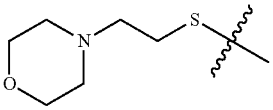
,
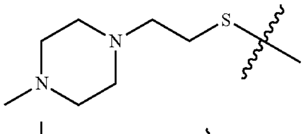
,
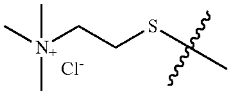
,
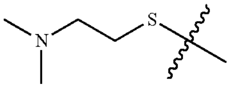
,
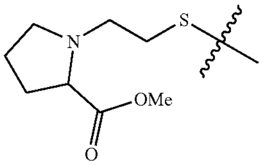
,

-continued

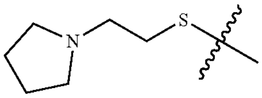
,
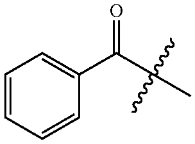
,

—S—($C_1$-$C_{10}$ aliphatic), $C_1$-$C_{10}$ aliphatic, aryl, $C_1$-$C_6$ heteroalkyl, heteroaryl and heterocyclyl. In some embodiments, R is

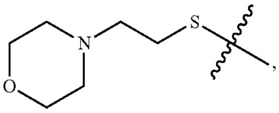
,
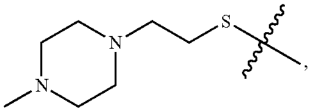
,
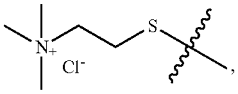
,
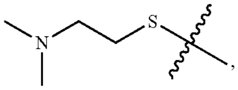
,
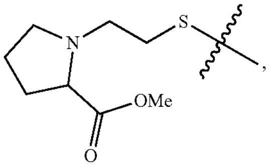
,
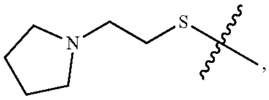
,
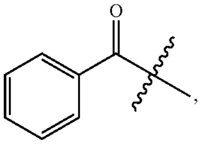
, or —S—($C_1$-$C_{10}$ aliphatic). In some embodiments, $R^1$ is,

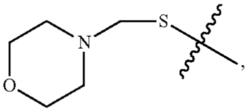
,
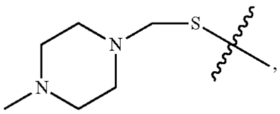
,
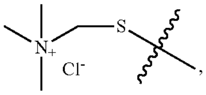
,
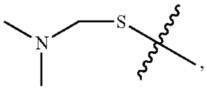
,
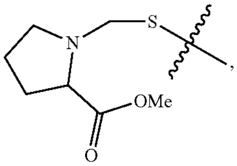
, or
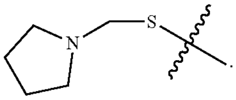
.

In some embodiments, $R^1$ is an optionally substituted group selected from —S—($C_1$-$C_6$ aliphatic), $C_1$-$C_{10}$ aliphatic, $C_1$-$C_6$ heteroaliphatic, aryl, heterocyclyl and heteroaryl.

In some embodiments, $R^1$ is

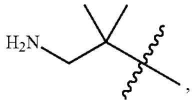,
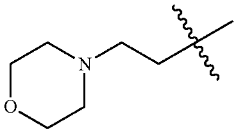,
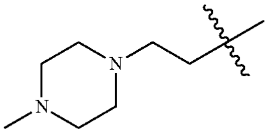,
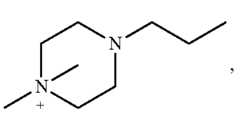,
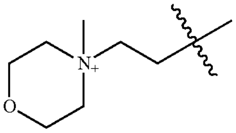,
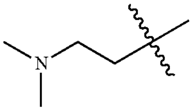,
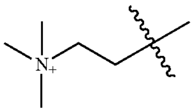,
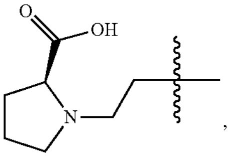,
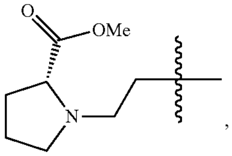,
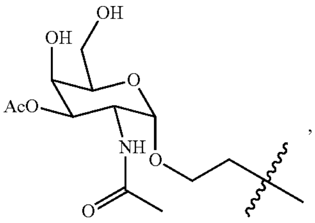,
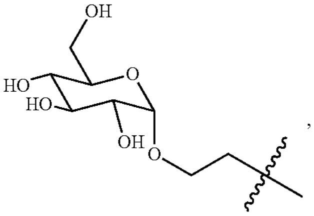, or
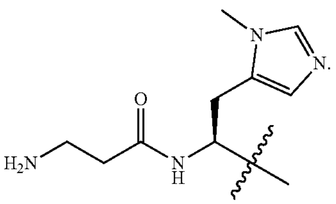

In some embodiments, the sulfur atom in the $R^1$ embodiments described above and herein is connected with the sulfur atom, G, E, or —C(O)— moiety in the L embodiments described above and herein. In some embodiments, the —C(O)— moiety in the $R^1$ embodiments described above and herein is connected with the sulfur atom, G, E, or —C(O)— moiety in the L embodiments described above and herein.

In some embodiments, $-L-R^1$ is any combination of the L embodiments and $R^1$ embodiments described above and herein.

In some embodiments, $-L-R^1$ is $-L^3-G-R^1$ wherein each variable is independently as defined above and described herein.

In some embodiments, $-L-R^1$ is $-L^4-G-R^1$ wherein each variable is independently as defined above and described herein.

In some embodiments, $-L-R^1$ is $-L^3-G-S—R^{L2}$, wherein each variable is independently as defined above and described herein.

In some embodiments, $-L-R^1$ is $-L^3-G-C(O)—R^{L2}$, wherein each variable is independently as defined above and described herein.

In some embodiments, $-L-R^1$ is

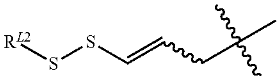,
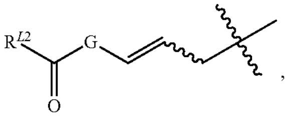,
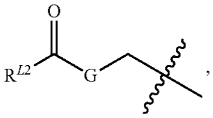, or 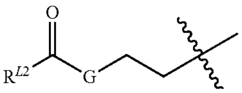, wherein $R^{L2}$ is an optionally substituted $C_1$-$C_9$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, and each G is independently as defined above and described herein.

In some embodiments, $-L-R^1$ is $—R^{L3}—S—S—R^{L2}$, wherein each variable is independently as defined above and described herein. In some embodiments, $-L-R^1$ is $—R^{L3}—C(O)—S—S—R^{L2}$, wherein each variable is independently as defined above and described herein.

In some embodiments, $-L-R^1$ has the structure of:

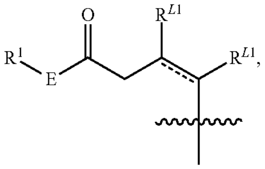

wherein each variable is independently as defined above and described herein.

In some embodiments, -L-$R^1$ has the structure of:

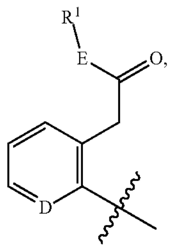

wherein each variable is independently as defined above and described herein.

In some embodiments, -L-$R^1$ has the structure of:

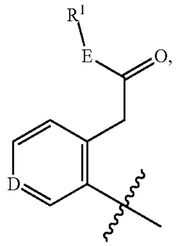

wherein each variable is independently as defined above and described herein.

In some embodiments, -L-$R^1$ has the structure of:

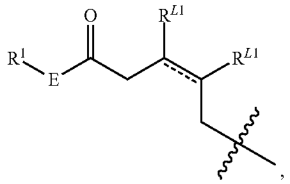

wherein each variable is independently as defined above and described herein.

In some embodiments, -L-$R^1$ has the structure of:

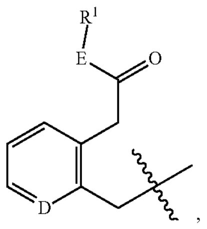

wherein each variable is independently as defined above and described herein.

In some embodiments, -L-$R^1$ has the structure of:

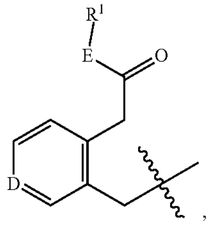

wherein each variable is independently as defined above and described herein.

In some embodiments, -L-$R^1$ has the structure of:

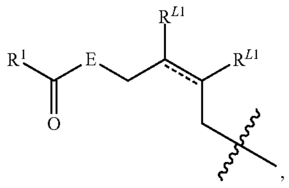

wherein each variable is independently as defined above and described herein.

In some embodiments, -L-$R^1$ has the structure of:

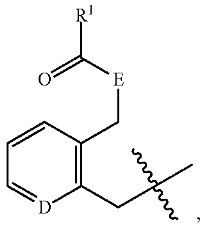

wherein each variable is independently as defined above and described herein.

In some embodiments, -L-$R^1$ has the structure of:

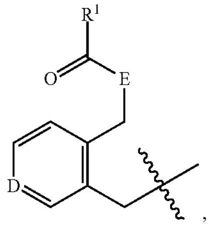

wherein each variable is independently as defined above and described herein.

In some embodiments, -L-$R^1$ has the structure of:

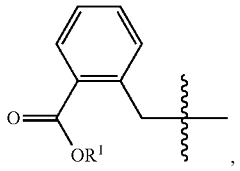

wherein each variable is independently as defined above and described herein.

In some embodiments, -L-$R^1$ has the structure of:

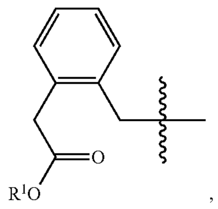

wherein each variable is independently as defined above and described herein.

In some embodiments, -L-$R^1$ has the structure of:

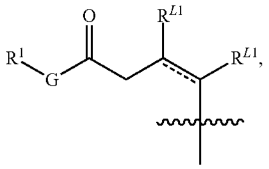

wherein each variable is independently as defined above and described herein.

In some embodiments, -L-$R^1$ has the structure of:

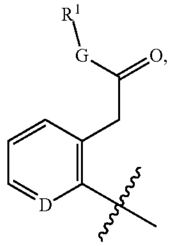

wherein each variable is independently as defined above and described herein.

In some embodiments, -L-$R^1$ has the structure of:

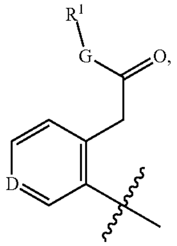

wherein each variable is independently as defined above and described herein.

In some embodiments, -L-$R^1$ has the structure of:

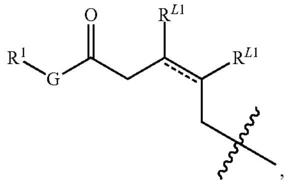

wherein each variable is independently as defined above and described herein.

In some embodiments, -L-$R^1$ has the structure of:

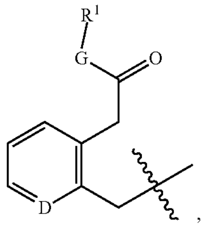

wherein each variable is independently as defined above and described herein.

In some embodiments, -L-$R^1$ has the structure of:

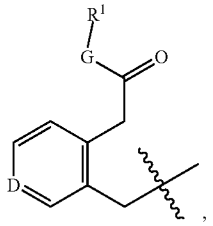

wherein each variable is independently as defined above and described herein.

In some embodiments, -L-$R^1$ has the structure of:

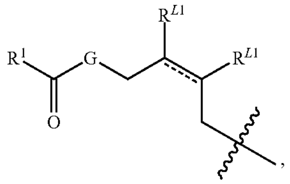

wherein each variable is independently as defined above and described herein.

In some embodiments, -L-$R^1$ has the structure of:

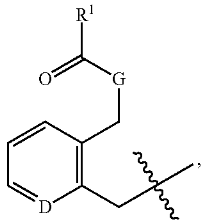

wherein each variable is independently as defined above and described herein.

In some embodiments, -L-$R^1$ has the structure of:

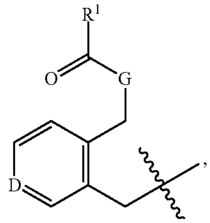

wherein each variable is independently as defined above and described herein.

In some embodiments, -L-$R^1$ has the structure of:

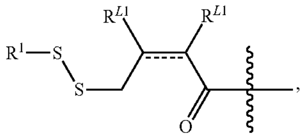

wherein each variable is independently as defined above and described herein.

In some embodiments, -L-$R^1$ has the structure of:

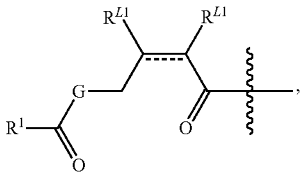

wherein each variable is independently as defined above and described herein.

In some embodiments, —X-L-$R^1$ has the structure of:

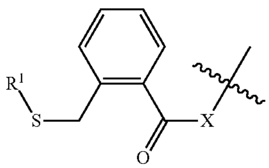

wherein:

the phenyl ring is optionally substituted, and each of $R^1$ and X is independently as defined above and described herein.

In some embodiments, -L-$R^1$ is

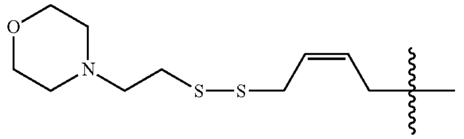

,

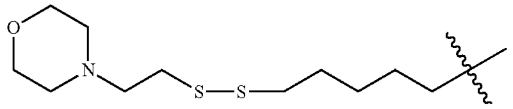

,

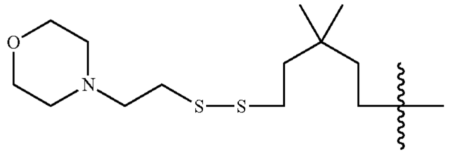

,

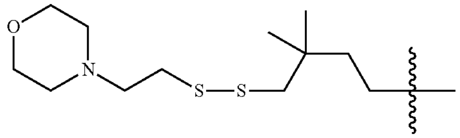

,

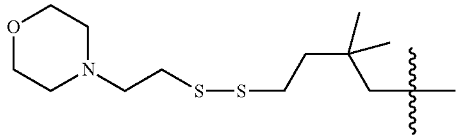

,

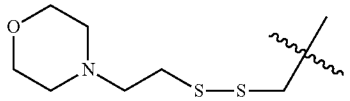

,

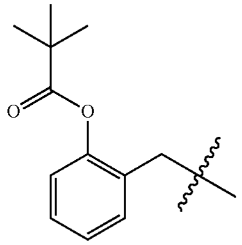

,

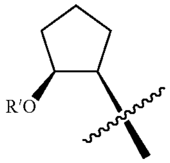

,

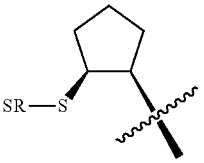

,

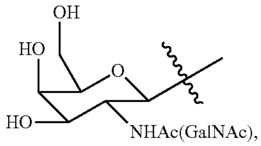

(GalNAc),

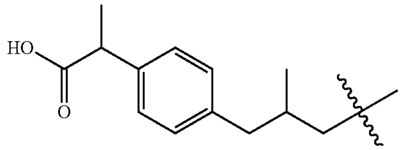

,

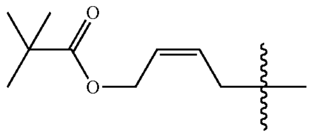

,

-continued
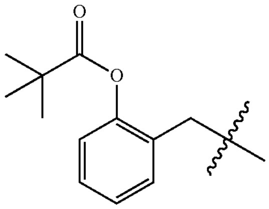,
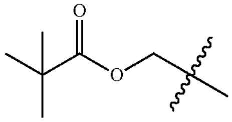,
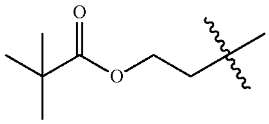,
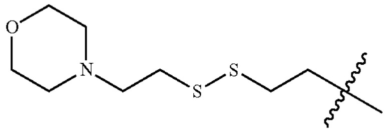,
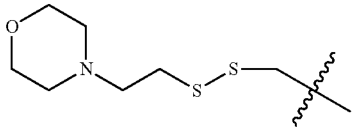,
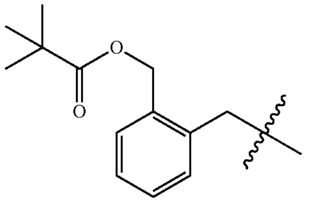,
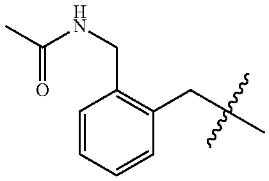,
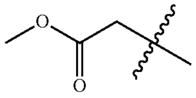, 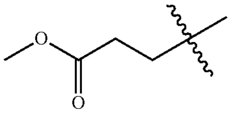,
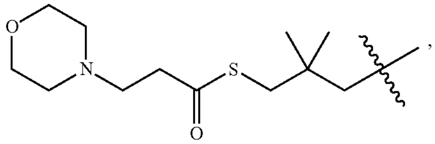,
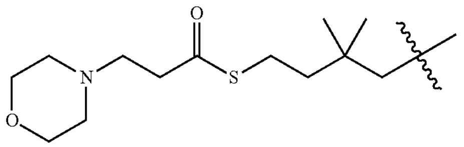,
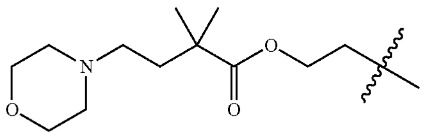,
-continued
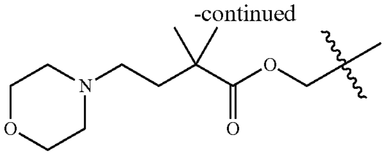,
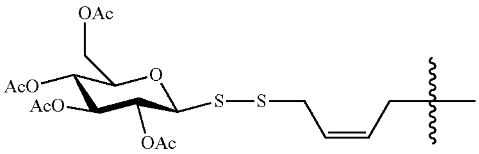,
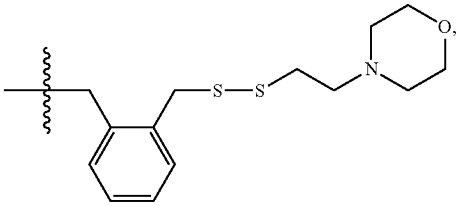
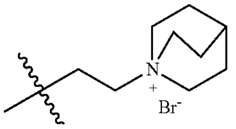, 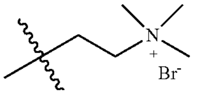,
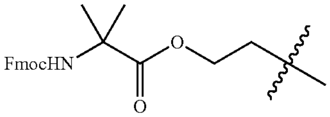,
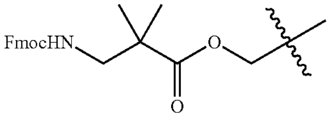,
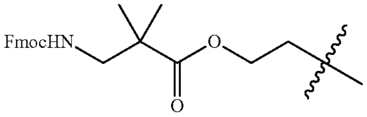,
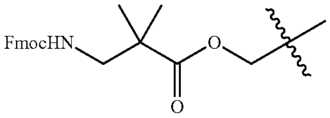,
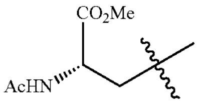,
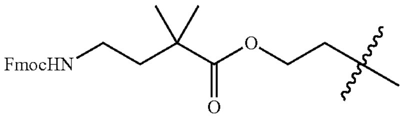,
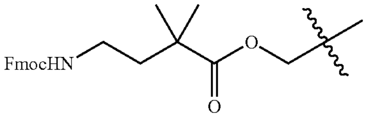,
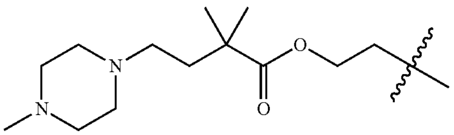,
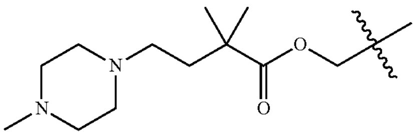

-continued
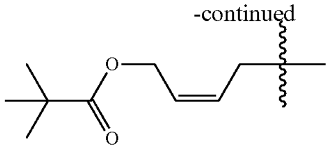
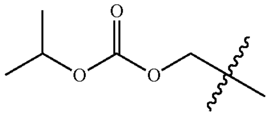, $CH_3$—,
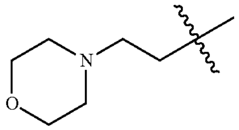, 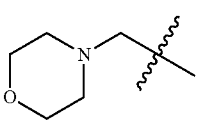,
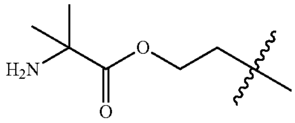,
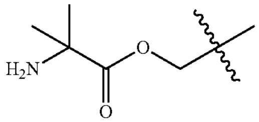, 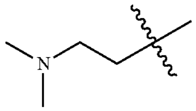,
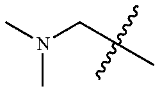, 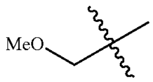, or
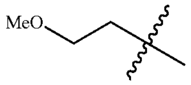.
In some embodiments, -L-R[1] is:
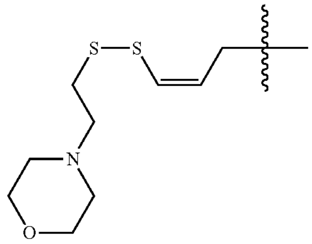,
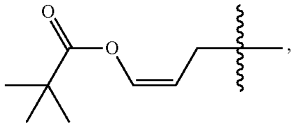, or
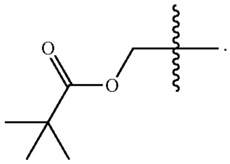.
In some embodiments, -L-R[1] is
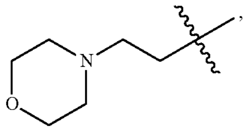,
-continued
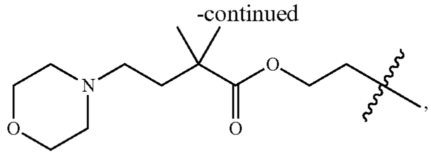,
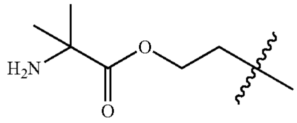,
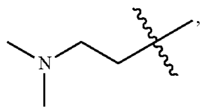, 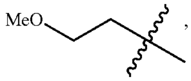, or
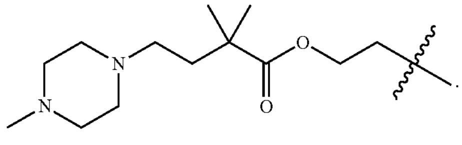.
In some embodiments, -L-R[1] is
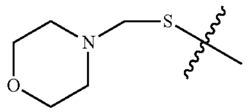,
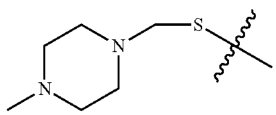, 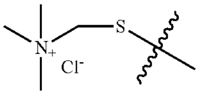,
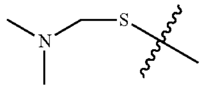, 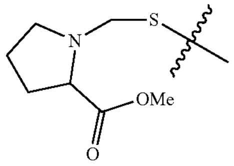, or
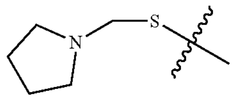.
In some embodiments, -L-R[1] comprises a terminal optionally substituted —$(CH_2)_2$-moiety which is connected to X. In some embodiments, -L-R[1] comprises a terminal —$(CH_2)_2$-moiety which is connected to X. Example such -L-R[1] moieties are depicted below:
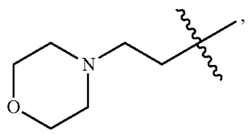,
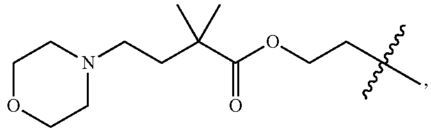,
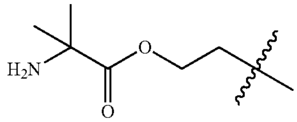, -continued
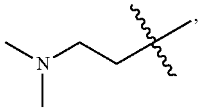,
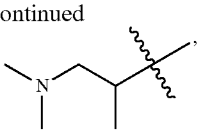,
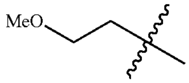, and
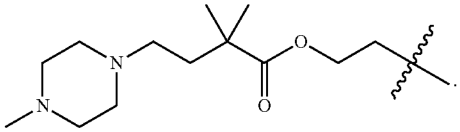.
In some embodiments, -L-R[1] comprises a terminal optionally substituted —$(CH_2)$— moiety which is connected to X. In some embodiments, -L-R[1] comprises a terminal —$(CH_2)$— moiety which is connected to X. Example such -L-R[1] moieties are depicted below:
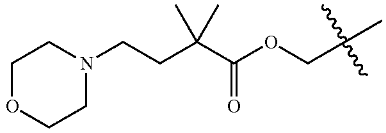,
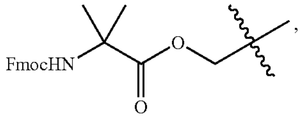,
-continued
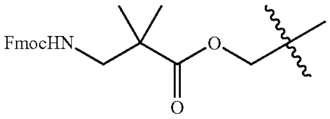,
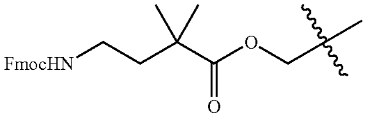,
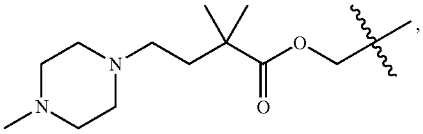,
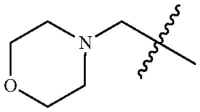,
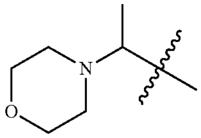,
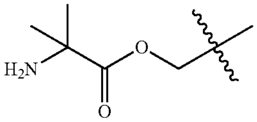,
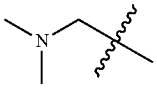, and
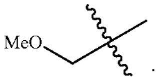.
In some embodiments, -L-R is
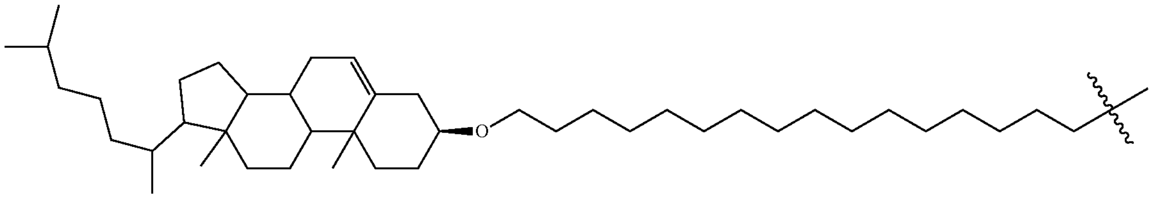,
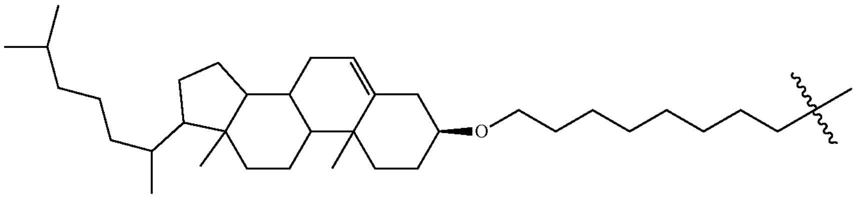, or
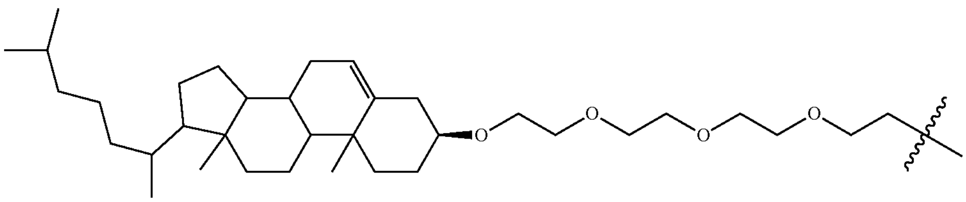.

In some embodiments, -L-$R^1$ is $CH_3$—,
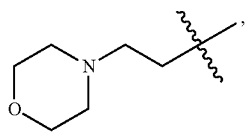,
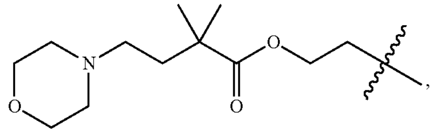,
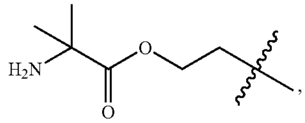,
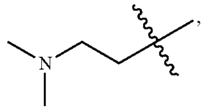, 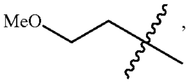,
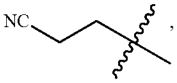, or
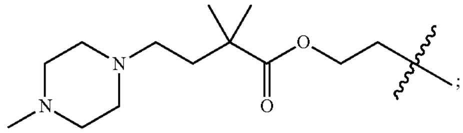;
and X is —S—.
In some embodiments, -L-$R^1$ is $CH_3$—,
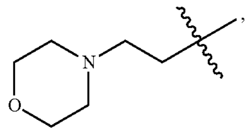,
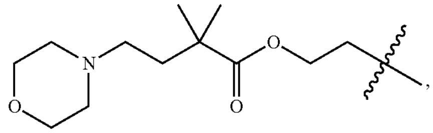,
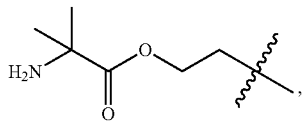,
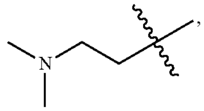, 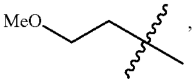, or
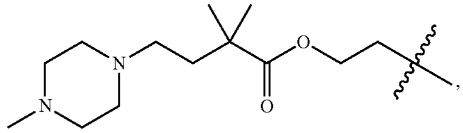,
X is —S—, W is O, Y is —O—, and Z is —O—.
In some embodiments, $R^1$ is
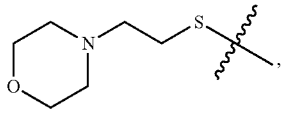,
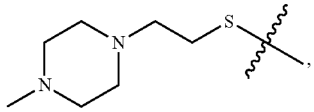,
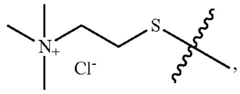, 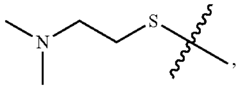,
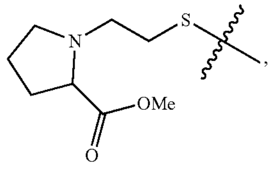,
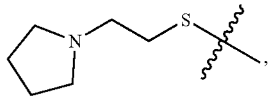, 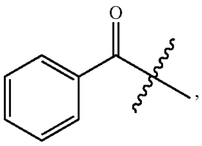,
or —S—($C_1$-$C_{10}$ aliphatic).
In some embodiments, $R^1$ is
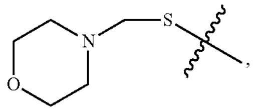,
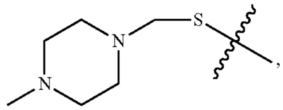,
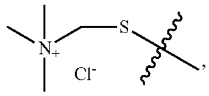, 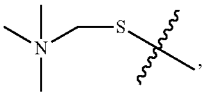,
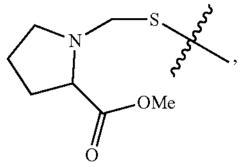, or
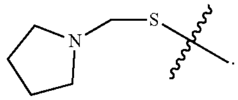.
In some embodiments, X is —O— or —S—, and $R^1$ is
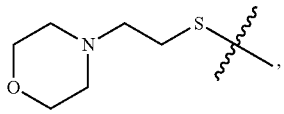, -continued
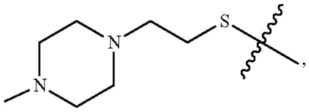,
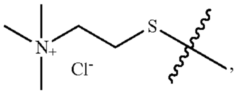, 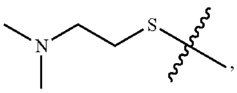,
-continued
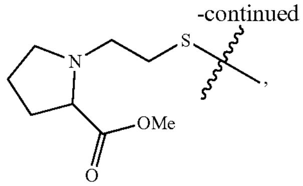,
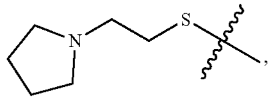, 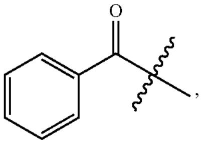,
or —S—($C_1$-$C_{10}$ aliphatic).
In some embodiments, X is —O— or —S—, and $R^1$ is
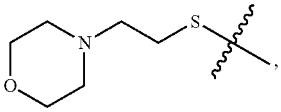, 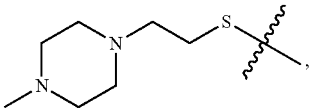, 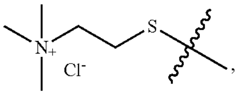, 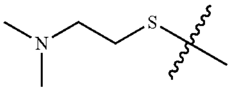,
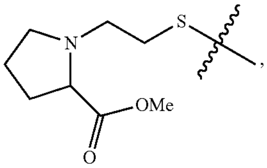, 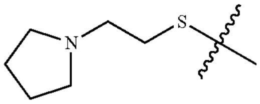, 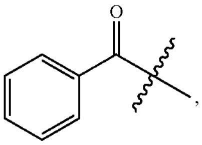,
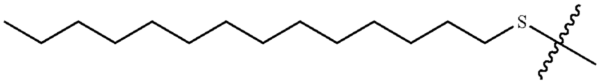,
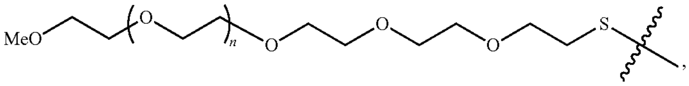,
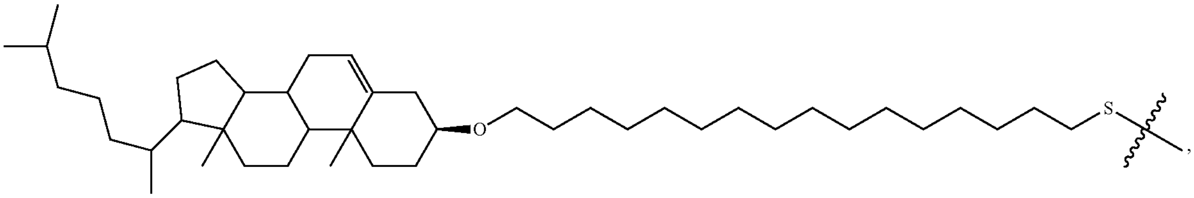,
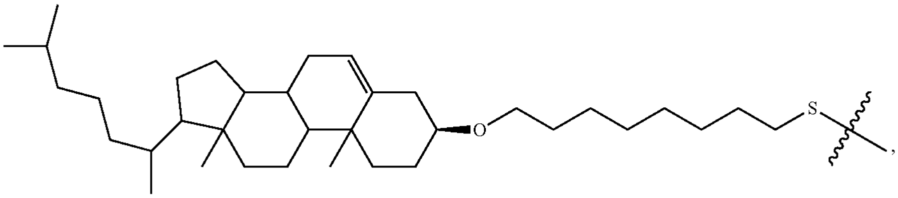,
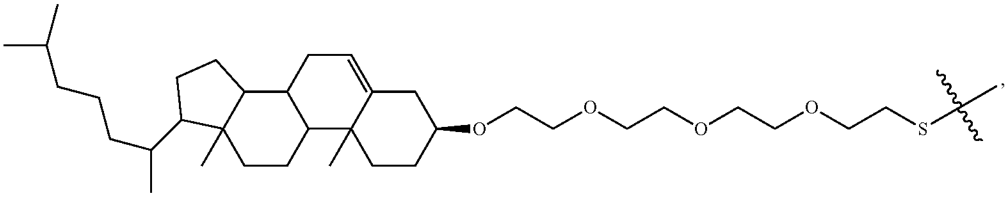,
—S—($C_1$-$C_{10}$ aliphatic) or —S—($C_1$-$C_{50}$ aliphatic).

In some embodiments, L is a covalent bond and -L-$R^1$ is $R^1$.
In some embodiments, -L-$R^1$ is not hydrogen.
In some embodiments, —X-L-$R^1$ is R is
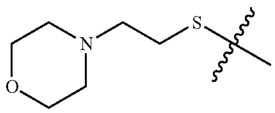,
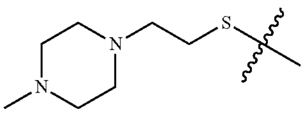,
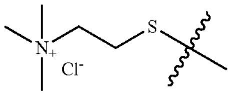,
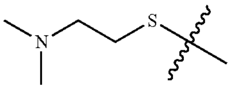,
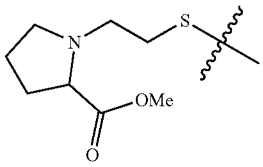,
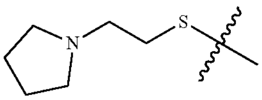,
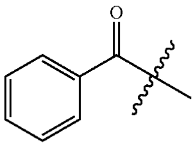,
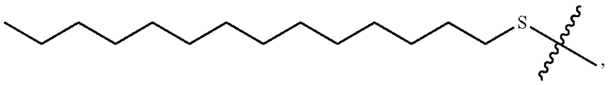,
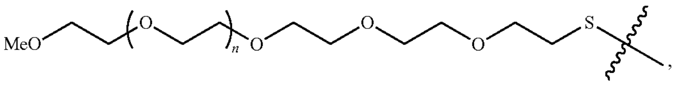,
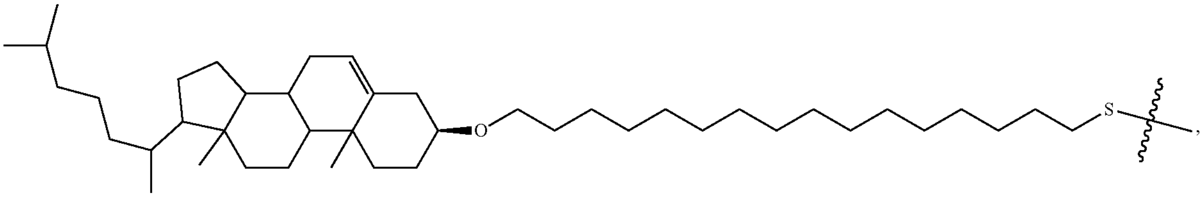,
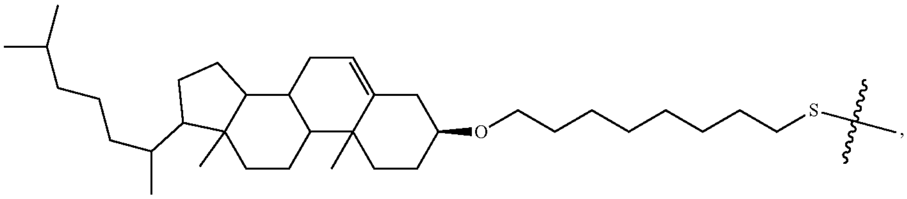,
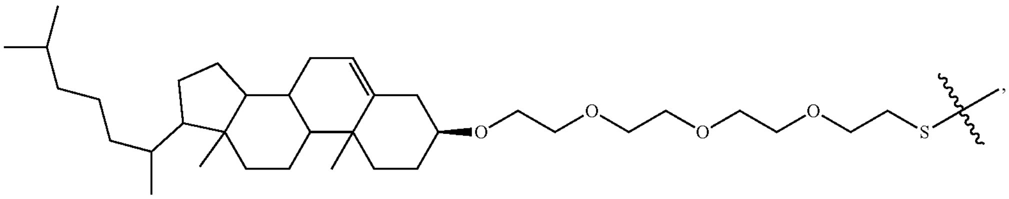,
—S—($C_1$-$C_{10}$ aliphatic) or —S—($C_1$-$C_{50}$ aliphatic).

In some embodiments, —X-L-$R^1$ has the structure of

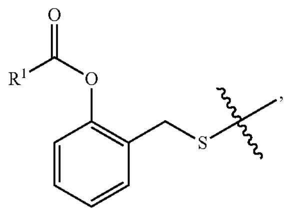

wherein the

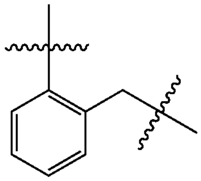 [SMILES: *Cc1ccccc1*]

moiety is optionally substituted. In some embodiments, —X-L-$R^1$ is

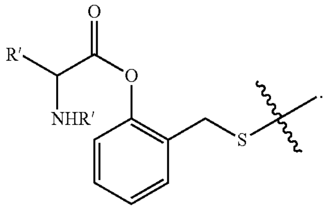

In some embodiments, —X-L-$R^1$ is

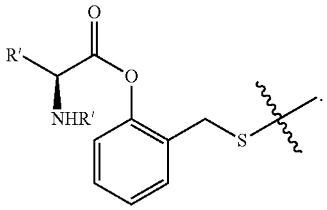

In some embodiments, —X-L-$R^1$ is

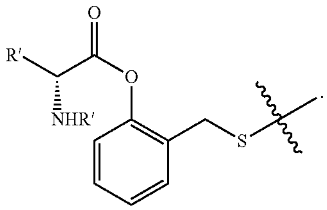

In some embodiments, —X-L-$R^1$ has the structure of

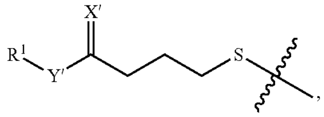

wherein X' is O or S, Y' is —O—, —S— or —NR'—, and the

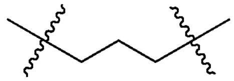 [SMILES: *CCC*]

moiety is optionally substituted. In some embodiments, Y' is —O—, —S— or —NH—. In some embodiments,

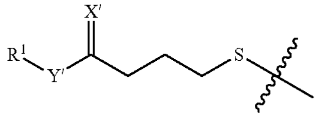

is

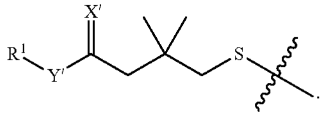

In some embodiments,

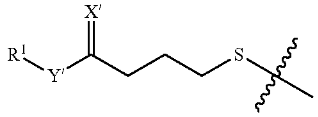

is

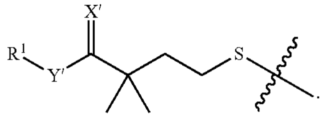

In some embodiments,

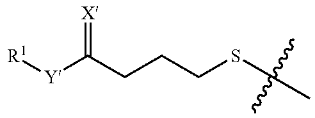

is

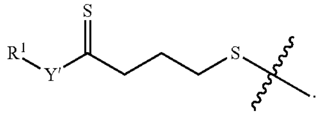

In some embodiments, —X-L-$R^1$ has the structure of

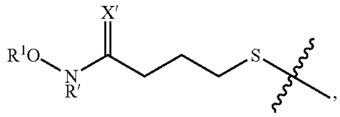

wherein X' is 0 or S, and the

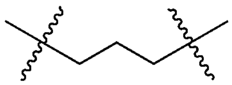 [SMILES: *CCC*]

moiety is optionally substituted. In some embodiments

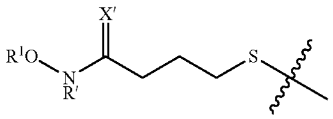

is

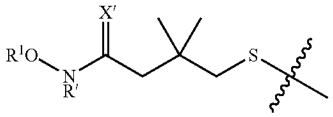

.

In some embodiments, —X-L-$R^1$ is

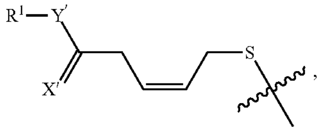

, wherein the

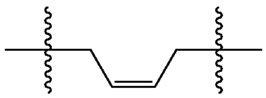 [SMILES: *C/C=C\C*]

is optionally substituted. In some embodiments, —X-L-$R^1$ is

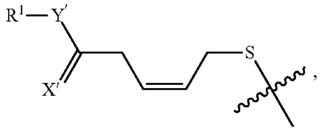

, wherein the

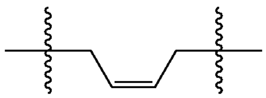 [SMILES: *C/C=C\C*]

is substituted. In some embodiments, —X-L-$R^1$ is

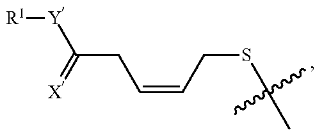

, wherein the

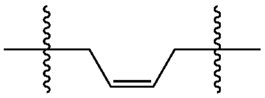

is unsubstituted.

In some embodiments, —X-L-$R^1$ is $R^1$—C(O)—S-$L^x$-S—, wherein $L^x$ is an optionally substituted group selected from

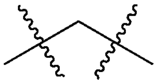

,

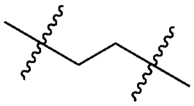

,

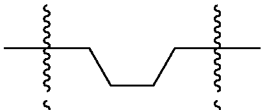

,

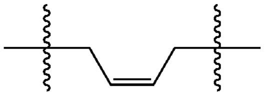

, and

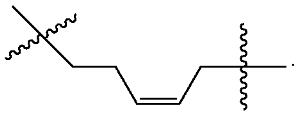

.

In some embodiments, $L^x$ is

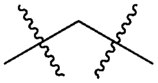

,

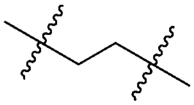

,

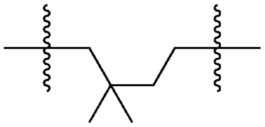

,

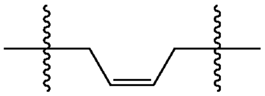

, and

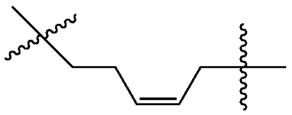

.

In some embodiments, —X-L-$R^1$ is $(CH_3)_3C$—S—S-$L^x$-S—. In some embodiments, —X-L-$R^1$ is $R^1$—C(=X')—Y'—$C(R)_2$—S-$L^x$-S—. In some embodiments, —X-L-$R^1$ is R—C(=X')—Y'—$CH_2$—S-$L^x$-S—.

In some embodiments, —X-L-$R^1$ is

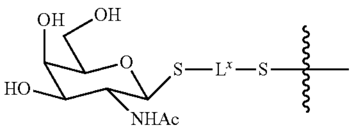

.

As will be appreciated by a person skilled in the art, many of the —X-L-$R^1$ groups described herein are cleavable and can be converted to —$X^-$ after administration to a subject. In some embodiments, —X-L-$R^1$ is cleavable. In some embodiments, —X-L-$R^1$ is —S-L-$R^1$, and is converted to —$S^-$ after administration to a subject. In some embodiments, the conversion is promoted by an enzyme of a subject. As appreciated by a person skilled in the art, methods of determining whether the —S-L-$R^1$ group is converted to —$S^-$ after administration is widely known and practiced in the art, including those used for studying drug metabolism and pharmacokinetics.

In some embodiments, the internucleotidic linkage having the structure of formula I is

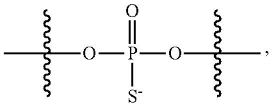

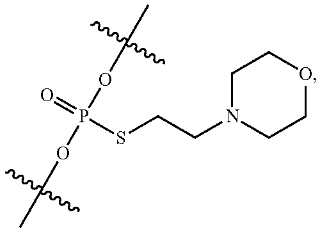

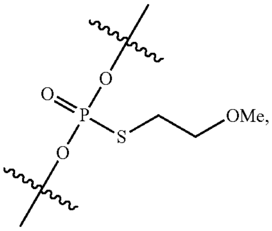

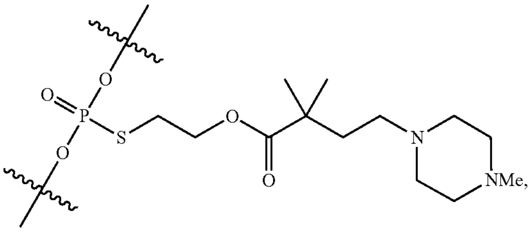

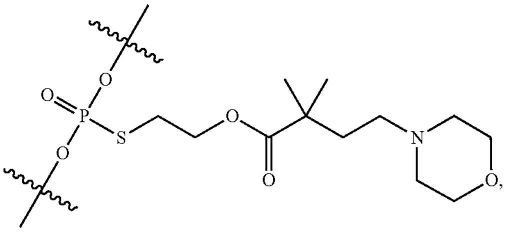

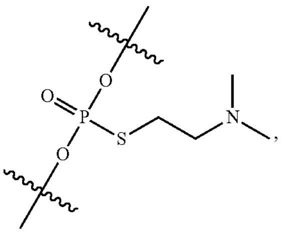

-continued

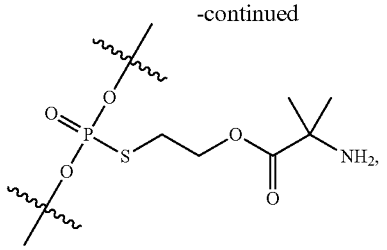

or

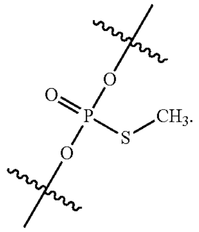 [SMILES: *OP(=O)(O*)SC]

In some embodiments, the internucleotidic linkage of formula I has the structure of formula I-a:

(I-a)

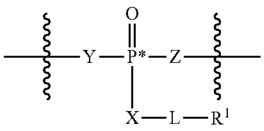

wherein each variable is independently as defined above and described herein.

In some embodiments, the internucleotidic linkage of formula I has the structure of formula I-b:

(I-b)

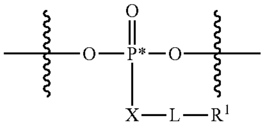

wherein each variable is independently as defined above and described herein.

In some embodiments, the internucleotidic linkage of formula I is an phosphorothioate triester linkage having the structure of formula I-c:

(I-c)

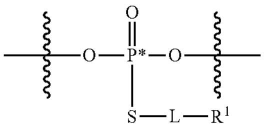

wherein:

P* is an asymmetric phosphorus atom and is either Rp or Sp;

L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —$C(R')_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

each R' is independently —R, —C(O)R, —CO$_2$R, or —SO$_2$R, or:

two R' on the same nitrogen are taken together with their intervening atoms to form an optionally substituted heterocyclic or heteroaryl ring, or two R' on the same carbon are taken together with their intervening atoms to form an optionally substituted aryl, carbocyclic, heterocyclic, or heteroaryl ring;

Cy- is an optionally substituted bivalent ring selected from phenylene, carbocyclylene, arylene, heteroarylene, or heterocyclylene;

each R is independently hydrogen, or an optionally substituted group selected from $C_1$-$C_6$ aliphatic, phenyl, carbocyclyl, aryl, heteroaryl, or heterocyclyl;

each

independently represents a connection to a nucleoside; and $R^1$ is not —H when L is a covalent bond.

In some embodiments, the internucleotidic linkage having the structure of formula I is

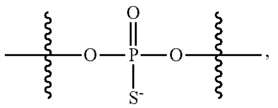

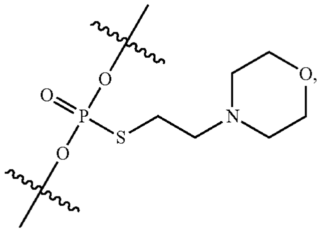

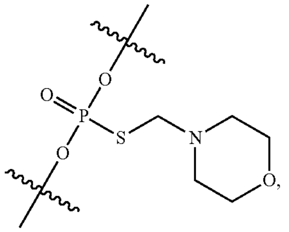

-continued

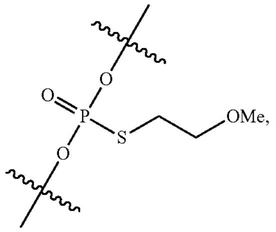

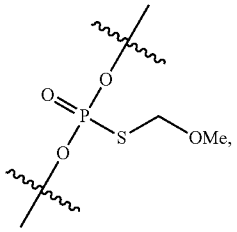

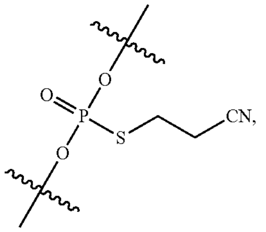

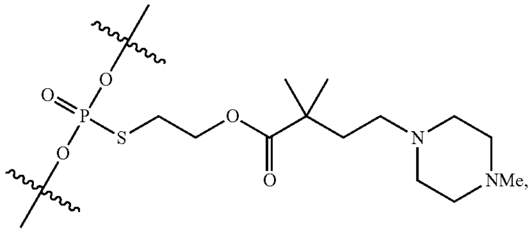

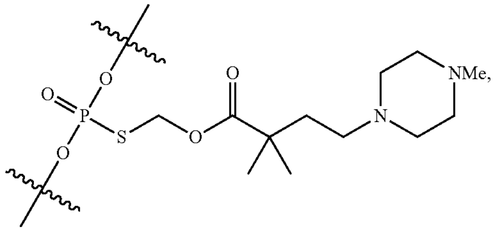

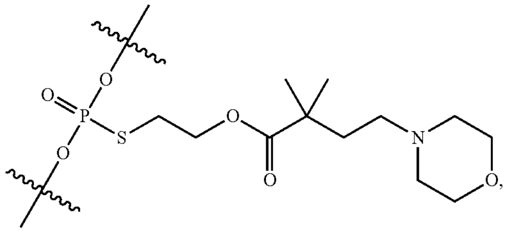

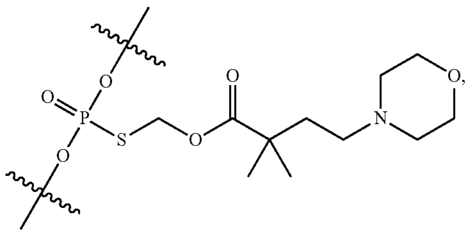

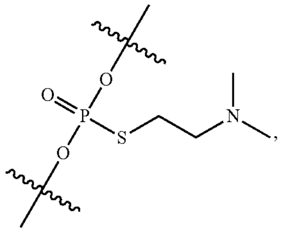

-continued
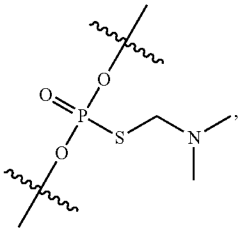
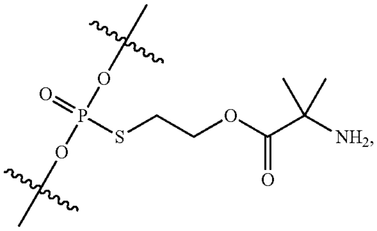
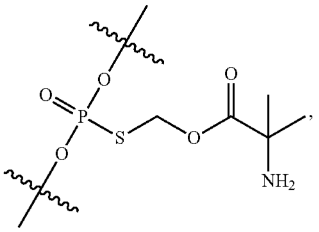
or
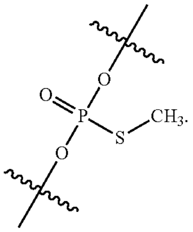
In some embodiments, the internucleotidic linkage having the structure of formula I-c is
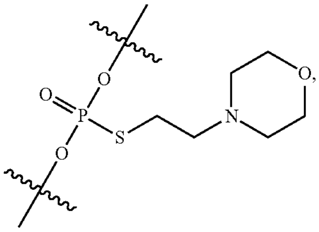
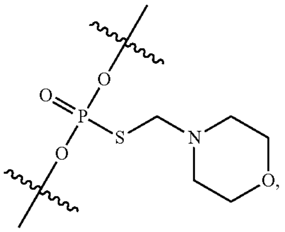
-continued
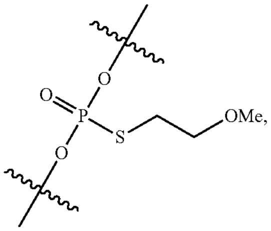
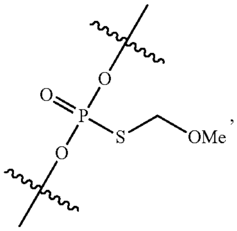
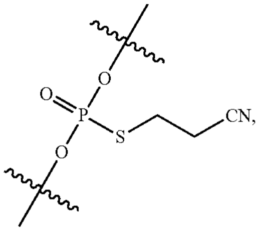
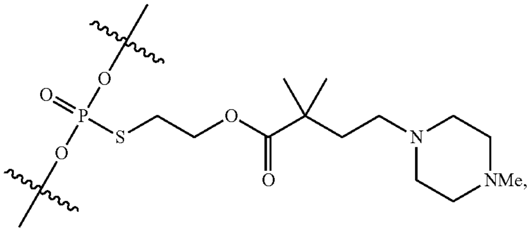
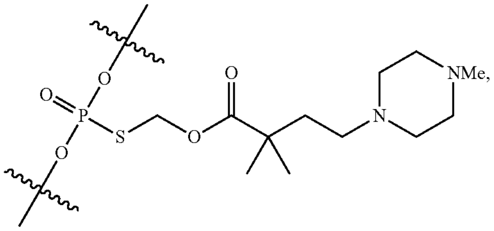
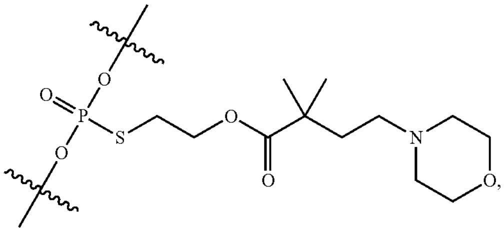
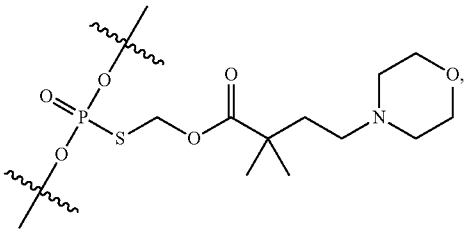
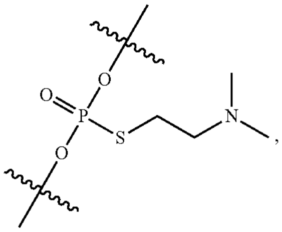

-continued

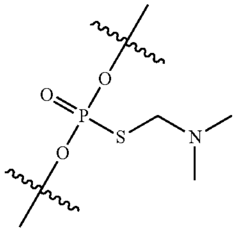

,

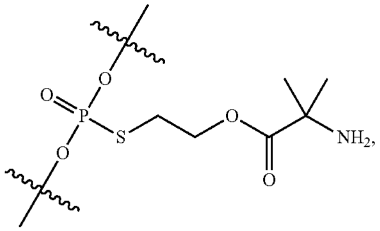

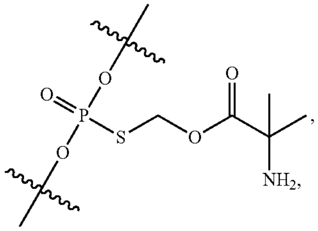

, or

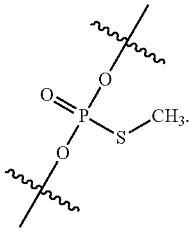

In some embodiments, the present disclosure provides a chirally controlled oligonucleotide comprising one or more phosphate diester linkages, and one or more modified internucleotide linkages having the formula of I-a, I-b, or I-c.

In some embodiments, the present disclosure provides a chirally controlled oligonucleotide comprising at least one phosphate diester internucleotidic linkage and at least one phosphorothioate triester linkage having the structure of formula I-c. In some embodiments, the present disclosure provides a chirally controlled oligonucleotide comprising at least one phosphate diester internucleotidic linkage and at least two phosphorothioate triester linkages having the structure of formula I-c. In some embodiments, the present disclosure provides a chirally controlled oligonucleotide comprising at least one phosphate diester internucleotidic linkage and at least three phosphorothioate triester linkages having the structure of formula I-c. In some embodiments, the present disclosure provides a chirally controlled oligonucleotide comprising at least one phosphate diester internucleotidic linkage and at least four phosphorothioate triester linkages having the structure of formula I-c. In some embodiments, the present disclosure provides a chirally controlled oligonucleotide comprising at least one phosphate diester internucleotidic linkage and at least five phosphorothioate triester linkages having the structure of formula I-c.

In some embodiments, the present disclosure provides a chirally controlled oligonucleotide comprising a sequence found in GGCACAAGGGCACAGACTTC (SEQ ID NO: 38). In some embodiments, the present disclosure provides a chirally controlled oligonucleotide comprising a sequence found in GGCACAAGGGCACAGACTTC (SEQ ID NO: 38), wherein the said sequence has over 50% identity with GGCACAAGGGCACAGACTTC (SEQ ID NO: 38). In some embodiments, the present disclosure provides a chirally controlled oligonucleotide comprising a sequence found in GGCACAAGGGCACAGACTTC (SEQ ID NO: 38), wherein the said sequence has over 60% identity with GGCACAAGGGCACAGACTTC (SEQ ID NO: 38). In some embodiments, the present disclosure provides a chirally controlled oligonucleotide comprising a sequence found in GGCACAAGGGCACAGACTTC (SEQ ID NO: 38), wherein the said sequence has over 70% identity with GGCACAAGGGCACAGACTTC (SEQ ID NO: 38). In some embodiments, the present disclosure provides a chirally controlled oligonucleotide comprising a sequence found in GGCACAAGGGCACAGACTTC (SEQ ID NO: 38), wherein the said sequence has over 80% identity with GGCACAAGGGCACAGACTTC (SEQ ID NO: 38). In some embodiments, the present disclosure provides a chirally controlled oligonucleotide comprising a sequence found in GGCACAAGGGCACAGACTTC (SEQ ID NO: 38), wherein the said sequence has over 90% identity with GGCACAAGGGCACAGACTTC (SEQ ID NO: 38). In some embodiments, the present disclosure provides a chirally controlled oligonucleotide comprising a sequence found in GGCACAAGGGCACAGACTTC (SEQ ID NO: 38), wherein the said sequence has over 95% identity with GGCACAAGGGCACAGACTTC (SEQ ID NO: 38). In some embodiments, the present disclosure provides a chirally controlled oligonucleotide comprising the sequence of GGCACAAGGGCACAGACTTC (SEQ ID NO: 38). In some embodiments, the present disclosure provides a chirally controlled oligonucleotide having the sequence of GGCACAAGGGCACAGACTTC.

In some embodiments, the present disclosure provides a chirally controlled oligonucleotide comprising a sequence found in GGCACAAGGGCACAGACTTC (SEQ ID NO: 38), wherein at least one internucleotidic linkage has a chiral linkage phosphorus. In some embodiments, the present disclosure provides a chirally controlled oligonucleotide comprising a sequence found in GGCACAAGGGCACAGACTTC (SEQ ID NO: 38), wherein at least one internucleotidic linkage has the structure of formula I. In some embodiments, the present disclosure provides a chirally controlled oligonucleotide comprising a sequence found in GGCACAAGGGCACAGACTTC (SEQ ID NO: 38), wherein each internucleotidic linkage has the structure of formula I. In some embodiments, the present disclosure provides a chirally controlled oligonucleotide comprising a sequence found in GGCACAAGGGCACAGACTTC (SEQ ID NO: 38), wherein at least one internucleotidic linkage has the structure of formula I-c. In some embodiments, the present disclosure provides a chirally controlled oligonucleotide comprising a sequence found in GGCACAAGGGCACAGACTTC (SEQ ID NO: 38), wherein each internucleotidic linkage has the structure of formula I-c. In some embodiments, the present disclosure provides a chirally controlled oligonucleotide comprising a sequence found in GGCACAAGGGCACAGACTTC (SEQ ID NO: 38), wherein at least one internucleotidic linkage is

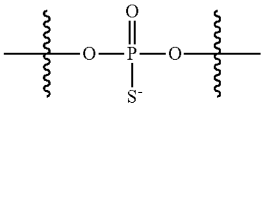

.

In some embodiments, the present disclosure provides a chirally controlled oligonucleotide comprising a sequence found in GGCACAAGGGCACAGACTTC (SEQ ID NO: 38), wherein each internucleotidic linkage is

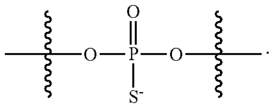

In some embodiments, the present disclosure provides a chirally controlled oligonucleotide comprising a sequence found in GGCACAAGGGCACAGACTTC (SEQ ID NO: 38), wherein at least one internucleotidic linkage is

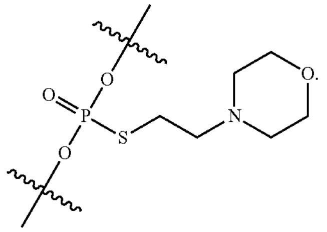

In some embodiments, the present disclosure provides a chirally controlled oligonucleotide comprising a sequence found in GGCACAAGGGCACAGACTTC (SEQ ID NO: 38), wherein each internucleotidic linkage is

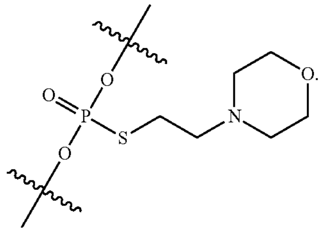

In some embodiments, the present disclosure provides a chirally controlled oligonucleotide comprising the sequence of GGCACAAGGGCACAGACTTC (SEQ ID NO: 38), wherein at least one internucleotidic linkage has a chiral linkage phosphorus. In some embodiments, the present disclosure provides a chirally controlled oligonucleotide comprising the sequence of GGCACAAGGGCACA-GACTTC (SEQ ID NO: 38), wherein at least one inter-nucleotidic linkage has the structure of formula I. In some embodiments, the present disclosure provides a chirally controlled oligonucleotide comprising the sequence of GGCACAAGGGCACAGACTTC (SEQ ID NO: 38), wherein each internucleotidic linkage has the structure of formula I. In some embodiments, the present disclosure provides a chirally controlled oligonucleotide comprising the sequence of GGCACAAGGGCACAGACTTC (SEQ ID NO: 38), wherein at least one internucleotidic linkage has the structure of formula I-c. In some embodiments, the present disclosure provides a chirally controlled oligonucle-otide comprising the sequence of GGCACAAGGGCACA-GACTTC (SEQ ID NO: 38), wherein each internucleotidic linkage has the structure of formula I-c. In some embodi-ments, the present disclosure provides a chirally controlled oligonucleotide comprising the sequence of GGCACAAGGGCACAGACTTC (SEQ ID NO: 38), wherein at least one internucleotidic linkage is

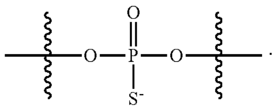

In some embodiments, the present disclosure provides a chirally controlled oligonucleotide comprising the sequence of GGCACAAGGGCACAGACTTC (SEQ ID NO: 38), wherein each internucleotidic linkage is

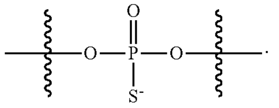

In some embodiments, the present disclosure provides a chirally controlled oligonucleotide comprising the sequence of GGCACAAGGGCACAGACTTC (SEQ ID NO: 38), wherein at least one internucleotidic linkage is

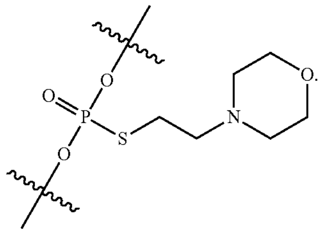

In some embodiments, the present disclosure provides a chirally controlled oligonucleotide comprising the sequence of GGCACAAGGGCACAGACTTC (SEQ ID NO: 38), wherein each internucleotidic linkage is

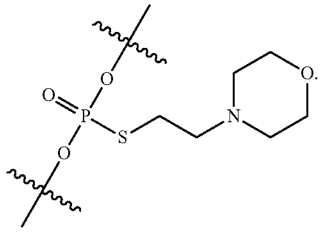

In some embodiments, the present disclosure provides a chirally controlled oligonucleotide having the sequence of GGCACAAGGGCACAGACTTC (SEQ ID NO: 38), wherein at least one internucleotidic linkage has a chiral linkage phosphorus. In some embodiments, the present disclosure provides a chirally controlled oligonucleotide having the sequence of GGCACAAGGGCACAGACTTC (SEQ ID NO: 38), wherein at least one internucleotidic linkage has the structure of formula I. In some embodiments, the present disclosure provides a chirally controlled oligo-nucleotide having the sequence of GGCACAAGGGCACA-GACTTC (SEQ ID NO: 38), wherein each internucleotidic linkage has the structure of formula I. In some embodiments, the present disclosure provides a chirally controlled oligonucleotide having the sequence of GGCACAAGGGCACAGACTTC (SEQ ID NO: 38), wherein at least one internucleotidic linkage has the structure of formula I-c. In some embodiments, the present disclosure provides a chirally controlled oligonucleotide having the sequence of GGCACAAGGGCACAGACTTC (SEQ ID NO: 38), wherein each internucleotidic linkage has the structure of formula I-c. In some embodiments, the present disclosure provides a chirally controlled oligonucleotide having the sequence of GGCACAAGGGCACAGACTTC (SEQ ID NO: 38), wherein at least one internucleotidic linkage is

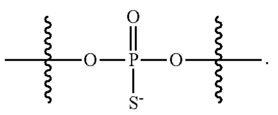 [SMILES: *OP(=O)([S-])O*]

In some embodiments, the present disclosure provides a chirally controlled oligonucleotide having the sequence of GGCACAAGGGCACAGACTTC (SEQ ID NO: 38), wherein each internucleotidic linkage is

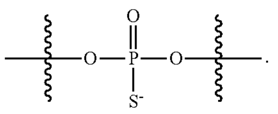 [SMILES: *OP(=O)([S-])O*]

In some embodiments, the present disclosure provides a chirally controlled oligonucleotide having the sequence of GGCACAAGGGCACAGACTTC (SEQ ID NO: 38), wherein at least one internucleotidic linkage is

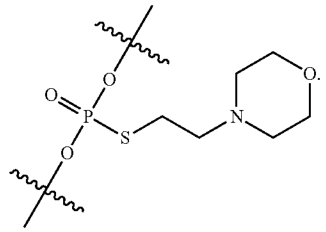

In some embodiments, the present disclosure provides a chirally controlled oligonucleotide having the sequence of GGCACAAGGGCACAGACTTC (SEQ ID NO: 38), wherein each internucleotidic linkage is

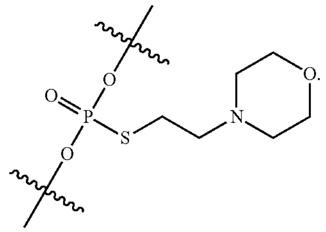

In some embodiments, the present disclosure provides a chirally controlled oligonucleotide having the sequence of GGCACAAGGGCACAGACTTC (SEQ ID NO: 38), wherein at least one linkage phosphorus is Rp. It is understood by a person of ordinary skill in the art that in certain embodiments wherein the chirally controlled oligonucleotide comprises an RNA sequence, each T is independently and optionally replaced with U. In some embodiments, the present disclosure provides a chirally controlled oligonucleotide having the sequence of GGCACAAGGGCACAGACTTC (SEQ ID NO: 38), wherein each linkage phosphorus is Rp. In some embodiments, the present disclosure provides a chirally controlled oligonucleotide having the sequence of GGCACAAGGGCACAGACTTC (SEQ ID NO: 38), wherein at least one linkage phosphorus is Sp. In some embodiments, the present disclosure provides a chirally controlled oligonucleotide having the sequence of GGCACAAGGGCACAGACTTC (SEQ ID NO: 38), wherein each linkage phosphorus is Sp. In some embodiments, the present disclosure provides a chirally controlled oligonucleotide having the sequence of GGCACAAGGGCACAGACTTC (SEQ ID NO: 38), wherein the oligonucleotide is a blockmer. In some embodiments, the present disclosure provides a chirally controlled oligonucleotide having the sequence of GGCACAAGGGCACAGACTTC (SEQ ID NO: 38), wherein the oligonucleotide is a stereoblockmer. In some embodiments, the present disclosure provides a chirally controlled oligonucleotide having the sequence of GGCACAAGGGCACAGACTTC (SEQ ID NO: 38), wherein the oligonucleotide is a P-modification blockmer. In some embodiments, the present disclosure provides a chirally controlled oligonucleotide having the sequence of GGCACAAGGGCACAGACTTC (SEQ ID NO: 38), wherein the oligonucleotide is a linkage blockmer. In some embodiments, the present disclosure provides a chirally controlled oligonucleotide having the sequence of GGCACAAGGGCACAGACTTC (SEQ ID NO: 38), wherein the oligonucleotide is an altmer. In some embodiments, the present disclosure provides a chirally controlled oligonucleotide having the sequence of GGCACAAGGGCACAGACTTC (SEQ ID NO: 38), wherein the oligonucleotide is a stereoaltmer. In some embodiments, the present disclosure provides a chirally controlled oligonucleotide having the sequence of GGCACAAGGGCACAGACTTC (SEQ ID NO: 38), wherein the oligonucleotide is a P-modification altmer. In some embodiments, the present disclosure provides a chirally controlled oligonucleotide having the sequence of GGCACAAGGGCACAGACTTC (SEQ ID NO: 38), wherein the oligonucleotide is a linkage altmer. In some embodiments, the present disclosure provides a chirally controlled oligonucleotide having the sequence of GGCACAAGGGCACAGACTTC (SEQ ID NO: 38), wherein the oligonucleotide is a unimer. In some embodiments, the present disclosure provides a chirally controlled oligonucleotide having the sequence of GGCACAAGGGCACAGACTTC (SEQ ID NO: 38), wherein the oligonucleotide is a stereounimer. In some embodiments, the present disclosure provides a chirally controlled oligonucleotide having the sequence of GGCACAAGGGCACAGACTTC (SEQ ID NO: 38), wherein the oligonucleotide is a P-modification unimer. In some embodiments, the present disclosure provides a chirally controlled oligonucleotide having the sequence of GGCACAAGGGCACAGACTTC (SEQ ID NO: 38), wherein the oligonucleotide is a linkage unimer. In some embodiments, the present disclosure provides a chirally controlled oligonucleotide having the sequence of GGCACAAGGGCACAGACTTC (SEQ ID NO: 38), wherein the oligonucleotide is a gapmer. In some embodiments, the present disclosure provides a chirally controlled oligonucleotide having the sequence of GGCACAAGGGCACAGACTTC (SEQ ID NO: 38), wherein the oligonucleotide is a skipmer.

In some embodiments, the present disclosure provides a chirally controlled oligonucleotide having the sequence of GGCACAAGGGCACAGACTTC (SEQ ID NO: 38), wherein each cytosine is optionally and independently replaced by 5-methylcytosine. In some embodiments, the present disclosure provides a chirally controlled oligonucleotide having the sequence of GGCACAAGGGCACAGACTTC (SEQ ID NO: 38), wherein at least one cytosine is optionally and independently replaced by 5-methylcytosine. In some embodiments, the present disclosure provides a chirally controlled oligonucleotide having the sequence of GGCACAAGGGCACAGACTTC (SEQ ID NO: 38), wherein each cytosine is optionally and independently replaced by 5-methylcytosine.

In some embodiments, a chirally controlled oligonucleotide is designed such that one or more nucleotides comprise a phosphorus modification prone to "autorelease" under certain conditions. That is, under certain conditions, a particular phosphorus modification is designed such that it self-cleaves from the oligonucleotide to provide, e.g., a phosphate diester such as those found in naturally occurring DNA and RNA. In some embodiments, such a phosphorus modification has a structure of —O-L-$R^1$, wherein each of L and $R^1$ is independently as defined above and described herein. In some embodiments, an autorelease group comprises a morpholino group. In some embodiments, an autorelease group is characterized by the ability to deliver an agent to the internucleotidic phosphorus linker, which agent facilitates further modification of the phosphorus atom such as, e.g., desulfurization. In some embodiments, the agent is water and the further modification is hydrolysis to form a phosphate diester as is found in naturally occurring DNA and RNA.

In some embodiments, the present disclosure provides a chirally controlled oligonucleotide comprising any sequence disclosed herein (including, as non-limiting examples, any sequence disclosed in any Table). In some embodiments, the present disclosure provides a chirally controlled oligonucleotide comprising a sequence having over 50% identity with any sequence disclosed herein. In some embodiments, the present disclosure provides a chirally controlled oligonucleotide comprising a sequence having over 60% identity with any sequence disclosed herein. In some embodiments, the present disclosure provides a chirally controlled oligonucleotide comprising a sequence having over 70% identity with any sequence disclosed herein. In some embodiments, the present disclosure provides a chirally controlled oligonucleotide comprising a sequence having over 80% identity with any sequence disclosed herein. In some embodiments, the present disclosure provides a chirally controlled oligonucleotide comprising a sequence having over 90% identity with any sequence disclosed herein. In some embodiments, the present disclosure provides a chirally controlled oligonucleotide comprising a sequence having over 95% identity with any sequence disclosed herein. In some embodiments, the present disclosure provides a chirally controlled oligonucleotide comprising any sequence disclosed herein. In some embodiments, the present disclosure provides a chirally controlled oligonucleotide having any sequence disclosed herein.

In some embodiments, the present disclosure provides a chirally controlled oligonucleotide comprising any sequence disclosed herein, wherein at least one internucleotidic linkage has a chiral linkage phosphorus. In some embodiments, the present disclosure provides a chirally controlled oligonucleotide comprising any sequence disclosed herein, wherein at least one internucleotidic linkage has the structure of formula I. In some embodiments, the present disclosure provides a chirally controlled oligonucleotide comprising any sequence disclosed herein, wherein each internucleotidic linkage has the structure of formula I. In some embodiments, the present disclosure provides a chirally controlled oligonucleotide comprising any sequence disclosed herein, wherein at least one internucleotidic linkage has the structure of formula I-c. In some embodiments, the present disclosure provides a chirally controlled oligonucleotide comprising any sequence disclosed herein, wherein each internucleotidic linkage has the structure of formula I-c. In some embodiments, the present disclosure provides a chirally controlled oligonucleotide comprising any sequence disclosed herein, wherein at least one internucleotidic linkage is

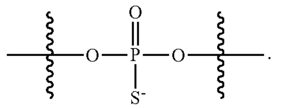

In some embodiments, the present disclosure provides a chirally controlled oligonucleotide comprising any sequence disclosed herein, wherein each internucleotidic linkage is

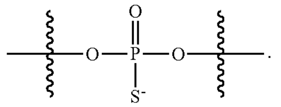

In some embodiments, the present disclosure provides a chirally controlled oligonucleotide comprising any sequence disclosed herein, wherein at least one internucleotidic linkage is

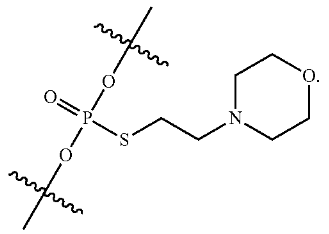

In some embodiments, the present disclosure provides a chirally controlled oligonucleotide comprising any sequence disclosed herein, wherein each internucleotidic linkage is

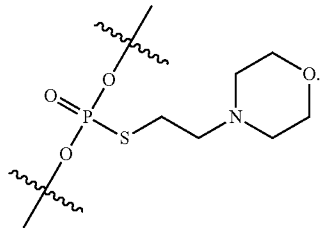

In some embodiments, the present disclosure provides a chirally controlled oligonucleotide comprising any sequence disclosed herein, wherein at least one internucleotidic linkage has a chiral linkage phosphorus. In some embodiments, the present disclosure provides a chirally controlled oligonucleotide comprising any sequence disclosed herein, wherein at least one internucleotidic linkage has the structure of formula I. In some embodiments, the present disclosure provides a chirally controlled oligonucleotide comprising any sequence disclosed herein, wherein each internucleotidic linkage has the structure of formula I. In some embodiments, the present disclosure provides a chirally controlled oligonucleotide comprising any sequence disclosed herein, wherein at least one internucleotidic linkage has the structure of formula I-c. In some embodiments, the present disclosure provides a chirally controlled oligonucleotide comprising any sequence disclosed herein, wherein each internucleotidic linkage has the structure of formula I-c. In some embodiments, the present disclosure provides a chirally controlled oligonucleotide comprising any sequence disclosed herein, wherein at least one internucleotidic linkage is

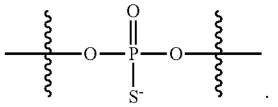

In some embodiments, the present disclosure provides a chirally controlled oligonucleotide comprising any sequence disclosed herein, wherein each internucleotidic linkage is

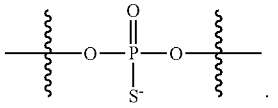 [SMILES: *OP(=O)([S-])O*]

In some embodiments, the present disclosure provides a chirally controlled oligonucleotide comprising any sequence disclosed herein, wherein at least one internucleotidic linkage is

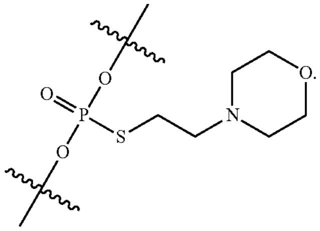

In some embodiments, the present disclosure provides a chirally controlled oligonucleotide comprising any sequence disclosed herein, wherein each internucleotidic linkage is

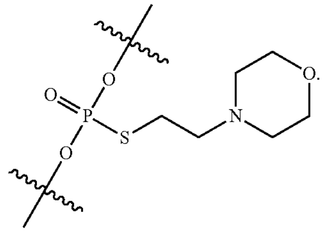

In some embodiments, the present disclosure provides a chirally controlled oligonucleotide having any sequence disclosed herein, wherein at least one internucleotidic linkage has a chiral linkage phosphorus. In some embodiments, the present disclosure provides a chirally controlled oligonucleotide having any sequence disclosed herein, wherein at least one internucleotidic linkage has the structure of formula I. In some embodiments, the present disclosure provides a chirally controlled oligonucleotide having any sequence disclosed herein, wherein each internucleotidic linkage has the structure of formula I. In some embodiments, the present disclosure provides a chirally controlled oligonucleotide having any sequence disclosed herein, wherein at least one internucleotidic linkage has the structure of formula I-c. In some embodiments, the present disclosure provides a chirally controlled oligonucleotide having any sequence disclosed herein, wherein each internucleotidic linkage has the structure of formula I-c. In some embodiments, the present disclosure provides a chirally controlled oligonucleotide having any sequence disclosed herein, wherein at least one internucleotidic linkage is

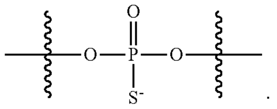

In some embodiments, the present disclosure provides a chirally controlled oligonucleotide having any sequence disclosed herein, wherein each internucleotidic linkage is

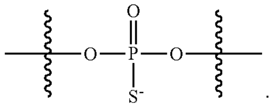

In some embodiments, the present disclosure provides a chirally controlled oligonucleotide having any sequence disclosed herein, wherein at least one internucleotidic linkage is

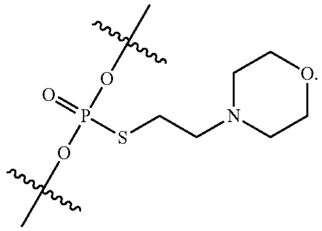

In some embodiments, the present disclosure provides a chirally controlled oligonucleotide having any sequence disclosed herein, wherein each internucleotidic linkage is

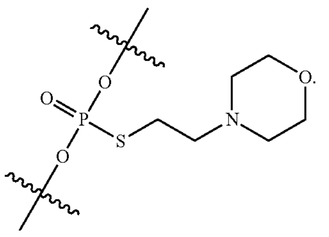

In some embodiments, the present disclosure provides a chirally controlled oligonucleotide having any sequence disclosed herein, wherein at least one linkage phosphorus is Rp. It is understood by a person of ordinary skill in the art that in certain embodiments wherein the chirally controlled oligonucleotide comprises an RNA sequence, each T is independently and optionally replaced with U. In some embodiments, the present disclosure provides a chirally controlled oligonucleotide having any sequence disclosed herein, wherein each linkage phosphorus is Rp. In some embodiments, the present disclosure provides a chirally controlled oligonucleotide having any sequence disclosed herein, wherein at least one linkage phosphorus is Sp. In some embodiments, the present disclosure provides a chirally controlled oligonucleotide having any sequence disclosed herein, wherein each linkage phosphorus is Sp. In some embodiments, the present disclosure provides a chirally controlled oligonucleotide having any sequence disclosed herein, wherein the oligonucleotide is a blockmer. In some embodiments, the present disclosure provides a chirally controlled oligonucleotide having any sequence disclosed herein, wherein the oligonucleotide is a stereoblockmer. In some embodiments, the present disclosure provides a chirally controlled oligonucleotide having any sequence disclosed herein, wherein the oligonucleotide is a P-modification blockmer. In some embodiments, the present disclosure provides a chirally controlled oligonucleotide having any sequence disclosed herein, wherein the oligonucleotide is a linkage blockmer. In some embodiments, the present disclosure provides a chirally controlled oligonucleotide having any sequence disclosed herein, wherein the oligonucleotide is an altmer. In some embodiments, the present disclosure provides a chirally controlled oligonucleotide having any sequence disclosed herein, wherein the oligonucleotide is a stereoaltmer. In some embodiments, the present disclosure provides a chirally controlled oligonucleotide having any sequence disclosed herein, wherein the oligonucleotide is a P-modification altmer. In some embodiments, the present disclosure provides a chirally controlled oligonucleotide having any sequence disclosed herein, wherein the oligonucleotide is a linkage altmer. In some embodiments, the present disclosure provides a chirally controlled oligonucleotide having any sequence disclosed herein, wherein the oligonucleotide is a unimer. In some embodiments, the present disclosure provides a chirally controlled oligonucleotide having any sequence disclosed herein, wherein the oligonucleotide is a stereounimer. In some embodiments, the present disclosure provides a chirally controlled oligonucleotide having any sequence disclosed herein, wherein the oligonucleotide is a P-modification unimer. In some embodiments, the present disclosure provides a chirally controlled oligonucleotide having any sequence disclosed herein, wherein the oligonucleotide is a linkage unimer. In some embodiments, the present disclosure provides a chirally controlled oligonucleotide having any sequence disclosed herein, wherein the oligonucleotide is a gapmer. In some embodiments, the present disclosure provides a chirally controlled oligonucleotide having any sequence disclosed herein, wherein the oligonucleotide is a skipmer.

In some embodiments, the present disclosure provides a chirally controlled oligonucleotide having any sequence disclosed herein, wherein each cytosine is optionally and independently replaced by 5-methylcytosine. In some embodiments, the present disclosure provides a chirally controlled oligonucleotide having any sequence disclosed herein, wherein at least one cytosine is optionally and independently replaced by 5-methylcytosine. In some embodiments, the present disclosure provides a chirally controlled oligonucleotide having any sequence disclosed herein, wherein each cytosine is optionally and independently replaced by 5-methylcytosine.

In various embodiments, any sequence disclosed herein can be combined with one or more of the following as disclosed herein or known in the art: pattern of backbone linkages; pattern of backbone chiral centers; and pattern of backbone P-modifications; pattern of base modification; pattern of sugar modification; pattern of backbone linkages; pattern of backbone chiral centers; and pattern of backbone P-modifications.

In some embodiments, a chirally controlled oligonucleotide is designed such that the resulting pharmaceutical properties are improved through one or more particular modifications at phosphorus. It is well documented in the art that certain oligonucleotides are rapidly degraded by nucleases and exhibit poor cellular uptake through the cytoplasmic cell membrane (Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1): 196-208; Bologna et al., (2002), Antisense & Nucleic Acid Drug Development 12:33-41). For instance, Vives et al., (Nucleic Acids Research (1999), 27(20):4071-76) found that tert-butyl SATE pro-oligonucleotides displayed markedly increased cellular penetration compared to the parent oligonucleotide.

In some embodiments, a modification at a linkage phosphorus is characterized by its ability to be transformed to a phosphate diester, such as those present in naturally occurring DNA and RNA, by one or more esterases, nucleases, and/or cytochrome P450 enzymes, including but not limited to, those listed in Table 1A, below.

TABLE 1A

Example enzymes.

| Family | Gene |
|---|---|
| CYP1 | CYP1A1, CYP1A2, CYP1B1 |
| CYP2 | CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1 |
| CYP3 | CYP3A4, CYP3A5, CYP3A7, CYP3A43 |
| CYP4 | CYP4A11, CYP4A22, CYP4B1, CYP4F2, CYP4F3, CYP4F8, CYP4F11, CYP4F12, CYP4F22, CYP4V2, CYP4X1, CYP4Z1 |
| CYP5 | CYP5A1 |
| CYP7 | CYP7A1, CYP7B1 |

TABLE 1A-continued

| Example enzymes. | |
|---|---|
| Family | Gene |
| CYP8 | CYP8A1 (prostacyclin synthase), CYP8B1 (bile acid biosynthesis) |
| CYP11 | CYP11A1, CYP11B1, CYP11B2 |
| CYP17 | CYP17A1 |
| CYP19 | CYP19A1 |
| CYP20 | CYP20A1 |
| CYP21 | CYP21A2 |
| CYP24 | CYP24A1 |
| CYP26 | CYP26A1, CYP26B1, CYP26C1 |
| CYP27 | CYP27A1 (bile acid biosynthesis), CYP27B1 (vitamin D3 1-alpha hydroxylase, activates vitamin D3), CYP27C1 (unknown function) |
| CYP39 | CYP39A1 |
| CYP46 | CYP46A1 |
| CYP51 | CYP51A1 (lanosterol 14-alpha demethylase) |

In some embodiments, a modification at phosphorus results in a P-modification moiety characterized in that it acts as a pro-drug, e.g., the P-modification moiety facilitates delivery of an oligonucleotide to a desired location prior to removal. For instance, in some embodiments, a P-modification moiety results from PEGylation at the linkage phosphorus. One of skill in the relevant arts will appreciate that various PEG chain lengths are useful and that the selection of chain length will be determined in part by the result that is sought to be achieved by PEGylation. For instance, in some embodiments, PEGylation is effected in order to reduce RES uptake and extend in vivo circulation lifetime of an oligonucleotide.

In some embodiments, a PEGylation reagent for use in accordance with the present disclosure is of a molecular weight of about 300 g/mol to about 100,000 g/mol. In some embodiments, a PEGylation reagent is of a molecular weight of about 300 g/mol to about 10,000 g/mol. In some embodiments, a PEGylation reagent is of a molecular weight of about 300 g/mol to about 5,000 g/mol. In some embodiments, a PEGylation reagent is of a molecular weight of about 500 g/mol. In some embodiments, a PEGylation reagent of a molecular weight of about 1000 g/mol. In some embodiments, a PEGylation reagent is of a molecular weight of about 3000 g/mol. In some embodiments, a PEGylation reagent is of a molecular weight of about 5000 g/mol.

In certain embodiments, a PEGylation reagent is PEG500. In certain embodiments, a PEGylation reagent is PEG1000. In certain embodiments, a PEGylation reagent is PEG3000. In certain embodiments, a PEGylation reagent is PEG5000.

In some embodiments, a P-modification moiety is characterized in that it acts as a PK enhancer, e.g., lipids, PEGylated lipids, etc.

In some embodiments, a P-modification moiety is characterized in that it acts as an agent which promotes cell entry and/or endosomal escape, such as a membrane-disruptive lipid or peptide.

In some embodiments, a P-modification moiety is characterized in that it acts as a targeting agent. In some embodiments, a P-modification moiety is or comprises a targeting agent. The phrase "targeting agent," as used herein, is an entity that is associates with a payload of interest (e.g., with an oligonucleotide or oligonucleotide composition) and also interacts with a target site of interest so that the payload of interest is targeted to the target site of interest when associated with the targeting agent to a materially greater extent than is observed under otherwise comparable conditions when the payload of interest is not associated with the targeting agent. A targeting agent may be, or comprise, any of a variety of chemical moieties, including, for example, small molecule moieties, nucleic acids, polypeptides, carbohydrates, etc. Targeting agents are described further by Adarsh et al., "Organelle Specific Targeted Drug Delivery—A Review," International Journal of Research in Pharmaceutical and Biomedical Sciences, 2011, p. 895.

Example such targeting agents include, but are not limited to, proteins (e.g. Transferrin), oligopeptides (e.g., cyclic and acylic RGD-containing oligopedptides), antibodies (monoclonal and polyclonal antibodies, e.g. IgG, IgA, IgM, IgD, IgE antibodies), sugars/carbohydrates (e.g., monosaccharides and/or oligosaccharides (mannose, mannose-6-phosphate, galactose, and the like)), vitamins (e.g., folate), or other small biomolecules. In some embodiments, a targeting moiety is a steroid molecule (e.g., bile acids including cholic acid, deoxycholic acid, dehydrocholic acid; cortisone; digoxigenin; testosterone; choleasterol; cationic steroids such as cortisone having a trimethylaminomethyl hydrazide group attached via a double bond at the 3-position of the cortisone ring, etc.). In some embodiments, a targeting moiety is a lipophilic molecule (e.g., alicyclic hydrocarbons, saturated and unsaturated fatty acids, waxes, terpenes, and polyalicyclic hydrocarbons such as adamantine and buckminsterfullerenes). In some embodiments, a lipophilic molecule is a terpenoid such as vitamin A, retinoic acid, retinal, or dehydroretinal. In some embodiments, a targeting moiety is a peptide.

In some embodiments, a P-modification moiety is a targeting agent of formula —X-L-$R^1$ wherein each of X, L, and $R^1$ are as defined in Formula I above.

In some embodiments, a P-modification moiety is characterized in that it facilitates cell specific delivery.

In some embodiments, a P-modification moiety is characterized in that it falls into one or more of the above-described categories. For instance, in some embodiments, a P-modification moiety acts as a PK enhancer and a targeting ligand. In some embodiments, a P-modification moiety acts as a pro-drug and an endosomal escape agent. One of skill in the relevant arts would recognize that numerous other such combinations are possible and are contemplated by the present disclosure.

Nucleobases

In some embodiments, a nucleobase present in a provided oligonucleotide is a natural nucleobase or a modified nucleobase derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Example modified nucleobases are disclosed in Chiu and Rana, R N A, 2003, 9, 1034-1048, Limbach et al. *Nucleic Acids Research,* 1994, 22, 2183-2196 and Revankar and Rao, *Comprehensive Natural Products Chemistry*, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

Compounds represented by the following general formulae are also contemplated as modified nucleobases:

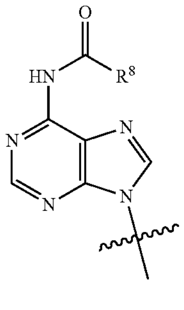
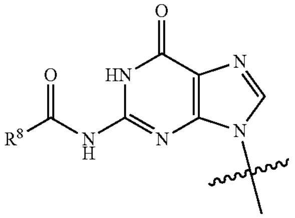
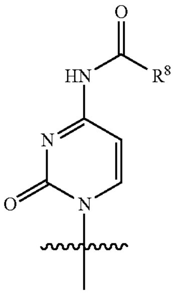
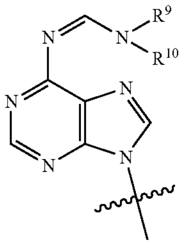
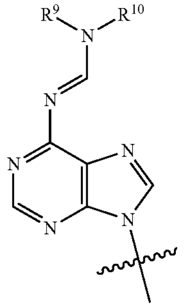
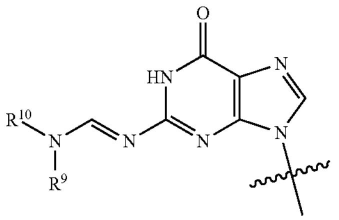
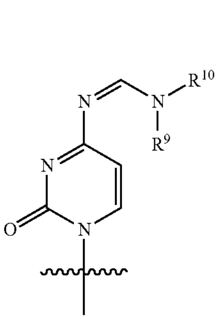
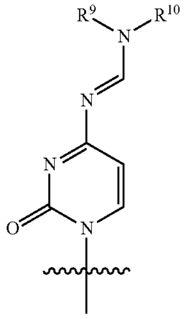

-continued

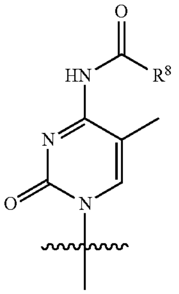
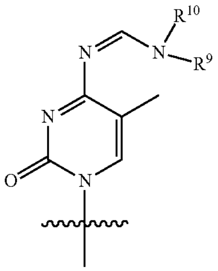
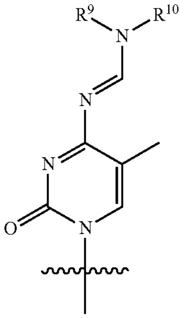

wherein $R^8$ is an optionally substituted, linear or branched group selected from aliphatic, aryl, aralkyl, aryloxylalkyl, carbocyclyl, heterocyclyl or heteroaryl group having 1 to 15 carbon atoms, including, by way of example only, a methyl, isopropyl, phenyl, benzyl, or phenoxymethyl group; and each of $R^9$ and $R^{10}$ is independently an optionally substituted group selected from linear or branched aliphatic, carbocyclyl, aryl, heterocyclyl and heteroaryl.

Modified nucleobases also include expanded-size nucleobases in which one or more aryl rings, such as phenyl rings, have been added. Nucleic base replacements described in the Glen Research catalog (www.glenresearch.com); Krueger A T et al, *Acc. Chem. Res.,* 2007, 40, 141-150; Kool, ET, *Acc. Chem. Res.,* 2002, 35, 936-943; Benner S. A., et al., *Nat. Rev. Genet.,* 2005, 6, 553-543; Romesberg, F. E., et al., *Curr. Opin. Chem. Biol.,* 2003, 7, 723-733; Hirao, I., *Curr. Opin. Chem. Biol.,* 2006, 10, 622-627, are contemplated as useful for the synthesis of the nucleic acids described herein. Some examples of these expanded-size nucleobases are shown below:

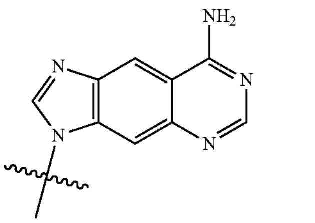
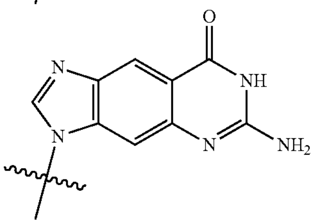

-continued

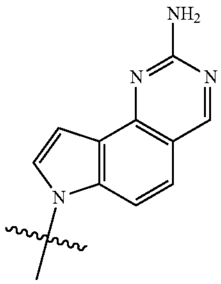
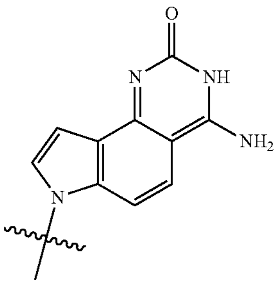

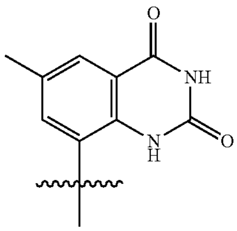
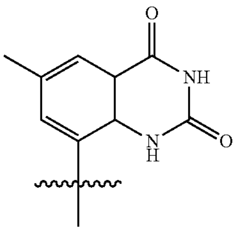

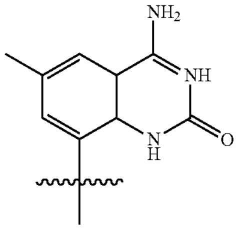
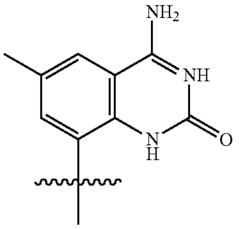

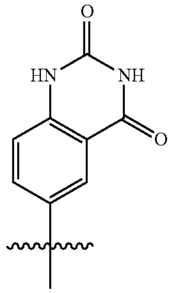
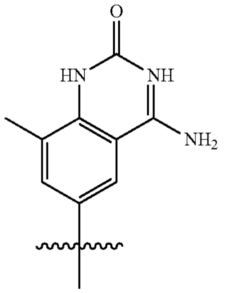

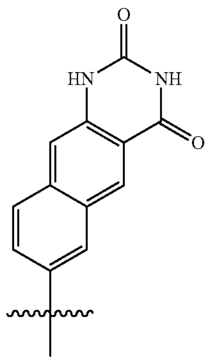
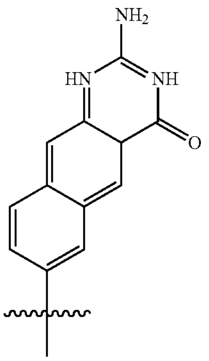

Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, ET, *Org. Lett.*, 2002, 4, 4377-4380. Shown below is an example of a porphyrin-derived ring which can be used as a base replacement:

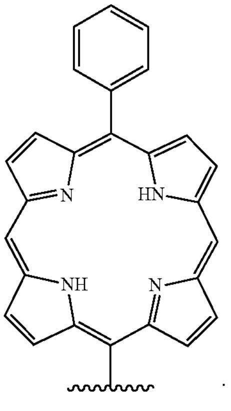 [SMILES: *c1c2nc(cc3ccc([nH]3)c(-c3ccccc3)c3nc(cc4ccc1[nH]4)C=C3)C=C2]

In some embodiments, modified nucleobases are of any one of the following structures, optionally substituted:

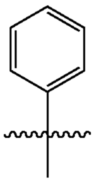
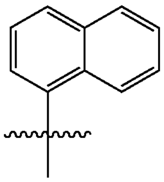
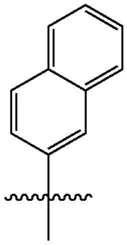

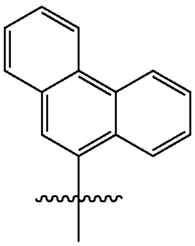
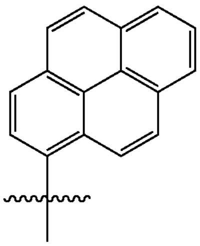

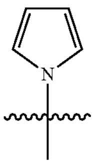
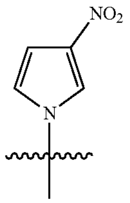
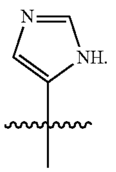

In some embodiments, a modified nucleobase is fluorescent. Example such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

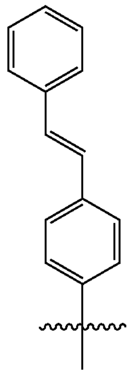
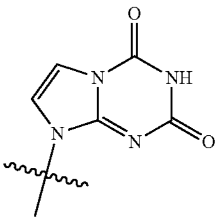
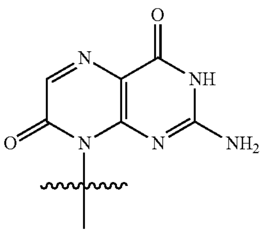
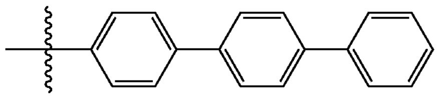
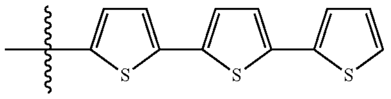
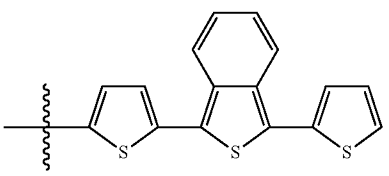
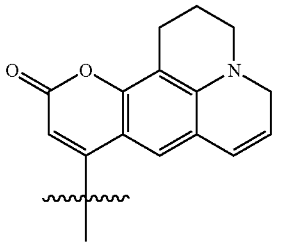
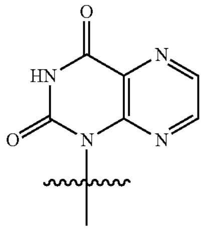
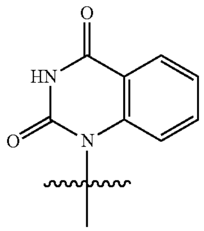
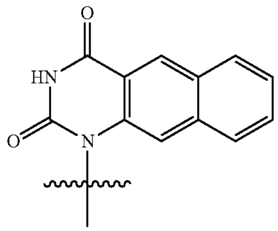
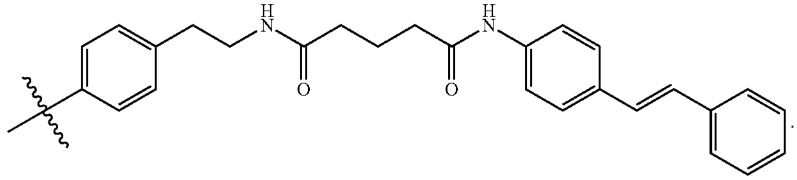

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, other nucleosides can also be used in the process disclosed herein and include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in US Patent Application Publication No. 20070287831.

In some embodiments, a nucleobase or modified nucleobase comprises one or more biomolecule binding moieties such as e.g., antibodies, antibody fragments, biotin, avidin, streptavidin, receptor ligands, or chelating moieties. In other embodiments, a nucleobase or modified nucleobase is 5-bromouracil, 5-iodouracil, or 2,6-diaminopurine. In some embodiments, a nucleobase or modified nucleobase is modified by substitution with a fluorescent or biomolecule binding moiety. In some embodiments, the substituent on a nucleobase or modified nucleobase is a fluorescent moiety.

In some embodiments, the substituent on a nucleobase or modified nucleobase is biotin or avidin.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the modified nucleobases, sugars, and internucleotidic linkages of each of which are incorporated by reference.

In some embodiments, a base is optionally substituted A, T, C, G or U, wherein one or more —$NH_2$ are independently and optionally replaced with —$C(-L-R^1)_3$, one or more —NH— are independently and optionally replaced with —$C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-R' are optionally taken together with their intervening atoms to form a 3-30 membered bicyclic or polycyclic ring having 0-10 heteroatom ring atoms. In some embodiments, a modified base is optionally substituted A, T, C, G or U, wherein one or more —$NH_2$ are independently and optionally replaced with —$C(-L-R^1)_3$, one or more —NH— are independently and optionally replaced with —$C(-L-R^1)_2$—, one or more =N— are independently and optionally replaced with —$C(-L-R^1)$—, one or more =CH— are independently and optionally replaced with =N—, and one or more =O are independently and optionally replaced with =S, =$N(-L-R^1)$, or =$C(-L-R^1)_2$, wherein two or more -L-$R^1$ are optionally taken together with their intervening atoms to form a 3-30 membered bicyclic or polycyclic ring having 0-10 heteroatom ring atoms, wherein the modified base is different than the natural A, T, C, G and U. In some embodiments, a base is optionally substituted A, T, C, G or U. In some embodiments, a modified base is substituted A, T, C, G or U, wherein the modified base is different than the natural A, T, C, G and U.

In some embodiments, a modified nucleotide or nucleotide analog is any modified nucleotide or nucleotide analog described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

Sugars

In some embodiments, provided oligonucleotides comprise one or more modified sugar moieties beside the natural sugar moieties.

The most common naturally occurring nucleotides are comprised of ribose sugars linked to the nucleobases adenosine (A), cytosine (C), guanine (G), and thymine (T) or uracil (U). Also contemplated are modified nucleotides wherein a phosphate group or linkage phosphorus in the nucleotides can be linked to various positions of a sugar or modified sugar. As non-limiting examples, the phosphate group or linkage phosphorus can be linked to the 2', 3', 4' or 5' hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with methods of the present disclosure.

Other modified sugars can also be incorporated within a provided oligonucleotide. In some embodiments, a modified sugar contains one or more substituents at the 2' position including one of the following: —F; —$CF_3$, —CN, —$N_3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl$)_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl$)_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl$)_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl$)_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein the alkyl, alkylene, alkenyl and alkynyl may be substituted or unsubstituted. Examples of substituents include, and are not limited to, —$O(CH_2)_nOCH_3$, and —$O(CH_2)$. $NH_2$, wherein n is from 1 to about 10, MOE, DMAOE, DMAEOE. Also contemplated herein are modified sugars described in WO 2001/088198; and Martin et al., *Helv. Chim. Acta,* 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the 2', 3', 4', 5', or 6' positions of the sugar or modified sugar, including the 3' position of the sugar on the 3'-terminal nucleotide or in the 5' position of the 5'-terminal nucleotide.

In some embodiments, the 2'-OH of a ribose is replaced with a substituent including one of the following: —H, —F;

—$CF_3$, —CN, —$N_3$, —NO, —$NO_2$, —OR', —SR', or —$N(R')_2$, wherein each R' is independently as defined above and described herein; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl)$_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein the alkyl, alkylene, alkenyl and alkynyl may be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —$OCH_2CH_2OMe$.

Modified sugars also include locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L- as defined herein. In some embodiments, -L- is —O—$CH_2$—, wherein —$CH_2$— is optionally substituted. In some embodiments, -L- is —O—$CH_2$—. In some embodiments, -L- is —O—CH(Et)-. In some embodiments, -L- is between $C_2$ and $C_4$ of a sugar moiety. In some embodiments, a locked nucleic acid has the structure indicated below. A locked nucleic acid of the structure below is indicated, wherein Ba represents a nucleobase or modified nucleobase as described herein, and wherein $R^{2s}$ is —$OCH_2$C4'-.

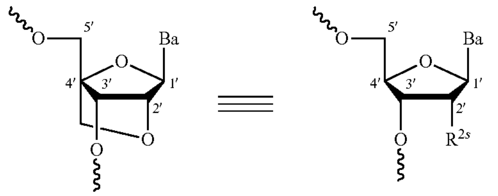

C2'$OCH_2$C4' = LNA
(Locked Nucleic Acid)

$R^{2s}$ = $OCH_2$C4'

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xenonucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

Non-limiting examples of modified sugars include glycerol, which form glycerol nucleic acid (GNA) analogues. One example of a GNA analogue is shown below and is described in Zhang, R et al., *J. Am. Chem. Soc.,* 2008, 130, 5846-5847; Zhang L, et al., *J. Am. Chem. Soc.,* 2005, 127, 4174-4175 and Tsai C H et al., *PNAS,* 2007, 14598-14603 (X=$O^-$):

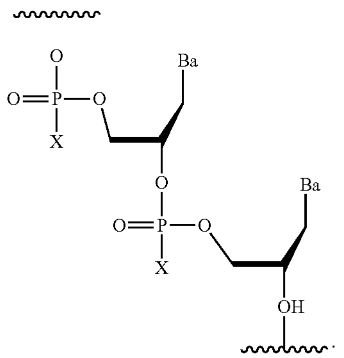

Another example of a GNA derived analogue, flexible nucleic acid (FNA) based on the mixed acetal aminal of formyl glycerol, is described in Joyce G F et al., *PNAS,* 1987, 84, 4398-4402 and Heuberger B D and Switzer C, *J. Am. Chem. Soc.,* 2008, 130, 412-413, and is shown below:

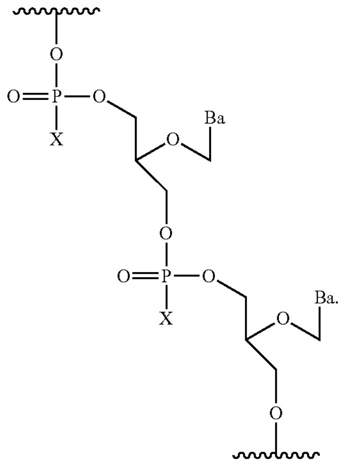

Additional non-limiting examples of modified sugars include hexopyranosyl (6' to 4'), pentopyranosyl (4' to 2'), pentopyranosyl (4' to 3'), or tetrofuranosyl (3' to 2') sugars. In some embodiments, a hexopyranosyl (6' to 4') sugar is of any one in the following formulae:

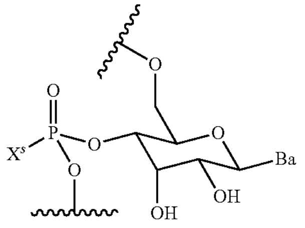

-continued

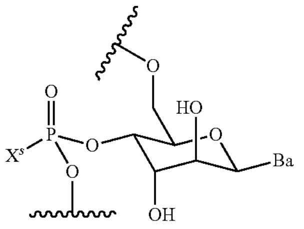

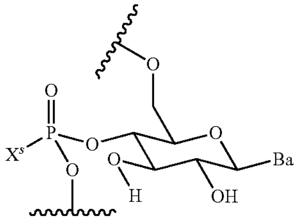

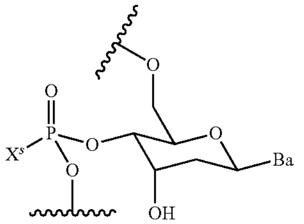

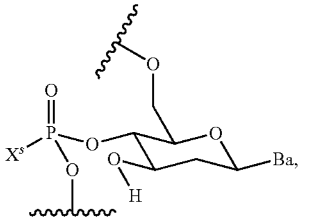

wherein $X^s$ corresponds to the P-modification group "—$XLR^1$" described herein and Ba is as defined herein.

In some embodiments, a pentopyranosyl (4' to 2') sugar is of any one in the following formulae:

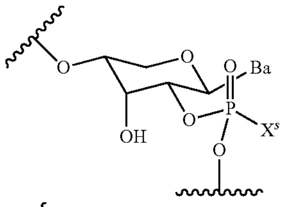

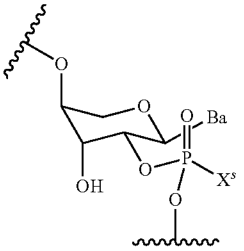

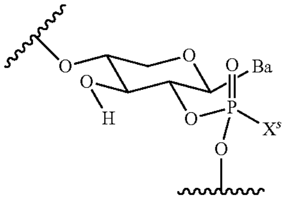

-continued

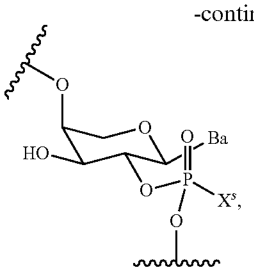

wherein $X^s$ corresponds to the P-modification group "—$XLR^1$" described herein and Ba is as defined herein.

In some embodiments, a pentopyranosyl (4' to 3') sugar is of any one in the following formulae:

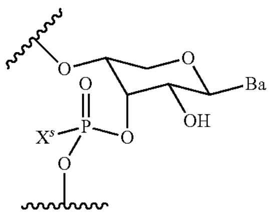

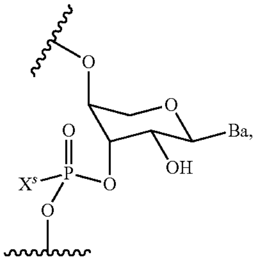

wherein $X^s$ corresponds to the P-modification group "—$XLR^1$" described herein and Ba is as defined herein.

In some embodiments, a tetrofuranosyl (3' to 2') sugar is of either in the following formulae:

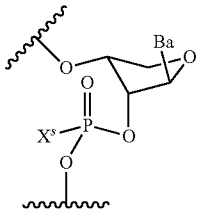

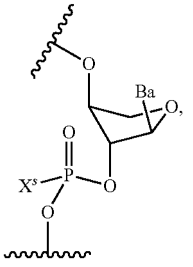

wherein $X^s$ corresponds to the P-modification group "—$XLR^1$" described herein and Ba is as defined herein.

In some embodiments, a modified sugar is of any one in the following formulae:

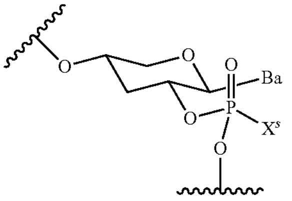

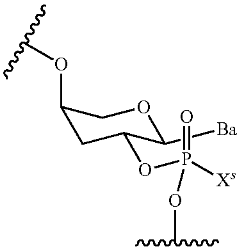

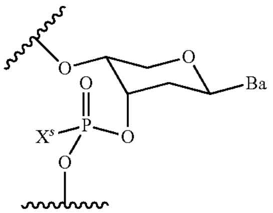

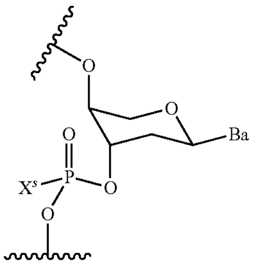

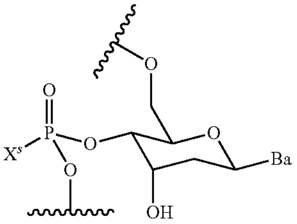

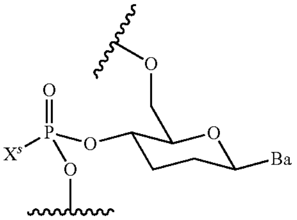

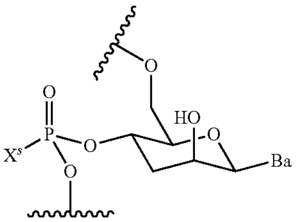

-continued

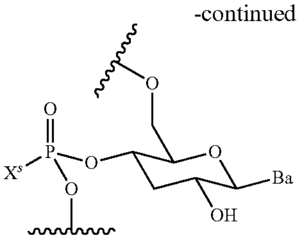

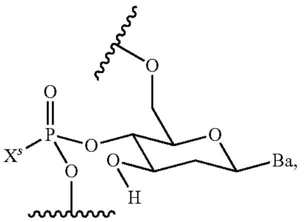

wherein $X^s$ corresponds to the P-modification group "—XLR$^1$" described herein and Ba is as defined herein.

In some embodiments, one or more hydroxyl group in a sugar moiety is optionally and independently replaced with halogen, R'—N(R')$_2$, —OR', or —SR', wherein each R' is independently as defined above and described herein.

In some embodiments, a sugar mimetic is as illustrated below, wherein $X^s$ corresponds to the P-modification group "—XLR$^1$" described herein, Ba is as defined herein, and $X^1$ is selected from —S—, —Se—, —CH$_2$—, —NMe-, —NEt- or —NiPr—.

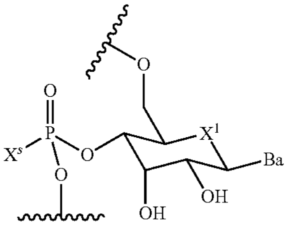

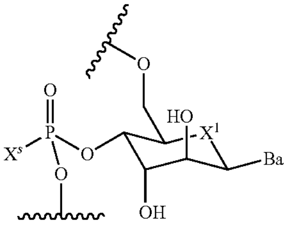

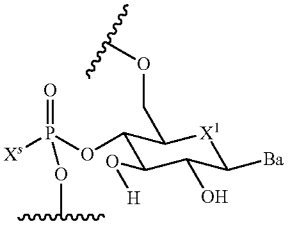

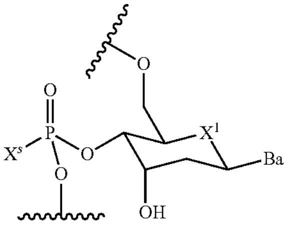

-continued
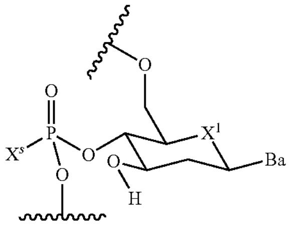
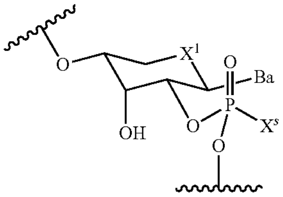
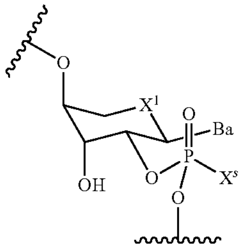
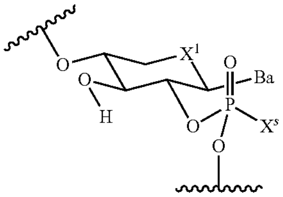
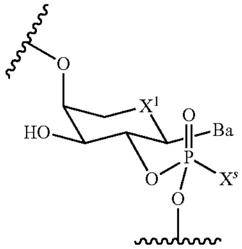
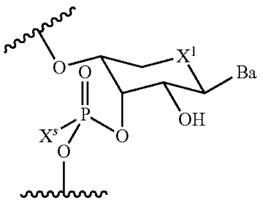
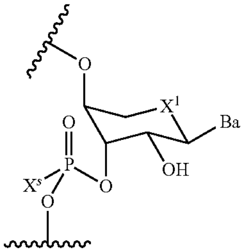
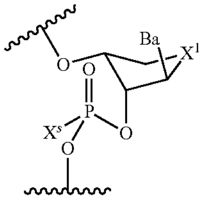
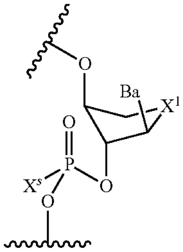
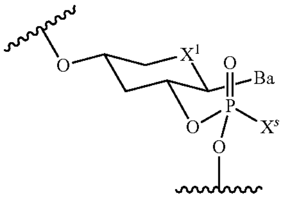
-continued
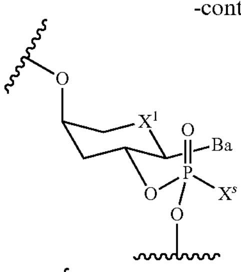
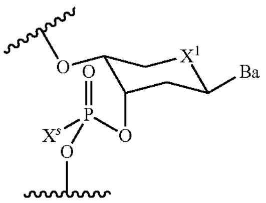
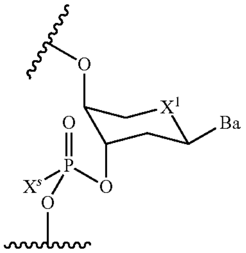
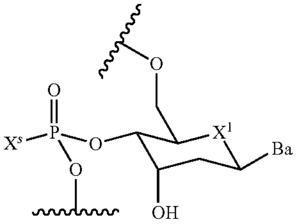
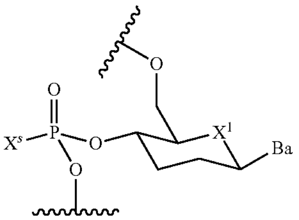
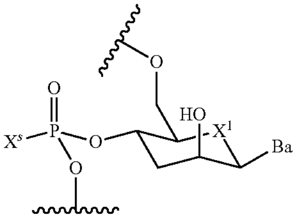
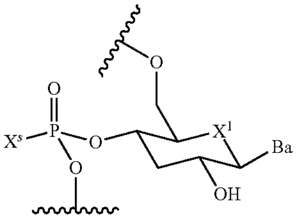
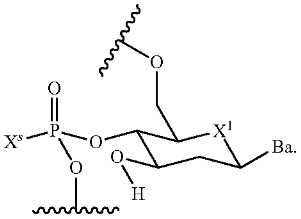
In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a chirally controlled oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

Modified sugars and sugar mimetics can be prepared by methods known in the art, including, but not limited to: A. Eschenmoser, Science (1999), 284:2118; M. Bohringer et al, Helv. Chim. Acta (1992), 75:1416-1477; M. Egli et al, *J. Am. Chem. Soc.* (2006), 128(33):10847-56; A. Eschenmoser in *Chemical Synthesis: Gnosis to Prognosis*, C. Chatgilialoglu and V. Sniekus, Ed., (Kluwer Academic, Netherlands, 1996), p. 293; K.-U. Schoning et al, *Science* (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, *J. Acc. Chem. Res.* 1999, 32, 301-310). In some embodiments, a modified sugar is any of those described in PCT Publication No. WO2012/030683, incorporated herein by reference, and depicted in the FIGS. 26-30 of the present application.

In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, an example modified internucleotidic linkage and/or sugar is selected from:

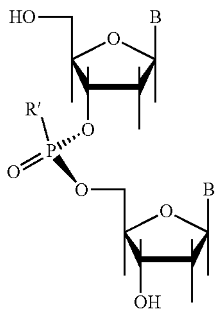

S
R' = $-OC_2H$
R' = $-CH_3$

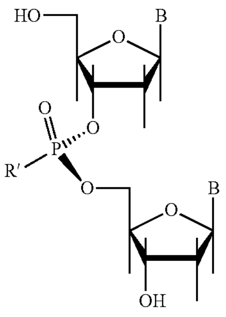

R
Np(Et)N
NpN

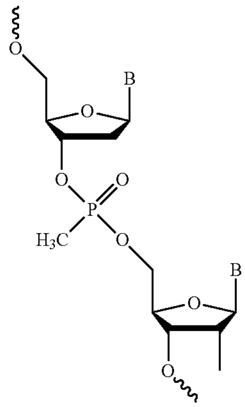

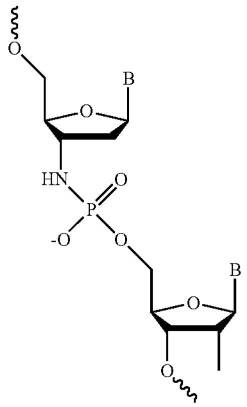

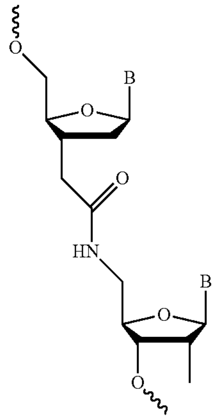

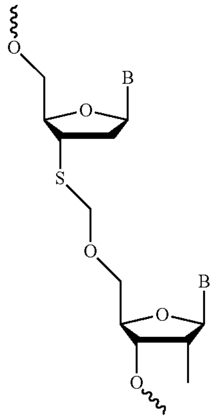

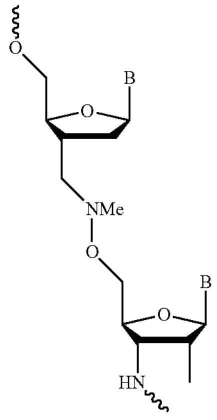

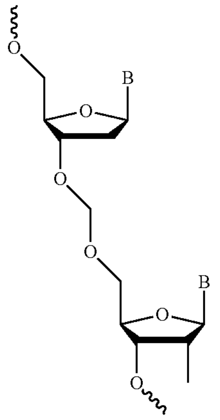

-continued
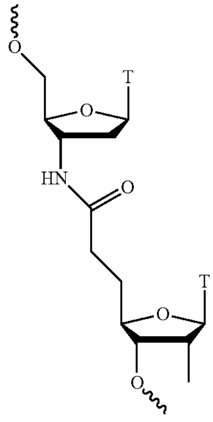
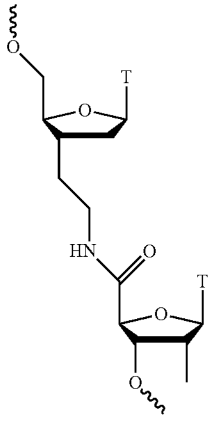
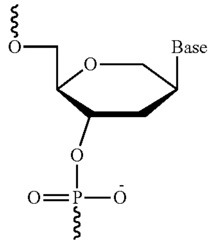
HNA
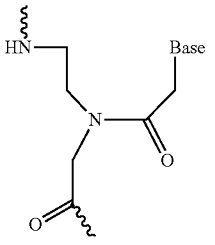
PNA
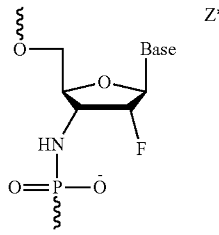
2′-Fluoro N3′-P5′-phosphoramidate
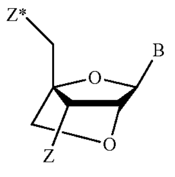
LNA
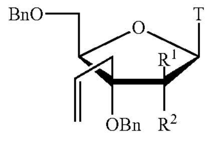
beta-D-oxy-LNA
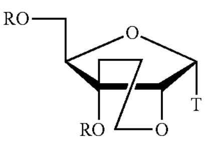
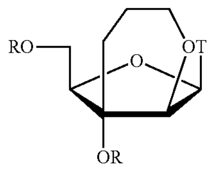
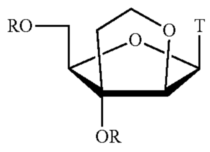
2′-O,3′-C-linked bicyclic
-continued
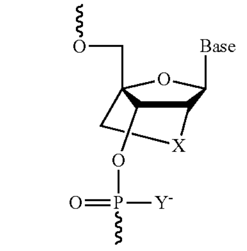
LNA: X = O, Y = O
2′-Thio-LNA: X = S, Y = O
2′-Phosphorothioate-LNA: X = O, Y = S
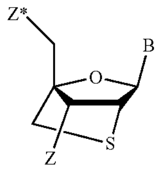
PS-LNA
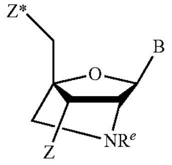
beta-D-thio-LNA
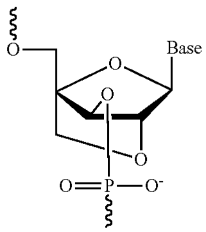
beta-D-amino-LNA
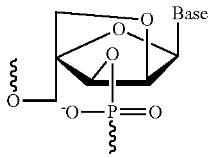
xylo-LNA [c]
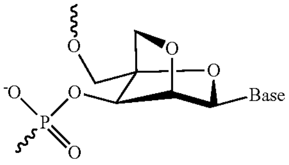
alpha-L-LNA
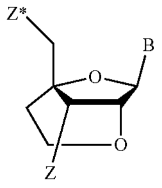
ENA
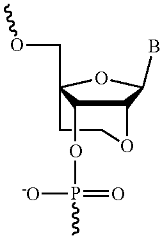
beta-D-ENA
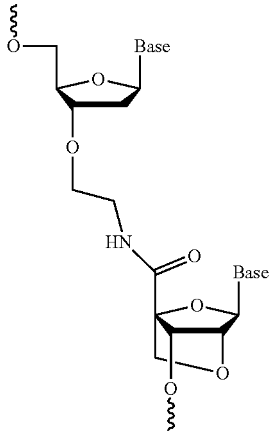
amide-linked LNA
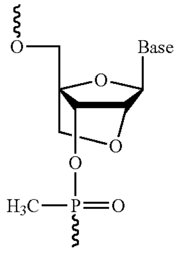
methylphosphonate-LNA -continued

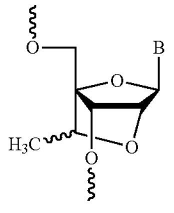

(R,S)-cEt

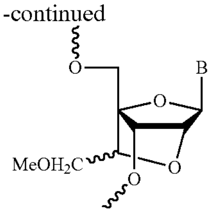

(R,S)-cMOE
(R,S)-cMOE

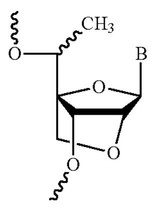

(R,S)-5'-Me-LNA

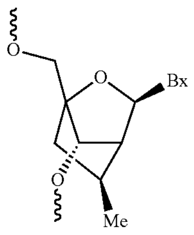

S-Me cLNA

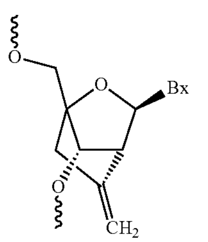

Methylene-cLNA

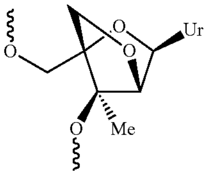

3'-Me-alpha-L-LNA

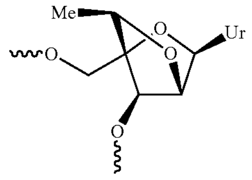

R-6'-Me-alpha-L-LNA

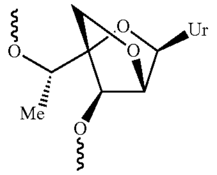

S-5'-Me-alpha-L-LNA

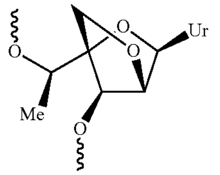

R-5'-Me-alpha-L-LNA

In some embodiments, $R^1$ is R as defined and described. In some embodiments, $R^2$ is R. In some embodiments, $R^e$ is R. In some embodiments, $R^e$ is H, $CH_3$, Bn, $COCF_3$, benzoyl, benzyl, pyren-1-ylcarbonyl, pyren-1-ylmethyl, 2-aminoethyl. In some embodiments, an example modified internucleotidic linkage and/or sugar is selected from those described in Ts'o et al. Ann. N. Y. Acad. Sci. 1988, 507, 220; Gryaznov, S.; Chen, J.-K. J. Am. Chem. Soc. 1994, 116, 3143; Mesmaeker et al. Angew. Chem., Int. Ed. Engl. 1994, 33, 226; Jones et al. J. Org. Chem. 1993, 58, 2983; Vasseur et al. J. Am. Chem. Soc. 1992, 114, 4006; Van Aerschot et al. 1995 Angew. Chem. Int. Ed. Engl. 34: 1338; Hendrix et al. 1997 Chem. Eur. J. 3: 110; Koshkin et al. 1998 Tetrahedron 54: 3607-3630; Hyrup et al. 1996 Bioorg. Med. Chem. 4: 5; Nielsen et al. 1997 Chem. Soc. Rev. 73; Schultz et al. 1996 Nucleic Acids Res. 24: 2966; Obika et al. 1997 Tetrahedron Lett. 38 (50): 8735-8; Obika et al. 1998 Tetrahedron Lett. 39: 5401-5404; Singh et al. 1998 Chem. Comm. 1247-1248; Kumar et al. 1998 Bioo. Med. Chem. Let. 8: 2219-2222; Nielsen et al. 1997 J. Chem. Soc. Perkins Transl. 1: 3423-3433; Singh et al. 1998 J. Org. Chem. 63: 6078-6079; Seth et al. 2010 J. Org. Chem. 75: 1569-1581; Singh et al. 1998 J. Org. Chem. 63: 10035-39; Sorensen 2003 Chem. Comm. 2130-2131; Petersen et al. 2003 TRENDS Biotech. 21: 74-81; Rajwanshi et al. 1999 Chem. Commun. 1395-1396; Jepsen et al. 2004 Oligo. 14: 130-146; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Koizumi et al. 2003 Nuc. Acids Res. 12: 3267-3273; Lauritsen et al. 2002 Chem. Comm. 5: 530-531; Lauritsen et al. 2003 Bioo. Med. Chem. Lett. 13: 253-256; WO 20070900071; Seth et al., Nucleic Acids Symposium Series (2008), 52(1), 553-554; Seth et al. 2009 J. Med. Chem. 52: 10-13; Seth et al. 2012 Mol. Ther-Nuc. Acids. 1, e47; Pallan et al. 2012 Chem. Comm. 48: 8195-8197; Seth et al. 2010 J. Med. Chem. 53: 8309-8318; Seth et al. 2012 Bioo. Med. Chem. Lett. 22: 296-299; WO 2016/079181; U.S. Pat. Nos. 6,326,199; 6,066,500; and 6,440,739, the base and sugar modifications of each of which is herein incorporated by reference.

Oligonucleotides

In some embodiments, the present disclosure provides oligonucleotides and oligonucleotide compositions that are chirally controlled. For instance, in some embodiments, a provided composition contains predetermined levels of one or more individual oligonucleotide types, wherein an oligonucleotide type is defined by: 1) base sequence; 2) pattern of backbone linkages; 3) pattern of backbone chiral centers; and 4) pattern of backbone P-modifications. In some embodiments, a particular oligonucleotide type may be defined by 1A) base identity; 1B) pattern of base modification; 1C) pattern of sugar modification; 2) pattern of backbone linkages; 3) pattern of backbone chiral centers; and 4) pattern of backbone P-modifications. In some embodiments, oligonucleotides of the same oligonucleotide type are identical.

In some embodiments, a provided oligonucleotide is a unimer. In some embodiments, a provided oligonucleotide is a P-modification unimer. In some embodiments, a provided oligonucleotide is a stereounimer. In some embodiments, a provided oligonucleotide is a stereounimer of configuration Rp. In some embodiments, a provided oligonucleotide is a stereounimer of configuration Sp.

In some embodiments, a provided oligonucleotide is an altmer. In some embodiments, a provided oligonucleotide is a P-modification altmer. In some embodiments, a provided oligonucleotide is a stereoaltmer.

In some embodiments, a provided oligonucleotide is a blockmer. In some embodiments, a provided oligonucleotide is a P-modification blockmer. In some embodiments, a provided oligonucleotide is a stereoblockmer.

In some embodiments, a provided oligonucleotide is a gapmer.

In some embodiments, a provided oligonucleotide is a skipmer.

In some embodiments, a provided oligonucleotide is a hemimer. In some embodiments, a hemimer is an oligonucleotide wherein the 5'-end or the 3'-end has a sequence that possesses a structure feature that the rest of the oligonucleotide does not have. In some embodiments, the 5'-end or the 3'-end has or comprises 2 to 20 nucleotides. In some embodiments, a structural feature is a base modification. In some embodiments, a structural feature is a sugar modification. In some embodiments, a structural feature is a P-modification. In some embodiments, a structural feature is stereochemistry of the chiral internucleotidic linkage. In some embodiments, a structural feature is or comprises a base modification, a sugar modification, a P-modification, or stereochemistry of the chiral internucleotidic linkage, or combinations thereof. In some embodiments, a hemimer is an oligonucleotide in which each sugar moiety of the 5'-end sequence shares a common modification. In some embodiments, a hemimer is an oligonucleotide in which each sugar moiety of the 3'-end sequence shares a common modification. In some embodiments, a common sugar modification of the 5' or 3' end sequence is not shared by any other sugar moieties in the oligonucleotide. In some embodiments, an example hemimer is an oligonucleotide comprising a sequence of substituted or unsubstituted 2'-O-alkyl sugar modified nucleosides, bicyclic sugar modified nucleosides, 3-D-ribonucleosides or 3-D-deoxyribonucleosides (for example 2'-MOE modified nucleosides, and LNA™ or ENA™ bicyclic sugar modified nucleosides) at one terminus and a sequence of nucleosides with a different sugar moiety (such as a substituted or unsubstituted 2'-O-alkyl sugar modified nucleosides, bicyclic sugar modified nucleosides or natural ones) at the other terminus. In some embodiments, a provided oligonucleotide is a combination of one or more of unimer, altmer, blockmer, gapmer, hemimer and skipmer. In some embodiments, a provided oligonucleotide is a combination of one or more of unimer, altmer, blockmer, gapmer, and skipmer. For instance, in some embodiments, a provided oligonucleotide is both an altmer and a gapmer. In some embodiments, a provided nucleotide is both a gapmer and a skipmer. One of skill in the chemical and synthetic arts will recognize that numerous other combinations of patterns are available and are limited only by the commercial availability and/or synthetic accessibility of constituent parts required to synthesize a provided oligonucleotide in accordance with methods of the present disclosure. In some embodiments, a hemimer structure provides advantageous benefits, as exemplified by FIG. 29. In some embodiments, provided oligonucleotides are 5'-hemmimers that comprises modified sugar moieties in a 5'-end sequence. In some embodiments, provided oligonucleotides are 5'-hemmimers that comprises modified 2'-sugar moieties in a 5'-end sequence.

In some embodiments, a provided oligonucleotide comprises one or more optionally substituted nucleotides. In some embodiments, a provided oligonucleotide comprises one or more modified nucleotides. In some embodiments, a provided oligonucleotide comprises one or more optionally substituted nucleosides. In some embodiments, a provided oligonucleotide comprises one or more modified nucleosides. In some embodiments, a provided oligonucleotide comprises one or more optionally substituted LNAs.

In some embodiments, a provided oligonucleotide comprises one or more optionally substituted nucleobases. In some embodiments, a provided oligonucleotide comprises one or more optionally substituted natural nucleobases. In some embodiments, a provided oligonucleotide comprises one or more optionally substituted modified nucleobases. In some embodiments, a provided oligonucleotide comprises one or more 5-methylcytidine; 5-hydroxymethylcytidine, 5-formylcytosine, or 5-carboxylcytosine. In some embodiments, a provided oligonucleotide comprises one or more 5-methylcytidine.

In some embodiments, a provided oligonucleotide comprises one or more optionally substituted sugars. In some embodiments, a provided oligonucleotide comprises one or more optionally substituted sugars found in naturally occurring DNA and RNA. In some embodiments, a provided oligonucleotide comprises one or more optionally substituted ribose or deoxyribose. In some embodiments, a provided oligonucleotide comprises one or more optionally substituted ribose or deoxyribose, wherein one or more hydroxyl groups of the ribose or deoxyribose moiety is optionally and independently replaced by halogen, R', —$N(R')_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen, R', —$N(R')_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen. In some embodiments, a provided oligonucleotide comprises one or more optionally substituted deoxyribose, wherein the 2' position of the deoxyribose is optionally and independently substituted with one or more —F. halogen. In some embodiments, a provided oligonucleotide comprises one or more optionally substituted deoxyribose, wherein the 2' position of the deoxyribose is optionally and independently substituted with —OR', wherein each R' is independently as defined above and described herein. In some embodiments, a provided oligonucleotide comprises one or more optionally substituted deoxyribose, wherein the 2' position of the deoxyribose is optionally and independently substituted with —OR', wherein each R' is independently an optionally substituted $C_1$-$C_6$ aliphatic. In some embodiments, a provided oligonucleotide comprises one or more optionally substituted deoxyribose, wherein the 2' position of the deoxyribose is optionally and independently substituted with —OR', wherein each R' is independently an optionally substituted $C_1$-$C_6$ alkyl. In some embodiments, a provided oligonucleotide comprises one or more optionally substituted deoxyribose, wherein the 2' position of the deoxyribose is optionally and independently substituted with —OMe. In some embodiments, a provided oligonucleotide comprises one or more optionally substituted deoxyribose, wherein the 2' position of the deoxyribose is optionally and independently substituted with —O-methoxyethyl.

In some embodiments, a provided oligonucleotide is single-stranded oligonucleotide.

In some embodiments, a provided oligonucleotide is a hybridized oligonucleotide strand. In certain embodiments, a provided oligonucleotide is a partially hydridized oligonucleotide strand. In certain embodiments, a provided oligonucleotide is a completely hydridized oligonucleotide strand. In certain embodiments, a provided oligonucleotide is a double-stranded oligonucleotide. In certain embodiments, a provided oligonucleotide is a triple-stranded oligonucleotide (e.g., a triplex).

In some embodiments, a provided oligonucleotide is chimeric. For example, in some embodiments, a provided oligonucleotide is DNA-RNA chimera, DNA-LNA chimera, etc.

In some embodiments, any one of the structures comprising an oligonucleotide depicted in WO2012/030683 can be modified in accordance with methods of the present disclosure to provide chirally controlled variants thereof. For example, in some embodiments the chirally controlled variants comprise a stereochemical modification at any one or more of the linkage phosphorus and/or a P-modification at any one or more of the linkage phosphorus. For example, in some embodiments, a particular nucleotide unit of an oligonucleotide of WO2012/030683 is preselected to be stereochemically modified at the linkage phosphorus of that nucleotide unit and/or P-modified at the linkage phosphorus of that nucleotide unit. In some embodiments, a chirally controlled oligonucleotide is of any one of the structures depicted in FIGS. 26-30. In some embodiments, a chirally controlled oligonucleotide is a variant (e.g., modified version) of any one of the structures depicted in FIGS. 26-30. The related disclosure of WO2012/030683 is herein incorporated by reference in its entirety.

In some embodiments, a provided oligonucleotide is a therapeutic agent.

In some embodiments, a provided oligonucleotide is an antisense oligonucleotide.

In some embodiments, a provided oligonucleotide is an antigene oligonucleotide.

In some embodiments, a provided oligonucleotide is a decoy oligonucleotide.

In some embodiments, a provided oligonucleotide is part of a DNA vaccine.

In some embodiments, a provided oligonucleotide is an immunomodulatory oligonucleotide, e.g., immunostimulatory oligonucleotide and immunoinhibitory oligonucleotide.

In some embodiments, a provided oligonucleotide is an adjuvant.

In some embodiments, a provided oligonucleotide is an aptamer.

In some embodiments, a provided oligonucleotide is a ribozyme.

In some embodiments, a provided oligonucleotide is a deoxyribozyme (DNAzymes or DNA enzymes).

In some embodiments, a provided oligonucleotide is an siRNA.

In some embodiments, a provided oligonucleotide is a microRNA, or miRNA.

In some embodiments, a provided oligonucleotide is a ncRNA (non-coding RNAs), including a long non-coding RNA (lncRNA) and a small non-coding RNA, such as piwi-interacting RNA (piRNA).

In some embodiments, a provided oligonucleotide is complementary to a structural RNA, e.g., tRNA.

In some embodiments, a provided oligonucleotide is a nucleic acid analog, e.g., GNA, LNA, PNA, TNA, GNA, ANA, FANA, CeNA, HNA, UNA, ZNA, or Morpholino. In some embodiments, a provided oligonucleotide is a nucleic acid analog, e.g., GNA, LNA, PNA, TNA and Morpholino.

In some embodiments, a provided oligonucleotide is a P-modified prodrug.

In some embodiments, a provided oligonucleotide is a primer. In some embodiments, a primers is for use in polymerase-based chain reactions (i.e., PCR) to amplify nucleic acids. In some embodiments, a primer is for use in any known variations of PCR, such as reverse transcription PCR (RT-PCR) and real-time PCR.

In some embodiments, a provided oligonucleotide is characterized as having the ability to modulate RNase H activation. For example, in some embodiments, RNase H activation is modulated by the presence of stereocontrolled phosphorothioate nucleic acid analogs, with natural DNA/RNA being more or equally susceptible than the Rp stereoisomer, which in turn is more susceptible than the corresponding Sp stereoisomer.

In some embodiments, a provided oligonucleotide is characterized as having the ability to indirectly or directly increase or decrease activity of a protein or inhibition or promotion of the expression of a protein. In some embodiments, a provided oligonucleotide is characterized in that it is useful in the control of cell proliferation, viral replication, and/or any other cell signaling process.

In some embodiments, a provided oligonucleotide is from about 2 to about 200 nucleotide units in length. In some embodiments, a provided oligonucleotide is from about 2 to about 180 nucleotide units in length. In some embodiments, a provided oligonucleotide is from about 2 to about 160 nucleotide units in length. In some embodiments, a provided oligonucleotide is from about 2 to about 140 nucleotide units in length. In some embodiments, a provided oligonucleotide is from about 2 to about 120 nucleotide units in length. In some embodiments, a provided oligonucleotide is from about 2 to about 100 nucleotide units in length. In some embodiments, a provided oligonucleotide is from about 2 to about 90 nucleotide units in length. In some embodiments, a provided oligonucleotide is from about 2 to about 80 nucleotide units in length. In some embodiments, a provided oligonucleotide is from about 2 to about 70 nucleotide units in length. In some embodiments, a provided oligonucleotide is from about 2 to about 60 nucleotide units in length. In some embodiments, a provided oligonucleotide is from about 2 to about 50 nucleotide units in length. In some embodiments, a provided oligonucleotide is from about 2 to about 40 nucleotide units in length. In some embodiments, a provided oligonucleotide is from about 2 to about 30 nucleotide units in length. In some embodiments, a provided oligonucleotide is from about 2 to about 29 nucleotide units in length. In some embodiments, a provided oligonucleotide is from about 2 to about 28 nucleotide units in length. In some embodiments, a provided oligonucleotide is from about 2 to about 27 nucleotide units in length. In some embodiments, a provided oligonucleotide is from about 2 to about 26 nucleotide units in length. In some embodiments, a provided oligonucleotide is from about 2 to about 25 nucleotide units in length. In some embodiments, a provided oligonucleotide is from about 2 to about 24 nucleotide units in length. In some embodiments, a provided oligonucleotide is from about 2 to about 23 nucleotide units in length. In some embodiments, a provided oligonucleotide is from about 2 to about 22 nucleotide units in length. In some embodiments, a provided oligonucleotide is from about 2 to about 21 nucleotide units in length. In some embodiments, a provided oligonucleotide is from about 2 to about 20 nucleotide units in length.

In some embodiments, a provided oligonucleotide is from about 4 to about 200 nucleotide units in length. In some embodiments, a provided oligonucleotide is from about 4 to about 180 nucleotide units in length. In some embodiments, a provided oligonucleotide is from about 4 to about 160 nucleotide units in length. In some embodiments, a provided oligonucleotide is from about 4 to about 140 nucleotide units in length. In some embodiments, a provided oligonucleotide is from about 4 to about 120 nucleotide units in length. In some embodiments, a provided oligonucleotide is from about 4 to about 100 nucleotide units in length. In some embodiments, a provided oligonucleotide is from about 4 to about 90 nucleotide units in length. In some embodiments, a provided oligonucleotide is from about 4 to about 80 nucleotide units in length. In some embodiments, a provided oligonucleotide is from about 4 to about 70 nucleotide units in length. In some embodiments, a provided oligonucleotide is from about 4 to about 60 nucleotide units in length. In some embodiments, a provided oligonucleotide is from about 4 to about 50 nucleotide units in length. In some embodiments, a provided oligonucleotide is from about 4 to about 40 nucleotide units in length. In some embodiments, a provided oligonucleotide is from about 4 to about 30 nucleotide units in length. In some embodiments, a provided oligonucleotide is from about 4 to about 29 nucleotide units in length. In some embodiments, a provided oligonucleotide is from about 4 to about 28 nucleotide units in length. In some embodiments, a provided oligonucleotide is from about 4 to about 27 nucleotide units in length. In some embodiments, a provided oligonucleotide is from about 4 to about 26 nucleotide units in length. In some embodiments, a provided oligonucleotide is from about 4 to about 25 nucleotide units in length. In some embodiments, a provided oligonucleotide is from about 4 to about 24 nucleotide units in length. In some embodiments, a provided oligonucleotide is from about 4 to about 23 nucleotide units in length. In some embodiments, a provided oligonucleotide is from about 4 to about 22 nucleotide units in length. In some embodiments, a provided oligonucleotide is from about 4 to about 21 nucleotide units in length. In some embodiments, a provided oligonucleotide is from about 4 to about 20 nucleotide units in length.

In some embodiments, a provided oligonucleotide is from about 5 to about 10 nucleotide units in length. In some embodiments, a provided oligonucleotide is from about 10 to about 30 nucleotide units in length. In some embodiments, a provided oligonucleotide is from about 15 to about 25 nucleotide units in length. In some embodiments, a provided oligonucleotide is from about 5, 6, 7, 8, 9, 10, 11, 12, 13, 14, 15, 16, 17, 18, 19, 20, 21, 22, 23, 24, or 25 nucleotide units in length.

In some embodiments, an oligonucleotide is at least 2 nucleotide units in length. In some embodiments, an oligonucleotide is at least 3 nucleotide units in length. In some embodiments, an oligonucleotide is at least 4 nucleotide units in length. In some embodiments, an oligonucleotide is at least 5 nucleotide units in length. In some embodiments, an oligonucleotide is at least 6 nucleotide units in length. In some embodiments, an oligonucleotide is at least 7 nucleotide units in length. In some embodiments, an oligonucleotide is at least 8 nucleotide units in length. In some embodiments, an oligonucleotide is at least 9 nucleotide units in length. In some embodiments, an oligonucleotide is at least 10 nucleotide units in length. In some embodiments, an oligonucleotide is at least 11 nucleotide units in length. In some embodiments, an oligonucleotide is at least 12 nucleotide units in length. In some embodiments, an oligonucleotide is at least 13 nucleotide units in length. In some embodiments, an oligonucleotide is at least 14 nucleotide units in length. In some embodiments, an oligonucleotide is at least 15 nucleotide units in length. In some embodiments, an oligonucleotide is at least 16 nucleotide units in length. In some embodiments, an oligonucleotide is at least 17 nucleotide units in length. In some embodiments, an oligonucleotide is at least 18 nucleotide units in length. In some embodiments, an oligonucleotide is at least 19 nucleotide units in length. In some embodiments, an oligonucleotide is at least 20 nucleotide units in length. In some embodiments, an oligonucleotide is at least 21 nucleotide units in length. In some embodiments, an oligonucleotide is at least 22 nucleotide units in length. In some embodiments, an oligonucleotide is at least 23 nucleotide units in length. In some embodiments, an oligonucleotide is at least 24 nucleotide units in length. In some embodiments, an oligonucleotide is at least 25 nucleotide units in length. In some other embodiments, an oligonucleotide is at least 30 nucleotide units in length. In some other embodiments, an oligonucleotide is a duplex of complementary strands of at least 18 nucleotide units in length. In some other embodiments, an oligonucleotide is a duplex of complementary strands of at least 21 nucleotide units in length.

In some embodiments, the 5'-end and/or the 3'-end of a provided oligonucleotide is modified. In some embodiments, the 5'-end and/or the 3'-end of a provided oligonucleotide is modified with a terminal cap moiety. Example such modifications, including terminal cap moieties are extensively described herein and in the art, for example but not limited to those described in US Patent Application Publication US 2009/0023675A1.

In some embodiments, oligonucleotides of an oligonucleotide type characterized by 1) a common base sequence and length, 2) a common pattern of backbone linkages, and 3) a common pattern of backbone chiral centers, have the same chemical structure. For example, they have the same base sequence, the same pattern of nucleoside modifications, the same pattern of backbone linkages (i.e., pattern of internucleotidic linkage types, for example, phosphate, phosphorothioate, etc), the same pattern of backbone chiral centers (i.e. pattern of linkage phosphorus stereochemistry (Rp/Sp)), and the same pattern of backbone phosphorus modifications (e.g., pattern of "—XLR$^1$" groups in formula I).

Example Oligonucleotides and Compositions

In some embodiments, the present disclosure provides oligonucleotides and/or oligonucleotide compositions that are useful for various purposes known in the art. In some embodiments, the present disclosure provides oligonucleotide compositions with improved properties, e.g., activities, toxicities, etc. Non-limiting example compositions are listed below:

TABLE 2

| Example Oligonucleotide and Compositions | |
|---|---|
| WV-459 | m5C*m5C*G*T*m5C*G*m5C*m5C*m5C*T*T*m5C*A*G*m5C*A*m5C*G*m5C*A (SEQ ID NO: 39) |
| WV-485 | m5C*Sm5C*SG*ST*Sm5C*SG*Sm5C*Sm5C*Sm5C*ST*ST*Sm5C*RA*SG*Sm5C*SA*Sm5C*SG*Sm5C*SA (SEQ ID NO: 40) |
| WV-458 | m5Ceo*m5Ceo*Geo*Teo*m5Ceo*G*m5C*m5C*m5C*T*T*m5C*A*G*m5C*Aeo*m5Ceo*Geo*m5Ceo*Aeo (SEQ ID NO: 41) |
| WV-486 | m5Ceo*Sm5Ceo*SGeo*STeo*Sm5Ceo*SG*Sm5C*Sm5C*Sm5C*ST*ST*Sm5C*SA*SG*Sm5C*SAeo*Sm5Ceo*SGeo*Sm5Ceo*SAeo (SEQ ID NO: 42) |
| WV-487 | m5Ceo*Sm5Ceo*SGeo*STeo*Sm5Ceo*SG*Sm5C*Sm5C*Sm5C*ST*ST*Sm5C*RA*SG*Sm5C*SAeo*Sm5Ceo*SGeo*Sm5Ceo*SAeo (SEQ ID NO: 43) |
| WV-488 | m5Ceo*Rm5Ceo*RGeo*RTeo*Rm5Ceo*RG*Sm5C*Sm5C*Sm5C*ST*ST*Sm5C*RA*SG*Sm5C*SAeo*Rm5Ceo*RGeo*Rm5Ceo*RAeo (SEQ ID NO: 44) |
| ONT-83 | Geo*Teo*m5Ceo*m5Ceo*m5Ceo*T*G*A*A*G*A*T*G*T*m5C*Aeo*Aeo*Teo*Geo*m5Ceo (SEQ ID NO: 45) |
| ONT-82 | Geo*RTeo*Rm5Ceo*Rm5Ceo*Rm5Ceo*RT*RG*RA*RA*RG*RA*RT*RG*RT*Rm5C*RAeo*RAeo*RTeo*RGeo*Rm5Ceo (SEQ ID NO: 46) |
| ONT-84 | Geo*STeo*Sm5Ceo*Sm5Ceo*Sm5Ceo*ST*SG*SA*SA*SG*SA*ST*SG*ST*Sm5C*SAeo*SAeo*STeo*SGeo*Sm5Ceo (SEQ ID NO: 47) |
| ONT-85 | Geo*RTeo*Rm5Ceo*Rm5Ceo*Rm5Ceo*RT*SG*SA*SA*SG*SA*ST*SG*ST*Sm5C*SAeo*RAeo*RTeo*RGeo*Rm5Ceo (SEQ ID NO: 48) |

TABLE 2-continued

| Example Oligonucleotide and Compositions | |
|---|---|
| ONT-86 | Geo*STeo*Sm5Ceo*Sm5Ceo*Sm5Ceo*ST*RG*RA*RA*RG*RA*RT*RG*RT*Rm5C*RAeo*SAeo*STeo*SGeo*Sm5Ceo (SEQ ID NO: 49) |
| WV-917 | mG*mG*mC*mA*mC*A*A*G*G*G*C*A*C*A*G*mA*mC*mU*mU*mC (SEQ ID NO: 50) |
| WV-1085 | mG*SmG*SmC*SmA*SmC*SA*SA*SG*SG*SG*SC*SA*SC*RA*SG*SmA*SmC*SmU*SmU*SmC (SEQ ID NO: 51) |
| WV-1086 | mG*RmG*RmC*RmA*RmC*SA*SA*SG*SG*SG*SC*SA*SC*RA*SG*SmA*RmC*RmU*RmU*RmC (SEQ ID NO: 52) |
| WV-1087 | mGmGmCmAmC*SA*SA*SG*SG*SG*SC*SA*SC*RA*SG*SmAmCmUmUmC (SEQ ID NO: 53) |
| WV-1091 | mG*RmGmGmCmAmC*SA*SA*SG*SG*SG*SC*SA*SC*RA*SG*SmAmCmUmU*RmC (SEQ ID NO: 54) |
| WV-1092 | mG*SmGmCmAmC*SA*SA*SG*SG*SG*SC*SA*SC*RA*SG*SmAmCmUmU*SmC (SEQ ID NO: 55) |
| WV-1510 | G*SmGmCmAmC*SA*SA*SG*SG*SG*SC*SA*SC*RA*SG*SmAmCmUmU*SC (SEQ ID NO: 56) |
| WV-1511 | G*mGmCmAmC*A*A*G*G*G*C*A*C*A*G*mAmCmUmU*C (SEQ ID NO: 57) |
| WV-1497 | mG*mGmCmAmC*A*A*G*G*G*C*A*C*A*G*mAmCmUmU*mC (SEQ ID NO: 58) |
| WV-1655 | Geo*Geom5CeoAeom5Ceo*A*A*G*G*G*C*A*C*A*G*Aeom5CeoTeoTeo*m5Ceo (SEQ ID NO: 59) |

TABLE 3

| Brief Description of Example Oligonucleotides and Compositions. | |
|---|---|
| WV-459 | All DNA, each cytidine is 5-methylated, Stereorandom |
| WV-485 | All DNA, each cytidine is 5-methylated, Stereopure, One Rp in DNA |
| WV-458 | 5-10-5 (2'-MOE-DNA-2'-MOE) Gapmer, each cytidine is 5-methylated, Stereorandom |
| WV-486 | 5-10-5 (2'-MOE-DNA-2'-MOE) Gapmer, each cytidine is 5-methylated, Stereopure |
| WV-487 | 5-10-5 (2'-MOE-DNA-2'-MOE) Gapmer, each cytidine is 5-methylated, Stereopure, One Rp in DNA |
| WV-488 | 5-10-5 (2'-MOE-DNA-2'-MOE) Gapmer, each cytidine is 5-methylated, Stereopure, One Rp in DNA and Rp wings |
| ONT-83 | 5-10-5 (2'-MOE-DNA-2'-MOE) Gapmer, each cytidine is 5-methylated, Stereorandom |
| ONT-82 | 5-10-5 (2'-MOE-DNA-2'-MOE) Gapmer, each cytidine is 5-methylated, Stereopure |
| ONT-84 | 5-10-5 (2'-MOE-DNA-2'-MOE) Gapmer, each cytidine is 5-methylated, Stereopure |
| ONT-85 | 5-10-5 (2'-MOE-DNA-2'-MOE) Gapmer, each cytidine is 5-methylated, Rp wings |
| ONT-86 | 5-10-5 (2'-MOE-DNA-2'-MOE) Gapmer, each cytidine is 5-methylated, Sp wings |
| WV-917 | 5-10-5 (2'-OMe-DNA-2'-OMe), Gapmer, Stereorandom |
| WV-1085 | 5-10-5 (2'-OMe-DNA-2'-OMe) Gapmer, Stereopure, One Rp in DNA |
| WV-1086 | 5-10-5 (2'-OMe-DNA-2'-OMe) Gapmer, Stereopure, One Rp in DNA and Rp wings |
| WV-1087 | 5-10-5 (2'-OMe-DNA-2'-OMe) Gapmer, Stereopure, One Rp in DNA, PO wings |
| WV-1091 | 5-10-5 (2'-OMe-DNA-2'-OMe) Gapmer, Stereopure, One Rp in DNA, PO wings with One Rp on each end |
| WV-1092 | 5-10-5 (2'-OMe-DNA-2'-OMe) Gapmer, Stereopure, One Rp in DNA, PO wings with One Sp on each end |

TABLE 3-continued

| Brief Description of Example Oligonucleotides and Compositions. | |
|---|---|
| WV-1510 | 1-4-10-4-1 (DNA-2'-OMe-DNA-2'-OMe-DNA) Gapmer, Stereopure, One Rp in DNA, PO wings with One Sp on each end |
| WV-1511 | 1-4-10-4-1 (DNA-2'-OMe-DNA-2'-OMe-DNA) Gapmer, Stereorandom |
| WV-1497 | 5-10-5 (2'-OMe-DNA-2'-OMe) Gapmer, Stereorandom, PO wings with One PS on each end |
| WV-1655 | 5-10-5 (2'-MOE-DNA-2'-MOE) Gapmer, Stereorandom, PO wings with One PS on each end |

In some embodiments, * only represents a stereorandom phosphorothioate linkage; *S represents an Sp phosphorothioate linkage; *R represents an Rp phosphorothioate linkage; all non-labeled linkage is a natural phosphate linkage; m preceding a base represents 2'-OMe; eo following a base represents 2'-MOE;

In some embodiments, a provided oligonucleotide composition is a chirally controlled oligonucleotide composition of an oligonucleotide type listed in Table 2. In some embodiments, a provided composition is of WV-1092. In some embodiments, a first plurality of oligonucleotides is a plurality of an oligonucleotide in Table 2. In some embodiments, a first plurality of oligonucleotides is a plurality of WV-1092.

The present disclosure provides compositions comprising or consisting of a plurality of provided oligonucleotides (e.g., chirally controlled oligonucleotide compositions). In some embodiments, all such provided oligonucleotides are of the same type, i.e., all have the same base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—XLR$^1$" groups in formula I). In some embodiments, all oligonucleotides of the same type are identical. In many embodiments, however, provided compositions comprise a plurality of oligonucleotides types, typically in pre-determined relative amounts.

In some embodiments, a provided chirally controlled oligonucleotide composition comprises a combination of one or more provided oligonucleotide types. One of skill in the chemical and medicinal arts will recognize that the selection and amount of each of the one or more types of provided oligonucleotides in a provided composition will depend on the intended use of that composition. That is to say, one of skill in the relevant arts would design a provided chirally controlled oligonucleotide composition such that the amounts and types of provided oligonucleotides contained therein cause the composition as a whole to have certain desirable characteristics (e.g., biologically desirable, therapeutically desirable, etc.).

In some embodiments, a provided chirally controlled oligonucleotide composition comprises a combination of two or more provided oligonucleotide types. In some embodiments, a provided chirally controlled oligonucleotide composition comprises a combination of three or more provided oligonucleotide types. In some embodiments, a provided chirally controlled oligonucleotide composition comprises a combination of four or more provided oligonucleotide types. In some embodiments, a provided chirally controlled oligonucleotide composition comprises a combination of five or more provided oligonucleotide types. In some embodiments, a provided chirally controlled oligonucleotide composition comprises a combination of six or more provided oligonucleotide types. In some embodiments, a provided chirally controlled oligonucleotide composition comprises a combination of seven or more provided oligonucleotide types. In some embodiments, a provided chirally controlled oligonucleotide composition comprises a combination of eight or more provided oligonucleotide types. In some embodiments, a provided chirally controlled oligonucleotide composition comprises a combination of nine or more provided oligonucleotide types. In some embodiments, a provided chirally controlled oligonucleotide composition comprises a combination of ten or more provided oligonucleotide types. In some embodiments, a provided chirally controlled oligonucleotide composition comprises a combination of fifteen or more provided oligonucleotide types.

In some embodiments, a provided chirally controlled oligonucleotide composition is a combination of an amount of chirally uniform mipomersen of the Rp configuration and an amount of chirally uniform mipomersen of the Sp configuration.

In some embodiments, a provided chirally controlled oligonucleotide composition is a combination of an amount of chirally uniform mipomersen of the Rp configuration, an amount of chirally uniform mipomersen of the Sp configuration, and an amount of one or more chirally pure mipomersen of a desired diastereomeric form.

In some embodiments, a provided oligonucleotide type is selected from those described in WO/2014/012081 and WO/2015/107425, the oligonucleotides, oligonucleotide types, oligonucleotide compositions, and methods thereof of each of which are incorporated herein by reference. In some embodiments, a provided chirally controlled oligonucleotide composition comprises oligonucleotides of an oligonucleotide type selected from those described in WO/2014/012081 and WO/2015/107425.

In some embodiments, provided oligonucleotides comprise base sequence, pattern of backbone linkages, pattern or backbone chiral centers, and/or pattern of chemical modifications (e.g., base modifications, sugar modifications, etc.) of any oligonucleotide disclosed herein.

Example Methods for Preparing Oligonucleotides and Compositions

Methods for preparing provided oligonucleotides and oligonucleotide compositions are widely known in the art, including but not limited to those described in WO/2010/064146, WO/2011/005761, WO/2013/012758, WO/2014/010250, US2013/0178612, WO/2014/012081 and WO/2015/107425, the methods and reagents of each of which is incorporated herein by reference.

Among other things, the present disclosure provides methods for making chirally controlled oligonucleotides and chirally controlled compositions comprising one or more specific nucleotide types. In some embodiments, the phrase "oligonucleotide type," as used herein, defines an oligonucleotide that has a particular base sequence, pattern of backbone linkages, pattern of backbone chiral centers, and pattern of backbone phosphorus modifications (e.g., "—$XLR^1$" groups). Oligonucleotides of a common designated "type" are structurally identical to one another with respect to base sequence, pattern of backbone linkages, pattern of backbone chiral centers, and pattern of backbone phosphorus modifications. In some embodiments, oligonucleotides of an oligonucleotide type are identical.

In some embodiments, a provided chirally controlled oligonucleotide in the disclosure has properties different from those of the corresponding stereorandom oligonucleotide mixture. In some embodiments, a chirally controlled oligonucleotide has lipophilicity different from that of the stereorandom oligonucleotide mixture. In some embodiments, a chirally controlled oligonucleotide has different retention time on HPLC. In some embodiments, a chirally controlled oligonucleotide may have a peak retention time significantly different from that of the corresponding stereorandom oligonucleotide mixture. During oligonucleotide purification using HPLC as generally practiced in the art, certain chirally controlled oligonucleotides will be largely if not totally lost. During oligonucleotide purification using HPLC as generally practiced in the art, certain chirally controlled oligonucleotides will be largely if not totally lost. One of the consequences is that certain diastereomers of a stereorandom oligonucleotide mixture (certain chirally controlled oligonucleotides) are not tested in assays. Another consequence is that from batches to batches, due to the inevitable instrumental and human errors, the supposedly "pure" stereorandom oligonucleotide will have inconsistent compositions in that diastereomers in the composition, and their relative and absolute amounts, are different from batches to batches. The chirally controlled oligonucleotide and chirally controlled oligonucleotide composition provided in this disclosure overcome such problems, as a chirally controlled oligonucleotide is synthesized in a chirally controlled fashion as a single diastereomer, and a chirally controlled oligonucleotide composition comprise predetermined levels of one or more individual oligonucleotide types.

One of skill in the chemical and synthetic arts will appreciate that synthetic methods of the present disclosure provide for a degree of control during each step of the synthesis of a provided oligonucleotide such that each nucleotide unit of the oligonucleotide can be designed and/or selected in advance to have a particular stereochemistry at the linkage phosphorus and/or a particular modification at the linkage phosphorus, and/or a particular base, and/or a particular sugar. In some embodiments, a provided oligonucleotide is designed and/or selected in advance to have a particular combination of stereocenters at the linkage phosphorus of the internucleotidic linkage.

In some embodiments, a provided oligonucleotide made using methods of the present disclosure is designed and/or determined to have a particular combination of linkage phosphorus modifications. In some embodiments, a provided oligonucleotide made using methods of the present disclosure is designed and/or determined to have a particular combination of bases. In some embodiments, a provided oligonucleotide made using methods of the present disclosure is designed and/or determined to have a particular combination of sugars. In some embodiments, a provided oligonucleotide made using methods of the present disclosure is designed and/or determined to have a particular combination of one or more of the above structural characteristics.

Methods of the present disclosure exhibit a high degree of chiral control. For instance, methods of the present disclosure facilitate control of the stereochemical configuration of every single linkage phosphorus within a provided oligonucleotide. In some embodiments, methods of the present disclosure provide an oligonucleotide comprising one or more modified internucleotidic linkages independently having the structure of formula I.

In some embodiments, methods of the present disclosure provide an oligonucleotide which is a mipomersen unimer. In some embodiments, methods of the present disclosure provide an oligonucleotide which is a mipomersen unimer of configuration Rp. In some embodiments, methods of the present disclosure provide an oligonucleotide which is a mipomersen unimer of configuration Sp.

In some embodiments, methods of the present disclosure provide a chirally controlled oligonucleotide composition, i.e., an oligonucleotide composition that contains predetermined levels of individual oligonucleotide types. In some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises a plurality of oligonucleotide types. Example chirally controlled oligonucleotide compositions made in accordance with the present disclosure are described herein.

In some embodiments, methods of the present disclosure provide chirally pure mipomersen compositions with respect to the configuration of the linkage phosphorus. That is to say, in some embodiments, methods of the present disclosure provide compositions of mipomersen wherein mipomersen exists in the composition in the form of a single diastereomer with respect to the configuration of the linkage phosphorus.

In some embodiments, methods of the present disclosure provide chirally uniform mipomersen compositions with respect to the configuration of the linkage phosphorus. That is to say, in some embodiments, methods of the present disclosure provide compositions of mipomersen in which all nucleotide units therein have the same stereochemistry with respect to the configuration of the linkage phosphorus, e.g., all nucleotide units are of the Rp configuration at the linkage phosphorus or all nucleotide units are of the Sp configuration at the linkage phosphorus.

In some embodiments, a provided chirally controlled oligonucleotide is over 50% pure. In some embodiments, a provided chirally controlled oligonucleotide is over about 55% pure. In some embodiments, a provided chirally controlled oligonucleotide is over about 60% pure. In some embodiments, a provided chirally controlled oligonucleotide is over about 65% pure. In some embodiments, a provided chirally controlled oligonucleotide is over about 70% pure. In some embodiments, a provided chirally controlled oligonucleotide is over about 75% pure. In some embodiments, a provided chirally controlled oligonucleotide is over about 80% pure. In some embodiments, a provided chirally controlled oligonucleotide is over about 85% pure. In some embodiments, a provided chirally controlled oligonucleotide is over about 90% pure. In some embodiments, a provided chirally controlled oligonucleotide is over about 91% pure. In some embodiments, a provided chirally controlled oligonucleotide is over about 92% pure. In some embodiments, a provided chirally controlled oligonucleotide is over about 93% pure. In some embodiments, a provided chirally controlled oligonucleotide is over about 94% pure. In some embodiments, a provided chirally controlled oligonucleotide is over about 95% pure. In some embodiments, a provided chirally controlled oligonucleotide is over about 96% pure. In some embodiments, a provided chirally controlled oligonucleotide is over about 97% pure. In some embodiments, a provided chirally controlled oligonucleotide is over about 98% pure. In some embodiments, a provided chirally controlled oligonucleotide is over about 99% pure. In some embodiments, a provided chirally controlled oligonucleotide is over about 99.5% pure. In some embodiments, a provided chirally controlled oligonucleotide is over about 99.6% pure. In some embodiments, a provided chirally controlled oligonucleotide is over about 99.7% pure. In some embodiments, a provided chirally controlled oligonucleotide is over about 99.8% pure. In some embodiments, a provided chirally controlled oligonucleotide is over about 99.9% pure. In some embodiments, a provided chirally controlled oligonucleotide is over at least about 99% pure.

In some embodiments, a chirally controlled oligonucleotide composition is a composition designed to comprise a single oligonucleotide type. In certain embodiments, such compositions are about 50% diastereomerically pure. In some embodiments, such compositions are about 50% diastereomerically pure. In some embodiments, such compositions are about 50% diastereomerically pure. In some embodiments, such compositions are about 55% diastereomerically pure. In some embodiments, such compositions are about 60% diastereomerically pure. In some embodiments, such compositions are about 65% diastereomerically pure. In some embodiments, such compositions are about 70% diastereomerically pure. In some embodiments, such compositions are about 75% diastereomerically pure. In some embodiments, such compositions are about 80% diastereomerically pure. In some embodiments, such compositions are about 85% diastereomerically pure. In some embodiments, such compositions are about 90% diastereomerically pure. In some embodiments, such compositions are about 91% diastereomerically pure. In some embodiments, such compositions are about 92% diastereomerically pure. In some embodiments, such compositions are about 93% diastereomerically pure. In some embodiments, such compositions are about 94% diastereomerically pure. In some embodiments, such compositions are about 95% diastereomerically pure. In some embodiments, such compositions are about 96% diastereomerically pure. In some embodiments, such compositions are about 97% diastereomerically pure. In some embodiments, such compositions are about 98% diastereomerically pure. In some embodiments, such compositions are about 99% diastereomerically pure. In some embodiments, such compositions are about 99.5% diastereomerically pure. In some embodiments, such compositions are about 99.6% diastereomerically pure. In some embodiments, such compositions are about 99.7% diastereomerically pure. In some embodiments, such compositions are about 99.8% diastereomerically pure. In some embodiments, such compositions are about 99.9% diastereomerically pure. In some embodiments, such compositions are at least about 99% diastereomerically pure.

Among other things, the present disclosure recognizes the challenge of stereoselective (rather than stereorandom or racemic) preparation of oligonucleotides. Among other things, the present disclosure provides methods and reagents for stereoselective preparation of oligonucleotides comprising multiple (e.g., more than 5, 6, 7, 8, 9, or 10) internucleotidic linkages, and particularly for oligonucleotides comprising multiple (e.g., more than 5, 6, 7, 8, 9, or 10) chiral internucleotidic linkages. In some embodiments, in a stereorandom or racemic preparation of oligonucleotides, at least one chiral internucleotidic linkage is formed with less than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 90:10, 95:5, 96:4, 97:3, or 98:2 diastereoselectivity. In some embodiments, for a stereoselective or chirally controlled preparation of oligonucleotides, each chiral internucleotidic linkage is formed with greater than 95:5 diastereoselectivity. In some embodiments, for a stereoselective or chirally controlled preparation of oligonucleotides, each chiral internucleotidic linkage is formed with greater than 96:4 diastereoselectivity. In some embodiments, for a stereoselective or chirally controlled preparation of oligonucleotides, each chiral internucleotidic linkage is formed with greater than 97:3 diastereoselectivity. In some embodiments, for a stereoselective or chirally controlled preparation of oligonucleotides, each chiral internucleotidic linkage is formed with greater than 98:2 diastereoselectivity. In some embodiments, for a stereoselective or chirally controlled preparation of oligonucleotides, each chiral internucleotidic linkage is formed with greater than 99:1 diastereoselectivity. In some embodiments, diastereoselectivity of a chiral internucleotidic linkage in an oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage.

In some embodiments, a chirally controlled oligonucleotide composition is a composition designed to comprise multiple oligonucleotide types. In some embodiments, methods of the present disclosure allow for the generation of a library of chirally controlled oligonucleotides such that a pre-selected amount of any one or more chirally controlled oligonucleotide types can be mixed with any one or more other chirally controlled oligonucleotide types to create a chirally controlled oligonucleotide composition. In some embodiments, the pre-selected amount of an oligonucleotide type is a composition having any one of the above-described diastereomeric purities.

In some embodiments, the present disclosure provides methods for making a chirally controlled oligonucleotide comprising steps of:

(1) coupling;
(2) capping;
(3) modifying;
(4) deblocking; and
(5) repeating steps (1)-(4) until a desired length is achieved.

When describing the provided methods, the word "cycle" has its ordinary meaning as understood by a person of ordinary skill in the art. In some embodiments, one round of steps (1)-(4) is referred to as a cycle.

In some embodiments, the present disclosure provides methods for making chirally controlled oligonucleotide compositions, comprising steps of:

(a) providing an amount of a first chirally controlled oligonucleotide; and
(b) optionally providing an amount of one or more additional chirally controlled oligonucleotides.

In some embodiments, a first chirally controlled oligonucleotide is an oligonucleotide type, as described herein. In some embodiments, a one or more additional chirally controlled oligonucleotide is a one or more oligonucleotide type, as described herein.

One of skill in the relevant chemical and synthetic arts will recognize the degree of versatility and control over structural variation and stereochemical configuration of a provided oligonucleotide when synthesized using methods of the present disclosure. For instance, after a first cycle is complete, a subsequent cycle can be performed using a nucleotide unit individually selected for that subsequent cycle which, in some embodiments, comprises a nucleobase and/or a sugar that is different from the first cycle nucleobase and/or sugar. Likewise, the chiral auxiliary used in the coupling step of the subsequent cycle can be different from the chiral auxiliary used in the first cycle, such that the second cycle generates a phosphorus linkage of a different stereochemical configuration. In some embodiments, the stereochemistry of the linkage phosphorus in the newly formed internucleotidic linkage is controlled by using stereochemically pure phosphoramidites. Additionally, the modification reagent used in the modifying step of a subsequent cycle can be different from the modification reagent used in the first or former cycle. The cumulative effect of this iterative assembly approach is such that each component of a provided oligonucleotide can be structurally and configurationally tailored to a high degree. An additional advantage to this approach is that the step of capping minimizes the formation of "n−1" impurities that would otherwise make isolation of a provided oligonucleotide extremely challenging, and especially oligonucleotides of longer lengths.

In some embodiments, an example cycle of the method for making chirally controlled oligonucleotides is illustrated in example schemes described in the present disclosure. In some embodiments, an example cycle of the method for making chirally controlled oligonucleotides is illustrated in Scheme I. In some embodiments, 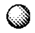 represents the solid support, and optionally a portion of the growing chirally controlled oligonucleotide attached to the solid support. The chiral auxiliary exemplified has the structure of formula 3-I:

Formula 3-I

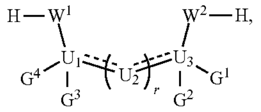

which is further described below. "Cap" is any chemical moiety introduced to the nitrogen atom by the capping step, and in some embodiments, is an amino protecting group. One of ordinary skill in the art understands that in the first cycle, there may be only one nucleoside attached to the solid support when started, and cycle exit can be performed optionally before deblocking. As understood by a person of skill in the art, $B^{PRO}$ is a protected base used in oligonucleotide synthesis. Each step of the above-depicted cycle of Scheme I is described further below.

Scheme I. Synthesis of chirally controlled oligonucleotide.

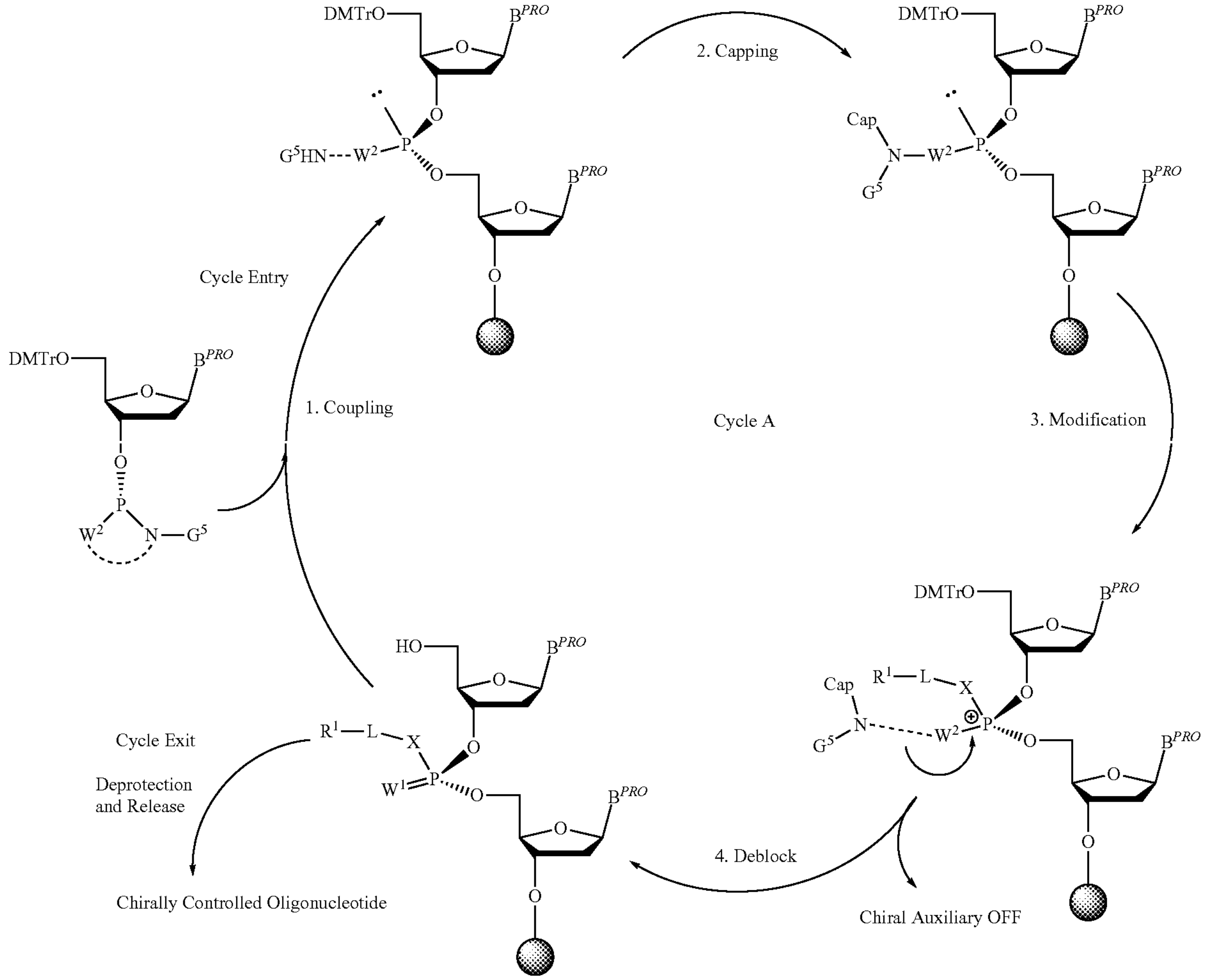

Synthesis on Solid Support

In some embodiments, the synthesis of a provided oligonucleotide is performed on solid phase. In some embodiments, reactive groups present on a solid support are protected. In some embodiments, reactive groups present on a solid support are unprotected. During oligonucleotide synthesis a solid support is treated with various reagents in several synthesis cycles to achieve the stepwise elongation of a growing oligonucleotide chain with individual nucleotide units. The nucleoside unit at the end of the chain which is directly linked to the solid support is termed "the first nucleoside" as used herein. A first nucleoside is bound to a solid support via a linker moiety, i.e. a diradical with covalent bonds between either of a CPG, a polymer or other solid support and a nucleoside. The linker stays intact during the synthesis cycles performed to assemble the oligonucleotide chain and is cleaved after the chain assembly to liberate the oligonucleotide from the support.

Solid supports for solid-phase nucleic acid synthesis include the supports described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262, 530; and Koster U.S. Pat. No. 4,725,677 (reissued as RE34, 069). In some embodiments, a solid phase is an organic polymer support. In some embodiments, a solid phase is an inorganic polymer support. In some embodiments, an organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In some embodiments, an inorganic polymer support is silica, alumina, controlled polyglass (CPG), which is a silica-gel support, or aminopropyl CPG. Other useful solid supports include fluorous solid supports (see e.g., WO/2005/070859), long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.*, 1983, 105, 661-663; G. R. Gough, M. J. Bruden and P. T. Gilham, *Tetrahedron Lett.*, 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis.

In addition to the attachment of a functional group to the membrane, the use of a linker or spacer group attached to the membrane is also used in some embodiments to minimize steric hindrance between the membrane and the synthesized chain.

Other suitable solid supports include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research,* 1991, 19, 1527), TentaGel Support—an aminopolyethyleneglycol derivatized support (see, e.g., Wright, et al., *Tetrahedron Lett.,* 1993, 34, 3373), and Poros-a copolymer of polystyrene/divinylbenzene.

Surface activated polymers have been demonstrated for use in synthesis of natural and modified nucleic acids and proteins on several solid supports mediums. A solid support material can be any polymer suitably uniform in porosity, having sufficient amine content, and sufficient flexibility to undergo any attendant manipulations without losing integrity. Examples of suitable selected materials include nylon, polypropylene, polyester, polytetrafluoroethylene, polystyrene, polycarbonate, and nitrocellulose. Other materials can serve as a solid support, depending on the design of the investigator. In consideration of some designs, for example, a coated metal, in particular gold or platinum can be selected (see e.g., US publication No. 20010055761). In one embodiment of oligonucleotide synthesis, for example, a nucleoside is anchored to a solid support which is functionalized with hydroxyl or amino residues. Alternatively, a solid support is derivatized to provide an acid labile trialkoxytrityl group, such as a trimethoxytrityl group (TMT). Without being bound by theory, it is expected that the presence of a trialkoxytrityl protecting group will permit initial detritylation under conditions commonly used on DNA synthesizers. For a faster release of oligonucleotide material in solution with aqueous ammonia, a diglycoate linker is optionally introduced onto the support.

In some embodiments, a provided oligonucleotide alternatively is synthesized from the 5' to 3' direction. In some embodiments, a nucleic acid is attached to a solid support through its 5' end of the growing nucleic acid, thereby presenting its 3' group for reaction, i.e. using 5'-nucleoside phosphoramidites or in enzymatic reaction (e.g. ligation and polymerization using nucleoside 5'-triphosphates). When considering the 5' to 3' synthesis the iterative steps of the present disclosure remain unchanged (i.e. capping and modification on the chiral phosphorus).

Linking Moiety

A linking moiety or linker is optionally used to connect a solid support to a compound comprising a free nucleophilic moiety. Suitable linkers are known such as short molecules which serve to connect a solid support to functional groups (e.g., hydroxyl groups) of initial nucleosides molecules in solid phase synthetic techniques. In some embodiments, the linking moiety is a succinamic acid linker, or a succinate linker (—CO—$CH_2$—$CH_2$—CO—), or an oxalyl linker (—CO—CO—). In some embodiments, the linking moiety and the nucleoside are bonded together through an ester bond. In some embodiments, a linking moiety and a nucleoside are bonded together through an amide bond. In some embodiments, a linking moiety connects a nucleoside to another nucleotide or nucleic acid. Suitable linkers are disclosed in, for example, *Oligonucleotides And Analogues A Practical Approach*, Ekstein, F. Ed., IRL Press, N.Y., 1991, Chapter 1 and Solid-Phase Supports for Oligonucleotide Synthesis, Pon, R. T., *Curr. Prot. Nucleic Acid Chem.,* 2000, 3.1.1-3.1.28.

A linker moiety is used to connect a compound comprising a free nucleophilic moiety to another nucleoside, nucleotide, or nucleic acid. In some embodiments, a linking moiety is a phosphodiester linkage. In some embodiments, a linking moiety is an H-phosphonate moiety. In some embodiments, a linking moiety is a modified phosphorus linkage as described herein. In some embodiments, a universal linker (UnyLinker) is used to attached the oligonucleotide to the solid support (Ravikumar et al., *Org. Process Res. Dev.,* 2008, 12 (3), 399-410). In some embodiments, other universal linkers are used (Pon, R. T., *Curr. Prot. Nucleic Acid Chem.,* 2000, 3.1.1-3.1.28). In some embodiments, various orthogonal linkers (such as disulfide linkers) are used (Pon, R. T., *Curr. Prot. Nucleic Acid Chem.,* 2000, 3.1.1-3.1.28).

Among other things, the present disclosure recognizes that a linker can be chosen or designed to be compatible with a set of reaction conditions employed in oligonucleotide synthesis. In some embodiments, to avoid degradation of oligonucleotides and to avoid desulfurization, auxiliary groups are selectively removed before de-protection. In some embodiments, DPSE group can selectively be removed by $F^-$ ions. In some embodiments, the present disclosure provides linkers that are stable under a DPSE de-protection condition, e.g., 0.1 M TBAF in MeCN, 0.5M HF-$Et_3N$ in THF or MeCN, etc. In some embodiments, a provided linker is the SP linker. In some embodiments, the present disclosure demonstrates that the SP linker is stable under a DPSE de-protection condition, e.g., 0.1M TBAF in MeCN, 0.5M HF-$Et_3N$ in THF or MeCN, etc.; they are also stable, e.g., under anhydrous basic conditions, such as om1M DBU in MeCN.

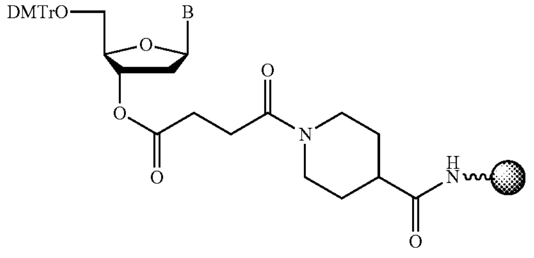

succinyl-piperidine (SP) linker

In some embodiments, an example linker is:

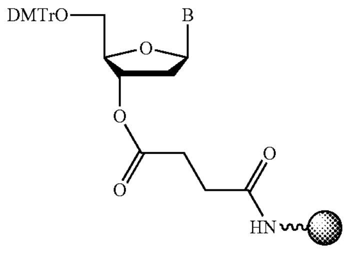

succinyl linker

-continued

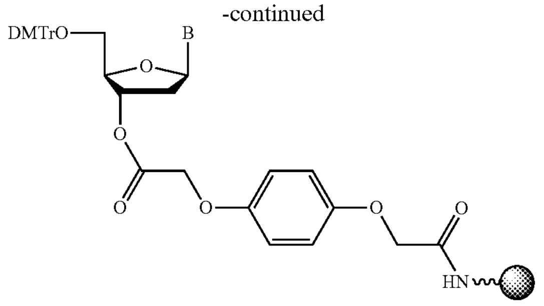

Q-linker

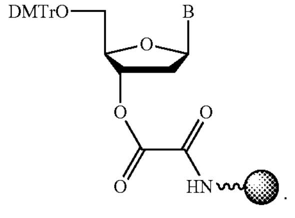

oxalyl linker

In some embodiments, the succinyl linker, Q-linker or oxalyl linker is not stable to one or more DPSE-deprotection conditions using $F^-$.

General Conditions—Solvents for Synthesis

Syntheses of provided oligonucleotides are generally performed in aprotic organic solvents. In some embodiments, a solvent is a nitrile solvent such as, e.g., acetonitrile. In some embodiments, a solvent is a basic amine solvent such as, e.g., pyridine. In some embodiments, a solvent is an ethereal solvent such as, e.g., tetrahydrofuran. In some embodiments, a solvent is a halogenated hydrocarbon such as, e.g., dichloromethane. In some embodiments, a mixture of solvents is used. In certain embodiments a solvent is a mixture of any one or more of the above-described classes of solvents.

In some embodiments, when an aprotic organic solvent is not basic, a base is present in the reacting step. In some embodiments where a base is present, the base is an amine base such as, e.g., pyridine, quinoline, or N,N-dimethylaniline. Example other amine bases include pyrrolidine, piperidine, N-methyl pyrrolidine, pyridine, quinoline, N,N-dimethylaminopyridine (DMAP), or N,N-dimethylaniline.

In some embodiments, a base is other than an amine base.

In some embodiments, an aprotic organic solvent is anhydrous. In some embodiments, an anhydrous aprotic organic solvent is freshly distilled. In some embodiments, a freshly distilled anhydrous aprotic organic solvent is a basic amine solvent such as, e.g., pyridine. In some embodiments, a freshly distilled anhydrous aprotic organic solvent is an ethereal solvent such as, e.g., tetrahydrofuran. In some embodiments, a freshly distilled anhydrous aprotic organic solvent is a nitrile solvent such as, e.g., acetonitrile.

Chiral Reagent/Chiral Auxiliary

In some embodiments, chiral reagents are used to confer stereoselectivity in the production of chirally controlled olignucleotides. Many different chiral reagents, also referred to by those of skill in the art and herein as chiral auxiliaries, may be used in accordance with methods of the present disclosure. Example such chiral reagents are described herein and in Wada I, II and III, referenced above. In certain embodiments, a chiral reagent is as described by Wada I. In some embodiments, a chiral reagent for use in accordance with the methods of the present disclosure are of Formula 3-I, below:

Formula 3-I

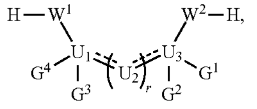

wherein $W^1$ and $W^2$ are any of —O—, —S—, or —$NG^5$-, $U_1$ and $U_3$ are carbon atoms which are bonded to $U_2$ if present, or to each other if r is 0, via a single, double or triple bond. $U_2$ is —C—, -$CG^8$-, -$CG^8G^8$-, —$NG^8$-, —N—, —O—, or —S— where r is an integer of 0 to 5 and no more than two heteroatoms are adjacent. When any one of $U_2$ is C, a triple bond must be formed between a second instance of $U_2$, which is C, or to one of $U_1$ or $U_3$. Similarly, when any one of $U_2$ is $CG^8$, a double bond is formed between a second instance of $U_2$ which is -$CG^8$- or —N—, or to one of $U_1$ or $U_3$. In some embodiments, —$U_1(G_3G_4)$—$(U_2)_r$—$U_3(G_1G_2)$- is -$CG^3G^4$-$CG^1G^2$-. In some embodiments, —$U_1$—$(U_2)_r$—$U_3$— is -$CG^3$═$CG^1$-. In some embodiments, —$U_1$—$(U_2)_r$—$U_3$— is —C≡C—. In some embodiments, —$U_1$—$(U_2)_r$—$U_3$— is -$CG^3$═$CG^8$-$CG^1G^2$-. In some embodiments, —$U_1$—$(U_2)_r$—$U_3$— is -$CG^3G^4$-O-$CG^1G^2$-. In some embodiments, —$U_1$—$(U_2)_r$—$U_3$— is -$CG^3G^4$-$NG^8$-$CG^1G^2$-. In some embodiments, —$U_1$—$(U_2)_r$—$U_3$— is -$CG^3G^4$-N-$CG^2$-. In some embodiments, —$U_1$—$(U_2)_r$—$U_3$— is -$CG^3G^4$-N═C $G^8$-$CG^1G^2$.

As defined herein, $G^1$, $G^2$, $G^3$, $G^4$, $G^5$, and $G^8$ are independently hydrogen, or an optionally substituted group selected from alkyl, aralkyl, cycloalkyl, cycloalkylalkyl, heterocyclyl, heteroaryl, and aryl; or two of $G^1$, $G^2$, $G^3$, $G^4$, and $G^5$ are $G^6$ (taken together to form an optionally substituted, saturated, partially unsaturated or unsaturated carbocyclic or heteroatom-containing ring of up to about 20 ring atoms which is monocyclic or polycyclic, and is fused or unfused). In some embodiments, a ring so formed is substituted by oxo, thioxo, alkyl, alkenyl, alkynyl, heteroaryl, or aryl moieties. In some embodiments, when a ring formed by taking two $G^6$ together is substituted, it is substituted by a moiety which is bulky enough to confer stereoselectivity during the reaction.

In some embodiments, a ring formed by taking two of $G^6$ together is optionally substituted cyclopentyl, pyrrolyl, cyclopropyl, cyclohexenyl, cyclopentenyl, tetrahydropyranyl, or piperazinyl. In some embodiments, a ring formed by taking two of $G^6$ together is optionally substituted cyclopentyl, pyrrolyl, cyclopropyl, cyclohexenyl, cyclopentenyl, tetrahydropyranyl, pyrrolidinyl, or piperazinyl.

In some embodiments, $G^1$ is optionally substituted phenyl. In some embodiments, $G^1$ is phenyl. In some embodiments, $G^2$ is methyl or hydrogen. In some embodiments, $G^1$ is optionally substituted phenyl and $G^2$ is methyl. In some embodiments, $G^1$ is phenyl and $G^2$ is methyl.

In some embodiments, r is 0.

In some embodiments, $W^1$ is —$NG^5$-. In some embodiments, one of $G^3$ and $G^4$ is taken together with $G^5$ to form an optionally substituted pyrrolidinyl ring. In some embodiments, one of $G^3$ and $G^4$ is taken together with $G^5$ to form a pyrrolidinyl ring.

In some embodiments, $W^2$ is —O—.

In some embodiments, a chiral reagent is a compound of Formula 3-AA:

Formula 3-AA

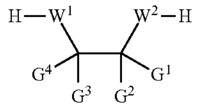

wherein each variable is independently as defined above and described herein.

In some embodiments of Formula 3AA, $W^1$ and $W^2$ are independently —$NG^5$-, —O—, or —S—; $G^1$, $G^2$, $G^3$, $G^4$, and $G^5$ are independently hydrogen, or an optionally substituted group selected from alkyl, aralkyl, cycloalkyl, cycloalkylalkyl, heterocyclyl, heteroaryl, or aryl; or two of $G^1$, $G^2$, $G^3$, $G^4$, and $G^5$ are $G^6$ (taken together to form an optionally substituted saturated, partially unsaturated or unsaturated carbocyclic or heteroatom-containing ring of up to about 20 ring atoms which is monocyclic or polycyclic, fused or unfused), and no more than four of $G^1$, $G^2$, $G^3$, $G^4$, and $G^5$ are $G^6$. Similarly to the compounds of Formula 3-I, any of $G^1$, $G^2$, $G^3$, $G^4$, or $G^5$ are optionally substituted by oxo, thioxo, alkyl, alkenyl, alkynyl, heteroaryl, or aryl moieties. In some embodiments, such substitution induces stereoselectivity in chirally controlled oligonucleotide production.

In some embodiments, a provided chiral reagent has the structure of

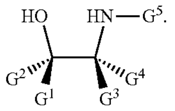

In some embodiments, a provided chiral reagent has the structure of

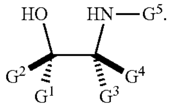

In some embodiments, a provided chiral reagent has the structure of

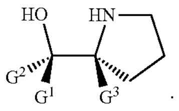

In some embodiments, a provided chiral reagent has the structure of

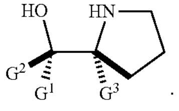

In some embodiments, a provided chiral reagent has the structure of

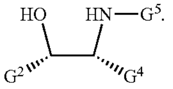

In some embodiments, a provided chiral reagent has the structure of

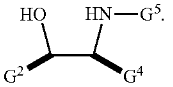

In some embodiments, a provided chiral reagent has the structure of

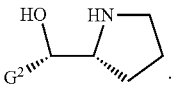

In some embodiments, a provided chiral reagent has the structure of

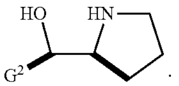

In some embodiments, $W^1$ is —$NG^5$, $W^2$ is O, each of $G^1$ and $G^3$ is independently hydrogen or an optionally substituted group selected from $C_1$-10 aliphatic, heterocyclyl, heteroaryl and aryl, $G^2$ is —$C(R)_2Si(R)_3$, and $G^4$ and $G^5$ are taken together to form an optionally substituted saturated, partially unsaturated or unsaturated heteroatom-containing ring of up to about 20 ring atoms which is monocyclic or polycyclic, fused or unfused. In some embodiments, each R is independently hydrogen, or an optionally substituted group selected from $C_1$-$C_6$ aliphatic, carbocyclyl, aryl, heteroaryl, and heterocyclyl. In some embodiments, $G^2$ is —$C(R)_2Si(R)_3$, wherein —$C(R)_2$— is optionally substituted —$CH_2$—, and each R of —$Si(R)_3$ is independently an optionally substituted group selected from $C_{1-10}$ aliphatic, heterocyclyl, heteroaryl and aryl. In some embodiments, at least one R of —$Si(R)_3$ is independently optionally substituted $C_{1-10}$ alkyl. In some embodiments, at least one R of —$Si(R)_3$ is independently optionally substituted phenyl. In some embodiments, one R of —$Si(R)_3$ is independently optionally substituted phenyl, and each of the other two R is independently optionally substituted $C_{1-10}$ alkyl. In some embodiments, one R of —$Si(R)_3$ is independently optionally substituted $C_{1-10}$ alkyl, and each of the other two R is independently optionally substituted phenyl. In some embodiments, $G^2$ is optionally substituted —$CH_2Si(Ph)(Me)_2$. In some embodiments, $G^2$ is optionally substituted —$CH_2Si(Me)(Ph)_2$. In some embodiments, $G^2$ is —$CH_2Si(Me)(Ph)_2$. In some embodiments, $G^4$ and $G^5$ are taken together to form an optionally substituted saturated 5-6 membered ring containing one nitrogen atom (to which $G^5$ is attached). In some embodiments, $G^4$ and $G^5$ are taken together to form an optionally substituted saturated 5-membered ring containing one nitrogen atom. In some embodiments, $G^1$ is hydrogen. In some embodiments, $G^3$ is hydrogen. In some embodiments, both $G^1$ and $G^3$ are hydrogen.

In some embodiments, a chiral reagent has one of the following formulae:

Formulae 3-AB

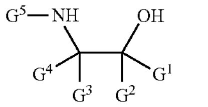

3-BB

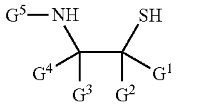

3-CC

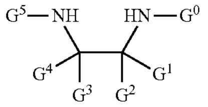

3-DD

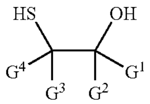

3-EE

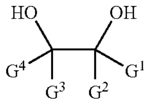

3-FF

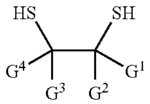

In some embodiments, a chiral reagent is an aminoalcohol. In some embodiments, a chiral reagent is an aminothiol. In some embodiments, a chiral reagent is an aminophenol. In some embodiments, a chiral reagent is (S)- and (R)-2-methylamino-1-phenylethanol, (1R, 2S)-ephedrine, or (1R, 2S)-2-methylamino-1,2-diphenylethanol.

In some embodiments of the disclosure, a chiral reagent is a compound of one of the following formulae:

Formula O

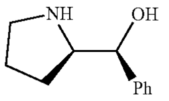

Formula P

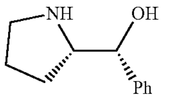

Formula Q

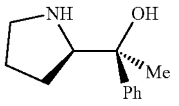

Formula R

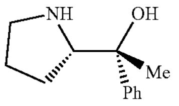

-continued

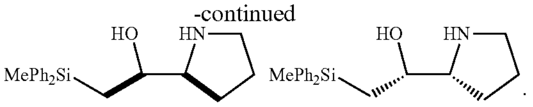

DPSE

As demonstrated herein, when used for preparing a chiral internucleotidic linkage, to obtain stereoselectivity generally stereochemically pure chiral reagents are utilized. Among other things, the present disclosure provides stereochemically pure chiral reagents, including those having structures described.

The choice of chiral reagent, for example, the isomer represented by Formula Q or its stereoisomer, Formula R, permits specific control of chirality at a linkage phosphorus. Thus, either an Rp or Sp configuration can be selected in each synthetic cycle, permitting control of the overall three dimensional structure of a chirally controlled oligonucleotide. In some embodiments, a chirally controlled oligonucleotide has all Rp stereocenters. In some embodiments of the disclosure, a chirally controlled oligonucleotide has all Sp stereocenters. In some embodiments of the disclosure, each linkage phosphorus in the chirally controlled oligonucleotide is independently Rp or Sp. In some embodiments of the disclosure, each linkage phosphorus in the chirally controlled oligonucleotide is independently Rp or Sp, and at least one is Rp and at least one is Sp. In some embodiments, the selection of Rp and Sp centers is made to confer a specific three dimensional superstructure to a chirally controlled oligonucleotide. Example such selections are described in further detail herein.

In some embodiments, a chiral reagent for use in accordance with the present disclosure is selected for its ability to be removed at a particular step in the above-depicted cycle. For example, in some embodiments it is desirable to remove a chiral reagent during the step of modifying the linkage phosphorus. In some embodiments, it is desirable to remove a chiral reagent before the step of modifying the linkage phosphorus. In some embodiments, it is desirable to remove a chiral reagent after the step of modifying the linkage phosphorus. In some embodiments, it is desirable to remove a chiral reagent after a first coupling step has occurred but before a second coupling step has occurred, such that a chiral reagent is not present on the growing oligonucleotide during the second coupling (and likewise for additional subsequent coupling steps). In some embodiments, a chiral reagent is removed during the “deblock” reaction that occurs after modification of the linkage phosphorus but before a subsequent cycle begins. Example methods and reagents for removal are described herein.

In some embodiments, removal of chiral auxiliary is achieved when performing the modification and/or deblocking step, as illustrated in Scheme I. It can be beneficial to combine chiral auxiliary removal together with other transformations, such as modification and deblocking. A person of ordinary skill in the art would appreciate that the saved steps/transformation could improve the overall efficiency of synthesis, for instance, with respect to yield and product purity, especially for longer oligonucleotides. One example wherein the chiral auxiliary is removed during modification and/or deblocking is illustrated in Scheme I.

In some embodiments, a chiral reagent for use in accordance with methods of the present disclosure is characterized in that it is removable under certain conditions. For instance, in some embodiments, a chiral reagent is selected for its ability to be removed under acidic conditions. In certain embodiments, a chiral reagent is selected for its ability to be removed under mildly acidic conditions. In certain embodiments, a chiral reagent is selected for its ability to be removed by way of an E1 elimination reaction (e.g., removal occurs due to the formation of a cation intermediate on the chiral reagent under acidic conditions, causing the chiral reagent to cleave from the oligonucleotide). In some embodiments, a chiral reagent is characterized in that it has a structure recognized as being able to accommodate or facilitate an E1 elimination reaction. One of skill in the relevant arts will appreciate which structures would be envisaged as being prone toward undergoing such elimination reactions.

In some embodiments, a chiral reagent is selected for its ability to be removed with a nucleophile. In some embodiments, a chiral reagent is selected for its ability to be removed with an amine nucleophile. In some embodiments, a chiral reagent is selected for its ability to be removed with a nucleophile other than an amine.

In some embodiments, a chiral reagent is selected for its ability to be removed with a base. In some embodiments, a chiral reagent is selected for its ability to be removed with an amine. In some embodiments, a chiral reagent is selected for its ability to be removed with a base other than an amine.

Additional chiral auxiliaries and their use can be found in e.g., Wada I (JP4348077; WO2005/014609; WO2005/092909), Wada II (WO2010/064146), Wada III (WO2012/039448), Chiral Control (WO2010/064146), etc.

Activation

An achiral H-phosphonate moiety is treated with the first activating reagent to form the first intermediate. In one embodiment, the first activating reagent is added to the reaction mixture during the condensation step. Use of the first activating reagent is dependent on reaction conditions such as solvents that are used for the reaction. Examples of the first activating reagent are phosgene, trichloromethyl chloroformate, bis(trichloromethyl)carbonate (BTC), oxalyl chloride, $Ph_3PCl_2$, $(PhO)_3PCl_2$, N,N'-bis(2-oxo-3-oxazolidinyl)phosphinic chloride (BopCl), 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP).

The example of achiral H-phosphonate moiety is a compound shown in the above Scheme. DBU represents 1,8-diazabicyclo[5.4.0]undec-7-ene. $H^+DBU$ may be, for example, ammonium ion, alkylammonium ion, heteroaromatic iminium ion, or heterocyclic iminium ion, any of which is primary, secondary, tertiary or quaternary, or a monovalent metal ion.

Reacting with Chiral Reagent

After the first activation step, the activated achiral H-phosphonate moiety reacts with a chiral reagent, which is represented by formula (Z-I) or (Z-I'), to form a chiral intermediate of formula (Z-Va), (Z-Vb), (Z-Va'), or (Z-Vb').

Stereospecific Condensation Step

A chiral intermediate of Formula Z-Va ((Z-Vb), (Z-Va'), or (Z-Vb')) is treated with the second activating reagent and a nucleoside to form a condensed intermediate. The nucleoside may be on solid support. Examples of the second activating reagent are 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole (ETT), 5-benzylthiotetrazole (BTT), 5-(4-nitrophenyl)tetrazole, N-cyanomethylpyrrolidinium triflate (CMPT), N-cyanomethylpiperidinium triflate, N-cyanomethyldimethylammonium triflate. A chiral intermediate of Formula Z-Va ((Z-Vb), (Z-Va'), or (Z-Vb')) may be isolated as a monomer. Usually, the chiral intermediate of Z-Va ((Z-Vb), (Z-Va'), or (Z-Vb')) is not isolated and undergoes a reaction in the same pot with a nucleoside or modified nucleoside to provide a chiral phosphite compound, a condensed intermediate. In other embodiments, when the method is performed via solid phase synthesis, the solid support comprising the compound is filtered away from side products, impurities, and/or reagents.

Capping Step

If the final nucleic acid is larger than a dimer, the unreacted —OH moiety is capped with a blocking group and the chiral auxiliary in the compound may also be capped with a blocking group to form a capped condensed intermediate. If the final nucleic acid is a dimer, then the capping step is not necessary.

Modifying Step

The compound is modified by reaction with an electrophile. The capped condensed intermediate may be executed modifying step. In some embodiments, the modifying step is performed using a sulfur electrophile, a selenium electrophile or a boronating agent. Examples of modifying steps are step of oxidation and sulfurization.

In some embodiments of the method, the sulfur electrophile is a compound having one of the following formulas:

$S_8$(Formula Z-B), $Z^{z1}$—S—S—$Z^{z2}$, or $Z^{z1}$—S—$V^z$—$Z^{z2}$;

wherein $Z^{z1}$ and $Z^{z2}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{z1}$ and $Z^{z2}$ are taken together to form a 3 to 8 membered alicyclic or heterocyclic ring, which may be substituted or unsubstituted; $V^z$ is $SO_2$, O, or $NR^f$; and $R^f$ is hydrogen, alkyl, alkenyl, alkynyl, or aryl.

In some embodiments of the method, the sulfur electrophile is a compound of following Formulae Z-A, Z-B, Z-C, Z-D, Z-E, or Z-F:

Formula Z-A

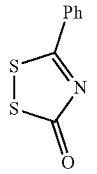

Formula Z-B $S_8$

Formula Z-C

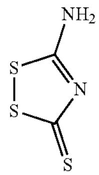

Formula Z-D

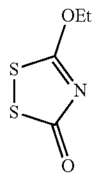

-continued

Formula Z-E

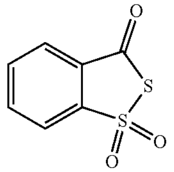

Formula Z-F

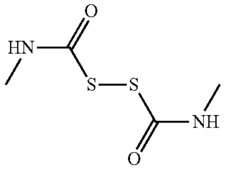

In some embodiments, a sulfurization reagent is 3-phenyl-1,2,4-dithiazolin-5-one.

In some embodiments, the selenium electrophile is a compound having one of the following formulae:

Se(Formula Z-G), $Z^{z3}$—Se—Se—$Z^{z4}$, or $Z^{z3}$—Se—$V^z$—$Z^{z4}$;

wherein $Z^{z3}$ and $Z^{z4}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{z3}$ and $Z^{z4}$ are taken together to form a 3 to 8 membered alicyclic or heterocyclic ring, which may be substituted or unsubstituted; $V^z$ is $SO_2$, S, O, or $NR^f$; and $R^f$ is hydrogen, alkyl, alkenyl, alkynyl, or aryl.

In some embodiments, the selenium electrophile is a compound of Formula Z-G, Z-H, Z-I, Z-J, Z-K, or Z-L.

Se Formula Z-G

KSeCN Formula Z-H

Formula Z-I

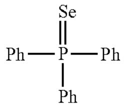

Formula Z-J

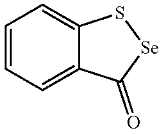

Formula Z-K

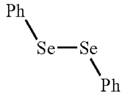

Formula Z-L

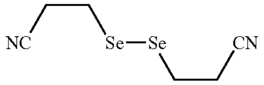

In some embodiments, the boronating agent is borane-N,N-diisopropylethylamine ($BH_3$ DIPEA), borane-pyridine ($BH_3$ Py), borane-2-chloropyridine ($BH_3$ CPy), borane-aniline ($BH_3$ An), borane-tetrahydrofiirane ($BH_3$ THF), or borane-dimethylsulfide ($BH_3$ $Me_2S$).

In some embodiments, after the modifying step, a chiral auxiliary group falls off from the growing oligonucleotide chain. In some embodiments, after the modifying step, a chiral auxiliary group remains connected to the internucleotidic phosphorus atom.

In some embodiments of the method, the modifying step is an oxidation step. In some embodiments of the method, the modifying step is an oxidation step using similar conditions as described above in this application. In some embodiments, an oxidation step is as disclosed in, e.g., JP 2010-265304 A and WO2010/064146.

Chain Elongation Cycle and De-Protection Step

The capped condensed intermediate is deblocked to remove the blocking group at the 5'-end of the growing nucleic acid chain to provide a compound. The compound is optionally allowed to re-enter the chain elongation cycle to form a condensed intermediate, a capped condensed intermediate, a modified capped condensed intermediate, and a 5'-deprotected modified capped intermediate. Following at least one round of chain elongation cycle, the 5'-deprotected modified capped intermediate is further deblocked by removal of the chiral auxiliary ligand and other protecting groups for, e.g., nucleobase, modified nucleobase, sugar and modified sugar protecting groups, to provide a nucleic acid. In other embodiments, the nucleoside comprising a 5'-OH moiety is an intermediate from a previous chain elongation cycle as described herein. In yet other embodiments, the nucleoside comprising a 5'-OH moiety is an intermediate obtained from another known nucleic acid synthetic method. In embodiments where a solid support is used, the phosphorus-atom modified nucleic acid is then cleaved from the solid support. In certain embodiments, the nucleic acids is left attached on the solid support for purification purposes and then cleaved from the solid support following purification.

In yet other embodiments, the nucleoside comprising a 5'-OH moiety is an intermediate obtained from another known nucleic acid synthetic method. In yet other embodiments, the nucleoside comprising a 5'-OH moiety is an intermediate obtained from another known nucleic acid synthetic method as described in this application. In yet other embodiments, the nucleoside comprising a 5'-OH moiety is an intermediate obtained from another known nucleic acid synthetic method comprising one or more cycles illustrated in Scheme I. In yet other embodiments, the nucleoside comprising a 5'-OH moiety is an intermediate obtained from another known nucleic acid synthetic method comprising one or more cycles illustrated in Scheme I-b, I-c or I-d.

In some embodiments, the present disclosure provides oligonucleotide synthesis methods that use stable and commercially available materials as starting materials. In some embodiments, the present disclosure provides oligonucleotide synthesis methods to produce stereocontrolled phosphorus atom-modified oligonucleotide derivatives using an achiral starting material.

In some embodiments, the method of the present disclosure does not cause degradations under the de-protection steps. Further the method does not require special capping agents to produce phosphorus atom-modified oligonucleotide derivatives.

Condensing Reagent

Condensing reagents ($C_R$) useful in accordance with methods of the present disclosure are of any one of the following general formulae:

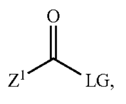

$C_R1$

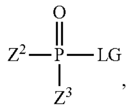

$C_R2$

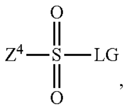

$C_R3$

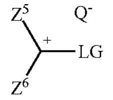

$C_R4$ or

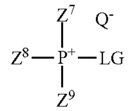

$C_R5$ wherein $Z^1$, $Z^2$, $Z^3$, $Z^4$, $Z^5$, $Z^6$, $Z^7$, $Z^8$, and $Z^9$ are independently optionally substituted group selected from alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^2$ and $Z^3$, $Z^5$ and $Z^6$, $Z^7$ and $Z^8$, $Z^8$ and $Z^9$, $Z^9$ and $Z^7$, or $Z^7$ and $Z^8$ and $Z^9$ are taken together to form a 3 to 20 membered alicyclic or heterocyclic ring; $Q^-$ is a counter anion; and LG is a leaving group.

In some embodiments, a counter ion of a condensing reagent $C_R$ is $C_1^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$. In some embodiments, a leaving group of a condensing reagent $C_R$ is F, Cl, Br, I, 3-nitro-1,2,4-triazole, imidazole, alkyltriazole, tetrazole, pentafluorobenzene, or 1-hydroxybenzotriazole.

Examples of condensing reagents used in accordance with methods of the present disclosure include, but are not limited to, pentafluorobenzoyl chloride, carbonyldiimidazole (CDI), 1-mesitylenesulfonyl-3-nitrotriazole (MSNT), 1-ethyl-3-(3'-dimethylaminopropyl)carbodiimide hydrochloride (EDCI-HCl), benzotriazole-1-yloxytris(dimethylamino)phosphonium hexafluorophosphate (PyBOP), N,N'-bis(2-oxo-3-oxazolidinyl)phosphinic chloride (BopCl), 2-(1H-7-azabenzotriazol-1-yl)-1,1,3,3-tetramethyluronium hexafluorophosphate (HATU), and O-benzotriazole-N,N,N',N'-tetramethyluronium hexafluorophosphate (HBTU), DIPCDI; N,N'-bis(2-oxo-3-oxazolidinyl)phosphinic bromide (BopBr), 1,3-dimethyl-2-(3-nitro-1,2,4-triazol-1-yl)-2-pyrrolidin-1-yl-1,3,2-diazaphospholidinium hexafluorophosphate (MNTP), 3-nitro-1,2,4-triazol-1-yl-tris(pyrrolidin-1-yl)phosphonium hexafluorophosphate (PyNTP), bromotripyrrolidinophosphonium hexafluorophosphate (PyBrOP); O-(benzotriazol-1-yl)-N,N,N',N'-tetramethyluronium tetrafluoroborate (TBTU); and tetramethylfluoroformamidinium hexafluorophosphate (TFFH). In certain embodiments, a counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$.

In some embodiments, a condensing reagent is 1-(2,4,6-triisopropylbenzenesulfonyl)-5-(pyridin-2-yl) tetrazolide, pivaloyl chloride, bromotrispyrrolidinophosphonium hexafluorophosphate, N,N'-bis(2-oxo-3-oxazolidinyl) phosphinic chloride (BopCl), or 2-chloro-5,5-dimethyl-2-oxo-1,3,2-dioxaphosphinane. In some embodiment, a condensing reagent is N,N'-bis(2-oxo-3-oxazolidinyl)phosphinic chloride (BopCl). In some embodiments, a condensing reagent is selected from those described in WO/2006/066260).

In some embodiments, a condensing reagent is 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP):

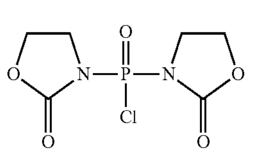

BopCl

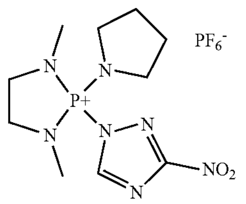

MNTP

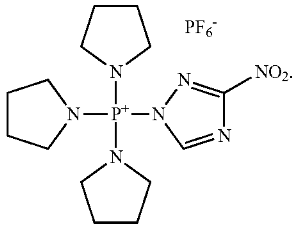

PyNTP

Selection of Base and Sugar of Nucleoside Coupling Partner

As described herein, nucleoside coupling partners for use in accordance with methods of the present disclosure can be the same as one another or can be different from one another. In some embodiments, nucleoside coupling partners for use in the synthesis of a provided oligonucleotide are of the same structure and/or stereochemical configuration as one another. In some embodiments, each nucleoside coupling partner for use in the synthesis of a provided oligonucleotide is not of the same structure and/or stereochemical configuration as certain other nucleoside coupling partners of the oligonucleotide. Example nucleobases and sugars for use in accordance with methods of the present disclosure are described herein. One of skill in the relevant chemical and synthetic arts will recognize that any combination of nucleobases and sugars described herein are contemplated for use in accordance with methods of the present disclosure.

Coupling Step

Example coupling procedures and chiral reagents and condensing reagents for use in accordance with the present disclosure are outlined in, inter alia, Wada I (JP4348077; WO2005/014609; WO2005/092909), Wada II (WO2010/064146), Wada III (WO2012/039448), and Chiral Control (WO2010/064146). Chiral nucleoside coupling partners for use in accordance with the present disclosure are also referred to herein as "Wada amidites." In some embodiments, a coupling partner has the structure of

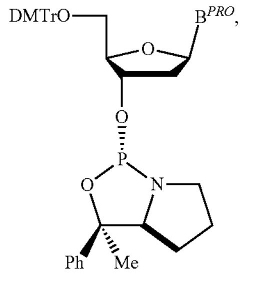

wherein $B^{PRO}$ is a protected nucleobase.

In some embodiments, a coupling partner has the structure of

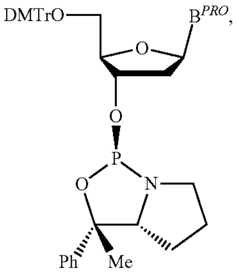

wherein $B^{PRO}$ is a protected nucleobase. In some embodiments, a coupling partner has the structure of

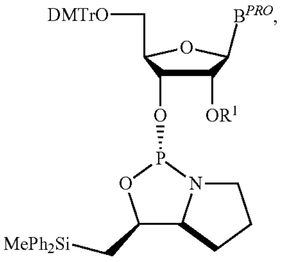

wherein $B^{PRO}$ is a protected nucleobase, and $R^1$ is as defined and described herein. In some embodiments, a coupling partner has the structure of

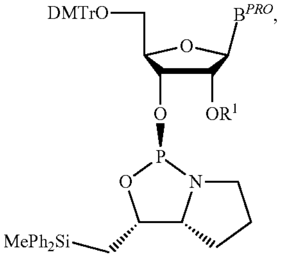

wherein $B^{PRO}$ is a protected nucleobase, and $R^1$ is as defined and described herein. In some embodiments, $R^1$ is optionally substituted $C_{1-6}$ alkyl. In some embodiments, $R^1$ is Me.

Example chiral phosphoramidites as coupling partner are depicted below:

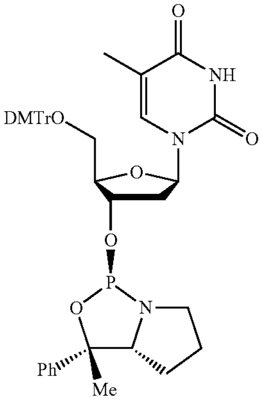

-continued

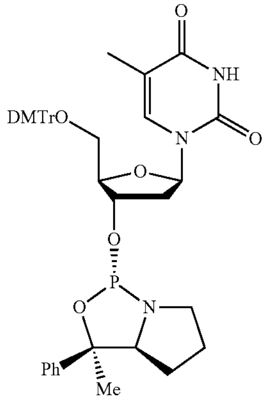

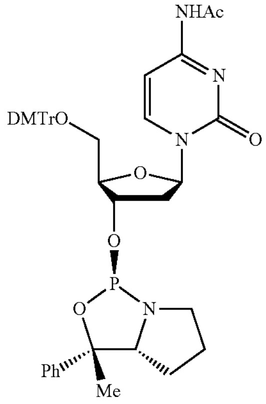

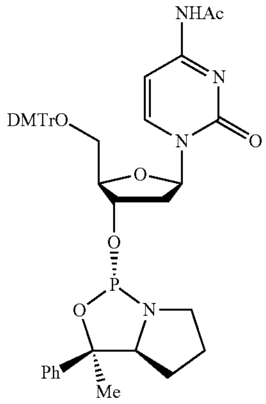

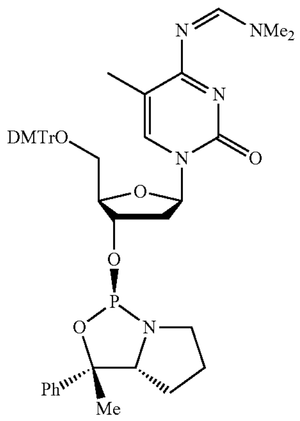

-continued
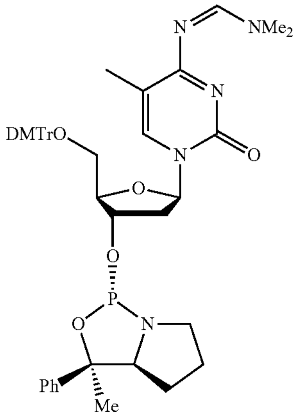
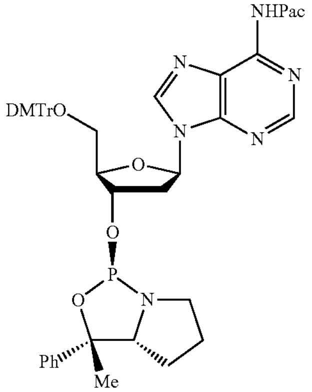
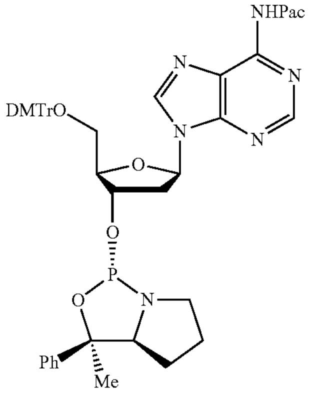
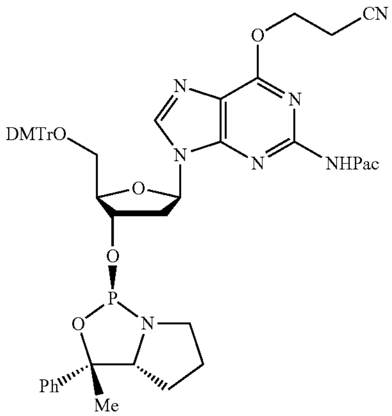
-continued
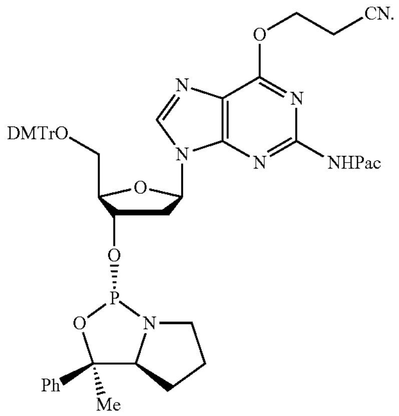
Additional examples are described in Chiral Control (WO2010/064146).
One of the methods used for synthesizing the coupling partner is depicted in Scheme II, below.
Scheme II. Example synthesis of coupling partner.
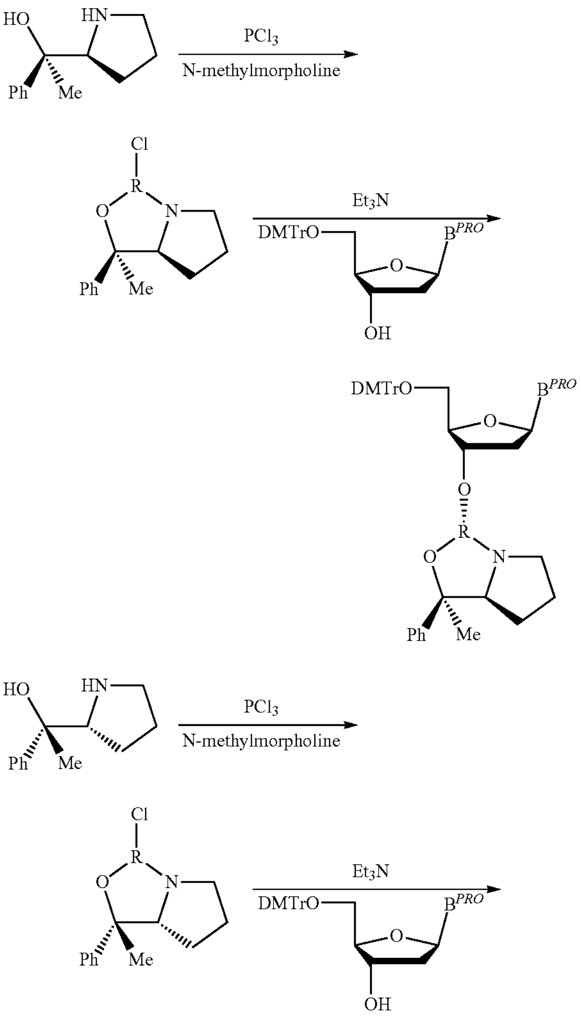

-continued

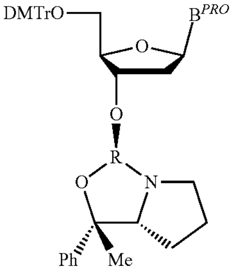

In some embodiments, the step of coupling comprises reacting a free hydroxyl group of a nucleotide unit of an oligonucleotide with a nucleoside coupling partner under suitable conditions to effect the coupling. In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

Once the appropriate hydroxyl group of the growing oligonucleotide has been deblocked, the support is washed and dried in preparation for delivery of a solution comprising a chiral reagent and a solution comprising an activator. In some embodiments, a chiral reagent and an activator are delivered simultaneously. In some embodiments, co-delivery comprises delivering an amount of a chiral reagent in solution (e.g., a phosphoramidite solution) and an amount of activator in a solution (e.g., a CMPT solution) in a polar aprotic solvent such as a nitrile solvent (e.g., acetonitrile).

In some embodiments, the step of coupling provides a crude product composition in which the chiral phosphite product is present in a diastereomeric excess of >95%. In some embodiments, the chiral phosphite product is present in a diastereomeric excess of >96%. In some embodiments, the chiral phosphite product is present in a diastereomeric excess of >97%. In some embodiments, the chiral phosphite product is present in a diastereomeric excess of >98%. In some embodiments, the chiral phosphite product is present in a diastereomeric excess of >99%.

Capping Step:

Provided methods for making chirally controlled oligonucleotides comprise a step of capping. In some embodiments, a step of capping is a single step. In some embodiments, a step of capping is two steps. In some embodiments, a step of capping is more than two steps.

In some embodiments, a step of capping comprises steps of capping the free amine of the chiral auxiliary and capping any residual unreacted 5' hydroxyl groups. In some embodiments, the free amine of the chiral auxiliary and the unreacted 5' hydroxyl groups are capped with the same capping group. In some embodiments, the free amine of the chiral auxiliary and the unreacted 5' hydroxyl groups are capped with different capping groups. In certain embodiments, capping with different capping groups allows for selective removal of one capping group over the other during synthesis of the oligonucleotide. In some embodiments, the capping of both groups occurs simultaneously. In some embodiments, the capping of both groups occurs iteratively.

In certain embodiments, capping occurs iteratively and comprises a first step of capping the free amine followed by a second step of capping the free 5' hydroxyl group, wherein both the free amine and the 5' hydroxyl group are capped with the same capping group. For instance, in some embodiments, the free amine of the chiral auxiliary is capped using an anhydride (e.g., phenoxyacetic anhydride, i.e., $Pac_2O$) prior to capping of the 5' hydroxyl group with the same anhydride. In certain embodiments, the capping of the 5' hydroxyl group with the same anhydride occurs under different conditions (e.g., in the presence of one or more additional reagents). In some embodiments, capping of the 5' hydroxyl group occurs in the presence of an amine base in an etherial solvent (e.g., NMI (N-methylimidazole) in THF). The phrase "capping group" is used interchangeably herein with the phrases "protecting group" and "blocking group".

In some embodiments, an amine capping group is characterized in that it effectively caps the amine such that it prevents rearrangement and/or decomposition of the intermediate phosphite species. In some embodiments, a capping group is selected for its ability to protect the amine of the chiral auxiliary in order to prevent intramolecular cleavage of the internucleotide linkage phosphorus.

In some embodiments, a 5' hydroxyl group capping group is characterized in that it effectively caps the hydroxyl group such that it prevents the occurrence of "shortmers," e.g., "n−m" (m and n are integers and m<n; n is the number of bases in the targeted oligonucleotide) impurities that occur from the reaction of an oligonucleotide chain that fails to react in a first cycle but then reacts in one or more subsequent cycles. The presence of such shortmers, especially "n−1", has a deleterious effect upon the purity of the crude oligonucleotide and makes final purification of the oligonucleotide tedious and generally low-yielding.

In some embodiments, a particular cap is selected based on its tendency to facilitate a particular type of reaction under particular conditions. For instance, in some embodiments, a capping group is selected for its ability to facilitate an E1 elimination reaction, which reaction cleaves the cap and/or auxiliary from the growing oligonucleotide. In some embodiments, a capping group is selected for its ability to facilitate an E2 elimination reaction, which reaction cleaves the cap and/or auxiliary from the growing oligonucleotide. In some embodiments, a capping group is selected for its ability to facilitate a β-elimination reaction, which reaction cleaves the cap and/or auxiliary from the growing oligonucleotide.

Modifying Step:

As used herein, the phrase "modifying step", "modification step" and "P-modification step" are used interchangeably and refer generally to any one or more steps used to install a modified internucleotidic linkage. In some embodiments, the modified internucleotidic linkage having the structure of formula I. A P-modification step of the present disclosure occurs during assembly of a provided oligonucleotide rather than after assembly of a provided oligonucleotide is complete. Thus, each nucleotide unit of a provided oligonucleotide can be individually modified at the linkage phosphorus during the cycle within which the nucleotide unit is installed.

In some embodiments, a suitable P-modification reagent is a sulfur electrophile, selenium electrophile, oxygen electrophile, boronating reagent, or an azide reagent.

For instance, in some embodiments, a selemium reagent is elemental selenium, a selenium salt, or a substituted diselenide. In some embodiments, an oxygen electrophile is elemental oxygen, peroxide, or a substituted peroxide. In some embodiments, a boronating reagent is a borane-amine (e.g., N,N-diisopropylethylamine ($BH_3$·DIPEA), borane-pyridine ($BH_3$·Py), borane-2-chloropyridine ($BH_3$·CPy), borane-aniline ($BH_3$·An)), a borane-ether reagent (e.g., borane-tetrahydrofuran ($BH_3$·THF)), a borane-dialkylsulfide reagent (e.g., $BH_3 \cdot Me_2S$), aniline-cyanoborane, or a triphenylphosphine-carboalkoxyborane. In some embodiments, an azide reagent is comprises an azide group capable of undergoing subsequent reduction to provide an amine group.

In some embodiments, a P-modification reagent is a sulfurization reagent as described herein. In some embodiments, a step of modifying comprises sulfurization of phosphorus to provide a phosphorothioate linkage or phosphorothioate triester linkage. In some embodiments, a step of modifying provides an oligonucleotide having an internucleotidic linkage of formula I.

In some embodiments, the present disclosure provides sulfurizing reagents, and methods of making, and use of the same.

In some embodiments, such sulfurizing reagents are thiosulfonate reagents. In some embodiments, a thiosulfonate reagent has a structure of formula S-I:

S-I

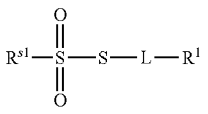

wherein:

$R^{s1}$ is R; and each of R, L and $R^1$ is independently as defined and described above and herein.

In some embodiments, the sulfurizing reagent is a bis (thiosulfonate) reagent. In some embodiments, the bis(thiosulfonate) reagent has the structure of formula S-II:

S-II

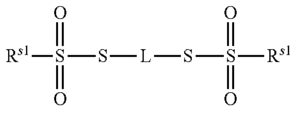

wherein each of $R^{s1}$ and L is independently as defined and described above and herein.

As defined generally above, $R^{s1}$ is R, wherein R is as defined and described above and herein. In some embodiments, $R^{s1}$ is optionally substituted aliphatic, aryl, heterocyclyl or heteroaryl. In some embodiments, $R^{s1}$ is optionally substituted alkyl. In some embodiments, $R^{s1}$ is optionally substituted alkyl. In some embodiments, $R^{s1}$ is methyl. In some embodiments, $R^{s1}$ is cyanomethyl. In some embodiments, $R^{s1}$ is nitromethyl. In some embodiments, $R^{s1}$ is optionally substituted aryl. In some embodiments, $R^{s1}$ is optionally substituted phenyl. In some embodiments, $R^{s1}$ is phenyl. In some embodiments, $R^{s1}$ is p-nitrophenyl. In some embodiments, $R^{s1}$ is p-methylphenyl. In some embodiments, $R^{s1}$ is p-chlorophenyl. In some embodiments, $R^{s1}$ is o-chlorophenyl. In some embodiments, $R^{s1}$ is 2,4,6-trichlorophenyl. In some embodiments, $R^{s1}$ is pentafluorophenyl. In some embodiments, $R^{s1}$ is optionally substituted heterocyclyl. In some embodiments, $R^{s1}$ is optionally substituted heteroaryl.

In some embodiments, $R^{s1}$—$S(O)_2S$— is

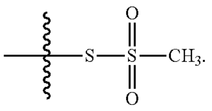

(MTS)

In some embodiments, $R^{s1}$—$S(O)_2S$— is

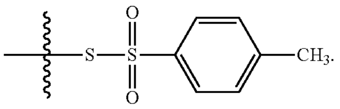

(TTS)

In some embodiments, $R^{s1}$—$S(O)_2S$— is

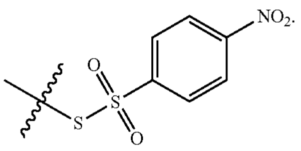

($NO_2$PheTS)

In some embodiments, $R^{s1}$—$S(O)_2S$— is

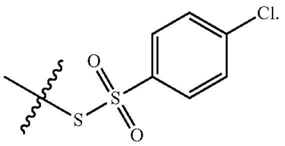

(p-ClPheTS)

In some embodiments, $R^{s1}$—$S(O)_2S$— is

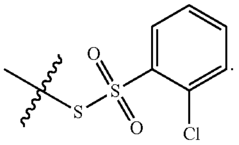

(o-ClPheTS)

In some embodiments, $R^{s1}$—$S(O)_2S$— is

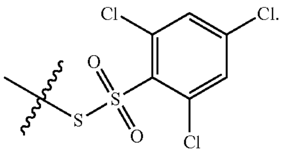

(2,4,6-TriClPheTS)

In some embodiments, $R^{s1}$—$S(O)_2S$— is

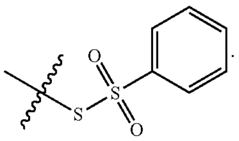

(PheTS)

In some embodiments, $R^{S1}$—$S(O)_2S$— is

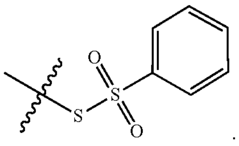

(PFPheTS)

In some embodiments, $R^{s1}$—$S(O)_2S$— is

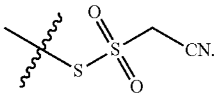

(a-CNMTS)

In some embodiments, $R^{s1}$—$S(O)_2S$— is

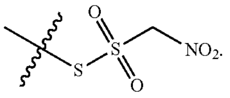

(a-NO2MTS)

In some embodiments, $R^{s1}$—$S(O)_2S$— is

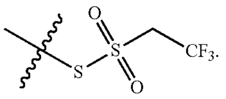

(a-CF3MTS)

In some embodiments, $R^{s1}$—$S(O)_2S$— is

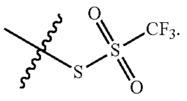

(a-CF3TS)

In some embodiments, $R^{s1}$—$S(O)_2S$— is

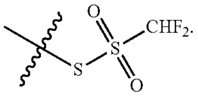

(a-CHF2TS)

In some embodiments, $R^{s1}$—$S(O)_2S$— is

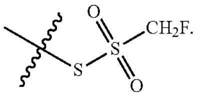

(a-CH2FTS)

In some embodiments, the sulfurizing reagent has the structure of S-I or S-II, wherein L is —S—$R^{L3}$— or —S—C(O)—$R^{L3}$—. In some embodiments, L is —S—$R^{L3}$— or —S—C(O)—$R^{L3}$—, wherein $R^{L3}$ is an optionally substituted $C_1$-$C_6$ alkylene. In some embodiments, L is —S—$R^{L3}$— or —S—C(O)—$R^{L3}$—, wherein $R^{L3}$ is an optionally substituted $C_1$-$C_6$ alkenylene. In some embodiments, L is —S—$R^{L3}$— or —S—C(O)—$R^{L3}$—, wherein $R^{L3}$ is an optionally substituted $C_1$-$C_6$ alkylene wherein one or more methylene units are optionally and independently replaced by an optionally substituted $C_1$-$C_6$ alkenylene, arylene, or heteroarylene. In some embodiments, In some embodiments, $R^{L3}$ is an optionally substituted —S—($C_1$-$C_6$ alkenylene)-, —S—($C_1$-$C_6$ alkylene)-, —S—($C_1$-$C_6$ alkylene)-arylene-($C_1$-$C_6$ alkylene)-, —S—CO-arylene-($C_1$-$C_6$ alkylene)-, or —S—CO—($C_1$-$C_6$ alkylene)-arylene-($C_1$-$C_6$ alkylene)-. In some embodiments, the sulfurizing reagent has the structure of S-I or S-II, wherein L is —S—$R^{L3}$— or —S—C(O)—$R^{L3}$—, and the sulfur atom is connected to $R^1$.

In some embodiments, the sulfurizing reagent has the structure of S-I or S-II, wherein L is alkylene, alkenylene, arylene or heteroarylene.

In some embodiments, the sulfurizing reagent has the structure of S-I or S-II, wherein L is

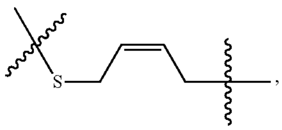

,

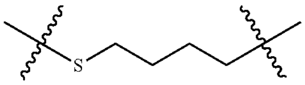

,

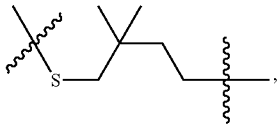

,

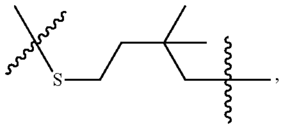

,

-continued
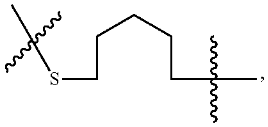
,
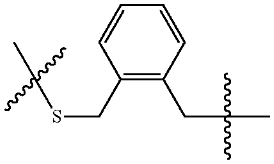
,
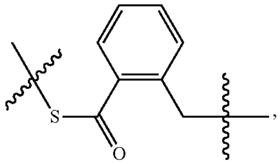
,
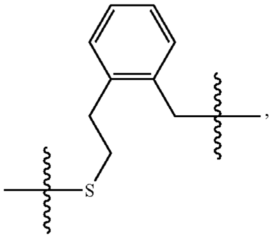
, or
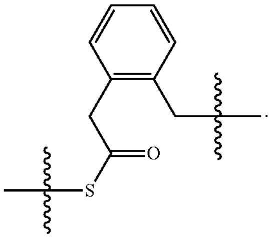
.
In some embodiments, L is
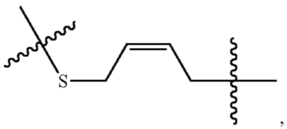
,
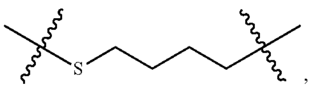
,
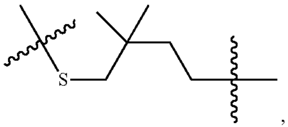
,
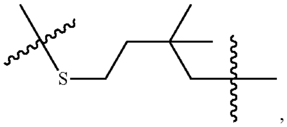
,
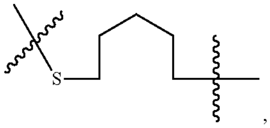
,
-continued
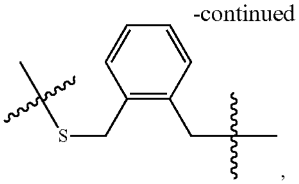
,
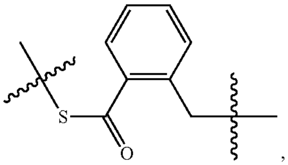
,
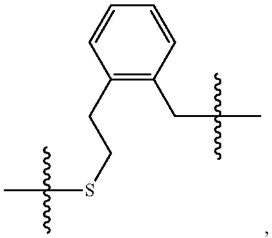
, or
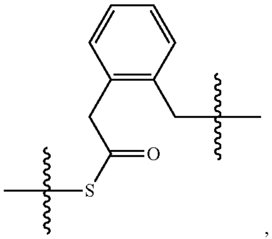
,
wherein the sulfur atom is connected to $R^1$. In some embodiments, the sulfurizing reagent has the structure of S-I or S-II, wherein $R^1$ is
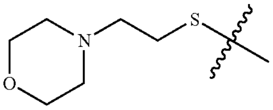
,
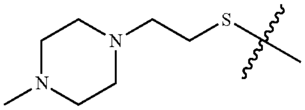
,
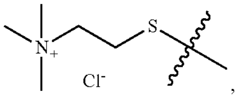
,
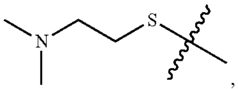
, or
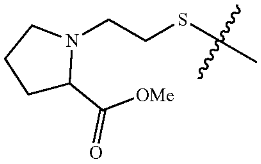
.
In some embodiments, $R^1$ is
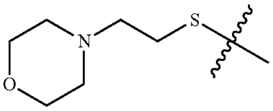
, -continued

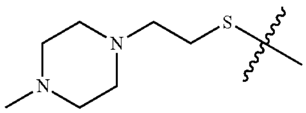

,

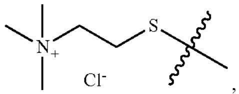

,

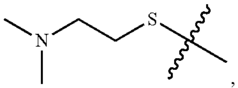

, or

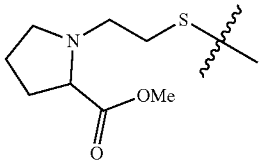

, wherein the sulfur atom is connected to L. In some embodiments, the sulfurizing reagent has the structure of S-I or S-II, wherein L is

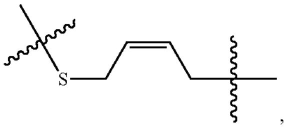

,

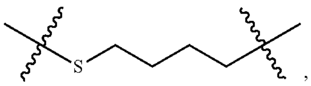

,

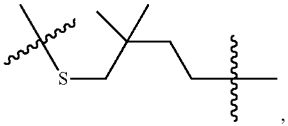

,

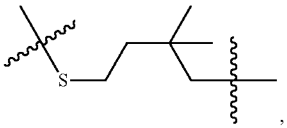

,

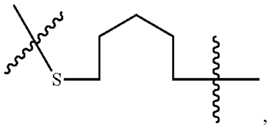

,

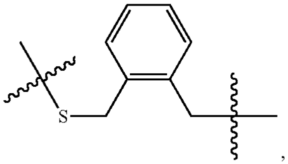

,

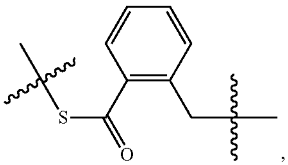

,

-continued

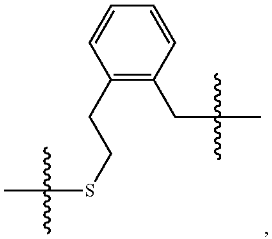

, or

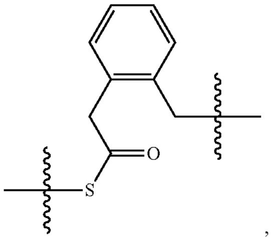

, wherein the sulfur atom is connected to $R^1$; and $R^1$ is

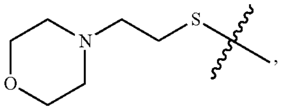

,

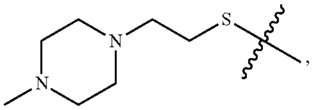

,

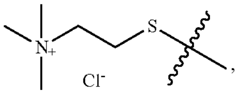

,

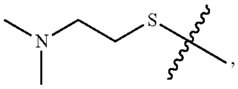

, or

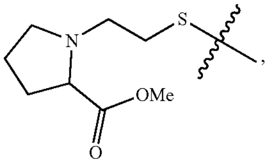

, wherein the sulfur atom is connected to L.

In some embodiments, the sulfurizing reagent has the structure of S-I or S-II, wherein $R^1$ is —S—$R^{L2}$, wherein $R^{L2}$ is as defined and described above and herein. In some embodiments, $R^{L2}$ is an optionally substituted group selected from —S—($C_1$-$C_6$ alkylene)-heterocyclyl, —S—($C_1$-$C_6$ alkenylene)-heterocyclyl, —S—($C_1$-$C_6$ alkylene)-N(R')$_2$, —S—($C_1$-$C_6$ alkylene)-N(R')$_3$, wherein each R' is as defined above and described herein.

In some embodiments, -L-$R^1$ is —$R^{L3}$—S—S—$R^{L2}$, wherein each variable is independently as defined above and described herein. In some embodiments, -L-$R^1$ is —$R^{L3}$—C(O)—S—S—$R^{L2}$, wherein each variable is independently as defined above and described herein.

Example bis(thiosulfonate) reagents of formula S-II are depicted below:

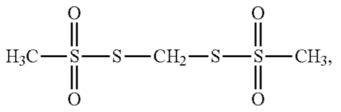

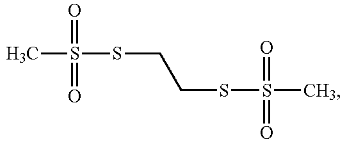

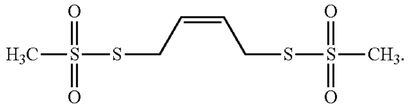

In some embodiments, the sulfurization reagent is a compound having one of the following formulae:

$S_8$, $R^{s2}$—S—S—$R^{s3}$, or $R^{s2}$—S—$X^s$—$R^{s3}$, wherein:

each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or $R^{s2}$ and $R^{s3}$ are taken together with the atoms to which they are bound to form an optionally substituted heterocyclic or heteroaryl ring;

$X^s$ is —$S(O)_2$—, —O—, or —N(R')—; and

R' is as defined and described above and herein.

In some embodiments, the sulfurization reagent is $S_8$,

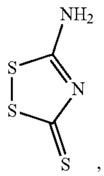 ,
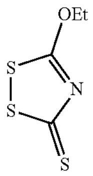 ,
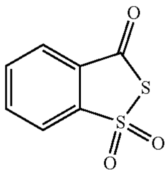 ,
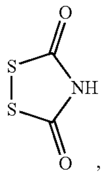 ,

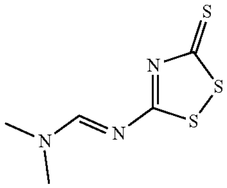 , or 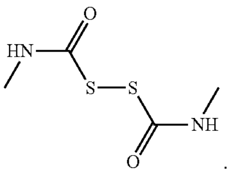 .

In some embodiments, the sulfurization reagent is $S_8$,

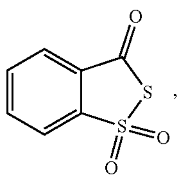 , or 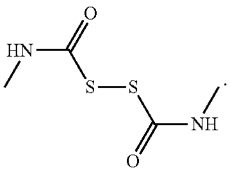

In some embodiments, the sulfurization reagent is

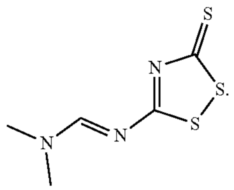

Example sulfuring reagents are depicted in Table 5 below.

TABLE 5

| Example sulfurization reagents. |
|---|
| 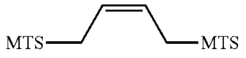 |
| 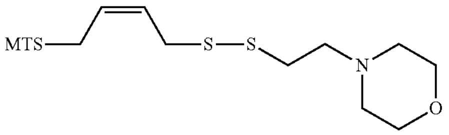 |
| 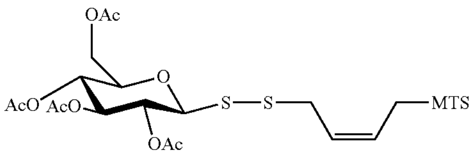 |
| 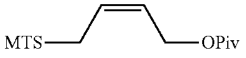 |
| 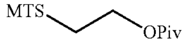 |
| 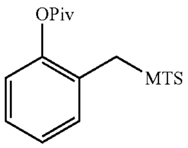 |
| 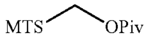 |
| 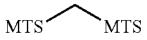 |
| 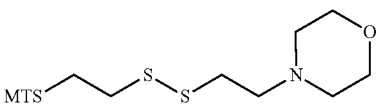 |
| 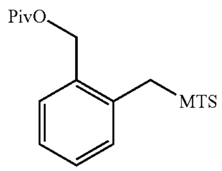 |
| 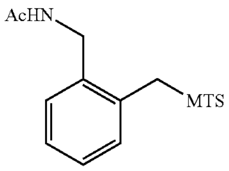 |

TABLE 5-continued
Example sulfurization reagents.
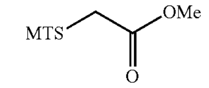
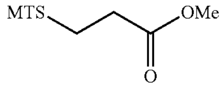
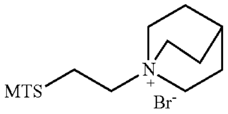
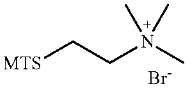
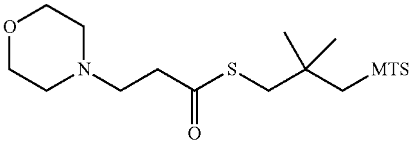
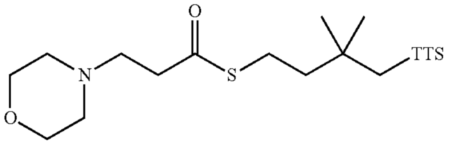
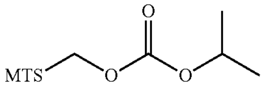
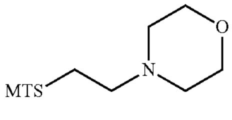
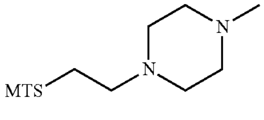
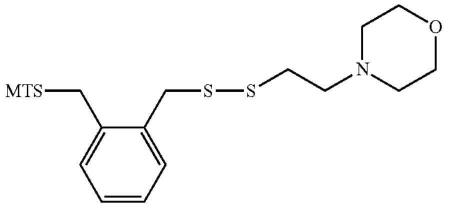
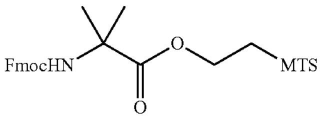
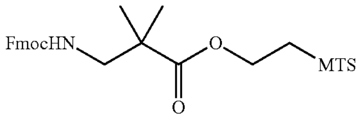
TABLE 5-continued
Example sulfurization reagents.
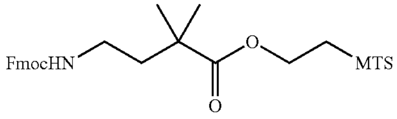
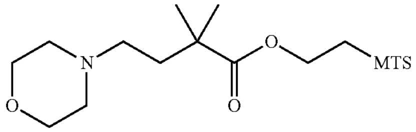
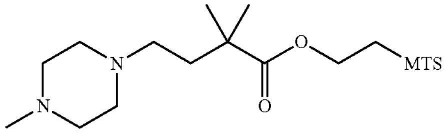
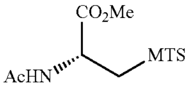
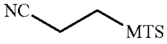
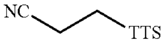
$S_8$
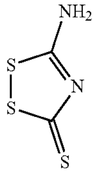
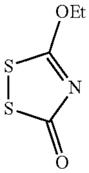
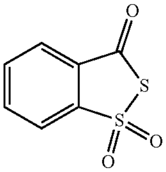 [SMILES: O=C1SS(=O)(=O)c2ccccc21]
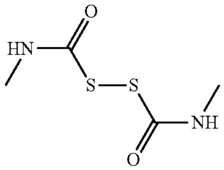
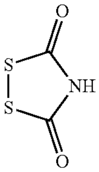

TABLE 5-continued

Example sulfurization reagents.

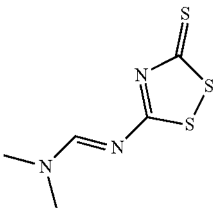

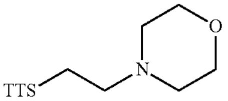

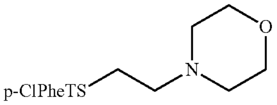

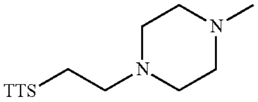

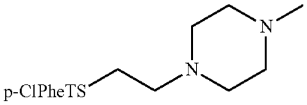

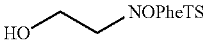

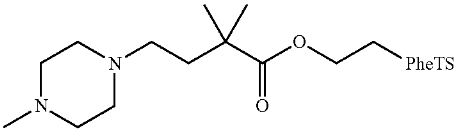

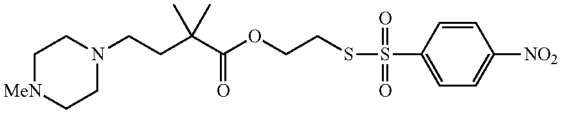 [SMILES: CN1CCN(CCC(C)(C)C(=O)OCCSS(=O)(=O)c2ccc([N+](=O)[O-])cc2)CC1]

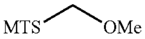

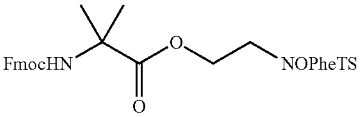

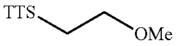

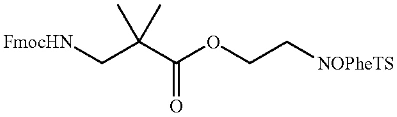

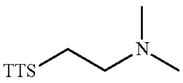

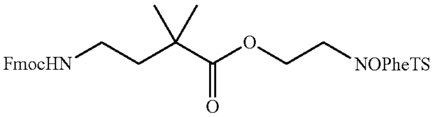

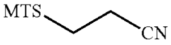

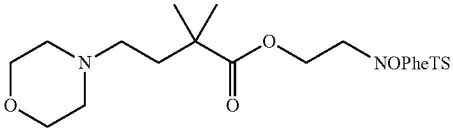

POS

In some embodiments, a provided sulfurization reagent is used to modify an H-phosphonate. For instance, in some embodiments, an H-phosphonate oligonucleotide is synthesized using, e.g., a method of Wada I or Wada II, and is modified using a sulfurization reagent of formula S-I or S-II:

S-I

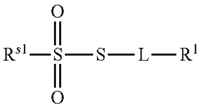

S-II

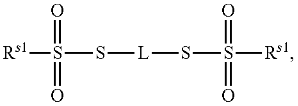

wherein each of $R^{S1}$, L, and $R^1$ are as described and defined above and herein.

In some embodiments, the present disclosure provides a process for synthesizing a phosphorothioate triester, comprising steps of:

i) reacting an H-phosphonate of structure:

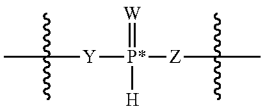

wherein each of W, Y, and Z are as described and defined above and herein, with a silylating reagent to provide a silyloxyphosphonate; and ii) reacting the silyloxyphosphonate with a sulfurization reagent of structure S-I or S-II:

S-I

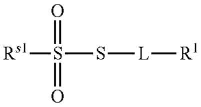

-continued

S-II

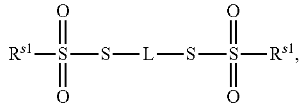

to provide a phosphorothiotriester.

In some embodiments, a selenium electrophile is used instead of a sulfurizing reagent to introduce modification to the internucleotidic linkage. In some embodiments, a selenium electrophile is a compound having one of the following formulae:

Se, $R^{s2}$—Se—Se—$R^{s3}$, or $R^{s2}$—Se—$X^{s}$—$R^{s3}$, wherein:

each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or $R^{s2}$ and $R^{s3}$ are taken together with the atoms to which they are bound to form an optionally substituted heterocyclic or heteroaryl ring;

$X^{s}$ is —$S(O)_2$—, —O—, or —N(R')—; and

R' is as defined and described above and herein.

In other embodiments, the selenium electrophile is a compound of Se, KSeCN,

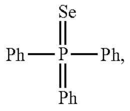

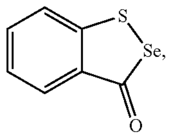

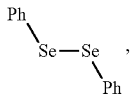

, or

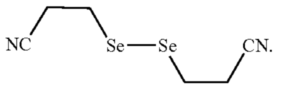

In some embodiments, the selenium electrophile is Se or

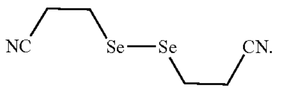

In some embodiments, a sulfurization reagent for use in accordance with the present disclosure is characterized in that the moiety transferred to phosphorus during sulfurization is a substituted sulfur (e.g., —SR) as opposed to a single sulfur atom (e.g., —$S^-$ or =S).

In some embodiments, a sulfurization reagent for use in accordance with the present disclosure is characterized in that the activity of the reagent is tunable by modifying the reagent with a certain electron withdrawing or donating group.

In some embodiments, a sulfurization reagent for use in accordance with the present disclosure is characterized in that it is crystalline. In some embodiments, a sulfurization reagent for use in accordance with the present disclosure is characterized in that it has a high degree of crystallinity. In certain embodiments, a sulfurization reagent for use in accordance with the present disclosure is characterized by ease of purification of the reagent via, e.g., recrystallization. In certain embodiments, a sulfurization reagent for use in accordance with the present disclosure is characterized in that it is substantially free from sulfur-containing impurities. In some embodiments, sulfurization reagents which are substantially free from sulfur-containing impurities show increased efficiency.

In some embodiments, the provided chirally controlled oligonucleotide comprises one or more phosphate diester linkages. To synthesize such chirally controlled oligonucleotides, one or more modifying steps are optionally replaced with an oxidation step to install the corresponding phosphate diester linkages. In some embodiments, the oxidation step is performed in a fashion similar to ordinary oligonucleotide synthesis. In some embodiments, an oxidation step comprises the use of $I_2$. In some embodiments, an oxidation step comprises the use of $I_2$ and pyridine. In some embodiments, an oxidation step comprises the use of 0.02 M $I_2$ in a THF/pyridine/water (70:20:10-v/v/v) co-solvent system. An example cycle is depicted in Scheme I-c.

In some embodiments, a phosphorothioate is directly formed through sulfurization by a sulfurization reagents, e.g., 3-phenyl-1,2,4-dithiazolin-5-one. In some embodiments, after a direct installation of a phosphorothioate, a chiral auxiliary group remains attached to the internucleotidic phosphorus atom. In some embodiments, an additional de-protecting step is required to remove the chiral auxiliary (e.g., for DPSE-type chiral auxiliary, using TBAF, HF-$Et_3N$, etc.).

In some embodiments, a phosphorothioate precursor is used to synthesize chirally controlled oligonucleotides comprising phosphorothioate linkages. In some embodiments, such a phosphorothioate precursor is

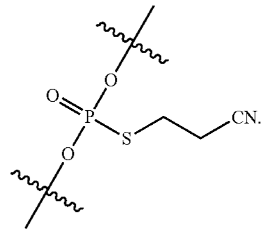 [SMILES: *OP(=O)(O*)SCCC#N]

In some embodiments,

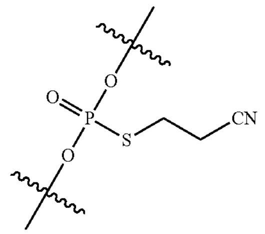 [SMILES: *OP(=O)(O*)SCCC#N]

is converted into phosphorothioate diester linkages during standard deprotection/release procedure after cycle exit. Examples are further depicted below.

In some embodiments, the provided chirally controlled oligonucleotide comprises one or more phosphate diester linkages and one or more phosphorothioate diester linkages. In some embodiments, the provided chirally controlled oligonucleotide comprises one or more phosphate diester linkages and one or more phosphorothioate diester linkages, wherein at least one phosphate diester linkage is installed after all the phosphorothioate diester linkages when synthesized from 3' to 5'. To synthesize such chirally controlled oligonucleotides, in some embodiments, one or more modifying steps are optionally replaced with an oxidation step to install the corresponding phosphate diester linkages, and a phosphorothioate precursor is installed for each of the phosphorothioate diester linkages. In some embodiments, a phosphorothioate precursor is converted to a phosphorothioate diester linkage after the desired oligonucleotide length is achieved. In some embodiments, the deprotection/release step during or after cycle exit converts the phosphorothioate precursors into phosphorothioate diester linkages. In some embodiments, a phosphorothioate precursor is characterized in that it has the ability to be removed by a beta-elimination pathway. In some embodiments, a phosphorothioate precursor is

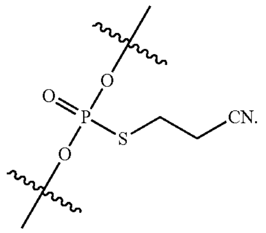 [SMILES: *OP(=O)(O*)SCCC#N]

As understood by one of ordinary skill in the art, one of the benefits of using a phosphorothioate precursor, for instance,

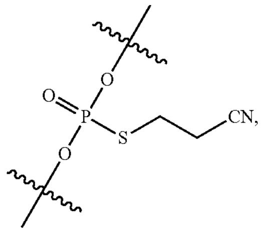 [SMILES: *OP(=O)(O*)SCCC#N]

during synthesis is that

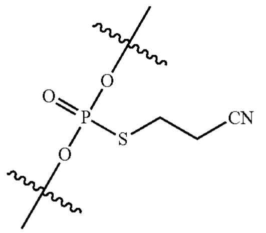 [SMILES: *OP(=O)(O*)SCCC#N]

is more stable than phosphorothioate in certain conditions.

In some embodiments, a phosphorothioate precursor is a phosphorus protecting group as described herein, e.g., 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, 4-[N-methyl-N-(2,2,2-trifluoroacetyl)amino]butyl. Examples are further depicted below.

As noted above, in some embodiments, sulfurization occurs under conditions which cleave the chiral reagent from the growing oligonucleotide. In some embodiments, sulfurization occurs under conditions which do not cleave the chiral reagent from the growing oligonucleotide.

In some embodiments, a sulfurization reagent is dissolved in a suitable solvent and delivered to the column. In certain embodiments, the solvent is a polar aprotic solvent such as a nitrile solvent. In some embodiments, the solvent is acetonitrile. In some embodiments, a solution of sulfurization reagent is prepared by mixing a sulfurization reagent (e.g., a thiosulfonate derivative as described herein) with BSTFA (N,O-bis-trimethylsilyl-trifluoroacetamide) in a nitrile solvent (e.g., acetonitrile). In some embodiments, BSTFA is not included. For example, the present inventors have found that relatively more reactive sulfurization reagents of general formula $R^{s2}$—S—$S(O)_2$—$R^{s3}$ can often successfully participate in sulfurization reactions in the absence of BSTFA. To give but one example, the inventors have demonstrated that where $R^{s2}$ is p-nitrophenyl and $R^{s3}$ is methyl then no BSTFA is required. In light of this disclosure, those skilled in the art will readily be able to determine other situations and/or sulfurization reagents that do not require BSTFA.

In some embodiments, the sulfurization step is performed at room temperature. In some embodiments, the sulfurization step is performed at lower temperatures such as about 0° C., about 5° C., about 10° C., or about 15° C. In some embodiments, the sulfurization step is performed at elevated temperatures of greater than about 20° C.

In some embodiments, a sulfurization reaction is run for about 1 minute to about 120 minutes. In some embodiments, a sulfurization reaction is run for about 1 minute to about 90 minutes. In some embodiments, a sulfurization reaction is run for about 1 minute to about 60 minutes. In some embodiments, a sulfurization reaction is run for about 1 minute to about 30 minutes. In some embodiments, a sulfurization reaction is run for about 1 minute to about 25 minutes. In some embodiments, a sulfurization reaction is run for about 1 minute to about 20 minutes. In some embodiments, a sulfurization reaction is run for about 1 minute to about 15 minutes. In some embodiments, a sulfurization reaction is run for about 1 minute to about 10 minutes. In some embodiments, a sulfurization reaction is run for about 5 minute to about 60 minutes.

In some embodiments, a sulfurization reaction is run for about 5 minutes. In some embodiments, a sulfurization reaction is run for about 10 minutes. In some embodiments, a sulfurization reaction is run for about 15 minutes. In some embodiments, a sulfurization reaction is run for about 20 minutes. In some embodiments, a sulfurization reaction is run for about 25 minutes. In some embodiments, a sulfurization reaction is run for about 30 minutes. In some embodiments, a sulfurization reaction is run for about 35 minutes. In some embodiments, a sulfurization reaction is run for about 40 minutes. In some embodiments, a sulfurization reaction is run for about 45 minutes. In some embodiments, a sulfurization reaction is run for about 50 minutes. In some embodiments, a sulfurization reaction is run for about 55 minutes. In some embodiments, a sulfurization reaction is run for about 60 minutes.

It was unexpectedly found that certain of the sulfurization modification products made in accordance with methods of the present disclosure are unexpectedly stable. In some embodiments, it the unexpectedly stable products are phosphorothioate triesters. In some embodiments, the unexpectedly stable products are chirally controlled oligonucleotides comprising one or more internucleotidic linkages having the structure of formula I-c.

One of skill in the relevant arts will recognize that sulfurization methods described herein and sulfurization reagents described herein are also useful in the context of modifying H-phosphonate oligonucleotides such as those described in Wada II (WO2010/064146).

In some embodiments, the sulfurization reaction has a stepwise sulfurization efficiency that is at least about 80%, 85%, 90%, 95%, 96%, 97%, or 98%. In some embodiments, the sulfurization reaction provides a crude dinucleotide product composition that is at least 98% pure. In some embodiments, the sulfurization reaction provides a crude tetranucleotide product composition that is at least 90% pure. In some embodiments, the sulfurization reaction provides a crude dodecanucleotide product composition that is at least 70% pure. In some embodiments, the sulfurization reaction provides a crude icosanucleotide product composition that is at least 50% pure.

Once the step of modifying the linkage phosphorus is complete, the oligonucleotide undergoes another deblock step in preparation for re-entering the cycle. In some embodiments, a chiral auxiliary remains intact after sulfurization and is deblocked during the subsequent deblock step, which necessarily occurs prior to re-entering the cycle. The process of deblocking, coupling, capping, and modifying, are repeated until the growing oligonucleotide reaches a desired length, at which point the oligonucleotide can either be immediately cleaved from the solid support or left attached to the support for purification purposes and later cleaved. In some embodiments, one or more protecting groups are present on one or more of the nucleotide bases, and cleavage of the oligonucleotide from the support and deprotection of the bases occurs in a single step. In some embodiments, one or more protecting groups are present on one or more of the nucleotide bases, and cleavage of the oligonucleotide from the support and deprotection of the bases occurs in more than one step. In some embodiments, deprotection and cleavage from the support occurs under basic conditions using, e.g., one or more amine bases. In certain embodiments, the one or more amine bases comprise propyl amine. In certain embodiments, the one or more amine bases comprise pyridine.

In some embodiments, cleavage from the support and/or deprotection occurs at elevated temperatures of about 30° C. to about 90° C. In some embodiments, cleavage from the support and/or deprotection occurs at elevated temperatures of about 40° C. to about 80° C. In some embodiments, cleavage from the support and/or deprotection occurs at elevated temperatures of about 50° C. to about 70° C. In some embodiments, cleavage from the support and/or deprotection occurs at elevated temperatures of about 60° C. In some embodiments, cleavage from the support and/or deprotection occurs at ambient temperatures.

Example purification procedures are described herein and/or are known generally in the relevant arts.

Noteworthy is that the removal of the chiral auxiliary from the growing oligonucleotide during each cycle is beneficial for at least the reasons that (1) the auxiliary will not have to be removed in a separate step at the end of the oligonucleotide synthesis when potentially sensitive functional groups are installed on phosphorus; and (2) unstable phosphorus-auxiliary intermediates prone to undergoing side reactions and/or interfering with subsequent chemistry are avoided. Thus, removal of the chiral auxiliary during each cycle makes the overall synthesis more efficient.

While the step of deblocking in the context of the cycle is described above, additional general methods are included below.

Deblocking Step

In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

In some embodiments, acidification is used to remove a blocking group. In some embodiments, the acid is a Brønsted acid or Lewis acid. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring and or other sugar ring. In some embodiments, an acid is selected from $R^{a1}COOH$, $R^{a1}SO_3H$, $R^{a3}SO_3H$

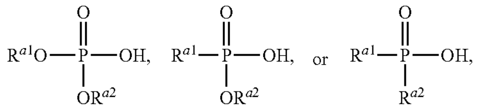

wherein each of $R^{a1}$ and $R^{a2}$ is independently hydrogen or an optionally substituted alkyl or aryl, and $R^a$ is an optionally substituted alkyl or aryl.

In some embodiments, acidification is accomplished by a Lewis acid in an organic solvent. Example such useful Lewis acids are $Zn(X^a)_2$ wherein $X^a$ is Cl, Br, I, or $CF_3SO_3$.

In some embodiments, the step of acidifying comprises adding an amount of a Brønsted or Lewis acid effective to remove a blocking group without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid or trichloroacetic acid in an organic solvent or 80% acetic acid in water. The concentration of any Brønsted or Lewis acid used in this step is selected such that the concentration of the acid does not exceed a concentration that causes cleavage of a nucleobase from a sugar moiety.

In some embodiments, acidification comprises adding 1% trifluoroacetic acid in an organic solvent. In some embodiments, acidification comprises adding about 0.1% to about 8% trifluoroacetic acid in an organic solvent. In some embodiments, acidification comprises adding 3% dichloroacetic acid or trichloroacetic acid in an organic solvent. In some embodiments, acidification comprises adding about 0.1% to about 10% dichloroacetic acid or trichloroacetic acid in an organic solvent. In some embodiments, acidification comprises adding 3% trichloroacetic acid in an organic solvent. In some embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to an acidic solvent. In certain embodiments, the cation scavengers can be triethylsilane or triisopropylsilane. In some embodiments, a blocking group is deblocked by acidification, which comprises adding 1% trifluoroacetic acid in an organic solvent. In some embodiments, a blocking group is deblocked by acidification, which comprises adding 3% dichloroacetic acid in an organic solvent. In some embodiments, a blocking group is deblocked by acidification, which comprises adding 3% trichloroacetic acid in an organic solvent. In some embodiments, a blocking group is deblocked by acidification, which comprises adding 3% trichloroacetic acid in dichloromethane.

In certain embodiments, methods of the present disclosure are completed on a synthesizer and the step of deblocking the hydroxyl group of the growing oligonucleotide comprises delivering an amount solvent to the synthesizer column, which column contains a solid support to which the oligonucleotide is attached. In some embodiments, the solvent is a halogenated solvent (e.g., dichloromethane). In certain embodiments, the solvent comprises an amount of an acid. In some embodiments, the solvent comprises an amount of an organic acid such as, for instance, trichloroacetic acid. In certain embodiments, the acid is present in an amount of about 1% to about 20% w/v. In certain embodiments, the acid is present in an amount of about 1% to about 10% w/v. In certain embodiments, the acid is present in an amount of about 1% to about 5% w/v. In certain embodiments, the acid is present in an amount of about 1 to about 3% w/v. In certain embodiments, the acid is present in an amount of about 3% w/v. Methods for deblocking a hydroxyl group are described further herein. In some embodiments, the acid is present in 3% w/v is dichloromethane.

In some embodiments, the chiral auxiliary is removed before the deblocking step. In some embodiments, the chiral auxiliary is removed during the deblocking step.

In some embodiments, cycle exit is performed before the deblocking step. In some embodiments, cycle exit is preformed after the deblocking step.

General Conditions for Blocking Group/Protecting Group Removal

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2nd Ed., John Wiley & Sons, New York, 1991). For example, amino groups can be blocked with nitrogen blocking groups such as phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin-4-yl (Fpmp), 1-(2-chloroethoxy)ethyl, 3-methoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), [4-(N-dichloroacetyl-N-methylamino)benzyloxy]methyl, 2-cyanoethyl (CN), pivaloyloxymethyl (PivOM), levunyloxymethyl (ALE). Other representative hydroxyl blocking groups have been described (see e.g., Beaucage et al., *Tetrahedron,* 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from nucleic acids. In some embodiments, all blocking groups are removed. In some embodiments, a portion of blocking groups are removed. In some embodiments, reaction conditions can be adjusted to selectively remove certain blocking groups.

In some embodiments, nucleobase blocking groups, if present, are cleavable with an acidic reagent after the assembly of a provided oligonucleotide. In some embodiment, nucleobase blocking groups, if present, are cleavable under neither acidic nor basic conditions, e.g. cleavable with fluoride salts or hydrofluoric acid complexes. In some embodiments, nucleobase blocking groups, if present, are cleavable in the presence of base or a basic solvent after the assembly of a provided oligonucleotide. In certain embodiments, one or more of the nucleobase blocking groups are characterized in that they are cleavable in the presence of base or a basic solvent after the assembly of a provided oligonucleotide but are stable to the particular conditions of one or more earlier deprotection steps occurring during the assembly of the provided oligonucleotide.

In some embodiments, blocking groups for nucleobases are not required. In some embodiments, blocking groups for nucleobases are required. In some embodiments, certain nucleobases require one or more blocking groups while other nucleobases do not require one or more blocking groups.

In some embodiments, the oligonucleotide is cleaved from the solid support after synthesis. In some embodiments, cleavage from the solid support comprises the use of propylamine. In some embodiments, cleavage from the solid support comprises the use of propylamine in pyridine. In some embodiments, cleavage from the solid support comprises the use of 20% propylamine in pyridine. In some embodiments, cleavage from the solid support comprises the use of propylamine in anhydrous pyridine. In some embodiments, cleavage from the solid support comprises the use of 20% propylamine in anhydrous pyridine. In some embodiments, cleavage from the solid support comprises use of a polar aprotic solvent such as acetonitrile, NMP, DMSO, sulfone, and/or lutidine. In some embodiments, cleavage from the solid support comprises use of solvent, e.g., a polar aprotic solvent, and one or more primary amines (e.g., a $C_{1-10}$ amine), and/or one or more of methoxylamine, hydrazine, and pure anhydrous ammonia.

In some embodiments, deprotection of oligonucleotide comprises the use of propylamine. In some embodiments, deprotection of oligonucleotide comprises the use of propylamine in pyridine. In some embodiments, deprotection of oligonucleotide comprises the use of 20% propylamine in pyridine. In some embodiments deprotection of oligonucleotide comprises the use of propylamine in anhydrous pyridine. In some embodiments, deprotection of oligonucleotide comprises the use of 20% propylamine in anhydrous pyridine.

In some embodiments, the oligonucleotide is deprotected during cleavage.

In some embodiments, cleavage of oligonucleotide from solid support, or deprotection of oligonucleotide, is performed at about room temperature. In some embodiments, cleavage of oligonucleotide from solid support, or deprotection of oligonucleotide, is performed at elevated temperature. In some embodiments, cleavage of oligonucleotide from solid support, or deprotection of oligonucleotide, is performed at above about 30° C., 40° C., 50° C., 60° C., 70° C., 80° C. 90° C. or 100° C. In some embodiments, cleavage of oligonucleotide from solid support, or deprotection of oligonucleotide, is performed at about 30° C., 40° C., 50° C., 60° C., 70° C., 80° C. 90° C. or 100° C. In some embodiments, cleavage of oligonucleotide from solid support, or deprotection of oligonucleotide, is performed at about 40-80° C. In some embodiments, cleavage of oligonucleotide from solid support, or deprotection of oligonucleotide, is performed at about 50-70° C. In some embodiments, cleavage of oligonucleotide from solid support, or deprotection of oligonucleotide, is performed at about 60° C.

In some embodiments, cleavage of oligonucleotide from solid support, or deprotection of oligonucleotide, is performed for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed for about 0.1-5 hrs. In some embodiments, cleavage of oligonucleotide from solid support, or deprotection of oligonucleotide, is performed for about 3-10 hrs. In some embodiments, cleavage of oligonucleotide from solid support, or deprotection of oligonucleotide, is performed for about 5-15 hrs. In some embodiments, cleavage of oligonucleotide from solid support, or deprotection of oligonucleotide, is performed for about 10-20 hrs. In some embodiments, cleavage of oligonucleotide from solid support, or deprotection of oligonucleotide, is performed for about 15-25 hrs. In some embodiments, cleavage of oligonucleotide from solid support, or deprotection of oligonucleotide, is performed for about 20-40 hrs. In some embodiments, cleavage of oligonucleotide from solid support, or deprotection of oligonucleotide, is performed for about 2 hrs. In some embodiments, cleavage of oligonucleotide from solid support, or deprotection of oligonucleotide, is performed for about 5 hrs. In some embodiments, cleavage of oligonucleotide from solid support, or deprotection of oligonucleotide, is performed for about 10 hrs. In some embodiments, cleavage of oligonucleotide from solid support, or deprotection of oligonucleotide, is performed for about 15 hrs. In some embodiments, cleavage of oligonucleotide from solid support, or deprotection of oligonucleotide, is performed for about 18 hrs. In some embodiments, cleavage of oligonucleotide from solid support, or deprotection of oligonucleotide, is performed for about 24 hrs.

In some embodiments, cleavage of oligonucleotide from solid support, or deprotection of oligonucleotide, is performed at room temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at room temperature for about 5-48 hrs. In some embodiments, cleavage of oligonucleotide from solid support, or deprotection of oligonucleotide, is performed at room temperature for about 10-24 hrs. In some embodiments, cleavage of oligonucleotide from solid support, or deprotection of oligonucleotide, is performed at room temperature for about 18 hrs. In some embodiments, cleavage of oligonucleotide from solid support, or deprotection of oligonucleotide, is performed at elevated temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at elevated temperature for about 0.5-5 hrs. In some embodiments, cleavage of oligonucleotide from solid support, or deprotection of oligonucleotide, is performed at about 60° C. for about 0.5-5 hrs. In some embodiments, cleavage of oligonucleotide from solid support, or deprotection of oligonucleotide, is performed at about 60° C. for about 2 hrs.

In some embodiments, cleavage of oligonucleotide from solid support, or deprotection of oligonucleotide comprises the use of propylamine and is performed at room temperature or elevated temperature for more than 0.1 hr, 1 hr, 2 hrs, 5 hrs, 10 hrs, 15 hrs, 20 hrs, 24 hrs, 30 hrs, or 40 hrs. Example conditions are 20% propylamine in pyridine at room temperature for about 18 hrs, and 20% propylamine in pyridine at 60° C. for about 18 hrs.

In some embodiments, prior to cleavage from solid support, a step is performed to remove a chiral auxiliary group, if one is still attached to an internucleotidic phosphorus atom. In some embodiments, for example, one or more DPSE type chiral auxiliary groups remain attached to internucleotidic phosphorus atoms during the oligonucleotide synthesis cycle. Suitable conditions for removing remaining chiral auxiliary groups are widely known in the art, e.g., those described in Wada I, Wada II, Wada III, Chiral Control, etc. In some embodiments, a condition for removing DPSE type chiral auxiliary is TBAF or $HF\text{-}Et_3N$, e.g., 0.1M TBAF in MeCN, 0.5M $HF\text{-}Et_3N$ in THF or MeCN, etc. In some embodiments, the present disclosure recognizes that a linker may be cleaved during the process of removing a chiral auxiliary group. In some embodiments, the present disclosure provides linkers, such as the SP linker, that provides better stability during chiral auxiliary group removal. Among other things, certain linkers provided by the present disclosure provided improved yield and/or purity.

In some embodiments, an activator is a "Wada" activator, i.e., the activator is from any one of Wada I, II, or III documents cited above.
Example activating groups are depicted below:
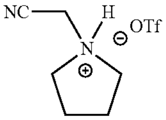
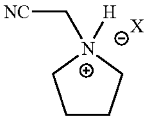
X = non nucleophilic anion
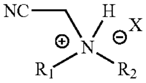
$X = {}^{-}OTf, BF_4^-$, $PF6^-$, $TfN^-$
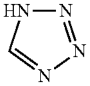
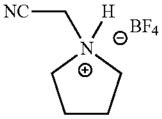
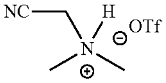
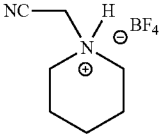
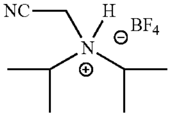
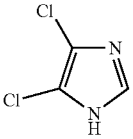
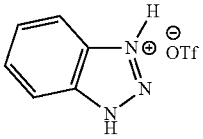
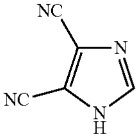
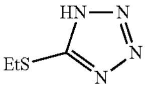
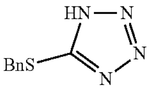
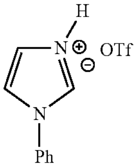
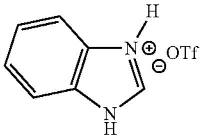
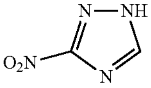
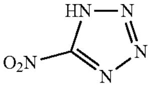
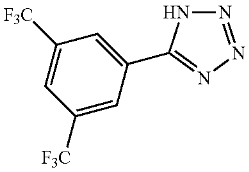
In some embodiments, an activating reagent is selected from
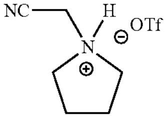
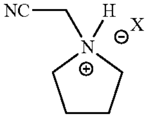
X = non nucleophilic anion
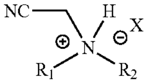
$X = {}^{-}OTf, BF_4^-$, $PF6^-$, $TfN^-$
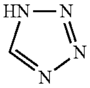
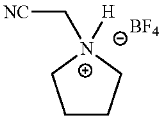
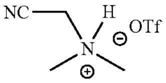
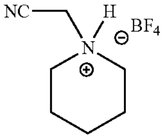
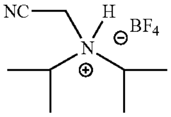
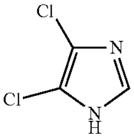
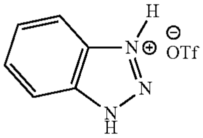
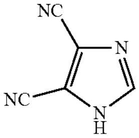
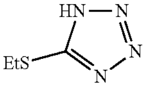
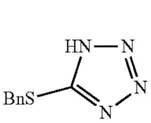
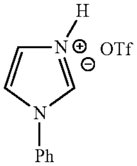
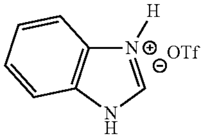
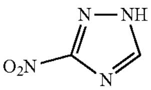
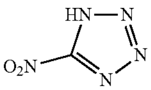

In some embodiments, an example cycle is depicted in Scheme I-b.
Scheme I-b. Installation of phosphorothioate linkages.
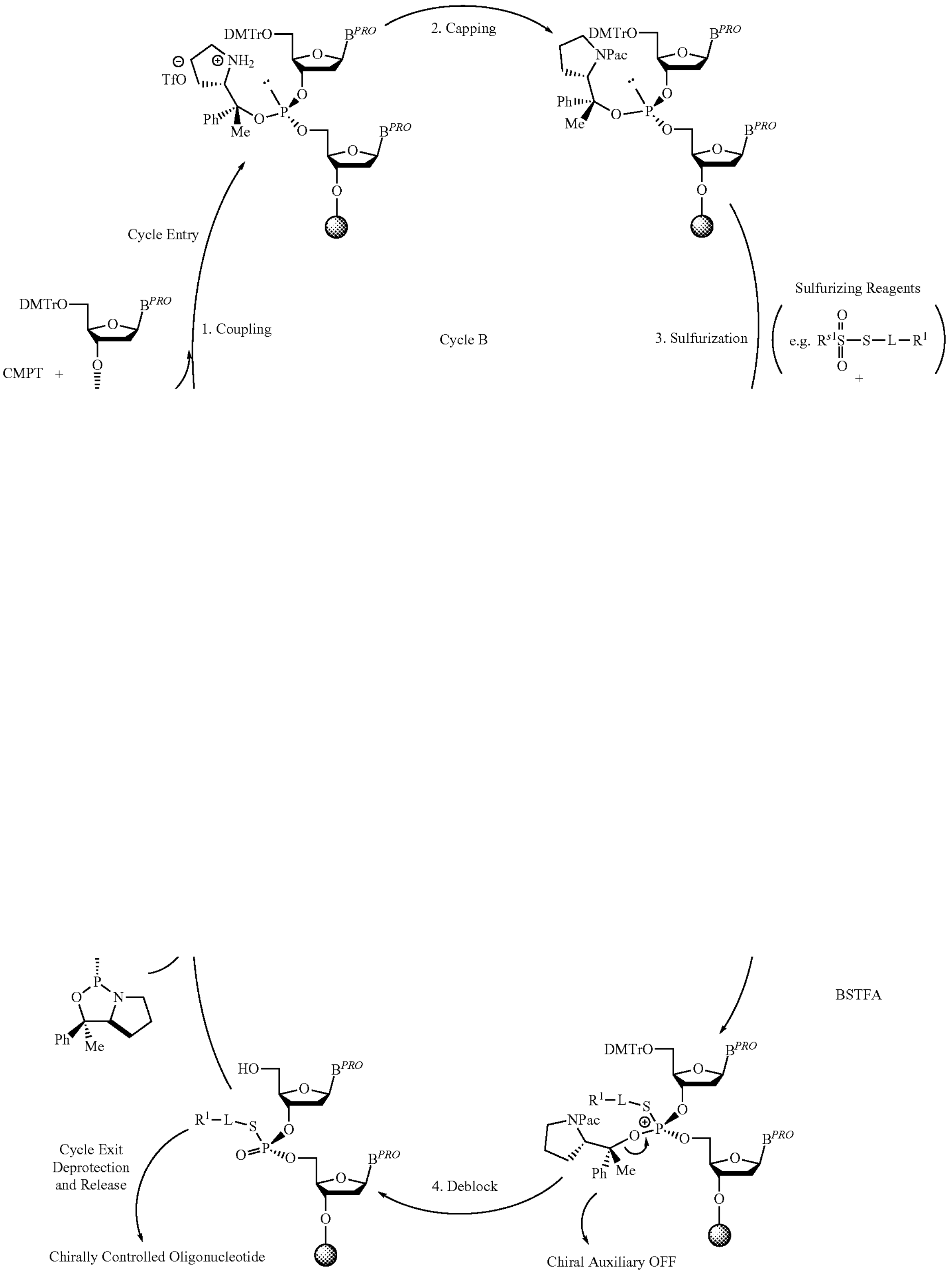

In some embodiments, an example cycle is illustrated in Scheme I-c.
Scheme I-c. Installation of both phosphate diester and modified internucleotidic linkages in a chirally controlled oligonucleotide.
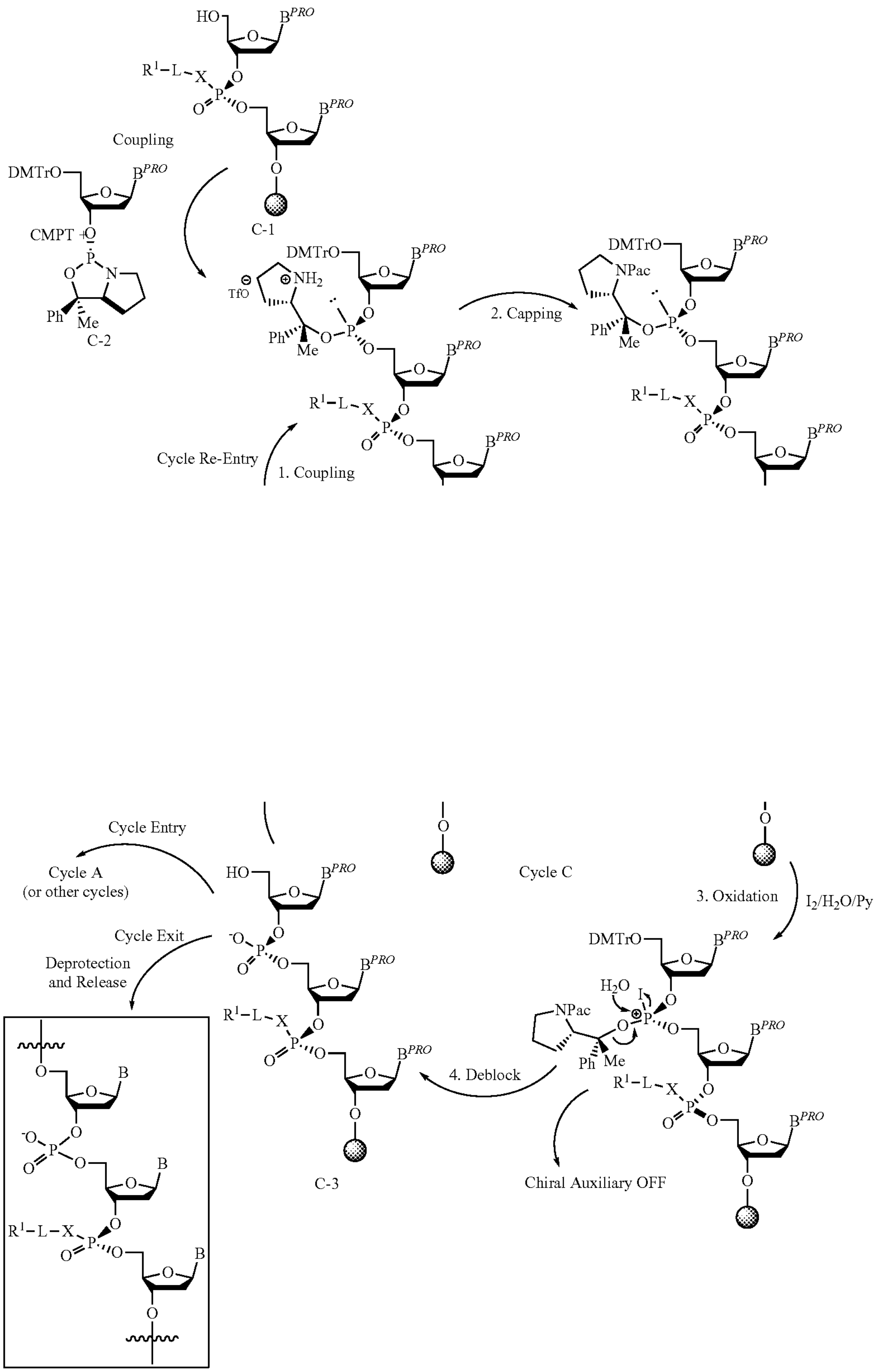

In Scheme I-c, oligonucleotide (or nucleotide, or oligonucleotide with modified internucleotidic linkage) on solid support (C-1) is coupled with phosphoramidite C-2. After coupling and capping, an oxidation step is performed. After deblocking, a phosphate diester linkage is formed. The cycle product C-3 can either re-enter cycle C to install more phosphate diester linkage, or enter other cycles to install other types of internucleotidic linkages, or go to cycle exit.

In some embodiments, non-chirally pure phosphoramidite can be used instead of C-2 in Scheme I-c. In some embodiments, β-cyanoethylphosphoramidites protected with DMTr is used. In some embodiments, the phosphoramidite being used has the structure of

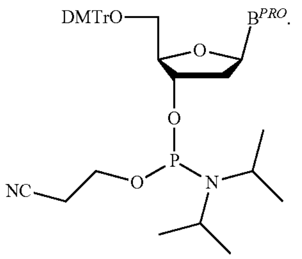

In some embodiments, the use of a phosphorothioate diester precursor increases the stability of oligonucleotide during synthesis. In some embodiments, the use of a phosphorothioate diester precursor improves the efficiency of chirally controlled oligonucleotide synthesis. In some embodiments, the use of a phosphorothioate diester precursor improves the yield of chirally controlled oligonucleotide synthesis. In some embodiments, the use of a phosphorothioate diester precursor improves the product purity of chirally controlled oligonucleotide synthesis.

In some embodiments, the phosphorothioate diester precursor in the above-mentioned methods is

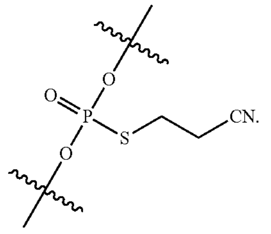 [SMILES: *OP(=O)(O*)SCCC#N]

In some embodiments,

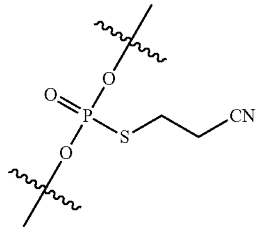

is converted to a phosphorothioate diester linkage during deprotection/release. In some embodiments, an example cycle is depicted in Scheme I-d. More examples are depicted below.

Scheme I-d. Phosphorothioate diester precursor in chirally controlled oligonucleotide synthesis.

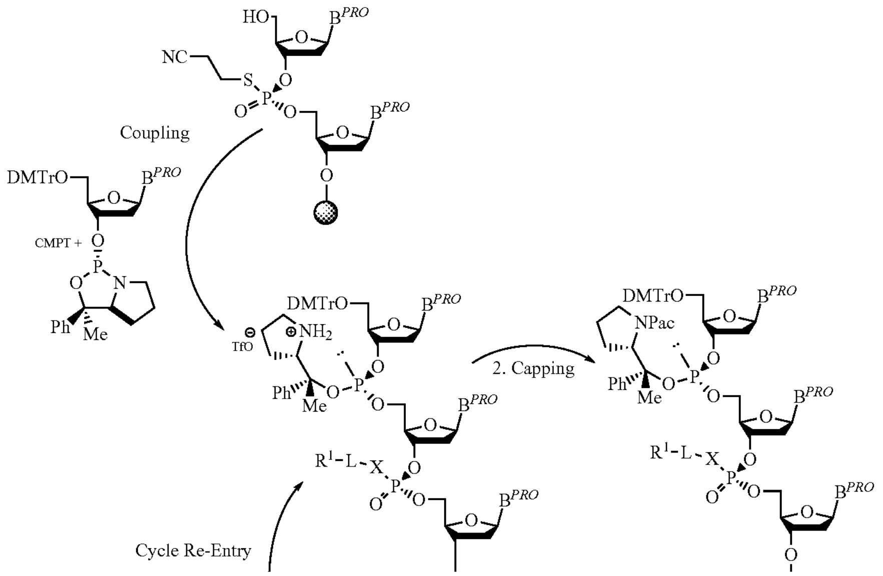

-continued

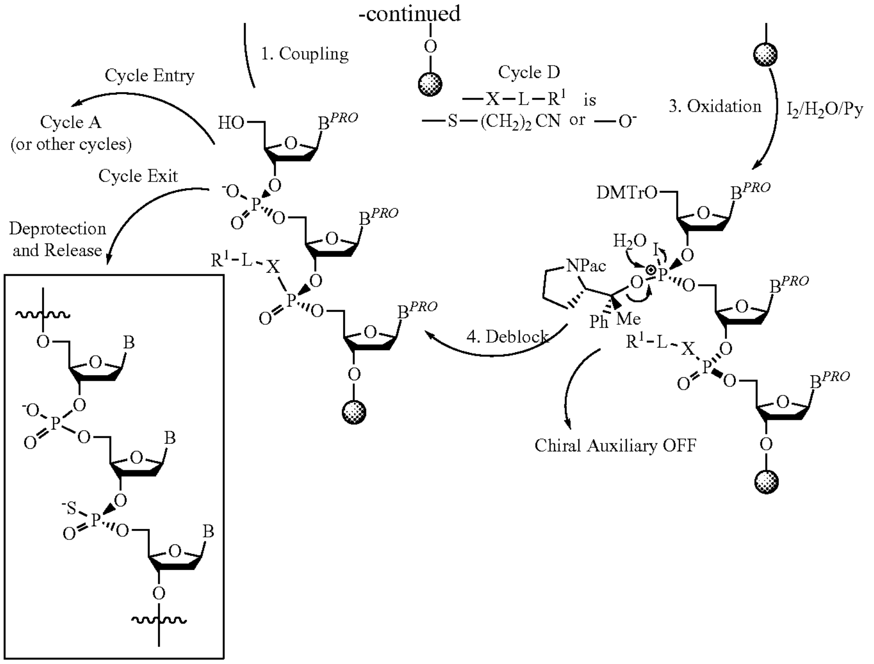

As illustrated in Scheme I-d, both phosphorothioate and phosphate diester linkages can be incorporated into the same chirally controlled oligonucleotide. As understood by a person of ordinary skill in the art, the provided methods do not require that the phosphorothioate diester and the phosphate diester to be consecutive—other internucleotidic linkages can form between them using a cycle as described above. In Scheme I-d, phosphorothioate diester precursors,

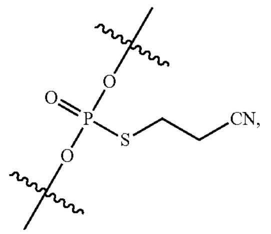

are installed in place of the phosphorothioate diester linkages. In some embodiments, such replacement provided increased synthesis efficiency during certain steps, for instance, the oxidation step. In some embodiments, the use of phosphorothioate diester precursors generally improve the stability of chirally controlled oligonucleotides during synthesis and/or storage. After cycle exit, during deprotection/release, the phosphorothioate diester precursor is converted to phosphorothioate diester linkage. In some embodiments, it is beneficial to use phosphorothioate diester precursor even when no phosphate diester linkage is present in the chirally controlled oligonucleotide, or no oxidation step is required during synthesis.

As in Scheme I-c, in some embodiments, non-chirally pure phosphoramidite can be used for cycles comprising oxidation steps. In some embodiments, β-cyanoethylphosphoramidites protected with DMTr is used. In some embodiments, the phosphoramidite being used has the structure of

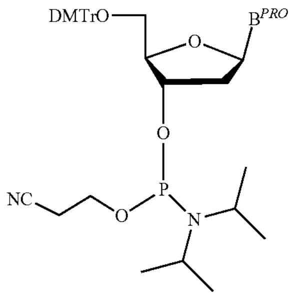

In some embodiments, methods of the present disclosure provide chirally controlled oligonucleotide compositions that are enriched in a particular oligonucleotide type.

In some embodiments, at least about 10% of a provided crude composition is of a particular oligonucleotide type. In some embodiments, at least about 20% of a provided crude composition is of a particular oligonucleotide type. In some embodiments, at least about 30% of a provided crude composition is of a particular oligonucleotide type. In some embodiments, at least about 40% of a provided crude composition is of a particular oligonucleotide type. In some embodiments, at least about 50% of a provided crude composition is of a particular oligonucleotide type. In some embodiments, at least about 60% of a provided crude composition is of a particular oligonucleotide type. In some embodiments, at least about 70% of a provided crude composition is of a particular oligonucleotide type. In some embodiments, at least about 80% of a provided crude composition is of a particular oligonucleotide type. In some embodiments, at least about 90% of a provided crude composition is of a particular oligonucleotide type. In some embodiments, at least about 95% of a provided crude composition is of a particular oligonucleotide type.

In some embodiments, at least about 1% of a provided composition is of a particular oligonucleotide type. In some embodiments, at least about 2% of a provided composition is of a particular oligonucleotide type. In some embodiments, at least about 3% of a provided composition is of a particular oligonucleotide type. In some embodiments, at least about 4% of a provided composition is of a particular oligonucleotide type. In some embodiments, at least about 5% of a provided composition is of a particular oligonucleotide type. In some embodiments, at least about 10% of a provided composition is of a particular oligonucleotide type. In some embodiments, at least about 20% of a provided composition is of a particular oligonucleotide type. In some embodiments, at least about 30% of a provided composition is of a particular oligonucleotide type. In some embodiments, at least about 40% of a provided composition is of a particular oligonucleotide type. In some embodiments, at least about 50% of a provided composition is of a particular oligonucleotide type. In some embodiments, at least about 60% of a provided composition is of a particular oligonucleotide type. In some embodiments, at least about 70% of a provided composition is of a particular oligonucleotide type. In some embodiments, at least about 80% of a provided composition is of a particular oligonucleotide type. In some embodiments, at least about 90% of a provided composition is of a particular oligonucleotide type. In some embodiments, at least about 95% of a provided composition is of a particular oligonucleotide type.

In some embodiments, an example cycle is depicted in Scheme I-e, below.

Scheme I-e. Example cycle using PhMe chiral auxiliary.

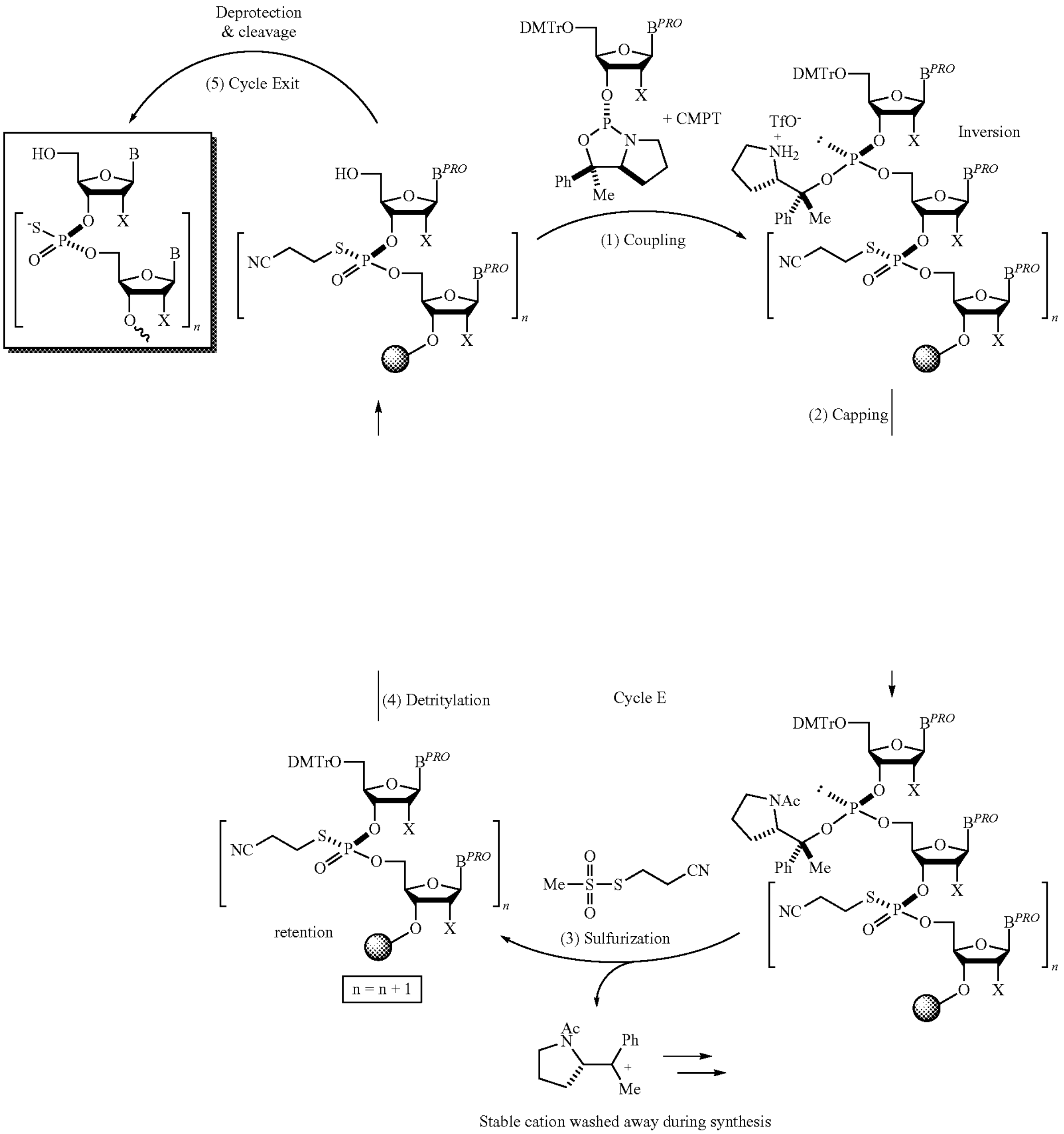

In some embodiments, X is H or a 2'-modification. In some embodiments, X is H or —$OR^1$, wherein $R^1$ is not hydrogen. In some embodiments, X is H or —$OR^1$, wherein $R^1$ is optionally substituted $C_{1-6}$ alkyl. In some embodiments, X is H. In some embodiments, X is —OMe. In some embodiments, X is —$OCH_2CH_2OCH_3$. In some embodiments, X is —F.

In some embodiments, an example cycle is depicted in Scheme I-f.

Scheme I-e. Example cycle using DPSE chiral auxiliary.

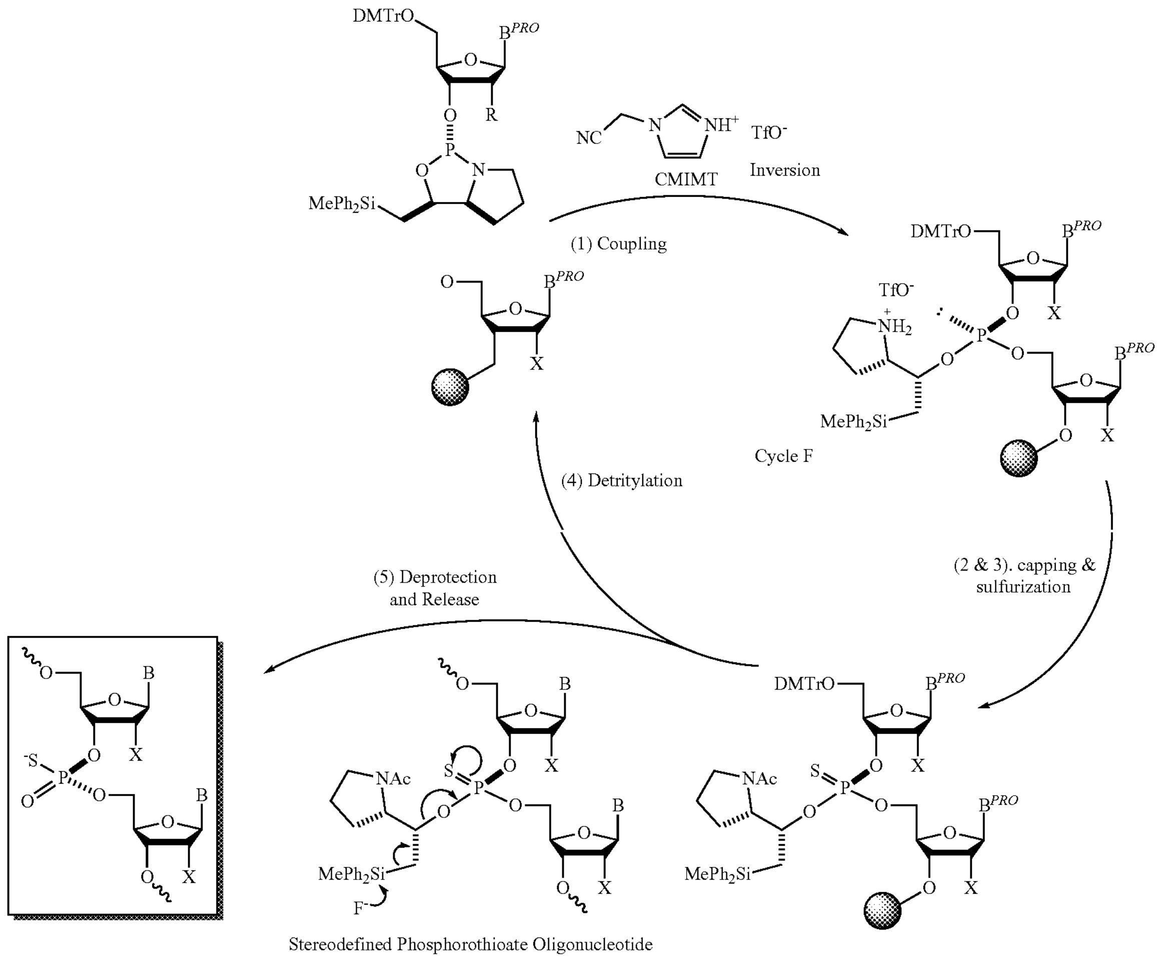

In some embodiments, X is H or a 2'-modification. In some embodiments, X is H or —$OR^1$, wherein $R^1$ is not hydrogen. In some embodiments, X is H or —$OR^1$, wherein $R^1$ is optionally substituted $C_{1-6}$ alkyl. In some embodiments, X is H. In some embodiments, X is —OMe. In some embodiments, X is —$OCH_2CH_2OCH_3$. In some embodiments, X is —F.

It is understood by a person having ordinary skill in the art that different types of cycles may be combined to provide complete control of the chemical modifications and stereochemistry of oligonucleotides. In some embodiments, for example, an oligonucleotide synthesis process may contain one or more Cycles A-F. In some embodiments, a provided method comprises at least one cycle using a DPSE-type chiral auxiliary.

In some embodiments, a provided method further comprises providing a fluoro-containing reagent. In some embodiments, a provided fluoro-containing reagent removes a chiral reagent, or a product formed from a chiral reagent, from oligonucleotides after synthesis. Various known fluoro-containing reagents, including those $F^-$ sources for removing —$SiR_3$ groups, can be utilized in accordance with the present disclosure, for example, TBAF, $HF_3$-$Et_3N$ etc. In some embodiments, a fluoro-containing reagent provides better results, for example, shorter treatment time, lower temperature, less de-sulfurization, etc, compared to traditional methods, such as concentrated ammonia. In some embodiments, for certain fluoro-containing reagent, the present disclosure provides linkers for improved results, for example, less cleavage of oligonucleotides from support during removal of chiral reagent (or product formed therefrom during oligonucleotide synthesis). In some embodiments, a provided linker is an SP linker. In some embodiments, the present disclosure demonstrated that a HF-base complex can be utilized, such as HF—$NR_3$, to control cleavage during removal of chiral reagent (or product formed therefrom during oligonucleotide synthesis). In some embodiments, HF—$NR_3$ is HF—$NEt_3$. In some embodiments, HF—$NR_3$ enables use of traditional linkers, e.g., succinyl linker.

In some embodiments, the present disclosure comprises a method for manufacturing an oligonucleotide composition directed to a selected target sequence, the method comprising manufacturing a provided oligonucleotide composition comprising a first plurality of oligonucleotides, each of which has a base sequence complementary to the target sequence. In some embodiments, a provided method further comprises providing a pharmaceutically acceptable carrier.

Biological Applications and Example Use

In some embodiments, the present disclosure recognizes that properties, e.g., activities, toxicities, etc. of oligonucleotides and compositions thereof can be optimized by chemical modifications and/or stereochemistry. In some embodiments, the present disclosure provides methods for optimizing oligonucleotide properties through chemical modifications and stereochemistry. In some embodiments, the present disclosure provides oligonucleotides and compositions and methods thereof with low toxicities. In some embodiments, the present disclosure provides oligonucleotides and compositions and methods thereof with low toxicities and enhanced activities (e.g., target-inhibition efficiency, specificity, cleavage rates, cleavage pattern, etc.). In some embodiments, the present disclosure provides oligonucleotides and compositions and methods thereof with improved protein binding profile. In some embodiments, the present disclosure provides oligonucleotides and compositions and methods thereof with improved protein binding profile and enhanced activities. In some embodiments, the present disclosure provides oligonucleotides and compositions and methods thereof with improved delivery and enhanced activities.

In some embodiments, provided oligonucleotides, compositions and methods have low toxicities, e.g., when compared to a reference composition. As widely known in the art, oligonucleotides can induce toxicities when administered to, e.g., cells, tissues, organism, etc. In some embodiments, oligonucleotides can induce undesired immune response. In some embodiments, oligonucleotide can induce complement activation. In some embodiments, oligonucleotides can induce activation of the alternative pathway of complement. In some embodiments, oligonucleotides can induce inflammation. Among other things, the complement system has strong cytolytic activity that can damages cells and should therefore be modulated to reduce potential injuries. In some embodiments, oligonucleotide-induced vascular injury is a recurrent challenge in the development of oligonucleotides for e.g., pharmaceutical use. In some embodiments, a primary source of inflammation when high doses of oligonucleotides are administered involves activation of the alternative complement cascade. In some embodiments, complement activation is a common challenge associated with phosphorothioate-containing oligonucleotides, and there is also a potential of some sequences of phosphorothioates to induce innate immune cell activation. In some embodiments, cytokine release is associated with administration of oligonucleotides. For example, in some embodiments, increases in interleukin-6 (IL-6) monocyte chemoattractant protein (MCP-1) and/or interleukin-12 (IL-12) is observed. See, e.g., Frazier, Antisense Oligonucleotide Therapies: The Promise and the Challenges from a Toxicologic Pathologist's Perspective. *Toxicol Pathol.,* 43: 78-89, 2015; and Engelhardt, et al., Scientific and Regulatory Policy Committee Points-to-consider Paper: Drug-induced Vascular Injury Associated with Nonsmall Molecule Therapeutics in Preclinical Development: Part 2. Antisense Oligonucleotides. *Toxicol Pathol.* 43: 935-944, 2015.

By controlling of chemical modifications and/or stereochemistry, the present disclosure provides improved oligonucleotide compositions and methods. In some embodiments, provided oligonucleotides comprise chemical modifications. In some embodiments, provided oligonucleotides comprise base modifications, sugar modifications, internucleotidic linkage modifications, or any combinations thereof. In some embodiments, provided oligonucleotides comprise base modifications. In some embodiments, provided oligonucleotides comprise sugar modifications. In some embodiments, provided oligonucleotides comprises 2'-modifications on the sugar moieties. In some embodiments, the present disclosure demonstrates that 2'-modifications can lower toxicity. In some embodiments, provided oligonucleotides comprises one or more modified internucleotidic linkages and one or more natural phosphate linkages. In some embodiments, the present disclosure demonstrates that incorporation of one or more natural phosphate linkages into oligonucleotides comprising one or more modified internucleotidic linkages can lower toxicity. A natural phosphate linkage can be incorporated into various locations of an oligonucleotide. In some embodiments, a natural phosphate linkage is incorporated into a wing region, or a region close to the 5'- or the 3'-end. In some embodiments, a natural phosphate linkage is incorporated into the middle of an oligonucleotide. In some embodiments, a natural phosphate linkage is incorporated into a core region. In some embodiments, the present disclosure demonstrates that stereochemistry, either alone or in combination with chemical modifications, can modulate toxicity. In some embodiments, the present disclosure demonstrates that stereochemistry, either alone or in combination with chemical modifications, can modulate immune response. In some embodiments, the present disclosure demonstrates that stereochemistry, either alone or in combination with chemical modifications, can modulate complement activation. It is surprisingly found that a chirally controlled oligonucleotide composition of an individual stereoisomer can have dramatically different toxicity profile, e.g., complement activation, compared to the corresponding stereorandom composition, and/or a chirally controlled oligonucleotide composition of another individual stereoisomer. For examples, see FIGS. 1-5. In some embodiments, the present disclosure demonstrates that stereochemistry, either alone or in combination with chemical modifications, can modulate complement activation via the alternative pathway. Example chemical modifications, stereochemistry and patterns thereof are extensively described in this disclosure, and they can be used in combinations. Example compositions and methods of are also extensively described in this disclosure. A person having ordinary skill in the art understands that methods and compositions described herein can be used to either increase or decrease immune responses, including complement activation, relative to a reference composition.

In some embodiments, the present disclosure provides a method of administering an oligonucleotide composition comprising a first plurality of oligonucleotides having a common nucleotide sequence, the improvement that comprises:

administering a provided oligonucleotide composition comprising the first plurality of oligonucleotides that is characterized by reduced toxicity relative to a reference oligonucleotide composition of the same common nucleotide sequence.

In some embodiments, the present disclosure provides a method of administering an oligonucleotide composition comprising a first plurality of oligonucleotides having a common nucleotide sequence, the improvement that comprises:

administering an oligonucleotide composition comprising the first plurality of oligonucleotides that is chirally controlled and that is characterized by reduced toxicity relative to a reference oligonucleotide composition of the same common nucleotide sequence.

In some embodiments, the present disclosure provides a method of administering an oligonucleotide composition comprising a first plurality of oligonucleotides having a common nucleotide sequence, the improvement that comprises:

administering an oligonucleotide composition in which each oligonucleotide in the plurality comprises one or more modified sugar moieties and the composition is characterized by reduced toxicity relative to a reference oligonucleotide composition of the same common nucleotide sequence but lacking at least one of the one or more modified sugar moieties.

In some embodiments, the present disclosure provides a method of administering an oligonucleotide composition comprising a first plurality of oligonucleotides having a common nucleotide sequence, the improvement that comprises:

administering an oligonucleotide composition in which each oligonucleotide in the plurality includes one or more natural phosphate linkages and one or more modified phosphate linkages;

wherein the oligonucleotide composition is characterized by reduced toxicity when tested in at least one assay that is observed with an otherwise comparable reference composition whose oligonucleotides comprise fewer natural phosphate linkages.

In some embodiments, the present disclosure provides a method of administering an oligonucleotide composition comprising a first plurality of oligonucleotides having a common nucleotide sequence, the improvement that comprises:

administering an oligonucleotide composition in which each oligonucleotide in the plurality includes one or more natural phosphate linkages and one or more modified phosphate linkages;

wherein the oligonucleotide composition is characterized by reduced toxicity when tested in at least one assay that is observed with an otherwise comparable reference composition whose oligonucleotides do not comprise natural phosphate linkages.

In some embodiments, the present disclosure provides a method of administering an oligonucleotide composition comprising a first plurality of oligonucleotides having a common nucleotide sequence, the improvement that comprises:

administering an oligonucleotide composition in which each oligonucleotide in the plurality comprises one or more modified sugar moieties and the composition is characterized by reduced toxicity relative to a reference oligonucleotide composition of the same common nucleotide sequence but lacking at least one of the one or more modified sugar moieties.

In some embodiments, the present disclosure provides a method comprising steps of administering to a subject an oligonucleotide composition comprising a first plurality of oligonucleotides each of which has a common base sequence and comprises a modified sugar moiety, wherein the oligonucleotide composition is characterized by reduced toxicity when tested in at least one assay that is observed with an otherwise comparable reference composition that comprises a reference plurality of oligonucleotides which have the same common base sequence but have no modified sugar moieties.

In some embodiments, the present disclosure provides a method comprising steps of administering to a subject an oligonucleotide composition comprising a first plurality of oligonucleotides each of which has a common base sequence and comprises one or more natural phosphate linkages and one or more modified phosphate linkages, wherein the oligonucleotide composition is characterized by reduced toxicity when tested in at least one assay that is observed with an otherwise comparable reference composition that comprises a reference plurality of oligonucleotides which have the same common base sequence but have no natural phosphate linkages.

In some embodiments, the present disclosure provides a method comprising steps of administering a chirally controlled oligonucleotide composition to a subject, wherein the chirally controlled oligonucleotide composition is characterized by reduced toxicity when tested in at least one assay that is observed with an otherwise comparable reference composition that includes a different chirally controlled oligonucleotide composition, or a stereorandom oligonucleotide composition, comprising oligonucleotides having the same base sequence.

In some embodiments, reduced toxicity is or comprises reduced complement activation. In some embodiments, reduced toxicity comprises reduced complement activation. In some embodiments, reduced toxicity is or comprises reduced complement activation. In some embodiments, reduced toxicity comprises reduced complement activation via the alternative pathway. In some embodiments, toxicity can be assessed through measuring levels of complement activation. In some embodiments, altered complement activation is observed in an assay that detects a protein whose level changes upon complement activation. In some embodiments, altered complement activation is observed in an assay that detects presence, absolute level and or relative levels of one or more complete-activation related product. In some embodiments, complement activation is observed in a serum. In some embodiments, complement activation is observed in human serum. In some embodiments, complement activation is observed in a primate serum. In some embodiments, complement activation is observed in monkey serum.

In some embodiments, complement activation is measured no more than 60 minutes after administration of oligonucleotides. In some embodiments, complement activation is measured no more than 50 minutes after administration of oligonucleotides. In some embodiments, complement activation is measured no more than 40 minutes after administration of oligonucleotides. In some embodiments, complement activation is measured no more than 30 minutes after administration of oligonucleotides. In some embodiments, complement activation is measured no more than 25 minutes after administration of oligonucleotides. In some embodiments, complement activation is measured no more than 20 minutes after administration of oligonucleotides. In some embodiments, complement activation is measured no more than 15 minutes after administration of oligonucleotides. In some embodiments, complement activation is measured no more than 10 minutes after administration of oligonucleotides. In some embodiments, complement activation is measured no more than 9 minutes after administration of oligonucleotides. In some embodiments, complement activation is measured no more than 8 minutes after administration of oligonucleotides. In some embodiments, complement activation is measured no more than 7 minutes after administration of oligonucleotides. In some embodiments, complement activation is measured no more than 6 minutes after administration of oligonucleotides. In some embodiments, complement activation is measured no more than 5 minutes after administration of oligonucleotides. In some embodiments, complement activation is measured no more than 4 minutes after administration of oligonucleotides. In some embodiments, complement activation is measured no more than 3 minutes after administration of oligonucleotides. In some embodiments, complement activation is measured no more than 2 minutes after administration of oligonucleotides. In some embodiments, complement activation is measured no more than 1 minute after administration of oligonucleotides. In some embodiments, complement activation is measured no more than 30 seconds after administration of oligonucleotides. In some embodiments, complement activation is measured no more than 20 seconds after administration of oligonucleotides. In some embodiments, complement activation is measured no more than 10 seconds after administration of oligonucleotides. In some embodiments, complement activation is measured no more than 5 seconds after administration of oligonucleotides.

In some embodiments, complement activation is measured 5 minutes after administration of oligonucleotides. In some embodiments, complement activation is measured 10 minutes after administration of oligonucleotides. In some embodiments, complement activation is measured 15 minutes after administration of oligonucleotides. In some embodiments, complement activation is measured 20 minutes after administration of oligonucleotides. In some embodiments, complement activation is measured 25 minutes after administration of oligonucleotides. In some embodiments, complement activation is measured 30 minutes after administration of oligonucleotides. In some embodiments, complement activation is measured 35 minutes after administration of oligonucleotides. In some embodiments, complement activation is measured 40 minutes after administration of oligonucleotides. In some embodiments, complement activation is measured 45 minutes after administration of oligonucleotides. In some embodiments, complement activation is measured 50 minutes after administration of oligonucleotides. In some embodiments, complement activation is measured 55 minutes after administration of oligonucleotides. In some embodiments, complement activation is measured 60 minutes after administration of oligonucleotides. In some embodiments, complement activation is measured at multiple time points after administration of oligonucleotides, for example, at two or more time points selected from 5, 10, 15, 20, 25, 30, 35, 40, 45, 50, 55, 60, 70, 80, 90, 100, 110 and 120 minutes after administration of oligonucleotides.

In some embodiments, complement activation is reduced by at least 10%, 20%, 30%, 40%, 50%, 60%, 70%, 80%, 90%, 95%, 96%, 97%, 98% or 99%. In some embodiments, complement activation is reduced by at least 5%. In some embodiments, complement activation is reduced by at least 10%. In some embodiments, complement activation is reduced by at least 15%. In some embodiments, complement activation is reduced by at least 20%. In some embodiments, complement activation is reduced by at least 25%. In some embodiments, complement activation is reduced by at least 30%. In some embodiments, complement activation is reduced by at least 35%. In some embodiments, complement activation is reduced by at least 40%. In some embodiments, complement activation is reduced by at least 45%. In some embodiments, complement activation is reduced by at least 50%. In some embodiments, complement activation is reduced by at least 55%. In some embodiments, complement activation is reduced by at least 60%. In some embodiments, complement activation is reduced by at least 65%. In some embodiments, complement activation is reduced by at least 70%. In some embodiments, complement activation is reduced by at least 75%. In some embodiments, complement activation is reduced by at least 80%. In some embodiments, complement activation is reduced by at least 85%. In some embodiments, complement activation is reduced by at least 90%. In some embodiments, complement activation is reduced by at least 95%. In some embodiments, complement activation is reduced by at least 96%. In some embodiments, complement activation is reduced by at least 97%. In some embodiments, complement activation is reduced by at least 98%. In some embodiments, complement activation is reduced by at least 99%. In some embodiments, complement activation is reduced to the same level of a negative control, e.g., water, a buffer not inducing complement activation, etc. In some embodiments, provided oligonucleotides, compositions and methods reduce injection site inflammation. In some embodiments, provided oligonucleotides, compositions and methods reduce induced vascular injury.

Markers that can be used to evaluate toxicity are widely known in the art, for example, CH50 (total complement), complement split products (e.g., Bb, C3a, C5a, etc.), MCP-1 and CRP, fibrinogen, haptoglobin, globulin, proteinuria, albuminuria, Angiopoietin-2, Endothelin-1, Eselectin, Thrombospondin-1, Vascular endothelial growth factor alpha, Calponin-1, Tissue inhibitor of metalloproteinase 1, Lipocalin 2, Cytokine-induced neutrophil chemoattractant 1, Alpha-1 acid glycoprotein 1, total nitric oxide, Von Willebrands factor, intercellular adhesion molecule (ICAM), vascular cellular adhesion molecule-1 (VCAM-1), interleukins, monocyte chemotactic protein-1, serum amyloid A, CRP, fibrinogen, plasminogen activator inhibitor-1, caveolin, matrix metalloproteinases (MMP-1, MMP-3, and MMP-9), vascular endothelial growth factor, thrombomodulin, E-selectin, P-selectin, complement pathway analysis and other inflammatory markers (i.e., CRP, MCP-1, MMP-3, and/or other cytokines or chemokines), markers of endothelial activation (e.g., VCAM), etc. For examples, see Frazier, Antisense Oligonucleotide Therapies: The Promise and the Challenges from a Toxicologic Pathologist's Perspective. *Toxicol Pathol.,* 43: 78-89, 2015; Engelhardt, et al., Scientific and Regulatory Policy Committee Points-to-consider Paper: Drug-induced Vascular Injury Associated with Nonsmall Molecule Therapeutics in Preclinical Development: Part 2. Antisense Oligonucleotides. *Toxicol Pathol.* 43: 935-944, 2015; etc. In some embodiments, a marker is protein in the complement pathway. In some embodiments, a marker is protein in the alternative complement pathway. In some embodiments, a marker is protein produced during complete activation. In some embodiments, a marker is protein produced during complete activation via the alternative pathway. In some embodiments, a marker is selected from C3a, Bb, C4a, C5a, C5b, C6, C7, C8 and C9. In some embodiments, a marker is selected from C4a, C5a, C5b, C6, C7, C8 and C9. In some embodiments, a marker is selected from C3a, C4a, C5a and Bb. In some embodiments, a marker is C3a or Bb. In some embodiments, a marker is C3a. In some embodiments, a marker is Bb.

Example assays are widely known in the art, including but not limited to those described in this disclosure and US2002/0082227; Frazier, Antisense Oligonucleotide Therapies: The Promise and the Challenges from a Toxicologic Pathologist's Perspective. *Toxicol Pathol.,* 43: 78-89, 2015; Engelhardt, et al., Scientific and Regulatory Policy Committee Points-to-consider Paper: Drug-induced Vascular Injury Associated with Nonsmall Molecule Therapeutics in Preclinical Development: Part 2. Antisense Oligonucleotides. *Toxicol Pathol.* 43: 935-944, 2015; etc.

The present disclosure demonstrates that chirally controlled oligonucleotide compositions of individual stereoisomers can have different complement activation profiles. In some embodiments, chirally controlled oligonucleotide compositions of oligonucleotides having all phosphorothioate linkages and a single Rp in the middle may demonstrate relatively high complement activation. As provided in this disclosure, various methods can be used to decrease the relatively high complement activation of these oligonucleotides, including but not limited to introduction of one or more natural phosphate linkages. For examples, see FIGS. 4 and 5.

With their improved properties, e.g., low toxicity, high activities, etc., provided oligonucleotides and compositions thereof are particularly useful for treating various diseases. In some embodiments, provided oligonucleotides, compositions and/or methods are particularly useful for reducing a target involved in the complement system. In some embodiments, provided oligonucleotides, compositions and/or methods are particularly useful for reducing complement activation by reducing levels of a target in the complement system as provided oligonucleotides, compositions and/or methods themselves only induce low, if any, complement activation compared to reference oligonucleotides, compositions and/or methods thereof. In some embodiments, a target involved in the complement system is C1, C1a, C1r, C1s, C1q, MASP-1, MASP-2, C3, C3-convertase, C3a, C3b, C3aR, C4b, C5, C5a, C5aR, Factor B, Factor D, Thrombin, Plasmin, Kallikrein, or FactorXIIa. In some embodiments, provided oligonucleotides, compositions and/or methods can provide improved treatment of associated diseases such as neuroinflammation and neurodegeneration, muscular inflammation, demyelination, vasculitis and nephritis. In some embodiments, a disease is a rare disease associated with complement; for examples, see Reis et al., Applying complement therapeutics to rare diseases, Clinical Immunology (2015), doi: 10.1016/j.clim.2015.08.009. In some embodiments, the present disclosure provides compositions of oligonucleotides targeting C5. In some embodiments, a provided composition is an siRNA composition targeting C5. In some embodiments, the present disclosure provides compositions of oligonucleotides targeting factor B. In some embodiments, the present disclosure provides compositions and methods targeting factor B for treatment of lupus nephritis. Example base sequences for targeting factor B include but are not limited to those described in Grossman et al. Inhibition of the alternative complement pathway by antisense oligonucleotides targeting complement factor B improves lupus nephritis in mice. *Immunobiology.* 2015 Aug. 10. pii: S0171-2985(15)30041-3. doi: 10.1016/j.imbio.2015.08.001.

In some embodiments, the present disclosure provides methods for modulating protein binding properties of oligonucleotides, for example, by adjusting chemical modifications and/or stereochemistry of oligonucleotides. Example chemical modifications, stereochemistry and combinations thereof are extensively described in this disclosure. In some embodiments, the present disclosure provides oligonucleotides and compositions thereof with improved protein binding profile.

In some embodiments, the present disclosure provides a method, comprising administering a composition comprising a first plurality of oligonucleotides, which composition displays altered protein binding as compared with a reference composition comprising a plurality of oligonucleotides, each of which also has the common base sequence but which differs structurally from the oligonucleotides of the first plurality in that:

individual oligonucleotides within the reference plurality differ from one another in stereochemical structure; and/or at least some oligonucleotides within the reference plurality have a structure different from a structure represented by the plurality of oligonucleotides of the composition; and/or at least some oligonucleotides within the reference plurality do not comprise a wing region and a core region.

In some embodiments, the present disclosure provides a method of administering an oligonucleotide composition comprising a first plurality of oligonucleotides having a common nucleotide sequence, the improvement that comprises:

administering an oligonucleotide composition comprising a first plurality of oligonucleotides that is characterized by altered protein binding relative to a reference oligonucleotide composition of the same common nucleotide sequence.

In some embodiments, provided oligonucleotides and compositions increase beneficial protein binding. In some embodiments, provided oligonucleotides and compositions decrease harmful protein binding. In some embodiments, provided oligonucleotides and compositions increase beneficial protein binding and decrease detrimental protein binding.

In some embodiments, improved protein binding profile lower toxicities and improve activities of provided oligonucleotides and compositions. In some embodiments, lowered binding to negative regulators of complement pathways contribute to decreased complement activation. In some embodiments, lowered binding to certain proteins are associated with lower toxicities and/or better activities. In some embodiments, increased binding to certain proteins contributes to lower toxicities and/or better activities.

Binding to various proteins, e.g., serum proteins, heparin sulfate-binding proteins, intracellular proteins, etc., by oligonucleotides can be modulated using oligonucleotides, compositions and methods provided in the present disclosure. Example proteins include but are not limited to Albumin, Complement Factor H, Factor IX, ApoE, Thrombin, Factor VIIIa, Heparin Cofactor II, alpha-2 macroglobulin, Fibroblast Growth Factor 1, Fibroblast Growth Factor 2, Hepatocyte Growth Factor/Scatter Factor, Vascular Endothelial Growth Factor, High-Mobility Group Protein B1, Cyclophilin B, IL-8 (CXCL8), Platelet Factor 4 (CXCL4), Stromal Cell-Derived Factor-1 (CXCL12), Monocyte Chemoattractant Protein-1 (CCL2), Fibroblast Growth Factor Receptor 1, Neuropilin-1, Receptor for Advanced Glycation End Products, Receptor Protein Tyrosine Phosphatase Sigma, Slit-2, ROBO1, Thrombin, Antithrombin, Protein C inhibitor, Amyloid precursor protein 1, Thrombospondin-1, Annexin A2, PDGF BB, PC4/Sub1, RNF163/ZNF9, Ku70, Ku80, TCP1-alpha, TCP1-beta, TCP1-epsilon, TCP1-gamma, TCP1-Theta, TCP1-delta, HSP90-AA1, HSP90-AB, HSP70-5/GRP78, HSPA1L, HSC70, ACTB, TBBB2C, Vimentin, CArG Binding Factor, DHX30, EIF2S2, EIF4H, GRSF1, hnRNP D1L, hnRNPA1, hnRNPA2, hnRNPH1, hnRNPK, hnRNPQ, hnRNPU, hnRNPUL, ILF2, ILF3, KHSRP, La/SSB, NCL, NPM1, P54nrb, PSF, PSPC1, RHA, YBX1, ACLY, VARS, ANXA2, NDKA, Thymidylate Kinase, JKBP1 delta 6, SHMT2, LRP-PRC, NARS, ATAD3A, KCTD12, CD4, GP120, aMb2 (Mac-1), VDAC-1, Ago2 PAZ domain, RAGE, AIM2, DHX36, DHX9, DDX41, IFI16, RIG-I, MDA5, LRRFIP1, DLM-1/ZBP1, TREX1, Laminin, and Fibronectin. In some embodiments, a plurality of oligonucleotides or an oligonucleotide composition can simultaneously modulate binding to multiple proteins, including maintaining the same binding levels to one group of proteins, decreasing binding levels to another group of proteins, and/or increasing binding level to yet another group of proteins. In some embodiments, provided oligonucleotides, compositions and methods provide increased binding to one or more serum proteins. In some embodiments, a serum protein is albumin. In some embodiments, provided oligonucleotides, compositions and methods provide decreased binding to one or more heparin sulfate-binding protein. In some embodiments, provided oligonucleotides, compositions and methods provide decreased binding to one or more Factor H.

In some embodiments, protein binding is decreased by more than 10%. In some embodiments, protein binding is decreased by more than 20%. In some embodiments, protein binding is decreased by more than 30%. In some embodiments, protein binding is decreased by more than 40%. In some embodiments, protein binding is decreased by more than 50%. In some embodiments, protein binding is decreased by more than 60%. In some embodiments, protein binding is decreased by more than 70%. In some embodiments, protein binding is decreased by more than 75%. In some embodiments, protein binding is decreased by more than 80%. In some embodiments, protein binding is decreased by more than 85%. In some embodiments, protein binding is decreased by more than 90%. In some embodiments, protein binding is decreased by more than 91%. In some embodiments, protein binding is decreased by more than 92%. In some embodiments, protein binding is decreased by more than 93%. In some embodiments, protein binding is decreased by more than 94%. In some embodiments, protein binding is decreased by more than 95%. In some embodiments, protein binding is decreased by more than 96%. In some embodiments, protein binding is decreased by more than 97%. In some embodiments, protein binding is decreased by more than 98%. In some embodiments, protein binding is decreased by more than 99%.

In some embodiments, protein binding is increased by more than 10%. In some embodiments, protein binding is increased by more than 20%. In some embodiments, protein binding is increased by more than 30%. In some embodiments, protein binding is increased by more than 40%. In some embodiments, protein binding is increased by more than 50%. In some embodiments, protein binding is increased by more than 60%. In some embodiments, protein binding is increased by more than 70%. In some embodiments, protein binding is increased by more than 80%. In some embodiments, protein binding is increased by more than 90%. In some embodiments, protein binding is increased by more than 100%. In some embodiments, protein binding is increased by more than 150%. In some embodiments, protein binding is increased by more than 2 folds. In some embodiments, protein binding is increased by more than 3 folds. In some embodiments, protein binding is increased by more than 4 folds. In some embodiments, protein binding is increased by more than 5 folds. In some embodiments, protein binding is increased by more than 6 folds. In some embodiments, protein binding is increased by more than 7 folds. In some embodiments, protein binding is increased by more than 8 folds. In some embodiments, protein binding is increased by more than 9 folds. In some embodiments, protein binding is increased by more than 10 folds. In some embodiments, protein binding is increased by more than 15 folds. In some embodiments, protein binding is increased by more than 20 folds. In some embodiments, protein binding is increased by more than 25 folds. In some embodiments, protein binding is increased by more than 30 folds. In some embodiments, protein binding is increased by more than 35 folds. In some embodiments, protein binding is increased by more than 40 folds. In some embodiments, protein binding is increased by more than 45 folds. In some embodiments, protein binding is increased by more than 50 folds. In some embodiments, protein binding is increased by more than 60 folds. In some embodiments, protein binding is increased by more than 70 folds. In some embodiments, protein binding is increased by more than 80 folds. In some embodiments, protein binding is increased by more than 90 folds. In some embodiments, protein binding is increased by more than 100 folds.

In some embodiments, the present disclosure provides assays for assessing protein binding. In some embodiments, protein binding can be assessed by binding to albumin. In some embodiments, protein binding can be assessed by binding to BSA. In some embodiments, protein binding can be assessed in vitro. Additional suitable assays are widely known in the art.

Chemical modifications, stereochemistry and combinations thereof that can improve protein binding profiles are extensively described in this disclosure. In some embodiments, more modified internucleotidic linkages can increase protein binding. In some embodiments, more phosphorothioate linkages can increase protein binding. In some embodiments, fewer modified internucleotidic linkages can decrease protein binding. In some embodiments, fewer phosphorothioate linkages can decrease protein binding. In some embodiments, more Sp chiral internucleotidic linkages increase protein binding. In some embodiments, fewer Sp chiral internucleotidic linkages decrease protein binding. In some embodiments, more modified bases increase protein binding. In some embodiments, fewer modified bases decrease protein binding. In some embodiments, one type of sugar modifications can increase protein binding compared to the other. In some embodiments, increased 2'-MOE content decrease protein biding when compared to 2'-OMe. The present disclosure provides numerous combinations of chemical modifications and/or stereochemistry patterns to improve protein binding profiles. In some embodiments, the present disclosure provides numerous combinations of chemical modifications and/or stereochemistry patterns to improve protein binding profiles while at the same time providing lower toxicities and/or better activities. Example oligonucleotides and compositions having these modifications, stereochemistry, or combinations thereof are described herein in this disclosure.

Delivery of oligonucleotides to targets can benefit from improved protein binding profile. In some embodiments, improved binding properties to certain proteins facilitate transportation of oligonucleotides to target cells, tissues, organs or organism. In some embodiments, improved binding properties to certain proteins promote release of oligonucleotides from proteins and other molecules so that they can perform their biological functions, including hybridization to target nucleic acid sequences, inhibition of functions of target nucleic acid sequences, cleavage of target nucleic acid sequences, etc. In some embodiments, provided oligonucleotides, compositions and methods provide improved uptake of oligonucleotides. In some embodiments, provided oligonucleotides, compositions and methods provide improved uptake of oligonucleotides.

In some embodiments, the present disclosure provides a method comprising administering a composition comprising a first plurality of oligonucleotides, which composition displays improved delivery as compared with a reference composition comprising a plurality of oligonucleotides, each of which also has the common base sequence but which differs structurally from the oligonucleotides of the first plurality in that:

individual oligonucleotides within the reference plurality differ from one another in stereochemical structure; and/or at least some oligonucleotides within the reference plurality have a structure different from a structure represented by the plurality of oligonucleotides of the composition; and/or at least some oligonucleotides within the reference plurality do not comprise a wing region and a core region.

In some embodiments, the present disclosure provides a method of administering an oligonucleotide composition comprising a first plurality of oligonucleotides having a common nucleotide sequence, the improvement that comprises:

administering an oligonucleotide comprising a first plurality of oligonucleotides that is characterized by improved delivery relative to a reference oligonucleotide composition of the same common nucleotide sequence.

In some embodiments, provided oligonucleotides, compositions and methods provide improved systemic delivery. In some embodiments, provided oligonucleotides, compositions and methods provide improved cytoplasmatic delivery. In some embodiments, improved delivery is to a population of cells. In some embodiments, improved delivery is to a tissue. In some embodiments, improved delivery is to an organ. In some embodiments, improved delivery is to an organism. Example structural elements (e.g., chemical modifications, stereochemistry, combinations thereof, etc.), oligonucleotides, compositions and methods that provide improved delivery are extensively described in this disclosure.

In some embodiments, the present disclosure provides methods for decreasing level of a target nucleic acid in a cell, tissue, and/or organism without low toxicity by contacting with a provided composition of this disclosure. In some embodiments, the present disclosure provides methods for decreasing level of a target nucleic acid in a cell, tissue, and/or organism without lower toxicity comparing to a reference composition by contacting with a provided composition of this disclosure. In some embodiments, the present disclosure provides methods for decreasing level of a target nucleic acid in a cell, tissue, and/or organism without significant complement activation by contacting with a provided composition of this disclosure. In some embodiments, the present disclosure provides methods for decreasing level of a target nucleic acid in a cell, tissue, and/or organism lower complement activation compared to a reference composition by contacting with a provided composition of this disclosure.

In some embodiments, the present disclosure provides methods for identifying and/or characterizing an oligonucleotide composition with improved properties, e.g., toxicities, activities, etc. In some embodiments, the present disclosure provides methods for identifying and/or characterizing an oligonucleotide composition with lower toxicities compared to a reference composition. In some embodiments, the present disclosure provides methods for identifying and/or characterizing an oligonucleotide composition with improved protein binding profiles compared to a reference composition.

In some embodiments, the present disclosure provides a method of identifying and/or characterizing an oligonucleotide composition, the method comprising steps of: providing at least one composition comprising a first plurality of oligonucleotides; and assessing toxicity relative to a reference composition.

In some embodiments, the present disclosure provides a method of identifying and/or characterizing an oligonucleotide composition, the method comprising steps of: providing at least one composition comprising a first plurality of oligonucleotides; and assessing complement activation relative to a reference composition.

In some embodiments, the present disclosure provides a method of identifying and/or characterizing an oligonucleotide composition, the method comprising steps of: providing at least one composition comprising a first plurality of oligonucleotides; and assessing protein binding profile relative to a reference composition.

In some embodiments, the present disclosure provides a method of identifying and/or characterizing an oligonucleotide composition, the method comprising steps of: providing at least one composition comprising a first plurality of oligonucleotides; and assessing delivery relative to a reference composition.

In some embodiments, the present disclosure provides a method of identifying and/or characterizing an oligonucleotide composition, the method comprising steps of: providing at least one composition comprising a first plurality of oligonucleotides; and assessing cellular uptake relative to a reference composition.

In some embodiments, properties of a provided oligonucleotide compositions are compared to a reference oligonucleotide composition. In some embodiments, a reference oligonucleotide composition comprises a reference plurality of oligonucleotides.

In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages.

In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a chirally un-controlled (or stereorandom) composition of oligonucleotides having the same base sequence and chemical modifications.

In some embodiments, a reference composition is a composition of oligonucleotides having the same base sequence but different chemical modifications. In some embodiments, a reference composition is a composition of oligonucleotides having the same base sequence, base modifications, internucleotidic linkage modifications but different sugar modifications. In some embodiments, a reference composition has fewer 2'-modified sugar modifications. In some embodiments, a reference composition is a composition of oligonucleotides having the same base sequence, base modifications, sugar modifications but different internucleotidic linkage modifications. In some embodiments, a reference composition has more internucleotidic linkage modifications. In some embodiments, a reference composition has fewer natural phosphate linkages. In some embodiments, a reference composition comprising oligonucleotides having no natural phosphate linkages.

In some embodiments, a reference composition is a composition comprising a reference plurality of oligonucleotides wherein individual oligonucleotides within the reference plurality differ from one another in stereochemical structure. In some embodiments, a reference composition is a composition comprising a reference plurality of oligonucleotides, wherein at least some oligonucleotides within the reference plurality have a structure different from a structure represented by a plurality of oligonucleotides of a composition compared to the reference composition. In some embodiments, a reference composition is a composition comprising a reference plurality of oligonucleotides wherein at least some oligonucleotides within the reference plurality do not comprise a wing region and a core region.

In some embodiments, a reference oligonucleotide composition comprises a reference plurality of oligonucleotides having the same common nucleotide sequence but lacking at least one of the one or more modified sugar moieties in oligonucleotides of the oligonucleotide composition compared to the reference composition. In some embodiments, a reference oligonucleotide composition comprises a reference plurality of oligonucleotides having the same common nucleotide sequence but have no modified sugar moieties. In some embodiments, a reference oligonucleotide composition comprises a reference plurality of oligonucleotides having the same common nucleotide sequence but do not comprise natural phosphate linkages. In some embodiments, a reference composition is a chirally controlled oligonucleotide composition of oligonucleotides having the same chemical modification patterns. In some embodiments, a reference composition is a chirally controlled oligonucleotide composition of another stereoisomer.

In some embodiments, oligonucleotides of the first plurality comprise one or more structural elements (e.g., modifications, stereochemistry, patterns, etc.) that oligonucleotides of the reference plurality do not all have. Such structural elements can be any one described in this disclosure.

In some embodiments, oligonucleotides of the first plurality comprise more phosphorothioate linkages than oligonucleotides of the reference composition. In some embodiments, oligonucleotides of the first plurality comprise more phosphorothioate linkages than oligonucleotides of the reference composition at the 5'-end region. In some embodiments, oligonucleotides of the first plurality comprise more phosphorothioate linkages than oligonucleotides of the reference composition at the 3'-end region. In some embodiments, oligonucleotides of the first plurality comprise more phosphorothioate linkages in a wing region than the corresponding region of oligonucleotides of the reference composition. In some embodiments, oligonucleotides of the first plurality comprise more phosphorothioate linkages in each wing region than the corresponding regions in oligonucleotides of the reference composition. In some embodiments, oligonucleotides of the first plurality comprise more Sp chiral internucleotidic linkages than oligonucleotides of the reference composition. In some embodiments, oligonucleotides of the first plurality comprise more Sp phosphorothioate linkages than oligonucleotides of the reference composition. In some embodiments, oligonucleotides of the first plurality comprise more Sp phosphorothioate linkages than oligonucleotides of the reference composition at the 5'-end region. In some embodiments, oligonucleotides of the first plurality comprise more Sp phosphorothioate linkages than oligonucleotides of the reference composition at the 3'-end region. In some embodiments, oligonucleotides of the first plurality comprise more Sp phosphorothioate linkages in a wing region than oligonucleotides of the reference composition. In some embodiments, oligonucleotides of the first plurality comprise more Sp phosphorothioate linkages in each wing region than oligonucleotides of the reference composition. In some embodiments, oligonucleotides of the first plurality comprise more modified bases than oligonucleotides of the reference composition. In some embodiments, oligonucleotides of the first plurality comprise more methylated bases than oligonucleotides of the reference composition. In some embodiments, oligonucleotides of the first plurality comprise more methylated bases than oligonucleotides of the reference composition at the 5'-end region. In some embodiments, oligonucleotides of the first plurality comprise more methylated bases than oligonucleotides of the reference composition at the 3'-end region. In some embodiments, oligonucleotides of the first plurality comprise more methylated bases than in a wing region than oligonucleotides of the reference composition. In some embodiments, oligonucleotides of the first plurality comprise more methylated bases than in each wing region than oligonucleotides of the reference composition. In some embodiments, oligonucleotides of the first plurality comprise fewer 2'-MOE modifications than oligonucleotides of the reference composition. In some embodiments, oligonucleotides of the first plurality comprise fewer 2'-MOE modifications than oligonucleotides of the reference composition. In some embodiments, oligonucleotides of the first plurality comprise fewer 2'-MOE modifications than oligonucleotides of the reference composition at the 5'-end region. In some embodiments, oligonucleotides of the first plurality comprise fewer 2'-MOE modifications than oligonucleotides of the reference composition at the 3'-end. In some embodiments, oligonucleotides of the first plurality comprise fewer 2'-MOE modifications than in a wing region than oligonucleotides of the reference composition. In some embodiments, oligonucleotides of the first plurality comprise fewer 2'-MOE modifications than in each wing region than oligonucleotides of the reference composition. In some embodiments, individual oligonucleotides within the reference plurality differ from one another in stereochemical structure. In some embodiments, at least some oligonucleotides within the reference plurality have a structure different from a structure represented by the plurality of oligonucleotides of the composition. In some embodiments, at least some oligonucleotides within the reference plurality do not comprise a wing region and a core region. In some embodiments, the reference composition is a substantially racemic preparation of oligonucleotides that share the base sequence. In some embodiments, the reference composition is a chirally controlled oligonucleotide composition of another oligonucleotide type. In some embodiments, oligonucleotides of the reference composition comprise more phosphorothioate linkages. In some embodiments, oligonucleotides of the reference composition comprise only phosphorothioate linkages. In some embodiments, oligonucleotides of the reference composition comprise fewer modified sugar moieties. In some embodiments, oligonucleotides of the reference composition comprise fewer modified sugar moieties, wherein the modification is 2'-OR$^1$. In some embodiments, oligonucleotides of the reference composition comprise more modified sugar moieties. In some embodiments, oligonucleotides of the reference composition comprise more modified sugar moieties, the modification is 2'-$OR^1$. In some embodiments, oligonucleotides of the reference composition comprise fewer phosphorothioate linkages. In some embodiments, oligonucleotides of the reference composition have a wing, and comprise fewer phosphorothioate linkages at the wing. In some embodiments, oligonucleotides of the reference composition comprise fewer Sp phosphorothioate linkages. In some embodiments, oligonucleotides of the reference composition have a wing, and comprise fewer Sp phosphorothioate linkages at the wing. In some embodiments, oligonucleotides of the reference composition comprise more Rp phosphorothioate linkages. In some embodiments, oligonucleotides of the reference composition have a wing, and comprise more Rp phosphorothioate linkages at the wing. In some embodiments, oligonucleotides of the reference composition comprise fewer methylated bases. In some embodiments, oligonucleotides of the reference composition comprise more 2'-MOE modifications. In some embodiments, oligonucleotides of the reference composition comprise fewer natural phosphate linkages. In some embodiments, oligonucleotides of the reference composition comprise fewer natural phosphate linkages at the 5'- and/or 3'-end. In some embodiments, oligonucleotides of the reference composition comprise fewer natural phosphate linkages in a region corresponding to a wing of oligonucleotides of the first plurality. In some embodiments, oligonucleotides of the first plurality comprise natural phosphate linkages in a wing, and oligonucleotides of the reference composition comprise fewer natural phosphate linkages at the corresponding wing region. In some embodiments, oligonucleotides of the first plurality comprises natural phosphate linkages in a wing, and oligonucleotides of the reference composition comprises modified internucleotidic linkages at one or more such natural phosphate linkage locations in a wing. In some embodiments, oligonucleotides of the first plurality comprise natural phosphate linkages in a wing, and oligonucleotides of the reference composition comprises phosphorothioate linkages at one or more such natural phosphate linkage locations in a wing. In some embodiments, oligonucleotides of the reference composition comprise no natural phosphate linkages. In some embodiments, oligonucleotides of the reference composition comprise no wing-core-wing structure. In some embodiments, oligonucleotides of the first plurality comprise a 5'-end wing region comprising a natural phosphate linkage between the two nucleosides at its 3'-end, and oligonucleotides of a reference plurality do not have a natural phosphate linkage at the same position. In some embodiments, oligonucleotides of the first plurality comprise a 3'-end wing region comprising a natural phosphate linkage between the two nucleosides at its 5'-end, and oligonucleotides of a reference plurality do not have a natural phosphate linkage at the same position.

In some embodiments, provided chirally controlled oligonucleotide compositions comprises oligonucleotides of one oligonucleotide type. In some embodiments, provided chirally controlled oligonucleotide compositions comprises oligonucleotides of only one oligonucleotide type. In some embodiments, provided chirally controlled oligonucleotide compositions has oligonucleotides of only one oligonucleotide type. In some embodiments, provided chirally controlled oligonucleotide compositions comprises oligonucleotides of two or more oligonucleotide types. In some embodiments, using such compositions, provided methods can target more than one target. In some embodiments, a chirally controlled oligonucleotide composition comprising two or more oligonucleotide types targets two or more targets. In some embodiments, a chirally controlled oligonucleotide composition comprising two or more oligonucleotide types targets two or more mismatches. In some embodiments, a single oligonucleotide type targets two or more targets, e.g., mutations. In some embodiments, a target region of oligonucleotides of one oligonucleotide type comprises two or more "target sites" such as two mutations or SNPs.

In some embodiments, oligonucleotides in a provided chirally controlled oligonucleotide composition optionally comprise modified bases or sugars. In some embodiments, a provided chirally controlled oligonucleotide composition does not have any modified bases or sugars. In some embodiments, a provided chirally controlled oligonucleotide composition does not have any modified bases. In some embodiments, oligonucleotides in a provided chirally controlled oligonucleotide composition comprise modified bases and sugars. In some embodiments, oligonucleotides in a provided chirally controlled oligonucleotide composition comprise a modified base. In some embodiments, oligonucleotides in a provided chirally controlled oligonucleotide composition comprise a modified sugar. Modified bases and sugars for oligonucleotides are widely known in the art, including but not limited in those described in the present disclosure. In some embodiments, a modified base is 5-mC. In some embodiments, a modified sugar is a 2'-modified sugar. Suitable 2'-modification of oligonucleotide sugars are widely known by a person having ordinary skill in the art. In some embodiments, 2'-modifications include but are not limited to 2'-$OR^1$, wherein $R^1$ is not hydrogen. In some embodiments, a 2'-modification is 2'-$OR^1$, wherein $R^1$ is optionally substituted $C_{1-6}$ aliphatic. In some embodiments, a 2'-modification is 2'-MOE. In some embodiments, a modification is 2'-halogen. In some embodiments, a modification is 2'-F. In some embodiments, modified bases or sugars may further enhance activity, stability and/or selectivity of a chirally controlled oligonucleotide composition, whose common pattern of backbone chiral centers provides unexpected activity, stability and/or selectivity.

In some embodiments, a provided chirally controlled oligonucleotide composition does not have any modified sugars. In some embodiments, a provided chirally controlled oligonucleotide composition does not have any 2'-modified sugars. In some embodiments, the present disclosure surprisingly found that by using chirally controlled oligonucleotide compositions, modified sugars are not needed for stability, activity, and/or control of cleavage patterns. Furthermore, in some embodiments, the present disclosure surprisingly found that chirally controlled oligonucleotide compositions of oligonucleotides without modified sugars deliver better properties in terms of stability, activity, turnover and/or control of cleavage patterns. For example, in some embodiments, it is surprisingly found that chirally controlled oligonucleotide compositions of oligonucleotides having no modified sugars dissociates much faster from cleavage products and provide significantly increased turnover than compositions of oligonucleotides with modified sugars.

As discussed in detail herein, the present disclosure provides, among other things, a chirally controlled oligonucleotide composition, meaning that the composition contains a plurality of oligonucleotides of at least one type. Each oligonucleotide molecule of a particular "type" is comprised of preselected (e.g., predetermined) structural elements with respect to: (1) base sequence; (2) pattern of backbone linkages; (3) pattern of backbone chiral centers; and (4) pattern of backbone P-modification moieties. In some embodiments, provided oligonucleotide compositions contain oligonucleotides that are prepared in a single synthesis process. In some embodiments, provided compositions contain oligonucleotides having more than one chiral configuration within a single oligonucleotide molecule (e.g., where different residues along the oligonucleotide have different stereochemistry); in some such embodiments, such oligonucleotides may be obtained in a single synthesis process, without the need for secondary conjugation steps to generate individual oligonucleotide molecules with more than one chiral configuration.

Oligonucleotide compositions as provided herein can be used as agents for modulating a number of cellular processes and machineries, including but not limited to, transcription, translation, immune responses, epigenetics, etc. In addition, oligonucleotide compositions as provided herein can be used as reagents for research and/or diagnostic purposes. One of ordinary skill in the art will readily recognize that the present disclosure herein is not limited to particular use but is applicable to any situations where the use of synthetic oligonucleotides is desirable. Among other things, provided compositions are useful in a variety of therapeutic, diagnostic, agricultural, and/or research applications.

In some embodiments, provided oligonucleotide compositions comprise oligonucleotides and/or residues thereof that include one or more structural modifications as described in detail herein. In some embodiments, provided oligonucleotide compositions comprise oligonucleoties that contain one or more nucleic acid analogs. In some embodiments, provided oligonucleotide compositions comprise oligonucleotides that contain one or more artificial nucleic acids or residues (e.g., a nucleotide analog), including but not limited to: a peptide nucleic acid (PNA), locked nucleic acid (LNA), morpholino, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA), threose nucleic acids (TNA), and/or Xeno nucleic acids (XNA), and any combination thereof.

In any of the embodiments, the disclosure is useful for oligonucleotide-based modulation of gene expression, immune response, etc. Accordingly, stereo-defined, oligonucleotide compositions of the disclosure, which contain oligonucleotides of predetermined type (i.e., which are chirally controlled, and optionally chirally pure), can be used in lieu of conventional stereo-random or chirally impure counterparts. In some embodiments, provided compositions show enhanced intended effects and/or reduced unwanted side effects. Certain embodiments of biological and clinical/therapeutic applications of the disclosure are discussed explicitly below.

Various dosing regimens can be utilized to administer provided chirally controlled oligonucleotide compositions. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is same as or different from the first dose (or another prior dose) amount. In some embodiments, a dosing regimen comprises administering at least one unit dose for at least one day. In some embodiments, a dosing regimen comprises administering more than one dose over a time period of at least one day, and sometimes more than one day. In some embodiments, a dosing regimen comprises administering multiple doses over a time period of at least week. In some embodiments, the time period is at least 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per week for more than one week. In some embodiments, a dosing regimen comprises administering one dose per week for 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose every two weeks for more than two week period. In some embodiments, a dosing regimen comprises administering one dose every two weeks over a time period of 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per month for one month. In some embodiments, a dosing regimen comprises administering one dose per month for more than one month. In some embodiments, a dosing regimen comprises administering one dose per month for 2, 3, 4, 5, 6, 7, 8, 9, 10, 11, 12, or more months. In some embodiments, a dosing regimen comprises administering one dose per week for about 10 weeks. In some embodiments, a dosing regimen comprises administering one dose per week for about 20 weeks. In some embodiments, a dosing regimen comprises administering one dose per week for about 30 weeks. In some embodiments, a dosing regimen comprises administering one dose per week for 26 weeks. In some embodiments, a chirally controlled oligonucleotide composition is administered according to a dosing regimen that differs from that utilized for a chirally uncontrolled (e.g., stereorandom) oligonucleotide composition of the same sequence, and/or of a different chirally controlled oligonucleotide composition of the same sequence. In some embodiments, a chirally controlled oligonucleotide composition is administered according to a dosing regimen that is reduced as compared with that of a chirally uncontrolled (e.g., stereorandom) oligonucleotide composition of the same sequence in that it achieves a lower level of total exposure over a given unit of time, involves one or more lower unit doses, and/or includes a smaller number of doses over a given unit of time. In some embodiments, a chirally controlled oligonucleotide composition is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, a chirally controlled oligonucleotide composition has a longer dosing regimen compared to the corresponding chirally uncontrolled oligonucleotide composition. In some embodiments, a chirally controlled oligonucleotide composition has a shorter time period between at least two doses compared to the corresponding chirally uncontrolled oligonucleotide composition. Without wishing to be limited by theory, Applicant notes that in some embodiments longer dosing regimen, and/or shorter time periods between doses, may be due to the improved safety of a chirally controlled oligonucleotide composition.

In some embodiments, with their low toxicity, provided oligonucleotides and compositions can be administered in higher dosage and/or with higher frequency. In some embodiments, with their improved delivery (and other properties), provided compositions can be administered in lower dosages and/or with lower frequency to achieve biological effects, for example, clinical efficacy.

A single dose can contain various amounts of oligonucleotides. In some embodiments, a single dose can contain various amounts of a type of chirally controlled oligonucleotide, as desired suitable by the application. In some embodiments, a single dose contains about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more (e.g., about 350, 400, 450, 500, 550, 600, 650, 700, 750, 800, 850, 900, 950, 1000 or more) mg of a type of chirally controlled oligonucleotide. In some embodiments, a single dose contains about 1 mg of a type of chirally controlled oligonucleotide. In some embodiments, a single dose contains about 5 mg of a type of chirally controlled oligonucleotide. In some embodiments, a single dose contains about 10 mg of a type of chirally controlled oligonucleotide. In some embodiments, a single dose contains about 15 mg of a type of chirally controlled oligonucleotide. In some embodiments, a single dose contains about 20 mg of a type of chirally controlled oligonucleotide. In some embodiments, a single dose contains about 50 mg of a type of chirally controlled oligonucleotide. In some embodiments, a single dose contains about 100 mg of a type of chirally controlled oligonucleotide. In some embodiments, a single dose contains about 150 mg of a type of chirally controlled oligonucleotide. In some embodiments, a single dose contains about 200 mg of a type of chirally controlled oligonucleotide. In some embodiments, a single dose contains about 250 mg of a type of chirally controlled oligonucleotide. In some embodiments, a single dose contains about 300 mg of a type of chirally controlled oligonucleotide. In some embodiments, a chirally controlled oligonucleotide is administered at a lower amount in a single dose, and/or in total dose, than a chirally uncontrolled oligonucleotide. In some embodiments, a chirally controlled oligonucleotide is administered at a lower amount in a single dose, and/or in total dose, than a chirally uncontrolled oligonucleotide due to improved efficacy. In some embodiments, a chirally controlled oligonucleotide is administered at a higher amount in a single dose, and/or in total dose, than a chirally uncontrolled oligonucleotide. In some embodiments, a chirally controlled oligonucleotide is administered at a higher amount in a single dose, and/or in total dose, than a chirally uncontrolled oligonucleotide due to improved safety.

Biologically Active Oligonucleotides

A provided oligonucleotide composition as used herein may comprise single stranded and/or multiply stranded oligonucleotides. In some embodiments, single-stranded oligonucleotides contain self-complementary portions that may hybridize under relevant conditions so that, as used, even single-stranded oligonucleotides may have at least partially double-stranded character. In some embodiments, an oligonucleotide included in a provided composition is single-stranded, double-stranded, or triple-stranded. In some embodiments, an oligonucleotide included in a provided composition comprises a single-stranded portion and a multiple-stranded portion within the oligonucleotide. In some embodiments, as noted above, individual single-stranded oligonucleotides can have double-stranded regions and single-stranded regions.

In some embodiments, provided compositions include one or more oligonucleotides fully or partially complementary to strand of: structural genes, genes control and/or termination regions, and/or self-replicating systems such as viral or plasmid DNA. In some embodiments, provided compositions include one or more oligonucleotides that are or act as siRNAs or other RNA interference reagents (RNAi agents or iRNA agents), shRNA, antisense oligonucleotides, self-cleaving RNAs, ribozymes, fragment thereof and/or variants thereof (such as Peptidyl transferase 23S rRNA, RNase P, Group I and Group II introns, GIR1 branching ribozymes, Leadzyme, Hairpin ribozymes, Hammerhead ribozymes, HDV ribozymes, Mammalian CPEB3 ribozyme, VS ribozymes, glmS ribozymes, CoTC ribozyme, etc.), microRNAs, microRNA mimics, supermirs, aptamers, antimirs, antagomirs, $U_1$ adaptors, triplex-forming oligonucleotides, RNA activators, long non-coding RNAs, short non-coding RNAs (e.g., piRNAs), immunomodulatory oligonucleotides (such as immunostimulatory oligonucleotides, immunoinhibitory oligonucleotides), GNA, LNA, ENA, PNA, TNA, HNA, TNA, XNA, HeNA, CeNA, morpholinos, G-quadruplex (RNA and DNA), antiviral oligonucleotides, and decoy oligonucleotides.

In some embodiments, provided compositions include one or more hybrid (e.g., chimeric) oligonucleotides. In the context of the present disclosure, the term "hybrid" broadly refers to mixed structural components of oligonucleotides. Hybrid oligonucleotides may refer to, for example, (1) an oligonucleotide molecule having mixed classes of nucleotides, e.g., part DNA and part RNA within the single molecule (e.g., DNA-RNA); (2) complementary pairs of nucleic acids of different classes, such that DNA:RNA base pairing occurs either intramolecularly or intermolecularly; or both; (3) an oligonucleotide with two or more kinds of the backbone or internucleotide linkages.

In some embodiments, provided compositions include one or more oligonucleotide that comprises more than one classes of nucleic acid residues within a single molecule. For example, in any of the embodiments described herein, an oligonucleotide may comprise a DNA portion and an RNA portion. In some embodiments, an oligonucleotide may comprise a unmodified portion and modified portion.

Provided oligonucleotide compositions can include oligonucleotides containing any of a variety of modifications, for example as described herein. In some embodiments, particular modifications are selected, for example, in light of intended use. In some embodiments, it is desirable to modify one or both strands of a double-stranded oligonucleotide (or a double-stranded portion of a single-stranded oligonucleoties). In some embodiments, the two strands (or portions) include different modifications. In some embodiments, the two strands include the same modifications. One of skill in the art will appreciate that the degree and type of modifications enabled by methods of the present disclosure allow for numerous permutations of modifications to be made. Example such modifications are described herein and are not meant to be limiting.

The phrase "antisense strand" as used herein, refers to an oligonucleotide that is substantially or 100% complementary to a target sequence of interest. The phrase "antisense strand" includes the antisense region of both oligonucleotides that are formed from two separate strands, as well as unimolecular oligonucleotides that are capable of forming hairpin or dumbbell type structures. The terms "antisense strand" and "guide strand" are used interchangeably herein.

The phrase "sense strand" refers to an oligonucleotide that has the same nucleoside sequence, in whole or in part, as a target sequence such as a messenger RNA or a sequence of DNA. The terms "sense strand" and "passenger strand" are used interchangeably herein.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant. In some embodiments, a target sequence is associated with a disease or disorder.

By "specifically hybridizable" and "complementary" is meant that a nucleic acid can form hydrogen bond(s) with another nucleic acid sequence by either traditional Watson-Crick or other non-traditional types. In reference to the nucleic molecules of the present disclosure, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, *CSH Symp. Quant. Biol. LIT* pp. 123-133; Frier et al., 1986, *Proc. Nat. Acad. Sci. USA* 83:9373-9377; Turner et al., 1987, *I. Ain. Chem. Soc.* 109:3783-3785)

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, e.g., under physiological conditions in the case of in vivo assays or therapeutic treatment, or in the case of in vitro assays, under conditions in which the assays are performed. In some embodiments, non-target sequences differ from corresponding target sequences by at least 5 nucleotides.

When used as therapeutics, a provided oligonucleotide is administered as a pharmaceutical composition. In some embodiments, the pharmaceutical composition comprises a therapeutically effective amount of a provided oligonucleotide comprising, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In another embodiment, the pharmaceutical composition is formulated for intravenous injection, oral administration, buccal administration, inhalation, nasal administration, topical administration, ophthalmic administration or optic administration. In further embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

Pharmaceutical Compositions

When used as therapeutics, a provided oligonucleotide or oligonucleotide composition described herein is administered as a pharmaceutical composition. In some embodiments, the pharmaceutical composition comprises a therapeutically effective amount of a provided oligonucleotides, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In some embodiments, the pharmaceutical composition is formulated for intravenous injection, oral administration, buccal administration, inhalation, nasal administration, topical administration, ophthalmic administration or optic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled oligonucleotide, or composition thereof, in admixture with a pharmaceutically acceptable excipient. One of skill in the art will recognize that the pharmaceutical compositions include the pharmaceutically acceptable salts of the chirally controlled oligonucleotide, or composition thereof, described above.

A variety of supramolecular nanocarriers can be used to deliver nucleic acids. Example nanocarriers include, but are not limited to liposomes, cationic polymer complexes and various polymeric. Complexation of nucleic acids with various polycations is another approach for intracellular delivery; this includes use of PEGlyated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, polymer micelles, quantum dots and lipoplexes.

Additional nucleic acid delivery strategies are known in addition to the example delivery strategies described herein.

In therapeutic and/or diagnostic applications, the compounds of the disclosure can be formulated for a variety of modes of administration, including systemic and topical or localized administration. Techniques and formulations generally may be found in Remington, The Science and Practice of Pharmacy, (20th ed. 2000).

Provided oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. Broad distribution of oligonucleotides and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with oligonucleotides of this disclosure. For example, chemotherapeutic agents or other anti-proliferative agents may be combined with the oligonucleotides of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

The function and advantage of these and other embodiments of the present disclosure will be more fully understood from the examples described below. The following examples are intended to illustrate the benefits of the present disclosure, but do not exemplify the full scope of the disclosure.

Lipids

In some embodiments, provided oligonucleotide compositions further comprise one or more lipids. In some embodiments, the lipids are conjugated to provided oligonucleotides in the compositions. In some embodiments, two or more same or different lipids can be conjugated to one oligonucleotide, through either the same or differently chemistry and/or locations. In some embodiments, a composition can comprise an oligonucleotide disclosed herein (as non-limiting examples, a chirally controlled oligonucleotide composition, or a chirally controlled oligonucleotide composition wherein the sequence of the oligonucleotide comprises, consists of or is the sequence of any oligonucleotide disclosed herein, or a chirally controlled oligonucleotide composition wherein the sequence of the oligonucleotide comprises, consists of or is the sequence of any oligonucleotide disclosed in Table 8 or any other Table herein, etc.) and a lipid. In some embodiments, a provided oligonucleotide comprises base sequence, pattern of backbone linkages, pattern or backbone chiral centers, and/or pattern of chemical modifications (e.g., base modifications, sugar modifications, etc.) of any oligonucleotide disclosed herein, and is conjugated to a lipid. In some embodiments, a provided composition comprises an oligonucleotide disclosed herein and a lipid, wherein the lipid is conjugated to the oligonucleotide.

In some embodiments, the present disclosure provides a composition comprising an oligonucleotide and a lipid. Many lipids can be utilized in provided technologies in accordance with the present disclosure.

In some embodiments, a lipid comprises an $R^{LD}$ group, wherein $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—, wherein:

each R' is independently —R, —C(O)R, —$CO_2$R, or —$SO_2$R, or:

two R' are taken together with their intervening atoms to form an optionally substituted aryl, carbocyclic, heterocyclic, or heteroaryl ring;

-Cy- is an optionally substituted bivalent ring selected from carbocyclylene, arylene, heteroarylene, and heterocyclylene; and each R is independently hydrogen, or an optionally substituted group selected from $C_1$-$C_6$ aliphatic, phenyl, carbocyclyl, aryl, heteroaryl, or heterocyclyl.

In some embodiments, a lipid comprises an $R^{LD}$ group, wherein $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—, wherein:

each R' is independently —R, —C(O)R, —$CO_2$R, or —$SO_2$R, or:

two R' are taken together with their intervening atoms to form an optionally substituted aryl, carbocyclic, heterocyclic, or heteroaryl ring;

-Cy- is an optionally substituted bivalent ring selected from carbocyclylene, arylene, heteroarylene, and heterocyclylene; and each R is independently hydrogen, or an optionally substituted group selected from $C_1$-$C_6$ aliphatic, phenyl, carbocyclyl, aryl, heteroaryl, or heterocyclyl.

In some embodiments, a lipid comprises an $R^{LD}$ group, wherein $R^{LD}$ is an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—, wherein:

each R' is independently —R, —C(O)R, —$CO_2$R, or —$SO_2$R, or:

two R' are taken together with their intervening atoms to form an optionally substituted aryl, carbocyclic, heterocyclic, or heteroaryl ring;

-Cy- is an optionally substituted bivalent ring selected from carbocyclylene, arylene, heteroarylene, and heterocyclylene; and each R is independently hydrogen, or an optionally substituted group selected from $C_1$-$C_6$ aliphatic, phenyl, carbocyclyl, aryl, heteroaryl, or heterocyclyl.

In some embodiments, $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

In some embodiments, $R^{LD}$ is an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

The aliphatic group of $R^{LD}$ can be a variety of suitable length. In some embodiments, it is $C_{10}$-$C_{80}$. In some embodiments, it is $C_{10}$-$C_{75}$. In some embodiments, it is $C_{10}$-$C_{70}$. In some embodiments, it is $C_{10}$-$C_{65}$. In some embodiments, it is $C_{10}$-$C_{60}$. In some embodiments, it is $C_{10}$-$C_{50}$. In some embodiments, it is $C_{10}$-$C_{40}$. In some embodiments, it is $C_{10}$-$C_{35}$. In some embodiments, it is $C_{10}$-$C_{30}$. In some embodiments, it is $C_{10}$-$C_{25}$. In some embodiments, it is $C_{10}$-$C_{24}$. In some embodiments, it is $C_{10}$—$C_{23}$. In some embodiments, it is $C_{10}$-$C_{22}$. In some embodiments, it is $C_{10}$-$C_{21}$. In some embodiments, it is $C_{12}$-$C_{22}$. In some embodiments, it is $C_{13}$-$C_{22}$. In some embodiments, it is $C_{14}$-$C_{22}$. In some embodiments, it is $C_{15}$-$C_{22}$. In some embodiments, it is $C_{16}$-$C_{22}$. In some embodiments, it is $C_{17}$-$C_{22}$. In some embodiments, it is $C_{18}$-$C_{22}$. In some embodiments, it is $C_{10}$-$C_{20}$. In some embodiments, the lower end of the range is $C_{10}$, $C_{11}$, $C_{12}$, $C_{13}$, $C_{14}$, $C_{15}$, $C_{16}$, $C_{17}$, or $C_{18}$. In some embodiments, the higher end of the range is $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{55}$, or $C_{60}$. In some embodiments, it is $C_{10}$. In some embodiments, it is $C_{11}$. In some embodiments, it is $C_{12}$. In some embodiments, it is $C_{13}$. In some embodiments, it is $C_{14}$. In some embodiments, it is $C_{15}$. In some embodiments, it is $C_{16}$. In some embodiments, it is $C_{17}$. In some embodiments, it is $C_{18}$. In some embodiments, it is $C_{19}$. In some embodiments, it is $C_{20}$. In some embodiments, it is $C_{21}$. In some embodiments, it is $C_{22}$. In some embodiments, it is $C_{23}$. In some embodiments, it is $C_{24}$. In some embodiments, it is $C_{25}$. In some embodiments, it is $C_{30}$. In some embodiments, it is $C_{35}$. In some embodiments, it is $C_{40}$. In some embodiments, it is $C_{45}$. In some embodiments, it is $C_{50}$. In some embodiments, it is $C_{55}$. In some embodiments, it is $C_{60}$.

In some embodiments, a lipid comprises no more than one $R^{LD}$ group. In some embodiments, a lipid comprises two or more $R^{LD}$ groups.

In some embodiments, a lipid is conjugated to a biologically active agent, optionally through a linker, as a moiety comprising an $R^{LD}$ group. In some embodiments, a lipid is conjugated to a biologically active agent, optionally through a linker, as a moiety comprising no more than one $R^{LD}$ group. In some embodiments, a lipid is conjugated to a biologically active agent, optionally through a linker, as an $R^{LD}$ group. In some embodiments, a lipid is conjugated to a biologically active agent, optionally through a linker, as a moiety comprising two or more $R^{LD}$ groups.

In some embodiments, $R^{LD}$ is an optionally substituted, $C_{10}$-$C_{40}$ saturated or partially unsaturated, aliphatic chain. In some embodiments, a lipid comprises an optionally substituted $C_{10}$-$C_{40}$ saturated or partially unsaturated, aliphatic chain.

In some embodiments, $R^{LD}$ is an optionally substituted $C_{10}$-$C_{40}$ linear, saturated or partially unsaturated, aliphatic chain. In some embodiments, a lipid comprises an optionally substituted $C_{10}$-$C_{40}$ linear, saturated or partially unsaturated, aliphatic chain.

In some embodiments, $R^{LD}$ is a $C_{10}$-$C_{40}$ linear, saturated or partially unsaturated, aliphatic chain, optionally substituted with one or more $C_{1-4}$ aliphatic groups. In some embodiments, a lipid comprises a $C_{10}$-$C_{40}$ linear, saturated or partially unsaturated, aliphatic chain, optionally substituted with one or more $C_{1-4}$ aliphatic groups. In some embodiments, $R^{LD}$ is a $C_{10}$-$C_{40}$ linear, saturated or partially unsaturated, aliphatic chain, optionally substituted with one or more $C_{1-2}$ aliphatic groups. In some embodiments, a lipid comprises a $C_{10}$-$C_{40}$ linear, saturated or partially unsaturated, aliphatic chain, optionally substituted with one or more $C_{1-2}$ aliphatic groups. In some embodiments, $R^{LD}$ is a $C_{10}$-$C_{40}$ linear, saturated or partially unsaturated, aliphatic chain, optionally substituted with one or more methyl groups. In some embodiments, a lipid comprises a $C_{10}$-$C_{40}$ linear, saturated or partially unsaturated, aliphatic chain, optionally substituted with one or more methyl groups.

In some embodiments, $R^{LD}$ is an unsubstituted $C_{10}$-$C_{40}$ linear, saturated or partially unsaturated, aliphatic chain. In some embodiments, a lipid comprises an unsubstituted $C_{10}$-$C_{40}$ linear, saturated or partially unsaturated, aliphatic chain.

In some embodiments, a lipid comprises no more than one optionally substituted $C_{10}$-$C_{40}$ linear, saturated or partially unsaturated, aliphatic chain. In some embodiments, a lipid comprises two or more optionally substituted $C_{10}$-$C_{40}$ linear, saturated or partially unsaturated, aliphatic chain.

In some embodiments, $R^{LD}$ is an optionally substituted, $C_{10}$-$C_{60}$ saturated or partially unsaturated, aliphatic chain. In some embodiments, a lipid comprises an optionally substituted $C_{10}$-$C_{60}$ saturated or partially unsaturated, aliphatic chain.

In some embodiments, $R^{LD}$ is an optionally substituted $C_{10}$-$C_{60}$ linear, saturated or partially unsaturated, aliphatic chain. In some embodiments, a lipid comprises an optionally substituted $C_{10}$-$C_{60}$ linear, saturated or partially unsaturated, aliphatic chain.

In some embodiments, $R^{LD}$ is a $C_{10}$-$C_{60}$ linear, saturated or partially unsaturated, aliphatic chain, optionally substituted with one or more $C_{1-4}$ aliphatic groups. In some embodiments, a lipid comprises a $C_{10}$-$C_{60}$ linear, saturated or partially unsaturated, aliphatic chain, optionally substituted with one or more $C_{1-4}$ aliphatic groups. In some embodiments, $R^{LD}$ is a $C_{10}$-$C_{60}$ linear, saturated or partially unsaturated, aliphatic chain, optionally substituted with one or more $C_{1-2}$ aliphatic groups. In some embodiments, a lipid comprises a $C_{10}$-$C_{60}$ linear, saturated or partially unsaturated, aliphatic chain, optionally substituted with one or more $C_{1-2}$ aliphatic groups. In some embodiments, $R^{LD}$ is a $C_{10}$-$C_{60}$ linear, saturated or partially unsaturated, aliphatic chain, optionally substituted with one or more methyl groups. In some embodiments, a lipid comprises a $C_{10}$-$C_{60}$ linear, saturated or partially unsaturated, aliphatic chain, optionally substituted with one or more methyl groups.

In some embodiments, $R^{LD}$ is an unsubstituted $C_{10}$-$C_{60}$ linear, saturated or partially unsaturated, aliphatic chain. In some embodiments, a lipid comprises an unsubstituted $C_{10}$-$C_{60}$ linear, saturated or partially unsaturated, aliphatic chain.

In some embodiments, a lipid comprises no more than one optionally substituted $C_{10}$-$C_{60}$ linear, saturated or partially unsaturated, aliphatic chain. In some embodiments, a lipid comprises two or more optionally substituted $C_{10}$-$C_{60}$ linear, saturated or partially unsaturated, aliphatic chain.

In some embodiments, $R^{LD}$ is an optionally substituted, $C_{10}$-$C_{80}$ saturated or partially unsaturated, aliphatic chain. In some embodiments, a lipid comprises an optionally substituted $C_{10}$-$C_{80}$ saturated or partially unsaturated, aliphatic chain.

In some embodiments, $R^{LD}$ is an optionally substituted $C_{10}$-$C_{80}$ linear, saturated or partially unsaturated, aliphatic chain. In some embodiments, a lipid comprises an optionally substituted $C_{10}$-$C_{80}$ linear, saturated or partially unsaturated, aliphatic chain.

In some embodiments, $R^{LD}$ is a $C_{10}$-Cao linear, saturated or partially unsaturated, aliphatic chain, optionally substituted with one or more $C_{1-4}$ aliphatic groups. In some embodiments, a lipid comprises a $C_{10}$-$C_{80}$ linear, saturated or partially unsaturated, aliphatic chain, optionally substituted with one or more $C_{1-4}$ aliphatic groups. In some embodiments, $R^{LD}$ is a $C_{10}$-$C_{80}$ linear, saturated or partially unsaturated, aliphatic chain, optionally substituted with one or more $C_{1-2}$ aliphatic groups. In some embodiments, a lipid comprises a $C_{10}$-$C_{80}$ linear, saturated or partially unsaturated, aliphatic chain, optionally substituted with one or more $C_{1-2}$ aliphatic groups. In some embodiments, $R^{LD}$ is a $C_{10}$-Cao linear, saturated or partially unsaturated, aliphatic chain, optionally substituted with one or more methyl groups. In some embodiments, a lipid comprises a $C_{10}$-$C_{80}$ linear, saturated or partially unsaturated, aliphatic chain, optionally substituted with one or more methyl groups.

In some embodiments, $R^{LD}$ is an unsubstituted $C_{10}$-Cao linear, saturated or partially unsaturated, aliphatic chain. In some embodiments, a lipid comprises an unsubstituted $C_{10}$-$C_{80}$ linear, saturated or partially unsaturated, aliphatic chain.

In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain.

In some embodiments, $R^{LD}$ is or comprises a $C_{10}$ saturated linear aliphatic chain. In some embodiments, $R^{LD}$ is or comprises a $C_{10}$ partially unsaturated linear aliphatic chain. In some embodiments, $R^{LD}$ is or comprises a $C_{11}$ saturated linear aliphatic chain. In some embodiments, $R^{LD}$ is or comprises a $C_{11}$ partially unsaturated linear aliphatic chain. In some embodiments, $R^{LD}$ is or comprises a $C_{12}$ saturated linear aliphatic chain. In some embodiments, $R^{LD}$ is or comprises a $C_{12}$ partially unsaturated linear aliphatic chain. In some embodiments, $R^{LD}$ is or comprises a $C_{13}$ saturated linear aliphatic chain. In some embodiments, $R^{LD}$ is or comprises a $C_{13}$ partially unsaturated linear aliphatic chain. In some embodiments, $R^{LD}$ is or comprises a $C_{14}$ saturated linear aliphatic chain. In some embodiments, $R^{LD}$ is or comprises a $C_{14}$ partially unsaturated linear aliphatic chain. In some embodiments, $R^{LD}$ is or comprises a $C_{15}$ saturated linear aliphatic chain. In some embodiments, $R^{LD}$ is or comprises a $C_{15}$ partially unsaturated linear aliphatic chain. In some embodiments, $R^{LD}$ is or comprises a $C_{16}$ saturated linear aliphatic chain. In some embodiments, $R^{LD}$ is or comprises a $C_{16}$ partially unsaturated linear aliphatic chain. In some embodiments, $R^{LD}$ is or comprises a $C_{17}$ saturated linear aliphatic chain. In some embodiments, $R^{LD}$ is or comprises a $C_{17}$ partially unsaturated linear aliphatic chain. In some embodiments, $R^{LD}$ is or comprises a $C_{18}$ saturated linear aliphatic chain. In some embodiments, $R^{LD}$ is or comprises a $C_{18}$ partially unsaturated linear aliphatic chain. In some embodiments, $R^{LD}$ is or comprises a $C_{19}$ saturated linear aliphatic chain. In some embodiments, $R^{LD}$ is or comprises a $C_{19}$ partially unsaturated linear aliphatic chain. In some embodiments, $R^{LD}$ is or comprises a $C_{20}$ saturated linear aliphatic chain. In some embodiments, $R^{LD}$ is or comprises a $C_{20}$ partially unsaturated linear aliphatic chain. In some embodiments, $R^{LD}$ is or comprises a $C_{21}$ saturated linear aliphatic chain. In some embodiments, $R^{LD}$ is or comprises a $C_{21}$ partially unsaturated linear aliphatic chain. In some embodiments, $R^{LD}$ is or comprises a $C_{22}$ saturated linear aliphatic chain. In some embodiments, $R^{LD}$ is or comprises a $C_{22}$ partially unsaturated linear aliphatic chain. In some embodiments, $R^{LD}$ is or comprises a $C_{23}$ saturated linear aliphatic chain. In some embodiments, $R^{LD}$ is or comprises a $C_{23}$ partially unsaturated linear aliphatic chain. In some embodiments, $R^{LD}$ is or comprises a $C_{24}$ saturated linear aliphatic chain. In some embodiments, $R^{LD}$ is or comprises a $C_{24}$ partially unsaturated linear aliphatic chain. In some embodiments, $R^{LD}$ is or comprises a $C_{25}$ saturated linear aliphatic chain. In some embodiments, $R^{LD}$ is or comprises a $C_{25}$ partially unsaturated linear aliphatic chain. In some embodiments, $R^{LD}$ is or comprises a $C_{26}$ saturated linear aliphatic chain. In some embodiments, $R^{LD}$ is or comprises a $C_{26}$ partially unsaturated linear aliphatic chain. In some embodiments, $R^{LD}$ is or comprises a $C_{27}$ saturated linear aliphatic chain. In some embodiments, $R^{LD}$ is or comprises a $C_{27}$ partially unsaturated linear aliphatic chain. In some embodiments, $R^{LD}$ is or comprises a $C_{28}$ saturated linear aliphatic chain. In some embodiments, $R^{LD}$ is or comprises a $C_{28}$ partially unsaturated linear aliphatic chain. In some embodiments, $R^{LD}$ is or comprises a $C_{29}$ saturated linear aliphatic chain. In some embodiments, $R^{LD}$ is or comprises a $C_{29}$ partially unsaturated linear aliphatic chain. In some embodiments, $R^{LD}$ is or comprises a $C_{30}$ saturated linear aliphatic chain. In some embodiments, $R^{LD}$ is or comprises a $C_{30}$ partially unsaturated linear aliphatic chain.

In some embodiments, a lipid has the structure of $R^{LD}$—OH. In some embodiments, a lipid has the structure of $R^{LD}$—C(O)OH. In some embodiments, $R^{LD}$ is

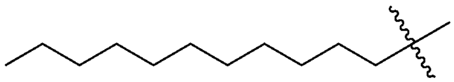,

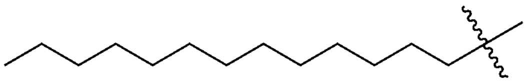,

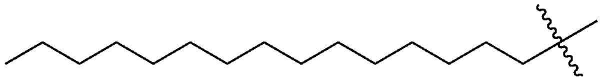,

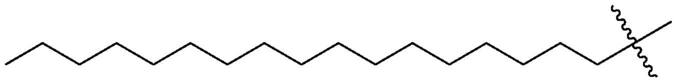,

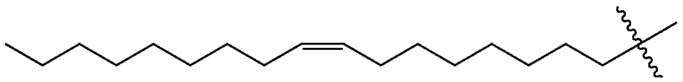,

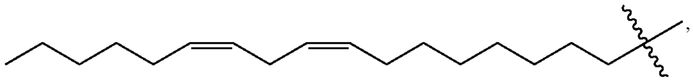,

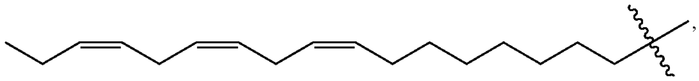,

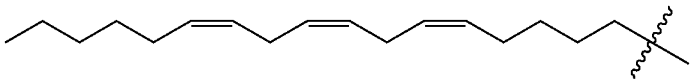,

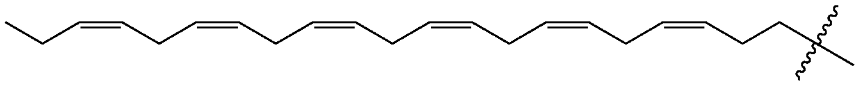,

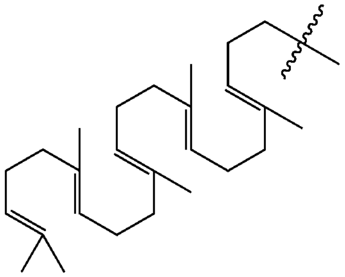, or

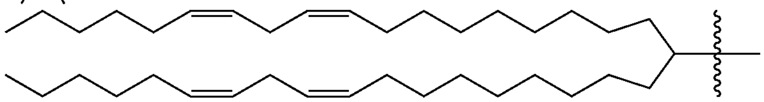.

In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid, arachidonic acid, and dilinoleyl. In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid, and dilinoleyl. In some embodiments, a lipid has a structure of:

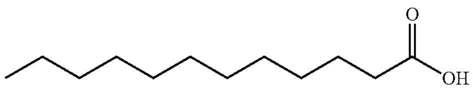

Lauric acid

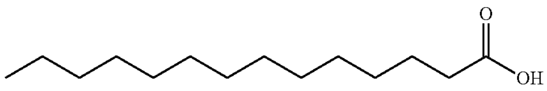

Myristic acid

-continued

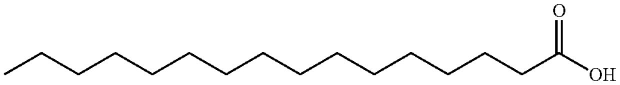

Palmitic acid

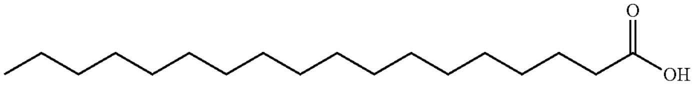

Stearic acid

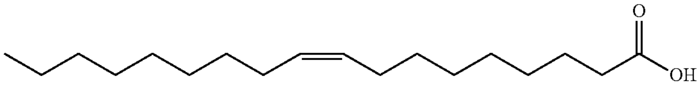

Oleic acid

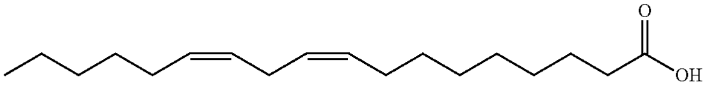

Linoleic acid

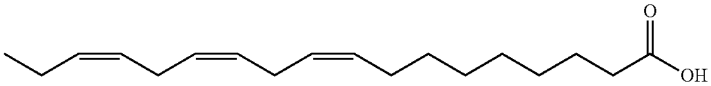

Alpha Linolenic acid

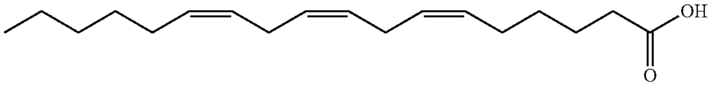

Gamma Linolenic acid

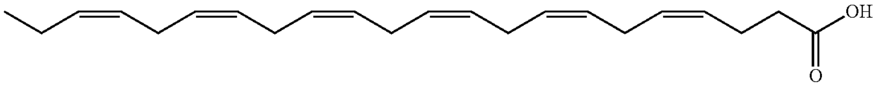

Docosahexaenoic acid

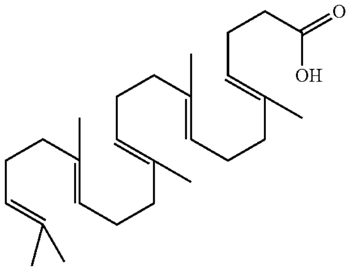

or

Turbinaric acid

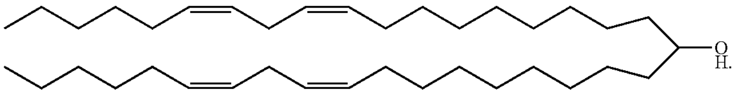

Dilinoleyl alcohol

In some embodiments, a lipid is, comprises or consists of any of: an at least partially hydrophobic or amphiphilic molecule, a phospholipid, a triglyceride, a diglyceride, a monoglyceride, a fat-soluble vitamin, a sterol, a fat and a wax. In some embodiments, a lipid is any of: a fatty acid, glycerolipid, glycerophospholipid, sphingolipid, sterol lipid, prenol lipid, saccharolipid, polyketide, and other molecule.

Lipids can be incorporated into provided technologies through many types of methods in accordance with the present disclosure. In some embodiments, lipids are physically mixed with provided oligonucleotides to form provided compositions. In some embodiments, lipids are chemically conjugated with oligonucleotides.

In some embodiments, provided compositions comprise two or more lipids. In some embodiments, provided oligonucleotides comprise two or more conjugated lipids. In some embodiments, the two or more conjugated lipids are the same. In some embodiments, the two or more conjugated lipids are different. In some embodiments, provided oligonucleotides comprise no more than one lipid. In some embodiments, oligonucleotides of a provided composition comprise different types of conjugated lipids. In some embodiments, oligonucleotides of a provided composition comprise the same type of lipids.

Lipids can be conjugated to oligonucleotides optionally through linkers. Various types of linkers in the art can be utilized in accordance of the present disclosure. In some embodiments, a linker comprise a phosphate group, which can, for example, be used for conjugating lipids through chemistry similar to those employed in oligonucleotide synthesis. In some embodiments, a linker comprises an amide, ester, or ether group. In some embodiments, a linker has the structure of -L-. In some embodiments, after conjugation to oligonucleotides, a lipid forms a moiety having the structure of -L-$R^{LD}$, wherein each of L and $R^{LD}$ is independently as defined and described herein.

In some embodiments, -L- comprises a bivalent aliphatic chain. In some embodiments, -L- comprises a phosphate group. In some embodiments, -L- comprises a phosphorothioate group. In some embodiments, -L- has the structure of $—C(O)NH—(CH_2)_6—OP(═O)(S—)—$.

Lipids, optionally through linkers, can be conjugated to oligonucleotides at various suitable locations. In some embodiments, lipids are conjugated through the 5'-OH group. In some embodiments, lipids are conjugated through the 3'-OH group. In some embodiments, lipids are conjugated through one or more sugar moieties. In some embodiments, lipids are conjugated through one or more bases. In some embodiments, lipids are incorporated through one or more internucleotidic linkages. In some embodiments, an oligonucleotide may contain multiple conjugated lipids which are independently conjugated through its 5'-OH, 3'-OH, sugar moieties, base moieties and/or internucleotidic linkages.

In some embodiments, a lipid is conjugated to an oligonucleotide optionally through a linker moiety. A person having ordinary skill in the art appreciates that various technologies can be utilized to conjugate lipids to an oligonucleotide in accordance with the present disclosure. For example, for lipids comprising carboxyl groups, such lipids can be conjugated through the carboxyl groups. In some embodiments, a lipid is conjugated through a linker having the structure of -L-, wherein L is as defined and described in formula I. In some embodiments, L comprises a phosphate diester or modified phosphate diester moiety. In some embodiments, a compound formed by lipid conjugation has the structure of ($R^{LD}$-L-$)_x$-(oligonucleotide), wherein x is 1 or an integer greater than 1, and each of $R^{LD}$ and L is independently as defined and described herein. In some embodiments, x is 1. In some embodiments, x is greater than 1. In some embodiments, an oligonucleotide is an oligonucleotide. For example, in some embodiments, a conjugate has the following structures:

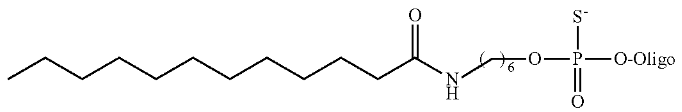

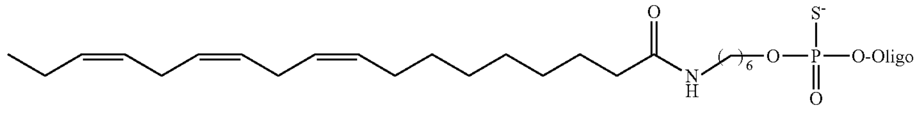

In some embodiments, a linker is selected from: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; and a linker comprising at least one peptide-based cleavage group.

In some embodiments, a lipid is not conjugated to an oligonucleotide.

In some embodiments, the present disclosure pertains to compositions and methods related to a composition comprising an oligonucleotide and a lipid comprising a $C_{10}$-$C_{40}$ linear, saturated or partially unsaturated, aliphatic chain, wherein the lipid is conjugated to the biologically active agent. In some embodiments, the present disclosure pertains to compositions and methods related to a composition comprising an oligonucleotide and a lipid comprising a $C_{10}$-$C_{40}$ linear, saturated or partially unsaturated, aliphatic chain, optionally substituted with one or more $C_{1-4}$ aliphatic group, wherein the lipid is conjugated to the biologically active agent.

In some embodiments, the present disclosure pertains to compositions and methods related to a composition comprising an oligonucleotide and a lipid comprising a $C_{10}$-$C_{40}$ linear, saturated or partially unsaturated, aliphatic chain, wherein the lipid is not conjugated to the biologically active agent. In some embodiments, the present disclosure pertains to compositions and methods related to a composition comprising an oligonucleotide and a lipid comprising a $C_{10}$-$C_{40}$ linear, saturated or partially unsaturated, aliphatic chain, optionally substituted with one or more $C_{14}$ aliphatic group, wherein the lipid is not conjugated to the biologically active agent.

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is not conjugated to the biologically active agent. In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is not conjugated to the biologically active agent.

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is conjugated to the biologically active agent. In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is conjugated to the biologically active agent.

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is directly conjugated to the biologically active agent (without a linker interposed between the lipid and the biologically active agent). In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is directly conjugated to the biologically active agent (without a linker interposed between the lipid and the biologically active agent).

In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl, wherein the lipid is indirectly conjugated to the biologically active agent (with a linker interposed between the lipid and the biologically active agent). In some embodiments, a composition comprises an oligonucleotide and a lipid selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, and dilinoleyl, wherein the lipid is indirectly conjugated to the biologically active agent (with a linker interposed between the lipid and the biologically active agent).

A linker is a moiety that connects two parts of a composition; as a non-limiting example, a linker physically connects an oligonucleotide to a lipid.

Non-limiting examples of suitable linkers include: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group.

In some embodiments, a linker comprises an uncharged linker or a charged linker.

In some embodiments, a linker comprises an alkyl.

In some embodiments, a linker comprises a phosphate. In various embodiments, a phosphate can also be modified by replacement of bridging oxygen, (i.e. oxygen that links the phosphate to the nucleoside), with nitrogen (bridged phosphoroamidates), sulfur (bridged phosphorothioates) and carbon (bridged methylenephosphonates). The replacement can occur at the either linking oxygen or at both the linking oxygens. When the bridging oxygen is the 3'-oxygen of a nucleoside, replacement with carbon can be done. When the bridging oxygen is the 5'-oxygen of a nucleoside, replacement with nitrogen can be done. In various embodiments, the linker comprising a phosphate comprises any one or more of: a phosphorodithioate, phosphoramidate, boranophosphonoate, or a compound of formula (I):

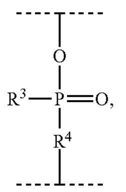

(I)

where $R^3$ is selected from OH, SH, $NH_2$, $BH_3$, $CH_3$, $C_{1-6}$ alkyl, $C_{6-10}$ aryl, $C_{1-6}$ alkoxy and $C_6$-io aryl-oxy, wherein $C_{1-6}$ alkyl and $C_6$-io aryl are unsubstituted or optionally independently substituted with 1 to 3 groups independently selected from halo, hydroxyl and $NH_2$; and $R^4$ is selected from O, S, NH, or $CH_2$.

In some embodiments, a linker comprises a direct bond or an atom such as oxygen or sulfur, a unit such as NR', C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynyl arylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheter ocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R_1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In some embodiments, a linker is a branched linker. In some embodiments, a branchpoint of the branched linker may be at least trivalent, but may be a tetravalent, pentavalent or hexavalent atom, or a group presenting such multiple valencies. In some embodiments, a branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branchpoint is glycerol or glycerol derivative.

In one embodiment, a linker comprises at least one cleavable linking group.

As a non-limiting example, a cleavable linking group can be sufficiently stable outside the cell, but which upon entry into a target cell is cleaved to release the two parts the linker is holding together. As a non-limiting example, a cleavable linking group is cleaved at least 10 times or more, at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum). Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

As a non-limiting example, a cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a desired pH, thereby releasing the cationic lipid from the ligand inside the cell, or into the desired compartment of the cell.

As a non-limiting example, a linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

As a non-limiting example, a linker can contain a peptide bond, which can be used when targeting cell types rich in peptidases, such as liver cells and synoviocytes.

As a non-limiting example, suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. As a non-limiting example, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In some embodiments, a linker comprises a redox cleavable linking group. As a non-limiting example, one class of cleavable linking groups are redox cleavable linking groups that are cleaved upon reduction or oxidation. A non-limiting example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. As a non-limiting example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. As a non-limiting example, candidate compounds are cleaved by at most 10% in the blood. As a non-limiting example, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

In some embodiments, a linker comprises a phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Additional non-limiting examples are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. An additional non-limiting examples is —O—P(O)(OH)—O—.

In some embodiments, a linker comprises an acid cleavable linking groups are linking groups that are cleaved under acidic conditions. As a non-limiting example, acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). In an additional non-limiting example, when the carbon attached to the oxygen of the ester (the alkoxy group) is an aryl group, substituted alkyl group, or tertiary alkyl group such as dimethyl pentyl or t-butyl.

In some embodiments, a linker comprises an ester-based linking groups. As a non-limiting example, ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

In some embodiments, a linker comprises a peptide-based cleaving group. Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. As a non-limiting example, peptide-based cleavable groups do not include the amide group (—C(O)NH—). The amide group can be formed between any alkylene, alkenylene or alkynylene. A peptide bond is a special type of amide bond formed between amino acids to yield peptides and proteins. As a non-limiting example, a peptide based cleavage group can be limited to the peptide bond (i.e., the amide bond) formed between amino acids yielding peptides and proteins and does not include the entire amide functional group. As a non-limiting example, a peptide-based cleavable linking groups can have the general formula —NHCHR$^A$C(O)NHCHR$^B$C(O)—, where R$^A$ and R$^B$ are the R groups of the two adjacent amino acids. These candidates can be evaluated using methods analogous to those described above.

Any linker reported in the art can be used, including, as non-limiting examples, those described in: U.S. Pat. App. No. 20150265708.

A non-limiting example of a method of conjugating a lipid and an oligonucleotide is presented in Example 1.

A non-limiting example of a linker is a C6 amino linker.

Target Components

In some embodiments, a provided composition further comprises a targeting component (targeting compound or moiety). A target component can be either conjugated or not conjugated to a lipid or a biologically active agent. In some embodiments, a target component is conjugated to a biologically active agent. In some embodiments, a biologically active agent is conjugated to both a lipid and a targeting component. As described in here, in some embodiments, a biologically active agent is a provided oligonucleotide. Thus, in some embodiments, a provided oligonucleotide composition further comprises, besides a lipid and oligonucleotides, a target elements. Various targeting components can be used in accordance with the present disclosure, e.g., lipids, antibodies, peptides, carbohydrates, etc.

Target components can be incorporated into provided technologies through many types of methods in accordance with the present disclosure. In some embodiments, target components are physically mixed with provided oligonucleotides to form provided compositions. In some embodiments, target components are chemically conjugated with oligonucleotides.

In some embodiments, provided compositions comprise two or more target components. In some embodiments, provided oligonucleotides comprise two or more conjugated target components. In some embodiments, the two or more conjugated target components are the same. In some embodiments, the two or more conjugated target components are different. In some embodiments, provided oligonucleotides comprise no more than one target component. In some embodiments, oligonucleotides of a provided composition comprise different types of conjugated target components. In some embodiments, oligonucleotides of a provided composition comprise the same type of target components.

Target components can be conjugated to oligonucleotides optionally through linkers. Various types of linkers in the art can be utilized in accordance of the present disclosure. In some embodiments, a linker comprise a phosphate group, which can, for example, be used for conjugating target components through chemistry similar to those employed in oligonucleotide synthesis. In some embodiments, a linker comprises an amide, ester, or ether group. In some embodiments, a linker has the structure of -L-. Target components can be conjugated through either the same or different linkers compared to lipids.

Target components, optionally through linkers, can be conjugated to oligonucleotides at various suitable locations. In some embodiments, target components are conjugated through the 5'-OH group. In some embodiments, target components are conjugated through the 3'-OH group. In some embodiments, target components are conjugated through one or more sugar moieties. In some embodiments, target components are conjugated through one or more bases. In some embodiments, target components are incorporated through one or more internucleotidic linkages. In some embodiments, an oligonucleotide may contain multiple conjugated target components which are independently conjugated through its 5'-OH, 3'-OH, sugar moieties, base moieties and/or internucleotidic linkages. Target components and lipids can be conjugated either at the same, neighboring and/or separated locations. In some embodiments, a target component is conjugated at one end of an oligonucleotide, and a lipid is conjugated at the other end.

In some embodiments, the present disclosure provides the following embodiments:

1. An oligonucleotide composition comprising a first plurality of oligonucleotides which:
   1) have a common base sequence; and
   2) comprise one or more wing regions and a core region;
   wherein:
   each wing region comprises at least one modified sugar moiety; and
   each core region comprises at least one un-modified sugar moiety.

2. An oligonucleotide composition comprising a first plurality of oligonucleotides comprising one or more wing regions and a core region, wherein:
   oligonucleotides of the first plurality have the same base sequence; and
   each wing region independently comprises one or more modified internucleotidic linkages and optionally one or more natural phosphate linkages, and the core region independently comprises one or more modified internucleotidic linkages; or
   each wing region independently comprises one or more modified sugar moieties, and the core region comprises one or more un-modified sugar moieties.

3. An oligonucleotide composition, comprising a first plurality of oligonucleotides of a particular oligonucleotide type defined by:
   1) base sequence;
   2) pattern of backbone linkages;
   3) pattern of backbone chiral centers; and
   4) pattern of backbone phosphorus modifications.
   which composition is chirally controlled in that it is enriched, relative to a substantially racemic preparation of oligonucleotides having the same base sequence, for oligonucleotides of the particular oligonucleotide type.

3a. An oligonucleotide composition, comprising a first plurality of oligonucleotides of a particular oligonucleotide type defined by:
   1) base sequence;
   2) pattern of backbone linkages;
   3) pattern of backbone chiral centers; and
   4) pattern of backbone phosphorus modifications.
   which composition is chirally controlled in that it is enriched, relative to a substantially racemic preparation of oligonucleotides having the same base sequence, for oligonucleotides of the particular oligonucleotide type,
   wherein the oligonucleotides of the first plurality comprise one or more natural phosphate linkages.

4. A composition of any one of the preceding embodiments, wherein the oligonucleotides comprise one or more wing regions and a core region, wherein:

oligonucleotides of the first plurality have the same base sequence;

each wing independently has a length of two or more bases, and independently comprises one or more modified internucleotidic linkages and optionally one or more natural phosphate linkages; and the core region independently has a length of two or more bases and independently comprises one or more modified internucleotidic linkages.

4a. A composition of any one of the preceding embodiments, wherein a wing has the same or lower percentage of modified internucleotidic linkages than the core.

4b. A composition of any one of the preceding embodiments, wherein each wing independently has the same or lower percentage of modified internucleotidic linkages than the core.

4c. A composition of any one of the preceding embodiments, wherein a wing has a lower percentage of modified internucleotidic linkages that the core.

4d. A composition of any one of the preceding embodiments, wherein a wing has one or more natural phosphate linkages.

4e. A composition of any one of the preceding embodiments, wherein each wing independently has one or more natural phosphate linkages.

4f. A composition of any one of the preceding embodiments, wherein has a wing to the 5' of the core has a modified internucleotidic linkage at its 5'-end.

4g. A composition of any one of the preceding embodiments, wherein has a wing to the 3' of the core has a modified internucleotidic linkage at its 3'-end.

4h. A composition of any one of the preceding embodiments, wherein a wing comprises a modified internucleotidic linkage followed by one or more natural phosphate linkages in the wing.

4i. A composition of any one of the preceding embodiments, wherein a wing to the 5' of a core comprises a modified internucleotidic linkage followed by one or more natural phosphate linkages in the wing.

4j. A composition of any one of the preceding embodiments, wherein, a wing to the 5' of a core comprises a modified internucleotidic linkage followed by two or more consecutive natural phosphate linkages in the wing.

4k. A composition of any one of the preceding embodiments, wherein a wing comprises a modified internucleotidic linkage preceded by one or more natural phosphate linkages in the wing.

4l. A composition of any one of the preceding embodiments, wherein a wing to the 3' of a core comprises a modified internucleotidic linkage preceded by one or more natural phosphate linkages in the wing.

4m. A composition of any one of the preceding embodiments, wherein a wing to the 3' of a core comprises a modified internucleotidic linkage preceded by two or more consecutive natural phosphate linkages in the wing.

4n. A composition of any one of the preceding embodiments, wherein a wing is to the 5'-end of the core and comprises a natural phosphate linkage between the two nucleosides at its 3'-end.

4o. A composition of any one of the preceding embodiments, wherein a wing is to the 3'-end of the core and comprises a natural phosphate linkage between the two nucleosides at its 5'-end;

5. A composition of embodiment 1, wherein the first plurality comprises at least about 10% of the oligonucleotides in the composition.

5a. A composition of embodiment 1, wherein the first plurality comprises at least about 20% of the oligonucleotides in the composition.

5b. A composition of embodiment 1, wherein the first plurality comprises at least about 50% of the oligonucleotides in the composition.

5c. A composition of embodiment 1, wherein the first plurality comprises at least about 60% of the oligonucleotides in the composition.

6. A composition of embodiment 1, wherein the first plurality comprises at least about 70% of the oligonucleotides in the composition.

7. A composition of embodiment 1, wherein the first plurality comprises at least about 80% of the oligonucleotides in the composition.

8. A composition of embodiment 1, wherein the first plurality comprises at least about 85% of the oligonucleotides in the composition.

9. A composition of embodiment 1, wherein the first plurality comprises at least about 90% of the oligonucleotides in the composition.

10. A composition of embodiment 1, wherein the first plurality comprises at least about 95% of the oligonucleotides in the composition.

11. A composition of any one of the preceding embodiments, comprising a first plurality of oligonucleotides of a particular oligonucleotide type defined by:

1) base sequence;

2) pattern of backbone linkages;

3) pattern of backbone chiral centers; and 4) pattern of backbone phosphorus modifications.

12. A composition of any one of the preceding embodiments, wherein the composition comprises a first plurality of oligonucleotides of a particular oligonucleotide type, wherein oligonucleotides of a particular oligonucleotide type have a common pattern of base modification and pattern of sugar modification.

13. A composition of any one of the preceding embodiments, wherein the composition comprises a first plurality of oligonucleotides of a particular oligonucleotide type, wherein oligonucleotides of a particular oligonucleotide type are structurally identical.

14. A composition of any one of the preceding embodiments, wherein the level of the first plurality of oligonucleotides is pre-determined.

15. A composition of any one of the preceding embodiments, wherein a first plurality of oligonucleotides comprise two wing regions and a core region.

15a. A composition of any one of the preceding embodiments, wherein a first plurality of oligonucleotides comprise no more than two wing regions and no more than one core region.

16. A composition of any one of the preceding embodiments, wherein a first plurality of oligonucleotides have a wing-core-wing structure.

17. A composition of any one of the preceding embodiments, wherein a first plurality of oligonucleotides are gapmers having a wing-core-wing structure.

18. A composition of any one of embodiments 1-13, wherein a first plurality of oligonucleotides comprise no more than one wing region and no more than one core region.

19. A composition of any one of embodiments 1-13, wherein a first plurality of oligonucleotides are hemimers having a wing-core structure.

20. A composition of any one of embodiments 1-13, wherein a first plurality of oligonucleotides are hemimers having a core-wing structure.

21. A composition of any one of the preceding embodiments, wherein a wing comprises a chiral internucleotidic linkage.

22. A composition of any one of the preceding embodiments, wherein a wing comprises no more than 20% chiral internucleotidic linkages.

23. A composition of any one of the preceding embodiments, wherein each wing independently comprises a chiral internucleotidic linkage.

24. A composition of any one of the preceding embodiments, wherein each wing independently comprises no more than 20% chiral internucleotidic linkages.

25. A composition of any one of embodiments 1-17 and 19-22, wherein a wing to the 5'-end of the core comprises a chiral internucleotidic linkage at the 5'-end of the wing.

26. A composition of any one of embodiments 1-16 and 18-22, wherein a wing to the 3'-end of the core comprises a chiral internucleotidic linkage at the 3'-end of the wing.

27. A composition of any one of the preceding embodiments, wherein a wing has only one chiral internucleotidic linkage, and each of the other internucleotidic linkages of the wing is a natural phosphate linkage

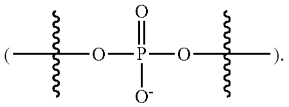 [SMILES: *OP(=O)([O-])O*]

28. A composition of any one of the preceding embodiments, wherein the chiral internucleotidic linkage has the structure of formula I.

29. A composition of any one of the preceding embodiments, wherein a chiral internucleotidic linkage has the structure of formula I, and wherein X is S, and Y and Z are O.

30. A composition of any one of the preceding embodiments, wherein a chiral internucleotidic linkage is a phosphorothioate linkage.

31. A composition of any one of the preceding embodiments, wherein a chiral internucleotidic linkage is Sp.

32. A composition of any one of the preceding embodiments, wherein each chiral internucleotidic linkage is Sp.

33. A composition of any one of embodiments 1-31, wherein a chiral internucleotidic linkage is Rp.

34. A composition of any one of embodiments 1-30, wherein each chiral internucleotidic linkage is Rp.

35. A composition of any one of embodiments 1-33, wherein a wing comprises an Sp phosphorothioate linkage.

36. A composition of any one of embodiments 1-33, wherein each wing independently comprises an Sp phosphorothioate linkage.

37. A composition of any one of embodiments 1-19, 21-33, and 35-36, wherein a wing is to the 5'-end of the core, and the wing has an Sp phosphorothioate linkage.

38. A composition of any one of embodiments 1-19, 21-33, and 35-37, wherein a wing is to the 5'-end of the core, and the wing has an Sp phosphorothioate linkage at the 5'-end of the wing.

39. A composition of any one of embodiments 1-19, 21-33, and 35-38, wherein a wing is to the 5'-end of the core, the wing has an Sp phosphorothioate linkage at the 5'-end of the wing, and each of the other internucleotidic linkages of the wing is a natural phosphate linkage

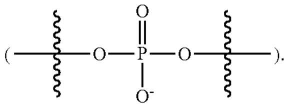 [SMILES: *OP(=O)([O-])O*]

40. A composition of any one of embodiments 1-18, 20-33 and 35-36, wherein a wing is to the 3'-end of the core, and the wing has an Sp phosphorothioate linkage at the 3'-end of the wing.

41. A composition of any one of embodiments 1-18, 20-33, 35-36 and 40, wherein a wing is to the 3'-end of the core, and the wing has an Sp phosphorothioate linkage at the 3'-end of the wing.

42. A composition of any one of embodiments 1-18, 20-33, 35-36 and 40-41, wherein one wing is to the 3'-end of the common core, the wing has an Sp phosphorothioate linkage at the 3'-end of the wing, and each of the other internucleotidic linkages of the wing is a natural phosphate linkage

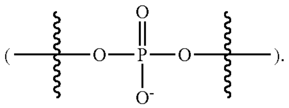 [SMILES: *OP(=O)([O-])O*]

43. A composition of any one of embodiments 1-31 and 33-42, wherein a wing comprises an Rp phosphorothioate linkage.

44. A composition of any one of embodiments 1-31 and 33-42, wherein each wing independently comprises an Rp phosphorothioate linkage.

45. A composition of any one of embodiments 1-19, 21-31 and 33-44, wherein a wing is to the 5'-end of the core, and the wing has an Rp phosphorothioate linkage.

46. A composition of any one of embodiments 1-19, 21-31 and 33-45, wherein a wing is to the 5'-end of the core, and the wing has an Rp phosphorothioate linkage at the 5'-end of the wing.

47. A composition of any one of embodiments 1-19, 21-31 and 33-46, wherein a wing is to the 5'-end of the core, the wing has an Rp phosphorothioate linkage at the 5'-end of the wing, and each of the other internucleotidic linkages of the wing is a natural phosphate linkage

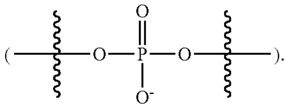 [SMILES: *OP(=O)([O-])O*]

48. A composition of any one of embodiments 1-18, 20-31 and 33-44, wherein a wing is to the 3'-end of the core, and the wing has an Rp phosphorothioate.

49. A composition of any one of embodiments 1-18, 20-31 and 33-44, wherein a wing is to the 3'-end of the core, and the wing has an Rp phosphorothioate linkage at the 3'-end of the wing.

50. A composition of any one of embodiments 1-18, 20-31 and 33-44, wherein one wing is to the 3'-end of the common core, the wing has an Rp phosphorothioate linkage at the 3'-end of the wing, and each of the other internucleotidic linkages of the wing is a natural phosphate linkage

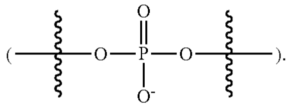 [SMILES: *OP(=O)([O-])O*]

51. A composition of any one of embodiments 1-30, wherein a wing is to the 5'-end of a core, and its 5'-end internucleotidic linkage is a chiral internucleotidic linkage.
52. A composition of any one of embodiments 1-30, wherein a wing is to the 5'-end of a core, and its 5'-end internucleotidic linkage is an Sp chiral internucleotidic linkage.
53. A composition of any one of embodiments 1-30, wherein a wing is to the 5'-end of a core, and its 5'-end internucleotidic linkage is an Rp chiral internucleotidic linkage.
54. A composition of any one of embodiments 1-30 and 51-53, wherein a wing is to the 3'-end of a core, and its 3'-end internucleotidic linkage is a chiral internucleotidic linkage.
55. A composition of any one of embodiments 1-30 and 51-53, wherein a wing is to the 3'-end of a core, and its 3'-end internucleotidic linkage is an Sp chiral internucleotidic linkage.
56. A composition of any one of embodiments 1-30 and 51-53, wherein a wing is to the 3'-end of a core, and its 3'-end internucleotidic linkage is an Rp chiral internucleotidic linkage.
57. A composition of any one of the preceding embodiments, wherein a wing independently comprises a natural phosphate linkage

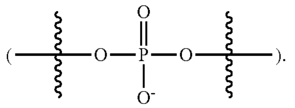 [SMILES: *OP(=O)([O-])O*]

58. A composition of any one of the preceding embodiments, wherein a wing independently comprises two or more natural phosphate linkages

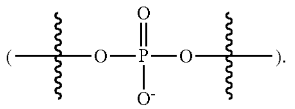 [SMILES: *OP(=O)([O-])O*]

59. A composition of any one of the preceding embodiments, wherein a wing independently comprises two or more natural phosphate linkages, and all natural phosphate linkages within a wing are consecutive.
60. A composition of any one of the preceding embodiments, wherein each wing independently comprises a natural phosphate linkage

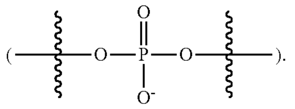 [SMILES: *OP(=O)([O-])O*]

61. A composition of any one of the preceding embodiments, wherein each wing independently comprises two or more natural phosphate linkages.
61a. A composition of any one of the preceding embodiments, wherein each wing independently comprises three or more natural phosphate linkages.
61b. A composition of any one of the preceding embodiments, wherein each wing independently comprises four or more natural phosphate linkages.
61c. A composition of any one of the preceding embodiments, wherein each wing independently comprises five or more natural phosphate linkages.
62. A composition of any one of the preceding embodiments, wherein each wing independently comprises two or more natural phosphate linkages, and all natural phosphate linkages within a wing are consecutive.
62a. A composition of any one of the preceding embodiments, wherein each wing independently comprises three or more natural phosphate linkages, and all natural phosphate linkages within a wing are consecutive.
62b. A composition of any one of the preceding embodiments, wherein each wing independently comprises four or more natural phosphate linkages, and all natural phosphate linkages within a wing are consecutive.
62c. A composition of any one of the preceding embodiments, wherein each wing independently comprises five or more natural phosphate linkages, and all natural phosphate linkages within a wing are consecutive.
63. A composition of any one of the preceding embodiments, wherein at least 5% of the internucleotidic linkages in a wing are natural phosphate linkages.
63a. A composition of any one of the preceding embodiments, wherein at least 10% of the internucleotidic linkages in a wing are natural phosphate linkages.
63b. A composition of any one of the preceding embodiments, wherein at least 20% of the internucleotidic linkages in a wing are natural phosphate linkages.
63c. A composition of any one of the preceding embodiments, wherein at least 30% of the internucleotidic linkages in a wing are natural phosphate linkages.
63c. A composition of any one of the preceding embodiments, wherein at least 40% of the internucleotidic linkages in a wing are natural phosphate linkages.
63e. A composition of any one of the preceding embodiments, wherein at least 50% of the internucleotidic linkages in a wing are natural phosphate linkages.
63f. A composition of any one of the preceding embodiments, wherein at least 60% of the internucleotidic linkages in a wing are natural phosphate linkages.
63g. A composition of any one of the preceding embodiments, wherein at least 70% of the internucleotidic linkages in a wing are natural phosphate linkages.
63h. A composition of any one of the preceding embodiments, wherein at least 80% of the internucleotidic linkages in a wing are natural phosphate linkages.
63i. A composition of any one of the preceding embodiments, wherein at least 90% of the internucleotidic linkages in a wing are natural phosphate linkages.
63j. A composition of any one of the preceding embodiments, wherein at least 95% of the internucleotidic linkages in a wing are natural phosphate linkages.
64. A composition of any one of the preceding embodiments, wherein at least 5% of the internucleotidic linkages in each wing are independently natural phosphate linkages.
64a. A composition of any one of the preceding embodiments, wherein at least 10% of the internucleotidic linkages in each wing are independently natural phosphate linkages.
64b. A composition of any one of the preceding embodiments, wherein at least 20% of the internucleotidic linkages in each wing are independently natural phosphate linkages.

64c. A composition of any one of the preceding embodiments, wherein at least 30% of the internucleotidic linkages in each wing are independently natural phosphate linkages.

64c. A composition of any one of the preceding embodiments, wherein at least 40% of the internucleotidic linkages in each wing are independently natural phosphate linkages.

64e. A composition of any one of the preceding embodiments, wherein at least 50% of the internucleotidic linkages in each wing are independently natural phosphate linkages.

64f. A composition of any one of the preceding embodiments, wherein at least 60% of the internucleotidic linkages in each wing are independently natural phosphate linkages.

64g. A composition of any one of the preceding embodiments, wherein at least 70% of the internucleotidic linkages in each wing are independently natural phosphate linkages.

64h. A composition of any one of the preceding embodiments, wherein at least 80% of the internucleotidic linkages in each wing are independently natural phosphate linkages.

64i. A composition of any one of the preceding embodiments, wherein at least 90% of the internucleotidic linkages in each wing are independently natural phosphate linkages.

64j. A composition of any one of the preceding embodiments, wherein at least 95% of the internucleotidic linkages in each wing are independently natural phosphate linkages.

65. A composition of any one of the preceding embodiments, wherein a wing comprises no more than 15 modified phosphate linkages.

65a. A composition of any one of the preceding embodiments, wherein a wing comprises no more than 10 modified phosphate linkages.

65b. A composition of any one of the preceding embodiments, wherein a wing comprises no more than 9 modified phosphate linkages.

65c. A composition of any one of the preceding embodiments, wherein a wing comprises no more than 8 modified phosphate linkages.

65d. A composition of any one of the preceding embodiments, wherein a wing comprises no more than 7 modified phosphate linkages.

65e. A composition of any one of the preceding embodiments, wherein a wing comprises no more than 6 modified phosphate linkages.

65f. A composition of any one of the preceding embodiments, wherein a wing comprises no more than 5 modified phosphate linkages.

65g. A composition of any one of the preceding embodiments, wherein a wing comprises no more than 4 modified phosphate linkages.

65h. A composition of any one of the preceding embodiments, wherein a wing comprises no more than 3 modified phosphate linkages.

65i. A composition of any one of the preceding embodiments, wherein a wing comprises no more than 2 modified phosphate linkages.

65j. A composition of any one of the preceding embodiments, wherein a wing comprises no more than 1 modified phosphate linkage.

66. A composition of any one of the preceding embodiments, wherein each wing independently comprises no more than 15 modified phosphate linkages.

66a. A composition of any one of the preceding embodiments, wherein each wing independently comprises no more than 10 modified phosphate linkages.

66b. A composition of any one of the preceding embodiments, wherein each wing independently comprises no more than 9 modified phosphate linkages.

66c. A composition of any one of the preceding embodiments, wherein each wing independently comprises no more than 8 modified phosphate linkages.

66d. A composition of any one of the preceding embodiments, wherein each wing independently comprises no more than 7 modified phosphate linkages.

66e. A composition of any one of the preceding embodiments, wherein each wing independently comprises no more than 6 modified phosphate linkages.

66f. A composition of any one of the preceding embodiments, wherein each wing independently comprises no more than 5 modified phosphate linkages.

66g. A composition of any one of the preceding embodiments, wherein each wing independently comprises no more than 4 modified phosphate linkages.

66h. A composition of any one of the preceding embodiments, wherein each wing independently comprises no more than 3 modified phosphate linkages.

66i. A composition of any one of the preceding embodiments, wherein each wing independently comprises no more than 2 modified phosphate linkages.

66j. A composition of any one of the preceding embodiments, wherein each wing independently comprises no more than 1 modified phosphate linkage.

67. A composition of any one of the preceding embodiments, wherein a wing comprises less than 100% modified phosphate linkages.

67a. A composition of any one of the preceding embodiments, wherein a wing comprises no more than 95% modified phosphate linkages.

67b. A composition of any one of the preceding embodiments, wherein a wing comprises no more than 90% modified phosphate linkages.

67c. A composition of any one of the preceding embodiments, wherein a wing comprises no more than 80% modified phosphate linkages.

67d. A composition of any one of the preceding embodiments, wherein a wing comprises no more than 70% modified phosphate linkages.

67e. A composition of any one of the preceding embodiments, wherein a wing comprises no more than 60% modified phosphate linkages.

67f. A composition of any one of the preceding embodiments, wherein a wing comprises no more than 50% modified phosphate linkages.

67g. A composition of any one of the preceding embodiments, wherein a wing comprises no more than 40% modified phosphate linkages.

67h. A composition of any one of the preceding embodiments, wherein a wing comprises no more than 30% modified phosphate linkages.

67i. A composition of any one of the preceding embodiments, wherein a wing comprises no more than 20% modified phosphate linkages.

67k. A composition of any one of the preceding embodiments, wherein a wing comprises no more than 10% modified phosphate linkage.

68. A composition of any one of the preceding embodiments, wherein each wing independently comprises less than 100% modified phosphate linkages.

68a. A composition of any one of the preceding embodiments, wherein each wing independently comprises no more than 95% modified phosphate linkages.

68b. A composition of any one of the preceding embodiments, wherein each wing independently comprises no more than 90% modified phosphate linkages.

68c. A composition of any one of the preceding embodiments, wherein each wing independently comprises no more than 80% modified phosphate linkages.

68d. A composition of any one of the preceding embodiments, wherein each wing independently comprises no more than 70% modified phosphate linkages.

68e. A composition of any one of the preceding embodiments, wherein each wing independently comprises no more than 60% modified phosphate linkages.

68f. A composition of any one of the preceding embodiments, wherein each wing independently comprises no more than 50% modified phosphate linkages.

68g. A composition of any one of the preceding embodiments, wherein each wing independently comprises no more than 40% modified phosphate linkages.

68h. A composition of any one of the preceding embodiments, wherein each wing independently comprises no more than 30% modified phosphate linkages.

68i. A composition of any one of the preceding embodiments, wherein each wing independently comprises no more than 20% modified phosphate linkages.

68j. A composition of any one of the preceding embodiments, wherein each wing independently comprises no more than 10% modified phosphate linkage.

69. A composition of any one of the preceding embodiments, wherein an internucleotidic linkage of a wing region is independently selected from a natural phosphate linkage and a modified phosphate linkage having the structure of formula I.

70. A composition of any one of the preceding embodiments, wherein an internucleotidic linkage of a wing region is independently selected from a natural phosphate linkage and a phosphorothioate linkage.

71. A composition of any one of embodiments 1-20, wherein each internucleotidic linkage within a wing is a natural phosphate linkage.

71a. A composition of any one of embodiments 1-20, wherein each internucleotidic linkage within each wing is a natural phosphate linkage.

72. A composition of any one of embodiments 1-20, wherein each internucleotidic linkage within a wing is a chiral internucleotidic linkage.

72a. A composition of any one of embodiments 1-20, wherein each internucleotidic linkage within each wing is a chiral internucleotidic linkage.

73. A composition of any one of the preceding embodiments, wherein a wing has a length of three or more bases.

73a. A composition of any one of the preceding embodiments, wherein one wing has a length of four or more bases.

73b. A composition of any one of the preceding embodiments, wherein one wing has a length of five or more bases.

73c. A composition of any one of the preceding embodiments, wherein one wing has a length of six or more bases.

73d. A composition of any one of the preceding embodiments, wherein one wing has a length of seven or more bases.

73e. A composition of any one of the preceding embodiments, wherein one wing has a length of eight or more bases.

73f. A composition of any one of the preceding embodiments, wherein one wing has a length of nine or more bases.

73g. A composition of any one of the preceding embodiments, wherein one wing has a length of ten or more bases.

74. A composition of any one of the preceding embodiments, wherein each wing independently has a length of three or more bases.

74a. A composition of any one of the preceding embodiments, wherein each wing independently has a length of four or more bases.

74b. A composition of any one of the preceding embodiments, wherein each wing independently has a length of five or more bases.

74c. A composition of any one of the preceding embodiments, wherein each wing independently has a length of six or more bases.

74d. A composition of any one of the preceding embodiments, wherein each wing independently has a length of seven or more bases.

74e. A composition of any one of the preceding embodiments, wherein each wing independently has a length of eight or more bases.

74f. A composition of any one of the preceding embodiments, wherein each wing independently has a length of nine or more bases.

74g. A composition of any one of the preceding embodiments, wherein each wing independently has a length of ten or more bases.

75. A composition of any one of embodiments 1-72, wherein a wing has a length of three bases.

76. A composition of any one of embodiments 1-72, wherein a wing has a length of four bases.

77. A composition of any one of embodiments 1-72, wherein a wing has a length of five bases.

78. A composition of any one of embodiments 1-72, wherein a wing has a length of six bases.

79. A composition of any one of embodiments 1-72, wherein a wing has a length of seven bases.

80. A composition of any one of embodiments 1-72, wherein a wing has a length of eight bases.

81. A composition of any one of embodiments 1-72, wherein a wing has a length of nine bases.

82. A composition of any one of embodiments 1-72, wherein a wing has a length of ten bases.

83. A composition of any one of embodiments 1-72, wherein a wing has a length of 11 bases.

84. A composition of any one of embodiments 1-72, wherein a wing has a length of 12 bases.

85. A composition of any one of embodiments 1-72, wherein a wing has a length of 13 bases.

86. A composition of any one of embodiments 1-72, wherein a wing has a length of 14 bases.

87. A composition of any one of embodiments 1-72, wherein a wing has a length of 15 bases.

88. A composition of any one of embodiments 1-72, wherein each wing has the same length.

89. A composition of any one of the preceding embodiments, wherein a wing is defined by sugar modifications relative to a core.

90. A composition of any one of the preceding embodiments, wherein each wing independently comprises a modified sugar moiety.

91. A composition of any one of the preceding embodiments, wherein each wing sugar moiety is independently a modified sugar moiety.

92. A composition of any one of the preceding embodiments, wherein a modified sugar moiety comprises a high-affinity sugar modification.

93. A composition of any one of the preceding embodiments, wherein a modified sugar moiety has a 2'-modification.

94. A composition of any one of the preceding embodiments, wherein a modified sugar moiety comprises a bicyclic sugar modification.

95. A composition of any one of the preceding embodiments, wherein a modified sugar moiety comprises a bicyclic sugar modification having a -L- or —O-L- bridge connecting two ring carbon atoms.

96. A composition of any one of the preceding embodiments, wherein a modified sugar moiety comprises a bicyclic sugar modification having a 4'-CH($CH_3$)—O-2' bridge.

97. A composition of any one of embodiments 1-93, wherein a modified sugar moiety comprises a 2'-modification, wherein a 2'-modification is 2'-$OR^1$.

98. A composition of any one of embodiments 1-93, wherein a modified sugar moiety comprises a 2'-modification, wherein a 2'-modification is 2'-$OR^1$, wherein $R^1$ is optionally substituted $C_{1-6}$ alkyl.

99. A composition of any one of embodiments 1-93, wherein a modified sugar moiety comprises a 2'-modification, wherein a 2'-modification is 2'-MOE.

100. A composition of any one of embodiments 1-93, wherein a modified sugar moiety comprises a 2'-modification, wherein a 2'-modification is 2'-OMe.

101. A composition of any one of embodiments 1-96, wherein a modified sugar moiety comprises a 2'-modification, wherein the 2'-modification is S-cEt.

102. A composition of any one of embodiments 1-93, wherein a modified sugar moiety comprises a 2'-modification, wherein the 2'-modification is FANA.

103. A composition of any one of embodiments 1-93, wherein a modified sugar moiety comprises a 2'-modification, wherein the 2'-modification is FRNA.

104. A composition of any one of embodiments 1-92, wherein a modified sugar moiety has a 5'-modification.

105. A composition of any one of embodiments 1-92, wherein a modified sugar moiety is R-5'-Me-DNA.

106. A composition of any one of embodiments 1-92, wherein a modified sugar moiety is S-5'-Me-DNA.

107. A composition of any one of embodiments 1-92, wherein a modified sugar moiety is FHNA.

108. A composition of any one of the preceding embodiments, wherein each wing sugar moiety is modified.

109. A composition of any one of the preceding embodiments, wherein all modified wing sugar moieties within a wing have the same modification.

110. A composition of any one of the preceding embodiments, wherein all modified wing sugar moieties have the same modification.

111. A composition of any one of embodiments 1-108, wherein at least one modified wing sugar moiety is different than another modified wing sugar moiety.

112. A composition of any one of the preceding embodiments, wherein a wing comprises a modified base.

113. A composition of any one of the preceding embodiments, wherein a wing comprises a 2S-dT.

114. A composition of any one of the preceding embodiments, wherein the core region has a length of five or more bases.

115. A composition of any one of the preceding embodiments, wherein the core region has a length of six or more bases.

116. A composition of any one of the preceding embodiments, wherein the core region has a length of seven or more bases.

117. A composition of any one of the preceding embodiments, wherein the core region has a length of eight or more bases.

118. A composition of any one of the preceding embodiments, wherein the core region has a length of nine or more bases.

119. A composition of any one of the preceding embodiments, wherein the core region has a length of ten or more bases.

120. A composition of any one of the preceding embodiments, wherein the core region has a length of 11 or more bases.

121. A composition of any one of the preceding embodiments, wherein the core region has a length of 12 or more bases.

122. A composition of any one of the preceding embodiments, wherein the core region has a length of 13 or more bases.

123. A composition of any one of the preceding embodiments, wherein the core region has a length of 14 or more bases.

124. A composition of any one of the preceding embodiments, wherein the core region has a length of 15 or more bases.

125. A composition of any one of 1-113, wherein the core region has a length of five bases.

126. A composition of any one of 1-113, wherein the core region has a length of six bases.

127. A composition of any one of 1-113, wherein the core region has a length of seven bases.

128. A composition of any one of 1-113, wherein the core region has a length of eight bases.

129. A composition of any one of 1-113, wherein the core region has a length of nine bases.

130. A composition of any one of 1-113, wherein the core region has a length of ten bases.

131. A composition of any one of 1-113, wherein the core region has a length of 11 bases.

132. A composition of any one of 1-113, wherein the core region has a length of 12 bases.

133. A composition of any one of 1-113, wherein the core region has a length of 13 bases.

134. A composition of any one of 1-113, wherein the core region has a length of 14 bases.

135. A composition of any one of 1-113, wherein the core region has a length of 15 bases.

136. A composition of any one of the preceding embodiments, wherein the core region does not have any 2'-modification.

153. A composition of any one of the preceding embodiments, wherein each core sugar moiety is not modified.

138. A composition of any one of the preceding embodiments, wherein each sugar moiety of the core region is the natural DNA sugar moiety.

139. A composition of any one of the preceding embodiments, wherein the core region comprises a chiral internucleotidic linkage.

140. A composition of any one of the preceding embodiments, wherein each internucleotidic linkage of the core region is a chiral internucleotidic linkage.

141. A composition of any one of the preceding embodiments, wherein each internucleotidic linkage of the core region is a chiral internucleotidic linkage having the structure of formula I.

142. A composition of any one of the preceding embodiments, wherein each internucleotidic linkage of the core region is a chiral internucleotidic linkage having the structure of formula I, and wherein X is S, and Y and Z are O.

143. A composition of any one of the preceding embodiments, wherein each internucleotidic linkage of the core region is a chiral internucleotidic linkage having the structure of formula I, and wherein one -L-$R^1$ is not —H.

144. A composition of any one of embodiments 1-142, wherein each internucleotidic linkage of the core region is a phosphorothioate linkage.

145. A composition of any one of the preceding embodiments, wherein the core region has a pattern of backbone chiral center comprises (Sp)m(Rp)n, wherein m is 1-50, and n is 1-10.

146. A composition of any one of the preceding embodiments, wherein the core region has a pattern of backbone chiral center comprises (Sp)m(Rp)n, wherein m is 1-50, n is 1-10, and m>n.

147. A composition of any one of the preceding embodiments, wherein the core region has a pattern of backbone chiral center comprises (Sp)m(Rp)n, wherein m is 2, 3, 4, 5, 6, 7 or 8, and n is 1.

148. A composition of any one of embodiments 1-144, wherein the core region has a pattern of backbone chiral centers comprising (Rp)n(Sp)m, wherein m is 1-50 and n is 1-10.

149. A composition of any one of embodiments 1-144 and 148, wherein the core region has a pattern of backbone chiral centers comprising Rp(Sp)m, wherein m is 2, 3, 4, 5, 6, 7 or 8.

150. A composition of any one of embodiments 1-144 and 148-149, wherein the core region has a pattern of backbone chiral centers comprising $Rp(Sp)_2$.

151. A composition of any one of embodiments 1-144, wherein the core region has a pattern of backbone chiral centers comprising (Np)t(Rp)n(Sp)m, wherein t is 1-10, n is 1-10, m is 1-50, and each Np is independent Rp or Sp.

152. A composition of any one of embodiments 1-144 and 151, wherein the core region has a pattern of backbone chiral centers comprising (Sp)t(Rp)n(Sp)m, wherein t is 1-10, n is 1-10, m is 1-50.

153. A composition of any one of embodiments 1-144 and 151-152, wherein n is 1.

154. A composition of any one of embodiments 1-144 and 151-153, wherein t is 2, 3, 4, 5, 6, 7 or 8.

155. A composition of any one of embodiments 1-144 and 151-154, wherein m is 2, 3, 4, 5, 6, 7 or 8.

156. A composition of any one of embodiments 1-144 and 151-155, wherein at least one of t and m is greater than 5.

157. A composition of any one of the preceding embodiments, wherein the core region has a pattern of backbone chiral centers comprising SpSpRpSpSp.

158. A composition of any one of the preceding embodiments, wherein 50% or more of the chiral internucleotidic linkages in the core region have Sp configuration.

159. A composition of any one of the preceding embodiments, wherein 60% or more of the chiral internucleotidic linkages in the core region have Sp configuration.

160. A composition of any one of the preceding embodiments, wherein 70% or more of the chiral internucleotidic linkages in the core region have Sp configuration.

161. A composition of any one of the preceding embodiments, wherein 80% or more of the chiral internucleotidic linkages in the core region have Sp configuration.

162. A composition of any one of the preceding embodiments, wherein 90% or more of the chiral internucleotidic linkages in the core region have Sp configuration.

163. A composition of any one of the preceding embodiments, wherein each internucleotidic linkage in the core region is chiral, the core region has only one Rp, and each of the other internucleotidic linkages in the core region is Sp.

164. A composition of any one of the preceding embodiments, wherein each base moiety in the core is not modified.

165. A composition of any one of embodiments 1-163, wherein the core region comprises a modified base.

166. A composition of any one of embodiments 1-163, wherein the core region comprises a modified base, wherein a modified base is substituted A, T, C or G.

167. A composition of any one of embodiments 1-164, wherein each base moiety in the core region is independently selected from A, T, C and G.

168. A composition of any one of embodiments 1-163, wherein the core region is a DNA sequence whose phosphate linkages are independently replaced with phosphorothioate linkages.

169. A composition of any one of the preceding embodiments, wherein the oligonucleotides are single stranded.

170. A composition of any one of the preceding embodiments, wherein the oligonucleotides are antisense oligonucleotide, antagomir, microRNA, pre-microRNs, antimir, supermir, ribozyme, U1 adaptor, RNA activator, RNAi agent, decoy oligonucleotide, triplex forming oligonucleotide, aptamer or adjuvant.

171. A composition of any one of the preceding embodiments, wherein the oligonucleotides are antisense oligonucleotides.

172. A composition of any one of embodiments 1-171, wherein the oligonucleotides have a length of greater than 10 bases.

173. A composition of any one of embodiments 1-171, wherein the oligonucleotides have a length of greater than 11 bases.

174. A composition of any one of embodiments 1-171, wherein the oligonucleotides have a length of greater than 12 bases.

175. A composition of any one of embodiments 1-171, wherein the oligonucleotides have a length of greater than 13 bases.

176. A composition of any one of embodiments 1-171, wherein the oligonucleotides have a length of greater than 14 bases.

177. A composition of any one of embodiments 1-171, wherein the oligonucleotides have a length of greater than 15 bases.

178. A composition of any one of embodiments 1-171, wherein the oligonucleotides have a length of greater than 16 bases.

179. A composition of any one of embodiments 1-171, wherein the oligonucleotides have a length of greater than 17 bases.

180. A composition of any one of embodiments 1-171, wherein the oligonucleotides have a length of greater than 18 bases.

181. A composition of any one of embodiments 1-171, wherein the oligonucleotides have a length of greater than 19 bases.

182. A composition of any one of embodiments 1-171, wherein the oligonucleotides have a length of greater than 20 bases.

183. A composition of any one of embodiments 1-171, wherein the oligonucleotides have a length of greater than 21 bases.

184. A composition of any one of embodiments 1-171, wherein the oligonucleotides have a length of greater than 22 bases.

185. A composition of any one of embodiments 1-171, wherein the oligonucleotides have a length of greater than 23 bases.

186. A composition of any one of embodiments 1-171, wherein the oligonucleotides have a length of greater than 24 bases.

187. A composition of any one of embodiments 1-171, wherein the oligonucleotides have a length of greater than 25 bases.

188. A composition of any one of the preceding embodiments, wherein the oligonucleotides have a length of less than about 200 bases.

189. A composition of any one of the preceding embodiments, wherein the oligonucleotides have a length of less than about 150 bases.

190. A composition of any one of the preceding embodiments, wherein the oligonucleotides have a length of less than about 100 bases.

191. A composition of any one of the preceding embodiments, wherein the oligonucleotides have a length of less than about 50 bases.

192. A composition of any one of the preceding embodiments, wherein the oligonucleotides have a length of less than about 40 bases.

193. A composition of any one of the preceding embodiments, wherein the oligonucleotides have a length of less than about 30 bases.

194. A composition of any one of embodiments 1-171, wherein the oligonucleotides have a length of 10 bases.

195. A composition of any one of embodiments 1-171, wherein the oligonucleotides have a length of 11 bases.

196. A composition of any one of embodiments 1-171, wherein the oligonucleotides have a length of 12 bases.

197. A composition of any one of embodiments 1-171, wherein the oligonucleotides have a length of 13 bases.

198. A composition of any one of embodiments 1-171, wherein the oligonucleotides have a length of 14 bases.

199. A composition of any one of embodiments 1-171, wherein the oligonucleotides have a length of 15 bases.

200. A composition of any one of embodiments 1-171, wherein the oligonucleotides have a length of 16 bases.

201. A composition of any one of embodiments 1-171, wherein the oligonucleotides have a length of 17 bases.

202. A composition of any one of embodiments 1-171, wherein the oligonucleotides have a length of 18 bases.

203. A composition of any one of embodiments 1-171, wherein the oligonucleotides have a length of 19 bases.

204. A composition of any one of embodiments 1-171, wherein the oligonucleotides have a length of 20 bases.

205. A composition of any one of embodiments 1-171, wherein the oligonucleotides have a length of 21 bases.

206. A composition of any one of embodiments 1-171, wherein the oligonucleotides have a length of 22 bases.

207. A composition of any one of embodiments 1-171, wherein the oligonucleotides have a length of 23 bases.

207a. A composition of any one of embodiments 1-171, wherein the oligonucleotides have a length of 24 bases.

207b. A composition of any one of embodiments 1-171, wherein the oligonucleotides have a length of 25 bases.

208. A composition of any one of the preceding embodiments, wherein oligonucleotides of a first plurality have a pattern of backbone chiral center comprises (Sp)m(Rp)n, wherein m is 1-50, and n is 1-10.

208a. A composition of any one of the preceding embodiments, wherein oligonucleotides of a first plurality a pattern of backbone chiral center comprises (Sp)m(Rp)n, wherein m is 1-50, n is 1-10, and m>n.

208b. A composition of any one of the preceding embodiments, wherein oligonucleotides of a first plurality a pattern of backbone chiral center comprises (Sp)m(Rp)n, wherein m is 2, 3, 4, 5, 6, 7 or 8, and n is 1.

208c. A composition of any one of embodiments 1-207, wherein oligonucleotides of a first plurality a pattern of backbone chiral centers comprising (Rp)n(Sp)m, wherein m is 1-50 and n is 1-10.

208d. A composition of any one of embodiments 1-207 and 208d, wherein oligonucleotides of a first plurality a pattern of backbone chiral centers comprising Rp(Sp)m, wherein m is 2, 3, 4, 5, 6, 7 or 8.

208e. A composition of any one of embodiments 1-207 and 208d-208e, wherein oligonucleotides of a first plurality a pattern of backbone chiral centers comprising $Rp(Sp)_2$.

208f. A composition of any one of embodiments 1-207, wherein oligonucleotides of a first plurality a pattern of backbone chiral centers comprising (Np)t(Rp)n(Sp)m, wherein t is 1-10, n is 1-10, m is 1-50, and each Np is independent Rp or Sp.

208g. A composition of any one of embodiments 1-207 and 208g, wherein oligonucleotides of a first plurality a pattern of backbone chiral centers comprising (Sp)t(Rp)n(Sp)m, wherein t is 1-10, n is 1-10, m is 1-50.

208h. A composition of any one of embodiments 1-207 and 208g-208f, wherein n is 1.

208i. A composition of any one of embodiments 1-207 and 208g-208g, wherein t is 2, 3, 4, 5, 6, 7 or 8.

208j. A composition of any one of embodiments 1-207 and 208g-208h, wherein m is 2, 3, 4, 5, 6, 7 or 8.

208k. A composition of any one of embodiments 1-207 and 208g-208i, wherein at least one of t and m is greater than 5.

208l. A composition of any one of the preceding embodiments, wherein the core region has a pattern of backbone chiral centers comprising SpSpRpSpSp.

209. A composition of any one of the preceding embodiments, wherein 50% or more of the chiral internucleotidic linkages in oligonucleotides of a first plurality have Sp configuration.

209a. A composition of any one of the preceding embodiments, wherein 60% or more of the chiral internucleotidic linkages in oligonucleotides of a first plurality have Sp configuration.

209b. A composition of any one of the preceding embodiments, wherein 70% or more of the chiral internucleotidic linkages in oligonucleotides of a first plurality have Sp configuration.

209c. A composition of any one of the preceding embodiments, wherein 80% or more of the chiral internucleotidic linkages in oligonucleotides of a first plurality have Sp configuration.

209d. A composition of any one of the preceding embodiments, wherein 90% or more of the chiral internucleotidic linkages in oligonucleotides of a first plurality have Sp configuration.

209e. A composition of any one of the preceding embodiments, wherein each internucleotidic linkage in oligonucleotides of a first plurality is chiral, the core region has only one Rp, and each of the other internucleotidic linkages in oligonucleotides of a first plurality is Sp.

210. A composition of any one of the preceding embodiments, wherein the oligonucleotide type is not (Sp, Sp, Rp, Sp, Sp, Rp, Sp, Sp, Rp, Sp, Sp)-d[5mCs1As1Gs1Ts15mCs1Ts1Gs15mCs1Ts1Ts15mCs1G] (SEQ ID NO: 60) or (Rp, Rp, Rp, Rp, Rp, Sp, Sp, Rp, Sp, Sp, Rp, Sp, Sp, Rp, Rp, Rp, Rp, Rp, Rp)-Gs5mCs5mCsTs5mCsAsGsTs5mCsTSGs5mCsTSTs5mCsGs5mCsAs5mCs-5mC (5R-(SSR)3-5R) (SEQ ID NO: 61), wherein in the underlined nucleotide are 2'-O-MOE modified.

211. A composition of any one of the preceding embodiments, wherein the oligonucleotide is not an oligonucleotide selected from: (Sp, Sp, Rp, Sp, Sp, Rp, Sp, Sp, Rp, Sp, Sp)-d [5mCs1As1Gs1Ts15mCs1Ts1Gs15mCs1Ts1Ts15mCs1G] (SEQ ID NO: 60) or (Rp, Rp, Rp, Rp, Rp, Sp, Sp, Rp, Sp, Sp, Rp, Sp, Sp, Rp, Rp, Rp, Rp, Rp, Rp)-Gs5mCs5mCs Ts5mCsAsGsTs5mCsTSGs5mCsTSTs5mCsGs5mCsAs5mCs5mC (5R-(SSR)3-5R) (SEQ ID NO: 61), wherein in the underlined nucleotide are 2'-O-MOE modified.

212. A composition of any one of the preceding embodiments, wherein the oligonucleotide is not an oligonucleotide selected from:

| | | |
|---|---|---|
| ONT-106 | (*R*p)-uucuAGAccuGuuuuGcuudT**s**dT (SEQ ID NO: 62) | PCSK9 sense |
| ONT-107 | (*S*p)-uucuAGAccuGuuuuGcuudT**s**dT (SEQ ID NO: 63) | PCSK9 sense |
| ONT-108 | (*R*p)-AAGcAAAAcAGGUCuAGAAdT**s**dT (SEQ ID NO: 64) | PCSK9 antisense |
| ONT-109 | (*S*p)-AAGcAAAAcAGGUCuAGAAdT**s**dT (SEQ ID NO: 65) | PCSK9 antisense |
| ONT-110 | (*R*p, *R*p)-a**s**AGcAAAAcAGGUCuAGAA dT**s**dT (SEQ ID NO: 66) | PCSK9 antisense |
| ONT-111 | (*S*p, *R*p)-a**s**GcAAAAcAGGUCuAGAAd T**s**dT (SEQ ID NO: 67) | PCSK9 antisense |
| ONT-112 | (*S*p, *S*p)-a**s**GcAAAAcAGGUCuAGAAd T**s**dT (SEQ ID NO: 68) | PCSK9 antisense |
| ONT-113 | (*R*p, *S*p)-a**s**GcAAAAcAGGUCuAGAAd T**s**dT (SEQ ID NO: 69) | PCSK9 antisense |

wherein lower case letters represent 2'OMe RNA residues; capital letters represent 2'OH RNA residues; and bolded and "s" indicates a phosphorothioate moiety; and

| | |
|---|---|
| PCSK9 (1) | (All (*S*p))-ususcsusAsGsAscscsusGsususu susGscsususdTsdT (SEQ ID NO: 70) |
| PCSK9 (2) | (All (*R*p))-ususcsusAsGsAscscsusGsususu susGscsususdTsdT (SEQ ID NO: 71) |
| PCSK9 (3) | (All (*S*p))-usucuAsGsAsccuGsuuuuGscuusd TsdT (SEQ ID NO: 72) |
| PCSK9 (4) | (All (*R*p))-usucuAsGsAsccuGsuuuuGscuusd TsdT (SEQ ID NO: 73) |
| PCSK9 (5) | (*R*p, *S*p, *R*p, *S*p, *R*p, *S*p, *R*p, *S*p, *R*p, *S*p, *R*p, *S*p, *R*p, *S*p, *R*p, *S*p, *R*p, *S*p, *R*p, *S*p)-ususcsusAsGsAscscsusGsusususGscsus usdTsdT (SEQ ID NO: 74) |
| PCSK9 (6) | (*S*p, *R*p, *S*p, *R*p, *S*p, *R*p, *S*p, *R*p, *S*p, *R*p, *S*p, *R*p, *S*p, *R*p, *S*p, *R*p, *S*p, *R*p, *S*p, *R*p)-ususcsusAsGsAscscsusGsusususGscsususdT sdT (SEQ ID NO: 75) |

wherein lower case letters represent 2'-OMe RNA residues; capital letters represent RNA residues; d=2'-deoxy residues; and "s" indicates a phosphorothioate moiety and

| | |
|---|---|
| PCSK9 (7) | (All (*R*p))-AsAsGscsAsAsAsAscsAsGsGsUs CsusAsGsAsAsdTsdT (SEQ ID NO: 76) |
| PCSK9 (8) | (All (*S*p))-AsAsGscsAsAsAsAscsAsGsGsUs CsusAsGsAsAsdTsdT (SEQ ID NO: 77) |
| PCSK9 (9) | (All (*R*p))-AsAGcAAAAcsAsGsGsUsCsusAsG sAsAsdTsdT (SEQ ID NO: 78) |
| PCSK9 (10) | (All (*S*p))-AsAGcAAAAcsAsGsGsUsCsusAsG sAsAsdTsdT (SEQ ID NO: 79) |
| PCSK9 (11) | (All (*R*p))-AAsGscsAsAsAsAscAGGUCuAGAA dTsdT (SEQ ID NO: 80) |
| PCSK9 (12) | (All (*S*p))-AAsGscsAsAsAsAscAGGUCuAGAA dTsdT (SEQ ID NO: 81) |
| PCSK9 (13) | (All (*R*p))-AsAsGscAsAsAsAscAsGsGsUsCs uAsGsAsAsdTsdT (SEQ ID NO: 82) |
| PCSK9 (14) | (All (*S*p))-AsAsGscAsAsAsAscAsGsGsUsCs uAsGsAsAsdTsdT (SEQ ID NO: 83) |
| PCSK9 (15) | (All (*R*p))-AsAGcAAAsAscAsGsGsUsCsusAs GsAsAsdTsdT (SEQ ID NO: 84) |
| PCSK9 (16) | (All (*S*p))-AsAGcAAAsAscAsGsGsUsCsusAs GsAsAsdTsdT (SEQ ID NO: 85) |
| PCSK9 (17) | (*R*p, *S*p, *R*p, *S*p, *R*p, *S*p, *R*p, *S*p, *R*p, *S*p, *R*p, *S*p, *R*p, *S*p)-AsAGcAAAsAscAsGsG sUsCsusAsGsAsAsdTsdT (SEQ ID NO: 86) |
| PCSK9 (18) | (*S*p, *R*p, *S*p, *R*p, *S*p, *R*p, *S*p, *R*p, *S*p, *R*p, *S*p, *R*p, *S*p, *R*p)-AsAGcAAAsAscAsGsGs UsCsusAsGsAsAsdTsdT (SEQ ID NO: 87) |

wherein lower case letters represent 2'-OMe RNA residues; capital letters represent RNA residues; d=2'-deoxy residues; "s" indicates a phosphorothioate moiety; and

| | |
|---|---|
| PCSK9 (19) | (All (*R*p))-UfsusCfsusAfsgsAfscsCfsus GfsusUfsusUfsgsCfsusUfsdTsdT (SEQ ID NO: 88) |
| PCSK9 (20) | (All (*S*p))-UfsusCfsusAfsgsAfscsCfsus GfsusUfsusUfsgsCfsusUfsdTsdT (SEQ ID NO: 89) |
| PCSK9 (21) | (All (*R*p))-UfsuCfsuAfsgAfscCfsuGfsuU fsuUfsgCfsuUfsdTsdT (SEQ ID NO: 90) |
| PCSK9 (22) | (All (*S*p))-UfsuCfsuAfsgAfscCfsuGfsuU fsuUfsgCfsuUfsdTsdT (SEQ ID NO: 91) |
| PCSK9 (23) | (*R*p, *S*p, *R*p, *S*p, *R*p, *S*p, *R*p, *S*p, *R*p, *S*p, *R*p, *S*p, *R*p, *S*p, *R*p, *S*p, *R*p, *S*p, *R*p, *S*p)-UfsusCfsusAfsgsAfscsCfsusGfs usUfsusUfsgsCfsusUfsdTsdT (SEQ ID NO: 92) |
| PCSK9 (24) | (*S*p, *R*p, *S*p, *R*p, *S*p, *R*p, *S*p, *R*p, *S*p, *R*p, *S*p, *R*p, *S*p, *R*p, *S*p, *R*p, *S*p, *R*p, *S*p,*R*p)-UfsusCfsusAfsgsAfscsCfsusGf susUfsusUfsgsCfsusUfsdTsdT (SEQ ID NO: 93) |

wherein lower case letters represent 2'-OMe RNA residues; capital letters represent 2'-F RNA residues; d=2'-deoxy residues; and "s" indicates a phosphorothioate moiety; and

| | |
|---|---|
| PCSK9 (25) | (All (*Rp*))-asAfsgsCfsasAfsasAfscsAfsgsGfsusCfsusAfsgsAfsasdTsdT (SEQ ID NO: 94) |
| PCSK9 (26) | (All (*Sp*))-asAfsgsCfsasAfsasAfscsAfsgsGfsusCfsusAfsgsAfsasdTsdT (SEQ ID NO: 95) |
| PCSK9 (27) | (All (*Rp*))-asAfgCfaAfaAfcsAfsgsGfsusCfsusAfsgsAfsasdTsdT (SEQ ID NO: 96) |
| PCSK9 (28) | (All (*Sp*))-asAfgCfaAfaAfcsAfsgsGfsusCfsusAfsgsAfsasdTsdT (SEQ ID NO: 97) |
| PCSK9 (29) | (All (*Rp*))-asAfsgCfsaAfsaAfscAfsgGfsuCfsuAfsgAfsadTsdT (SEQ ID NO: 98) |
| PCSK9 (30) | (All (*Sp*))-asAfsgCfsaAfsaAfscAfsgGfsuCfsuAfsgAfsadTsdT (SEQ ID NO: 99) |
| PCSK9 (31) | (*Rp*, *Sp*, *Rp*, *Sp*, *Rp*, *Sp*, *Rp*, *Sp*, *Rp*, *Sp*, *Rp*, *Sp*, *Rp*, *Sp*)-asAfgCfaAfasAfscAfsgsGfsusCfsusAfsgsAfsasdTsdT (SEQ ID NO: 100) |
| PCSK9 (32) | (*Sp*, *Rp*, *Sp*, *Rp*, *Sp*, *Rp*, *Sp*, *Rp*, *Sp*, *Rp*, *Sp*, *Rp*, *Sp*, *Rp*)-asAfgCfaAfasAfscAfsgsGfsusCfsusAfsgsAfsasdTsdT (SEQ ID NO: 101) |

213. A composition of any one of the preceding embodiments, wherein the oligonucleotide is not an oligonucleotide selected from:

$d[A_RC_SA_RC_SA_RC_SA_RC_SA_RC]$ (SEQ ID NO: 102), $d[C_SC_SC_SC_RC_RC_SC_SC_SC_SC]$ (SEQ ID NO: 103), $d[C_SC_SC_SC_SC_SC_SC_RC_RC_SC]$ (SEQ ID NO: 104) and $d[C_SC_SC_SC_SC_SC_RC_RC_SC_SC]$ (SEQ ID NO: 105), wherein R is Rp phosphorothioate linkage, and S is Sp phosphorothioate linkage.

214. A composition of any one of the preceding embodiments, wherein the oligonucleotide is not an oligonucleotide selected from: $GGA_RT_SG_RT_ST_R{}^mC_STCGA$ (SEQ ID NO: 106), $GGA_RT_RG_ST_ST_R{}^mC_RTCGA$ (SEQ ID NO: 107), $GGA_ST_SG_RT_RT_S{}^mC_STCGA$ (SEQ ID NO: 108), wherein R is Rp phosphorothioate linkage, S is Sp phosphorothioate linkage, all other linkages are PO, and each $^mC$ is a 5-methyl cytosine modified nucleoside.

215. A composition of any one of the preceding embodiments, wherein the oligonucleotide is not an oligonucleotide selected from: $T_kT_k{}^mC_kAGT^mCATGA^mCT_kT^mC_k{}^mC_k$ (SEQ ID NO: 109), wherein each nucleoside followed by a subscript 'k' indicates a (S)-cEt modification, R is Rp phosphorothioate linkage, S is Sp phosphorothioate linkage, each $^mC$ is a 5-methyl cytosine modified nucleoside, and all internucleoside linkages are phosphorothioates (PS) with stereochemistry patterns selected from RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

216. A composition of any one of the preceding embodiments, wherein the oligonucleotide is not an oligonucleotide selected from:

(SEQ ID NO: 110)

$T_kT_k{}^mC_k\underline{AGT^mCATGA^mCT}T_k{}^mC_k{}^mC_k$, wherein each nucleoside followed by a subscript 'k' indicates a (S)-cEt modification, R is Rp phosphorothioate linkage, S is Sp phosphorothioate linkage, each $^mC$ is a 5-methyl cytosine modified nucleoside and all internucleoside linkages in the underlined core are phosphorothioates (PS) with stereochemistry patterns selected from: RSSSRSRRRS, RSSSSSSSSS, SRRSRSSSSR, SRSRSSRSSR, RRRSSSRSSS, RRRSRSSRSR, RRSSSRSRSR, SRSSSRSSSS, SSRRSSRSRS, SSSSSSRRSS, RRRSSRRRSR, RRRRSSSSRS, SRRSRRRRRR, RSSRSSRRRR, RSRRSRRSRR, RRSRSSRSRS, SSRRRRRSRR, RSRRSRSSSR, RRSSRSRRRR, RRSRSRRSSS, RRSRSSSRRR, RSRRRRSRSR, SSRSSSRRRS, RSSRSRSRSR, RSRSRSSRSS, RRRSSRRSRS, SRRSSRRSRS, RRRRSRSRRR, SSSSRRRRSR, RRRRRRRRRR and SSSSSSSSSS.

217. A composition of embodiment 215 or 216, wherein each phosphorothioate moiety of each nucleotide comprising (S)-cEt modification is stereorandom.

218. A composition of any one of the preceding embodiments, wherein oligonucleotides of a first plurality comprise two or more natural phosphate linkages.

218a. A composition of any one of the preceding embodiments, wherein oligonucleotides of a first plurality comprise three or more natural phosphate linkages.

218b. A composition of any one of the preceding embodiments, wherein oligonucleotides of a first plurality comprise four or more natural phosphate linkages.

218c. A composition of any one of the preceding embodiments, wherein oligonucleotides of a first plurality comprise five or more natural phosphate linkages.

218d. A composition of any one of the preceding embodiments, wherein oligonucleotides of a first plurality comprise six or more natural phosphate linkages.

218e. A composition of any one of the preceding embodiments, wherein oligonucleotides of a first plurality comprise seven or more natural phosphate linkages.

218f. A composition of any one of the preceding embodiments, wherein oligonucleotides of a first plurality comprise eight or more natural phosphate linkages.

218g. A composition of any one of the preceding embodiments, wherein oligonucleotides of a first plurality comprise nine or more natural phosphate linkages.

218h. A composition of any one of the preceding embodiments, wherein oligonucleotides of a first plurality comprise ten or more natural phosphate linkages.

219. A composition of any one of the preceding embodiments, wherein oligonucleotides of a first plurality comprise two or more modified phosphate linkages.

219a. A composition of any one of the preceding embodiments, wherein oligonucleotides of a first plurality comprise three or more modified phosphate linkages.

219b. A composition of any one of the preceding embodiments, wherein oligonucleotides of a first plurality comprise four or more modified phosphate linkages.

219c. A composition of any one of the preceding embodiments, wherein oligonucleotides of a first plurality comprise five or more modified phosphate linkages.

219d. A composition of any one of the preceding embodiments, wherein oligonucleotides of a first plurality comprise six or more modified phosphate linkages.

219e. A composition of any one of the preceding embodiments, wherein oligonucleotides of a first plurality comprise seven or more modified phosphate linkages.

219f. A composition of any one of the preceding embodiments, wherein oligonucleotides of a first plurality comprise eight or more modified phosphate linkages.

219g. A composition of any one of the preceding embodiments, wherein oligonucleotides of a first plurality comprise nine or more modified phosphate linkages.

219i. A composition of any one of the preceding embodiments, wherein oligonucleotides of a first plurality comprise ten or more modified phosphate linkages.

220. A composition of any one of embodiments 219-219i, wherein each modified phosphate linkage is a phosphorothioate linkage.

221. A composition of any one of the preceding embodiments, wherein a first plurality of oligonucleotides comprises a modified base, wherein a modified base is substituted A, T, C, U or G.

222. A composition of any one of the preceding embodiments, wherein each base moiety in an oligonucleotide of the first plurality is optionally substituted A, T, C, U, or G.

223. A composition of any one of the preceding embodiments, wherein each base moiety in an oligonucleotide of the first plurality is independently selected from A, T, C, U, 5-MeC and G.

224. A composition of any one of the preceding embodiments, wherein each chiral internucleotidic linkage is formed with greater than 90:10 diastereomeric selectivity.

225. A composition of any one of the preceding embodiments, wherein each chiral internucleotidic linkage is formed with greater than 95:5 diastereomeric selectivity.

226. A composition of any one of the preceding embodiments, wherein each chiral internucleotidic linkage is formed with greater than 96:4 diastereomeric selectivity.

227. A composition of any one of the preceding embodiments, wherein each chiral internucleotidic linkage is formed with greater than 97:3 diastereomeric selectivity.

228. A composition of any one of the preceding embodiments, wherein each chiral internucleotidic linkage is formed with greater than 98:2 diastereomeric selectivity.

229. A composition of any one of the preceding embodiments, wherein each chiral internucleotidic linkage is formed with greater than 98:2 diastereomeric selectivity.

230. A composition of any one of embodiments 224-229, wherein the diastereomeric selectivity for forming a chiral internucleotidic linkage is measured by forming a dimeric oligonucleotide comprising the chiral internucleotidic linkage and the nucleosides to both sides of the chiral internucleotidic linkage under the same or comparable reaction conditions.

231. A composition of any one of the preceding embodiments, which composition displays reduced toxicity as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

231a. A composition of any one of the preceding embodiments, which composition displays reduced immune activation as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

231b. A composition of any one of the preceding embodiments, which composition displays reduced complement activation as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

231c. A composition of any one of the preceding embodiments, which composition displays reduced injection site inflammation as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

232. A composition of any one of the preceding embodiments, wherein the reduced complement activation is observed in an assay that detects a protein whose level changes upon complement activation.

233. A composition of any one of the preceding embodiments, wherein the reduced complement activation is observed in an assay that detects presence, absolute level and or relative levels of one or more complete-activation related product.

234. A composition of any one of the preceding embodiments, wherein the reduced complement activation is observed in an assay that detects presence, absolute level and or relative levels of one or more complete-activation related product selected from the group consisting of C3a, Bb, C4a, C5a, C5b, C6, C7, C8 and C9.

234a. A composition of any one of the preceding embodiments, wherein the reduced complement activation is observed in an assay that detects presence, absolute level and or relative levels of C3a.

234b. A composition of any one of the preceding embodiments, wherein the reduced complement activation is observed in an assay that detects presence, absolute level and or relative levels of C4a.

234c. A composition of any one of the preceding embodiments, wherein the reduced complement activation is observed in an assay that detects presence, absolute level and or relative levels of C5a.

234d. A composition of any one of the preceding embodiments, wherein the reduced complement activation is observed in an assay that detects presence, absolute level and or relative levels of Bb.

235. A composition of any one of the preceding embodiments, wherein the reduced complement activation is observed in monkey serum.

236. A composition of any one of the preceding embodiments, wherein complement activation is reduced by 5%.

236a. A composition of any one of the preceding embodiments, wherein complement activation is reduced by 10%.

236b. A composition of any one of the preceding embodiments, wherein complement activation is reduced by 20%.

236c. A composition of any one of the preceding embodiments, wherein complement activation is reduced by 30%.

236d. A composition of any one of the preceding embodiments, wherein complement activation is reduced by 40%.

236e. A composition of any one of the preceding embodiments, wherein complement activation is reduced by 50%.

236f. A composition of any one of the preceding embodiments, wherein complement activation is reduced by 60%.

236g. A composition of any one of the preceding embodiments, wherein complement activation is reduced by 70%.

236h. A composition of any one of the preceding embodiments, wherein complement activation is reduced by 80%.

236i. A composition of any one of the preceding embodiments, wherein complement activation is reduced by 90%.

236j. A composition of any one of the preceding embodiments, wherein complement activation is reduced by 95%.

236k. A composition of any one of the preceding embodiments, wherein complement activation is reduced by 96%.

236l. A composition of any one of the preceding embodiments, wherein complement activation is reduced by 97%.

236m. A composition of any one of the preceding embodiments, wherein complement activation is reduced by 98%.

236n. A composition of any one of the preceding embodiments, wherein complement activation is reduced by 99%.

237. A composition of any one of the preceding embodiments, wherein complement activation is measured at a time point less than 60 minutes after the composition is administered.

237a. A composition of any one of the preceding embodiments, wherein complement activation is measured at a time point within 0-40 minutes after the composition is administered.

237b. A composition of any one of the preceding embodiments, wherein complement activation is measured at multiple time points.

238. A composition of any one of the preceding embodiments, wherein complement activation is measured at a time point as measured by C3a levels at a time point within the range of 5-60 minutes after the composition is added to monkey serum.

239. A composition of any one of the preceding embodiments, which composition displays altered protein binding as compared with a reference composition comprising a plurality of oligonucleotides, each of which also has the common base sequence but which differs structurally from the oligonucleotides of the first plurality in that:

individual oligonucleotides within the reference plurality differ from one another in stereochemical structure; and/or at least some oligonucleotides within the reference plurality have a structure different from a structure represented by the plurality of oligonucleotides of the composition; and/or at least some oligonucleotides within the reference plurality do not comprise a wing region and a core region.

240. A composition of any one of the preceding embodiments, wherein the composition displays altered binding as compared with a reference composition to one or more proteins selected from serum proteins, heparin sulfate-binding proteins, and intracellular proteins.

241. A composition of any one of the preceding embodiments, wherein the composition displays altered binding as compared with a reference composition to one or more proteins selected from Albumin, Complement Factor H, Factor IX, ApoE, Thrombin, Factor VIIIa, Heparin Cofactor II, alpha-2 macroglobulin, Fibroblast Growth Factor 1, Fibroblast Growth Factor 2, Hepatocyte Growth Factor/Scatter Factor, Vascular Endothelial Growth Factor, High-Mobility Group Protein B1, Cyclophilin B, IL-8 (CXCL8), Platelet Factor 4 (CXCL4), Stromal Cell-Derived Factor-1 (CXCL12), Monocyte Chemoattractant Protein-1 (CCL2), Fibroblast Growth Factor Receptor 1, Neuropilin-1, Receptor for Advanced Glycation End Products, Receptor Protein Tyrosine Phosphatase Sigma, Slit-2, ROBO1, Thrombin, Antithrombin, Protein C inhibitor, Amyloid precursor protein 1, Thrombospondin-1, Annexin A2, PDGF BB, PC4/Sub1, RNF163/ZNF9, Ku70, Ku80, TCP1-alpha, TCP1-beta, TCP1-epsilon, TCP1-gamma, TCP1-Theta, TCP1-delta, HSP90-AA1, HSP90-AB, HSP70-5/GRP78, HSPA1L, HSC70, ACTB, TBBB2C, Vimentin, CArG Binding Factor, DHX30, EIF2S2, EIF4H, GRSF1, hnRNP D1L, hnRNPA1, hnRNPA2, hnRNPH1, hnRNPK, hnRNPQ, hnRNPU, hnRNPUL, ILF2, ILF3, KHSRP, La/SSB, NCL, NPM1, P54nrb, PSF, PSPC1, RHA, YBX1, ACLY, VARS, ANXA2, NDKA, Thymidylate Kinase, JKBP1 delta 6, SHMT2, LRPPRC, NARS, ATAD3A, KCTD12, CD4, GP120, aMb2 (Mac-1), VDAC-1, Ago2 PAZ domain, RAGE, AIM2, DHX36, DHX9, DDX41, IFI16, RIG-I, MDA5, LRRFIP1, DLM-1/ZBP1, TREX1, Laminin, and Fibronectin.

242. A composition of any one of the preceding embodiments, wherein the composition displays decreased binding as compared with a reference composition to one or more proteins.

242a. A composition of any one of the preceding embodiments, wherein the composition displays decreased binding as compared with a reference composition to one or more proteins by more than 10%.

242b. A composition of any one of the preceding embodiments, wherein the composition displays decreased binding as compared with a reference composition to one or more proteins by more than 20%.

242c. A composition of any one of the preceding embodiments, wherein the composition displays decreased binding as compared with a reference composition to one or more proteins by more than 30%.

242d. A composition of any one of the preceding embodiments, wherein the composition displays decreased binding as compared with a reference composition to one or more proteins by more than 40%.

242e. A composition of any one of the preceding embodiments, wherein the composition displays decreased binding as compared with a reference composition to one or more proteins by more than 50%.

242f. A composition of any one of the preceding embodiments, wherein the composition displays decreased binding as compared with a reference composition to one or more proteins by more than 60%.

242g. A composition of any one of the preceding embodiments, wherein the composition displays decreased binding as compared with a reference composition to one or more proteins by more than 70%.

242h. A composition of any one of the preceding embodiments, wherein the composition displays decreased binding as compared with a reference composition to one or more proteins by more than 80%.

242i. A composition of any one of the preceding embodiments, wherein the composition displays decreased binding as compared with a reference composition to one or more proteins by more than 90%.

242j. A composition of any one of the preceding embodiments, wherein the composition displays decreased binding as compared with a reference composition to one or more proteins by more than 95%.

242k. A composition of any one of the preceding embodiments, wherein the composition displays decreased binding as compared with a reference composition to one or more proteins by more than 96%.

242l. A composition of any one of the preceding embodiments, wherein the composition displays decreased binding as compared with a reference composition to one or more proteins by more than 97%.

242m. A composition of any one of the preceding embodiments, wherein the composition displays decreased binding as compared with a reference composition to one or more proteins by more than 98%.

242n. A composition of any one of the preceding embodiments, wherein the composition displays decreased binding as compared with a reference composition to one or more proteins by more than 99%.

243. A composition of any one of the preceding embodiments, wherein the composition displays decreased binding as compared with a reference composition to Factor H.

243a. A composition of any one of the preceding embodiments, wherein the composition displays decreased binding as compared with a reference composition to a heparin sulfate binding protein.

244. A composition of any one of the preceding embodiments, wherein the composition displays increased binding as compared with a reference composition to one or more proteins.

245. A composition of any one of the preceding embodiments, wherein the composition displays increased binding as compared with a reference composition to albumin.

245a. A composition of any one of the preceding embodiments, wherein the increased protein binding is observed in a BSA binding assay, wherein the first plurality of oligonucleotides have increased BSA binding that the reference plurality.

246. A composition of any one of the preceding embodiments, wherein the composition displays increased binding as compared with a reference composition by 5% or more.

246a. A composition of any one of the preceding embodiments, wherein the composition displays increased binding as compared with a reference composition by 10% or more.

246b. A composition of any one of the preceding embodiments, wherein the composition displays increased binding as compared with a reference composition by 20% or more.

246c. A composition of any one of the preceding embodiments, wherein the composition displays increased binding as compared with a reference composition by 30% or more.

246d. A composition of any one of the preceding embodiments, wherein the composition displays increased binding as compared with a reference composition by 40% or more.

246e. A composition of any one of the preceding embodiments, wherein the composition displays increased binding as compared with a reference composition by 50% or more.

246f. A composition of any one of the preceding embodiments, wherein the composition displays increased binding as compared with a reference composition by 60% or more.

246g. A composition of any one of the preceding embodiments, wherein the composition displays increased binding as compared with a reference composition by 70% or more.

246h. A composition of any one of the preceding embodiments, wherein the composition displays increased binding as compared with a reference composition by 80% or more.

246i. A composition of any one of the preceding embodiments, wherein the composition displays increased binding as compared with a reference composition by 90% or more.

246j. A composition of any one of the preceding embodiments, wherein the composition displays increased binding as compared with a reference composition by 100% or more.

246k. A composition of any one of the preceding embodiments, wherein the composition displays increased binding as compared with a reference composition by 2 folds or more.

246l. A composition of any one of the preceding embodiments, wherein the composition displays increased binding as compared with a reference composition by 5 folds or more.

246m. A composition of any one of the preceding embodiments, wherein the composition displays increased binding as compared with a reference composition by 10 folds or more.

246n. A composition of any one of the preceding embodiments, wherein the composition displays increased binding as compared with a reference composition by 50 folds or more.

246o. A composition of any one of the preceding embodiments, wherein the composition displays increased binding as compared with a reference composition by 100 folds or more.

246p. A composition of any one of the preceding embodiments, wherein protein binding is measured in vitro.

247. A composition of any one of the preceding embodiments, which the composition displays improved oligonucleotide delivery as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

247a. A composition of any one of the preceding embodiments, wherein the composition displays improved systemic delivery.

247b. A composition of any one of the preceding embodiments, wherein the composition displays improved cytoplasmatic delivery.

247c. A composition of any one of the preceding embodiments, wherein the composition displays improved delivery to a target.

247d. A composition of any one of the preceding embodiments, wherein the composition displays improved delivery to a population of cells.

247e. A composition of any one of the preceding embodiments, wherein the composition displays improved delivery to a tissue.

247f. A composition of any one of the preceding embodiments, wherein the composition displays improved delivery to an organ.

248. A composition of any one of the preceding embodiments, further comprising a pharmaceutically acceptable carrier.

248a. A composition of any one of the preceding embodiments, wherein oligonucleotides of the first plurality are for treatment of a disease associated with complement.

248b. A composition of any one of the preceding embodiments, wherein oligonucleotides of the first plurality are for treatment of neuroinflammation, neurodegeneration, muscular inflammation, demyelination, vasculitis or nephritis.

248c. A composition of any one of the preceding embodiments, wherein oligonucleotides of the first plurality are for treatment of lupus nephritis.

248d. A composition of any one of the preceding embodiments, wherein oligonucleotides of the first plurality target C1, C1a, C1r, C1s, C1q, MASP-1, MASP-2, C3, C3-convertase, C3a, C3b, C3aR, C4b, C5, C5a, C5aR, Factor B, Factor D, Thrombin, Plasmin, Kallikrein, or FactorXIIa.

248e. A composition of any one of the preceding embodiments, wherein oligonucleotides of the first plurality target C5.

248f. A composition of any one of the preceding embodiments except embodiment 248e, wherein oligonucleotides of the first plurality target factor B.

248g. A composition of any one of the preceding embodiments, comprising one or more lipids.

248h. A composition of any one of the preceding embodiments, wherein at least one lipid is conjugated to the oligonucleotides of the composition.

248i. A composition of any one of the preceding embodiments, wherein at least one lipid is covalently conjugated to the oligonucleotides of the composition.

248j. A composition of any one of the preceding embodiments, comprising one or more targeting components.

248k. A composition of any one of the preceding embodiments, wherein at least one target component is conjugated to the oligonucleotides of the composition.

248l. A composition of any one of the preceding embodiments, wherein at least one target component is covalently conjugated to the oligonucleotides of the composition.

249. In a method of administering an oligonucleotide composition comprising a first plurality of oligonucleotides having a common nucleotide sequence, the improvement that comprises: administering an oligonucleotide composition comprising the first plurality of oligonucleotides that is characterized by reduced toxicity relative to a reference oligonucleotide composition of the same common nucleotide sequence.

249a. In a method of administering an oligonucleotide composition comprising a first plurality of oligonucleotides having a common nucleotide sequence, the improvement that comprises: administering an oligonucleotide composition comprising the first plurality of oligonucleotides that is chirally controlled and that is characterized by reduced toxicity relative to a reference oligonucleotide composition of the same common nucleotide sequence.

249b. In a method of administering an oligonucleotide composition comprising a first plurality of oligonucleotides having a common nucleotide sequence, the improvement that comprises: administering an oligonucleotide composition of any one of the preceding embodiments.

249c. In a method of administering an oligonucleotide composition comprising a first plurality of oligonucleotides having a common nucleotide sequence, the improvement that comprises: administering an oligonucleotide composition in which each oligonucleotide in the plurality comprises one or more modified sugar moieties and the composition is characterized by reduced toxicity relative to a reference oligonucleotide composition of the same common nucleotide sequence but lacking at least one of the one or more modified sugar moieties.

249d. In a method of administering an oligonucleotide composition comprising a first plurality of oligonucleotides having a common nucleotide sequence, the improvement that comprises: administering an oligonucleotide composition in which each oligonucleotide in the plurality includes one or more natural phosphate linkages and one or more modified phosphate linkages; wherein the oligonucleotide composition is characterized by reduced toxicity when tested in at least one assay that is observed with an otherwise comparable reference composition whose oligonucleotides do not comprise natural phosphate linkages.

250. In a method of administering an oligonucleotide composition comprising a first plurality of oligonucleotides having a common nucleotide sequence, the improvement that comprises: administering an oligonucleotide composition in which each oligonucleotide in the plurality comprises one or more modified sugar moieties and the composition is characterized by reduced toxicity relative to a reference oligonucleotide composition of the same common nucleotide sequence but lacking at least one of the one or more modified sugar moieties.

251. A method comprising steps of administering to a subject an oligonucleotide composition comprising a first plurality of oligonucleotides each of which has a common base sequence and comprises a modified sugar moiety, wherein the oligonucleotide composition is characterized by reduced toxicity when tested in at least one assay that is observed with an otherwise comparable reference composition that comprises a reference plurality of oligonucleotides which have the same common base sequence but have no modified sugar moieties.

252. A method comprising steps of administering to a subject an oligonucleotide composition comprising a first plurality of oligonucleotides each of which has a common base sequence and comprises one or more natural phosphate linkages and one or more modified phosphate linkages, wherein the oligonucleotide composition is characterized by reduced toxicity when tested in at least one assay that is observed with an otherwise comparable reference composition that comprises a reference plurality of oligonucleotides which have the same common base sequence but have no natural phosphate linkages.

253. A method comprising steps of administering a chirally controlled oligonucleotide composition to a subject, wherein the chirally controlled oligonucleotide composition is characterized by reduced toxicity when tested in at least one assay that is observed with an otherwise comparable reference composition that includes a different chirally controlled oligonucleotide composition, or a stereorandom oligonucleotide composition, comprising oligonucleotides having the same base sequence.

254. A method of administering an oligonucleotide composition comprising a first plurality of oligonucleotides having a common nucleotide sequence, comprising:

administering an oligonucleotide composition comprising the first plurality of oligonucleotides that is characterized by reduced toxicity relative to a reference oligonucleotide composition comprising a reference plurality of oligonucleotides of the same common nucleotide sequence.

254a. A method of administering an oligonucleotide composition comprising a first plurality of oligonucleotides having a common nucleotide sequence, comprising:

administering an oligonucleotide composition comprising the first plurality of oligonucleotides that is characterized by reduced complement activation relative to a reference oligonucleotide composition comprising a reference plurality of oligonucleotides of the same common nucleotide sequence.

254b. A method of administering an oligonucleotide composition comprising a first plurality of oligonucleotides having a common nucleotide sequence, comprising:

administering an oligonucleotide composition comprising the first plurality of oligonucleotides that is characterized by altered protein binding relative to a reference oligonucleotide composition comprising a reference plurality of oligonucleotides of the same common nucleotide sequence.

254c. The method of embodiment 254b, wherein the altered protein binding comprises improved binding to albumin.

254d. A method of administering an oligonucleotide composition comprising a first plurality of oligonucleotides having a common nucleotide sequence, comprising:

administering an oligonucleotide composition comprising the first plurality of oligonucleotides that is characterized by reduced injection site inflammation relative to a reference oligonucleotide composition comprising a reference plurality of oligonucleotides of the same common nucleotide sequence.

254e. A method of any one of the preceding embodiments, wherein the reduced toxicity is or comprises reduced complement activation.

254f. A method of any one of the preceding embodiments, wherein the reduced toxicity is assessed in a complement activation assay.

254g. A method of any one of the preceding embodiments, wherein the reduced complement activation is observed in an assay that detects a protein whose level changes upon complement activation.

254h. A method of any one of the preceding embodiments, wherein the reduced complement activation is observed in an assay that detects presence, absolute level and or relative levels of one or more complete-activation related product.

254i. A method of any one of the preceding embodiments, wherein the reduced complement activation is observed in an assay that detects presence, absolute level and or relative levels of one or more complete-activation related product selected from the group consisting of C3a, Bb or combinations thereof.

254j. A method of any one of the preceding embodiments, wherein the reduced complement activation is observed in monkey serum.

255. A method of any one of the preceding embodiments, wherein oligonucleotides of the administered oligonucleotide compositions are for treatment of a disease associated with complement.

255a. A method of any one of the preceding embodiments, wherein oligonucleotides of the administered oligonucleotide compositions are for treatment of neuroinflammation, neurodegeneration, muscular inflammation, demyelination, vasculitis or nephritis.

255b. A method of any one of the preceding embodiments, wherein oligonucleotides of the administered oligonucleotide compositions are for treatment of lupus nephritis.

255c. A method of any one of the preceding embodiments, wherein oligonucleotides of the administered oligonucleotide compositions target C1, C1a, C1r, C1s, C1q, MASP-1, MASP-2, C3, C3-convertase, C3a, C3b, C3aR, C4b, C5, C5a, C5aR, Factor B, Factor D, Thrombin, Plasmin, Kallikrein, or FactorXIIa.

255d. A method of any one of the preceding embodiments, wherein oligonucleotides of the administered oligonucleotide compositions target C5.

255e. A method of any one of the preceding embodiments except embodiment 255d, wherein oligonucleotides of the administered oligonucleotide compositions target factor B.

256. A method of any one of the preceding embodiments, wherein complement activation is reduced by at least 5%.

256a. A method of any one of the preceding embodiments, wherein complement activation is reduced by at least 10%.

256b. A method of any one of the preceding embodiments, wherein complement activation is reduced by at least 20%.

256c. A method of any one of the preceding embodiments, wherein complement activation is reduced by at least 30%.

256d. A method of any one of the preceding embodiments, wherein complement activation is reduced by at least 40%.

256e. A method of any one of the preceding embodiments, wherein complement activation is reduced by at least 50%.

256f. A method of any one of the preceding embodiments, wherein complement activation is reduced by at least 60%.

256g. A method of any one of the preceding embodiments, wherein complement activation is reduced by at least 70%.

256h. A method of any one of the preceding embodiments, wherein complement activation is reduced by at least 80%.

256i. A method of any one of the preceding embodiments, wherein complement activation is reduced by at least 90%.

256j. A method of any one of the preceding embodiments, wherein complement activation is reduced by at least 95%.

256k. A method of any one of the preceding embodiments, wherein complement activation is reduced by at least 96%.

256l. A method of any one of the preceding embodiments, wherein complement activation is reduced by at least 97%.

256m. A method of any one of the preceding embodiments, wherein complement activation is reduced by at least 98%.

256n. A method of any one of the preceding embodiments, wherein complement activation is reduced by at least 99%.

256o. A method of any one of the preceding embodiments, wherein complement activation is reduced to a level comparable to a negative control.

256p. A method of any one of the preceding embodiments, wherein complement activation is reduced to a level comparable to water.

257. A method of any one of the preceding embodiments, wherein complement activation is measured at a time point no more than 60 minutes after the composition is added to monkey serum.

257a. A method of any one of the preceding embodiments, wherein complement activation is measured at a time point 0-40 minutes after the composition is added to monkey serum.

258. A method of any one of the preceding embodiments, wherein complement activation is measured at a time point as measured by C3a levels at a time point within the range of 5-60 minutes after the composition is added to monkey serum.

259. A method of any one of the preceding embodiments, wherein the composition of the first plurality of oligonucleotides displays reduced injection site inflammation as compared with a reference composition.

260. A method, comprising administering a composition comprising a first plurality of oligonucleotides, which composition displays reduced injection site inflammation as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

260a. In a method of administering an oligonucleotide composition comprising a first plurality of oligonucleotides having a common nucleotide sequence, the improvement that comprises: administering an oligonucleotide comprising a first plurality of oligonucleotides that is characterized by reduced injection site inflammation relative to a reference oligonucleotide composition of the same common nucleotide sequence.

261. A method of any one of the preceding embodiments, wherein the composition of the first plurality of oligonucleotides displays altered protein binding.

262. A method, comprising administering a composition comprising a first plurality of oligonucleotides, which composition displays altered protein binding as compared with a reference composition comprising a plurality of oligonucleotides, each of which also has the common base sequence but which differs structurally from the oligonucleotides of the first plurality in that:

- individual oligonucleotides within the reference plurality differ from one another in stereochemical structure; and/or
- at least some oligonucleotides within the reference plurality have a structure different from a structure represented by the plurality of oligonucleotides of the composition; and/or
- at least some oligonucleotides within the reference plurality do not comprise a wing region and a core region.

262a. In a method of administering an oligonucleotide composition comprising a first plurality of oligonucleotides having a common nucleotide sequence, the improvement that comprises: administering an oligonucleotide composition comprising a first plurality of oligonucleotides that is characterized by altered protein binding relative to a reference oligonucleotide composition of the same common nucleotide sequence.

263. A method of any one of the preceding embodiments, wherein the composition comprising the first plurality of oligonucleotides displays altered binding as compared with a reference composition to one or more proteins selected from serum proteins, heparin sulfate-binding proteins, and intracellular proteins.

264. A method of any one of the preceding embodiments, wherein the composition comprising the first plurality of oligonucleotides displays altered binding as compared with a reference composition to one or more proteins selected from Albumin, Complement Factor H, Factor IX, ApoE, Thrombin, Factor VIIIa, Heparin Cofactor II, alpha-2 macroglobulin, Fibroblast Growth Factor 1, Fibroblast Growth Factor 2, Hepatocyte Growth Factor/Scatter Factor, Vascular Endothelial Growth Factor, High-Mobility Group Protein B1, Cyclophilin B, IL-8 (CXCL8), Platelet Factor 4 (CXCL4), Stromal Cell-Derived Factor-1 (CXCL12), Monocyte Chemoattractant Protein-1 (CCL2), Fibroblast Growth Factor Receptor 1, Neuropilin-1, Receptor for Advanced Glycation End Products, Receptor Protein Tyrosine Phosphatase Sigma, Slit-2, ROBO1, Thrombin, Antithrombin, Protein C inhibitor, Amyloid precursor protein 1, Thrombospondin-1, Annexin A2, PDGF BB, PC4/Sub1, RNF163/ZNF9, Ku70, Ku80, TCP1-alpha, TCP1-beta, TCP1-epsilon, TCP1-gamma, TCP1-Theta, TCP1-delta, HSP90-AA1, HSP90-AB, HSP70-5/GRP78, HSPA1L, HSC70, ACTB, TBBB2C, Vimentin, CArG Binding Factor, DHX30, EIF2S2, EIF4H, GRSF1, hnRNP D1L, hnRNPA1, hnRNPA2, hnRNPH1, hnRNPK, hnRNPQ, hnRNPU, hnRNPUL, ILF2, ILF3, KHSRP, La/SSB, NCL, NPM1, P54nrb, PSF, PSPC1, RHA, YBX1, ACLY, VARS, ANXA2, NDKA, Thymidylate Kinase, JKBP1 delta 6, SHMT2, LRPPRC, NARS, ATAD3A, KCTD12, CD4, GP120, aMb2 (Mac-1), VDAC-1, Ago2 PAZ domain, RAGE, AIM2, DHX36, DHX9, DDX41, IFI16, RIG-I, MDA5, LRRFIP1, DLM-1/ZBP1, TREX1, Laminin, and Fibronectin.

265. A method of any one of the preceding embodiments, wherein the composition comprising the first plurality of oligonucleotides displays decreased binding as compared with a reference composition to one or more proteins.

265a. A method of any one of the preceding embodiments, wherein the composition comprising the first plurality of oligonucleotides displays decreased binding as compared with a reference composition to one or more proteins by more than 10%.

265b. A method of any one of the preceding embodiments, wherein the composition comprising the first plurality of oligonucleotides displays decreased binding as compared with a reference composition to one or more proteins by more than 20%.

265c. A method of any one of the preceding embodiments, wherein the composition comprising the first plurality of oligonucleotides displays decreased binding as compared with a reference composition to one or more proteins by more than 30%.

265d. A method of any one of the preceding embodiments, wherein the composition comprising the first plurality of oligonucleotides displays decreased binding as compared with a reference composition to one or more proteins by more than 40%.

265e. A method of any one of the preceding embodiments, wherein the composition comprising the first plurality of oligonucleotides displays decreased binding as compared with a reference composition to one or more proteins by more than 50%.

265f. A method of any one of the preceding embodiments, wherein the composition comprising the first plurality of oligonucleotides displays decreased binding as compared with a reference composition to one or more proteins by more than 60%.

265g. A method of any one of the preceding embodiments, wherein the composition comprising the first plurality of oligonucleotides displays decreased binding as compared with a reference composition to one or more proteins by more than 70%.

265h. A method of any one of the preceding embodiments, wherein the composition comprising the first plurality of oligonucleotides displays decreased binding as compared with a reference composition to one or more proteins by more than 80%.

265i. A method of any one of the preceding embodiments, wherein the composition comprising the first plurality of oligonucleotides displays decreased binding as compared with a reference composition to one or more proteins by more than 90%.

265j. A method of any one of the preceding embodiments, wherein the composition comprising the first plurality of oligonucleotides displays decreased binding as compared with a reference composition to one or more proteins by more than 95%.

265k. A method of any one of the preceding embodiments, wherein the composition comprising the first plurality of oligonucleotides displays decreased binding as compared with a reference composition to one or more proteins by more than 96%.

265l. A method of any one of the preceding embodiments, wherein the composition comprising the first plurality of oligonucleotides displays decreased binding as compared with a reference composition to one or more proteins by more than 97%.

265m. A method of any one of the preceding embodiments, wherein the composition comprising the first plurality of oligonucleotides displays decreased binding as compared with a reference composition to one or more proteins by more than 98%.

265n. A method of any one of the preceding embodiments, wherein the composition comprising the first plurality of oligonucleotides displays decreased binding as compared with a reference composition to one or more proteins by more than 99%.

266. A method of any one of the preceding embodiments, wherein the composition comprising the first plurality of oligonucleotides displays decreased binding as compared with a reference composition to Factor H.

266. A method of any one of the preceding embodiments, wherein the composition comprising the first plurality of oligonucleotides displays decreased binding as compared with a reference composition to a heparin sulfate binding protein.

267. A method of any one of the preceding embodiments, wherein the composition comprising the first plurality of oligonucleotides displays increased binding as compared with a reference composition to one or more proteins.

268. A method of any one of the preceding embodiments, wherein the composition comprising the first plurality of oligonucleotides displays increased binding as compared with a reference composition to albumin.

268a. A method of any one of the preceding embodiments, wherein the increased protein binding is observed in a BSA binding assay, wherein the first plurality of oligonucleotides have increased BSA binding that the reference plurality.

269. A method of any one of the preceding embodiments, wherein the composition comprising the first plurality of oligonucleotides displays increased binding as compared with a reference composition by 5% or more.

269a. A method of any one of the preceding embodiments, wherein the composition comprising the first plurality of oligonucleotides displays increased binding as compared with a reference composition by 10% or more.

269b. A method of any one of the preceding embodiments, wherein the composition comprising the first plurality of oligonucleotides displays increased binding as compared with a reference composition by 20% or more.

269c. A method of any one of the preceding embodiments, wherein the composition comprising the first plurality of oligonucleotides displays increased binding as compared with a reference composition by 30% or more.

269d. A method of any one of the preceding embodiments, wherein the composition comprising the first plurality of oligonucleotides displays increased binding as compared with a reference composition by 40% or more.

269e. A method of any one of the preceding embodiments, wherein the composition comprising the first plurality of oligonucleotides displays increased binding as compared with a reference composition by 50% or more.

269f. A method of any one of the preceding embodiments, wherein the composition comprising the first plurality of oligonucleotides displays increased binding as compared with a reference composition by 60% or more.

269g. A method of any one of the preceding embodiments, wherein the composition comprising the first plurality of oligonucleotides displays increased binding as compared with a reference composition by 70% or more.

269h. A method of any one of the preceding embodiments, wherein the composition comprising the first plurality of oligonucleotides displays increased binding as compared with a reference composition by 80% or more.

269i. A method of any one of the preceding embodiments, wherein the composition comprising the first plurality of oligonucleotides displays increased binding as compared with a reference composition by 90% or more.

269j. A method of any one of the preceding embodiments, wherein the composition comprising the first plurality of oligonucleotides displays increased binding as compared with a reference composition by 100% or more.

269k. A method of any one of the preceding embodiments, wherein the composition comprising the first plurality of oligonucleotides displays increased binding as compared with a reference composition by 2 folds or more.

269l. A method of any one of the preceding embodiments, wherein the composition comprising the first plurality of oligonucleotides displays increased binding as compared with a reference composition by 5 folds or more.

269m. A method of any one of the preceding embodiments, wherein the composition comprising the first plurality of oligonucleotides displays increased binding as compared with a reference composition by 10 folds or more.

269n. A method of any one of the preceding embodiments, wherein the composition comprising the first plurality of oligonucleotides displays increased binding as compared with a reference composition by 50 folds or more.

269o. A method of any one of the preceding embodiments, wherein the composition comprising the first plurality of oligonucleotides displays increased binding as compared with a reference composition by 100 folds or more.

270. A method of any one of the preceding embodiments, wherein protein binding is measured in vitro.

271. A method of any one of the preceding embodiments, wherein the composition comprising the first plurality of oligonucleotides displays improved delivery.

272. A method, comprising administering a composition comprising a first plurality of oligonucleotides, which composition displays improved delivery as compared with a reference composition comprising a plurality of oligonucleotides, each of which also has the common base sequence but which differs structurally from the oligonucleotides of the first plurality in that:

individual oligonucleotides within the reference plurality differ from one another in stereochemical structure; and/or at least some oligonucleotides within the reference plurality have a structure different from a structure represented by the plurality of oligonucleotides of the composition; and/or at least some oligonucleotides within the reference plurality do not comprise a wing region and a core region.

273. In a method of administering an oligonucleotide composition comprising a first plurality of oligonucleotides having a common nucleotide sequence, the improvement that comprises: administering an oligonucleotide comprising a first plurality of oligonucleotides that is characterized by improved delivery relative to a reference oligonucleotide composition of the same common nucleotide sequence.

274. A method of any one of the preceding embodiments, wherein the composition comprising the first plurality of oligonucleotides displays improved systemic delivery.

274a. A method of any one of the preceding embodiments, wherein the composition comprising the first plurality of oligonucleotides displays improved cytoplasmatic delivery.

275. A method of any one of the preceding embodiments, wherein the composition comprising the first plurality of oligonucleotides displays improved delivery to a target.

276. A method of any one of the preceding embodiments, wherein the composition comprising the first plurality of oligonucleotides displays improved delivery to a population of cells.

276a. A method of any one of the preceding embodiments, wherein the composition comprising the first plurality of oligonucleotides displays improved delivery to a tissue.

276b. A method of any one of the preceding embodiments, wherein the composition comprising the first plurality of oligonucleotides displays improved delivery to an organ.

277. A method of any one of the preceding embodiments, wherein oligonucleotides of the first plurality comprise more modified internucleotidic linkages than oligonucleotides of the reference composition.

277a. A method of any one of the preceding embodiments, wherein oligonucleotides of the first plurality comprise more phosphorothioate linkages than oligonucleotides of the reference composition.

277b. A method of any one of the preceding embodiments, wherein oligonucleotides of the first plurality comprise more phosphorothioate linkages than oligonucleotides of the reference composition at the 5'-end.

277c. A method of any one of the preceding embodiments, wherein oligonucleotides of the first plurality comprise more phosphorothioate linkages than oligonucleotides of the reference composition at the 3'-end.

277d. A method of any one of the preceding embodiments, wherein oligonucleotides of the first plurality comprise more phosphorothioate linkages in a wing region than oligonucleotides of the reference composition.

277e. A method of any one of the preceding embodiments, wherein oligonucleotides of the first plurality comprise more phosphorothioate linkages in each wing region than oligonucleotides of the reference composition.

278. A method of any one of the preceding embodiments, wherein oligonucleotides of the first plurality comprise more Sp chiral internucleotidic linkages than oligonucleotides of the reference composition.

278a. A method of any one of the preceding embodiments, wherein oligonucleotides of the first plurality comprise more Sp phosphorothioate linkages than oligonucleotides of the reference composition.

278b. A method of any one of the preceding embodiments, wherein oligonucleotides of the first plurality comprise more Sp phosphorothioate linkages than oligonucleotides of the reference composition at the 5'-end.

278c. A method of any one of the preceding embodiments, wherein oligonucleotides of the first plurality comprise more Sp phosphorothioate linkages than oligonucleotides of the reference composition at the 3'-end.

278d. A method of any one of the preceding embodiments, wherein oligonucleotides of the first plurality comprise more Sp phosphorothioate linkages in a wing region than oligonucleotides of the reference composition.

278e. A method of any one of the preceding embodiments, wherein oligonucleotides of the first plurality comprise more Sp phosphorothioate linkages in each wing region than oligonucleotides of the reference composition.

279. A method of any one of the preceding embodiments, wherein oligonucleotides of the first plurality comprise more modified bases than oligonucleotides of the reference composition.

279a. A method of any one of the preceding embodiments, wherein oligonucleotides of the first plurality comprise more methylated bases than oligonucleotides of the reference composition.

279b. A method of any one of the preceding embodiments, wherein oligonucleotides of the first plurality comprise more methylated bases than oligonucleotides of the reference composition at the 5'-end.

279c. A method of any one of the preceding embodiments, wherein oligonucleotides of the first plurality comprise more methylated bases than oligonucleotides of the reference composition at the 3'-end.

279d. A method of any one of the preceding embodiments, wherein oligonucleotides of the first plurality comprise more methylated bases than in a wing region than oligonucleotides of the reference composition.

279e. A method of any one of the preceding embodiments, wherein oligonucleotides of the first plurality comprise more methylated bases than in each wing region than oligonucleotides of the reference composition.

280. A method of any one of the preceding embodiments, wherein oligonucleotides of the first plurality comprise fewer 2'-MOE modifications than oligonucleotides of the reference composition.

280a. A method of any one of the preceding embodiments, wherein oligonucleotides of the first plurality comprise fewer 2'-MOE modifications than oligonucleotides of the reference composition.

281. A method of any one of the preceding embodiments, wherein oligonucleotides of the first plurality comprise fewer 2'-MOE modifications than oligonucleotides of the reference composition at the 5'-end.

282. A method of any one of the preceding embodiments, wherein oligonucleotides of the first plurality comprise fewer 2'-MOE modifications than oligonucleotides of the reference composition at the 3'-end.

283. A method of any one of the preceding embodiments, wherein oligonucleotides of the first plurality comprise fewer 2'-MOE modifications than in a wing region than oligonucleotides of the reference composition.

284. A method of any one of the preceding embodiments, wherein oligonucleotides of the first plurality comprise fewer 2'-MOE modifications than in each wing region than oligonucleotides of the reference composition.

285. A composition or method of any one of the preceding embodiments, wherein individual oligonucleotides within the reference plurality differ from one another in stereochemical structure.

286. A composition or method of any one of the preceding embodiments, wherein at least some oligonucleotides within the reference plurality have a structure different from a structure represented by the plurality of oligonucleotides of the composition.

287. A composition or method of any one of the preceding embodiments, wherein at least some oligonucleotides within the reference plurality do not comprise a wing region and a core region.

288. A method of any one of the preceding embodiments, wherein a composition of a first plurality of oligonucleotides is a composition of any one of the preceding embodiments.

289. A method of decreasing level of a target nucleic acid in a cell, tissue, and/or organism without significant complement activation by contacting with a composition of any one of the preceding embodiments.

290. A method of directing RNase H cleavage of a target nucleic acid without significant complement activation by contacting the target nucleic acid with a composition of any one of the preceding embodiments.

291. A method of any one of the preceding embodiments, wherein the method is performed under conditions and for a time sufficient to reduce level of the target nucleic acid sequence.

292. A method of identifying and/or characterizing an oligonucleotide composition, the method comprising steps of:
- providing at least one composition of any one of the preceding embodiments;
- assessing complement activation relative to a reference composition.

293. A method of identifying and/or characterizing an oligonucleotide composition, the method comprising steps of:
- providing at least one composition of any one of the preceding embodiments;
- assessing injection site inflammation relative to a reference composition.

294. A method of identifying and/or characterizing an oligonucleotide composition, the method comprising steps of:
- providing at least one composition of any one of the preceding embodiments;
- assessing protein binding relative to a reference composition.

295. A method of identifying and/or characterizing an oligonucleotide composition, the method comprising steps of:
- providing at least one composition of any one of the preceding embodiments;
- assessing delivery relative to a reference composition.

296. A method or composition of any one of the preceding embodiments, wherein the reference composition is a substantially racemic preparation of oligonucleotides that share the base sequence.

297. A method or composition of any one of the preceding embodiments, wherein the reference composition is a chirally controlled oligonucleotide composition of another oligonucleotide type.

298. A method or composition of any one of the preceding embodiments, wherein oligonucleotides of the reference composition comprise more phosphorothioate linkages.

299. A method or composition of any one of the preceding embodiments, wherein oligonucleotides of the reference composition comprise only phosphorothioate linkages.

300. A method or composition of any one of the preceding embodiments, wherein oligonucleotides of the reference composition comprise fewer modified sugar moieties.

301. A method or composition of any one of the preceding embodiments, wherein oligonucleotides of the reference composition comprise fewer modified sugar moieties, wherein the modification is 2'-$OR^1$.

302. A method or composition of any one of the preceding embodiments, wherein oligonucleotides of the reference composition comprise more modified sugar moieties.

303. A method or composition of any one of the preceding embodiments, wherein oligonucleotides of the reference composition comprise more modified sugar moieties, wherein the modification is 2'-$OR^1$.

304. A method or composition of any one of the preceding embodiments, wherein oligonucleotides of the reference composition comprise fewer phosphorothioate linkages.

305. A method or composition of any one of the preceding embodiments, wherein oligonucleotides of the reference composition have a wing, and comprise fewer phosphorothioate linkages at the wing.

306. A method or composition of any one of the preceding embodiments, wherein oligonucleotides of the reference composition comprise fewer Sp phosphorothioate linkages.

307. A method or composition of any one of the preceding embodiments, wherein oligonucleotides of the reference composition have a wing, and comprise fewer Sp phosphorothioate linkages at the wing.

308. A method or composition of any one of the preceding embodiments, wherein oligonucleotides of the reference composition comprise more Rp phosphorothioate linkages.

309. A method or composition of any one of the preceding embodiments, wherein oligonucleotides of the reference composition have a wing, and comprise more Rp phosphorothioate linkages at the wing.

310. A method or composition of any one of the preceding embodiments, wherein oligonucleotides of the reference composition comprise fewer methylated bases.

311. A method or composition of any one of the preceding embodiments, wherein oligonucleotides of the reference composition comprise more 2'-MOE modifications.

312. A method or composition of any one of the preceding embodiments, wherein oligonucleotides of the reference composition share the same:
1) base sequence;
2) pattern of backbone linkages; and
3) pattern of backbone phosphorus modifications.

313. A method or composition of any one of the preceding embodiments, wherein oligonucleotides of the reference composition comprise fewer natural phosphate linkages.

314. A method or composition of any one of the preceding embodiments, wherein oligonucleotides of the reference composition comprise fewer natural phosphate linkages at the 5'- and/or 3'-end.

315. A method or composition of any one of the preceding embodiments, wherein oligonucleotides of the reference composition comprise fewer natural phosphate linkages in a region corresponding to a wing of oligonucleotides of the first plurality.

316. A method or composition of any one of the preceding embodiments, wherein oligonucleotides of the first plurality comprise natural phosphate linkages in a wing, and oligonucleotides of the reference composition comprise fewer natural phosphate linkages at the corresponding wing region.

317. A method or composition of any one of the preceding embodiments, wherein oligonucleotides of the first plurality comprise natural phosphate linkages in a wing, and oligonucleotides of the reference composition comprises modified internucleotidic linkages at one or more such natural phosphate linkage locations in a wing.

318. A method or composition of any one of the preceding embodiments, wherein oligonucleotides of the first plurality comprise natural phosphate linkages in a wing, and oligonucleotides of the reference composition comprises phosphorothioate linkages at one or more such natural phosphate linkage locations in a wing.

319. A method or composition of any one of the preceding embodiments, wherein oligonucleotides of the reference composition comprise no natural phosphate linkages.

320. A method or composition of any one of the preceding embodiments, wherein oligonucleotides of the reference composition comprise no wing-core-wing structure.

321. A method for manufacturing an oligonucleotide composition directed to a selected target sequence, the method comprising steps of:

- manufacturing an oligonucleotide composition comprising a first plurality of oligonucleotides of any one of the preceding embodiments, each of which has a base sequence complementary to the target sequence.

322. A method of embodiment 321, further comprising providing a pharmaceutically acceptable carrier.

EXEMPLIFICATION

The foregoing has been a description of certain non-limiting embodiments of the disclosure. Accordingly, it is to be understood that the embodiments of the disclosure herein described are merely illustrative of the application of the principles of the disclosure. Reference herein to details of the illustrated embodiments is not intended to limit the scope of the claims.

Methods for preparing provided oligonucleotides and oligonucleotide compositions are widely known in the art, including but not limited to those described in WO/2010/064146, WO/2011/005761, WO/2013/012758, WO/2014/010250, US2013/0178612, WO/2014/012081 and WO/2015/107425, the methods and reagents of each of which is incorporated herein by reference. Applicant describes herein example methods for making provided oligonucleotides.

Example 1. Example Preparation of Linkers

In some embodiments, an SP linker was prepared following the scheme below:

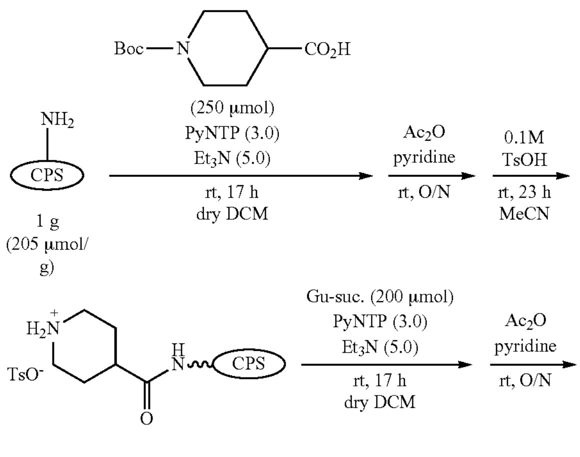

-continued

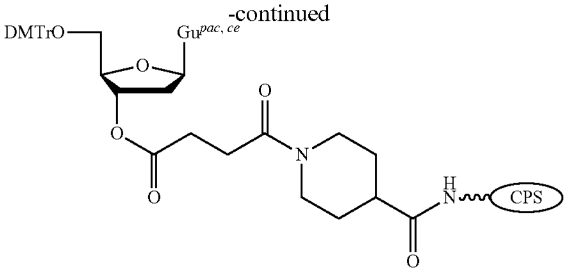

160 μmol/g

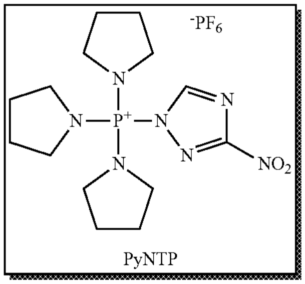

PyNTP

Example 2. Example Methods for Preparing Oligonucleotides and Compositions

ABBREVIATION

AMA: conc. $NH_3$— 40% $MeNH_2$ in $H_2O$ (1:1, v/v)
CMIMT: N-cyanomethylimidazolium triflate
DBU: 1,8-diazabicyclo[5.4.0]undec-7-ene
DCA: dichloroacetic acid
DCM: dichloromethane, $CH_2Cl_2$
DMTr: 4,4'-dimethoxytrityl
DVB: divinylbenzene
HCP: highly cross-linked polystyrene (contains 50% DVB, non-swelling polystyrene)
MeIm: N-methylimidazole
MQ: water obtained from "Milli-Q Reference"
PhIMT: N-phenylimidazolium triflate
POS: 3-phenyl-1,2,4-dithiazolin-5-one
PS200: primer support 200, commercially available from GE Healthcare
PS5G: primer support 5G, commercially available from GE Healthcare
TBAF: tetrabutylammonium fluoride
TBHP: tert-butylhydroperoxide
TEAA: triethylammonium aceate Solid support: Various types of solid support (varied nucleosides loading) were tested. In some embodiments, HCP>PS5G≈PS200≥CPG. In some embodiments, a solid support is HCP. In some embodiments, a solid support is PS5G. In some embodiments, a solid support is PS200. In some embodiments, a solid support is CPG. For nucleosides loading, various range (30-300 μmol/g) were tested. In some embodiments, 70-80 μmol/g loading performed than others. In some embodiments, nucleoside loading is 70-80 μmol/g. CPG was purchased from various suppliers (GlenReseach, LinkTechnologies, ChemGenes, PrimeSynthesis, and 3-Prime).

Various linkers were tested and can be used. In some embodiments, during preparation of chirally controlled oligonucleotide compositions by using DPSE-type chemistry, SP-linker was used.

Various activators were prepared and/or purchased, and evaluated. In some embodiments, for DPSE-type chemistry, CMIMT was used.

Example Analytical Conditions:

RP-UPLC-MS

System: Waters, Aquity UPLC I-Class, Xevo G2-Tof

Column: Waters, BEH C18, 1.7 μm, 2.1×150 mm

Temp. & Flow rate: 55° C., 0.3 mL/min

Buffer: A: 0.1M TEAA; B: MeCN

Gradient: % B: 1-30%/30 min

AEX-HPLC

System: Waters, Alliance e2695

Column: Thermo, DNAPac PA-200, 4×250 mm

Temp. & Flow rate: 50° C., 1 mL/min

Buffer: A: 20 mM NaOH; B: A+1M $NaClO_4$

Gradient: % B: 10-50%/30 min

Example Procedure for the Synthesis of Chrial-Oligos (1 μMol Scale):

Automated solid-phase synthesis of chiral-oligos was performed according to example cycles shown herein. After the synthesis cycles, the resin was treated with 0.1M TBAF in MeCN (1 mL) for 2 h (30 min usually enough) at room temperature, washed with MeCN, dried, and add AMA (1 mL) for 30 min at 45° C. The mixture was cooled to room temperature and the resin was removed by membrane filtration. The filtrate was concentrated under reduced pressure to about 1 mL. The residue was diluted with 1 mL of $H_2O$ and analyzed by AEX-HPLC and RP-UPLC-MS (example conditions: refer to the analytical conditions).

| step | operation | reagents and solvent | volume | waiting time |
|---|---|---|---|---|
| 1 | detritylation | 3% DCA in toluene | 10 mL | 65 s |
| 2 | coupling | 0.15M monomer in $^{i}$PrCN + 0.5M CMIMT in MeCN | 0.5 mL | 5 min |
| 3 | capping | 20% $Ac_2O$, 30% 2,6-lutidine in MeCN + 20% MeIm in MeCN | 1.2 mL | 60 s |
| 4 | oxidation or sulfurization | 1.1M TBHP in DCM-decane or 0.1M POS in MeCN | 1.0 mL | 300 s |

As described, in some embodiments, TBAF treatment can provide better results, for example, less desulfurization. In some embodiments, SP linker provided better yields and/or purity through, without the intention to be limited by theory, better stability during chiral auxiliary removal as described. In some embodiments, fluoro-containing reagents such as HF—$NR_3$ (e.g., HF-TEA (triethylamine)), provided better yields and/or purity when succinyl linker was used by, without the intention to be limited by theory, less cleavage during chiral auxiliary removal. In some embodiments, after synthesis, the resin was treated with 1M TEA-HF in DMF-$H_2O$ (3:1, v/v; 1 mL) for 2 h at 50° C. PS5G support was washed with MeCN, $H_2O$, and add AMA (conc. $NH_3$— 40% $MeNH_2$ (1:1, v/v)) (1 mL) for 45 min at 50° C. The mixture was cooled to room temperature and the resin was removed by membrane filtration (washed with $H_2O$ for 2 mL). The filtrate was concentrated under reduced pressure until it becomes about 1 mL. The residue was diluted with 1 mL of $H_2O$ and analyzed by AEX-HPLC and RP-UPLC-MS (conditions: refer to the analytical conditions section).

Example procedure for the purification of chrial-oligos (1 μmol scale): in some embodiments, crude oligos were purified by AEX-MPLC according to the following example conditions:

System: AKTA Purifier-10

Column: TOHSOH, DNA STAT, 4.6×100 mm

Temp. & Flow rate: 60° C., 0.5 mL/min

Buffer: A: 20 mM Tris-HCl (pH 9.0)+20% MeCN, B: A+1.5M NaCl

Gradient: % B: 20-70%/25CV (2%/CV)

All fractions were analyzed by analytical AEX-HPLC, and fractions containing chiral oligo more than 80% purity were corrected and desalted by Sep-Pak Plus tC18 (WAT036800) using example conditions below:

Conditioning Sep-Pak Plus with 15 mL of MeCN.

Rinse cartridge with 15 mL of 50% MeCN/MQ.

Equilibrate cartridge with 30 mL of MQ.

Load sample, and wash with 40 mL of MQ.

Elute chiral oligos with 10 mL of 50% MeCN/MQ.

Eluted sample were evaporated under reduced pressure to remove MeCN, and lyophilized. The product were dissolved in MQ (1 mL), filtered by 0.2 m mesh syringe filter, and analyzed. After yield calculation by UV absorbance, the preparation was lyophilized again.

Example methods, conditions and reagents were described in, e.g., JP 2002-33436, WO2005/092909, WO2010/064146, WO2012/039448, WO2011/108682, WO2014/010250, WO2014/010780, WO2014/012081, etc., and may be useful for preparing provided oligonucleotides and/or compositions.

Provided compositions, among other things, demonstrated improved properties including improved stability and activities. For example, provided oligonucleotide compositions provided increased cleavage rates, increased selectivity, enhanced cleavage pattern, etc. The examples here demonstrated that provided compositions also have low toxicities and improved protein binding profiles.

Example 3. Measurement of Cynomolgus Monkey Serum Complement Activation In Vitro Effects of oligonucleotides on complement activation were measured in vitro in Cynomolgus monkey serum. The third complement component, C3, is central to the classical, alternative and lectin pathways of complement activation. During complement activation, C3 is proteolytically cleaved resulting in release of the anaphylatoxic peptide C3a. Upon activation of the alternative pathway, Factor B is cleaved by complement Factor D yielding the noncatalytic chain Ba and the catalytic subunit Bb. The active subunit Bb is a serine protease that associates with C3b to form the alternative pathway C3 convertase.

Serum from 3 individual Cynomolgus male monkeys was pooled and the pool was used. The time course of C3a and Bb complement activation was measured by incubating oligonucleotides at 37° C. at a final concentration of 330 ug/ml in Cynomolgus monkey serum (1:10 ratio, V/V) and taking aliquots at the indicated time points. Specifically, 9.24 μL of 10 mg/mL stock of oligonucleotide were added to 270.76 μL of pooled serum, incubated at 37° C. At the indicated time points, 20 μL aliquots were taken out and the reaction was immediately terminated by addition of 2.2 μL of 18 mg/mL EDTA (Sigma-Aldrich).

For the dose response curves six ⅓ serial dilutions (10× concentrated) of oligonucleotides in water were prepared starting from 1 mg/mL. 2 μL of diluted oligonucleotide solutions were then added to 18 μL of Cynomolgus monkey serum and incubated at 37° C. After 40 min the reaction was immediately terminated by addition of 2.2 μL of 18 mg/mL EDTA (Sigma-Aldrich). C3a and Bb were measured using MicroVue C3a Plus and Bb Plus Enzyme Immunoassays from (Quidel, San Diego, CA) at 1:3000 (C3a) and 1:40 (Bb) dilution.

Example results were presented in FIGS. 1-5. In some embodiments, provided compositions have altered levels of complement activation compared the reference stereorandom composition. In some embodiments, provided compositions have dramatically lower complement activation. In some embodiments, provided compositions have essentially no more complement activation than the negative control water.

Example 4. Example Methods for Preparing Oligonucleotides and Compositions

Oligonucleotides were diluted in distilled water to 100 μM to make stock solution. Human Serum Albumin (Fatty acid free, Globulin free, Sigma-Aldrich A3782) was diluted with PBST (1×PBS+0.1% Tween) to 5 mg/mL. Oligonucleotides were diluted 100 times into PBST or 5 mg/mL-Albumin solution to make 1 μM working solution. Oligonucleotide-PBST samples provided estimates of efficiency of oligonucleotide recovery after ultrafiltration, and were used to normalize oligonucleotide concentrations in flow-through of Albumin-binding solution. The 1 μM working solutions were incubated at 37° C. for half an hour. 100 μL of protein/1 μM oligonucleotide complex was put into ultrafiltration tubes (Amicon Ultra 50 kDa cut-off, regenerated cellulose) and centrifuged at 9,000×g for 3 min. The flow-through was collected and assayed for presence of oligonucleotides.

To detect single strand oligonucleotides, OliGreen dye was used. The dilution buffer was TE. Each oligonucleotide had its own standard curve made. Oligonucleotide was diluted to 0.5 μM (200× dilution from 100 μM stock), then seven 1:1 serial dilutions were made in duplicate. 20 μL of each diluted oligonucleotide standard was added to UV transparent half-area 96 well plate. All samples of ultrafiltration flow-through, including original 1 μM Oligonucleotide/PBST and 1 μM Oligonucleotide/protein, were 1:1 serial diluted starting at 4 folds of dilution. 20 μl of each sample was added along with its respective standard. Quant-iT OliGreen dye (Life Technologies, 07582) was diluted 200 times to make working solution. 20 μl of OliGreen working solution was mixed with each oligonucleotide samples and incubated at room temperature. The plate was read using fluorescence microplate reader (excitation=480 nm; emission=520 nm).

The concentration of oligonucleotide was calculated according to its own standard curve. Recovery of free oligonucleotide was calculated as $R_{oligo}=C_{P\text{-}FT}/C_{P\text{-}orig}$ ($R_{oligo}$ is the recovery of free oligonucleotide; $C_{P\text{-}FT}$ is concentration of PBST-flowthrough; $C_{P\text{-}orig}$ is concentration of PBST original working stock). Albumin bound oligonucleotide concentration was normalized as $C_{A\text{-}UB}=C_{A\text{-}FT}/R_{oligo}$; ($C_{A\text{-}UB}$ is Albumin unbound oligo concentration normalized; $C_{A\text{-}FT}$ is measured concentration of oligonucleotide in flow-through in Albumin treated sample). Percentage of unbound free oligonucleotide in Albumin samples was calculated as $P_{A\text{-}UB}=100*C_{A\text{-}UB}/C_{A\text{-}orig}$ ($P_{A\text{-}UB}$ is percentage of unbound free oligonucleotide of Albumin samples; $C_{A\text{-}orig}$ is concentration of Albumin original working stock). % Bound=100−$P_{A\text{-}UB}$.

Figure 6:
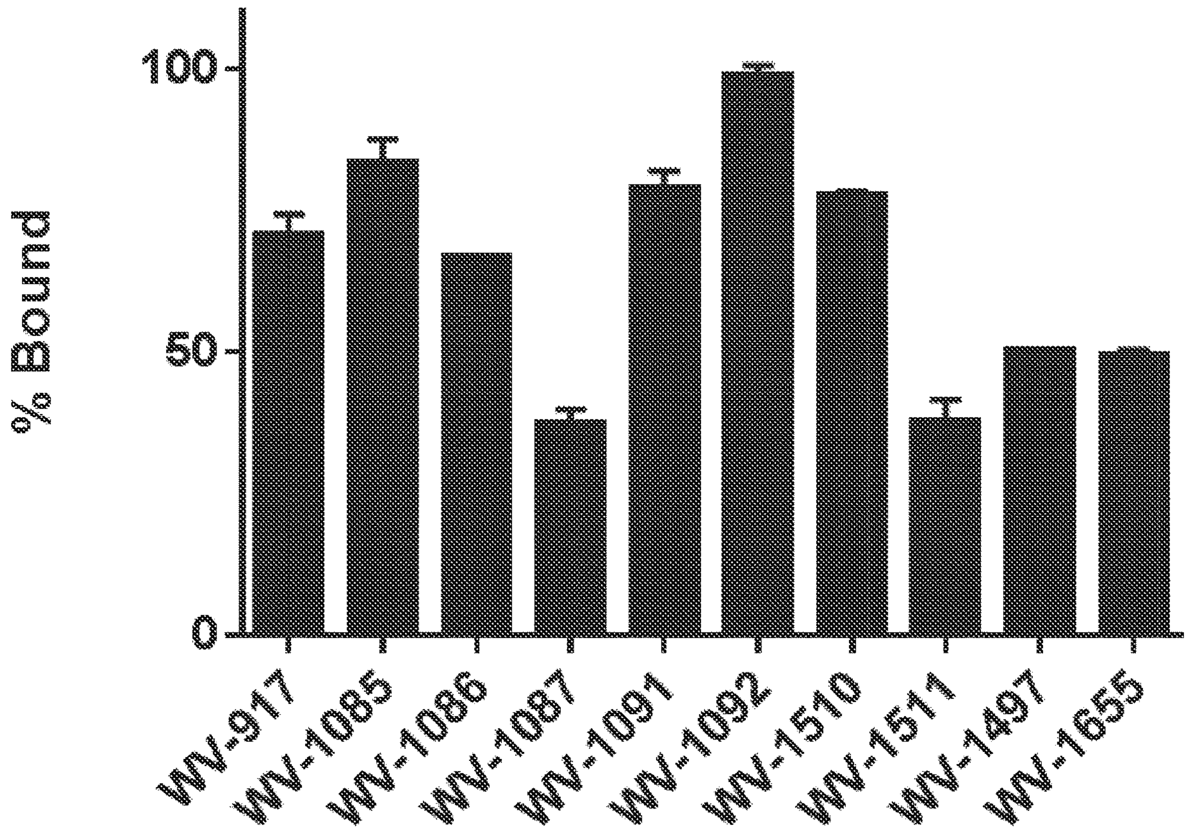
FIG. 6. Example albumin binding by oligonucleotides targeting human HTT.
Figure 7:
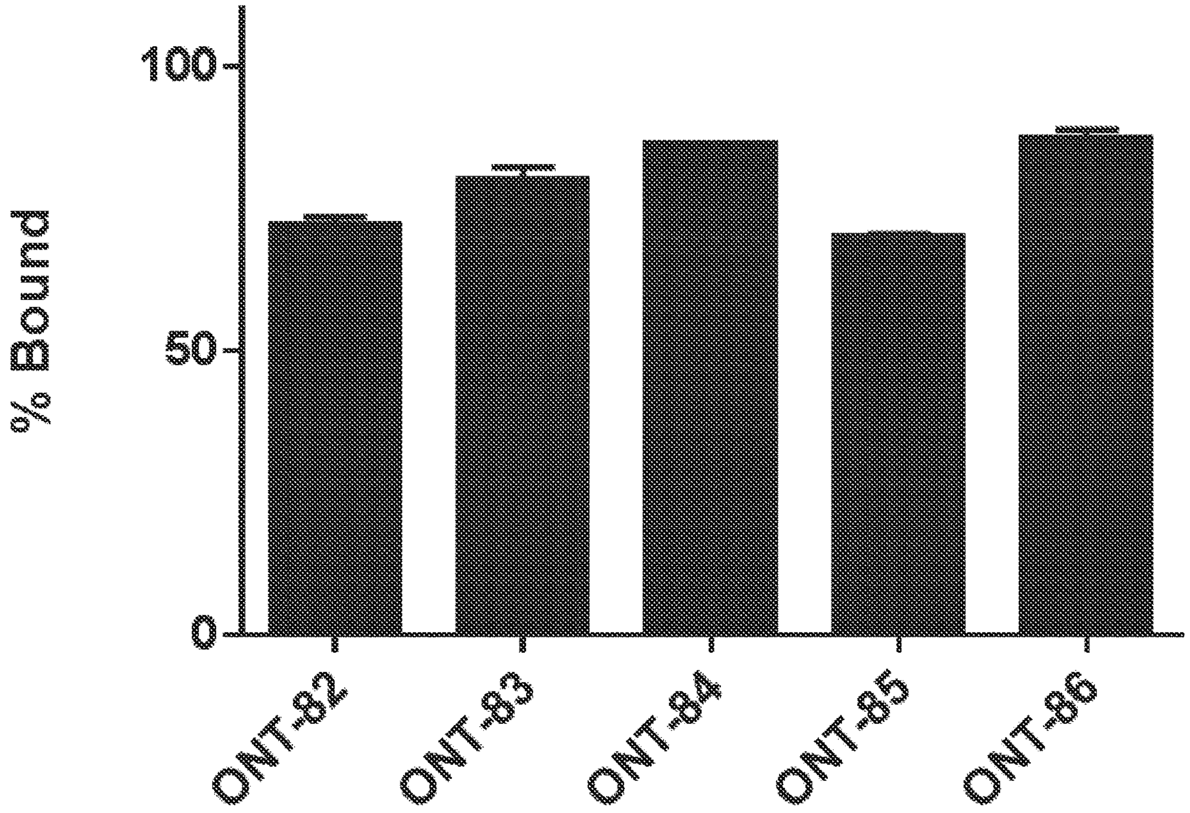
FIG. 7. Example albumin binding by oligonucleotides targeting mouse ApoB
Figure 8:
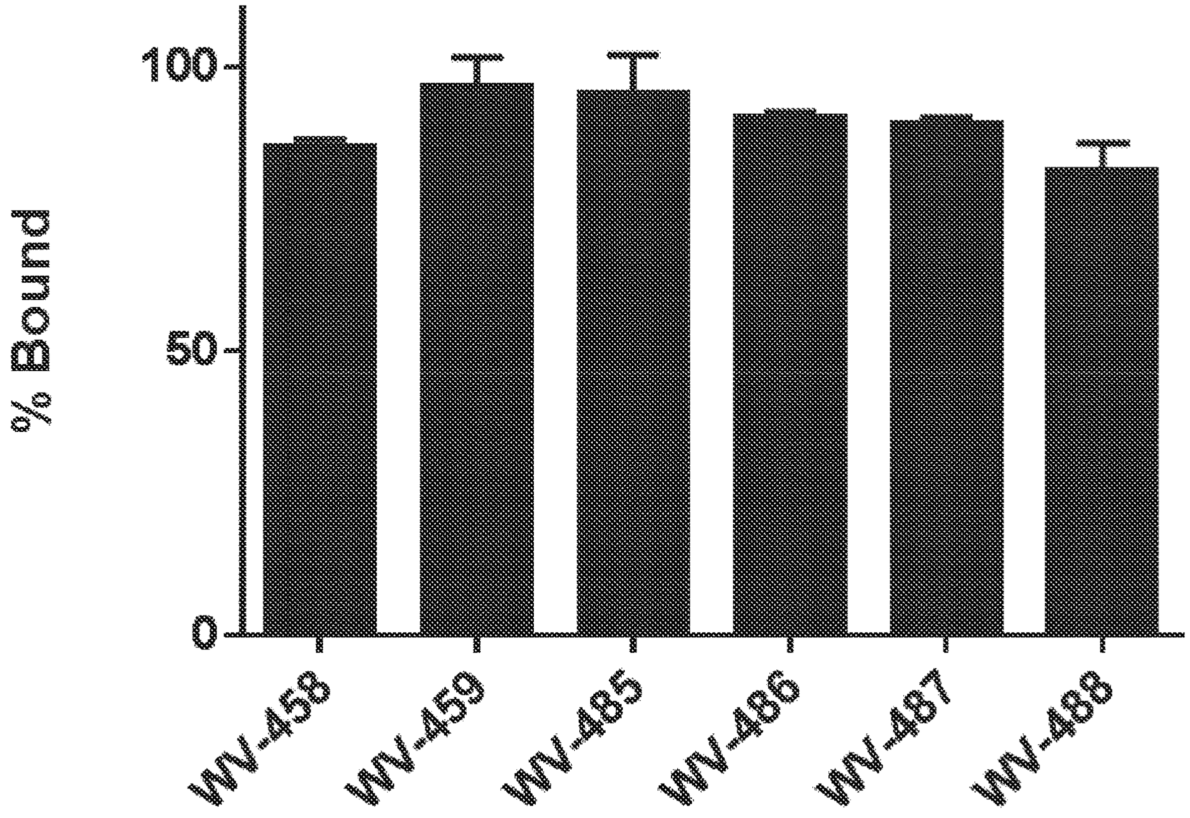
FIG. 8. Example albumin binding by oligonucleotides targeting human SOD1

Example results are presented in FIGS. 6-8. Provided compositions, for example, WV-1092, demonstrated increased binding to albumin which can facilitate oligonucleotide delivery.

EQUIVALENTS

Having described some illustrative embodiments of the disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the disclosure. The present disclosure is not to be limited in scope by examples provided, since the examples are intended as a single illustration of one aspect of the disclosure and other functionally equivalent embodiments are within the scope of the disclosure. Various modifications of the disclosure in addition to those shown and described herein will become apparent to those skilled in the art from the foregoing description and fall within the scope of the appended claims. The advantages and objects of the disclosure are not necessarily encompassed by each embodiment of the disclosure.

The invention claimed is:

1. A method for identifying a chirally controlled oligonucleotide composition that has reduced complement activation relative to a reference oligonucleotide composition, the method comprising:

providing at least one chirally controlled oligonucleotide composition comprising a plurality of oligonucleotides;

assessing complement activation of each of the at least one chirally controlled oligonucleotide composition relative to the reference oligonucleotide composition; and identify a chirally controlled oligonucleotide composition that displays reduced complement activation relative to the reference oligonucleotide composition;

wherein:

each of the at least one chirally controlled oligonucleotide composition is independently an oligonucleotide composition comprising a plurality of oligonucleotides of a particular oligonucleotide type which are structurally identical and is defined by:

1) base sequence;

2) pattern of backbone linkages;

3) pattern of backbone chiral centers; and 4) pattern of backbone phosphorus modifications;

which composition is chirally controlled in that it is enriched, relative to a substantially racemic preparation of oligonucleotides of the particular oligonucleotide type;

in the identified chirally controlled oligonucleotide composition, oligonucleotides of the plurality comprises 5 or more phosphorothioate internucleotidic linkages, wherein at least about 50% phosphorothioate internucleotidic linkages are Sp; and the reference oligonucleotide composition is a substantially racemic preparation of oligonucleotides of the particular type.

2. The method of claim 1, wherein the reduced complement activation is observed in an assay that detects the presence, absolute level and/or relative level of C3a or Bb.

3. The method of claim 1, wherein the pattern of backbone chiral centers comprise at least one Rp and at least one Sp.

4. The method of claim 3, wherein the pattern of backbone chiral centers comprise Rp(Sp)m, wherein m is 2.

5. The method of claim 4, wherein the pattern of backbone chiral centers comprise Rp(Sp)m, wherein m is 3.

6. The method of claim 4, wherein the pattern of backbone chiral centers comprise Rp(Sp)m, wherein m is 4.

7. The method of claim 4, wherein the pattern of backbone chiral centers comprise Rp(Sp)m, wherein m is 5.

8. The method of claim 4, wherein the pattern of backbone chiral centers comprise Rp(Sp)m, wherein m is 6.

9. The method of claim 4, wherein the pattern of backbone chiral centers comprise Rp(Sp)m, wherein m is 7.

10. The method of claim 4, wherein the pattern of backbone chiral centers comprise Rp(Sp)m, wherein m is 8.

11. The method of claim 4, wherein the pattern of backbone chiral centers comprise RpSpSp.

12. The method of claim 11, wherein the pattern of backbone chiral centers comprise (Np)t(Rp)(Sp)m, wherein t is 1, m is 2, and each Np is independent Rp or Sp.

13. The method of claim 12, wherein the pattern of backbone chiral centers comprise SpRpSpSp.

14. The method of claim 12, wherein the pattern of backbone chiral centers comprise SpSpRpSpSp.

15. The method of claim 4, wherein oligonucleotides of the first plurality comprise one or more natural phosphate linkages.

* * * * *